United States Patent
Fouser et al.

(10) Patent No.: US 8,906,375 B2
(45) Date of Patent: *Dec. 9, 2014

(54) METHODS OF USING ANTIBODIES AGAINST HUMAN IL-22

(75) Inventors: Lynette A. Fouser, Action, MA (US); Martin Hegen, Brookline, MA (US); Deborah P. Luxenberg, Melrose, MA (US); Margot O'Toole, Newtonville, MA (US)

(73) Assignee: Wyeth LLC, Madison, NJ (US)

( * ) Notice: Subject to any disclaimer, the term of this patent is extended or adjusted under 35 U.S.C. 154(b) by 966 days.

This patent is subject to a terminal disclaimer.

(21) Appl. No.: 12/951,734

(22) Filed: Nov. 22, 2010

(65) Prior Publication Data

US 2011/0091478 A1    Apr. 21, 2011

Related U.S. Application Data

(60) Continuation of application No. 12/474,479, filed on May 29, 2009, now Pat. No. 7,846,444, which is a division of application No. 11/707,986, filed on Feb. 20, 2007, now Pat. No. 7,811,567.

(60) Provisional application No. 60/774,595, filed on Feb. 21, 2006.

(51) Int. Cl.
| A61K 39/395 | (2006.01) |
| A61P 37/06 | (2006.01) |
| A61P 37/08 | (2006.01) |
| C07K 16/24 | (2006.01) |
| A61K 39/00 | (2006.01) |

(52) U.S. Cl.
CPC ........... *C07K 16/244* (2013.01); *C07K 2317/73* (2013.01); *C07K 2317/76* (2013.01); *C07K 2317/92* (2013.01); *A61K 2039/505* (2013.01); *C07K 2317/21* (2013.01); *C07K 2317/622* (2013.01); *Y10S 514/861* (2013.01)
USPC .................. 424/158.1; 424/145.1; 424/130.1; 424/141.1; 514/9.4; 514/861; 530/351; 530/389.1

(58) Field of Classification Search
None
See application file for complete search history.

(56) References Cited

U.S. PATENT DOCUMENTS

| 5,350,836 A | 9/1994 | Kipchick et al. |
| 5,536,637 A | 7/1996 | Jacobs |
| 5,674,487 A | 10/1997 | Smith et al. |
| 5,837,232 A | 11/1998 | De Waal Malefyt et al. |
| 5,863,796 A | 1/1999 | Moore et al. |
| 6,143,867 A | 11/2000 | Akerblom |
| 6,225,117 B1 | 5/2001 | Gately et al. |
| 6,274,710 B1 | 8/2001 | Dumoutier et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,939,545 B2 | 9/2005 | Jacobs et al. |
| 7,279,559 B2 | 10/2007 | Jacobs et al. |
| 7,307,161 B1 | 12/2007 | Jacobs et al. |
| 7,459,533 B2 | 12/2008 | Jacobs et al. |
| 7,811,567 B2 | 10/2010 | Fouser et al. |
| 2001/0006637 A1 | 7/2001 | Akahoshi et al. |
| 2001/0023070 A1 | 9/2001 | Ebner et al. |
| 2001/0024652 A1 | 9/2001 | Dumoutier et al. |
| 2002/0012669 A1 | 1/2002 | Presnell et al. |
| 2002/0102723 A1 | 8/2002 | Gurney et al. |
| 2002/0177165 A1 | 11/2002 | Ashkenazi et al. |
| 2002/0187523 A1 | 12/2002 | Tang et al. |
| 2003/0003545 A1 | 1/2003 | Ebner et al. |
| 2003/0012788 A1 | 1/2003 | Renauld et al. |
| 2003/0092133 A1 | 5/2003 | Ebner et al. |
| 2003/0170823 A1 | 9/2003 | Presnell et al. |
| 2004/0023341 A1 | 2/2004 | Xu et al. |
| 2004/0110189 A1 | 6/2004 | Dumoutier et al. |
| 2004/0152125 A1 | 8/2004 | Presnell et al. |
| 2004/0180399 A1 | 9/2004 | Renauld et al. |
| 2005/0042220 A1 | 2/2005 | Li et al. |

FOREIGN PATENT DOCUMENTS

| WO | WO 94/01548 | 1/1994 |
| WO | 9404678 | 3/1994 |
| WO | 9425591 | 11/1994 |
| WO | 9749805 | 12/1997 |
| WO | WO 99/61617 | 12/1999 |
| WO | WO 00/24758 | 5/2000 |
| WO | Wo 00/70049 | 11/2000 |
| WO | WO 00/73457 | 12/2000 |
| WO | WO 00/77037 | 12/2000 |
| WO | WO 01/46422 | 6/2001 |
| WO | WO 02/10393 | 2/2002 |
| WO | WO 02/16611 | 2/2002 |
| WO | WO 02/68476 | 9/2002 |
| WO | WO 2005/000897 | 1/2005 |

OTHER PUBLICATIONS

Norgales et al, Journal of Allergy Clinical Immunology, 2009, vol. 123, No. 6, pp. 1244-1252.*
Rheumatism, 43[2], p. 309 (2003) translated into Engiish cited in Office Action dated Feb. 28, 2012 in Japanese Patent Application No. 2008-556435.
Report of Annual Meeting of the Japanese Society for Immunology, 34 p. 159 (2004) translated into English cited in Office Action dated Feb. 28, 2012 in Japanese Patent Application No. 2008-556435.

(Continued)

*Primary Examiner* — Elizabeth C Kemmerer
*Assistant Examiner* — Fozia Hamud
(74) *Attorney, Agent, or Firm* — MH2 Technology Law Group, LLP

(57) ABSTRACT

The present application provides human antibodies and antigen binding fragments thereof that specifically bind to the human interleukin-22 (IL-22) and methods of using those antibodies, for example, in diagnosing, treating or preventing inflammatory disorders, autoimmune diseases, allergies, septic shock, infectious disorders, transplant rejection, cancer, and other immune system disorders.

29 Claims, 140 Drawing Sheets

(56) References Cited

OTHER PUBLICATIONS

Recombinant Antibodies, Benfen Shen, ed., Science Press, First edition on May 2005, p. 225, paragraph 2 (translated into English) cited in Office Action dated Mar. 14, 2012 in Chinese Patent Application 200780015768.0.
Nuttall, S. et al., "A naturally occurring NAR variable domain binds the Kgp protease from *Porphyromonas gingivalis*", FEBS Letters, vol. 516, 2002, pp. 80-86.
Ward, E. et al., "Binding activities of a repertoire of single immunoglobulin variable domains secreted from *Escherichia coli*", Nature. vol. 341, Oct. 12, 1989. pp. 544-546.
Winkler, K. et al., "Changing the antigen binding specificity by single point mutations of art anti-p24 (HIV-1) antibody", The Journal of Immunology, vol. 165, 2000, pp. 4505-4514, XP002579393.
Sugimoto et al. Gastroenterology: 2006: 130; 4: Suppl. 2: A41.
Sugimoto et al. Gastroenterology: 2005: 128: Suppl. 2: A18.
Van Deventer et al. Reaserach and Clinical Forums. 1998; 20; 11-18.
Andoh et al., "Interleukin-22, a member of the IL-10 subfamily, induces inflammatory responses in colonic subepithelial myofibroblasts", Gastroenterology: 2005 129:969-84.
Brand et al. Am. J. Physiol. Gastrointest. Liver Physiol.: 2006: 290:G827-38.
Sugimoto et al., "IL-22 Ameliorates intestinal inmflammation in a mouse model of ulcerative colitis", The Journal of Clinical Investigation: 2008: 118:534-44.
Mahairas G. et al., Database Est. Accession No. AQ104025. Aug. 1998.
Waterston R. et al., Database GenEmbl. Accession No. AC006734. Feb. 25, 1999.
Wilson R. et. al. J. Mol. Biol. 261:155-172, 1996.
Bork et al., Trends in Genetics 12:425-427, 1996.
Vukicevic et al., PNAS USA 93:9021-26, 1996.
Massague, J. Cell 49:437-8, 1987.
Pilbeam et al., Bone 14:717-720, 1993.
Skolnick et al., Trends in Biotech. 18:34-39, 2000.
Syrbe et al., (1999) Springer Seminars in Immunopathology, 21:263-85.
Dumoutier, L. et al., GenBank Accession No. NM_016971 for *Mus musculus* interleukin 10-related T cell-derived inducible factor (iltif). Jun. 8, 2000.
Aoki, I., et at Comparison of the amino acid and nucleotide sequences between human and two guinea pig major basic proteins,: FEBS Lett. 282(1):56-60, 1991.
Dumoutier, L. et al., "IL-TIF/IL-22: genomic organization and mapping of the human and mouse genes," Genes Immun. 1:488-494, 2000.
Ozaki, T. et al. GenBank Accession No. D13973 for *Dictyostelium discoideum* DNA for Dp87 protein, 1993. Feb. 1, 2000.
Aoki, I., et al. GenBank Accession No. P35709 for Eosinophil granule major basic protein 2 precursor (mbp-2). May 30, 2000.
Xie, M. et al. GenBank Accession No. AF279437 for *Homo sapiens* interleukin 22 (IL22). Oct. 9, 2000.
Dumoutier, L., et al., GenBank Accession No. AJ294727 for *Mus musculus* ILTIFa gene for IL TIE alpha protein (Li-21), exons la. Dec. 21, 2000.
Dumoutier, L., et al., Gen Bank Accession No. NP_065386 for Interleukin 22; Interleukin 21; IL-10-related T-cell-derived inducible factor (*Homo sapiens*). Nov. 2, 2000.
Ozaki, T., et al., Developmental regulation of transcription of a novel prespore-specific gene (Dp87) in *Dictyostelium doscoideum*,: Development. 117(4):1299-308, 1993.
Sambrook, J. et al., Molecular Cloning. A Laboratory fvlanual, 2d ed. Cold Spring Harbor Laboratory Press, 1989, Ch. 17.
Kotenko, Sergei V. et al., Journal of Biological Chemistry, American Society of Biological Chemists, Baltimore, MD, US, vol. 276, No. 4, Jan. 26, 2001, pp. 2727-2732.
Dumoutier, L. et al., "IL-TIF induces acute phase reactant production by heatocytes through 11-10Rbeta." Immunology Letters, vol. 73, No. 2-3 Sep. 2000, p. 261.
Lambert, A. et al., Toxicologic Pathology, vol. 29, No. 6, Nov. 2001, p. 712.
Bork, P., Genome Research 10:398-400, 2000.
Doerks, et al., Trends in Genetics 14:248-250, 1998.
Smith, et al., Nature Biotechnology 15:1222-1223, 1997.
Brenner, S. E., Trends in Genetics 15:132-133, 1999.
Mahairas, et al., PNAS, USA, 96(17) 739-9744 (1999).
Simon L.S., et al., (Jun. 2000), New and future drug therapies for rheumatoid arthritis, Rheumatology 39: 36-42.
Llorente L., et al. (2000) Arthritis and Rheumatism 43(8): 1790-1800.
Dumoutier, L. et al., (2000), J. of Immunol, 164:1814-1819.
Dumoutier, L. et al., PNAS 97(18): 10144-9, 2000.
Xie, M. et al., J. Biol. Chem. 275(40):31335-9, 2000.
Van Den Berg, W. (1998), Joint inflammation and carilage destruction may occur uncoupled, Springer Sem Immunopathol. 20:149-164.
R&D Systems, Catalog NR, AF582, XP002307633, "Anti-Mouse IL-22 Antibody", Aug. 22, 2002.
Kotenko, Sergei, Cytokine and Growth Factor Reviews, vol. 13, No. 3, Jun. 2002, pp. 223-240.
Radaeva, Svetlana, et al., Hepatology, vol. 39, No. 5, May 2004, pp. 1332-1342.
Resmini, C., et al., European Cytokine Network, vol. 14, No. Sup. 3, Sep. 2003, p. 129 and Annual Meeting of Int'l Cytokine Society; Dublin, Sep. 20-24, 2003. ISSN:1448-5493.
Li, J., et al, International Immunopharmacology, Elsevier, Amsterdam, NL, vol. 4, No. 5, May 2004, pp. 693-708.
Amelizad Z et al. Accession No. A60822, Biochem. Pharmacol. 37, 3245-3249, 1988.
International Search Report from PCT/US2007/004692, Apr. 1, 2008.
International Report on Patentability and Written Opinion of the International Searching Authority for PCT/US2007/004692, Aug. 26, 2008.
International Search Report from PCT/US2007/004430, Jul. 31, 2007.
International Report on Patentability and Written Opinion of the International Searching Authority for PCT/US2007/004430, Aug. 26, 2008.
Paul, Fundamental Immunology, 3rd Edition, 1993, pp. 292-295.
Lederman et al., Molecular Immunology, 1991, vol. 28, pp. 1171-1181.
Li et al., Proc Natol Acad Sci USA, 1980, vol. 77, pp. 3211-3214.
Daniel et al., Virology, 1994, vol. 202, pp. 540-549.
Mikayama et al., Proc. Natl. Acad. Sci. USA (1993) 90:10056-60.
Voet et al, Biochemistry, John Wiley & Sons, Inc. (1990) pp. 126-128.
Rudikoff et al., Proc. Natl. Acad, Sci. USA (1982) 79:1979-83.
Boniface et al., J. Immunol. (2005) 174:3695-702.
Zheng et al., Nature (2007) 445:648-51 and S1-S15.
Ikeuchi et al., Arthritis Rheumatism (2005) 52:1037-46.
Wirtz et al., Nature Protocols (2007) 2:541-46.
Zenewicz et al., Immunity (2008) 29:947-57.
Carvahlo et al., Inflamm Bowel Dis. (2008) 14:1051-60.
Dumoutier et al., "Absence of IL-22 aggravates dextran-sulfate [DSS] induced colitis," Abstract #42, Cyokine, (2008) 43:243-262.
Ouyang et al., Mucosal Immunology (2008) 1:335-338.
Wolk et al., J. Immunology (2007) 178:5973-81.
Schmechel et al., Inflamm Bowel Dis. (2008) 14:204-12.
Communication Pursuant to Article 94(3) EPC dated Nov. 10, 2009 from European Patent Application No. 07 751 904.4.

* cited by examiner

SEQ ID NO:1

```
  1 MAALQKSVSS FLMGTLATSC LLLLALLVQG GAAAPISSHC RLDKSNFQQP
 51 YITNRTFMLA KEASLADNNT DVRLIGEKLF HGVSMSERCY LMKQVLNFTL
101 EEVLFPQSDR FQPYMQEWPF LARLSNRLST CHIEGDDLHI QRNVQKLKD
151 TVKKLGESGE IKAIGELDLL FMSLRNACI
```

SEQ ID NO:2

```
   1 GAATTCGGCC AAAGAGGCCT ACAGGTTCTC CTTCCCCAGT CACCAGTTGC
  51 TCGAGTTAGA ATTGTCTGCA ATGGCCGCCC TGCAGAAATC TGTGAGCTCT
 101 TTCCTTATGG GGACCCTGGC CACCAGCTGC CTCCTTCTCT TGGCCCTCTT
 151 GGTACAGGGA GGAGCAGCTG CGCCCATCAG CTCCCACTGC AGGCTTGACA
 201 AGTCCAACTT CCAGCAGCCC TATATCACCA ACCGCACCTT CATGCTGGCT
 251 AAGGAGGCTA GCTTGGCTGA TAACAACACA GACGTTCGTC TCATTGGGGA
 301 GAAACTGTTC CACGGAGTCA GTATGAGTGA GCGCTGCTAT CTGATGAAGC
 351 AGGTGCTGAA CTTCACCCTT GAAGAAGTGC TGTTCCCTCA ATCTGATAGG
 401 TTCCAGCCTT ATATGCAGGA GGTGGTGCCC TTCCTGGCCA GGCTCAGCAA
 451 CAGGCTAAGC ACATGTCATA TTGAAGGTGA TGACCTGCAT ATCCAGAGGA
 501 ATGTGCAAAA GCTGAAGGAC ACAGTGAAAA AGCTTGGAGA GAGTGGAGAG
 551 ATCAAAGCAA TTGGAGAACT GGATTTGCTG TTTATGTCTC TGAGAAATGC
 601 CTGCATTTGA CCAGAGCAAA GCTGAAAAAT GAATAACTAA CCCCCTTTCC
 651 CTGCTAGAAA TAACAATTAG ATGCCCCAAA GCGATTTTTT TTAACCAAAA
 701 GGAAGATGGG AAGCCAAACT CCATCATGAT GGGTGGATTC CAAATGAACC
 751 CCTGCGTTAG TTACAAAGGA AACCAATGCC ACTTTTGTTT ATAAGACCAG
 801 AAGGTAGACT TTCTAAGCAT AGATATTTAT TGATAACATT TCATTGTAAC
 851 TGGTGTTCTA TACACAGAAA ACAATTTATT TTTTAAATAA TTGTCTTTTT
 901 CCATAAAAAA GATTACTTTC CATTCCTTTA GGGGAAAAAA CCCCTAAATA
 951 GCTTCATGTT TCCATAATCA GTACTTTATA TTTATAAATG TATTTATTAT
1001 TATTATAAGA CTGCATTTTA TTTATATCAT TTTATTAATA TGGATTTATT
1051 TATAGAAACA TCATTCGATA TTGCTACTTG AGTGTAAGGC TAATATTGAT
1101 ATTTATGACA ATAATTATAG AGCTATAACA TGTTTATTTG ACCTCAATAA
1151 ACACTTGGAT ATCCTAAAAA AAAAAAAAAA AAAGCGGCCG C
```

FIG. 5

SEQ ID NO:3

MAVLQKSMSFSLMGTLAASCLLLIALWAQEANALPVNTRCKLEVSNFQQPYI
VNRTFMLAKEASLADNNTDVRLIGEKLFRGVSAKDQCYLMKQVLNFTLEDVL
LPQSDRFQPYMQEVVPFLTKLSNQLSSCHISGDDQNIQKNVRRLKETVKKLG
ESGEIKAIGELDLLFMSLRNACV

SEQ ID NO:4

ATGGCTGTCCTGCAGAAATCTATGAGTTTTTCCCTTATGGGGACTTTGGC
CGCCAGCTGCCTGCTTCTCATTGCCCTGTGGGCCCAGGAGGCAAATGCGC
TGCCCGTCAACACCCGGTGCAAGCTTGAGGTGTCCAACTTCCAGCAGCCG
TACATCGTCAACCGCACCTTTATGCTGGCCAAGGAGGCCAGCCTTGCAGA
TAACAACACAGACGTCCGGCTCATCGGGGAGAAACTGTTCCGAGGAGTCA
GTGCTAAAGATCAGTGCTACCTGATGAAGCAGGTGCTCAACTTCACCCTG
GAAGACGTTCTGCTCCCCCAGTCAGACAGGTTCCAGCCCTACATGCAGGA
GGTGGTACCTTTCCTGACCAAACTCAGCAATCAGCTCAGCTCCTGTCACA
TCAGCGGTGACGACCAGAACATCCAGAAGAATGTCAGAAGGCTGAAGGAG
ACAGTGAAAAAGCTTGGAGAGAGTGGAGAGATCAAGGCGATTGGGGAACT
GGACCTGCTGTTTATGTCTCTGAGAAATGCTTGCGTCTGA

FIG. 6

GIL01

V_H (SEQ ID NO:5) with H1, H2, and H3 underlined (SEQ ID NO:8-10, respectively)

```
E V Q L V E S G G G L V T P G G S L R L S C A A S G F T F S
D Y Y M S W I R Q A P G R G L E W V S A I S G G G S T Y Y
A D S V K G R I T I S R D N A K N D L Y L Q M S L R S E D
T A V Y Y C A R G L W V W D P L D Y W G R G T L V T V S S
```

V_H (SEQ ID NO:14) with H1, H2, and H3 underlined (SEQ ID NO:17-19, respectively)

GAGGTGCAGCTTGTGGAGTCTGGGGGAGGCTTGGTCACGCCTGGAGGGTCCCTGAGACTCTCCTGTGCAGCCTCTGGATTCACCTTCAGTGACTACTACATGAGCTGGATCCGCCAGGCTCCAGG
GAGGGGGCTGGAGTGGGTCTCAGCTATTAGTGGTGGTGGTAGCACATACTACGCAGACTCCGTGAAGGGCCGGATCACCATCTCCAGAGACAACGCCAAGAACTCACTGTATCTGCAAATGA
GCAGCCTGAGATCTGAGGACACGGCCGTGTATTACTGTGCGAGAGGGCTTTGGGTTTGGGATCCTCTTGACTACTGGGGCCAGGGAACCCTGGTCACCGTCTCCTCA

V_L (SEQ ID NO:6) with L1, L2, and L3 underlined (SEQ ID NO:11-13, respectively)

```
D I Q M T Q S P S T L S A S I G D R V T I T C R A S E G I Y H
W L A W Y Q Q K P G K A P K L L I Y K A S S L A S G A P S R F
S G S G T D F T L T I S S L Q P D D F A T Y Y C Q Q Y S N
Y P L T F G G G T K L E I K R
```

V_L (SEQ ID NO:15) with L1, L2, and L3 underlined (SEQ ID NO:20-22, respectively)

GACATCCAGATGACCCAGTCTCCTTCCACCCTGTCTGCATCTATTGGAGACAGAGTCACCATCACCTGCCGGGCCAGTGAGGGTATTTATCACTGGTTGGCCTGGTATCAGCAGAAGCCAGG
GAAAGCCCCTAAACTCCTGATCTATAAGGCCTCTAGTTTAGCCAGTGGGGCCCCATCAAGGTTCAGCGGCAGTGGATCTGGGACAGATTTCACTCTCACCATCAGCAGCCTGCAGCCTGATG
ATTTTGCAACTTATTACTGCCAACAATATAGTAATTATCCGCTCACTTTCGGCGGAGGGACCAAGCTGGAGATCAAACGT

FIG. 7A

GIL16

V_H (SEQ ID NO:23) with H1, H2, and H3 underlined (SEQ ID NO:26-28, respectively)

Q V Q L V E S G A E V K K P G A S V K V S C K A S G Y T F T S Y G I
S W V R Q A P G Q G L E W M G W I S A Y T G N T N Y A Q K F Q G R V
T M T T D T S T S T A Y M E L R S L R S D D T A V Y Y C A R D R G Y
Y D A F D I W G Q G T L V T V S S

V_H (SEQ ID NO:32) with H1, H2, and H3 underlined (SEQ ID NO:35-37, respectively)

CAGGTGCAGCTGGTGGAGTCTGGAGCTGAGGTGAAGAAGCCTGGGGCCTCAGTGAAGGTCTCCTGCAAGGCTTCTGGTTACACCTTTACCAGTTATGGTATC
AGCTGGGTGCGACAGGCCCCCGGACAAGGGCTTGAGTGGATGGGATGGATCAGCGCTTACACAGAAACTATGCACAGAAGTTCCAGGGCAGAGTC
ACCATGACCACAGACACATCGACAAGCACAGCTTACATGGAACTGAGGAGCCTGAGATCTGACGACACGGCCGTGTATTACTGTGCGAGAGATCGTGGATAC
TATGATGCTTTTGATATCTGGGGCCAAGGGACCACCCTGGTCACCGTCTCCTCA

V_L (SEQ ID NO:24) with L1, L2, and L3 underlined (SEQ ID NO:29-31, respectively)

D I Q M T Q S P S T L S A S I G D R V T I T C R A S E G I Y H W L A
W Y Q Q K P G K A P K L L I Y K A S S L A S G A P S R F S G S G S G
T D F T L T I S S L Q P D D F A T Y Y C Q Q Y S N Y P L T F G G G T
K L E I K R

V_L (SEQ ID NO:33) with L1, L2, and L3 underlined (SEQ ID NO:38-40, respectively)

GACATCCAGATGACCCAGTCTCCTTCCACCCTGTCTGCATCTATTGGAGACAGAGTCACCATCACTTGCCGGGCCAGTGAGGGTATTTATCACTGGTTGGCC
TGGTATCAGCAGAAACCAGGAAAGCCCCTAAACTCCTGATCTATAAGGCCTCAGTTTAGCCAGTGGGGCCCATCAAGGTTCAGCGGCAGTGGATCTGGG
ACAGATTTCACTCTCACCATCAGCAGCCTGCAGCCTGATGATTTTGCAACTTATTACTGCCAACAATATAGTAATTATCCGCTCACTTTCGGCGGAGGGACC
AAGCTGGAGATCAAACGT

FIG. 7B

GIL45

$V_H$ (SEQ ID NO:41) with H1, H2, and H3 underlined (SEQ ID NO:44-46, respectively)

Q M Q L V Q S G G G V V Q P G R S L R L S C A A S G F I F S N Y G M Y W V R Q
A P G K G L E W V A H I W Y D G S N E K Y A D S V K G R M T V S R D N S R N T
L Y L Q M N S L R A E D T A V Y Y C A T E Q H W I T A F D I W G K G T L V T V
S S $V_H$ (SEQ ID NO:50) with H1, H2, and H3 underlined (SEQ ID NO:53-55, respectively)

CAGATGCAGCTGGTGCAGTCTGGGGGAGGCGTGGTCCAGCCTGGGAGGTCCCTGAGACTCTCCTGTGCAGCCTCTGGATTCACCTTCAGTAACTATGGCATGTACTGGGTCCGCCA
GGCTCCAGGCAAGGGGCTGGAGTGGGTGGCACATATTTGGTATGATGGAAGTAATGAAAAGTACGCAGACTCCGTGAAGGGCCGATTCACCGTCTCCAGAGACAATTCCAGGAACA
CGTTGTATTTGCAAATGAACAGCCTGAGAGCCGAGGACACGGCTGTGTATTACTGTGCCACAGAGCAACACTGGATTACTGCTTTTGATATCTGGGGCAAAGGCACCCTGGTCACCGTCTCCTCA $V_L$ (SEQ ID NO:42) with L1, L2, and L3 underlined (SEQ ID NO:47-49, respectively)

Q S V L T Q P A S V S G S P G Q S I T I S C T G T S S D V G G Y N Y V S W Y Q
Q H P G K A P K L M I Y E G S K R P S G V S N R F S G S K S G N T A S L T I S
G L Q A E D E A D Y Y C S S Y T T R S T R V F G G G T K L T V L G $V_L$ (SEQ ID NO:51) with L1, L2, and L3 underlined (SEQ ID NO:56-58, respectively)

CAGTCTGTGCTGACTCAGCCACCCTCCGCTGTGTCTGGGTCTCCTGGACAGTCGATCACCATCTCCTGCACTGGAACCAGCAGTGACGTTGGTGGTTATAACTATGTCTCCTGGTACCA
ACAACACCCAGGCAAGGCCCCCAAACTCATGATTTATGAGGGCAGTAAGCGGCCCTCAGGGGTTTCTAATCGCTTCTCTGGCTCCAAGTCTGGCAACACGGCCTCCCTGACAATCT
CTGGGCTCCAGGCTGAGGACGAGGCTGATTATTACTGCAGCTCATATACAACACGGAGCACTCGAGTTTTCGGCGGAGGGACCAAGCTGACCGTCCTAGGT

*FIG. 7C*

GIL60

V_H (SEQ ID NO:59) with H1, H2, and H3 underlined (SEQ ID NO:62-64, respectively)

E V Q L V E S G G G V V R P G G S L R L S C A A S G F T F D D Y G M N
W M R Q A P G K G L E W V S G V N W N G G T R D Y A A S V K G R F T I
S R D N A K N S L Y L Q M N S L R A E D T A L Y Y C A R G W Y S G S F
Y F G Y W G R G T L V T V S S

V_H (SEQ ID NO:68) with H1, H2, and H3 underlined (SEQ ID NO:71-73, respectively)

GAGGTGCAGCTGGTGGAGTCCGGGGGAGGTGTGGTACGGCCTGGGGGGTCCCTGAGACTCTCCTGTGCAGCCTCTGGATTCACCTTTGACGATTATGGCATGAA
CTGGGTCCGCCAAGCTCCAGGGAAGGGGCTGGAGTGGGTCTCTGGTGTTAATTGGAATGTGGTACCAGAGATTATGCAGCCGATTCACCA
TCTCCAGAGACAACGCCAAGAACTCCCTGTATCTGCAAATGAACAGTCTGAGAGCCGAGGACACGGCCCTTGTATTACTGTGCGAGAGGATGGTATAGTGGGAGC
TTCTACTACTTTGGCTACTGGGGCCGAGGAACCCTGGTCACCGTCTCCTCA

V_L (SEQ ID NO:60) with L1, L2, and L3 underlined (SEQ ID NO:65-67, respectively)

Q A V L T Q P S S V S G S P G Q S I T I S C T G A S G D V G A Y N F V
S W Y Q Q H P G K T P K L I I Y D V N K R P S G V S N R F S G S K S G
N T A S L T I S G L Q A E D E S D Y Y C S S Y T S T F S V V F G G G T
K V T V L G

V_L (SEQ ID NO:69) with L1, L2, and L3 underlined (SEQ ID NO:74-76, respectively)

CAGGCTGTGCTGACTCAGCCGTCCTCCGTGTCTGGGTCTCCTGGACAGTCGATCACCATCTCCTGCACTGGAGCCGGTGACGTTGGTGCTTATAACTTTGT
CTCCTGGTACCAACAACACCCAGGCAAAACCCCCAAACTCATAATTTATGATGTCAATAAGCGGCCCTCAGGGGTTTCTAATCGCTTCTCTGGCTCCAAGTCTG
GCAACACGGCCTCCCTGACCATCTCTGGGCTCCAGGCTGAGGACGAGTCTGATTATTACTGCAGCTCATATACAAGCACCTTCTCTGTGGTATTTGGCGGAGGG
ACCAAGGTCACCGTCCTAGGT

FIG. 7D

GIL68

$V_H$ (SEQ ID NO:77) with H1, H2, and H3 underlined. (SEQ ID NO:80-82, respectively)

E V Q L V Q S G A E V K K P G A S V K V S C Q A S G Y T F S D V I H W V R Q T P G
Q G F E W M G W V N P D T G E T R Y A Q K F Q G W V T M T R D M S N T A Y M E L P
R L R D D T A V Y Y C A R D L T G E D P F D I W G Q G T L V T V S S $V_H$ (SEQ ID NO:86) with H1, H2, and H3 underlined (SEQ ID NO:89-91, respectively)

GAGGTGCAGCTGGTGCAGTCTGGGGCTGAGGTGAAGAAGCCTGGGGCCTCAGTGAAGGTCTCCTGTCAGGCTTCTGGATACACCTTCAGCGATGTAATATTCACTGGGTGCGACAGACCCCTGGA
CAAGGGTTTGAGTGGATGGGATGGGTCAACCCTGACACTGGTGAGCACAAGATATGCGCAGAAGTTTCAGGGCTGGGTCACAATGACCAGGGACATGTCCAACACAGCCTACATGGAGCTGCCC
AGGCTGAGAGACGACACGGCCGTATATTACTGTGCGAGAGATCTAACTGGGGAACCCTGGTCACCGTCTCCTCA $V_L$ (SEQ ID NO:78) with L1, L2, and L3 underlined (SEQ ID NO:83-85, respectively)

Q S V L T Q P P S V S V A P G K T A T I T C G G N N F R N K R V H W Y Q Q R P G Q A
P V L V I Y Y D S D R P S G I P E R F S G S R S G N T A T L T I S R V E A G D E A D
F Y C Q V W D S S T E R P L F G G G T K L T V L G $V_L$ (SEQ ID NO:87) with L1, L2, and L3 underlined (SEQ ID NO:92-94, respectively)

CAGTCTGTGCTGACTCAGCCACCCTCAGTGTCAGTGGCCCCAGGAAAGACGGCCACCATCACTTGCGGGGGAAACAACTTTCGAAATAAAAGAGTACACTGGTATCAGCAGAGGCCAGG
CCCCTGTCCTGGTCATCTATTATGATTCAGACAGGCCCTCAGGGATCCCTGAGCGATTCTCTGGCTCCCGCTCCGGGAACAGGCCACCCTGACCATCAGCAGGGTCGAGGCGGGATGAGGC
CGACTTTTACTGTCAGGTGTGGGATAGTAGTACTGAGAGGCCGCTGTTCGGCGGAGGGACCAAGCTGACCGTCCTAGGT

FIG. 7E

GIL92

V_H (SEQ ID NO:95) with H1, H2, and H3 underlined (SEQ ID NO:98-100, respectively)

Q V Q L V Q S G A E V K K P G A S V K V S C K A S G Y T F T D Y Y
M H W V R Q A P G Q G L E W M G W I N P Y T G G A F Y A Q K F R G
R V T M T R D T S I N T A Y M E L S R L G S D D T A V Y Y C A R E
P E K F D F W G G D N W G R G T M V T V S S

V_H (SEQ ID NO:104) with H1, H2, and H3 underlined (SEQ ID NO:107-109, respectively)

CAGGTCCAGCTGGTGCAGTCTGGGGCTGAGGTGAAGAAGCCTGGGGCCTCAGTGAAGGTCTCCTGCAAGGCTTCTGGATACACCTTCACCGACTACTA
TATGCACTGGGTGCGACAGGCCCCTGGACAAGGGCTTGAGTGGATGGGATGGATCAACCCTTATACTGGTGGCGCATTCTATGCACAGAAGTTTCGGG
GCAGGGTCACAATGACCAGGGACACGTCCATCAACACAGCCTACATGGAGCTGAGCAGACTGGGATCTGACGACACTGCCGTGTATTATTGTGCGAGA
GAACCTGAAAAATTCGATTTTTGGGGGTGACAACTGGGGCCGGGGCACCATGGTCACCGTCTCCTCA

V_L (SEQ ID NO:96) with L1, L2, and L3 underlined (SEQ ID NO:101-103, respectively)

Q A V L T Q P S S V S G A P G Q R V T I S C T G S S S N I G A G Y
G V H W Y Q Q L P G T A P K L L I Y G N S N R P S G V P D R F S G
S K S G T S A S L A I T G L Q A E D E A D Y Y C Q S Y D S S L S G
Y V F G T G T Q L T V L G

V_L (SEQ ID NO:105) with L1, L2, and L3 underlined (SEQ ID NO:110-112, respectively)

CAGGCTGTGCTGACTCAGCCGTCCTCAGTGTCTGGGGCCCCAGGGCAGAGGGTCACCATCTCCTGCACTGGGAGCAGCTCCAACATCGGGGCAGGTTA
TGGTGTACACTGGTACCAGCAGCTTCCAGGAACAGCCCCCAAACTCCTCATCTATGGTAACAGCAATCGGCCCTCAGGGGTCCCTGACCGATTCTCTG
GCTCCAAGTCTGGCACCTCGGCCTCCCTGGCCATCACTGGGCTCCAGGCTGAGGATGAGGCTGATTATTACTGCCAGTCCTATGACAGCAGCCTGAGT
GGTTATGTCTTCGGAACTGGGACCCAGCTCACCGTCCTAGGT

V_H (SEQ ID NO:113) with H1, H2, and H3 underlined (SEQ ID NO:116-118, respectively)

E V Q L V E S G G G L V T P G G S L R L S C A A S G F T F S D Y Y M
<u>S</u> W V R Q A P G R G L E W V S <u>A I S G G S T Y Y A D S V K G</u> R I
T I S R D N A K N S L Y L Q M S S L R S E D T A V Y Y C A R <u>G L W V</u>
<u>W D P L D Y</u> W G R G T L V T V S S

V_H (SEQ ID NO:122) with H1, H2, and H3 underlined (SEQ ID NO:125-127, respectively)

GAGGTGCAGCTGGTGGAGTCTGGGGGAGGCTTGGTCACGCCTGGAGGGTCCCTGAGACTCTCCTGTGCAGCCTCTGGATTCACCTTCAGTGACTACTACATG
AGCTGGGTCCGCCAGGCTCCAGGGGAGGGGCTGGAGTGGGTCTCA<u>GCTATTAGTGGTGGTAGCACATACTACGCAGACTCCGTGAAGGGC</u>CGGATC
ACCATCTCCAGAGACAACGCCAAGAACTCACTGTATCTGCAAATGAGCAGCCTGAGATCTGAGGACACGGCCGTGTATTACTGTGCGAGAGGGCTTTGGGTT
TGGGATCCTCTTGACTACTGGGGCCAGGGAACCCTGGTCACCGTCTCCTCA

V_L (SEQ ID NO:114) with L1, L2, and L3 underlined (SEQ ID NO:119-121, respectively)

D I Q M T Q S P S T L S A S I G D R V T I T C R A <u>S E G I Y H W L A</u>
W Y Q Q K P G K A P K L L I Y <u>K A S S L A S</u> G A P S R F S G S G S G
T D F T L T I S S L Q P D D F A T Y Y C <u>Q Q Y S E F A W T</u> F G G G T
K L E I K R

V_L (SEQ ID NO:123) with L1, L2, and L3 underlined (SEQ ID NO:128-130, respectively)

GACATCCAGATGACCCAGTCTCCTTCCACCCTGTCTGCATCTATTGGAGACAGAGTCACCATCACCTGC<u>CGGGCCAGTGAGGTATTTATCACTGTTGCC</u>
TGGTATCAGCAGAAGCCAGGGAAAGCCCCTAAACTCCTGATCTATA<u>AGGCCTCTAGTTTAGCC</u>AGTGGGGCCCCATCAAGGTTCAGCGGCAGTGGATTTGGG
ACCGATTTCACTCTCACCATCAGCAGCCTGCAGCCTGATGATTTTGCAACTTATTACTGC<u>CAACAATACAGCGAGTTCGCCTGGACC</u>TTCGGCGGAGGGACC
AAGCTGGAGATCAAACGT

V_H (SEQ ID NO:131) with H1, H2, and H3 underlined (SEQ ID NO:134-136, respectively)

Q V Q L V E S G A E V K K P G A S V K V S C K A S G Y T F T S Y G I
S W V R Q A P G Q G L E W M G W V S A Y T G N T N Y A Q K F Q G R V
T M T T D T S T S T A Y M E L R G L R S D D T A V Y Y C A R D R G Y
Y D A F D I W G Q G T L V T V S S

V_H (SEQ ID NO:84) with H1, H2, and H3 underlined (SEQ ID NO:143-145, respectively)

AGGTGCAGCTGGTGGAGTCTGGGGCTGAGGTGAAGAAGCCTGGGGCCTCAGTGAAGGTTTCCTGCAAGGCTTCTGGTTACACCTTTACCAGTTATGGTATCA
GCTGGGTGCGACAGGCCCCTGGACAAGGGCTTGAGTGGATGGGATGGGTCAGCGCTTACACTGGTAACACAAACTATGCACAGAAGTTCCAGGGCAGAGTCA
CCATGACCACAGACACATCCACGAGCACAGCCTACATGGAACTGAGGGGCCTGAGATCTGACGACACGGCCGTGTATTACTGTGCGAGAGATCGTGGATACT
ATGATGCTTTTGATATCTGGGGCCAAGGGACCCTGGTCACCGTCTCCTCA

L (SEQ ID NO:132) with L1, L2, and L3 underlined (SEQ ID NO:137-139, respectively)

I Q M T Q S P S T L S A S I G D R V T I T C R A S E G I Y H W L A W
Y Q Q K P G K A P K L L I Y K A S S L A S G A P S R F S G S G S G T
D F T L T I S S L Q P D D F A T Y Y C Q Q M G E Y N A T I G G G T K
L E I K R

L (SEQ ID NO:141) with L1, L2, and L3 underlined (SEQ ID NO:146-148, respectively)

ACATCCAGATGACCCAGTCTCCTTCCACCCTGTCTGCATCTATTGGAGACAGAGTCACCATCACTTGCCGGGCCAGTGAGGGTATTTATCACTGGTTGGCCT
GGTATCAGCAGAAACCAGGGAAAGCCCCTAAACTCCTGATCTATAAGGCCTCTAGTTTAGCCAGTGGGGCCCCATCAAGGTTCAGCGGCAGTGGATTTGGGA
CAGATTTCACTCTCACCATCAGCAGCCTGCAGCCTGATGATTTTGCAACTTATTATTGCCAACAAATGGGCGAGTACAACGCCACCATCGGCGGAGGGACCA
AGCTGGAGATCAAACGT

V_H (SEQ ID NO:149) with H1, H2, and H3 underlined (SEQ ID NO:152-154, respectively)

Q V Q L V E S G A E V K K P G A S V K V S C K A S G Y T F T S Y G I S
W V R Q A P G Q G L E W M G W I S A Y T G N T N Y A Q K F Q G R V T M
T T D T S T A Y M E L R S L R S D D T A V Y Y C A R D R G Y Y D A
F D I W G Q G T L V T V S S

V_H (SEQ ID NO:158) with H1, H2, and H3 underlined (SEQ ID NO:161-163, respectively)

CAGGTGCAGCTGGTGGAGTCTGGAGCTGAGGTGAAGAAGCCTGGGGCCTCAGTGAAGGTCTCCTGCAAGGCTTCTGGTTACACCTTTACCAGTTATGGTATCAGC
TGGGTGCGACAGGCCCCTGGACAAGGGCTTGAGTGGATGGGATGGATCAGCGCTTACACAGAAGTTCAGGGCAGAGTCACCATG
ACCACAGACACATCCACGAGCACAGCCTACATGGAACTGAGGAGCCTGAGATCTGACGACACGGCCGTGTATTACTGTGCGAGAGATCGTGGATACTATGATGCT
TTCGATATCTGGGGCCAAGGGACCACCCTGGTCACCGTCTCCTCA

V_L (SEQ ID NO:150) with L1, L2, and L3 underlined (SEQ ID NO:155-157, respectively)

D I Q M T Q S P S T L S A S I G D R V T I T C R A S E G I Y H W L A W
Y Q Q K P G K A P K L L I Y K A S S L A S G A P S R F S G S G S G T D
F T L T I S S L Q P D D F A T Y Y C Q Q M G E W K A A F G G G T K L E
I K R

V_L (SEQ ID NO:159) with L1, L2, and L3 underlined (SEQ ID NO:164-166, respectively)

GACATCCAGATGACCCAGTCTCCTTCCACCCTGTCTGCATCTATTGGAGACAGAGTCACCATCACCTGCCGGGCCAGTGAGGGTATTTATCACTGGTTGGCCTGG
TATCAGCAGAAACCAGGGAAAGCCCCTAAACTCCTGATCTATAAGGCCTCTAGTTTAGCCAGTGGGGCCCCATCAAGGTTCAGCGGCAGTGGATTTGGGACAGAT
TTCACTCTCACCATCAGCAGCCTGCAGCCTGATGATTTTGCAACTTATTACTGCCAACAAATGGGGGAGTGGAAGGCGGCCTTCGGCGGAGGGACCAAGCTGGAGATCAAACGT

V_H (SEQ ID NO:167) with H1, H2, and H3 underlined (SEQ ID NO:170-172, respectively)

E V Q L V E S G G G V V R P G G S L R L S C A A S G F T F D D Y G M N
W V R Q A P G K G L E W V S G V W N G G T R D Y A A S V K G R F T I
S R D N A K N S L Y L Q M N S L R A E D T A L Y Y C A R G W Y S G A A
W N M G Y W G R G T L V T V S S

V_H (SEQ ID NO:176) with H1, H2, and H3 underlined (SEQ ID NO:179-181, respectively)

GAGGTGCAGCTGGTGGAGTCTGGGGGAGGTGTGGTACGGCCTGGGGGGTCCCTGAGACTCTCCTGTGCAGCCTCTGGATTCACCTTTGACGATTATGGCATGAAC
TGGGTCCGCCAAGCTCCAGGGAAGGGGCTGGAGTGGGTCTCTGGTGTTAATTGGAATGGTGGTACCAGAGATTATGCAGCCTCCGTGAAGGGCCGATTCACCATC
TCCAGAGACAACGCCAAGAACTCCCTGTATCTGCAAATGAACAGTCTGAGAGCCGAGGACACGGCCTTGTATTACTGTGCGAGAGGATGGTATAGTGGGGCCGCG
TGGAACATGGGCTACTGGGGCCGAGGAACCCTGGTCACCGTCTCCTCA

V_L (SEQ ID NO:168) with L1, L2, and L3 underlined (SEQ ID NO:173-175, respectively)

Q A V L T Q P S S V S G S P G Q S I T I S C T G A S G D V G A Y N F V
S W Y Q Q H P G K T P K L I I Y D V N K R P S G V S N R F S G S K S
N T A S L T I S G L Q A E D E S D Y Y C S S Y T S T F S V V F G G G T
K V T V L G

V_L (SEQ ID NO:177) with L1, L2, and L3 underlined (SEQ ID NO:182-184, respectively)

CAGGCTGTGCTGACTCAGCCGTCCTCAGCCTCTGGGGTCTCCTGGGTCTCCTGGTGGGTCTGAGAACCTCCTGACACTGACTGAGCCCAGCCAGTTGTGTCTTATAACTTTGTC
TCCTGGTACCAACAACACCCAGGCAAAACCCCCAAAACTCATAATTTATGATGTCAATAAGCGGCCCTCAGGGGTTTCTAATCGCTTCTCTGGCTCCAAGTCTAGC
AACACGGCCTCCCTGACCATCTCTGGGCTCCAGGCTGAGGACGAGTCTGATTATTACTGCAGCTCATATACAAGCACTTCTCTGTGGTATTGGCGGAGGGACC
AAGGTCACCGTCCTAGGT

$V_H$ (SEQ ID NO:185) with H1, H2, and H3 underlined (SEQ ID NO:188-190, respectively)

E V Q L V E S G G G V V R P G G S L R L S C A A S G F T F D D Y G M N W V
R Q A P G K G L E W V S G V N N G G T R D Y A A S V K G R F T I S R D N
A K N S L Y L Q M N S L R A E D T A L Y Y C A R G W Y S G S P W S L G H W
G R G T L V T V S S $V_H$ (SEQ ID NO:194) with H1, H2, and H3 underlined (SEQ ID NO:197-199, respectively)

GAGGTGCAGCTGGTGGAGTCCGGGGGAGGTGTGGTACGGCCTGGGGGGTCCCTGAGACTCTCCTGTGCAGCCTCTGGATTCACCTTTGACGATTATGGCATGAACTGGGT
CCGCCAAGCTCCAGGGAAGGGGCTGGAGTGGGTCTCTGGTGTTAATTGGAATGGCACCAGAGATTATGCAGCCTCCGTGAAGGGCCGATTCACCATCTCCAGAGACA
ACGCCAAGAACTCCCTGTATCTGCAAATGAACAGTGTAAGAGCTGAGGACACAGCCCTGTATTACTGTGCGAGAGGATGGTATAGTGGCCCGTGGTCGCTGGGCCAC
TGGGGCCAGGGAACCCTGGTCACCGTCTCCTCA $V_L$ (SEQ ID NO:186) with L1, L2, and L3 underlined (SEQ ID NO:191-193, respectively)

Q A V L T Q P S S V S G S P G Q S V T I S C T G A S G D V G A Y N E V S W
Y Q H P G K T P K L I I Y D V N K R P S G V S N R F S G S K S G N T A S
L T I S R L Q A E D E S D Y Y C S S Y T S R Y T T E F G G G T K V T V L G $V_L$ (SEQ ID NO:195) with L1, L2, and L3 underlined (SEQ ID NO:200-202, respectively)

CAGGCTGTGCTGACTCAGCCGTCCTCAGTCTCTGGGTCTCCTGGACAGTCGGTCACCATCTCCTGCACTGGAGCCAGCGGTGACGTTGGTGCTTATAACTTGTCTCCTG
GTACCAACAACAACCCCAGGCAAAACCCCCAAACTCATAATTTATGATGTCAATAAGCGGCCCTCAGGGGTTTCTAATCGCTTCTCTGGCTCCAAGTCTGGCAACACGGCCT
CCCTGACCATCTCTAGGCTCCAGGCTGAGGACGAGTCTGATTATTACTGCAGCTCATATACAGAGTACGACCAGTTGGCGAGGACCAAGTCACCGTCCTAGGT

V_H (SEQ ID NO:203) with H1, H2, and H3 underlined (SEQ ID NO:206-208, respectively)

E V Q L V E S G G G L V Q P G G S L R L S C A A S G F T F D D Y G M N W
V R Q A P G K G L E W V S G V N W N G G T R D Y A A S V K G R F T I S R
D N A K N S L Y L Q M N S L R A E D T A L Y Y C A R G W Y S G A A W N M
G Y W G R G T L V T V S S

V_H (SEQ ID NO:212) with H1, H2, and H3 underlined (SEQ ID NO:215-217, respectively)

GAGGTGCAGCTGGTGGAGTCCGGGGGAGGTCTGGTACAGCCTGGGGGGTCCCTGAGACTCTCCTGTGCAGCCTCTGGATTCACCTTTGACGATTATGGCATGAACTG
GGTCCGCCAGGCTCCAGGGAAGGGGCTGGAGTGGGTCTCTGGTGTTAATTGGAATGGTGGAACAGAGATTATGCAGCCTCCGTGAAGGGCCGATTCACCATCTCCA
GAGACAACGCCAAGAACTCCCTGTATCTGCAAATGAACAGTCTGAGAGCCGAGGACACGGCCCTTGTATTACTGTGCGAGAGATGTATAGTGGGGCCGCCGTGGAAC
ATGGGCTACTGGGGCCGAGGAACCCTGGTCACCGTCTCCTCA

V_L (SEQ ID NO:204) with L1, L2, and L3 underlined (SEQ ID NO:209-211, respectively)

Q A V L T Q P S S V S G S P G Q S I T I S C T G A S G D V G A Y N F V S
W Y Q Q H P G K T P K L I I Y D V N K R P S G V S N R F S G S K S G N T
A S L T I S G L Q A E D E S D Y Y C A S L V S D F S V V F G G G T K V T
V L G

V_L (SEQ ID NO:213) with L1, L2, and L3 underlined (SEQ ID NO:218-220, respectively)

CAGGCTGTGCTGACTCAGCCGTCCTCCGTGTCTGGGTCCCCTGGACAGTCGATCACCATCTCCTGCACTGGAGCCAGCGGTGACGTTGGTGCTTATAACTTTGTCTC
CTGGTACCAACAACACCCAGGCAAAACCCCCAAACTCATAATTTATGATGTCAATAAGCGGCCCTCAGGGGTTTCTAATCGCTTCTCTGGCTCCAAGTCTGGCAACA
CGGCCTCCCTGACCATCTCTGGGCTCCAGGCTGAGGACGAGTCTGATTATTACTGCGCTTCTCTTGTGAGTGACTTCTCTGTTGTATTTGGCGGAGGGACCAAGGTCACCGTCCTAGGT

V_H (SEQ ID NO:221) with H1, H2, and H3 underlined (SEQ ID NO:224-226, respectively)

E V Q L V Q S G A E V K K P G A S V K V S C Q A S G Y T F S D Y Y I H W
V R Q T P G Q G F E W M G W V N P D T G G T R Y A Q K F Q G W V T M T R
D M S N T T A Y M E L P R L R D D D T A V Y Y C A R D L T G F D P F D I
W G Q G T L V T V S S

V_H (SEQ ID NO:230) with H1, H2, and H3 underlined (SEQ ID NO:233-235, respectively)

GAGGTGCAGCTGGTGCAGTCTGGGGCTGAGGTGAAGAAGCCTGGGGCCTCAGTGAAGGTCTCCTGTCAGGCTTCAGGATACACCTTCAGCGATTACTATATTCACTG
GGTGCGACAGACCCCTGGACAAGGGTTTGAGTGGATGGGATGGGTCAACCCTGACACTGGTGGCACAGATACGGCAGAAGTTTCAGGGCTGGGTCACAATGACCA
GGGACATGTCCAACACCACAGCCTACATGGAGCTGCCCAGGCTGAGAGATGACGACGACACGGCCGTATATTACTGTGCGAGAGATCTAACTGGATTTGATCCTTTTGAT
ATCTGGGGCCAGGGAACCCTGGTCACCGTCTCCTCA

V_L (SEQ ID NO:222) with L1, L2, and L3 underlined (SEQ ID NO:227-229, respectively)

Q S V L T Q P P S V S V A P G K T A I T C G G N F R N K R V H W Y Q
Q R P G Q A P V L V I Y Y D S D R P S G I P E R F S G S R S G N T A T L
T I S R V E A G D E A D F Y C Q V W D L F N D N G V F G G G T K L T V L
G

V_L (SEQ ID NO:231) with L1, L2, and L3 underlined (SEQ ID NO:236-238, respectively)

CAGTCTGTGCTGACTCAGCCACCCTCAGTGTCAGTGGCCCCAGGAAAGACGGCCACAGTTACCTGTGGGGGAAACAACTTTCGAAATAAAAGAGTACTGTATCA
GCAGAGGCCAGGCCAGGCCCCCGTGCTGGTCATCTATTATGACTCAGACCGCCCCTCAGGGATCCCTGAGCGATTCTCTGGCTCCCGCTCTGGGAACACGGCCACCC
TGACCATCAGCAGGGTCGAGGCCGGGGATGAGGCCGACTTTTACTGTCAGGTGTGGGATCTCTTCAACGACAACGGCGTGTTCGGCGGAGGGACCAAGCTGACCGTCCTAGGT

V_H (SEQ ID NO:239) with H1, H2, and H3 underlined (SEQ ID NO:242-244, respectively)

E V Q L V Q S G A E V K K P G A S V K V S C Q A S G Y T F S D Y Y I H W V
R Q T P G Q G F E W M G W V N P D T G T R Y A Q K F Q G W V T M T R D M
S N T A Y M E L P R L R D D D T A V Y Y C A R D L T G F D P F D I W G Q
G T L V T V S S

V_H (SEQ ID NO:248) with H1, H2, and H3 underlined (SEQ ID NO:251-253, respectively)

GAGGTGCAGCTGGTGCAGTCTGGGGCTGAGGTGAAGAAGCCTGGGGCCTCAGTGAAGGTCTCCTGTCAGGCTTCTGGATACACCTTCAGCGATTACTATATTCACTGGGT
GCGACAGACCCCTGGACAAGGGTTTGAGTGGATGGGATGGGTCAACCCTGACACTGGTGCACAAGATACGGCAGAAGTTTCAGGGCTGGGTCACAATGACAGGACA
TGTCCAACACCACAGCCTACATGGAGCTGCCAAGGCTGAGAGATGACGACGCCGTATATTACTGTGCGAGAGATCTAACTGGATTTGATCCTTTTGATATCTGGGGC
CAGGGAACCCTGGTCACCGTCTCCTCA

V_L (SEQ ID NO:240) with L1, L2, and L3 underlined (SEQ ID NO:245-247, respectively)

Q S V L T Q P P S V S V A P G K T A T I T C G N E R N K R V H W Y Q Q
R P G Q A P V L V I Y Y D S D R P S G I P E R F S G S R S G N T A T L T I
S R V E A G D E A D F Y C Q V W D F L T D S G S F G G G T K L T V L G

V_L (SEQ ID NO:249) with L1, L2, and L3 underlined (SEQ ID NO:254-256, respectively)

CAGTCTGTGCTGACTCAGCCACCCTCAGTGTCAGTGGCCCCAGGAAAGACGGCCACAATTACCTGTGGGGGAAACAACTTTGAAATAAAAGAGTACACTGTATCAGCA
GAGGCCAGGCCAGGCCCCTGTCCTGGTCATCTATTATGATAGCGATCCTCAGGATCCTGAGCGATTCTCTGGCTCCCGCTCTGGGAACACGGCCACCCTGACCA
TCAGCAGGGTCGAGGCCGGGGATGAGGCCGACTTTTACTGTCAGGTGTGGGATTTCCTCACGGACTCGGGGTCGTTCGGCGGAGGGACCAAGCTGACCGTCCTAGGT

V_H (SEQ ID NO:257) with H1, H2, and H3 underlined (SEQ ID NO:260-262, respectively)

E V Q L V Q S G A E V K K P G A S V K V S C Q A S G Y T F S D Y Y I H W
V R Q T P G Q G F E W M G W V N P D T G G T R Y A Q K F Q G W V T M T R
D M S N T T A Y M E L P R L R D D D T A V Y Y C A R D L T G Y D Y Y D R
W G Q G T L V T V S S

V_H (SEQ ID NO:266) with H1, H2, and H3 underlined (SEQ ID NO:269-271, respectively)

GAGGTGCAGCTGGTGCAGTCTGGGGCTGAGGTGAAGAAGCCTGGGGCCTCAGTGAAGGTCTCCTGTCAGGCTTCAGGATACACCTTCAGCGATTACTATATTCACTG
GGTGCGACAGACCCCTGGACAAGGGTTTGAGTGGATGGGATGGGTCAACCCTGACACTGGTGGCACAAGATACGCCCAGAAGTTTCAGGGCTGGGTCACAATGACCA
GGGACATGTCCAACACCACAGCCTACATGGAGCTGCCCAGGCTGAGAGACGACGACACGGCCGTATATTACTGTGCGAGAGATCTAACTGGATACGACTACTACGAC
CGGTGGGGCCAGGGAACCCTGGTCACCGTCTCCTCA

V_L (SEQ ID NO:258) with L1, L2, and L3 underlined (SEQ ID NO:263-265, respectively)

Q S V L T Q P P S M S V A P G K T A T I T C G G N F R N K R V H W Y Q
Q R P G Q A P V L V I Y Y D S D R P S G I P E R F S G S R S G N T A T L
T I S R V E A G D E A D F Y C Q V W D F L A D E A M F G G G T K L T V L

V_L (SEQ ID NO:267) with L1, L2, and L3 underlined (SEQ ID NO:272-274, respectively)

CAGTCTGTGCTGACTCAGCCGCCCTCAGCCTCAGTGTCCCTGGGACAGACAGCCAGGATCACATGTGGGGGAAACAACTTTCGAAATAAAAGAGTACACTGGTATCA
GCAGAGGCCAGGCCAGGCCCCTGTCCTGGTCATCTATTATGATTCAGACCGGCCCTCAGGGATCCCTGAGCGATTCTCTGGCTCCCGCTCGGGAACACGGCCACCC
TGACCATCAGCAGGGTCGAGGGCGGGGATGAGGCCGACTTTTACTGTCAGGTGTGGGATTTCCTGGCCGACGAGGCGATGTTCGGCGGAGGGACCAAGCTGACCGTCCTAGGT

V_H (SEQ ID NO:275) with H1, H2, and H3 underlined (SEQ ID NO:278-280, respectively)

E V Q L V Q S G A E V K K P G A S V K V S C Q A S G Y T F S D Y Y I H
W V R Q T P G Q G F E W M G W V N P D T G G T R Y A Q K F Q G W V T M
T R D M S N T T A Y M E L P G L R D D D T A V Y Y C A R D L T G Y D Q
Y T A W G Q G T L V T V S S

V_H (SEQ ID NO:284) with H1, H2, and H3 underlined (SEQ ID NO:287-289, respectively)

GAGGTGCAGCTGGTGCAGTCTGGGGCTGAGGTGAAGAAGCCTGGGGCCTCAGTGAAGGTCTCCTGCCAGGCTTCAGGCTACACCTTCAGTGATTACTATATTCA
CTGGGTGCGACAGACCCCAGGACAAGGGTTTGAGTGGATGGGATGGGTCAACCCTGACACTGGTGGCACAGATACGGCCCAGAAGTTCAGGGCTGGGTCACAA
TGACCAGGGACATGTCCAACACCACAGCCTACATGGAGCTGCCGGGCCTGAGAGACGACGACACGGCCGTATATTACTGTGCGAGAGATCTAACTGGTACGAC
CAGTACACGGCCTGGGGCCAGGGAACCCTGGTCACCGTCTCCTCA

V_L (SEQ ID NO:276) with L1, L2, and L3 underlined (SEQ ID NO:281-283, respectively)

Q S V L T Q P P S V S V A P G K T A T I T C G G N F R N K R V H W Y
Q Q R P G Q A P V L V I Y D S D R P S G I P E R F S G S R S G N T A
T L T I S R V E A G D E A D F Y C S T F D P F T D R P L F G G G T K L
T V L G

V_L (SEQ ID NO:285) with L1, L2, and L3 underlined (SEQ ID NO:290-292, respectively)

CAGTCTGTGCTGACTCAGCCACCCTCAGTGTCCGTGGCCCCAGGAAAGACGGCCACGATTACCTGTGGGGGAAACAACTTTCGAAATAAAAGAGTACACTGGTA
TCAGCAGAGGCCAGGCCAGGCCCCTGTCCTGGTCATCTATTATGATTCAGACCGCCCTCAGGGGATCCCTGAGCGATTCTCTGGCTCCCGCTCTGGGAACACGG
CCACCCTGACCATCAGCAGGGTCGAGGCCGGGGATGAGGCCGACTTTTACTGTAGCACCTTCGACCCCTTCACTGATCGCCCGCTGTTCGGCGGAGGGACCAAG
CTGACCGTCCTAGGT

V_H (SEQ ID NO:293) with H1, H2, and H3 underlined (SEQ ID NO:296-298, respectively)

QVQLVQSGAEKKPGASVKVSCKASGYTFT<u>DYYMH</u>WVRQAPGQGLEWVG<u>WINPYTGGAFYAQKFRG</u>RVTMTRDTSINTAYMELSRLGSDDTAVYYCARE<u>PEREGGSTG QVWGRGTMVTVSS</u>

V_H (SEQ ID NO:302) with H1, H2, and H3 underlined (SEQ ID NO:305-307, respectively)

CAGGTCCAGTTGGTGCAGTCTGGGGCTGAGGTGAAGAAGCCTGGGGCCTCAGTGAAGGTCTCCTGCAAGGCTTCTGGATACACCTTCACCGACTACTATATGCACTG
GGTGCGACAGGCCCCTGGACAAGGGCTTGAGTGGGTGGGATGGATCAACCCTTATACTGGTGGGGCCATTCTATGCACAGAAGTTCGGGGCAGGGTCACAATGACCA
GGGACACGTCCATCAACACAGCCTACATGGAGCTAAGCAGACTGAGACTCTGACGACACGGCCGTGTATTATTGTGCGAGAGAACCTGAAAGATTCGGCGACTCCACG
GGGCAGGTCTGGGGCCGGGGACAATGGTCACCGTCTCGAGT

V_L (SEQ ID NO:294) with L1, L2, and L3 underlined (SEQ ID NO:299-301, respectively)

QAVLTQPSSVSGAPRQRVTISC<u>TGSSSNIGAGYGVH</u>WYQQLPGTAPKLLIY<u>GNSNRPS</u>GVPDRFSGSKSGTSASLAITGLQAEDEADYCY<u>HWDKEQSGVF</u>GTGTQLTVLSA

V_L (SEQ ID NO:303) with L1, L2, and L3 underlined (SEQ ID NO:308-310, respectively)

CAGGCTGTGCTGACTCAGCCGTCCTCAGTGTCTGGGGCCCCAAGGCAGAGGGTCACCATCTCCTGCACTGGGAGCAGCTCCAACATCGGGGCAGTTATGGTGTACA
CTGGTACCAACAGCTTCCAGGAACAGCCCCCAAACTCCTCATCTATGGTAACAGCAATCGGCCCTCAGGGGTCCCTGACCGATTCTCTGGCTCCAAGTCTGGCACCT
CAGCCTCCCTGGCCATCACTGGGCTCCAGGCTGAGGATGAGGCTGATTATTACTGCTACCACTGGGACAAGGAGCAAGAGCAGAGTGGTTATGCTGTTCTTCGAACTGGGACCCAG
CTCACCGTTTTAAGTGCG

V<sub>H</sub> (SEQ ID NO:311) with H1, H2, and H3 underlined (SEQ ID NO:314-316, respectively)

EVQLVQSGAEVKKPGASVKVSCQASGYTFTDYYMHWVRQAPGQGLEWVGWINPYTGSAFYAQKFRGRATMTRNTSINTAYMELSRLGSDDTAVYYCAREPEKFGES
SGQLWGRGTMVTISS

V<sub>H</sub> (SEQ ID NO:320) with H1, H2, and H3 underlined (SEQ ID NO:323-325, respectively)

GAAGTGCAGCTGGTGCAGTCTGGGGCTGAGGTGAAGAAGCCTGGGGCCTCAGTGAAGGTCTCCTGTCAGGCTTCTGGATACACCTTCACCGACTACTATATGCACT
GGGTGCGACAGGCCCCTGGACAAGGGCTTGAGTGGATGGGATGGATCAACCCTTATACTGGTAGCCATTCTATGCCACAGAAGTTTCGGGGACAGGCCACAATGAC
CAGGAACACGTCCATCAACACAGCGTACATGGAGCTGAGCAGACTGAGCGGATCTGACGACACGGCCGTGTATTATTGTGCGAGAGAACCTGAAAAATTCGGCGAGTCC
AGCGGGCCAGTTGTGGGGCGGGGGACAATGGTCACCATCTCGAGT

V<sub>L</sub> (SEQ ID NO:312) with L1, L2, and L3 underlined (SEQ ID NO:317-319, respectively)

QAVLTQPSSVSGAPGQRVTISCTGSSSNIGPGYGVHWYQQLPGTAPKLLIYGDSNRPSGVPDRFSGSKSGTSASLAITGLQAEDEADYYCQSYDSGLSGYVFGTGTQLTVLSA

V<sub>L</sub> (SEQ ID NO:321) with L1, L2, and L3 underlined (SEQ ID NO:326-328, respectively)

CAGGCTGTGCTGACTCAGCCGTCCTCAGTGTCTGGGGCCCCAGGGCAGAGGGTCACCATCTCCTGCACTGGGAGCAGCTCCAACATCGGGGCCAGGTTATGGTGTAC
ACTGGTACCAACAGCTTCCAGGAACAGCCCCCAAACTCCTCATCTATGGTGACAGCAATCGGCCCTCAGGGGTCCCTGACCGATTCTCTGGCTCCAAGTCTGGCAC
CTCAGCCTCCCTGGCCATCACTGGGCTCCAGGCTGAGGATGAGGCTGATTATTACTGCCAGTCCTATGACAGCCTGAGTGGTTATGTCTTCGGAACTGGGACC
CAGCTCACCGTTTTAAGTGCG

V_H (SEQ ID NO:329) with H1, H2, and H3 underlined (SEQ ID NO:332-334, respectively)

QVQLVQSGAEVKKPGASVKVSCKASGYTFTHYMHWVRQAPGQGLEWVGWINPYTGGAFYAQKFQGRVTMTRDTSINTAYMELSRLGSDDTAVYYCAREPEKEDSPN
AEIWGRGRGTMVTISS

V_H (SEQ ID NO:338) with H1, H2, and H3 underlined (SEQ ID NO:341-343, respectively)

CAGGTCCAGCTGGTGCAGTCTGGGGCTGAGGTGAAGAAGCCTGGGGCCTCAGTGAAGGTCTCCTGCAAGGCTTCTGGATACACCTTCACCCACTACTATATGCACTG
GGTGCGACAGGCCCCTGGACAAGGGCTTGAGTGGGTGGGATGGATCAACCCTTATACTGGTGGCGCATTCTATGCACAGAAGTTTCAGGGCAGGGTCACAATGACCA
GGGACACGTCCATCAACACAGCCTACATGGAGCTGAGCAGACTGAGAGGCGGACACGGGCCGTGTATTATTGTGCGAGAGAACCTGAAAAATTCGACTCGCCGAAC
GCCGAGATCTGGGGCCGGGGAACCATGGTCACCATCTCGAGT

V_L (SEQ ID NO:330) with L1, L2, and L3 underlined (SEQ ID NO:335-337, respectively)

QAVLTQPSSVSGAPGQRVTISCTGSSSNIGAGYGVHWYQQLPGTAPKLLIYGNSNRPSGVPDRFSGSKSGTSASLAITGLQAEDEADYYCQSYDSSLSGYVFGTGTQLTVLSA

V_L (SEQ ID NO:339) with L1, L2, and L3 underlined (SEQ ID NO:344-346, respectively)

CAGGCTGTGCTGACTCAGCCGTCCTCAGTGTCTGGGGCCCCAGGGCAGAGGGTCACCATCTCCTGCACTGGGAGCAGCTCCAACATCGGGGCAGGTTATGGTGTACA
CTGGTACCAACAGCTTCCAGGAACAGCCCCCAAACTCCTCATCTATGGTAACAGCAATCGGCCCTCAGGGGTCCCTGACCGATTCTCTGGCTCCAAGTCTGGCACCT
CAGCCTCCCTGGCCATCACTGGGCTCCAGGCTGAGGATGAGGCTGATTATTACTGCCAGTCCTATGACAGCAGCCTGAGTGGTTATGTCTTCGGAACCGGGACCCAG
CTCACCGTTTTAAGTGCG

$V_H$ (SEQ ID NO:347) with H1, H2, and H3 underlined (SEQ ID NO:350-352, respectively)

QVQLVQSGAEVKKPGASVKVSCKASGYTFTNYYMHWVRQAPGQGLEWVGWINPYTGSAFYAQKFRGRVTMTRDTSINTAYMELSRLGSDDTAVYYCAREPF KFDSDDSDVWGRGTMVTVSG $V_H$ (SEQ ID NO:356) with H1, H2, and H3 underlined (SEQ ID NO:359-361, respectively)

CAGGTTCAGCTGGTGCAGTCTGGGGCTGAGGTGAAGAAGCCTGGGGCCTCAGTGAAGGTCTCCTGCAAGGCTTCTGGATACACCTTCACCAACTACTATAT GCACTGGGTGCGACAGGCCCCTGGACAAGGGCTTGAGTGGGTGGGATGGATCAACCCTTATACTGGTAGCACACGGCCCCTATGCACAGAAGTTTCGGGCAGG TTACAATGACAGACACGTCCATCAACACAGCCTACATGGAGCTGAGCAGACTGGAGGATCTGAGCGACTGAGCGTGTATTATTGTGCGAGAGAACCTGAA AAATTCGACTCCGACGACTCCGACGTCTGGGGCCGCGGGGACCAATGGTCACCGTCTCGGGT $V_L$ (SEQ ID NO:348) with L1, L2, and L3 underlined (SEQ ID NO:353-355, respectively)

QAVLTQPPSVSGAPGQRVTISCTGSSSNIGAGYGVHWYQQLPGTAPKLIIYGDSSRPSGVPDRFSGSKSGTSASLAITGLQAEDEADYCQSYDNSLSGYVFGTGTQLTVLSA $V_L$ (SEQ ID NO:357) with L1, L2, and L3 underlined (SEQ ID NO:362-364, respectively)

CAGGCTGTGCTGACTCAGCCGCCCTCAGTGTCTGGGGCCCCAGGGCAGAGGGTCACCATCTCCTGCACTGGGAGCAGCTCCAACATCGGGGCAGGTTATGG TGTACACTGGTACCAACAGCTTCCAGGAACAGCCCCCAAACTCATCATCTATGGTGACAGCAGTCGGCCCTCAGGGGTCCCTGACCGATTCTCTGGCTCCA AGTCTGGCACCTGGCACCTCAGCCTCCCTGGCCATCACTGGGCTCCAGGCTGAGGATGAGGCTGATTATTACTGCCAGTCCTATGACAACAGCCTGAGCGGTTATGTC TTCGGAACTGGGACCCAGCTCACCGTTTTAAGTGCG

FIG. 7T

GIL01

V_H (SEQ ID NO:365) with H1, H2, and H3 underlined (SEQ ID NO:368-370, respectively)

Q V Q L V E S G G G L V K P G G S L R L S C A A S G F T F S D Y Y M S W I R Q
A P G K G L E W V S A I S G S G G S T Y Y A D S V K G R I T I S R D N A K N S
L Y L Q M N S L R A E D T A V Y Y C A R G L W V W D P L D Y W G R G T L V T V
S S

V_H (SEQ ID NO:374) with H1, H2, and H3 underlined (SEQ ID NO:377-379, respectively)

CAAGTGCAGCTGGTGGAGTCTGGGGGAGGCTTGGTCAAGCCTGGAGGGTCCCTGAGACTCTCCTGTGCAGCCTCTGGATTCACCTTCAGT<u>GACTACTACATGAGC</u>TGGATCCGCCA
GGCTCCAGGGAAGGGGCTGGAGTGGGTCTCAGCT<u>ATTAGTGGTAGTGGTGGTAGCACATACTACGCAGACTCCGTGAAGGGC</u>CGGATCACCATCTCCAGAGACAACGCCAAGAACT
CACTGTATCTGCAAATGAACAGCCTGAGAGCCGAGGACACGGCCGTGTATTAC<u>TGTGCGAGAGGGCTTTGGGTTTGGGATCCTCTTGACTAC</u>TGGGGCCAGGGAACCCTGGTCACCGTCTCTTCA

V_L (SEQ ID NO:366) with L1, L2, and L3 underlined (SEQ ID NO:371-373, respectively)

D I Q M T Q S P S T L S A S V G D R V T I T C R A S E G I Y H W L A W Y Q Q K
P G K A P K L L I Y K A S S L A S G V P S R F S G S G S G T E F T L T I S S L
Q P D D F A T Y Y C Q Q Y S N Y P L T F G G G T K V E I K R

V_L (SEQ ID NO:375) with L1, L2, and L3 underlined (SEQ ID NO:380-382, respectively)

GACATCCAGATGACCCAGTCTCCTTCCACCCTGTCTGCATCTGTTGGAGACAGAGTCACCATCACCTGC<u>CGGGCCAGTGAGGGTATTTATCACTGGTTGGCC</u>TGGTATCAGCAGAA
GCCAGGGAAAGCCCCTAAACTCCTGATCTATAAGGCCTCTAGTTTAGCCAGT<u>GGGGTCCCATCAAGGTTCAGCGGCAGTGGATCTGGGACAGAGTTCACTCTCACCATCAGCAGCC
TGCAGCCTGATGATTTTGCAACTTATTACTGCCAACAATATAGTAATTATCCGCTCACT<u>TTCGGCGGAGGGACCAAGGTGGAGATCAAACGT

FIG. 8A

GIL16

$V_H$ (SEQ ID NO:383) with H1, H2, and H3 underlined (SEQ ID NO:386-388, respectively)

QVQLVQSGAEVKKPGASVKVSCKASGYTFTSYGISWV
RQAPGQGLEWMGWISAYTGNTNYAQKFQGRVTMTDT
STSTAYMELRSLRSDDTAVYYCARDRGYYDAFDIWGQ
GTLVTVSS $V_H$ (SEQ ID NO:392) with H1, H2, and H3 underlined (SEQ ID NO:395-397, respectively)

CAGGTGCAGCTGGTGCAGTCTGGAGCTGAGGTGAAGAAGCCTGGGGCCTCAGTGAAGGTCTCCTGCAAGGCTTCTGGTT
ACACCTTTACCAGTTATGGTATCAGCTGGGT
GCGACAGGCCCCTGGACAAGGGCTTGAGTGGATGGGATGGATCAGTGCTTACACTGGTAACACAAACTATGCCCAGAAG
TTCCAGGGCAGAGTCACCATGACCACAGACA
CATCCACGAGCACAGCCTACATGGAACTGAGGAGCCTGAGATCTGACGACACGGCCGTGTATTACTGTGCGAGAGATCGTGGATACTATGCTTTTGATATCTGGGGC
CAAGGCACCCTGGTCACCGTCTCCTCA $V_L$ (SEQ ID NO:384) with L1, L2, and L3 underlined (SEQ ID NO:389-391, respectively)

DIQMTQSPSTLSASVGDRVTITCRASEGIYHWLAWYQ
QKPGKAPKLLIYKASSLASGVPSRFSGSGSGTEFTLT
ISSLQPDDFATYYCQQYSNYPLTFGGGTKVEIKR $V_L$ (SEQ ID NO:393) with L1, L2, and L3 underlined (SEQ ID NO:398-400, respectively)

GACATCCAGATGACCCAGTCTCCTTCCACCCTGTCTGCATCTGTTGGAGACAGAGTCACCATCACCTGCCGGGCCAGTGAGGGTATTTATCACTGGTTGGCCTGGTATCA
GCAGAAACCAGGGAAAGCCCCTAAGCTCCTGATCTATAAGGCCTCTAGTTTAGCCAGTGGGGTCCCATCAAGGTTCAGCGGCAGTGGATCTGGGACAGAGTTCACTCTCA
CCATCAGCAGCCTGCAGCCTGATGATTTTGCAACTTATTACTGCCAACAATATAGTAATTATCCGCTCACTTTCGGCGGAGGGACCAAGGTGGAGATCAAACGT

FIG. 8B

GIL45

V_H (SEQ ID NO:401) with H1, H2, and H3 underlined (SEQ ID NO:404-406, respectively)

Q M Q L V E S G G G V V Q P G R S L R L S C A A S G F T F S N Y G M
Y W V R Q A P G K G L E W V A H I W Y D G S N E K Y A D S V K G R M
T V S R D N S K N T L Y L Q M N S L R A E D T A V Y Y C A T E Q H W
L T A F D I W G K G T L V T V S S

V_H (SEQ ID NO:410) with H1, H2, and H3 underlined (SEQ ID NO:413-415, respectively)

CAGATGCAGCTGGTGGAGTCTGGGGGAGGCGTGGTCCAGCCTGGGAGGTCCCTGAGACTCTCCTGTGCAGCCTCTGGATTCACCTTCAGTAACTATGGCAT
GTACTGGGTCCGCCAGGCTCCAGGCAAGGGGCTGGAGTGGGTGGCACATATTTGGTATGATGGAAGTAATGAAAAGTACGCAGACTCCGTGAAGGGCCGAA
TGACCGTCTCCAGAGACAACAGCAAGAACACGCTGTATCTGCAAATGAACAGCCTGAGAGCCGAGGACACGGCTGTGTATTACTGTGCGACAGAGCAACAC
TGGATTACTGCTTTTGATATCTGGGGCCAAGGAACCCTGGTCACCGTCTCCTCA

V_L (SEQ ID NO:402) with L1, L2, and L3 underlined (SEQ ID NO:407-409, respectively)

Q S A L T Q P A S V S G S P G Q S I T I S C T G T S S D V G G Y N Y
V S W Y Q Q H P G K A P K L M I Y E G S K R P S G V S N R F S G S K
S G N T A S L T I S G L Q A E D E A D Y Y C S S Y T T R S T R V F G
G G T K L T V L G

V_L (SEQ ID NO:411) with L1, L2, and L3 underlined (SEQ ID NO:416-418, respectively)

CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTA
TGTCTCCTGGTACCAACAACACCCCGGCAAAGCCCCCAAACTCATGATTTATGAGGGCAGTAAGCGGCCCTCAGGGGTTTCTAATCGCTTCTCTGGCTCCA
AGTCTGGCAACACGGCCTCCCTGACAATCTCTGGGCTCCAGGCTGAGGACGAGGCTGATTACTACTGCAGCTCATATACAACCAGACACTCGAGTTTTC
GGCGGAGGGACCAAGCTGACCGTCCTAGGT

FIG. 8C

GIL60

V$_H$ (SEQ ID NO:419) with H1, H2, and H3 underlined (SEQ ID NO:422-424, respectively)

E V Q L V E S G G G V V R P G G S L R L S C A A S G F T F D D Y G M N W V
R Q A P G K G L E W V S G V N W N G G T R D Y A A S V K G R F T I S R D N
A K N S L Y L Q M N S L R A E D T A L Y H C A R G W Y S G S F Y Y F G Y W
G R G T L V T V S S

V$_H$ (SEQ ID NO:428) with H1, H2, and H3 underlined (SEQ ID NO:431-433, respectively)

GAGGTGCAGCTGGTGGAGAGCGGGGGAGGTGTGGTACGGCCTGGGGGTCCCTGAGACTCTCCTGTGCAGCCTCTGGATTCACCTTTGACGATTATGGCATGAACTGGGTC
CGCCAAGCTCCAGGGAAGGGGCTGGAGTGGGTCTCTGGTGTTAATTGGAATGGCGGTACCAGAGATTATGCCGCGTCCGTGAAGGGCCGATTCACCATCTCCAGAGACAAC
GCCAAGAACTCCCTGTATCTGCAAATGAACAGTCTGAGAGCCGAGGACACGGCCCTTGTATCACTGTGCGAGAGGATGGTATAGTGGGAGCTTCTACTACTTTGGCTACTGG
GGCCGAGGAACCCTGGTCACCGTCTCCTCA

V$_L$ (SEQ ID NO:420) with L1, L2, and L3 underlined (SEQ ID NO:425-427, respectively)

Q A A L T Q P A S V S G S P G Q S I T I S C T G A S G D V G A Y N F V S W
Y Q Q H P G K A P K L I I Y D V N K R P S G V S N R F S G S K S G N T A S
L T I S G L Q A E D E A D Y Y C S S Y T S T F S V V F G G G T K L T V L G

V$_L$ (SEQ ID NO:429) with L1, L2, and L3 underlined (SEQ ID NO:434-436, respectively)

CAGGCTGCGCTGACTCAGCCGGCCTCAGTGTCTGGGTCTCCGGGACAGTCGATCACCATCTCCTGCACTGGAGCCAGCGGTGACGTTGGTGCTTATAACTTTGTCTCCTGG
TACCAACAACACCCAGGCAAAGCCCCCAAACTCATAATTTATGATGTCAATAAGCGGCCCTCAGGGGTTTCTAATCGCTTCTCTGGCTCCAAGTCTGGCAACACGGCCTCC
CTGACCATCTCTGGGCTCCAGGCTGAGGACGAGGCTGATTATTACTGCAGCTCATATACAAGCACCTTCTCTGTGTATTGGCGGAGGAACCAAGCTGACCGTCCTAGGT

*FIG. 8D*

GIL68

V<sub>H</sub> (SEQ ID NO:437) with H1, H2, and H3 underlined (SEQ ID NO:440-442, respectively)

Q V Q L V Q S G A E V K K P G A S V K V S C K A S G Y T F S D Y Y I H W V R Q
A P G Q G L E W M G W V N P D T G G T R Y A Q K F Q G R V T M T R D M S I S T
A Y M E L S R L R S D D T A V Y Y C A R D L T G F D P F D I W G Q G T L V T V
S S

V<sub>H</sub> (SEQ ID NO:446) with H1, H2, and H3 underlined (SEQ ID NO:449-451, respectively)

CAGGTCCAACTGGTGCAGTCTGGGGCTGAGGTGAAGAAGCCTGGGGCCTCAGTGAAGGTCTCCTGTAAGGCTTCTGGATACACCTTCAGCGATTACTATATTCACTGGGTGCGACA
GGCCCCTGGACAAGGGCTTGAGTGGATGGGATGGAATCCTGACACTGGTGGCACAGATACGCGCAGAAGTTTCAGGGCCGAGTCACAATGACCAGGGACATGTCCATCTCA
GCCTACATGGAGCTGAGCCGTCTGAGATCTGACGACGACGGCCGTATATTACTGTGCGAGAGATCTAACTGATTTGATCCTTTTGATATCTGGGGCCAGGGAACCCTGGTCACCGTCTCCTCA

V<sub>L</sub> (SEQ ID NO:438) with L1, L2, and L3 underlined (SEQ ID NO:443-445, respectively)

S S V L T Q P P S V S V A P G K T A R I T C G G N F R N K R V H W Y Q Q K P
G Q A P V L V I Y Y D S D R P S G I P E R F S G S R S G N T A T L T I S R V E
A G D E A D Y Y C Q V W D S S T D R P L F G G G T K L T V L G

V<sub>L</sub> (SEQ ID NO:447) with L1, L2, and L3 underlined (SEQ ID NO:452-454, respectively)

TCGTCTGTGCTGACTCAGCCACCCTCAGTGTCTGTGGCCCCAGGAAAACGGCCCGCATTACCTGTGGGGGAAACAACTTTCGAAATAAAAGAGTACACTGTATCAGCAGAAGCC
AGGCCAGGCCCCTGTCCTGGTCATCTATTATGATTCAGACGCCCCTCAGGAGATTCCTGAGCGATTCTCTGGCTCCCGCTCGGGAACAACGGCCACCCTGACCATCAGCAGGGTCG
AGGCCGGGGATGAGGCCGACTATTACTGTCAGGTGTGGGATAGTAGTACTGATCGTCCGCTGTTCGGCGGAGGGACCAAGCTGACCGTCCTAGGT

FIG. 8E

GIL92

V_H (SEQ ID NO:455) with H1, H2, and H3 underlined (SEQ ID NO:458-460, respectively)

Q V Q L V Q S G A E V K K P G A S V K V S C K A S G Y T F T D Y Y M H W V R
Q A P G Q G L E W V G W I N P Y T G G A F Y A Q K F R G R V T M T R D T S I
S T A Y M E L S R L R S D D T A V Y Y C A R E P E K F D F W G G D N W G R G
T L V T V S S

V_H (SEQ ID NO:464) with H1, H2, and H3 underlined (SEQ ID NO:467-469, respectively)

CAGGTGCAGCTGGTGCAGTCTGGGGCTGAGGTGAAGAAGCCTGGGGCCTCAGTGAAGGTCTCCTGCAAGGCTTCAGGATACACCTTCACCGACTACTATATGCACTGGGTGCG
ACAGGCCCCTGGACAAGGGCTTGAGTGGGTGGGATGGATCAACCCTTATACTGGTGGCGCATTCTATGCACAGAAGTTTCGGGGCAGGGTCACAATGACCAGGGACACGTCCA
TCAGCACAGCCTACATGGAGCTGAGCAGACTGAGATCTGACGACACGGCCGTGTATTATTGTGCGAGAGAACCTGAAAAATTCGATTTTTGGGGGGGTGACAACTGGGGCCGG
GGGACATTGGTCACCGTCTCCTCA

V_L (SEQ ID NO:456) with L1, L2, and L3 underlined (SEQ ID NO:461-463, respectively)

Q A V L T Q P P S V S G A P G Q R V T I S C T G S S N I G A G Y G V H W Y
Q Q L P G T A P K L L I Y G N S N R P S G V P D R F S G S K S G T S A S L
I T G L Q A E D E A D Y Y C Q S Y D S S L S G Y V F G G G T Q L T V L G

V_L (SEQ ID NO:465) with L1, L2, and L3 underlined (SEQ ID NO:470-472, respectively)

CAGGCTGTGCTGACTCAGCCGCCCTCAGTGTCTGGGGCCCCAGGGCAGAGGGTCACCATCTCCTGCACTGGGAGCAGCAACATCGGGGCAGGTTATGGTGTACACTGGTA
CCAACAGCTTCCAGGAACAGCCCCCAAACTCCTCATCTATGGTAACAGCAATCGGCCCTCAGGGGTCCCTGACCGATTCTCGGCTCCAAGTCTGGCCACCTCAGCCTCCCTGG
CCATCACTGGGCTCCAGGCTGAGGATGAGGCTGATTATTACTGCCAGTCCTATGACAGCAGCCTGAGTGGTTATGTCTTCGGAGGTGGGACCCAGCTCACCGTCCTAGGT

V_H (SEQ ID NO:473) with H1, H2, and H3 underlined (SEQ ID NO:476-478, respectively)

Q V Q L V Q S G A E V K K P G A S V K V S C K A S G Y T F T S Y G I S W
V R Q A P G Q G L E W M G W V S A Y T G N T N Y A Q K F Q G R V T M T T
D T S T A Y M E L R S L R S D D T A V Y Y C A R D R G Y Y D A F D I
W G Q G T L V T V S S

V_H (SEQ ID NO:482) with H1, H2, and H3 underlined (SEQ ID NO:485-487, respectively)

CAGGTGCAGCTGGTGCAGTCTGGGGCTGAGGTGAAGAAGCCTGGGGCCTCAGTGAAGGTTTCCTGCAAGGCTTCTGGTTACACCTTTACCAGTTATGGTATCAGCTG
GGTGCGACAGGCCCCTGGACAAGGGCTTGAGTGGATGGGATGGGTCAGCGCTTACACTGGTAACACAAACTACGCACAGAAGTTCCAGGGCAGAGTCACGATGACCA
CAGACACATCCACGAGCACAGCCTACATGGAACTGAGGAGCCTGAGATCTGATGACACGGCCGTGTATTACTGTGCGAGAGATCGTGGATACTATGATGCTTTTGAT
ATCTGGGGCCAAGGGACCCTGGTCACCGTCTCCTCA

V_L (SEQ ID NO:474) with L1, L2, and L3 underlined (SEQ ID NO:479-481, respectively)

D I Q M T Q S P S T L S A S V G D R V T I T C R A S E G I Y H W L A W Y
Q Q K P G K A P K L L I Y K A S S L A S G V P S R F S G S G S G T E F T
L T I S S L Q P D D F A T Y Y C Q Q M G E Y N A T F G G G T K V E I K R

V_L (SEQ ID NO:483) with L1, L2, and L3 underlined (SEQ ID NO:488-490, respectively)

GACATCCAGATGACCCAGTCTCCTTCCACCCTGTCTGCATCTGTTGGAGACAGAGTCACCATCACTTGCCGGGCCAGTGAGGGTATTTATCACTGGTTGGCCTGGTA
TCAGCAGAAACCAGGGAAAGCCCCTAAACTCCTGATCTATAAGGCCTCTAGTTTAGCCAGTGGGGTCCCATCAAGGTTCAGCGGCAGTGGATCTGGGACAGAGTTCA
CTCTCACCATCAGCAGCCTGCAGCCTGATGATTTTGCAACTTATTACTGCCAACAAATGGGCGAGTACAACGCCACCTTCGGCGGAGGGACCAAGGTGGAGATCAAACGT

V_H (SEQ ID NO:491) with H1, H2, and H3 underlined (SEQ ID NO:494-496, respectively)

E V Q L V E S G G G V V R P G G S L R L S C A A S G F T F D D Y G M N W V
R Q A P G K G L E W V S G V N W N G G T R D Y A A S V K G R F T I S R D N
A K N S L Y L Q M N S L R A E D T A L Y H C A R G W Y S G A A W N M G Y W
G R G T L V T V S S

V_H (SEQ ID NO:500) with H1, H2, and H3 underlined (SEQ ID NO:503-505, respectively)

GAGGTGCAGCTGGTGGAGAGCGGGGGAGGTGTGGTTCGGCCTGGGGGGTCCCTGAGACTCTCCTGTGCAGCCTCTGGATTCACCTTTGACGATTATGGCATGAACTGGGTC
CGCCAAGCTCCAGGGAAGGGGCTGGAGTGGGTCTCTGGTGTTAATTGGAATGGTGGTACCAGAGATTATGCAGCCGCATTCACCATCTCCAGAGACAAC
GCCAAGAACTCCCTGTATCTGCAAATGAACAGTCTGCGTGCCCTTGAGAGACTGTGCGAGGATGTATGTGCGAGAGAGGGGCGTGGAACATGGGCTACTGG
GGCCGAGGAACCCTGGTCACCGTCTCCTCA

V_L (SEQ ID NO:492) with L1, L2, and L3 underlined (SEQ ID NO:497-499, respectively)

Q A A L T Q P A S V S G S P G Q S I T I S C T G A S G D V G A Y N F V S W
Y Q Q H P G K A P K L I I Y D V N K R P S G V S N R F S G S K S G N T A S
L T I S G L Q A E D E A D Y Y C S S Y T S T F S V V F G G G T K L T V L G

V_L (SEQ ID NO:501) with L1, L2, and L3 underlined (SEQ ID NO:506-508, respectively)

CAGGCTGCGCTGACTCAGCCGCCCTCCGTGTCAGGGTCTCCGGGACAGTCGATCACCATCTCCTGCACTGGAGCCAGCGGTGACGTTGGTGCTTATAACTTTGTCTCTGG
TACCAACAACACCAGGCAAAGCCCCCAAACTCTCAATCATGTCAATAAGCGGCCCCTCAGGGGTTTCTAATCGCTTCTGCCTCTGGGACAAGATCGGGCAACACGCCTCC
CTGACCATCTCTGGGCTCCAGGCTGAGGACGAGGCTGATTATTACTGCAGCCTCATATACAAGCACCTTCTCTGTGTATTGGCGGACCAAGCTGACCGTCCTAGGT

V_H (SEQ ID NO:509) with H1, H2, and H3 underlined (SEQ ID NO:512-514, respectively)

Q V Q L V Q S G A E V K K P G A S V K V S C K A S G Y T F S D Y Y I H W V
R Q A P G Q L E W M G W V N P D T G G T R Y A Q K F Q G R V T M T R D M
S I S T A Y M E L S R L R S D D T A V Y Y C A R D L T G F D P F D I W G Q
G T L V T V S S

V_H (SEQ ID NO:518) with H1, H2, and H3 underlined (SEQ ID NO:521-523, respectively)

CAGGTCCAGCTGGTGCAGTCTGGGGCTGAGGTGAAGAAGCCTGGGGCCTCAGTGAAGGTCTCCTGTAAGGCTTCAGGATACACCTTCAGCGATTACTATATTCACTGGGT
GCGACAGGCCCCTGGACAAGGGCTTGAGTGGATGGGATGGGTTAACCCTGACACTGGTGGCACAAGATACGCGCAGAAGTTTCAGGGCCGGGTCACAATGACCAGGGACA
TGTCCATCTCCACAGCCTACATGGAGCTGAGCAGGCTGAGATCTGACGACACGGCCGTATATTACTGTGCGAGAGATCTAACTGGATTTGATCCTTTTGATATCTGGGGC
CAGGGAACCCTGGTCACCGTCTCCTCA

V_L (SEQ ID NO:510) with L1, L2, and L3 underlined (SEQ ID NO:515-517, respectively)

S S V L T Q P P S V S V A P G K T A R I T C G G N F R N K V H W Y Q Q K
P G Q A P V L V I Y Y D S D R P S G I P E R F S G S R S G N T A T L T I S
R V E A G D E A D Y Y C Q V W D L F N D N G V F G G G T K L T V L G

V_L (SEQ ID NO:519) with L1, L2, and L3 underlined (SEQ ID NO:524-526, respectively)

TCGTCTGTGCTGACTCAGCCACCCTCAGTGTCAGTGGCCCCAGGAAAGACGGCCCGCATTACCTGTGGGGGAAATAAAAGATACACTTCGAAATAACAACTTTCAGTGGTATCAGCA
GAAGCCAGGCCAGGCCCCTGTCCTGGTCATCTATTATGATTCAGACCGGCCCTCAGGGATCCCTGAGCGATTCTCTGGCTCCCGCTCCGGGAACAACGGCCACCCTGACCA
TCAGCAGGGTCGAGGCCGGGGATGAGGCCGACTATTACTGTCAGGTGTGGGATCTCTTCAACGACAACGGCGTGTTCGGCGGAGGGACCAAGCTGACCGTCCTAGGT

V_H (SEQ ID NO:527) with H1, H2, and H3 underlined (SEQ ID NO:530-532, respectively)

Q V Q L V Q S G A E V K K P G A S V K V S C K A S G Y T F S D Y Y I H W V R
Q A P G Q G L E W M G W V N P D T G T R Y A Q K F Q G R V T M T R D M S I
S T A Y M E L S R L R S D D T A V Y Y C A R D L T G F D P F D I W G Q G T L
V T V S S

V_H (SEQ ID NO:536) with H1, H2, and H3 underlined (SEQ ID NO:539-541, respectively)

CAGGTCCAGCTGGTGCAGTCTGGGGCTGAGGTGAAGAAGCCTGGGGCCTCAGTGAAGGTTTCCTGTAAGGCTTCAGGATACACCTTCAGCGATTACTATATTCACTGGGTGCG
ACAGGCCCCTGGACAAGGGTTGGAGTGGATGGGATGGGTCAACCCTGACACTGGCACAAGATACGCGAGTTTCAGGGCCAGAAGTTCACAATGACCAGGGACATGTCCA
TCTCCACAGCCTACATGGAGCTGTCCAGGCTGAGATCTGACGACGCTGTGTATTACTGTGCGAGAGATCTAACTGGATTTGATCCTTTTGATATCTGGGGCCAGGGAACC
CTGGTCACCGTCTCCTCA

V_L (SEQ ID NO:528) with L1, L2, and L3 underlined (SEQ ID NO:533-535, respectively)

S S V L T Q P P S V S V A P G K T A R I T C G G N F R N K R V H W Y Q Q K
P G Q A P V L V I Y Y D S D R P S G I P E R F S G S R S G N T A T L T I S R
V E A G D E A D Y Y C Q V W D F L T D S G F G G G T K L T V L G

V_L (SEQ ID NO:537) with L1, L2, and L3 underlined (SEQ ID NO:542-544, respectively)

TCGTCTGTGCTGACTCAGCCACCCTCAGTGTCAGTGGCCCCAGGAAAGACGGCCAGGATTACCTGTGGGGGAAACAACTTTCGAAATAAAAGAGTACACGGCCACCCTAGT
GCCAGGCCAGGCCCCTGTCCTGGTCATCTATTATGATTCAGACCGGCCCTCAGGGATCCCTGAGCGATTCTCTGGCTCCCGCTCCGGGAACACGGCCACCCTGACCATCAGCA
GGGTCGAGGCCGGGGATGAGGCCGATTATTACTGTCAGGTGTGGGATTTCCTGACTGACTCGGGGTTCGGCGGAGGGACCAAGCTGACCGTCCTAGGT

V_H (SEQ ID NO:545) with H1, H2, and H3 underlined (SEQ ID NO:548-550, respectively)

Q V Q L V Q S G A E V K K P G A S V K V S C K A S G Y T F T D Y Y M H W V R
Q A P G Q G L E W V G W I N P Y T G G A E Y A Q K F R G R V T M T R D T S I
S T A Y M E L S R L R S D D T A V Y Y C A R E P E R F G D S T G Q W G R G
T L V T V S S

V_H (SEQ ID NO:554) with H1, H2, and H3 underlined (SEQ ID NO:557-559, respectively)

CAGGTGCAGCTGGTGCAGTCTGGGGCTGAGGTGAAGAAGCCTGGGGCCTCAGTGAAGGTTTCCTGCAAGGCTTCTGGATACACCTTCACCGACTACTATATGCACTGGGTGCG
ACAGGCCCCTGGACAAGGGCTTGAGTGGGTGGGATGGATCAACCCTTATACTGGTGGCGCATTCTATGCACAGAAGTTTCGGGGCAGGGTCACAATGACCAGGGACACGTCCA
TCAGCACAGCCTACATGGAGCTGAGCAGACTGAGATCTGACGACACGGCCGTGTATTATTGTGCGAGAGAACCTGAAAGATTCGGGGATTCCACCGGGCAGTCTGGGCCGG
GGGACATTGGTCACCGTCTCCTCA

V_L (SEQ ID NO:546) with L1, L2, and L3 underlined (SEQ ID NO:551-553, respectively)

Q A V L T Q P P S V S G A P G Q R V T I S C T G S S N I G A G Y G V H W Y
Q Q L P G T A P K L L I Y G N S N R P S G V P D R F S G S K S G T S A S L A
I T G L Q A E D E A D Y Y C Y H W D K E Q S G Y V F G G G T Q L T V L G

V_L (SEQ ID NO:555) with L1, L2, and L3 underlined (SEQ ID NO:560-562, respectively)

CAGGCTGTGCTGACTCAGCCGCCCTCAGTGTCCGGGGCCCCAGGGCAGAGGGTCACCATCTCCTGCACTGGGAGCAGCAACATCGGGGCAGGTTATGGTGTACACTGGTA
CCAACAGCTTCCAGGAACAGCCCCCAAACTCCTCATCTATGGTAACAGCAATCGGCCCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCTACCACTGGGACAAGGAGCAAGTGTTATGTCTTCGGAGGTGGGACCCAGCTGACCGTCCTAGGT

V_H (SEQ ID NO:563) with H1, H2, and H3 underlined (SEQ ID NO:566-568, respectively)

Q V Q L V Q S G A E V K K P G A S V K V S C K A S G Y T F T D Y Y M H W V
R Q A P G Q G L E W V G W I N P Y T G A S F Y A Q K F R G R V T M T R D T
S I S T A Y M E L S R L R S D D T A V Y Y C A R E P E K F G E S S G Q L W
G R G T L V T V S S

V_H (SEQ ID NO:572) with H1, H2, and H3 underlined (SEQ ID NO:575-577, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCGACTACTATATGCACTGGGTG
CGACAGGCCCCTGGACAAGGGCTTGAGTGGGTGGGATGGATCAACCCTTATACTGGTGCATCATTTATGCACAGAAGTTTCGGGGCAGGTCACAATGACCAGGGACACG
TCCATCAGCACAGCCTACATGGAGCTGAGCAGACTGAGATCTGACGACACGGCCGTGTATTATTGTGCGAGAGAACCTGAAAAATTCGGAGAGTCCAGCGGCCAGTTGTGG
GGCCGGGGACATTGGTCACCGTCTCCTCA

V_L (SEQ ID NO:564) with L1, L2, and L3 underlined (SEQ ID NO:569-571, respectively)

Q A V L T Q P P S V S G A P G Q R V T I S C T G S S N I G A G Y G V H W
Y Q Q L P G T A P K L L I Y G D S N R P S G V P D R F S G S K S G T S A S
L A I T G L Q A E D E A D Y Y C Q S Y D S L S G Y V F G G G T Q L T V L
G

V_L (SEQ ID NO:573) with L1, L2, and L3 underlined (SEQ ID NO:578-580, respectively)

CAGGCTGTGCTGACTCAGCCGCCCTCAGTGTCTGGGGCCCCAGGGCAGAGGGTCACCATCTCCTGCACTGGGAGCAGCTCCAACATCGGGGCAGGTTATGGTGTACACTGG
TACCAACAGCTTCCAGGAACAGCCCCCAAACTCCTCATCTATGGTGACAGCAATCGGCCCTCAGGGGTCCCTGACCGATTCTCTGGCTCCAAGTCTGGCACCTCAGCCTCC
CTGGCCATCACTGGGCTCCAGGCTGAGGATGAGGCTGATTATTACTGCCAGTCCTATGACAGCCTGAGTGGTTATGTCTTCGGAGGTGGGACCCAGCTGACCGTCCTAGGT

V_H (SEQ ID NO:581) with H1, H2, and H3 underlined (SEQ ID NO:584-586, respectively)

Q V Q L V Q S G A E V K K P G A S V K V S C K A S G Y T F T H Y Y
M H W V R Q A P G Q G L E W V G W I N P Y T G G A F Y A Q K F Q G
R V T M T R D T S I S T A Y M E L S R L R S D D T A V Y Y C A R E
P K F D S P N A E I W G R G T L V T V S S

V_H (SEQ ID NO:590) with H1, H2, and H3 underlined (SEQ ID NO:593-595, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCCACTACTAT
ATGCACTGGGTGCGACAGGCCCCTGGACAAGGGCTTGAGTGGGTGGGATGGATCAACCCTTATACTGGTGGCGCATTCTATGCACAGAAGTTTCAGGGC
AGGGTCACAATGACCAGGGACACGTCCATCAGCACAGCCTACATGGAGCTGAGCAGGCTGAGATCTGACGATACGGCCGTGTATTATTGTGCGAGAGAA
CCTGAAAAATTCGACTCGCCAAACGCCGAGATCTGGGGCCGGGGACATTGGTCACCGTCTCCTCA

V_L (SEQ ID NO:582) with L1, L2, and L3 underlined (SEQ ID NO:587-589, respectively)

Q A V L T Q P P S V S G A P G Q R V T I S C T G S S N I G A G Y
G V H W Y Q Q L P G T A P K L L I Y G N S N R P S G V P D R F S G
S K S G T S A S L A I T G L Q A E D E A D Y Y C Q S Y D S S L S G
Y V F G G G T Q L T V L G

V_L (SEQ ID NO:591) with L1, L2, and L3 underlined (SEQ ID NO:596-598, respectively)

CAGGCTGTGCTGACTCAGCCGCCCTCAGTGTCTGGGGCCCCAGGGCAGAGGGTCACCATCTCCTGCACTGGGAGCAGCTCCAACATCGGGGCCAGGTTAT
GGTGTACACTGGTACCAACAGCTTCCAGGAACAGCCCCAAACTCCTCATCTATGGTAACAGCAATCGGCCCTCAGGGGTCCCTGACCGATTCTCTGGC
TCCAAGTCTGGCACCTCGGCCTCCCTGGCCATCACTGGGCTCCAGGCTGAGGATGAGGCTGATTATTACTGCCAGTCCTATGACAGCAGCCTGAGTGGT
TATGTCTTCGGAGGTGGGACCCAGCTGACCGTCCTAGGT

V_H (SEQ ID NO:599) with H1, H2, and H3 underlined (SEQ ID NO:602-604, respectively)

Q V Q L V Q S G A E V K K P G A S V K V S C K A S G Y T F T N Y Y M H W
V R Q A P G Q G L E W M G W I N P Y T G S A F Y A Q K F R G R V T M T R
D T S I S T A Y M E L S R L R S D D T A V Y Y C A R E P E K F D S D D S
D V W G R G T L V T V S S

V_H (SEQ ID NO:608) with H1, H2, and H3 underlined (SEQ ID NO:611-613, respectively)

CAGGTGCAGCTGGTGCAGTCTGGGGCTGAGGTGAAGAAGCCTGGGGCCTCAGTGAAGGTCTCCTGCAAGGCTTCTGGATACACCTTCACCAACTACTATATGCACTGG
GTGCGACAGGCCCCTGGACAAGGGCTTGAGTGGATGGGATGGATCAACCCTTATACTGGCACAGAAGTTTCGGGGCAGGGTCACAATGACCAGG
GACACGTCCATCAGCACAGCCTACATGGAGCTGAGCAGACTGAGATCTGAGGACACGGCCGTGTATTATTGTGCGAGAGAACCTGAAAAATTCGACTCCGACGACTCC
GACGTCTGGGGCCGCGGCACCATTGGTCACCGTCTCCTCA

V_L (SEQ ID NO:600) with L1, L2, and L3 underlined (SEQ ID NO:605-607, respectively)

Q A V L T Q P P S V S G A P G Q R V T I S C T G S S N I G A G Y G V H
W Y Q Q L P G T A P K L L I Y G D S N R P S G V P D R F S G S K S G T S
A S L A I T G L Q A E D E A D Y Y C Q S Y D N S L S G Y V F G G G T Q L
T V L G

V_L (SEQ ID NO:609) with L1, L2, and L3 underlined (SEQ ID NO:614-616, respectively)

CAGGCTGTGCTGACTCAGCCGCCCTCAGTGTCTGGGGCCCCAGGGCAGAGGGTCACCATCTCCTGCACTGGGAGCAGCAACATCGGGGCAGGTTATGGTGTACAC
TGGTACCAACAGCTTCCAGGAACAGCCCCCAAACTCCTCATCTATGGTGACAGCAATCGGCCCTCAGGGGTCCCTGACCGATTCTCTGGCTCCAAGTCTGGCACCTCA
GCCTCCCTGGCCATCACTGGGCTCCAGGCTGAGGATGAGGCTGATTATTACTGCCAGTCCTATGACAACAGCCTGAGCGGTTATGTCTTCGGAGGTGGGACCCAGCTGACCGTCCTAGGT

V$_H$ (SEQ ID NO:617) with H1, H2, and H3 underlined (SEQ ID NO:620-622, respectively)

EVQLVESGGG VVRPGGSLRL SCAASGFTFD <u>DYGMNWVRQA PGKGLEWVSG</u>
<u>VNWNGGTRDY AASVKGRFTI</u> SRDNAKNSLY LQMNSLRAED TALYHCARGW
<u>YSGAAWNMGY</u> WGRGTLVTVS S

V$_H$ (SEQ ID NO:626) with H1, H2, and H3 underlined (SEQ ID NO:629-631, respectively)

GAGGTGCAGCTGGTGGAGAGCGGCGGAGGCGTGGTGAGACCAGGCGGCAGCCTGAGACTGAGCTGCGCCGCCAGCGGCTTCACCTTCGACGACTACGGCATGAA
CTGGGTGAGGCAGGCCCCAGGCAAGGGCCTGGAGTGGGTGTCCGGCGTGAACTGAACTGGAACGGCACCAGAGACTACGCCGCCGTGAAGGGCAGATTCACCA
TCAGCCGGGACAACGCCAAGAACAGCCTGTACCTGCAGATGAACAGCCTGAGAGCCGAGGACACCGCCCTGTACCACTGCGCCAGAGGCTGGTACAGCGGAGCC
GCCTGGAACATGGGCTACTGGGGCCAGGGCACCCTGGTGACCGTGTCCAGC

V$_L$ (SEQ ID NO:618) with L1, L2, and L3 underlined (SEQ ID NO:623-625, respectively)

QAALTQPASV SGSPGQSITI <u>SCTGASGDVG AYNFVSWYQQ HPGKAPKLII</u>
<u>YDVNKRPSGV</u> SNRFSGSKSG NTASLTISGL QAEDEADYC <u>ASLVSDFSVV</u>
FGGGTKLTVL

V$_L$ (SEQ ID NO:627) with L1, L2, and L3 underlined (SEQ ID NO:632-634, respectively)

CAGGCCGCCCTGACCCAGCCCGCCAGCGTGTCTGGCAGCCCAGGCCAGAGCATCACCATCAGCTGCACCGGCGCCAGCGGCGATGTGGGCGCCTACAACTTCGT
GTCCTGGTATCAGCAGCACCCCGGCAAGGCCCCCAAGCTGATCATCTACGACGTGAACAAGAGACCCAGCGGCGTGTCCAACAGATTCAGCGGCAGCAAGAGCG
GCAACACCGCCAGCCTGACCATCAGCGGACTGCAGGCCGAGGACGAGGCCGACTACTGCGCCAGCCTGGTGTCCGACTTCAGCGTGGTGTTCGGCGGAGGC
ACCAAGCTGACCGTGCTG

*FIG. 80*

GIL01

SEQ ID NO:7

E V Q L V E S G G G L V T P G G S L R L S C A A S G F T F
S D Y Y M S W I R Q A P G R D N A K N D L Y W V S A I S G G G S T Y
Y A D S V K G R F T I S R D N A K N S L Y L Q M N S L R
S E D T A V Y Y C A R G L W V D G G S G F T F T L R
V S S G G G D R V T I K A S L A S E G I H W L A W Y Q Q K P
S S A P K L L I Y S A P R F S G S G S G T
G K A P K L L I Y S L Q P D D F A T Y Y C Q Q Y S N Y P L T F
D F T L T I S S L E I K R A A A
G G G T K

SEQ ID NO:16

GAAGTGCAGCTGGTGGAGTCTGGGGGAGGCTTGGTCACGCCTGGAGGGT
CCCTGAGACTCTCCTGTGCCGCCAGCTCTGGATTCACCTTCAGTGACTACTA
CATGAGCTGGATCCGCCAGGCTCCAGGGAGGGGCTGGAGTGGGTCTCA
GCTATTAGTGGTAGTGGTGGTAGCACATACGCCGACTCCGTGAAGG
GCCGGATCACCATCTCTAGAGAGACAATGCCAAGAACTCACTGTATCTGCA
AATGAACAGCCTGAGAGCCGAGGACACGGCCGTGTATTACTGTGCGAGA
GGGCTTTGGGTTCTTCAGGTGGATCCTCTTGGAGGCGGTTCAGGCGGTT
TCACCGTCTCTCTCAGGTGGACATCCAGATGACCCATCACCTGCC
TCTATTGGAGACAGAGTCACCATCAGTTTAGCCAGTGGCCAGGAATGGGGAATT
ATCACTGGTTGGCCTGTATAAGGCCTCTAGTTTAGCCAGTGGGGCCCATCAGCAGGTTC
AGCGGCAGTGGATCTGGGACAGATTTCACTCTCACCATCAGCAGCTGC
AGCCTGATGATTTTGCAACTTATTACTGCCAACAATATATATAGTAATTATCC
GCTCACTTTCGGCGGAGGGACCAAGCTGGAGATCAAACGTGCGGCCGCA

FIG. 9A

GIL16

SEQ ID NO:25

Q V Q L V E S G A E V K K P G A S V K V S C K A S G Y T F T
S Y G I S W V R Q A P G Q G L E W M G W I S A Y M E L R S G Y
N Y A Q K F Q G R V T M T T D Y S T A Y M E Q M T Q W G S L V T
S D T A V Y Y C A R D R G S G G Y D I Q W H L A Q G Y P Q G T L R
V S S I G D R V H I S E G I H W L A S R F S G S Y S P T L F
S A K L T I S L K A S L A P S P D D F A T Y Y C Q Y N P L T F
G G G T K L E I K R A A

SEQ ID NO:34

CAGGTGCAGCTGGTGGAGTCTGGAGCTGAGGTGAAGAAGCCTGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGATGGATGG
ATCAGCGCTTACACTGGGTAACACAAACTATGCACAGAAGTTCCAGGCAG
AGTCACCATGACCACAGACTACTCCACGAGCACAGCCTACATGGAACTGA
GGAGCCTGAGATCTGACGACACGGCCGTGTATTACTGTGCGAGAGATCGT
GGATACTATGATGCTTTTGATATCTCAGGTTCAGGCGGTTATCACCGT
CTCCTCAGGTGGAGGCGGTTCAGGCGGAGGTGGCTCTGGCGGTGGCGGAT
CGGACATCCAGATGACCCAGTCTCCTTCCTCCGGGCTGTCGTGTCTCTGGG
ACAGAGTCACCATCACCTGCCGGGCCAGTCTAGGGCATGGAAGCCCCCATCAG
GCCCTGGTATCAGCAGAAGCCAGGGAAAGCCCCTAAGGTTCAGCCTAATA
AGGCCCTCTAGTTTAGCCAGTGGGGTCCCATCCCAGCAGCCCTGATTTTT
TCTGGACAGATTTCACTCTCCAACAATAATCGAATAATTCCGCTCACTTTCGGCG
TGCAACTTATTACTGCCAACAATATAGTAATTATCCGCTCACTTTCGGCG
GAGGGACCAAGCTGGAGATCAAACGTGCGGCCGCA

*FIG. 9B*

GIL45

SEQ ID NO:43

Q M Q L V Q S G G G V V Q P G R S L R L S C A A S G F T F S D
N Y G M Y W V R Q A P G K G L E W V A H I W Y D G N S R T F Y
A D S V K G R M T A T E Q H I T A F D I W G Q G T L V T V S S
T A V Y Y C A T G G G S G Q S V N Y L T P A S V Q H P G K A P
G G G S T H S C T G T S S D V G G Y N Y V S W Y Q Q K S G T K
S I H I Y E G S K R P S G V S N R F S G S K S T R V F G G G T
K L M I Q A E D E A D Y Y C S S Y T R S T V L H
I S G L Q L G A A A H
L T V L G A

SEQ ID NO:52

CAGATGCAGCTGGTGCAGTCTGGGGGAGGCGTGGTCCAGCCTGGGAGGT
CCCTGAGACTCTCCTGTGCAGCCTCTGGATTCACCTTCAGTGACTATGG
CATGTACTGGGTCCGCCAGGCTCCAGGCAAGGGGCTGGAGTGGGTGGCA
CATATTTGGTATGATGGAAGTAATGAAAGTATGCAGGAACACGTTGTGCA
GCCGAATGACCGTCTCCAGAGACAGCCGAGACACGCTGTATTCTGCGACA
AATGAACAACACTGGATTACTGCTTTTGATATCTGGGGCCAAGGTACCCTG
GTCACCGTCTCCTCAGGTGGCGGATCGCAGTCTGTGCTGACTCAGCCACC
CTGGAGACAGTCGATCACCATCTCCTGCACTGGAACCAGCAGTGACGTTG
GTGGTTATAACTATGTCTCCTGGTACCAACAAAAGTCAGGCACCAAGCCCC
CAAACTCATGATTTATGAGGGCAGTAAGCGGCCCTCAGGGGTTTCTAAT
CGCTTCTCTGGCTCCAAGTCTGGCAACACGCGCCTCCCTGACAATCTCTG
GGCTCCAGGCTGAGGACGAGGCTGATTATTACTGCAGCTCATATACAAC
CAGGAGCACTCGAGTTTTTCGGCGGAGGGACCAAGCTGACCGTCCTAGGT
GCGGCCGCA

*FIG. 9C*

GIL60

SEQ ID NO:61

E V Q L V E S G G G V V R P G G S L R L S C A A S G F T F D D Y
D Y G M N W V R Q A P G K G L E W V S L R V S L Y F G A Q A Y N M R Q G N S L R A E D T F D Y
A A S V K Y C A R G G S F Y Y S G S G D V G A Y N R F S G V S
T A L Y Y C A R G G S T H I C T G A S G D V G A Y N R F S G V S
S P G Q S T H I C T G A S G D V N K R P S G Y Y C
K T P K L I H Y D V N K R P S A E D Y Y C
S L T I S G L Q A E D A A
G T K V T V L G A A

SEQ ID NO:70

GAGGTGCAGCTGGTGGAGTCCGGGGGAGGTGTGGTACGGCCTGGGGGGT
CCCTGAGACTCTCCTGTGCAGCCTCTGGATTCACCTTTGACGATTATGG
CATGAACTGGGTCCGCCAAGCTCCAGGGAAGGGGCTGGAGTGGGTCTCT
GGTGTGTTAATGGTAATGGTGTACCAGAGACAACGCCCAAGAACTCTGCA
GCCGATTCACCATCTCGAGAGTCTGAGAGCCCGAGGACACGGCCTTGTATTACTGTGCA
AATGAACAGTCTGAGAGTGGGAGCTTCTGAGTCTGAGCGCGGGTTCAGGCGCGGAGCTC
GGATGGTATAGTGGGAGCTTCTGAGTCTGAGCGCGGGTTCAGGCGCGGAGCTC
CCCTGGTGTCACCGTCTCCTCAGGCGAAGTGCACAGTGCATCAGCCGTCTCCGTG
TGGCCGTGGCGAAGTGCACAGTGCATCAGCCGTCTCCGTG
TCTGGGCTCCTGACAGTGCTTATAACTTTGTCTCCTGGTACCAACACACCCAGG
GTGACGTTGGTGTCTTATAACTTTATGATGTCAATAAGGGCCCTCAGGG
CAAACCCCAAACTCATAATTTATGATGTCAATAAGGGCCCTCCCTGA
GTTTCTAATCGCTTCTCTGGCTCCAAGTCTGGCAACGCCTCCAGCTC
CCATCTCGGGCTCCAGGGACGAGTCTGATTATTACTGCAGCTC
ATATACAAGCACCTTCTCTGTGGTATTTGGCGGAGGGACCAAGGTCACC
GTCCTAGGTGCGGCC

FIG. 9D

GIL68

SEQ ID NO:79

E V Q L V Q S G A E V K K P G F E W K P G A S V K V S C Q A S G Y T F S D
Y Y I H W V R Q T P G Q G L E W M A Y V N P D T R Y A Q
K F Q G W V T R D M S N T T A Y M E L P R L V S D G G K T H G G
Y C A R D L T G F D P F I W G Q G T L V T V S S A S T K G P S V F P L A P
G G G S G G S A Q S V L T Q P P S V S G A P G Q R V T I S C S G S S S N I
T C G G N F R N K R V H W Y Q Q L P G T A P K L L I Y D D D
D R P S G I P E R F S G S R S G T S A S L A I T G L Q A E D E
A D F Y C Q V W D S S T D R P L F G G G T K L T V L S

SEQ ID NO:88

GAAGTGCAGCTGGTGCAGTCTGGGGCTGAGGTGAAGAAGCCTGGGCCTC
AGTGAAGGTCTCCTGTCAGGCTTCAGGATACACCTTCAGCGATTACTATA
TTCACTGGGTGCGACAGAGACCCCTGGACAAGGGCTTGAGTGGATGGCT
GTCAACCCTGACACTGTGGCACAAGATACGCCAGAAGTTTCAGGGCTG
GGTCACCAGGGACATGACCAGGACACAGCCTACATGGAGCTGC
CCAGGCTGAGAGCTGAGAGACGAGGCCGTATATTACTGTGCGAGAGATCTA
ACTGGATTTGATCCTTTTGATATCTGGGGCCAGGGAACCCTGGTCACCGT
CTCGAGTGGAGGCGGGCGGCTCAGGTGGAGGCGGGGCCCCCGGA
AAGACGGCCACAGTCTGTGCTGACTCAGCCACCCTCAGTGTCCGGGGCC
ACACTGGTATCAGCAGAGACCAGGCCATCAGCAGGTCCCCTGGCTCCCGC
ATGATTATGATGATGATCGGCCCTCAGGGGATTCCTGAGCGGTTCTCTGGCT
TCGGGCGACTTTTACTGTCAGGGCGTGGATAGTAGTACTGATCGCTGTGT
GGCCGACTTTACGTGTCAAGCCCTGGAGCCCGTCCCTAGGTGCGGGCCGCA
TCGGCGGCCGAGGGACCAAGCTGACCGTCCTAGGTGCGGCCGCA

FIG. 9E

GIL92

SEQ ID NO:97

```
Q V Q L V Q S G A E V K K P G A S V K V S C K A S G Y T F T D Y Y
M H W V R Q A P G Q G L E W M G W I N P Y T G G A F Y A Q K F R G
R V T M T R D T S I N T A Y M E L S R L G S D D T A V Y Y C A R E
P E K F D F W G Q G T L V T V S S A S T K G P S V F P L A P S S
G G S A Q A V L Q S S G L Y S L S S V V T V P S S S L G T Q T Y
I G A G Y G V H W Y Q Q L P G T A P K L L I Y G N S N R P S G V P
D R F S G S K S G T S A S L A I T G L Q T E D E A D Y Y C Q S Y D
S S L S G Y V F G T G T Q L T V L S
```

SEQ ID NO:106

CAGGTCCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGGCGCATTCTATGCACAGAAGTTTCGGGGCAG
GGTCACCATGACCAGGGACACGTCCATCAACACAGCCTACATGGAGCTGA
GCAGACTGGGATCTGACGACACGGCCGTGTATTATTGTGCCAGAGAACCT
GAAAAATTCGATTTTTGGGGTCAGGGGACAATGGT
CACCGTCTCGAGTGCACAGGCTGTTCAGCTCAGCCGTCCTCAGTGTCTGG
GCGAAGTGCACAGAGGGTCACCATCTCCTGCACTGGTACCAACAGCCCCA
CCAGGCAGAGGGGTCACTGTGTACTATTCCTGCTACCAACATCGGCCCCA
GGCAGGTTATGGTGTACAGTCTGTAACAGCAATCGGCCCTCCCTGGGCT
AACTCCTCATCTATGGTAACAATCGGCTCCAGCTCCAGGAACATGGGCTT
TCTCTGGCTCGAGTCTGGCAACTCCAGCGTCCTATGCCAGTCCTATGACAGCC
CCAGGCTGAGGATGAGGCTGATTATTACTGCCAGTCCTATGACAGCAGCC
TGAGTGGTTATGTCTTCGGAACTGGGACCCAGCTCACCGTTTTAAGTGCG
GCCGCA

SEQ ID NO:115

EVQLVESGGGLVTPGGSLRLSCAASGFTFSDYYMSWVRQAPGRGLEWVSAIS
GSGGSTYYADSVKGRITISRDNAKNSLYLQMSSLRSEDTAVYYCARGLWVWD
PLDYWGRGTLVTVSSGGGGSGGGGSGGGGSDIQMTQSPSTLSASIGDRVTIT
CRASEGIYHWLAWYQQKPGKAPKLLIYKASSLASGAPSRFSGSGFGTDFTLT
ISSLQPDDFATYYCQQYSEFAWTFGGGTKLEIKRAAAH

SEQ ID NO:124

GAGGTGCAGCTGGTGGAGTCTGGGGGAGGCTTGGTCACGCCTGGAGGGT
CCCTGAGACTCTCCTGTGCAGCCTCTGGATTCACCTTCAGTGACTACTA
CATGAGCTGGGTCCGCCAGGCTCCAGGGAAGGGGCTGGAGTGGGTCTCA
GCTATTAGTGGTAGTGGTAGCACATACTACGCAGACTCCGTGAAGG
GCCGGATCACCATCTCCAGAGACAACGCCAAGAACTCACTGTATCTGCA
AATGAGCAGCCTGAGATCTGAGGACACGGCCGTGTATTACTGTGCGAGA
GGGCTTTGGGTTTGGATCCTCTGACTACTGGGGCCAGGAAACCCTGG
TCACCGTCTCTTCAGGTGGCGGTTCAGGCGGAGGTGGCAGCGGCGG
TGGCGGATCGGACATCCAGATGACCCAGTCTCCTTCCACCCTGTCTGCA
TCTATTGGAGACAGAGTCACCATCACCTGCCGGGCCAGTGAGGGTATTT
ATCACTGGTTGGCCTGGTATCAGCAGAAGCCAGGGAAAGCCCCCTAAACT
CCTGATCTATAAGGCCTCTAGTTTAGCCAGTGGGGCCCCATCAAGGTTC
AGCGGCAGTGGATTTGGGACAGATTTCACTCTCACCATCAGCAGCCTGC
AGCCTGATGATTTTGCAACTTATTACTGCCAACAATACAGCGAGTTCGC
CTGGACCTTCGGCGGAGGGACCAAGCTGGAGATCAAACGTGCGGCCGCA
CAT

SEQ ID NO:133

QVQLVESGAEVKKPGASVKVSCKASGYTFTSYGISWVRQAPGQGLEWMGWV
SAYTGNTNYAQKFQGRVTMTDTSTSTAYMELRGLRSDDTAVYYCARDRGY
YDAYDIWGQGTLVTVSSGGGGSGGGGSGGGGSDIQMTQSPSTLSASIGDRV
TITCRASEGIYHWLAWYQQKPGKAPKLLIYKASSLASGAPSRFSGSGFGTD
FTLTISSLQPDDFATYYCQQMGEYNATIGGGTKLEIKRAAAH

SEQ ID NO:142

CAGGTGCAGCTGGTGGAGTCTGGGGCTGAGGTGAAGAAGCCTGGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
GTCAGCGCTTACACTGGTAACACAAACTATGCACAGAAGTTCCAGGGCAG
AGTCACCATGACCGACACAAGCACATCCACGGCCGTGTATTACTGTGCGA
GGGGCCTGAGATCTGACGACAGGACGGCCGTGTATTACTGTGCGAGAGATCGT
GGATACTATGATGCTTATGATATCTGGGGCCAAGGCACCCTGGTCACCGT
CTCCTCAGGTGGAGGCGGTTCAGGCGGAGGTGGCAGCGGCGGTGGCGGAT
CGGACATCCAGATGACCCAGTCTCCTTCCACCCTGTCTGCAGGGTATTGGA
GACAGAGTCACCATCACCTGCCGGGCCAGTGAGGGTTATCACTGGTT
GGCCTGGTATCAGCAGAAGCCAGGAAAGCCCCTAAACTCCTGATCTATA
AGGCCTCTAGTTTAGCCAGTGGGGCCCCATCAGCAGCCTGAGCCTGGAGC
TTTGGGACAGATTTCACTCTGCCAACAAATGGGCTGAGTACAACGCCAC
TGCAACTTATTACTGCCAACAAATGGGCTGAGTACAACGCCACCATCGGCG
GAGGGACCAAGCTGGAGATCAAAACGTGCGGCCGCACAT

SEQ ID NO:151

QVQLVESGAEVKKPGASVKVSCKASGYTFTSYGISWVRQAPGQGLEWMGWI
SAYTGNTNYAQKFQGRVTMTTDTSTSTAYMELRSLRSDDTAVYYCARDRGY
YDAFDIWGQGTLVTVSSGGGGSGGGGSGGGGSDIQMTQSPSTLSASIGDRV
TITCRASEGIYHWLAWYQQKPGKAPKLLIYKASSLASGAPSRFSGSGFGTD
FTLTISSLQPDDFATYYCQQMGEWKAAFGGGTKLEIKRAAAH

SEQ ID NO:160

CAGGTGCAGCTGGTGGAGTCTGGAGCTGAGGTGAAGAAGCCTGGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
ATCAGCGCTTACACTGGTAACACAAACTATGCACAGAAGTTCCAGGGCAG
AGTCACCATGACCACAGACACATCCACGAGCACAGCCTACATGGAACTGA
GGAGCCTGAGATCTGACGACACGGCCGTGTATTACTGTGCGAGAGATCGT
GGATACTATGATGCTTTCGATATCTGGGGCCAAGGGACCACCGTCACCGT
CTCCTCAGGTGGGGGCGGTTCAGGCGGAGGTGGCAGCGGCGGTGGCGGAT
CGGACATCCAGATGACCCAGTCTCCTTCCACCCTGTCTGCATCTATTGGA
GACAGAGTCACCATCACCTGCCGGGCCAGTGAGGGTATTTATCACTGGTT
GGCCTGGTATCAGCAGAAGCCAGGGAAAGCCCCCATCCAAGGTTCTCCTAATA
AGGCCTCTAGTTTAGCCAGTGGGGCCCCATCAAGGTTGCAGCCTGATTT
TGCAACTTATTACTGCCAACAAATGGGGGAGTGGAAGGCCGCCTTCGGCG
GAGGGACCAAGCTGGAGATCAAACGTGCGGCCGCACAT

SEQ ID NO:169

EVQLVESGGGVRPGGSLRLSCAASGFTFDDYGMNWVRQAPGKGLEWVSGV
NMNGGTRDYAASVKGRFTISRDNAKNSLYLQMNSLRAEDTALYYCARGWYS
GAAWNMGYWGRGTLVTVSSGGGGSGGGGSGGGGSAQAVLTQPSSVSGSPGQ
SITISCTGASGDVGAYNFVSWYQQHPGKTPKLIIYDVNKRPSGVSNRFSGS
KSSNTASLTISGLQAEDESDYCSSYTSTESVVFGGGTKVTVLGAAAH

SEQ ID NO:178

CGAGGTGCAGCTGGTGGAGTCCGGGGAGGTGTGTAACGGCCTGGGGGTCCCTG
AGACTCTCCTGTGCAGCCTCTGGATTCACCTTTGACGATTATGGCATGAACTGGG
TCCGCCAAGCTCCAGGGAAGGGGCTGGAGTGGGTCTCTGGTGTTAATTGGAATGG
TGGTACCAGAGATTATGCAGCCTCCGTGAAGGGCCGATTCACCATCTCCAGAGAC
AACGCCAAGAACTCCCTGTATCTGCAAATGAACAGTCTGAGAGCCGAGGACACGG
CCTTGTATTACTGTGCGAGAGGATGGTATAGTGGGGCCGCGTGAACATGGGCTA
CTGGGGCCGAGGAACCCTGGTCACCGTCTCCTCAGGTGGAGGCGGTTCAGGCGGA
GGTGGCTCTGGCGGTGGCGGAAGTGCACAGGCTGTGCTACTCAGCCGTCCTCCG
TGTCTGGGTCTCCTGGACAGTCGATCACCATCTCCTGCACTGGAGCCAGCGGTGA
CGTTGGTGCTTATAACTTTGTCTCCTGGTACCAACACCACCCCAGGGAAACCCCC
AAACTCATAATTTATGATGTCAATAAGCGGCCCTCAGGGGTTTCTAATCGCTTCT
CTGGCTCCAAGTCCAATACACGGCCTCCCTGACCATCTCTGGGCTCCAGGCCGA
GGACGAGTCTGATTATTACTGCAGCTCATATACAAGCACCTTCTGTGGTATTT
GGCGGAGGGACCAAGGTCACCGTCCTAGGTGCGGCCGCACAT

367D04

SEQ ID NO:187

EVQLVESGGGVVRPGGSLRLSCAASGFTFDDYGMNWVRQAPGKGLEWVSG
VNWNGGTRDYAASVKGRFTISRDNAKNSLYLQMNSLRAEDTALYYCARGW
YSGSPWSLGHWGRGTLVTVSSGGGGSGGGGSGGGGSGGGGSGGGGSGGGS
GGGGSAQAVLTQPSSVSGSPGQSVTISCTGASGDVGAYNFVSWYQQHPGK
TPKLIIYDVNKRPSGVSNRFSGSKSGNTASLTISRLQAEDESDYCSSYT
SRYTEFGGGTKVTVLGAAAH

SEQ ID NO:196

GAGGTGCAGCTGGTCGAGTCCGGGGAGGTGTGGTACGGCCCTGGGGGT
CCCTGAGACTCTCCTGTGCAGCCTCTGATTCACCTTTGACGATTATGG
CATGAACTGGGTCCGCCAAGCTCCAGGGAAGGGCTGGAGTGGTCTCT
GGTGTTAATTGGAATGGTGGTACCAGAGATTATGCAGCCTCCGTGAAGG
GCCGATTCACCATCTCCAGAGACAACGCCAAGAACTCCCTGTATCTGCA
AATGAACAGTCTGAGAGCCGAGGACACGGCCTTGTATTACTGTGCGAGA
GGATGGTATAGTGGGAGCCCGTGGTCGCCGGGGCCACTGGGGCGAGGAA
CCCTGGTCACCGTCTCCTCAGGTGGCGGAGGTTCGGCCGGAGGTGGCTC
TGGCGGTAGCGGAGGTGGCTCTGGCGGAGGTGGCTCTAGCGGAGGTGGA
GGTGGCTCTGGCGGTGGCGGAAGTGCACAGGCTGTGCTGACTCAGCCGT
CCTCCGTGTCCGGGTCTCCTGGACAGTCGTCGGTCACCATCTCCTGCACTGG
AGCCAGCGGTGACGTTGGTGCTTATAACTTTGTCTCCTGGTACCAACAA
CACCCAGGCAAAACCCCCAAATCGTTCTCCTGGCTCCAAGTCTGCAACGGC
CCTCAGGGGTTTCTAATCGCTCTAGGCTCCAGGCTCCGAGGACGAGTCTGATTATAC
CTCCCTGACCATCTCAGGCTCCAGGCTCCGAGGACGAGTCTGATTATAC
TGCAGCTCATATACATGAGTGACACGACCGAGTTTTGGCGGAGGGACCA
AGGTCACCGTCCTAGGTGCGGCCCGCACAT

SEQ ID NO:205

EVQLVESGGGVVRPGGSLRLSCAASGFTFDDYGMNWVRQAPGKGLEWVSG
VNWNGGTRDYAASVKGRFTISRDNAKNSLYLQMNSLRAEDTALYCARGW
YSGAAWNMGYWGRGTLVTVSSGGGGSGGGGSGGGGSGGGGSGGGGS
AQAVLTQPSSVSGSPGQSITISCTGASGDVGAYNFVSWYQQHPGKTPKLI
IYDVNKRPSGVSNRFSGSKSGNTASLTISGLQAEDESDYCASLVSDFSV
VFGGGTKVTVLGAAAH

SEQ ID NO:214

GAGGTGCAGCTGGTGGAGTCCGGGGGAGGTGTGGTACGGCCTGGGGGT
CCCTGAGACTCTCCTGTGCAGCCTCTGGATTCACCTTTGACGATTATGG
CATGAACTGGGTCCGCCAAGCTCCAGGGAAGGGGCTGGAGTGGTCTCT
GGTGTTAATTGGAATGGTGGTACCAGAGATTATGCAGCCTCCGTGAAGG
GCCGATTCACCATCTCCAGAGACAACGCCAAGAACTCCCTGTATCTGCA
AATGAACAGTCTGAGAGCCGAGGACACGGCCTTGTATTACTGTGCCGAGA
GGATGGTATAGTGGGCGCCGAGTCGGAGGCGGGTTCAGGCGGAGGTGGCTC
CGGTGGTAGCGGAGGTGGCTCTGGCGGTGGCGGATCGCAGGCTGTGCTGACT
CAGCCGAAGTGCACAGGCTGCGATCACCATCTCCTGCACTGGAGCCAGCGGTGACGT
CGGGTGCTTATAACTTTGTCTCCTGGTACCAACACCCAGGCAAAACC
CCCAAACTCATAATTTATGATGTCAATAAGCGCCCCTCAGGGTTTCTA
ATCGCTTCTCTGGCTCCAAGTCTGGCAACACGGCCTCCCTGACCATCTC
TGGGCTCCAGGCCGAGGACGAGTCTGATTATTACTGCGCCTCCCTCGTC
TCCGACTTCTCTGTGTTTTGGCGGAGGGACCAAGGTCACCGTCCTAG
GTGCGGGCCGCACAT

SEQ ID NO:223

EVQLVQSGAEVKKPGASVKVSCQASGYTFSDYYIHWVRQTPGQGFEWMGWV
NPDTGGTRYAQKFQGWVTMTRDMSNTTAYMELPRLRDDDTAVYYCARDLTG
FDPEDIWGQGTLVTVSSGGGGSGGGGSGGGGSAQSVLTQPPSVSVAPGKTA
TITCGGNNFRNKRVHWYQQRPGQAPVLVIYDSDRPSGIPERFSGSRSGNT
ATLTISRVEAGDEADFYCQVWDLFNDNGVFGGGTKLTVLGAAAH

SEQ ID NO:232

GAAGTGCAGCTGGTGCAGTCTGGGGCTGAGGTGAAGAAGCCTGGGGCCTC
AGTGAAGGTCTCCTGTCAGGCTTCAGGCTACACCTTCAGCGATTACTATA
TTCACTGGGTGCGACAGGCCCCTGGACAAGGGCTTGAGTGGATGGGATGG
GTCAACCCTGACACTGGTGGCACAAGATACGCGCAGAAGTTTCAGGGCTG
GGTCACAATGACCAGGGACATGTCCAACACCACAGCCTACATGGAGCTGC
CCAGGCTGAGAGACGACGACACGGCCGTATATTACTGTGCGAGAGATCTA
ACTGGATTTGATCCTTTTGATATCTGGGGCCAGGGAACCCTGGTCACCGT
CTCGAGTGGAGGCGGCAGTTCAGGCGGAGGTGGCTCTGGCGGTGGCGGAA
GTGCACAGTCTGTGCTGACTCAGCCACCCTCAGTGTCAGTGGCCCCAGGA
AAGACGGCCACGATTACCTGTGGGGGAAACAACTTTCGAAATAAAGAGT
ACACTGGTATCAGACCGGCCCTGGCCAGGCCAGCCCTGTCCTGGTCATCTATT
ATGATTCAGACCGGCCCTCAGGGATCCCTGAGCGATTCTCTGGCTCCCGC
TCTGGGAACACGGCCACCCTGACCATCAGCAGGGTCGAGGCCGGGATGA
GGCCGACTTTTACTGTCAGGTGTGGGATCTCTTCAACGACAACGGCGTGT
TCGGCGGAGGGACCAAGCTGACCGTCCTAGGTGCGGCCGCACAT

166G05

SEQ ID NO:241

EVQLVQSGAEVKKPGASVKVSCQASGYTFSDYYIHWVRQTPGQGFEWMGWV
NPDTGGTRYAQKFQGWVTMTRDMSNTTAYMELPRLRDDDTAVYYCARDLTG
FDPFDIWGQGTLVTVSSGGGGSGGGGSGGGGSAQSVLTQPPSVSVAPGKTA
TITCGGNNFRNKRVHWYQQRPGQAPVLVIYYDSDRPSGIPERFSGSRSGNT
ATLTISRVEAGDEADFYCQVWDELTDSGSFGGGTKLTVLGAAAH

SEQ ID NO:250

GAAGTGCAGCTGGTGCAGTCTGGGGCTGAGGTGAAGAAGCCTGGGGCCTC
AGTGAAGGTCTCCTGCAAGGCTTCAGGTTACACCTTCAGCGATTACTATA
TTCACTGGGTGCGACAGACCCCTGGACAAGGGTTTGAGTGGATGGGATGG
GTCAACCCTGACACTGGTGGCACAAGATACGCGCAGAAGTTTCAGGGCTG
GGTCACAATGACCAGGGACATGTCCAACACCACAGCCTACATGGAGCTGC
CCAGGCTGAGAGACGACGACACGGCCGTATATTACTGTGCGAGAGATCTA
ACTGGATTTGATCCTTTTGATATCTGGGGCCAGGGAACCCTGGTCACCGT
CTCGAGTGGAGGCGGCGGTTCAGGCGGAGGTGGCTCTGGCGGTGGCGGAA
GTGCACAGTCTGTGCTGACTCAGCCACCCTCAGTGTCAGTGGCCCCAGGA
AAGACGGCCACAGTCACCATTACCTGTGGGGGAAACAACTTTCGAAATAAAAGAGT
ACACTGGTATCAGCAGAGGCCCTGGCCAGGCGCCTGTCCTGGTCATCTATT
ATGATTCAGACAGGCCCTCAGGGATCCCTGAGCGTTTCTCTGGCTCCCGC
TCTGGGAACACGGCCACCCTGACCATCAGCAGGGTTGAGGCTGAGGCTGA
GGCCGACTTTTACTGTCAGGTGTGGGATTCCTACCGATGACTCGGGGTCGT
TCGGCGGAGGGACCAAGCTGACCGTCCTAGGTGCGGCCGCACAT

SEQ ID NO:259

EVQLVQSGAEVKKPGASVKVSCQASGYTFSDYYIHWVRQTPGQGFEWMGW
VNPDTGGTRYAQKFQGWVTMTRDMSNTTAYMELPRLRDDDTAVYYCARDL
TGYDYDRWGQGTLVTVSSGGGGSGGGGSGGGGSGGGGSAQ
SVLTQPPSMSVAPGKTATITCGGNNFRNKRVHWYQQRPGQAPVLVIYDS
DRPSGIPERFSGSRSGNTATLTISRVEAGDEADFYCQVWDFLADEAMFGG
GTKLTVLGAAAH

SEQ ID NO:268

GAAGTGCAGCTGGTGCAGTCTGGGGCTGAGGTGAAGAAGCCTGGGGCCTC
AGTGAAGGTCTCCTGTGCCACAGAGTCCTCAGGCTTCAGCGATTACTATA
TTCACTGGGTGCGACAGAGACCCCTGGACAAGGGTTTGAGTGGATGGG
GTCAACCCTGACACTGGTGCACAAGATACGCGCAGAAGTTTCAGGGCTG
GGTCACAATGACCAGGGACATGTCCAACACCACAGCCTACATGGAGCTGC
CCAGGCTGCGAGAGACGACGACGCCGTGTATTACTGTGCGAGAGATCTA
ACTGGATACGACTACGACCGTGGGGCCAGGGAACCCTGGTCACCGT
CTCGAGTGGAGGCGGCGGCAGTCTGGGCGGTGGCGGATCGGGCGGTGGAG
GTGGCTCTGCGGGTGGCGGAGGTGGCTCTGCGCGGTGGCGGAAGTGCACAG
TCTGTGCTGACTCAGCCGCCCTCAATGTCAGTGCCCCAGGAAAGACGGC
CACGATTACCTGTGGGGGAAACAACTTTCGAAATAAAGAGTACACTGGT
ATCAGCAGAGGCCCAGGCCAGGCCCCTGTCCTTGTCATCTATGATTCA
GACCGGCCCTCAGGGATCCCTGAGCAGGTTCTCTGGCTCCCGCTCTGGAA
CACGGCCACCCTGACCATCAGCAGGGTCGAGGCCGAGGATGAGGCCGACT
TTTACTGTCAGGTGTGGGATTTCCTGGCCGACGAGGCGATGTTCGGCGGA
GGGACCAAGCTGACCGTCCTAGGTGCCGGCCGCACAT

SEQ ID NO:277

EVQLVQSGAEVKKPGASVKVSCQASGYTFSDYYIHWVRQTPGQGFEWMGW
VNPDTGGTRYAQKFQGWVTMTRDMSNTTAYMELPGLRDDDTAVYYCARDL
TGYDQYTAWGQGTLVTVSSGGGGSGGGGSGGGGSAQSVLTQPPSVSAPG
KTATITCGGNNFRNKRVHWYQQRPGQAPVLVIYDSDRPSGIPERFSGSR
SGNTATLTISRVEAGDEADFYCSTFDPFTDRPLFGGGTKLTVLGAAAH

SEQ ID NO:286

GAAGTGCAGCTGGTGCAGTCTGGGGCTGAGGTGAAGAAGCCTGGGGCCTC
AGTGAAGGTCTCCTGCAAGGCTTCTGGATACACCTTCAGCGATTACTATA
TTCACTGGGTGCGACAGAGACCCAGGACAAGGGTTTGAGTGGATGGGATGG
GTCAACCCTGACACTGGTGGCACAGAGATACGCGCAGAAGTTTCAGGGCTG
GGTCACAATGACCAGGGACGAGATCCAACACCACAGCCTACATGGAGCTG
CCGGGCTGAGAGACGACACGGCCGTGTATTACTGTGCGAGAGATCTA
ACTGGGTACGACCAGTACCTGGGGCCTGGGGCCAGGGAACCCTGGTCACCGT
CTCGAGTGGAGGCGGCGGTTCAGGCGGAGGTGGCTCTGGCGGTGGCGGAA
GTGCACAGTCTGTGCTGACTCAGCCACCCTCAGTGTCAGTGGCCCCAGGA
AAGACGGCCACAGATTACCTGTGGGGGAAACAACTTTCGAAATAAAAGAGT
ACACTGGTATCAGCAGAGGCCAGGCCAGGTCCCTGAGCGATTCTCTGCTCATCTATT
ATGATTCAGACAGGCCACACCTTGACCACTTTGACCACCTTCACTGTCTCCGCTGT
TCTGGGAACACGGCCACCATCAGCAGGGTCGAGGCCGGGATGA
GGCCGACTTTTACTGTAGCACCTTTGACCCTTCACTGATCGTCCGCTGT
TCGGCGGAGGGACCAAGCTGACCGTCCTAGGTGCGGCCGCACAT

SEQ ID NO:295

QVQLVQSGAEKKPGASVKVSCKASGYTFTDYYMHWVRQAPGQGLEWVGWIN
PYTGGAFYAQKFRGRVTMTRDTSINTAYMELSRLGSDDTAVYYCAREPERF
GDSTGQVWGRGTMVTVSSGGGGSGGGGSGGGGSRSAQAVLTQPSSVSGAPRQR
VTISCTGSSSNIGAGYGVHWYQQLPGTAPKLLIYGNSNRPSGVPDRFSGSK
SGTSASLAITGLQAEDEADYYCYHWDKEQSGYVFGTGTQLTVLSA

SEQ ID NO:304

CAGGTCCAGTTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGGCGCATTCTATGCACAGAAGTTTCGGGGCAG
GGTCACAATGACCAGGGACACGTCCATCAACACAGCCTACATGGAGCTAA
GCAGACTGGGATCTGACGACACGGCCGTGTATTATTGTGCGAGAGAACCT
GAAAGATTCGGCGACTCCACGGGGCGGCCAGGTTCAGGCGGCCGGAGGCG
CACCGGTCTCGAGTGGGGCGGCGGCGGCGGCGGCCAGGCTGTGCTGACTC
CCAAGGCAGAGGGTCACCATCTCCTGCACTGGGAGCAGCTCCAACATCGG
GGCAGGTTATGGTGTACACTGGTACCAACAGCTTCCAGGAACAGCCCCCA
AACTCCTCATCTATGGTAACAGCAATCGGCCCTCAGGGGTCCCTGACCGA
TTCTCTGGCTCCAAGTCTGGCACCTCAGCCTCCCTGGCCATCACTGGGCT
CCAGGCTGAGGATGAGGCTGATTATTACTGCTACCACTGGGACAAGGAGC
AGAGTGGTTATGTCTTCGGAACTGGGACCCAGCTCACCGTTTTAAGTGCG

SEQ ID NO:313

EVQLVQSGAEVKKPGASVKVSCQASGYTFTDYYMHWVRQAPGQGLEWVGWI
NPYTGSAFYAQKFRGRATMTRNTSINTAYMELSRLGSDDTAVYYCAREPEK
FGESSGQLWGRGTMVTISSGGGGSGGGGSGGGGSAQAVLTQPSSVSGAPGQ
RVTISCTGSSSNIGPYGVHWYQQLPGTAPKLLIYGDSNRPSGVPDRFSGS
KSGTSASLAITGLQAEDEADYYCQSYDSGLSGYVFGTGTQLTVLSA

SEQ ID NO:322

GAAGTGCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGGTGGGATGG
ATCAACCCTTATACTGGTAGCGCATTCTATGCACAGAAGTTTCGGGGCAG
GGCCACAATGACCAGGAACACGTCCATCAACGCCTACATGGAGCTGA
GCAGACTGGGATCTGACGACACGGCCGTGTATTATTGTGCGAGAGAACCT
GAAAAATTCGGAGTCGAGTCTTCAGGCGGCGGTGGCTCTGGCGGTA
CACCATCTCGAGTGGAGGCGGCGGTTCAGCGGAGGTGGCTCTGGCGGTA
GCGAAGTGCACAGGCTGTGCTGACTCAGCCGTCCAGTCTCGGGGCC
CCAGGGCAGAGGGTCACCATCTCCTGCACTGGGAGCAGCTCCAACATCGG
GGCAGGTTATGGTGTACACTGGTACCAACAGCTTCCAGGAACACAGCCCCA
AACTCCTCATCTATGGTGACAGCAATCGGCCCTCAGGGGTCCCTGACCGA
TTCTCTGGCTCCAAGTCTGGCACCTCAGCCTCCCTGGCCATCACTGGGCT
CCAGGCCGAGGATGAGGCTGATTATTACTGCCAGTCCTATGACAGCGGCC
TGAGTGGTTATGTCTTCGGAACTGGGACCCAGCTCACCGTTTTAAGTGCG

SEQ ID NO:322

SEQ ID NO:331

QVQLVQSGAEVKKPGASVKVSCKASGYTFTHYYMHWVRQAPGQGLEWVGWI
NPYTGGAFYAQKFQGRVTMTRDTSINTAYMELSRLGSDDTAVYYCAREPEK
FDSPNAEIWGRGTMVTISSEGGSGGSGGSGGSGGSAQAVLTQPSSVSGAPGQ
RVTISCTGSSSNIGAGYGVHWYQQLPGTAPKLLIYGNSNRPSGVPDRFSGS
KSGTSASLAITGLQAEDEADYYCQSYDSSLSGYVFGTGTQLTVLSA

SEQ ID NO:340

CAGGTCCAGCTGGTGCAGTCTGGGGCTGAGGTGAAAAAGCCTGGGGCCTC
AGTGAAGGTCTCCTGCAAGGCTTCTGGATACACCTTCACCCACTACTATA
TGCACTGGGTGCGACAGGCCCCTGAGACAAGGGCTTGAGTGGGTGGGATGG
ATCAACCCTTATACTGGTGGCGCAGGAGACAGTCCATCAACACACAGCCAG
GGTCACAATGACCAGGGACACGGTCACCATTATTGTGCAGAGACTGA
GCAGACTGGGATCTGACGACGACAGCCCGTGTATTATTGTGCAGAGAACCT
GAAAAATTCGACTCGCCGAACGCGCCAGATCTGGGGCCGGAGTGGCTCTGGCGGTA
CCACCATCTCGAGTGAAGGCGGCGGTTCAGGCGGAGGTGGCTCTGGCGGC
GCGGAAGTGCACAGGCGTGTCTGACTCAGCCTTCCTCTGTCTGGGGCC
CCAGGGCAGAGGGTCACCATCTCCTGCACTGGGAGCAGCTCCAACATCGG
GGCAGGTTATGGTGTACACTGGTACCAACAGCTTCCAGGAACAGCCCCCA
AACTCCTCATCTATGGTAACAGCAATCGGCCCTCAGGGGTCCCTGACCGA
TTCTCTGGCTCCAAGTCTGGCACCTCAGCTCCCTGGCCATCACTGGGCT
CCAGGCTGAGGATGAGGCTGATTATTACTGCCAGTCCTATGACAGCAGCC
TGAGTGGTTATGTCTTCGGAACCGGGACCCAGCTCACCGTTTTAAGTGCG

356A11

SEQ ID NO:349

QVQLVQSGAEVKKPGASVKVSCKASGYTFTNYYMHWVRQAPGQGLEWVGWI
NPYTGSAFYAQKFRGRVTMTRDTSINTAYMELSRLGSDDTAVYYCAREPEK
FDSDDSDVWGRGTMVTVSGGGGSSGGGGSSGGGGSAQAVLTPPSVSGAPGQR
VTISCTGSSSNIGAGYGVHWYQQLPGTAPKLIIYGDSSRPSGVPDRFSGSK
SGTSASLAITGLQAEDEADYYCQSYDNSLSGYVFGTGTQLTVLSA

SEQ ID NO:358

CAGGTTCAGCTGGTGCAGTCTGGGGCTGAGGTGAAGAAGCCTGGGGCCTC
AGTGAAGGTCTCCTGCAAGGCTTCTGGATACACCTTCACCAACTACTATA
TGCACTGGGTGCGACAGGCCCCTGGACAAGGGCTTGAGTGGATGGGATGG
ATCAACCCTTATACTGGTAGCGCATTCTATGCACAGAAGTTTCGGGGCAG
GGTTACAATGACCAGGGACACGTCCATCAACACAGCCTACATGGAGCTGA
GCAGACTGGGATCTGACGACACGGCCGTGTATTATTGTGCGAGAGAACCT
GAAAAATTCGACTCCGACGACTCCGACGTCTGGGGCCGCGGGACAATGGT
CACCGTCTCGGGTGGAGGCGGCAGTTCAGGCGGAGGTGGCTCTGGCGGTA
GCGGAAGTGCACAGGCTGTGCTGACTCCTGCACCATCCCTGGGAGCCCCG
CCAGGGCAGAGGGTCACCATCTCCTGCACTGGGAGCAGCTCCAACATCGG
GGCAGGTTATGGTGTACACTGGTACCAACAGCTTCCAGGAACAGCCCCCA
AACTCATCATCTATGGTGACAGCAGTCGGCCCTCAGGGGTCCCTGACCGA
TTCTCTGGCTCCAAGTCTGGCACCTCAGCCTCCCTGGCCATCACTGGGCT
CCAGGCTGAGGATGAGGCTGATTATTACTGCCAGTCCTATGACAACAGCC
TGAGCGGTTATGTCTTCGGAACTGGGACCCAGCTCACCGTTTTAAGTGCG

FIG. 9T

GIL01

SEQ ID NO:367

QVQLVESGGGLVKPGGSLRLSCAASGFTFSDYYMSWIRQAPGKGLEWVSAIS
GSGGSTYYADSVKGRITISRDNAKNSLYLQMNSLRAEDTAVYYCARGLWVWD
PLDYWGRGTLVTVSSGGGGSGGGGSGGGGSDIQMTQSPSTLSASVGDRVTIT
CRASEGIYHWLAWYQQKPGKAPKLLIYKASSLASGVPSRFSGSGSGTDFTLT
ISSLQPDDFATYYCQQYSNYPLTFGGGTKVEIKRA

SEQ ID NO:376

CAAGTGCAGCTGGTGGAGTCTGGGGGAGGCTTGGTCAAGCCTGGAGGGTC
CCTGAGACTCTCCTGTGCCGCCAGCTCTGGATTCACCTTCAGTGACTACTACA
TGAGCTGGATCCGCCAGGCTCCAGGGAAGGGGCTGGAGTGGGTCTCAGCT
ATTAGTGGTAGTGGTGGTAGCACATACTACGCAGACTCCGTGAAGGGCCG
GATCACCATCTCCAGAGACAACGCCAAGAACTCACTGTATCTGCAAATGA
ACAGCCTGAGAGCTGAGGACACGGCCGTGTATTACTGTGCGAGAGGGCTT
TGGGTTTGGGATCCTCTAGACTACTGGGGCCGGGGAACCCTGGTCACCGT
CTCTTCAGGTGGCGGTGGCTCGGGCGGTGGTGGGTCGGGTGGCGGCGGAT
CGGACATCCAGATGACCCAGTCTCCTTCCACCCTGTCTGCATCTGTTGGA
GACAGAGTCACCATCACTTGCCGGGCCAGTGAGGGTATTTATCACTGGTT
GGCCTGGTATCAGCAGAAACCAGGGAAAGCCCCTAAACTCCTGATCTATA
AGGCCTCTAGTTTAGCCAGTGGGGTCCCATCAGCAGCCTTCAGCGGCAGTGGA
TCTGGGACAGATTTCACTCTCACCATCAGCAGCCTGCAGCCTGATGATTT
TGCAACTTATTACTGCCAACATATAGTAATTATCCGCTCACTTTCGGCG
GAGGGACCAAGGTGGAGATCAAACGTGCG

FIG. 10B

GIL16

SEQ ID NO:385

QVQLVQSGAEVKKPGASVKVSCKASGYTFTSYGISWVRQAPGQGLEWMGWI
SAYTGNTNYAQKFQGRVTMTTDTSTSTAYMELRSLRSDDTAVYYCARDRGY
YDAFDIWGQGTLVTVSSGGGGSGGGGSGGGGSDIQMTQSPSTLSASVGDRV
TITCRASEGIYHWLAWYQQKPGKAPKLLIYKASSLASGVPSRFSGSGSGTE
FTLTISSLQPDDFATYYCQQYSNYPLTFGGGTKVEIKRA

SEQ ID NO:394

CAGGTTCAGCTGGTGCAGTCTGGAGCTGAAGTTAAGAAGCCTGGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
ATCAGCGCTTACACTGGTAACACAAACTATGCACAGAAGTTCCAGGGCAG
AGTCACCATGACCACAGACACATCCACGAGCACAGCCTACATGGAACTGA
GGAGCCTGAGATCTGACGACACGGCCGTGTATTACTGTGCGAGAGATCGT
GGATACTATGATGCTTTTGATATCTGGGGCCAAGGGACACCCTGGTCACCGT
CTCCTCAGGTGGAGGCGGTTCAGGCGGAGGTGGCAGCGGCGGTGGCGGAT
CGGACATCCAGATGACCCAGTCTCCTTCCACCCTGTCTGCATCTGTTGGA
GACAGAGTCACCATCACTTGCCGGGCCAGTGAGGGTATTATCACCGTT
GGCCTGGTATCAGCAGAAGCCAGGGAAAGCCCCTAAACTCCTGATCTATA
AGGCCTCTAGTTTAGCCAGTGGGGTCCCATCAGCAGCCTGATTT
TCTGGGACAGAGTTCACTCTCACCATCAGCAGCCTGCAGCCTGATGATTT
TGCAACTTATTACTGCCAACAATATAGTAATTATCCGCTCACTTTCGGCG
GAGGGACCAAGGTGGAGATCAAACGTGCG

FIG. 10C

GIL45

SEQ ID NO:403

QMQLVESGGGVVQPGRSLRLSCAASGFTFSNYGMYWVRQAPGKGLEWVAHI
WYDGSNEKYADSVKGRMTVSRDNSKNTLYLQMNSLRAEDTAVYYCATEQHW
ITAFDIWGKGTLVTVSSGGGGSGGGGSGGGGSQSALTQPASVSGSPGQSIT
ISCTGTSSDVGGYNYVSWYQQHPGKAPKLMIYEGSKRPSGVSNRFSGSKSG
NTASLTISGLQAEDEADYCSSYTTRSTRVFGGGTKLTVLGA

SEQ ID NO:412

CAGATGCAGCTGGTGGAGTCTGGGGGAGGCCTGGTCCAGCCTGGGAGGT
CCCTGAGACTCTCCTGTGCAGCCTCTGATTCACCTTCAGTAACTATGG
CATGTACTGGGTCCGCCAGGCTCCAGGGAAGGGGCTGGAGTGGGTGGCA
CATATTGGTATGATGGAAGTAATGAAAAGTATGCAGACTCCGTGAAGG
GCCGAATGACCGTCTCCAGAGACAATTCCAAGAACACGTTGTATTTGCA
AATGAACAGCCTGAGAGCCGAGGACACGGCTGTGTATTACTGTGCGACA
GAGCAACACTGGATTACTGCTTTTGATATCTGGGGCAAAGGCACCCTGG
TCACCGTCTCCTCAGGTGGAGGCGGTTCAGGCGGAGGTGGCTCAGGCGG
TGGCGGATCACAGTCTGCGCTGACTCAGCCTGCCTCTGTCTGGGTCT
CCTGGACAGTCGATCACCATCTCCTGTGTACCAACACAGGCAAGCCCC
GTGGTTATAACTATGTCTCCTGGTACCAACAGCATCCAGGCAAAGCCCC
CAAACTCATGATTTATGAGGGCAGTAAGCGGCCCTCAGGGGTTTCTAAT
CGCTTCTCTGGCTCCAAGTCTGGCAACACGGCCTCCCTGACAATCTCTG
GGCTCCAGGCTGAGGACGAGGCTGATTATTACTGCAGCTCATATACAAC
CAGGAGCACTCGAGTTTTCGGCGGAGGGACCAAGCTGACCGTCCTAGGT
GCG

FIG. 10D

GIL60

SEQ ID NO:421

EVQLVESGGGVVRPGGSLRLSCAASGFTFDDYGMNWVRQAPGKGLEWVSG
VNWNGGTRDYAASVKGRFTISRDNAKNSLYLQMNSLRAEDTALYHCARGW
YSGSFYFGYWMGRGTLVTVSSGGGGSGGGGSGGGGSAQAALTQPASVSGS
PGQSITISCTGASGDVGAYNFVSWYQQHPGKAPKLIIYDVNKRPSGVSNR
FSGSKSGNTASLTISGLQAEDEADYYCSSYTSFSVVFGGGTKLTVLGA

SEQ ID NO:430

GAGGTGCAGCTGGTGGAGTCCGGGGGAGGTGTGGTACGGCCTGGGGGTC
CCTGAGACTCTCCTGTGCAGCCTCTGGATTCACCTTTGACGATTATGGCA
TGAACTGGGTCCGCCAAGCTCCAGGGAAGGGGCTGGAGTGGGTCTCTGGT
GTTAATTGGAATGGTGGTACCAGAGATTATGCAGCCTCCGTGAAGGGCCG
ATTCACCATCTCCAGAGACAACGCCAAGAACTCCCTGTATCTGCAAATGA
ACAGTCTGAGAGCCGAGGACACGGCTCTGTATCACTGTGCGAGAGGATGG
TATAGTGGGAGCTTCTACTACTTTGGCTACTGGGGCCGAGGAACCCTGGT
CACCGTCTCGAGTGGAGGCGGTTCAGGCGGAGGTGGCTCTGGCGGTGGTG
GCGAAGTGCACAGGCTGCGCTGACTCAGCCGGCCTCTGTCCTGGTCT
CCTGACAGTCGATCACCATCTCCTGCACTGGAGCCAGCGGTGACGTTGG
TGCTTATAACTTTGTCTCCTGGTACCAATAAGCGCCCTCAGGGGTTTCTAATCGC
AACTCATAATTTATGATGTCAATAAGCGGCCCTCAGTCTGCAGTTTCTAATCGC
TTCTCTGGCTCCAAGTCTGGCAACACCGGCCTCCCTGACCATCTCTGGCT
CCAGGCCGAGGACGAGGCTGATTATTACTGCAGCTCATATACAAGCACCT
TCTCTGTGGTATTTGGCGGAGGGACCAAGCTCACCGTCCTAGGTGCG

FIG. 10E

GIL68

SEQ ID NO: 439

QVQLVQSGAEVKKPGASVKVSCKASGYTFSDYYIHWVRQAPGQGLEWMGWV
NPDTGGTRYAQKFQGRVTMTRDMSISTAYMELSRLRSDDTAVYYCARDLIG
FDPFDIWGQGTLVTVSSGGGGSGGGGSGGGGSASSVLTQPPSVSVAPGKTA
RITCGGNNFRNKRVHWYQQKPGQAPVLVIYDSDRPSGIPERFSGSRSGNT
ATLTISRVEAGDEADYCQVWDSSTDRPLFGGGTKLTVLGA

SEQ ID NO:448

CAAGTGCAGCTGGTGCAGTCTGGGGCTGAGGTGAAGAAGCCTGGGGCCTC
AGTGAAGGTCTCCTGTAAGGCTTCTGGATACACCTTCAGCGATTACTATA
TTCACTGGGTGCGACAGGCCCCTGGACAAGGGTTGGAGTGGATGGGATGG
GTCAACCCTGACACTGGTGGCACAAGATACGCGCAGAAGTTTCAGGGCCG
GGTCACAATGACCAGGGACATGTCCATCTCCACAGCCTACATGGAGCTGT
CCAGGCTGAGAAGCGACGACACGGCCGTATATTACTGTGCGAGAGATCTA
ACTGGATTTGATCCTTTTGATATCTGGGGCCAGGGAACCCTGGTCGTCGT
CTCGAGTGGAGGCGGTTCAGGCGGAGGTGGCTCTGGCGGTGGCGGAA
GTGCATCGTCTGTGCTGACTCAGCCACCCTCAGTGTCAGTGGCCCCAGGA
AAGACGGCCCGCATTACCTGTGGGGAAACAACTTTCGAAATAAAAGAGT
ACACTGGTATCAGCAGAAGCCAGGCCAGGCCCCTGTCCTGGTCATCTATT
ATGATTCAGACCGGCCCTCAGGGATCCCTGAGCGATTCTCTGGCTCCCGC
TCTGGGAACACGGCCACCCTGACCATCAGCAGGGTCGAGGCCGGGGATGA
GGCCGACTATTACTGTCAGGTGTGGGATAGTAGTACTGATAGGCCTAGTG
TCGGCGGAGGGACCAAGCTGACCGTCCTAGGTGCG

FIG. 10F

GIL92

SEQ ID NO:457

QVQLVQSGAEVKKPGASVKVSCKASGYTFTDYYMHWVRQAPGQGLEWVGWI
NPYTGGAFYAQKFRGRVTMTRDTSISTAYMELSRLRSDDTAVYYCAREPEK
FDFWGGDNWGRGTLVTVSSGGGGSGGGGSGGGGSAQAVLTQPPSVSGAPGQ
RVTISCTGSSNIGAGYGVHWYQQLPGTAPKLLIYGNSNRPSGVPDRFSGS
KSGTSASLAITGLQAEDEADYYCQSYDSSLSGYVFGGGTQLTVLSA

SEQ ID NO:466

CAGGTCCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGGCGCAGGACACGTCCATCAGCAGCAGTTCGGGCAG
GGTCACAATGACCAGGGACACGTCCATCAGCAGCAGTACATGGAGCTGA
GCAGACTGAGATCTGACGACACGGCCGTGTATTATTGTGCGAGAGAACCT
GAAAAATTCGATTTTTGGGGGGGTGACAACTGGGGCCGGGGACATTGGT
CACCGTCTCGAGTGGAGGCGGCGGTTCAGGCGGAGGTGGCTCTGGCGGTG
GCGGAAGTGCACAGGCTGTGCTGACTCAGCCTCCACTCACTGTCTGGGCC
CCAGGGCAGAGGGTCACCATCTCCTGCACTGGGAGCAGCAACATCGG
GGCAGGTTATGGTGTACACTGGTACCAACAGCTTCCAGGAACAGCCCCCA
AACTCCTCATCTATGGTAACAGCAATCGGCCCTCAGGGGTCCCTGACCGA
TTCTCTGGCTCCAAGTCTGGCACCTCAGCTCTCGGCCATCACTGGGCT
CCAGGCTGAGGATGAGGCTGATTATTACTGCCAGTCCTATGACAGCAGCC
TGAGTGGTTATGTCTTCGGAGGTGGGACCCAGCTCACCGTTTAAGTGCG

062A09

SEQ ID NO: 475

Q V Q L V Q S G A E V K K P G A S V K V S C K A S G Y T
F T S Y G I S W F Q Q A V R Q A P G Q G L E W M G W V S A Y M E L R
N T N Y A Q K F Q G R Y C A P T A R D R G G S T A Y M E Q Q G
S L R S D D T A V Y Y G G D P K L I H S L Q P D F A T Y Y C Q
S P S T L V S A S E G T E F T L T I K A S L Q P D F A T Y Y C Q
W Y Q Q S P G K A P K L L I Y K A S S L Q P D F A T Y Y C Q
S G S G T E F T L T I S S L Q P D D F A T Y Y C Q
M G E Y N A T F G G G T K V E I K R

SEQ ID NO: 484

CAGGTGCAGCTGGTGCAGTCTGGAGCTGAGGTGAAGAAGCCTGGGGCCTC
AGTGAAGGTCTCCTGCAAGGCTTCTGGTTACACCTTTACCAGTTATGGTA
TCAGCTGGGTGCGACAGGCCCCTGGACAAGGGCTTGAGTGGATGGGATGG
GTCAGCGCTTACATGGAACTGAGGCAGGGCAGAGTCACCATGACCAGGGA
CAGAGTCACCATGACCAGGGACACATCCACGAGCACAGCCTACATGGAGCTGAGGAGCCTGAGATCTGACGACACGGCCGTGTATTACTGTGCGAGAGATCGT
GGATACTATGATGCTTTTGATATCTGGGGCCAAGGGACCACCGTGGTCACCGT
CTCCTCAGGTGGAGGCGGTTCAGGCGGAGGTGGCAGCGGCGGTGGCGGAT
CTGGAGACATCCAGATGACCCAGTCTCCTTCCTCCGTGTCTGCATCTGTTGGA
GACAGAGTCACCATCACCTGCCGGGCCAGTGAGGGTATTATCACTGGTT
GGCCTGGTATCAGCAGAAAGCCAGGAAAGCCCCTAAGCTCCTGATCTATA
AGGCCTCTAGTTTAGCCAGTGGGGTCCCATCAGCAGCCTGCAGCCTGATGATTT
TGCAACTTATTACTGCCAACAAATGGGCGAGTACAACGCCACCTTCGGCG
GAGGGACCAAGGTGGAGATCAAACGT

SEQ ID NO:493

E V Q L V E S G G G V V R P G G S L R L S C A A S G F T F D D Y G M N W V R Q A P G K G L E W V S G I R S L Y A A S G F T R D Y A A S V K G R F T I S R D N A K N S M G V N W M G R T L V S G H P G T A L Y H C A R G W Y S G A A W N S L Y Q A T Q P A S V Q N T A S G G G S T H I S G G G S G D V G S W Y S K S V F G G P G Q S I H I Y D V N K R P S G V C S S Y T S T F S S D K A P K L I S G L Q A E D E A D Y Y C S L T I S G L Q A E D E A D Y Y C S L T V L G
G T K L T V L G

SEQ ID NO:502

GAGGTGCAGCTGGTGGAGAGCGGGGGAGGTGTGGTACGGCCTGGGGGGTC
CCTGAGACTCTCCTGTGCCAAGCTCTCCAGGATTCACCCTTTGACGATTATGGCA
TGAACTGGGTCCGCCAAGCTCCAGGGAAGGGGCTGGAGTGGGTCTCTGGT
GTTAATTGGAATGGTGTGGTGCAGAGATTATGCAGCCTCCGTGAAGGGCCG
ATTCACCATCTCCAGAGACAACGCCAAGAACTCCCTGTATCTGCAAATGA
ACAGTCTGAGAGCCGAGGACACGGCCGTGTATCACTGTGCGAGAGAATGG
TATAGTGGGGCCGCGTGGAACATGGGCTACGTCAGGGGAGGTTCAGGGG
CACCGTCTCCTCAGGAGGTGGCTCTGGCGGTGGCGGATCGGGAGGTGGCGGTG
GCGGAAGTGACAGCTGCGCTGACTCAGCCGCTCCTCAGCCGGGTTGG
CCTGGACAGTCGATCACCATCTCCTGCACTGGAACCAGCAGTGACGTTGG
TGCTTATAACTTTGTCTCTGTACCAACAACACCCTCAGGGTTTCTAATCGC
AACTCATAATTTATGATGTCAATAAGCGGCCCTCAGGGGTTTCTAATCGC
TTCTCTGGCTCCAAGTCTGGCAACACGGCCTCCCTGACCATCTCGGCT
CCAGGCCGAGGACGAGGCTGATTATTACTGCAGCTCATATACAAGCACCT
TCTCTGTGGTATTTGGCGGAGGGACCAAGCTGACCGTCCTAGGT

SEQ ID NO:511

Q V Q L V Q S G A E V K K P G A S V K V S C K A S G Y T
F S D Y Y I H W F Q Q A P G Q M T R D M S I D P F D I W V N P D T G
G T R Y A Q K F Q R V C Y S K T A P V L T I S R V L T K L T H G V
R L R S D D T A V Y G S G G S A R I T C S G S N F R N K R V H
T L V T S S V A P G Q P A T L Y D R P S G I P E R F
Q P P S V K P G Q N T A H I S R V L T K L T H G V
W Y Q Q R S G N T A F G G T K L T V L G
S G S R S G D L F N D N G V F G G T K L T V L G
W D L F N G

SEQ ID NO:520

CAGGTCCAGCTGGTGCAGTCTGGGGCTGAGGTGAAGAAGCCTGGGGCCTC
AGTGAAGGTCTCCTGTAAGGCTTCTGGATACACCTTCAGCGATTACTATA
TTCACTGGGTGCGACAGGCCCCTGGACAAGGGCTTGAGTGGATGGGATGG
GTCAACCCTGACAATGACCAGGACACATGTCCATCTCCACAGCTGGAGCTGT
GGTCACAGGACGGCGACGAAGCCACGGTCACCATTACTGTGCGAGAGATCTA
CCAGGCTGAGAATTTGATCCTTTTGATATCTGGGGCCAGGGAACCCTGGTCACCGT
CTCCTCAGCAGTTCAGCTCAGTGACTCAGTGCTGCTCGCCCCAGGA
GTGCATCGTCTGTGCTCAGCAGCCTCAGTCTCCTCAGTGTGGCCCCAGGA
AAGAGACGGCCCGCATTACCTGTGGGGGAAACAGCCCCTGAGCGATTCTCTGGCTCCGC
ACACTGGTATCAGACCGGCCCCTCAGGGATCCCCTGACCATCAGCAGGGTCGAGGCCGGGATGA
ATGATTCAGAACACGGCTATTACTGTCAGTGTGGATCTGGGATGTGTGGATGA
TCTGGAACGGGACTATTACTGTCAGTGTGGATCTGGTGTGGATGA
GGCCGACTATTACTGTCAGTGTGGATCTGGGATGA
TCGGCGGAGGGACCAAGCTGACCGTCCTAGGT

166G05

SEQ ID NO:529

Q V Q L V Q S G A E V K K P G A S V K V S C K A S G Y T
F S D Y Y I H W V R Q A P G Q G L E W M G W V N P D T G
G T R Y A Q K F Q G R V T M T R D M S T A Y M E L S Q L
R L R S D D T A V Y Y C A R D L T G G S A S W G V L T H
T L V T V S S V A P G Q K T A L V H S G N F R N K R V H
Q P P S V Q K P G Q A P V L T I S G I P E R F
W Y Q Q K P G N T A T L T G G T K L T F G
S G S R L T D S G S F R S D E A G D Y Y C Q V
W D F L

SEQ ID NO:538

CAGGTCCAGCTGGTGCAGTCTGGGGCTGAGGTGAAGAAGCCTGGGGCCTC
AGTGAAGGTCTCCTGTAAGGCTTCTGGATACACCTTCAGCGATTACTATA
TTCACTGGGTGCGACAGGCCCCTGGACAAGGGCTTGAGTGGATGGGATGG
GTCAACCCTGACACTGGTGGCACAGATACGCCAGAAGTTTCAGGGCCG
GGTCACAATGACCAGGGACGAGCCGTATATTACTGTGCAGAGATCTA
CCAGGCTGAGAAGGACGACGAGCCGTATATTACTGTGCAGAGATCTA
ACTGGATTTGATCCTTTGATATCTCAGGGAACCCTGGTCACCGT
CTCCTCAGGAGGCGCGTTCAGTCAGCTGTGCCCCAGGA
GTGCATCGTCTGTCTGTACAACTTCACGGGGAACAACTTCAGGCTG
AAGACGGCCCCGCATTACCTGTGGGAACAACTTTCGAAATAAAAGAGT
ACACTGGTATCAGCAGAAGCCAGGCCAGATCCCCTGAGCCATCAGCAGGT
ATGATTCAGAACCGGCACCCTGAGGTGTGAGGATTTCCTCCCGC
TCTCGGGGAGGAGGACCAAGCTGGGATTTCCTCACCGACTCGGGTCGT
GGCCGACTATTACTGTCAGGTGTGGATTTTCCTCACCGACTCGGGGTCGT
TCGGCGGAGGGACCAAGCTGACCGTCCTAGGT

SEQ ID NO:547

```
Q V Q L V Q S G A E V K K P G A S V K V S C K A S G Y T F T
D Y Y M H W V R Q A P G Q G L E W M G W I N P Y T G A F D D
A Q K F R G R V T M T R D T S I S T A Y M E L S R L R S D D
T A V Y Y C A R E P E R F G D S R S A Q A V L G R T L V T S
S G G G S Y C G S S G G G S S N I G A G Y G V H W Y Q Q L P G
P G Q R V T I S C T G S S S N R P S G V P D R F S G S K S G T S
T A P K L L I Y H D L Q A E D E A D Y Y C Y H W D K E Q S G Y V F G
S L A I T G L T Q Q T D
G G T Q L T V L G
```

SEQ ID NO:556

```
CAGGTGCAGCTGGTGCAGTCTGGGGCTGAGGTGAAGAAGCCTGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGATGG
ATCAACCCTTATACTGGTGCGCATTCTATGACGACGCAGAGTTTCGGGGCAG
GGTCACACAATGACCAGGGACACGTCCATCAGCACAGCCTACATGGAGCTGA
GCAGACTGAGATCTGACGACACGGCCGTGTATTATTGTGCGAGAGAACCT
GAAAGATTCGGGGACTCAGGGGGCGGGTGGGCTGCTAGCCAGTCTCTGGCGTA
CACCGTCTCCTCAGGTGGCACAGCAGCGTGTCTGACTCAGCCCCCTCAGT
GCAGAAGTGCAGGAGGGTCACCATCTCCTGCACTGGGAGCAGCTCCAACATCGG
GGCAGGTTATGCTACAGTAGTACACTGGTACCAGCAGCTTCCAGGAACAGCCCCA
AACTCCTCATCTATGGTAACGATCAGCGGCCCTCAGGGGTCCCTGATCGA
TTCTCTGGCTCCAAGTCTGGCACCTCAGCCTCCCTGGCCATCACTGGGCT
CCAGGCTGAGGATGAGGCTGATTATTACTGTTACCACTGGGACAAGGAGC
AGAGTGGTTATGTCTTCGGAGGTGGGACCCCAGCTCACCGTCCTAGGT
```

SEQ ID NO:565

QVQLVQSGAEVKKPGASVKVSCKASGYT
FTDYYMHWVRQAPGQGLEWMINPYTG
SAFYAQKFRGRVTMTRDTSISTAYMELS
RLRSDDTAVYYCARGPEKGGSAQLWGA
RGTLVTVSSGAPGGSGGGSGGGSSNIGA
LTQPPSVSQLPGTAPKLLIYGDSNRPSG
GYGVHWYQQLPGTAPKLLIYGDSNRPSG
VPDRFSGSKSGTSASLAITGLQAEDEAD
YYCQSYDSGLSGYVFGGGTQLTVLG

SEQ ID NO:574

CAGGTGCAGCTGGTGCAGTCTGGGGCTGAGGTGAAGAAGCCTGGGGCCTC
AGTGAAGGTCTCCTGCAAGGCTTCTGGATACACCTTCACCGACTACTATA
TGCACTGGGTGCGACAGGCCCCTGGACAAGGGCTTGAGTGGATGGGGATGG
ATCAACCCTTATACTGGTAGCGCTTTCTATGCACAGAAGTTTCGGGGCAG
GGTCACAATGACCAGGGACACGTCCATCAGCACAGCCTACATGGAGCTGA
GCAGACTGAGATCTGACGACACGGCCGTGTATTATTGTGCGGGGAGAACCT
GAAAAATTCGGGGAGTGGCGGCGCGCCCAGTTGTGGGCCGGGAGGCTCTGGCGGTA
CACCGTCTCCTCAGGAGGCGGCGGTTCAGGCGGCGGCGGCTCTGGCGGTA
GCGGAAGTGCACAGAGCTGTGCTGACTCAGCCGCCCACTCTGCCCTGGGT
CCAGGGCAGAGGGTCACCATCTCCTGCACTGGGAGCAGCTCCAACATCGG
GGCAGGTTATGGTGTACACTGGTACCAACAGCTTCCAGGAACAGCCCCCA
AACTCCTCATCTATGGTGACAGCAATCGGCCCTCAGGGGTCCCTGACCGA
TTCTCTGGCTCCAAGTCTGGCACCTCAGCCTCCCTGGCCATCACTGGGCT
CCAGGCTGAGGATGAGGCTGATTATTACTGCCAGTCCTATGACAGCGGCC
TGAGTGGTTATGTCTTCGGAGGTGGGACCCAGCTCACCGTCCTAGGT

355E04

SEQ ID NO:583

| Q | V | Q | L | V | Q | S | G | A | E | V | K | K | P | G | A | S | V | K | V | S | C | K | A | S | G | Y | T |
| F | T | H | Y | M | H | W | V | R | Q | A | P | G | Q | R | L | E | W | M | G | W | I | N | P | Y | T | L | G |
| G | A | F | Y | A | Q | K | F | Q | G | R | V | T | M | T | R | D | T | S | I | S | T | A | Y | M | E | L | S |
| R | L | R | S | D | D | T | A | V | Y | Y | C | A | R | E | P | E | K | G | S | S | G | S | A | Q | G | A | V |
| R | G | T | L | V | T | V | S | S | G | G | G | G | S | G | G | G | G | S | G | G | G | G | S | N | I | G | A |
| G | L | Q | P | P | S | V | S | Q | A | P | G | Q | R | V | T | I | S | C | T | G | N | S | N | R | P | S | G |
| G | Y | G | V | H | W | Y | Q | Q | K | S | G | T | A | P | K | L | L | I | T | Y | G | L | Q | A | E | D | E | A |
| V | P | D | R | F | S | G | S | K | S | G | T | S | A | S | L | A | I | T | G | L | Q | A | E | D | E | A | D |
| Y | Y | C | Q | S | Y | D | S | S | L | S | G | Y | V | F | G | G | G | T | Q | L | T | V | L | G | | | |

SEQ ID NO:592

CAGGTGCAGCTGGTGCAGTCTGGGGCTGAGGTGAAGAAGCCTGGGGCCTC
AGTGAAGGTCTCCTGCAAGGCTTCTGGATACACCTTCACCCACTACTATA
TGCACTGGGTGCGACAGGCCCCTGGACAAGGGCTTGAGTGGATGGGATGG
ATCAACCCTTATACTGGTGGCGCACGTGTACTATGCACAGCTACATGGAGCTGA
GGTCACAATGACCAGGGACACGTCCATCAGCACAGCCTACATGGAGCTGA
GCAGACTGAGATCTGACGACACGGCCGTGTATTATTGTGCGAGAGAACCT
GAAAAATTGCACTCGCCGAAGCGCCGAGATCTGGGGCGGAGGTGGCTCTGGCGGTA
CACCGGTCTCCCCAGGGTGCCAGGTCTGTGGCTCAGTGACTCAGCCCACCCTC
GCGGAAGTGCACAGGCTGTGCTGACTCAGCCCACCACTGTGTCTGGGGCC
CCAGGGCAGAGGGTCACCATCTCCTGCACTGGTAACAGCAACAGCAGCCA
GGCAGGTTATGGTGTACACTATGTAACAGCACACTGGCACCCTCCAGGCT
AACTCCTCTGCTGGGGATGAGGCTGATTATTACTGCCAGTCCTATGACAGCAGCC
TTCTCTGGCTCCAAGTCTGGCACCTCAGCCTCCCTGGCCATCACTGGGCT
CCAGGCTGAGGATGAGGCTGATTATTACTGCCAGTCCTATGACAGCAGCC
TGAGTGGTTATGTCTTCGGAGGTGGGACCCAGCTCACCGTCCTAGGT

SEQ ID NO: 601

Q V Q L V Q S G A E V K K P G A S V K V S C K A S G Y T
F T N Y Y M H W V R Q A P G Q G L E W M I N P Y T G
S A F Y A Q K F R G R V T M T R D T S T A Y M E L S
R L R S D D T A V Y Y C A R E P K G S D D S S N I G A
G Y P D R F S G S G S G T D F T L T I S S L Q A E D E A D
V Y Y C Q S Y D N S L S G Y V F G Q G T Q L T V L G

SEQ ID NO: 610

CAGGTGCAGCTGGTGCAGTCTGGGGCTGAGGTGAAGAAGCCTGGGGCCTC
AGTGAAGGTCTCCTGCAAGGCTTCTGGATACACCTTCACCAACTACTATA
TGCACTGGGTGCGACAGGCCCCTGGACAAGGGCTTGAGTGGATGGGGATGG
ATCAACCCTTATACTGGTAGCGCACACGTCTATGCACAGAAGTTTCGGGCAG
GGTCACAATGACCAGGGACACGTCCATCAGCACAGCCTACATGGAGCTGA
GCAGACTGAGATCTGACGACACGGCCGTGTATTATTGTGCGAGAGAACCT
GAAAAATTCGACTCCGACAGTTCAGGGAGCGTCTGGGCGCGGAGGACATTGGT
CACCGTCTCCTCAGGAGAGTGCACAGCTGTGCTGACTCCTGCACCATCTCCT
GCGGAAGTGCAGAGGGTCACCATCTCCTGCAGCAGCTCCAACATCGG
CCAGGGCAGTTATGTGCACTGGTACCAACAGCTTCCAGGAACAGCCCCCA
AACTCCTCATCTATGGTGACAGTCTGGCACCTCCCTCAGGGTCCCTGACCGA
TTCTCTGGCTCCACAGTCTGGCAACTCTGGGACCCTGGCCATCACTGGGCT
CCAGGCTGAGGATGAGGCTGATTATTACTGCCAGTCCTATGACAACAGCC
TGAGCGGTTATGTCTTCGGAACTGGGACCCCAGCTGACCGTCCTAGGT

SEQ ID NO:619

EVQLVESGGGVVRPGGSLRLSCAASGFTFDDYGMNWVRQAPGKGLEWVSGV
NWNGGTRDYAASVKGRFTISRDNAKNSLYLQMNSLRAEDTALYHCARGWYS
GAAWNMGYWGRGTLVTVSSGGGGSGGGGSGGGGSGGGGSGGGGSAQA
ALTQPASVSGSPGQSITISCTGASGDVGAYNFVSWYQQHPGKAPKLIIYDV
NKRPSGVSNRFSGSKSGNTASLTISGLQAEDEADYYCASLVSDFSVVFGGG
TKLTVL

SEQ ID NO:628

GAGGTGCAGCTGGTGGAGAGCGGGGGCGGAGGCGTGGTGAGACCAGGCGGCA
GCCTGAGACTGAGCTGCGCCGCCAGCGGCTTCACCTTCGACGACTACGG
CATGAACTGGGTGCGCCAGGCCCCAGGCAAGGGCCTGGAGTGGGTGTCC
GGCGTGAACTGGAACGGCGGCACCCGGGACTACGCCGCCTCTGTGAAGG
GCAGATTCACCATCAGCCGGGACAACGCCAAGAACAGCCTGTACCTGCA
GATGAACAGCCTGAGAGCCGAGGACACCGCCCTGTACCACTGCGCCAGA
GGCTGGTACAGCGGCGCCGCCTGGAACATGGGCTACTGGGGCAGAGGCA
CCCTGGTGACCGTGTCCAGCGGCGGAGGCGGTTCAGGCGGAGGTGGCTC
TGGTGGTGGAGGTTCAGGCGGCGGAGGCCCGGGCCGGAGCTGGT
GGCGAAGTGCACAGGCCCAGCCATCACCATCAGCTGCACCGGCGCCAGC
GGCGACGTGGGCGCCTACAACTTCGTGTCCTGGTATCAGCAGCACCCCG
GGCGCCCAAGCTGCTGATCATCTACGACGTGAACAAGAGACCCAGCGGCGTCCA
ACAGATTCAGCGGCAGCAAGAGCGGCAACACCGCCAGCCTGACCATCAG
CGGACTGCAGGCCGAGGACGAGGCCGACTACTACTGCGCCAGCCTGGTG
TCCGACTTCAGCGTGGTGTTCGGCGGAGGCACCAAGCTGACCGTGCTG

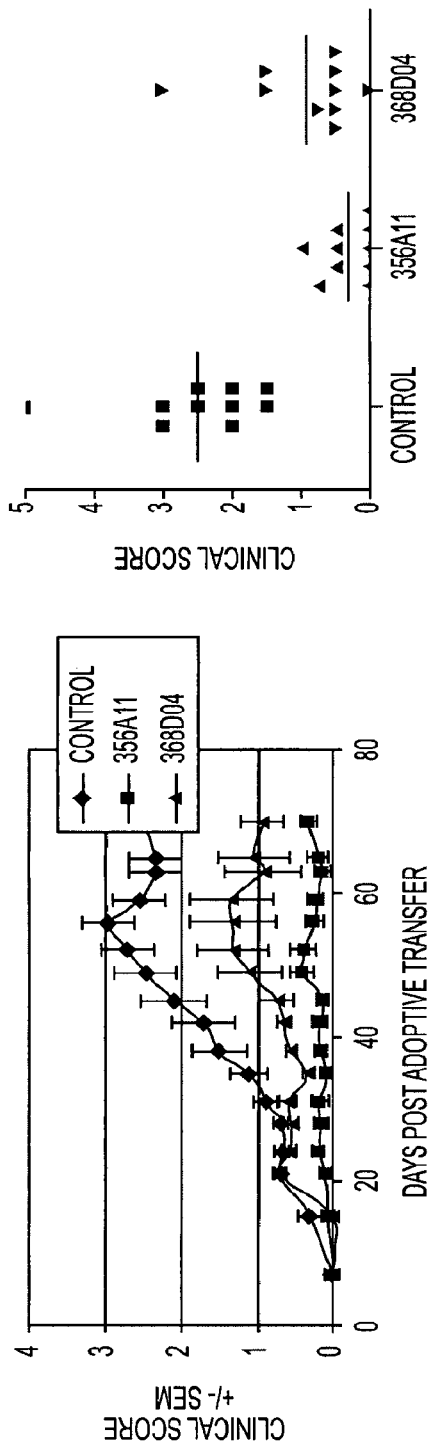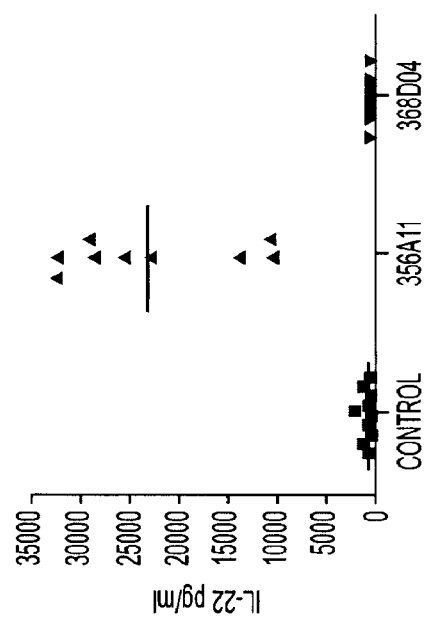

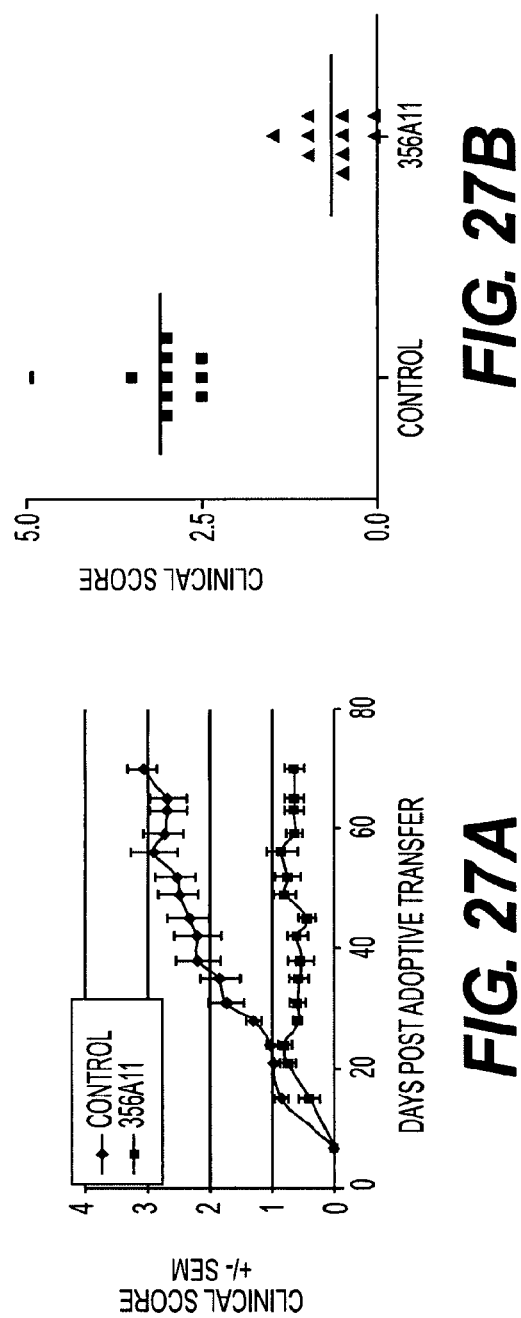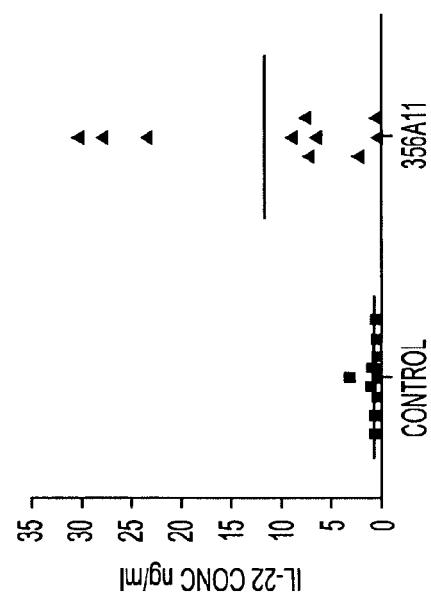

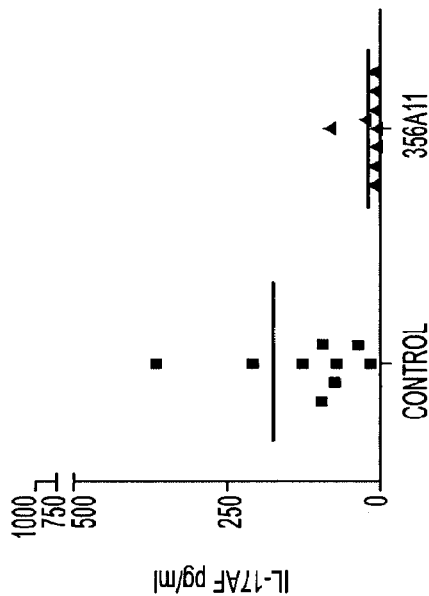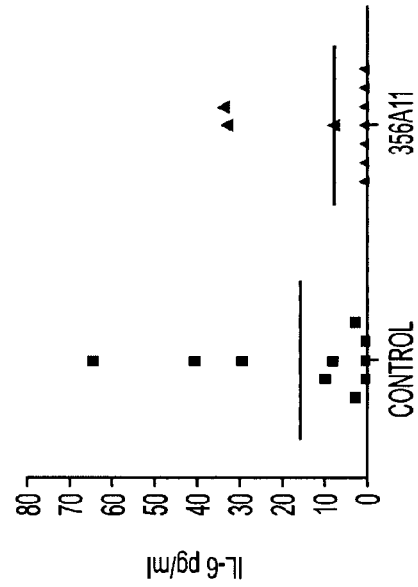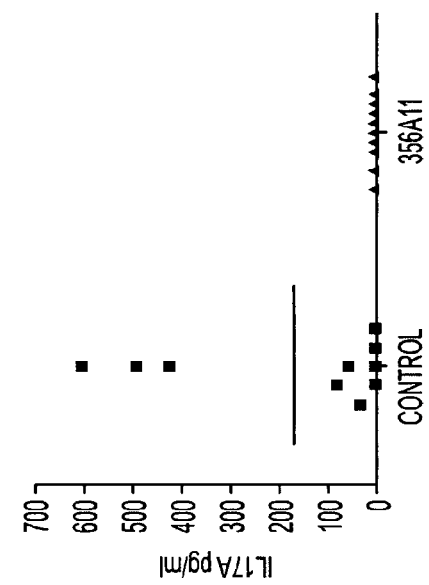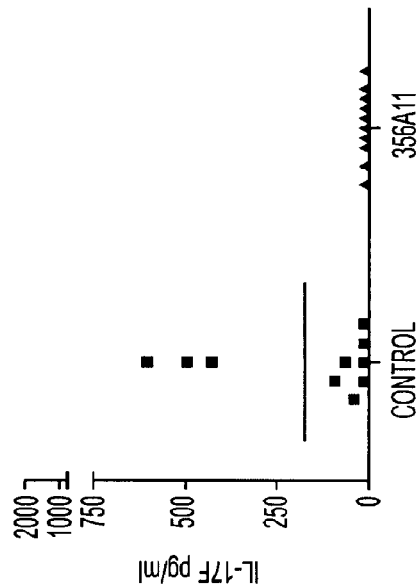

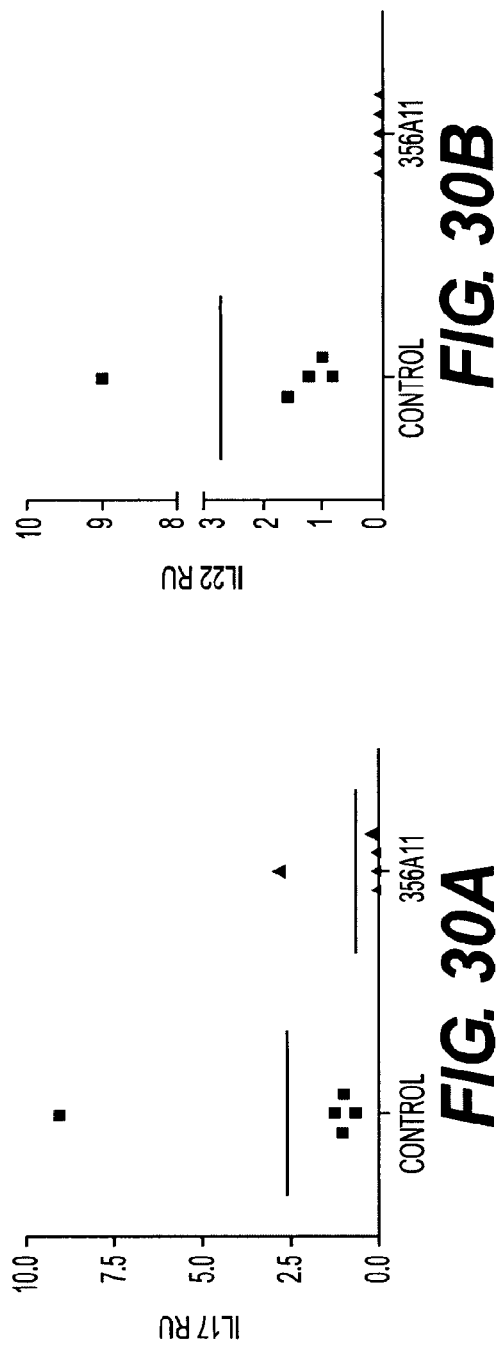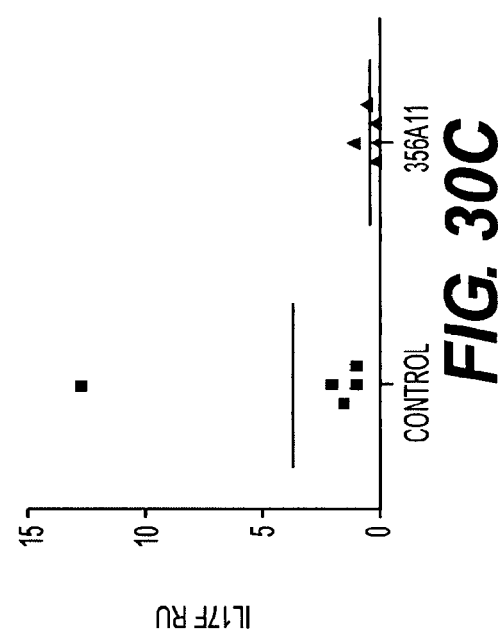

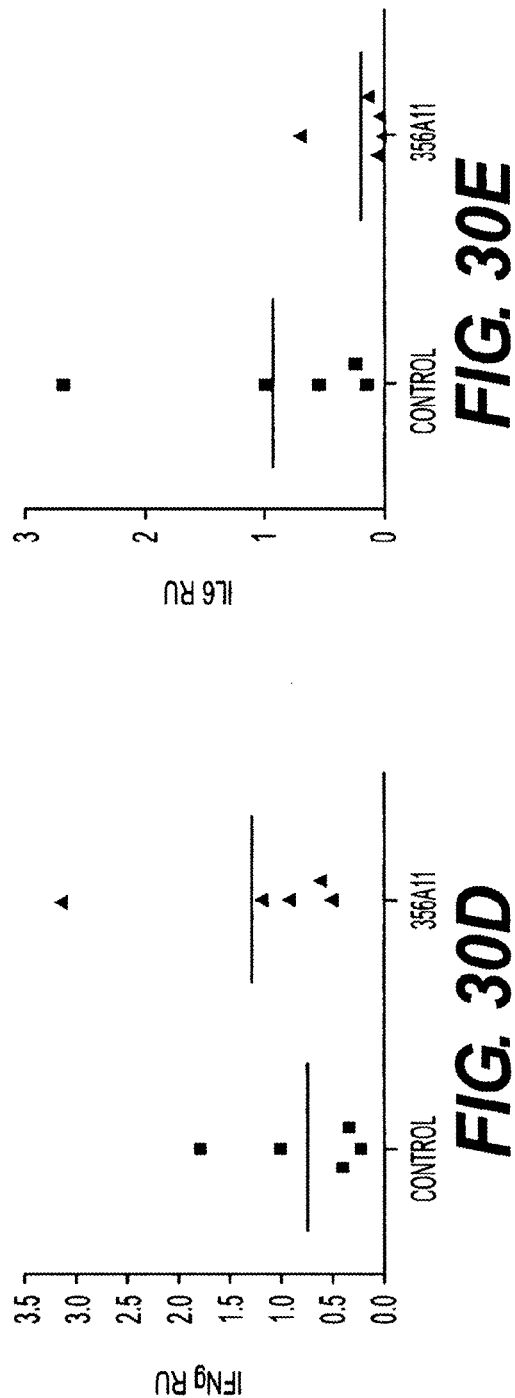

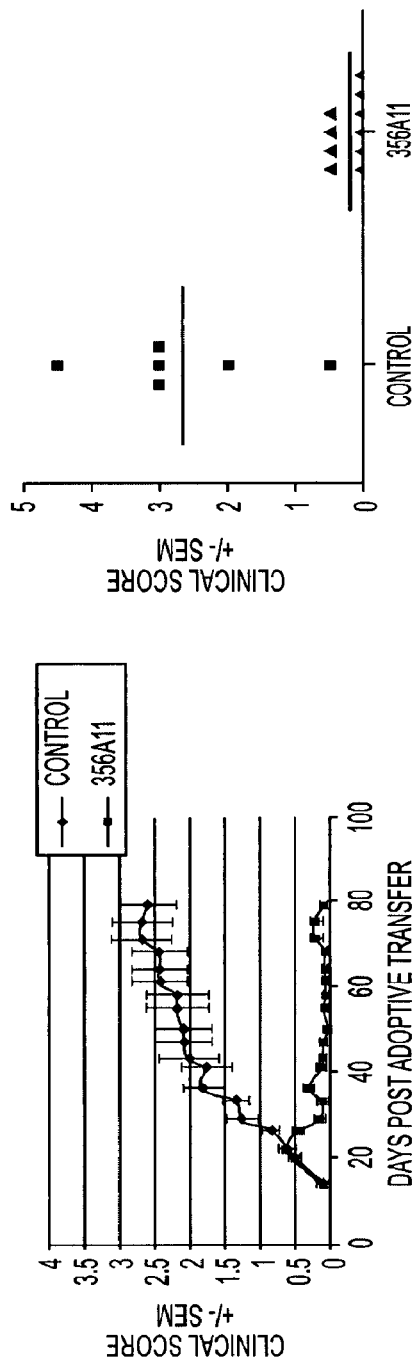
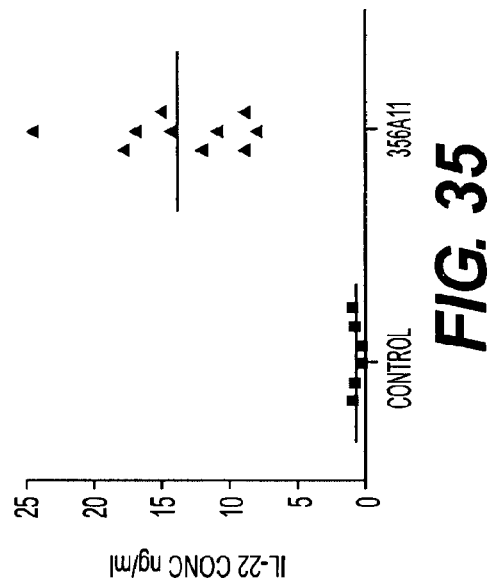
FIG. 34A
FIG. 34B
FIG. 35

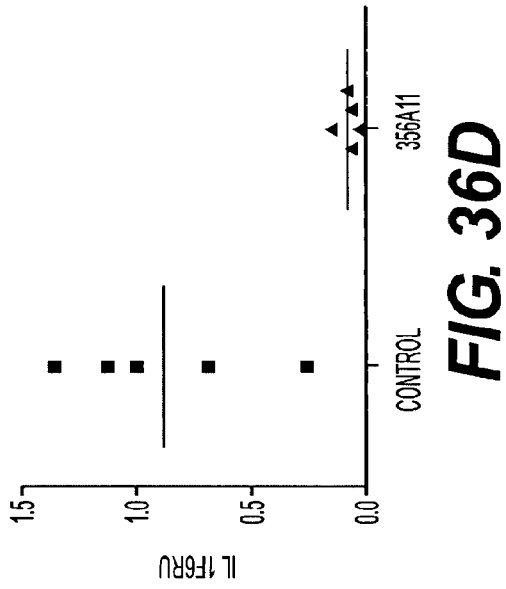
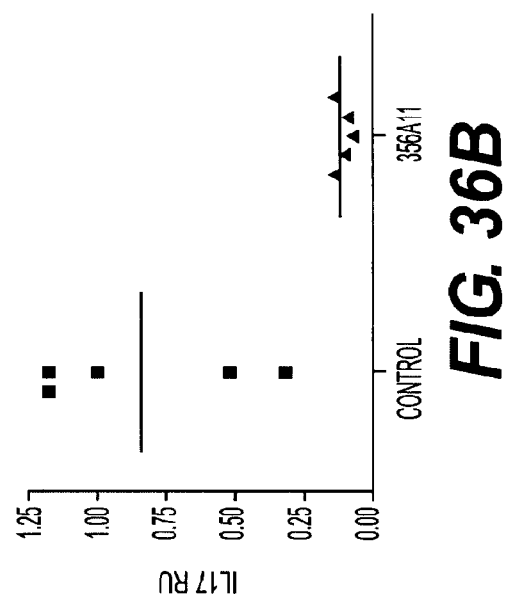
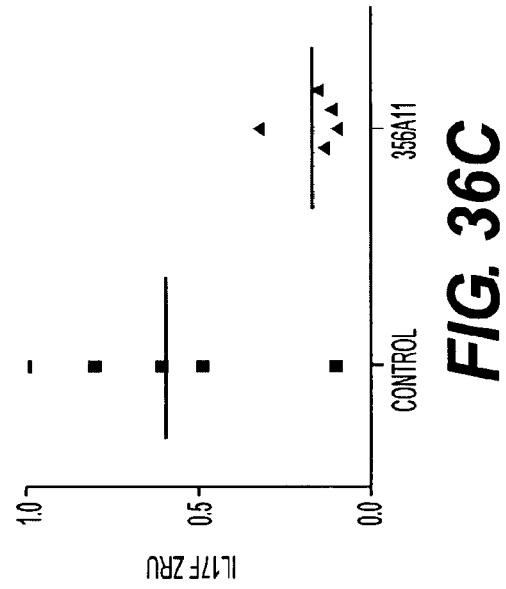
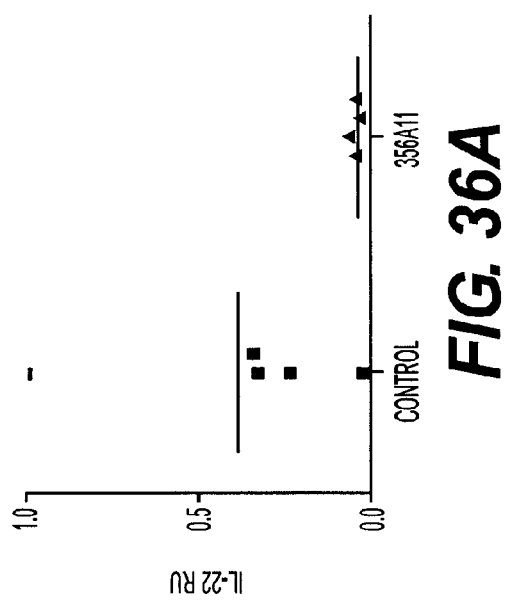

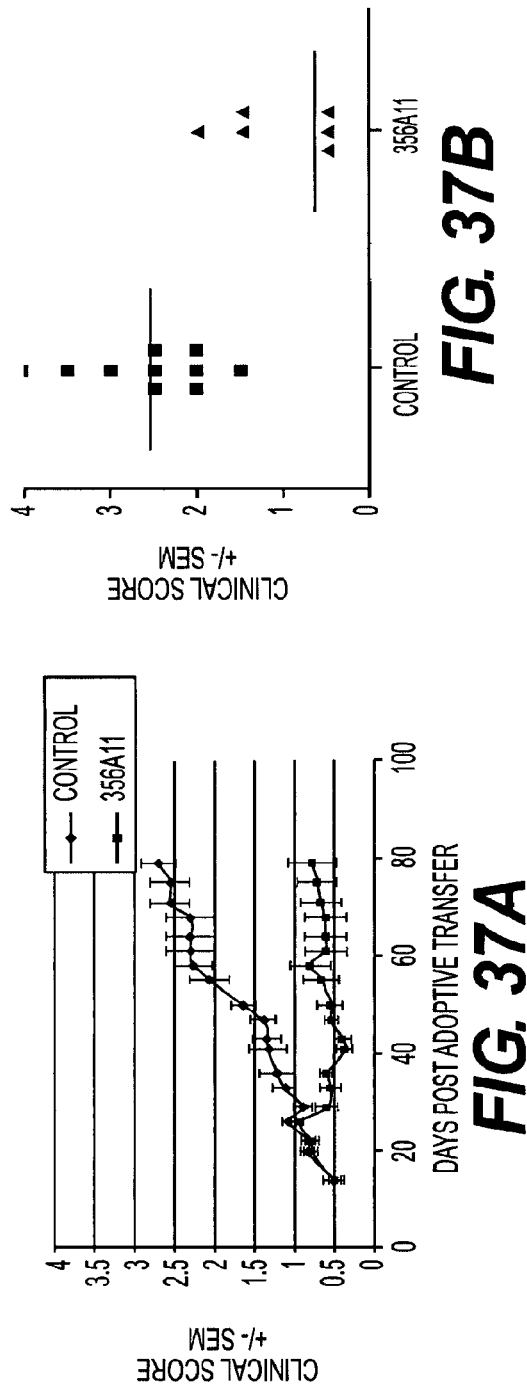

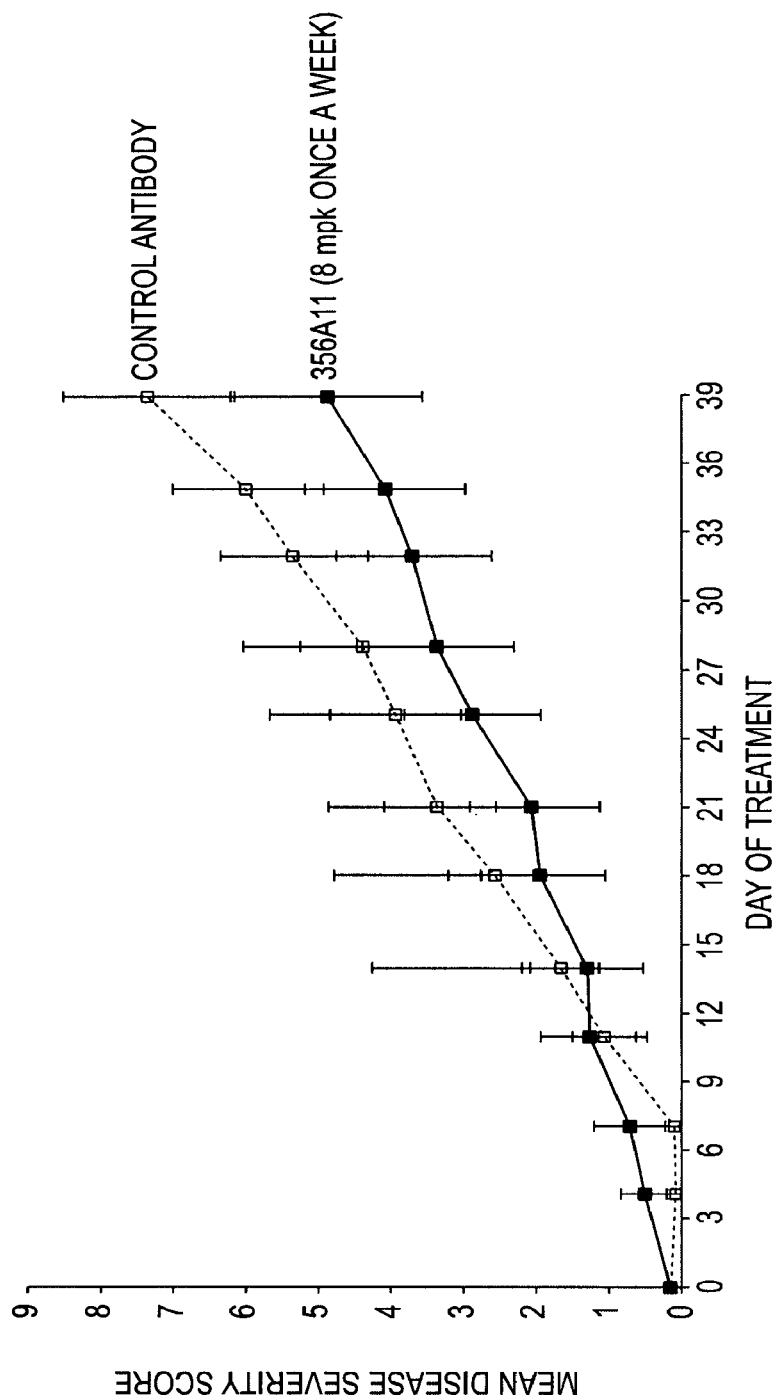

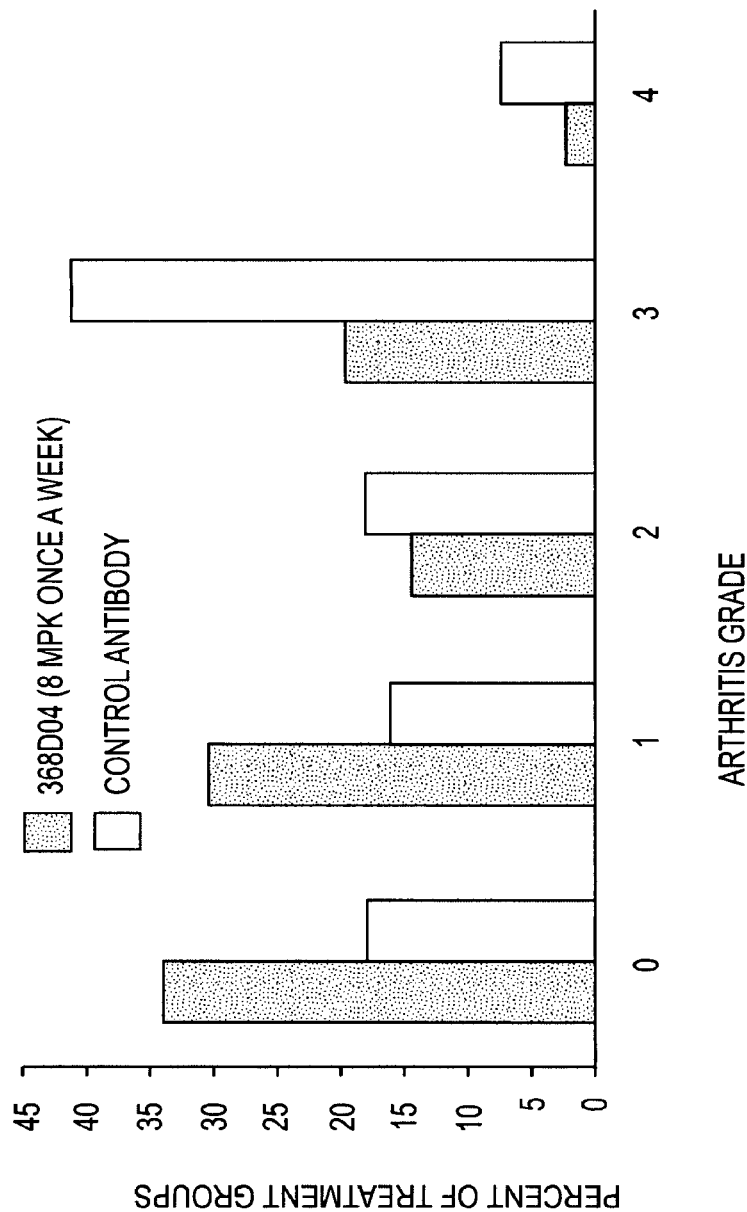

SEQUENCE LISTING

<160> NUMBER OF SEQ ID NOS: 634

<210> SEQ ID NO 1
<211> LENGTH: 178
<212> TYPE: PRT
<213> ORGANISM: Homo sapiens

<400> SEQUENCE: 1

```
Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Trp Pro Phe Leu Ala Arg Leu Ser Asn Arg Leu
        115                 120                 125

Ser Thr Cys His Ile Glu Gly Asp Asp Leu His Ile Gln Arg Asn Val
    130                 135                 140

Gln Lys Leu Lys Asp Thr Val Lys Lys Leu Gly Glu Ser Gly Glu Ile
145                 150                 155                 160

Lys Ala Ile Gly Glu Leu Asp Leu Leu Phe Met Ser Leu Arg Asn Ala
                165                 170                 175

Cys Ile
```

<210> SEQ ID NO 2
<211> LENGTH: 1191
<212> TYPE: DNA
<213> ORGANISM: Homo sapiens

<400> SEQUENCE: 2

```
gaattcggcc aaagaggcct acaggttctc cttccccagt caccagttgc tcgagttaga     60
attgtctgca atgccgccc tgcagaaatc tgtgagctct ttccttatgg ggaccctggc    120
caccagctgc ctccttctct tggccctctt ggtacaggga ggagcagctg cgcccatcag    180
ctcccactgc aggcttgaca gtccaactt ccagcagccc tatatcacca accgcacctt    240
catgctggct aaggaggcta gcttggctga taacaacaca gacgttcgtc tcattgggga    300
gaaactgttc cacggagtca gtatgagtga gcgctgctat ctgatgaagc aggtgctgaa    360
cttcacccct gaagaagtgc tgttccctca atctgatagg ttccagcctt atatgcagga    420
ggtggtgccc ttcctggcca ggctcagcaa caggctaagc acatgtcata ttgaaggtga    480
tgacctgcat atccagagga atgtgcaaaa gctgaaggac acagtgaaaa agcttggaga    540
gagtggagag atcaaagcaa ttggagaact ggatttgctg tttatgtctc tgagaaatgc    600
ctgcatttga ccagagcaaa gctgaaaaat gaataactaa ccccctttcc ctgctagaaa    660
taacaattag atgccccaaa gcgatttttt ttaaccaaaa ggaagatggg aagccaaact    720
ccatcatgat gggtggattc caaatgaacc cctgcgttag ttacaaagga aaccaatgcc    780
```

```
acttttgttt ataagaccag aaggtagact ttctaagcat agatatttat tgataacatt    840
tcattgtaac tggtgttcta tacacagaaa acaatttatt ttttaaataa ttgtcttttt    900
ccataaaaaa gattactttc cattccttta ggggaaaaaa cccctaaata gcttcatgtt    960
tccataatca gtactttata tttataaatg tatttattat tattataaga ctgcatttta   1020
tttatatcat tttattaata tggatttatt tatagaaaca tcattcgata ttgctacttg   1080
agtgtaaggc taatattgat atttatgaca ataattatag agctataaca tgtttatttg   1140
acctcaataa acacttggat atcctaaaaa aaaaaaaaaa aaagcggccg c            1191
```

<210> SEQ ID NO 3
<211> LENGTH: 179
<212> TYPE: PRT
<213> ORGANISM: Mus musculus

<400> SEQUENCE: 3

```
Met Ala Val Leu Gln Lys Ser Met Ser Phe Ser Leu Met Gly Thr Leu
1               5                   10                  15

Ala Ala Ser Cys Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val
```

<210> SEQ ID NO 4
<211> LENGTH: 540
<212> TYPE: DNA
<213> ORGANISM: Mus musculus

<400> SEQUENCE: 4

```
atggctgtcc tgcagaaatc tatgagtttt tcccttatgg ggactttggc cgccagctgc     60
ctgcttctca ttgccctgtg ggcccaggag gcaaatgcgc tgcccgtcaa cacccggtgc    120
aagcttgagg tgtccaactt ccagcagccg tacatcgtca accgcacctt tatgctggcc    180
aaggaggcca gccttgcaga taacaacaca gacgtccggc tcatcgggga gaaactgttc    240
cgaggagtca gtgctaaaga tcagtgctac ctgatgaagc aggtgctcaa cttcacccty    300
gaagacgttc tgctccccca gtcagacagg ttccagccct acatgcagga ggtggtacct    360
ttcctgacca aactcagcaa tcagctcagc tcctgtcaca tcagcggtga cgaccagaac    420
```

```
atccagaaga atgtcagaag gctgaaggag acagtgaaaa agcttggaga gagtggagag    480
atcaaggcga ttgggggaact ggacctgctg tttatgtctc tgagaaatgc ttgcgtctga    540
```

<210> SEQ ID NO 5
<211> LENGTH: 119
<212> TYPE: PRT
<213> ORGANISM: Homo sapiens

<400> SEQUENCE: 5

```
Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Arg Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Ile Thr Ile Ser Arg Asp Asn Ala Lys Asn Ser Leu Tyr
65                  70                  75                  80

Leu Gln Met Ser Ser Leu Arg Ser Glu Asp Thr Ala Val Tyr Tyr Cys
                85                  90                  95

Ala Arg Gly Leu Trp Val Trp Asp Pro Leu Asp Tyr Trp Gly Arg Gly
            100                 105                 110

Thr Leu Val Thr Val Ser Ser
        115
```

<210> SEQ ID NO 6
<211> LENGTH: 108
<212> TYPE: PRT
<213> ORGANISM: Homo sapiens

<400> SEQUENCE: 6

```
Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys Arg
            100                 105
```

<210> SEQ ID NO 7
<211> LENGTH: 245
<212> TYPE: PRT
<213> ORGANISM: Homo sapiens

<400> SEQUENCE: 7

```
Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30
```

-continued

```
Tyr Met Ser Trp Ile Arg Gln Ala Pro Gly Arg Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Ile Thr Ile Ser Arg Asp Asn Ala Lys Asn Ser Leu Tyr
 65                  70                  75                  80

Leu Gln Met Ser Ser Leu Arg Ser Glu Asp Thr Ala Val Tyr Tyr Cys
                 85                  90                  95

Ala Arg Gly Leu Trp Val Trp Asp Pro Leu Asp Tyr Trp Gly Arg Gly
            100                 105                 110

Thr Leu Val Thr Val Ser Ser Gly Gly Gly Ser Gly Gly Gly
            115                 120                 125

Ser Gly Gly Gly Ser Asp Ile Gln Met Thr Gln Ser Pro Ser Thr
            130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Ser Gly Thr Asp Phe Thr Leu Thr
            195                 200                 205

Ile Ser Ser Leu Gln Pro Asp Asp Phe Ala Thr Tyr Tyr Cys Gln Gln
210                 215                 220

Tyr Ser Asn Tyr Pro Leu Thr Phe Gly Gly Gly Thr Lys Leu Glu Ile
225                 230                 235                 240

Lys Arg Ala Ala Ala
            245
```

<210> SEQ ID NO 8
<211> LENGTH: 5
<212> TYPE: PRT
<213> ORGANISM: Homo sapiens

<400> SEQUENCE: 8

```
Asp Tyr Tyr Met Ser
 1               5
```

<210> SEQ ID NO 9
<211> LENGTH: 17
<212> TYPE: PRT
<213> ORGANISM: Homo sapiens

<400> SEQUENCE: 9

```
Ala Ile Ser Gly Ser Gly Gly Ser Thr Tyr Tyr Ala Asp Ser Val Lys
 1               5                   10                  15

Gly
```

<210> SEQ ID NO 10
<211> LENGTH: 10
<212> TYPE: PRT
<213> ORGANISM: Homo sapiens

<400> SEQUENCE: 10

```
Gly Leu Trp Val Trp Asp Pro Leu Asp Tyr
 1               5                   10
```

<210> SEQ ID NO 11

<211> LENGTH: 11
<212> TYPE: PRT
<213> ORGANISM: Homo sapiens

<400> SEQUENCE: 11

Arg Ala Ser Glu Gly Ile Tyr His Trp Leu Ala
1               5                   10

<210> SEQ ID NO 12
<211> LENGTH: 7
<212> TYPE: PRT
<213> ORGANISM: Homo sapiens

<400> SEQUENCE: 12

Lys Ala Ser Ser Leu Ala Ser
1               5

<210> SEQ ID NO 13
<211> LENGTH: 9
<212> TYPE: PRT
<213> ORGANISM: Homo sapiens

<400> SEQUENCE: 13

Gln Gln Tyr Ser Asn Tyr Pro Leu Thr
1               5

<210> SEQ ID NO 14
<211> LENGTH: 357
<212> TYPE: DNA
<213> ORGANISM: Homo sapiens

<400> SEQUENCE: 14

```
gaggtgcagt tggtggagtc tgggggaggc ttggtcacgc ctggagggtc cctgagactc      60
tcctgtgcag cctctggatt caccttcagt gactactaca tgagctggat ccgccaggct     120
ccagggaggg ggctggagtg ggtctcagct attagtggta gtggtggtag cacatactac     180
gcagactccg tgaagggccg gatcaccatc tccagagaca acgccaagaa ctcactgtat     240
ctgcaaatga gcagcctgag atctgaggac acggccgtgt attactgtgc gagagggctt     300
tgggtttggg atcctcttga ctactgggc agaggaaccc tggtcaccgt ctcctca        357
```

<210> SEQ ID NO 15
<211> LENGTH: 324
<212> TYPE: DNA
<213> ORGANISM: Homo sapiens

<400> SEQUENCE: 15

```
gacatccaga tgacccagtc tccttccacc ctgtctgcat ctattggaga cagagtcacc      60
atcacctgcc gggccagtga gggtatttat cactggttgg cctggtatca gcagaagcca     120
gggaaagccc ctaaactcct gatctataag gcctctagtt tagccagtgg ggccccatca     180
aggttcagcg gcagtggatc tgggacagat ttcactctca ccatcagcag cctgcagcct     240
gatgattttg caacttatta ctgccaacaa tatagtaatt atccgctcac tttcggcgga     300
gggaccaagc tggagatcaa acgt                                            324
```

<210> SEQ ID NO 16
<211> LENGTH: 735
<212> TYPE: DNA
<213> ORGANISM: Homo sapiens

<400> SEQUENCE: 16

```
gaagtgcagc tggtggagtc tgggggaggc ttggtcacgc ctggagggtc cctgagactc      60
tcctgtgcag cctctggatt caccttcagt gactactaca tgagctggat ccgccaggct     120
ccagggaggg ggctggagtg ggtctcagct attagtggta gtggtggtag cacatactac     180
gcagactccg tgaagggccg gatcaccatc tccagagaca acgccaagaa ctcactgtat     240
ctgcaaatga gcagcctgag atctgaggac acggccgtgt attactgtgc gagagggctt     300
tgggtttggg atcctcttga ctactggggc agaggaaccc tggtcaccgt ctcttcaggt     360
ggaggcggtt caggcggagg tggcagcggc ggtggcggat cggacatcca gatgacccag     420
tctccttcca ccctgtctgc atctattgga gacagagtca ccatcacctg ccgggccagt     480
gagggtattt atcactggtt ggcctggtat cagcagaagc cagggaaagc ccctaaactc     540
ctgatctata aggcctctag tttagccagt ggggccccat caaggttcag cggcagtgga     600
tctgggacag atttcactct caccatcagc agcctgcagc ctgatgattt tgcaacttat     660
tactgccaac aatatagtaa ttatccgctc actttcggcg gagggaccaa gctggagatc     720
aaacgtgcgg ccgca                                                     735
```

```
<210> SEQ ID NO 17
<211> LENGTH: 15
<212> TYPE: DNA
<213> ORGANISM: Homo sapiens

<400> SEQUENCE: 17
gactactaca tgagc                                                      15

<210> SEQ ID NO 18
<211> LENGTH: 51
<212> TYPE: DNA
<213> ORGANISM: Homo sapiens

<400> SEQUENCE: 18
gctattagtg gtagtggtgg tagcacatac tacgcagact ccgtgaaggg c              51

<210> SEQ ID NO 19
<211> LENGTH: 30
<212> TYPE: DNA
<213> ORGANISM: Homo sapiens

<400> SEQUENCE: 19
gggctttggg tttgggatcc tcttgactac                                      30

<210> SEQ ID NO 20
<211> LENGTH: 33
<212> TYPE: DNA
<213> ORGANISM: Homo sapiens

<400> SEQUENCE: 20
cgggccagtg agggtattta tcactggttg gcc                                  33

<210> SEQ ID NO 21
<211> LENGTH: 21
<212> TYPE: DNA
<213> ORGANISM: Homo sapiens

<400> SEQUENCE: 21
aaggcctcta gtttagccag t                                               21

<210> SEQ ID NO 22
<211> LENGTH: 27
```

```
<212> TYPE: DNA
<213> ORGANISM: Homo sapiens

<400> SEQUENCE: 22
caacaatata gtaattatcc gctcact                                              27

<210> SEQ ID NO 23
<211> LENGTH: 119
<212> TYPE: PRT
<213> ORGANISM: Homo sapiens

<400> SEQUENCE: 23
```

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
                100                 105                 110

Thr Leu Val Thr Val Ser Ser
        115

```
<210> SEQ ID NO 24
<211> LENGTH: 108
<212> TYPE: PRT
<213> ORGANISM: Homo sapiens

<400> SEQUENCE: 24
```

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Leu Glu Ile Lys Arg
            100                 105

```
<210> SEQ ID NO 25
<211> LENGTH: 245
<212> TYPE: PRT
<213> ORGANISM: Homo sapiens

<400> SEQUENCE: 25
```

Gln Val Gln Leu Val Glu Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
         35                  40                  45
Gly Trp Ile Ser Ala Tyr Thr Gly Asn Thr Asn Tyr Ala Gln Lys Phe
 50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Asp Arg Gly Tyr Tyr Asp Ala Phe Asp Ile Trp Gly Gln Gly
            100                 105                 110
Thr Leu Val Thr Val Ser Ser Gly Gly Gly Ser Gly Gly Gly
         115                 120                 125
Ser Gly Gly Gly Gly Ser Asp Ile Gln Met Thr Gln Ser Pro Ser Thr
130                 135                 140
Leu Ser Ala Ser Ile Gly Asp Arg Val Thr Ile Thr Cys Arg Ala Ser
145                 150                 155                 160
Glu Gly Ile Tyr His Trp Leu Ala Trp Tyr Gln Gln Lys Pro Gly Lys
                165                 170                 175
Ala Pro Lys Leu Leu Ile Tyr Lys Ala Ser Ser Leu Ala Ser Gly Ala
            180                 185                 190
Pro Ser Arg Phe Ser Gly Ser Gly Ser Gly Thr Asp Phe Thr Leu Thr
        195                 200                 205
Ile Ser Ser Leu Gln Pro Asp Asp Phe Ala Thr Tyr Tyr Cys Gln Gln
210                 215                 220
Tyr Ser Asn Tyr Pro Leu Thr Phe Gly Gly Gly Thr Lys Leu Glu Ile
225                 230                 235                 240
Lys Arg Ala Ala Ala
            245

<210> SEQ ID NO 26
<211> LENGTH: 5
<212> TYPE: PRT
<213> ORGANISM: Homo sapiens

<400> SEQUENCE: 26

Ser Tyr Gly Ile Ser
1               5

<210> SEQ ID NO 27
<211> LENGTH: 17
<212> TYPE: PRT
<213> ORGANISM: Homo sapiens

<400> SEQUENCE: 27

Trp Ile Ser Ala Tyr Thr Gly Asn Thr Asn Tyr Ala Gln Lys Phe Gln
1               5                   10                  15
Gly

<210> SEQ ID NO 28
<211> LENGTH: 10
<212> TYPE: PRT
<213> ORGANISM: Homo sapiens

<400> SEQUENCE: 28

Asp Arg Gly Tyr Tyr Asp Ala Phe Asp Ile
1               5                   10
```

<210> SEQ ID NO 29
<211> LENGTH: 11
<212> TYPE: PRT
<213> ORGANISM: Homo sapiens

<400> SEQUENCE: 29

Arg Ala Ser Glu Gly Ile Tyr His Trp Leu Ala
1               5                   10

<210> SEQ ID NO 30
<211> LENGTH: 7
<212> TYPE: PRT
<213> ORGANISM: Homo sapiens

<400> SEQUENCE: 30

Lys Ala Ser Ser Leu Ala Ser
1               5

<210> SEQ ID NO 31
<211> LENGTH: 9
<212> TYPE: PRT
<213> ORGANISM: Homo sapiens

<400> SEQUENCE: 31

Gln Gln Tyr Ser Asn Tyr Pro Leu Thr
1               5

<210> SEQ ID NO 32
<211> LENGTH: 357
<212> TYPE: DNA
<213> ORGANISM: Homo sapiens

<400> SEQUENCE: 32
caggtgcagc tggtggagtc tggagctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg atcagcgctt acactggtaa cacaaactat      180
gcacagaagt tccagggcag agtcaccatg accacagaca catccacgag cacagcctac     240
atggaactga ggagcctgag atctgacgac acggccgtgt attactgtgc gagagatcgt     300
ggatactatg atgcttttga tatctggggc caaggcaccc tggtcaccgt ctcctca        357

<210> SEQ ID NO 33
<211> LENGTH: 324
<212> TYPE: DNA
<213> ORGANISM: Homo sapiens

<400> SEQUENCE: 33
gacatccaga tgacccagtc tccttccacc ctgtctgcat ctattggaga cagagtcacc      60
atcacctgcc gggccagtga gggtatttat cactggttgg cctggtatca gcagaagcca     120
gggaaagccc ctaaactcct gatctataag gcctctagtt tagccagtgg ggccccatca     180
aggttcagcg gcagtggatc tgggacagat ttcactctca ccatcagcag cctgcagcct     240
gatgattttg caactattact tgccaacaa tatagtaatt atccgctcac tttcggcgga     300
gggaccaagc tggagatcaa acgt                                            324

<210> SEQ ID NO 34
<211> LENGTH: 735
<212> TYPE: DNA
<213> ORGANISM: Homo sapiens

<400> SEQUENCE: 34

```
caggtgcagc tggtggagtc tggagctgag gtgaagaagc ctggggcctc agtgaaggtc      60
tcctgcaagg cttctggtta cacctttacc agttatggta tcagctgggt gcgacaggcc    120
cctggacaag gcttgagtg gatgggatgg atcagcgctt acactggtaa cacaaactat    180
gcacagaagt tccagggcag agtcaccatg accacagaca catccacgag cacagcctac    240
atggaactga ggagcctgag atctgacgac acggccgtgt attactgtgc gagagatcgt    300
ggatactatg atgcttttga tatctggggc caaggcaccc tggtcaccgt ctcctcaggt    360
ggaggcggtt caggcggagg tggcagcggc ggtggcggat cggacatcca gatgacccag    420
tctccttcca ccctgtctgc atctattgga gacagagtca ccatcacctg ccgggccagt    480
gagggtattt atcactggtt ggcctggtat cagcagaagc cagggaaagc ccctaaactc    540
ctgatctata aggcctctag tttagccagt ggggccccat caaggttcag cggcagtgga    600
tctgggacag atttcactct caccatcagc agcctgcagc tgatgatttt gcaacttat    660
tactgccaac aatatagtaa ttatccgctc actttcggcg gagggaccaa gctggagatc    720
aaacgtgcgg ccgca                                                     735
```

```
<210> SEQ ID NO 35
<211> LENGTH: 15
<212> TYPE: DNA
<213> ORGANISM: Homo sapiens
```

<400> SEQUENCE: 35

```
agttatggta tcagc                                                      15
```

```
<210> SEQ ID NO 36
<211> LENGTH: 51
<212> TYPE: DNA
<213> ORGANISM: Homo sapiens
```

<400> SEQUENCE: 36

```
tggatcagcg cttacactgg taacacaaac tatgcacaga gttccaggg c               51
```

```
<210> SEQ ID NO 37
<211> LENGTH: 30
<212> TYPE: DNA
<213> ORGANISM: Homo sapiens
```

<400> SEQUENCE: 37

```
gatcgtggat actatgatgc ttttgatatc                                      30
```

```
<210> SEQ ID NO 38
<211> LENGTH: 33
<212> TYPE: DNA
<213> ORGANISM: Homo sapiens
```

<400> SEQUENCE: 38

```
cgggccagtg agggtattta tcactggttg gcc                                  33
```

```
<210> SEQ ID NO 39
<211> LENGTH: 21
<212> TYPE: DNA
<213> ORGANISM: Homo sapiens
```

<400> SEQUENCE: 39

```
aaggcctcta gtttagccag t                                               21
```

<210> SEQ ID NO 40
<211> LENGTH: 27
<212> TYPE: DNA
<213> ORGANISM: Homo sapiens

<400> SEQUENCE: 40
caacaatata gtaattatcc gctcact                                          27

<210> SEQ ID NO 41
<211> LENGTH: 119
<212> TYPE: PRT
<213> ORGANISM: Homo sapiens

<400> SEQUENCE: 41

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala His Ile Trp Tyr Asp Gly Ser Asn Glu Lys Tyr Ala Asp Ser Val
    50                  55                  60

Lys Gly Arg Met Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gln His Trp Ile Thr Ala Phe Asp Ile Trp Gly Lys Gly
            100                 105                 110

Thr Leu Val Thr Val Ser Ser
        115

<210> SEQ ID NO 42
<211> LENGTH: 111
<212> TYPE: PRT
<213> ORGANISM: Homo sapiens

<400> SEQUENCE: 42

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Thr Val Leu Gly
            100                 105                 110

<210> SEQ ID NO 43
<211> LENGTH: 249
<212> TYPE: PRT
<213> ORGANISM: Homo sapiens

<400> SEQUENCE: 43

```
Gln Met Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala His Ile Trp Tyr Asp Gly Ser Asn Glu Lys Tyr Ala Asp Ser Val
    50                  55                  60

Lys Gly Arg Met Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gln His Trp Ile Thr Ala Phe Asp Ile Trp Gly Lys Gly
            100                 105                 110

Thr Leu Val Thr Val Ser Ser Gly Gly Gly Ser Gly Ala Gly Gly
            115                 120                 125

Ser Gly Gly Gly Ser Gln Ser Val Leu Thr Gln Pro Ala Ser Val
    130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Glu Gly Ser Lys Arg Pro Ser
            180                 185                 190

Gly Val Ser Asn Arg Phe Ser Gly Ser Lys Ser Gly Asn Thr Ala Ser
        195                 200                 205

Leu Thr Ile Ser Gly Leu Gln Ala Glu Asp Glu Ala Asp Tyr Tyr Cys
    210                 215                 220

Ser Ser Tyr Thr Thr Arg Ser Thr Arg Val Phe Gly Gly Gly Thr Lys
225                 230                 235                 240

Leu Thr Val Leu Gly Ala Ala Ala His
                245

<210> SEQ ID NO 44
<211> LENGTH: 5
<212> TYPE: PRT
<213> ORGANISM: Homo sapiens

<400> SEQUENCE: 44

Asn Tyr Gly Met Tyr
1               5

<210> SEQ ID NO 45
<211> LENGTH: 17
<212> TYPE: PRT
<213> ORGANISM: Homo sapiens

<400> SEQUENCE: 45

His Ile Trp Tyr Asp Gly Ser Asn Glu Lys Tyr Ala Asp Ser Val Lys
1               5                   10                  15

Gly

<210> SEQ ID NO 46
<211> LENGTH: 10
<212> TYPE: PRT
<213> ORGANISM: Homo sapiens

<400> SEQUENCE: 46
```

Glu Gln His Trp Ile Thr Ala Phe Asp Ile
1               5                   10

<210> SEQ ID NO 47
<211> LENGTH: 14
<212> TYPE: PRT
<213> ORGANISM: Homo sapiens

<400> SEQUENCE: 47

Thr Gly Thr Ser Ser Asp Val Gly Gly Tyr Asn Tyr Val Ser
1               5                   10

<210> SEQ ID NO 48
<211> LENGTH: 7
<212> TYPE: PRT
<213> ORGANISM: Homo sapiens

<400> SEQUENCE: 48

Glu Gly Ser Lys Arg Pro Ser
1               5

<210> SEQ ID NO 49
<211> LENGTH: 10
<212> TYPE: PRT
<213> ORGANISM: Homo sapiens

<400> SEQUENCE: 49

Ser Ser Tyr Thr Thr Arg Ser Thr Arg Val
1               5                   10

<210> SEQ ID NO 50
<211> LENGTH: 357
<212> TYPE: DNA
<213> ORGANISM: Homo sapiens

<400> SEQUENCE: 50
cagatgcagc tggtgcagtc tgggggaggc gtggtccagc ctggggaggtc cctgagactc      60 tcctgtgcag cctctggatt caccttcagt aactatggca tgtactgggt ccgccaggct     120
ccaggcaagg ggctggagtg ggtggcacat atttggtatg atggaagtaa tgaaaagtat     180
gcagactccg tgaagggccg aatgaccgtc tccagagaca attccaggaa cacgttgtat     240
ttgcaaatga acagcctgag agccgaggac acggctgtgt attactgtgc gacagagcaa     300
cactggatta ctgcttttga tatctggggc aaaggcaccc tggtcaccgt ctcctca       357

<210> SEQ ID NO 51
<211> LENGTH: 333
<212> TYPE: DNA
<213> ORGANISM: Homo sapiens

<400> SEQUENCE: 51
cagtctgtgc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca agcccccaa actcatgatt tatgagggca gtaagcggcc ctcagggggtt     180 tctaatcgct tctctggctc caagtctggc aacacggccc cctgacaat ctctgggctc     240 caggctgagg acgaggctga ttattactgc agctcatata caaccaggag cactcgagtt     300
ttcggcggag ggaccaagct gaccgtccta ggt                                  333

<210> SEQ ID NO 52

<211> LENGTH: 744
<212> TYPE: DNA
<213> ORGANISM: Homo sapiens

<400> SEQUENCE: 52

```
cagatgcagc tggtgcagtc tgggggaggc gtggtccagc ctgggaggtc cctgagactc      60
tcctgtgcag cctctggatt caccttcagt aactatggca tgtactgggt ccgccaggct     120
ccaggcaagg ggctggagtg ggtggcacat atttggtatg atggaagtaa tgaaaagtat     180
gcagactccg tgaagggccg aatgaccgtc tccagagaca attccaggaa cacgttgtat     240
ttgcaaatga acagcctgag agccgaggac acggctgtgt attactgtgc gacagagcaa     300
cactggatta ctgcttttga tatctggggc aaaggcaccc tggtcaccgt ctcctcaggt     360
ggaggcggtt caggcgcagg tggcagcggc ggtggcggat cgcagtctgt gctgactcag     420
cctgcctccg tgtctgggtc tcctggacag tcgatcacca tctcctgcac tggaaccagc     480
agtgacgttg gtggttataa ctatgtctcc tggtaccaac aacacccagg caaagccccc     540
aaactcatga tttatgaggg cagtaagcgg ccctcagggg tttctaatcg cttctctggc     600
tccaagtctg gcaacacggc ctccctgaca atctctgggc tccaggctga ggacgaggct     660
gattattact gcagctcata taacccagg agcactcgag ttttcggcgg agggaccaag     720
ctgaccgtcc taggtgcggc cgca                                            744
```

<210> SEQ ID NO 53
<211> LENGTH: 15
<212> TYPE: DNA
<213> ORGANISM: Homo sapiens

<400> SEQUENCE: 53

```
aactatggca tgtac                                                       15
```

<210> SEQ ID NO 54
<211> LENGTH: 51
<212> TYPE: DNA
<213> ORGANISM: Homo sapiens

<400> SEQUENCE: 54

```
catatttggt atgatggaag taatgaaaag tatgcagact ccgtgaaggg c                51
```

<210> SEQ ID NO 55
<211> LENGTH: 30
<212> TYPE: DNA
<213> ORGANISM: Homo sapiens

<400> SEQUENCE: 55

```
gagcaacact ggattactgc ttttgatatc                                       30
```

<210> SEQ ID NO 56
<211> LENGTH: 42
<212> TYPE: DNA
<213> ORGANISM: Homo sapiens

<400> SEQUENCE: 56

```
actggaacca gcagtgacgt tggtggttat aactatgtct cc                          42
```

<210> SEQ ID NO 57
<211> LENGTH: 21
<212> TYPE: DNA
<213> ORGANISM: Homo sapiens

<400> SEQUENCE: 57
gagggcagta agcggccctc a                    21

<210> SEQ ID NO 58
<211> LENGTH: 30
<212> TYPE: DNA
<213> ORGANISM: Homo sapiens

<400> SEQUENCE: 58
agctcatata caaccaggag cactcgagtt           30

<210> SEQ ID NO 59
<211> LENGTH: 121
<212> TYPE: PRT
<213> ORGANISM: Homo sapiens

<400> SEQUENCE: 59

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ser Phe Tyr Tyr Phe Gly Tyr Trp Gly
            100                 105                 110

Arg Gly Thr Leu Val Thr Val Ser Ser
        115                 120

<210> SEQ ID NO 60
<211> LENGTH: 111
<212> TYPE: PRT
<213> ORGANISM: Homo sapiens

<400> SEQUENCE: 60

Gln Ala Val Leu Thr Gln Pro Ser Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Thr Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ser Asp Tyr Tyr Cys Ser Ser Tyr Thr Ser Thr
                85                  90                  95

Phe Ser Val Val Phe Gly Gly Gly Thr Lys Val Thr Val Leu Gly
            100                 105                 110

<210> SEQ ID NO 61
<211> LENGTH: 250
<212> TYPE: PRT
<213> ORGANISM: Homo sapiens

```
<400> SEQUENCE: 61

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Gly Asn Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ser Phe Tyr Tyr Phe Gly Tyr Trp Gly
            100                 105                 110

Arg Gly Thr Leu Val Thr Val Ser Ser Gly Gly Gly Ser Gly Gly
            115                 120                 125

Gly Gly Ser Gly Gly Gly Ser Ala Gln Ala Val Leu Thr Gln Pro
        130                 135                 140

Ser Ser Val Ser Gly Ser Pro Gly Gln Ser Ile Thr Ile Ser Cys Thr
145                 150                 155                 160

Gly Ala Ser Gly Asp Val Gly Ala Tyr Asn Phe Val Ser Trp Tyr Gln
                165                 170                 175

Gln His Pro Gly Lys Thr Pro Lys Leu Ile Ile Tyr Asp Val Asn Lys
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Ser Asp
210                 215                 220

Tyr Tyr Cys Ser Ser Tyr Thr Ser Thr Phe Ser Val Val Phe Gly Gly
225                 230                 235                 240

Gly Thr Lys Val Thr Val Leu Gly Ala Ala
            245                 250

<210> SEQ ID NO 62
<211> LENGTH: 5
<212> TYPE: PRT
<213> ORGANISM: Homo sapiens

<400> SEQUENCE: 62

Asp Tyr Gly Met Asn
1               5

<210> SEQ ID NO 63
<211> LENGTH: 17
<212> TYPE: PRT
<213> ORGANISM: Homo sapiens

<400> SEQUENCE: 63

Gly Val Asn Trp Asn Gly Gly Thr Arg Asp Tyr Ala Ala Ser Val Lys
1               5                   10                  15

Gly

<210> SEQ ID NO 64
<211> LENGTH: 12
<212> TYPE: PRT
```

<213> ORGANISM: Homo sapiens

<400> SEQUENCE: 64

Gly Trp Tyr Ser Gly Ser Phe Tyr Tyr Phe Gly Tyr
1               5                   10

<210> SEQ ID NO 65
<211> LENGTH: 14
<212> TYPE: PRT
<213> ORGANISM: Homo sapiens

<400> SEQUENCE: 65

Thr Gly Ala Ser Gly Asp Val Gly Ala Tyr Asn Phe Val Ser
1               5                   10

<210> SEQ ID NO 66
<211> LENGTH: 7
<212> TYPE: PRT
<213> ORGANISM: Homo sapiens

<400> SEQUENCE: 66

Asp Val Asn Lys Arg Pro Ser
1               5

<210> SEQ ID NO 67
<211> LENGTH: 10
<212> TYPE: PRT
<213> ORGANISM: Homo sapiens

<400> SEQUENCE: 67

Ser Ser Tyr Thr Ser Thr Phe Ser Val Val
1               5                   10

<210> SEQ ID NO 68
<211> LENGTH: 363
<212> TYPE: DNA
<213> ORGANISM: Homo sapiens

<400> SEQUENCE: 68
gaggtgcagc tggtggagtc cgggggaggt gtggtacggc ctgggggtc cctgagactc      60 tcctgtgcag cctctggatt cacctttgac gattatggca tgaactgggt ccgccaagct     120
ccagggaagg gctggagtg gtctctggt gttaattgga atggtggtac cagagattat      180
gcagcctccg tgaagggccg attcaccatc tccagagaca cgccaagaa ctccctgtat     240 ctgcaaatga acagtctgag agccgaggac acggccttgt attactgtgc gagaggatgg    300
tatagtggga gcttctacta ctttggctac tggggccgag aaccctggt caccgtctcc    360 tca                                                                   363

<210> SEQ ID NO 69
<211> LENGTH: 333
<212> TYPE: DNA
<213> ORGANISM: Homo sapiens

<400> SEQUENCE: 69
caggctgtgc tgactcagcc gtcctccgtg tctgggtctc ctggacagtc gatcaccatc     60
tcctgcactg gagccagcgg tgacgttggt gcttataact tgtctcctg gtaccaacaa     120 cacccaggca aaccccccaa actcataatt tatgatgtca ataagcggcc ctcaggggtt    180
tctaatcgct tctctggctc caagtctggc aacacggcct ccctgaccat ctctgggctc    240
caggccgagg acgagtctga ttattactgc agctcatata caagcacctt ctctgtggta    300

```
tttggcggag ggaccaaggt caccgtccta ggt                                  333
```

<210> SEQ ID NO 70
<211> LENGTH: 750
<212> TYPE: DNA
<213> ORGANISM: Homo sapiens

<400> SEQUENCE: 70

```
gaggtgcagc tggtggagtc cggggggaggt gtggtacggc ctgggggggtc cctgagactc    60
tcctgtgcag cctctggatt cacctttgac gattatggca tgaactgggt ccgccaagct    120
ccagggaagg ggctggagtg ggtctctggt gttaatggga atggtggtac cagagattat    180
gcagcctccg tgaagggccg attcaccatc tccagagaca acgccaagaa ctccctgtat    240
ctgcaaatga acagtctgag agccgaggac acggccttgt attactgtgc gagaggatgg    300
tatagtggga gcttctacta ctttggctac tggggccgag aaccctggt caccgtctcg    360
agtggaggcg gcggttcagg cggaggtggc tctggcggtg gcggaagtgc acaggctgtg    420
ctgactcagc cgtcctccgt gtctgggtct cctggacagt cgatcaccat ctcctgcact    480
ggagccagcg tgacgttgg tgcttataac tttgtctcct ggtaccaaca acacccaggc    540
aaaaccccca aactcataat ttatgatgtc aataagcggc cctcaggggt ttctaatcgc    600
ttctctggct ccaagtctgg caacacggcc tccctgacca tctctgggct ccaggccgag    660
gacgagtctg attattactg cagctcatat acaagcacct tctctgtggt atttggcgga    720
gggaccaagg tcaccgtcct aggtgcggcc                                     750
```

<210> SEQ ID NO 71
<211> LENGTH: 15
<212> TYPE: DNA
<213> ORGANISM: Homo sapiens

<400> SEQUENCE: 71

```
gattatggca tgaac                                                      15
```

<210> SEQ ID NO 72
<211> LENGTH: 51
<212> TYPE: DNA
<213> ORGANISM: Homo sapiens

<400> SEQUENCE: 72

```
ggtgttaatt ggaatggtgg taccagagat tatgcagcct ccgtgaaggg c              51
```

<210> SEQ ID NO 73
<211> LENGTH: 36
<212> TYPE: DNA
<213> ORGANISM: Homo sapiens

<400> SEQUENCE: 73

```
ggatggtata gtgggagctt ctactacttt ggctac                               36
```

<210> SEQ ID NO 74
<211> LENGTH: 42
<212> TYPE: DNA
<213> ORGANISM: Homo sapiens

<400> SEQUENCE: 74

```
actggagcca gcggtgacgt tggtgcttat aactttgtct cc                        42
```

<210> SEQ ID NO 75

<211> LENGTH: 21
<212> TYPE: DNA
<213> ORGANISM: Homo sapiens

<400> SEQUENCE: 75
gatgtcaata agcggccctc a                                                   21

<210> SEQ ID NO 76
<211> LENGTH: 30
<212> TYPE: DNA
<213> ORGANISM: Homo sapiens

<400> SEQUENCE: 76
agctcatata caagcacctt ctctgtggta                                          30

<210> SEQ ID NO 77
<211> LENGTH: 119
<212> TYPE: PRT
<213> ORGANISM: Homo sapiens

<400> SEQUENCE: 77

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 78
<211> LENGTH: 109
<212> TYPE: PRT
<213> ORGANISM: Homo sapiens

<400> SEQUENCE: 78

Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Ser Ser Thr Asp Arg
                85                  90                  95

Pro Leu Phe Gly Gly Gly Thr Lys Leu Thr Val Leu Gly
            100                 105

```
<210> SEQ ID NO 79
<211> LENGTH: 247
<212> TYPE: PRT
<213> ORGANISM: Homo sapiens

<400> SEQUENCE: 79

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Ser Gly Gly Gly
        115                 120                 125

Ser Gly Gly Gly Ser Ala Gln Ser Val Leu Thr Gln Pro Pro Ser
    130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
        195                 200                 205

Ile Ser Arg Val Glu Ala Gly Asp Glu Ala Asp Phe Tyr Cys Gln Val
    210                 215                 220

Trp Asp Ser Ser Thr Asp Arg Pro Leu Phe Gly Gly Thr Lys Leu
225                 230                 235                 240

Thr Val Leu Gly Ala Ala Ala
                245

<210> SEQ ID NO 80
<211> LENGTH: 5
<212> TYPE: PRT
<213> ORGANISM: Homo sapiens

<400> SEQUENCE: 80

Asp Tyr Tyr Ile His
1               5

<210> SEQ ID NO 81
<211> LENGTH: 17
<212> TYPE: PRT
<213> ORGANISM: Homo sapiens

<400> SEQUENCE: 81

Trp Val Asn Pro Asp Thr Gly Gly Thr Arg Tyr Ala Gln Lys Phe Gln
1               5                   10                  15

Gly
```

<210> SEQ ID NO 82
<211> LENGTH: 10
<212> TYPE: PRT
<213> ORGANISM: Homo sapiens

<400> SEQUENCE: 82

Asp Leu Thr Gly Phe Asp Pro Phe Asp Ile
1               5                   10

<210> SEQ ID NO 83
<211> LENGTH: 11
<212> TYPE: PRT
<213> ORGANISM: Homo sapiens

<400> SEQUENCE: 83

Gly Gly Asn Asn Phe Arg Asn Lys Arg Val His
1               5                   10

<210> SEQ ID NO 84
<211> LENGTH: 7
<212> TYPE: PRT
<213> ORGANISM: Homo sapiens

<400> SEQUENCE: 84

Tyr Asp Ser Asp Arg Pro Ser
1               5

<210> SEQ ID NO 85
<211> LENGTH: 11
<212> TYPE: PRT
<213> ORGANISM: Homo sapiens

<400> SEQUENCE: 85

Gln Val Trp Asp Ser Ser Thr Asp Arg Pro Leu
1               5                   10

<210> SEQ ID NO 86
<211> LENGTH: 357
<212> TYPE: DNA
<213> ORGANISM: Homo sapiens

<400> SEQUENCE: 86

```
gaggtgcagc tggtgcagtc tggggctgag gtgaagaagc ctggggcctc agtgaaggtc      60
tcctgtcagg cttctggata caccttcagc gattactata ttcactgggt gcgacagacc     120
cctggacaag gtttgagtg gatgggatgg gtcaaccctg acactggtgg cacaagatac     180
gcgcagaagt ttcagggctg gtcacaatg accagggaca tgtccaacac cacagcctac     240
atggagctgc ccaggctgag agacgacgac acggccgtat attactgtgc gagagatcta     300
actggatttg atccttttga tatctggggc cagggaaccc tggtcaccgt ctcctca        357
```

<210> SEQ ID NO 87
<211> LENGTH: 327
<212> TYPE: DNA
<213> ORGANISM: Homo sapiens

<400> SEQUENCE: 87

```
cagtctgtgc tgactcagcc accctcagtg tcagtggccc caggaaagac ggccacgatt      60
acctgtgggg gaaacaactt tcgaaataaa agagtacact ggtatcagca gaggccaggc     120
caggcccctg tcctggtcat ctattatgat tcagaccggc cctcagggat ccctgagcga     180
```

```
ttctctggct cccgctctgg gaacacggcc accctgacca tcagcagggt cgaggccggg    240
gatgaggccg acttttactg tcaggtgtgg gatagtagta ctgatcgtcc gctgttcggc    300
ggagggacca agctgaccgt cctaggt                                        327
```

<210> SEQ ID NO 88
<211> LENGTH: 741
<212> TYPE: DNA
<213> ORGANISM: Homo sapiens

<400> SEQUENCE: 88

```
gaagtgcagc tggtgcagtc tggggctgag gtgaagaagc ctggggcctc agtgaaggtc     60
tcctgtcagg cttctggata caccttcagc gattactata ttcactgggt gcgacagacc    120
cctggacaag gctttgagtg gatgggatgg gtcaaccctg acactggtgg cacaagatac    180
gcgcagaagt tcagggctgg ggtcaccatg accaggggaca tgtccaacac cacagcctac    240
atggagctgc ccaggctgag agacgacgac acggccgtat attactgtgc gagagatcta    300
actggatttg atccttttga tatctggggc cagggaaccc tggtcaccgt ctcgagtgga    360
ggcggcggtt caggcggagg tggctctggc ggtggcggaa gtgcacagtc tgtgctgact    420
cagccaccct cagtgtcagt ggccccagga aagacggcca cgattacctg tgggggaaac    480
aactttcgaa ataaaagagt acactggtat cagcagaggc caggccaggc ccctgtcctg    540
gtcatctatt atgattcaga ccggccctca gggatccctg agcgattctc tggctcccgc    600
tctgggaaca cggccaccct gaccatcagc agggtcgagg ccggggatga ggccgacttt    660
tactgtcagg tgtgggatag tagtactgat cgtccgctgt tcggcggagg gaccaagctg    720
accgtcctag gtgcggccgc a                                              741
```

<210> SEQ ID NO 89
<211> LENGTH: 15
<212> TYPE: DNA
<213> ORGANISM: Homo sapiens

<400> SEQUENCE: 89

```
gattactata ttcac                                                      15
```

<210> SEQ ID NO 90
<211> LENGTH: 51
<212> TYPE: DNA
<213> ORGANISM: Homo sapiens

<400> SEQUENCE: 90

```
tgggtcaacc ctgacactgg tggcacaaga tacgcgcaga gtttcaggg c               51
```

<210> SEQ ID NO 91
<211> LENGTH: 30
<212> TYPE: DNA
<213> ORGANISM: Homo sapiens

<400> SEQUENCE: 91

```
gatctaactg gatttgatcc ttttgatatc                                      30
```

<210> SEQ ID NO 92
<211> LENGTH: 33
<212> TYPE: DNA
<213> ORGANISM: Homo sapiens

<400> SEQUENCE: 92

```
gggggaaaca actttcgaaa taaaagagta cac                                  33
```

<210> SEQ ID NO 93
<211> LENGTH: 21
<212> TYPE: DNA
<213> ORGANISM: Homo sapiens

<400> SEQUENCE: 93
tatgattcag accggccctc a					21

<210> SEQ ID NO 94
<211> LENGTH: 33
<212> TYPE: DNA
<213> ORGANISM: Homo sapiens

<400> SEQUENCE: 94
caggtgtggg atagtagtac tgatcgtccg ctg					33

<210> SEQ ID NO 95
<211> LENGTH: 121
<212> TYPE: PRT
<213> ORGANISM: Homo sapiens

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Asp Phe Trp Gly Gly Asp Asn Trp Gly
            100                 105                 110

Arg Gly Thr Met Val Thr Val Ser Ser
        115                 120

<210> SEQ ID NO 96
<211> LENGTH: 112
<212> TYPE: PRT
<213> ORGANISM: Homo sapiens

<400> SEQUENCE: 96

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Gln Leu Thr Val Leu Gly
            100                 105                 110

<210> SEQ ID NO 97
<211> LENGTH: 252
<212> TYPE: PRT
<213> ORGANISM: Homo sapiens

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Asn Thr Ala Tyr
65                  70                  75                  80

Met Glu Leu Ser Arg Leu Gly Ser Asp Thr Ala Val Tyr Tyr Cys
                85                  90                  95

Ala Arg Glu Pro Glu Lys Phe Asp Phe Trp Gly Asp Asn Trp Gly
            100                 105                 110

Arg Gly Thr Met Val Thr Val Ser Ser Gly Gly Gly Ser Gly Gly
            115                 120                 125

Gly Gly Ser Gly Gly Gly Ser Ala Gln Ala Val Leu Thr Gln Pro
        130                 135                 140

Ser Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Gly Tyr Val Phe Gly
225                 230                 235                 240

Thr Gly Thr Gln Leu Thr Val Leu Ser Ala Ala Ala
            245                 250

<210> SEQ ID NO 98
<211> LENGTH: 5
<212> TYPE: PRT
<213> ORGANISM: Homo sapiens

<400> SEQUENCE: 98

Asp Tyr Tyr Met His
1               5

<210> SEQ ID NO 99
<211> LENGTH: 17
<212> TYPE: PRT
<213> ORGANISM: Homo sapiens

<400> SEQUENCE: 99

Trp Ile Asn Pro Tyr Thr Gly Gly Ala Phe Tyr Ala Gln Lys Phe Arg 1               5                   10                  15

Gly

<210> SEQ ID NO 100
<211> LENGTH: 12
<212> TYPE: PRT
<213> ORGANISM: Homo sapiens

<400> SEQUENCE: 100

Glu Pro Glu Lys Phe Asp Phe Trp Gly Gly Asp Asn
1               5                   10

<210> SEQ ID NO 101
<211> LENGTH: 14
<212> TYPE: PRT
<213> ORGANISM: Homo sapiens

<400> SEQUENCE: 101

Thr Gly Ser Ser Ser Asn Ile Gly Ala Gly Tyr Gly Val His
1               5                   10

<210> SEQ ID NO 102
<211> LENGTH: 7
<212> TYPE: PRT
<213> ORGANISM: Homo sapiens

<400> SEQUENCE: 102

Gly Asn Ser Asn Arg Pro Ser
1               5

<210> SEQ ID NO 103
<211> LENGTH: 11
<212> TYPE: PRT
<213> ORGANISM: Homo sapiens

<400> SEQUENCE: 103

Gln Ser Tyr Asp Ser Ser Leu Ser Gly Tyr Val
1               5                   10

<210> SEQ ID NO 104
<211> LENGTH: 363
<212> TYPE: DNA
<213> ORGANISM: Homo sapiens

<400> SEQUENCE: 104
caggtccagc tggtgcagtc tggggctgag gtgaagaagc ctggggcctc agtgaaggtc      60
tcctgcaagg cttctggata caccttcacc gactactata tgcactgggt gcgacaggcc     120
cctggacaag gcttgagtg gtgggatgg atcaacccctt atactggtgg cgcattctat     180
gcacagaagt ttcggggcag ggtcacaatg accagggaca cgtccatcaa cacagcctac     240
atggagctga gcagactggg atctgacgac acgccgtgt attattgtgc gagagaacct     300
gaaaaattcg attttggggg ggtgacaac tggggccggg gacaatggt caccgtctcc     360
tca                                                                  363

<210> SEQ ID NO 105
<211> LENGTH: 336
<212> TYPE: DNA
<213> ORGANISM: Homo sapiens

<400> SEQUENCE: 105
caggctgtgc tgactcagcc gtcctcagtg tctggggccc cagggcagag ggtcaccatc      60

```
tcctgcactg ggagcagctc caacatcggg gcaggttatg gtgtacactg gtaccaacag    120
cttccaggaa cagcccccaa actcctcatc tatggtaaca gcaatcggcc ctcagggtc    180 cctgaccgat tctctggctc caagtctggc acctcagcct ccctggccat cactgggctc    240
caggctgagg atgaggctga ttattactgc cagtcctatg acagcagcct gagtggttat    300
gtcttcggaa ctgggaccca gctcaccgtc ctaggt                              336
```

<210> SEQ ID NO 106
<211> LENGTH: 756
<212> TYPE: DNA
<213> ORGANISM: Homo sapiens

<400> SEQUENCE: 106

```
caggtccagc tggtgcagtc tggggctgag gtgaagaagc ctggggcctc agtgaaggtc     60
tcctgcaagg cttctggata caccttcacc gactactata tgcactgggt gcgacaggcc    120
cctggacaag gcttgagtg gtgggatgg atcaaccctt atactggtgg cgcattctat    180
gcacagaagt tcggggcag ggtcaccatg accagggaca cgtccatcaa cacagcctac    240
atggagctga gcagactggg atctgacgac acggccgtgt attattgtgc gagagaacct    300
gaaaaattcg attttggggg ggtgacaac tggggccggg gacaatggt caccgtctcg    360 agtggaggcg cgcggttcag cggaggtggc tctggcggtg gcggaagtgc acaggctgtg    420
ctgactcagc cgtcctcagt gtctggggcc ccagggcaga gggtcaccat ctcctgcact    480
gggagcagct ccaacatcgg ggcaggttat ggtgtacact ggtaccaaca gcttccagga    540
acagccccca aactcctcat ctatggtaac agcaatcggc cctcagggt ccctgaccga    600 ttctctggct ccaagtctgg cacctcagcc tccctggcca tcactgggct ccaggctgag    660
gatgaggctg attattactg ccagtcctat gacagcagcc tgagtggtta tgtcttcgga    720
actgggaccc agctcaccgt tttaagtgcg gccgca                              756
```

<210> SEQ ID NO 107
<211> LENGTH: 15
<212> TYPE: DNA
<213> ORGANISM: Homo sapiens

<400> SEQUENCE: 107

```
gactactata tgcac                                                      15
```

<210> SEQ ID NO 108
<211> LENGTH: 51
<212> TYPE: DNA
<213> ORGANISM: Homo sapiens

<400> SEQUENCE: 108

```
tggatcaacc cttatactgg tggcgcattc tatgcacaga agtttcgggg c              51
```

<210> SEQ ID NO 109
<211> LENGTH: 36
<212> TYPE: DNA
<213> ORGANISM: Homo sapiens

<400> SEQUENCE: 109

```
gaacctgaaa aattcgattt tggggggt gacaac                                36
```

<210> SEQ ID NO 110
<211> LENGTH: 42
<212> TYPE: DNA

<213> ORGANISM: Homo sapiens

<400> SEQUENCE: 110
actgggagca gctccaacat cggggcaggt tatggtgtac ac              42

<210> SEQ ID NO 111
<211> LENGTH: 21
<212> TYPE: DNA
<213> ORGANISM: Homo sapiens

<400> SEQUENCE: 111
ggtaacagca atcggccctc a                                     21

<210> SEQ ID NO 112
<211> LENGTH: 33
<212> TYPE: DNA
<213> ORGANISM: Homo sapiens

<400> SEQUENCE: 112
cagtcctatg acagcagcct gagtggttat gtc                        33

<210> SEQ ID NO 113
<211> LENGTH: 119
<212> TYPE: PRT
<213> ORGANISM: Homo sapiens

<400> SEQUENCE: 113

Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Arg Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Ile Thr Ile Ser Arg Asp Asn Ala Lys Asn Ser Leu Tyr
65                  70                  75                  80

Leu Gln Met Ser Ser Leu Arg Ser Glu Asp Thr Ala Val Tyr Tyr Cys
                85                  90                  95

Ala Arg Gly Leu Trp Val Trp Asp Pro Leu Asp Tyr Trp Gly Arg Gly
            100                 105                 110

Thr Leu Val Thr Val Ser Ser
        115

<210> SEQ ID NO 114
<211> LENGTH: 108
<212> TYPE: PRT
<213> ORGANISM: Homo sapiens

<400> SEQUENCE: 114

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Phe Gly Thr Asp Phe Thr Leu Thr Ile Ser Ser Leu Gln Pro

```
                65                  70                  75                  80
Asp Asp Phe Ala Thr Tyr Tyr Cys Gln Gln Tyr Ser Glu Phe Ala Trp
                    85                  90                  95

Thr Phe Gly Gly Gly Thr Lys Leu Glu Ile Lys Arg
                100                 105

<210> SEQ ID NO 115
<211> LENGTH: 246
<212> TYPE: PRT
<213> ORGANISM: Homo sapiens

<400> SEQUENCE: 115

Glu Val Gln Leu Val Glu Ser Gly Gly Gly Leu Val Thr Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Val Arg Gln Ala Pro Gly Arg Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Ile Thr Ile Ser Arg Asp Asn Ala Lys Asn Ser Leu Tyr
65                  70                  75                  80

Leu Gln Met Ser Ser Leu Arg Ser Glu Asp Thr Ala Val Tyr Tyr Cys
                85                  90                  95

Ala Arg Gly Leu Trp Val Trp Asp Pro Leu Asp Tyr Trp Gly Arg Gly
                100                 105                 110

Thr Leu Val Thr Val Ser Ser Gly Gly Gly Gly Ser Gly Gly Gly Gly
            115                 120                 125

Ser Gly Gly Gly Gly Ser Asp Ile Gln Met Thr Gln Ser Pro Ser Thr
        130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
                180                 185                 190

Pro Ser Arg Phe Ser Gly Ser Gly Phe Gly Thr Asp Phe Thr Leu Thr
            195                 200                 205

Ile Ser Ser Leu Gln Pro Asp Asp Phe Ala Thr Tyr Tyr Cys Gln Gln
        210                 215                 220

Tyr Ser Glu Phe Ala Trp Thr Phe Gly Gly Gly Thr Lys Leu Glu Ile
225                 230                 235                 240

Lys Arg Ala Ala Ala His
                245

<210> SEQ ID NO 116
<211> LENGTH: 5
<212> TYPE: PRT
<213> ORGANISM: Homo sapiens

<400> SEQUENCE: 116

Asp Tyr Tyr Met Ser
1               5

<210> SEQ ID NO 117
<211> LENGTH: 17
<212> TYPE: PRT
```

<210> SEQ ID NO 117
<211> LENGTH: (not shown)
<212> TYPE: PRT
<213> ORGANISM: Homo sapiens

<400> SEQUENCE: 117

Ala Ile Ser Gly Ser Gly Gly Ser Thr Tyr Tyr Ala Asp Ser Val Lys
1               5                   10                  15
Gly

<210> SEQ ID NO 118
<211> LENGTH: 10
<212> TYPE: PRT
<213> ORGANISM: Homo sapiens

<400> SEQUENCE: 118

Gly Leu Trp Val Trp Asp Pro Leu Asp Tyr
1               5                   10

<210> SEQ ID NO 119
<211> LENGTH: 11
<212> TYPE: PRT
<213> ORGANISM: Homo sapiens

<400> SEQUENCE: 119

Arg Ala Ser Glu Gly Ile Tyr His Trp Leu Ala
1               5                   10

<210> SEQ ID NO 120
<211> LENGTH: 7
<212> TYPE: PRT
<213> ORGANISM: Homo sapiens

<400> SEQUENCE: 120

Lys Ala Ser Ser Leu Ala Ser
1               5

<210> SEQ ID NO 121
<211> LENGTH: 9
<212> TYPE: PRT
<213> ORGANISM: Homo sapiens

<400> SEQUENCE: 121

Gln Gln Tyr Ser Glu Phe Ala Trp Thr
1               5

<210> SEQ ID NO 122
<211> LENGTH: 357
<212> TYPE: DNA
<213> ORGANISM: Homo sapiens

<400> SEQUENCE: 122

```
gaggtgcagc tggtggagtc tgggggaggc ttggtcacgc ctggagggtc cctgagactc      60
tcctgtgcag cctctggatt caccttcagt gactactaca tgagctgggt ccgccaggct     120
ccagggaggg gctggagtg gtctcagct attagtggta gtggtggtag cacatactac      180
gcagactccg tgaagggccg gatcaccatc tccagagaca acgccaagaa ctcactgtat     240
ctgcaaatga gcagcctgag atctgaggac acggccgtgt attactgtgc gagagggctt     300
tgggtttggg atcctcttga ctactggggc agaggaaccc tggtcaccgt ctcctca        357
```

<210> SEQ ID NO 123
<211> LENGTH: 324
<212> TYPE: DNA
<213> ORGANISM: Homo sapiens

```
<400> SEQUENCE: 123
gacatccaga tgacccagtc tccttccacc ctgtctgcat ctattggaga cagagtcacc    60
atcacctgcc gggccagtga gggtatttat cactggttgg cctggtatca gcagaagcca   120
gggaaagccc ctaaactcct gatctataag gcctctagtt tagccagtgg ggccccatca   180
aggttcagcg gcagtggatt tgggaccgat ttcactctca ccatcagcag cctgcagcct   240
gatgattttg caacttatta ctgccaacaa tacagcgagt tcgcctggac cttcggcgga   300
gggaccaagc tggagatcaa acgt                                          324

<210> SEQ ID NO 124
<211> LENGTH: 738
<212> TYPE: DNA
<213> ORGANISM: Homo sapiens

<400> SEQUENCE: 124
gaggtgcagc tggtggagtc tgggggaggc ttggtcacgc ctggagggtc cctgagactc    60
tcctgtgcag cctctggatt caccttcagt gactactaca tgagctgggt ccgccaggct   120
ccagggaggg gctggagtg gtctcagct attagtggta gtggtggtag cacatactac   180
gcagactccg tgaagggccg gatcaccatc tccagagaca cgccaagaa ctcactgtat   240 ctgcaaatga gcagcctgag atctgaggac acggccgtgt attactgtgc gagagggctt   300
tgggtttggg atcctcttga ctactggggc agaggaaccc tggtcaccgt ctcttcaggt   360 ggggcggtt caggcggagg tggcagcggc ggtggcggat cggacatcca gatgacccag   420
tccccttcca ccctgtctgc atctattgga gacagagtca ccatcacctg ccgggccagt   480
gagggtattt atcactggtt ggcctggtat cagcagaagc cagggaaagc ccctaaactc   540
ctgatctata aggcctctag tttagccagt gggcccccat caaggttcag cggcagtgga   600
tttgggacag atttcactct caccatcagc agcctgcagc ctgatgattt tgcaacttat   660
tactgccaac aatacagcga gttcgcctgg accttcggcg gagggaccaa gctggagatc   720
aaacgtgcgg ccgcacat                                                 738

<210> SEQ ID NO 125
<211> LENGTH: 15
<212> TYPE: DNA
<213> ORGANISM: Homo sapiens

<400> SEQUENCE: 125
gactactaca tgagc                                                    15

<210> SEQ ID NO 126
<211> LENGTH: 51
<212> TYPE: DNA
<213> ORGANISM: Homo sapiens

<400> SEQUENCE: 126
gctattagtg gtagtggtgg tagcacatac tacgcagact ccgtgaaggg c             51

<210> SEQ ID NO 127
<211> LENGTH: 30
<212> TYPE: DNA
<213> ORGANISM: Homo sapiens

<400> SEQUENCE: 127
gggctttggg tttgggatcc tcttgactac                                    30
```

-continued

```
<210> SEQ ID NO 128
<211> LENGTH: 33
<212> TYPE: DNA
<213> ORGANISM: Homo sapiens

<400> SEQUENCE: 128
cgggccagtg agggtattta tcactggttg gcc                              33

<210> SEQ ID NO 129
<211> LENGTH: 21
<212> TYPE: DNA
<213> ORGANISM: Homo sapiens

<400> SEQUENCE: 129
aaggcctcta gtttagccag t                                           21

<210> SEQ ID NO 130
<211> LENGTH: 27
<212> TYPE: DNA
<213> ORGANISM: Homo sapiens

<400> SEQUENCE: 130
caacaataca gcgagttcgc ctggacc                                     27

<210> SEQ ID NO 131
<211> LENGTH: 119
<212> TYPE: PRT
<213> ORGANISM: Homo sapiens

<400> SEQUENCE: 131
```

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Val Ser Ala Tyr Thr Gly Asn Thr Asn Tyr Ala Gln Lys Phe
        50                  55                  60

Gln Gly Arg Val Thr Met Thr Thr Asp Thr Ser Thr Ser Thr Ala Tyr
65                  70                  75                  80

Met Glu Leu Arg Gly Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
                100                 105                 110

Thr Leu Val Thr Val Ser Ser
        115

```
<210> SEQ ID NO 132
<211> LENGTH: 108
<212> TYPE: PRT
<213> ORGANISM: Homo sapiens

<400> SEQUENCE: 132
```

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Ala Ser Gly Ala Pro Ser Arg Phe Ser Gly

```
                    50                  55                  60
Ser Gly Phe Gly Thr Asp Phe Thr Leu Thr Ile Ser Ser Leu Gln Pro
 65                  70                  75                  80

Asp Asp Phe Ala Thr Tyr Tyr Cys Gln Gln Met Gly Glu Tyr Asn Ala
                 85                  90                  95

Thr Ile Gly Gly Gly Thr Lys Leu Glu Ile Lys Arg
            100                 105
```

<210> SEQ ID NO 133
<211> LENGTH: 246
<212> TYPE: PRT
<213> ORGANISM: Homo sapiens

<400> SEQUENCE: 133

```
Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Val Ser Ala Tyr Thr Gly Asn Thr Asn Tyr Ala Gln Lys Phe
 50                  55                  60

Gln Gly Arg Val Thr Met Thr Thr Asp Thr Ser Thr Ser Thr Ala Tyr
 65                  70                  75                  80

Met Glu Leu Arg Gly Leu Arg Ser Asp Asp Thr Ala Val Tyr Tyr Cys
                 85                  90                  95

Ala Arg Asp Arg Gly Tyr Tyr Asp Ala Tyr Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Asp Ile Gln Met Thr Gln Ser Pro Ser Thr
130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
            180                 185                 190

Pro Ser Arg Phe Ser Gly Ser Gly Phe Gly Thr Asp Phe Thr Leu Thr
        195                 200                 205

Ile Ser Ser Leu Gln Pro Asp Asp Phe Ala Thr Tyr Tyr Cys Gln Gln
210                 215                 220

Met Gly Glu Tyr Asn Ala Thr Ile Gly Gly Gly Thr Lys Leu Glu Ile
225                 230                 235                 240

Lys Arg Ala Ala Ala His
                245
```

<210> SEQ ID NO 134
<211> LENGTH: 5
<212> TYPE: PRT
<213> ORGANISM: Homo sapiens

<400> SEQUENCE: 134

```
Ser Tyr Gly Ile Ser
  1               5
```

<210> SEQ ID NO 135
<211> LENGTH: 17
<212> TYPE: PRT
<213> ORGANISM: Homo sapiens

<400> SEQUENCE: 135

Trp Val Ser Ala Tyr Thr Gly Asn Thr Asn Tyr Ala Gln Lys Phe Gln
1               5                   10                  15
Gly

<210> SEQ ID NO 136
<211> LENGTH: 10
<212> TYPE: PRT
<213> ORGANISM: Homo sapiens

<400> SEQUENCE: 136

Asp Arg Gly Tyr Tyr Asp Ala Phe Asp Ile
1               5                   10

<210> SEQ ID NO 137
<211> LENGTH: 11
<212> TYPE: PRT
<213> ORGANISM: Homo sapiens

<400> SEQUENCE: 137

Arg Ala Ser Glu Gly Ile Tyr His Trp Leu Ala
1               5                   10

<210> SEQ ID NO 138
<211> LENGTH: 7
<212> TYPE: PRT
<213> ORGANISM: Homo sapiens

<400> SEQUENCE: 138

Lys Ala Ser Ser Leu Ala Ser
1               5

<210> SEQ ID NO 139
<211> LENGTH: 9
<212> TYPE: PRT
<213> ORGANISM: Homo sapiens

<400> SEQUENCE: 139

Gln Gln Met Gly Glu Tyr Asn Ala Thr
1               5

<210> SEQ ID NO 140
<211> LENGTH: 357
<212> TYPE: DNA
<213> ORGANISM: Homo sapiens

<400> SEQUENCE: 140
caggtgcagc tggtggagtc tggggctgag gtgaagaagc ctggggcctc agtgaaggtc      60
tcctgcaagg cttctggtta caccttacc agttatggta tcagctgggt gcgacaggcc     120
cctggacaag gcttgagtg gatgggatgg gtcagcgctt acactggtaa cacaaactat     180
gcacagaagt tccagggcag agtcaccatg accacagaca catccacgag cacagcctac     240
atggaactga ggggcctgag atctgacgac acggccgtgt attactgtgc gagagatcgt     300
ggatactatg atgctttga tatctggggc caaggcaccc tggtcaccgt ctcctca        357

<210> SEQ ID NO 141
<211> LENGTH: 324

<212> TYPE: DNA
<213> ORGANISM: Homo sapiens

<400> SEQUENCE: 141

```
gacatccaga tgacccagtc tccttccacc ctgtctgcat ctattggaga cagagtcacc    60
atcacctgcc gggccagtga gggtatttat cactggttgg cctggtatca gcagaagcca   120
gggaaagccc ctaaactcct gatctataag gcctctagtt tagccagtgg ggccccatca   180
aggttcagcg gcagtggatt tgggacagat ttcactctca ccatcagcag cctgcagcct   240
gatgattttg caacttatta ctgccaacaa atgggcgagt acaacgccac catcggcgga   300
gggaccaagc tggagatcaa acgt                                          324
```

<210> SEQ ID NO 142
<211> LENGTH: 738
<212> TYPE: DNA
<213> ORGANISM: Homo sapiens

<400> SEQUENCE: 142

```
caggtgcagc tggtggagtc tggggctgag gtgaagaagc ctggggcctc agtgaaggtc    60
tcctgcaagg cttctggtta cacctttacc agttatggta tcagctgggt gcgacaggcc   120
cctggacaag gcttgagtg gatgggatgg gtcagcgctt acactggtaa cacaaactat   180
gcacagaagt tccagggcag agtcaccatg accacagaca catccacgag cacagcctac   240
atggaactga ggggcctgag atctgacgac acggccgtgt attactgtgc gagagatcgt   300
ggatactatg atgcttatga tatctggggc caaggcaccc tggtcaccgt ctcctcaggt   360
ggaggcggtt caggcggagg tggcagcggc ggtggcggat cggacatcca gatgacccag   420
tctccttcca ccctgtctgc atctattgga gacagagtca ccatcacctg ccgggccagt   480
gagggtattt atcactggtt ggcctggtat cagcagaagc cagggaaagc ccctaaactc   540
ctgatctata aggcctctag tttagccagt ggggccccat caaggttcag cggcagtgga   600
tttgggacag atttcactct caccatcagc agcctgcagc ctgatgattt tgcaacttat   660
tactgccaac aaatgggcga gtacaacgcc accatcggcg agggaccaa gctggagatc   720
aaacgtgcgg ccgcacat                                                 738
```

<210> SEQ ID NO 143
<211> LENGTH: 15
<212> TYPE: DNA
<213> ORGANISM: Homo sapiens

<400> SEQUENCE: 143

```
agttatggta tcagc                                                    15
```

<210> SEQ ID NO 144
<211> LENGTH: 51
<212> TYPE: DNA
<213> ORGANISM: Homo sapiens

<400> SEQUENCE: 144

```
tgggtcagcg cttacactgg taacacaaac tatgcacaga agttccaggg c            51
```

<210> SEQ ID NO 145
<211> LENGTH: 30
<212> TYPE: DNA
<213> ORGANISM: Homo sapiens

<400> SEQUENCE: 145

```
gatcgtggat actatgatgc ttttgatatc                                      30
```

```
<210> SEQ ID NO 146
<211> LENGTH: 33
<212> TYPE: DNA
<213> ORGANISM: Homo sapiens

<400> SEQUENCE: 146
cgggccagtg agggtattta tcactggttg gcc                                  33

<210> SEQ ID NO 147
<211> LENGTH: 21
<212> TYPE: DNA
<213> ORGANISM: Homo sapiens

<400> SEQUENCE: 147
aaggcctcta gtttagccag t                                               21

<210> SEQ ID NO 148
<211> LENGTH: 27
<212> TYPE: DNA
<213> ORGANISM: Homo sapiens

<400> SEQUENCE: 148
caacaaatgg gcgagtacaa cgccacc                                         27

<210> SEQ ID NO 149
<211> LENGTH: 119
<212> TYPE: PRT
<213> ORGANISM: Homo sapiens

<400> SEQUENCE: 149
```

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser
        115

```
<210> SEQ ID NO 150
<211> LENGTH: 108
<212> TYPE: PRT
<213> ORGANISM: Homo sapiens

<400> SEQUENCE: 150
```

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile

```
                35                  40                  45
Tyr Lys Ala Ser Ser Leu Ala Ser Gly Ala Pro Ser Arg Phe Ser Gly
 50                  55                  60

Ser Gly Phe Gly Thr Asp Phe Thr Leu Thr Ile Ser Ser Leu Gln Pro
 65                  70                  75                  80

Asp Asp Phe Ala Thr Tyr Tyr Cys Gln Gln Met Gly Glu Trp Lys Ala
                 85                  90                  95

Ala Phe Gly Gly Gly Thr Lys Leu Glu Ile Lys Arg
                100                 105
```

<210> SEQ ID NO 151
<211> LENGTH: 246
<212> TYPE: PRT
<213> ORGANISM: Homo sapiens

<400> SEQUENCE: 151

```
Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
                 35                  40                  45

Gly Trp Ile Ser Ala Tyr Thr Gly Asn Thr Asn Tyr Ala Gln Lys Phe
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Arg Gly Tyr Tyr Asp Ala Phe Asp Ile Trp Gly Gln Gly
                100                 105                 110

Thr Leu Val Thr Val Ser Ser Gly Gly Gly Ser Gly Gly Gly Gly
                115                 120                 125

Ser Gly Gly Gly Gly Ser Asp Ile Gln Met Thr Gln Ser Pro Ser Thr
130                 135                 140

Leu Ser Ala Ser Ile Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Ala
                180                 185                 190

Pro Ser Arg Phe Ser Gly Ser Gly Phe Gly Thr Asp Phe Thr Leu Thr
                195                 200                 205

Ile Ser Ser Leu Gln Pro Asp Asp Phe Ala Thr Tyr Tyr Cys Gln Gln
                210                 215                 220

Met Gly Glu Trp Lys Ala Ala Phe Gly Gly Gly Thr Lys Leu Glu Ile
225                 230                 235                 240

Lys Arg Ala Ala Ala His
                245
```

<210> SEQ ID NO 152
<211> LENGTH: 5
<212> TYPE: PRT
<213> ORGANISM: Homo sapiens

<400> SEQUENCE: 152

Ser Tyr Gly Ile Ser

```
<210> SEQ ID NO 153
<211> LENGTH: 17
<212> TYPE: PRT
<213> ORGANISM: Homo sapiens

<400> SEQUENCE: 153

Trp Ile Ser Ala Tyr Thr Gly Asn Thr Asn Tyr Ala Gln Lys Phe Gln
1               5                   10                  15
Gly

<210> SEQ ID NO 154
<211> LENGTH: 10
<212> TYPE: PRT
<213> ORGANISM: Homo sapiens

<400> SEQUENCE: 154

Asp Arg Gly Tyr Tyr Asp Ala Phe Asp Ile
1               5                   10

<210> SEQ ID NO 155
<211> LENGTH: 11
<212> TYPE: PRT
<213> ORGANISM: Homo sapiens

<400> SEQUENCE: 155

Arg Ala Ser Glu Gly Ile Tyr His Trp Leu Ala
1               5                   10

<210> SEQ ID NO 156
<211> LENGTH: 7
<212> TYPE: PRT
<213> ORGANISM: Homo sapiens

<400> SEQUENCE: 156

Lys Ala Ser Ser Leu Ala Ser
1               5

<210> SEQ ID NO 157
<211> LENGTH: 9
<212> TYPE: PRT
<213> ORGANISM: Homo sapiens

<400> SEQUENCE: 157

Gln Gln Met Gly Glu Trp Lys Ala Ala
1               5

<210> SEQ ID NO 158
<211> LENGTH: 357
<212> TYPE: DNA
<213> ORGANISM: Homo sapiens

<400> SEQUENCE: 158
caggtgcagc tggtggagtc tggagctgag gtgaagaagc ctggggcctc agtgaaggtc      60
tcctgcaagg cttctggtta ccctttacc agttatggta tcagctgggt gcgacaggcc     120
cctggacaag gcttgagtg gatgggatgg atcagcgctt acactggtaa cacaaactat     180
gcacagaagt tccagggcag agtcaccatg accacagaca catccacgag cacagcctac    240
atggaactga ggagcctgag atctgacgac acggccgtgt attactgtgc gagagatcgt    300
ggatactatg atgctttcga tatctggggc caaggcaccc tggtcaccgt ctcctca       357
```

<210> SEQ ID NO 159
<211> LENGTH: 324
<212> TYPE: DNA
<213> ORGANISM: Homo sapiens

<400> SEQUENCE: 159

```
gacatccaga tgacccagtc tccttccacc ctgtctgcat ctattggaga cagagtcacc      60
atcacctgcc gggccagtga gggtatttat cactggttgg cctggtatca gcagaagcca     120
gggaaagccc ctaaactcct gatctataag gcctctagtt tagccagtgg ggccccatca     180
aggttcagcg gcagtggatt tgggacagat ttcactctca ccatcagcag cctgcagcct     240
gatgattttg caacttatta ctgccaacaa atgggggagt ggaaggcggc cttcggcgga     300
gggaccaagc tggagatcaa acgt                                            324
```

<210> SEQ ID NO 160
<211> LENGTH: 738
<212> TYPE: DNA
<213> ORGANISM: Homo sapiens

<400> SEQUENCE: 160

```
caggtgcagc tggtggagtc tggagctgag gtgaagaagc ctggggcctc agtgaaggtc      60
tcctgcaagg cttctggtta ccctttacc agttatggta tcagctgggt gcgacaggcc     120
cctggacaag gcttgagtg gatgggatgg atcagcgctt acactggtaa cacaaactat     180
gcacagaagt tccagggcag agtcaccatg accacagaca catccacgag cacagcctac     240
atggaactga ggagcctgag atctgacgac acggccgtgt attactgtgc gagagatcgt     300
ggatactatg atgctttcga tatctggggc caaggcaccc tggtcaccgt ctcctcaggt     360
gggggcggtt caggcggagg tggcagcggc ggtggcggat cggacatcca gatgacccag     420
tctccttcca ccctgtctgc atcattggga cagagtca ccatcacctg ccgggccagt     480
gagggtattt atcactggtt ggcctggtat cagcagaagc cagggaaagc ccctaaactc     540
ctgatctata aggcctctag tttagccagt ggggccccat caaggttcag cggcagtgga     600
tttgggacag atttcactct caccatcagc agcctgcagc ctgatgattt tgcaacttat     660
tactgccaac aaatggggga gtggaaggcg gccttcggcg gagggaccaa gctggagatc     720
aaacgtgcgg ccgcacat                                                   738
```

<210> SEQ ID NO 161
<211> LENGTH: 15
<212> TYPE: DNA
<213> ORGANISM: Homo sapiens

<400> SEQUENCE: 161

```
agttatggta tcagc                                                       15
```

<210> SEQ ID NO 162
<211> LENGTH: 51
<212> TYPE: DNA
<213> ORGANISM: Homo sapiens

<400> SEQUENCE: 162

```
tggatcagcg cttacactgg taacacaaac tatgcacaga gttccaggg c                51
```

<210> SEQ ID NO 163
<211> LENGTH: 30
<212> TYPE: DNA
<213> ORGANISM: Homo sapiens
```

<400> SEQUENCE: 163
gatcgtggat actatgatgc tttcgatatc                                    30

<210> SEQ ID NO 164
<211> LENGTH: 33
<212> TYPE: DNA
<213> ORGANISM: Homo sapiens

<400> SEQUENCE: 164
cgggccagtg agggtattta tcactggttg gcc                                33

<210> SEQ ID NO 165
<211> LENGTH: 21
<212> TYPE: DNA
<213> ORGANISM: Homo sapiens

<400> SEQUENCE: 165
aaggcctcta gtttagccag t                                             21

<210> SEQ ID NO 166
<211> LENGTH: 27
<212> TYPE: DNA
<213> ORGANISM: Homo sapiens

<400> SEQUENCE: 166
caacaaatgg gggagtggaa ggcggcc                                       27

<210> SEQ ID NO 167
<211> LENGTH: 5
<212> TYPE: PRT
<213> ORGANISM: Homo sapiens

<400> SEQUENCE: 167

Asp Tyr Gly Met Asn
1               5

<210> SEQ ID NO 168
<211> LENGTH: 111
<212> TYPE: PRT
<213> ORGANISM: Homo sapiens

<400> SEQUENCE: 168

Gln Ala Val Leu Thr Gln Pro Ser Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Thr Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Ser Asn Thr Ala Ser Leu Thr Ile Ser Gly Leu
65                  70                  75                  80

Gln Ala Glu Asp Glu Ser Asp Tyr Tyr Cys Ser Ser Tyr Thr Ser Thr
                85                  90                  95

Phe Ser Val Val Phe Gly Gly Gly Thr Lys Val Thr Val Leu Gly
            100                 105                 110

<210> SEQ ID NO 169
<211> LENGTH: 252
<212> TYPE: PRT

<213> ORGANISM: Homo sapiens

<400> SEQUENCE: 169

Glu Val Gln Leu Val Glu Ser Gly Gly Val Val Arg Pro Gly
1               5                   10                  15
Gly

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
            35                  40                  45

Ser Gly Val Asn Trp Asn Gly Gly Thr Arg Asp Tyr Ala Ala Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Gly Gly Gly Ser Gly Gly
            115                 120                 125

Gly Gly Ser Gly Gly Gly Ser Ala Gln Ala Val Leu Thr Gln Pro
        130                 135                 140

Ser Ser Val Ser Gly Ser Pro Gly Gln Ser Ile Thr Ile Ser Cys Thr
145                 150                 155                 160

Gly Ala Ser Gly Asp Val Gly Ala Tyr Asn Phe Val Ser Trp Tyr Gln
                165                 170                 175

Gln His Pro Gly Lys Thr Pro Lys Leu Ile Ile Tyr Asp Val Asn Lys
            180                 185                 190

Arg Pro Ser Gly Val Ser Asn Arg Phe Ser Gly Ser Lys Ser Ser Asn
        195                 200                 205

Thr Ala Ser Leu Thr Ile Ser Gly Leu Gln Ala Glu Asp Glu Ser Asp
210                 215                 220

Tyr Tyr Cys Ser Ser Tyr Thr Ser Thr Phe Ser Val Val Phe Gly Gly
225                 230                 235                 240

Gly Thr Lys Val Thr Val Leu Gly Ala Ala Ala His
            245                 250

<210> SEQ ID NO 170
<211> LENGTH: 5
<212> TYPE: PRT
<213> ORGANISM: Homo sapiens

<400> SEQUENCE: 170

Asp Tyr Gly Met Asn
1               5

<210> SEQ ID NO 171
<211> LENGTH: 17
<212> TYPE: PRT
<213> ORGANISM: Homo sapiens

<400> SEQUENCE: 171

Gly Val Asn Trp Asn Gly Gly Thr Arg Asp Tyr Ala Ala Ser Val Lys
1               5                   10                  15
Gly

<210> SEQ ID NO 172
<211> LENGTH: 12

```
<212> TYPE: PRT
<213> ORGANISM: Homo sapiens

<400> SEQUENCE: 172

Gly Trp Tyr Ser Gly Ala Ala Trp Asn Met Gly Tyr
1               5                   10

<210> SEQ ID NO 173
<211> LENGTH: 14
<212> TYPE: PRT
<213> ORGANISM: Homo sapiens

<400> SEQUENCE: 173

Thr Gly Ala Ser Gly Asp Val Gly Ala Tyr Asn Phe Val Ser
1               5                   10

<210> SEQ ID NO 174
<211> LENGTH: 7
<212> TYPE: PRT
<213> ORGANISM: Homo sapiens

<400> SEQUENCE: 174

Asp Val Asn Lys Arg Pro Ser
1               5

<210> SEQ ID NO 175
<211> LENGTH: 10
<212> TYPE: PRT
<213> ORGANISM: Homo sapiens

<400> SEQUENCE: 175

Ser Ser Tyr Thr Ser Thr Phe Ser Val Val
1               5                   10

<210> SEQ ID NO 176
<211> LENGTH: 363
<212> TYPE: DNA
<213> ORGANISM: Homo sapiens

<400> SEQUENCE: 176
gaggtgcagc tggtggagtc cggggggaggt gtggtacggc ctgggggggtc cctgagactc    60 tcctgtgcag cctctggatt cacctttgac gattatggca tgaactgggt ccgccaagct   120
ccagggaagg ggctggagtg gtctctggt gttaattgga atggtggtac cagagattat   180
gcagcctccg tgaagggccg attcaccatc tccagagaca cgccaagaa ctccctgtat   240 ctgcaaatga acagtctgag agccgaggac acggccttgt attactgtgc gagaggatgg   300
tatagtgggg ccgcgtggaa catgggctac tggggccgag aaccctggt caccgtctcc   360 tca                                                                  363

<210> SEQ ID NO 177
<211> LENGTH: 333
<212> TYPE: DNA
<213> ORGANISM: Homo sapiens

<400> SEQUENCE: 177
caggctgtgc tgactcagcc gtcctccgtg tctgggtctc ctggacagtc gatcaccatc    60
tcctgcactg gagccagcgg tgacgttggt gcttataact ttgtctcctg gtaccaacaa   120
cacccaggca aaccccccaa actcataatt tatgatgtca ataagcggcc ctcaggggtt   180
tctaatcgct tctctggctc caagtctagc aacacggcct ccctgaccat ctctgggctc   240
```

```
caggccgagg acgagtctga ttattactgc agctcatata caagcacctt ctctgtggta    300
tttggcggag ggaccaaggt caccgtccta ggt                                  333

<210> SEQ ID NO 178
<211> LENGTH: 757
<212> TYPE: DNA
<213> ORGANISM: Homo sapiens

<400> SEQUENCE: 178
cgaggtgcag ctggtggagt ccggggggagg tgtggtacgg cctgggggggt ccctgagact    60 ctcctgtgca gcctctggat tcacctttga cgattatggc atgaactggg tccgccaagc    120
tccagggaag gggctggagt gggtctctgg tgttaattgg aatggtggta ccagagatta   180
tgcagcctcc gtgaagggcc gattcaccat ctccagagac aacgccaaga actccctgta   240
tctgcaaatg aacagtctga gagccgagga cacggccttg tattactgtg cgagaggatg   300
gtatagtggg gccgcgtgga acatgggcta ctggggccga ggaacccctgg tcaccgtctc   360 gagtggaggc ggcggttcag gcggaggtgg ctctggcggt ggcggaagtg cacaggctgt   420
gctgactcag ccgtcctccg tgtctgggtc tcctggacag tcgatcacca tctcctgcac   480
tggagccagc ggtgacgttg gtgcttataa ctttgtctcc tggtaccaac aacacccagg   540
caaaaccccc aaactcataa tttatgatgt caataagcgg ccctcagggg tttctaatcg   600
cttctctggc tccaagtcta gcaacacggc ctccctgacc atctctgggc tccaggccga   660
ggacgagtct gattattact gcagctcata caagcacc ttctctgtgg tatttggcgg   720
agggaccaag gtcaccgtcc taggtgcggc cgcacat                              757

<210> SEQ ID NO 179
<211> LENGTH: 15
<212> TYPE: DNA
<213> ORGANISM: Homo sapiens

<400> SEQUENCE: 179
gattatggca tgaac                                                     15

<210> SEQ ID NO 180
<211> LENGTH: 51
<212> TYPE: DNA
<213> ORGANISM: Homo sapiens

<400> SEQUENCE: 180
ggtgttaatt ggaatggtgg taccagagat tatgcagcct ccgtgaaggg c               51

<210> SEQ ID NO 181
<211> LENGTH: 36
<212> TYPE: DNA
<213> ORGANISM: Homo sapiens

<400> SEQUENCE: 181
ggatggtata gtggggccgc gtggaacatg ggctac                              36

<210> SEQ ID NO 182
<211> LENGTH: 42
<212> TYPE: DNA
<213> ORGANISM: Homo sapiens

<400> SEQUENCE: 182
actggagcca gcggtgacgt tggtgcttat aactttgtct cc                        42
```

<210> SEQ ID NO 183
<211> LENGTH: 21
<212> TYPE: DNA
<213> ORGANISM: Homo sapiens

<400> SEQUENCE: 183
gatgtcaata agcggccctc a                                      21

<210> SEQ ID NO 184
<211> LENGTH: 30
<212> TYPE: DNA
<213> ORGANISM: Homo sapiens

<400> SEQUENCE: 184
agctcatata caagcacctt ctctgtggta                             30

<210> SEQ ID NO 185
<211> LENGTH: 121
<212> TYPE: PRT
<213> ORGANISM: Homo sapiens

<400> SEQUENCE: 185

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ser Pro Trp Ser Leu Gly His Trp Gly
            100                 105                 110

Arg Gly Thr Leu Val Thr Val Ser Ser
        115                 120

<210> SEQ ID NO 186
<211> LENGTH: 111
<212> TYPE: PRT
<213> ORGANISM: Homo sapiens

<400> SEQUENCE: 186

Gln Ala Val Leu Thr Gln Pro Ser Ser Val Ser Gly Ser Pro Gly Gln
1               5                   10                  15

Ser Val Thr Ile Ser Cys Thr Gly Ala Ser Gly Asp Val Gly Ala Tyr
            20                  25                  30

Asn Phe Val Ser Trp Tyr Gln Gln His Pro Gly Lys Thr Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Arg Leu
65                  70                  75                  80

Gln Ala Glu Asp Glu Ser Asp Tyr Tyr Cys Ser Ser Tyr Thr Ser Arg
                85                  90                  95

Tyr Thr Thr Glu Phe Gly Gly Gly Thr Lys Val Thr Val Leu Gly
            100                 105                 110

<210> SEQ ID NO 187
<211> LENGTH: 271
<212> TYPE: PRT
<213> ORGANISM: Homo sapiens

<400> SEQUENCE: 187

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ser Pro Trp Ser Leu Gly His Trp Gly
            100                 105                 110

Arg Gly Thr Leu Val Thr Val Ser Gly Gly Gly Ser Gly Gly
        115                 120                 125

Gly Gly Ser Gly Gly Ser Gly Gly Ser Gly Gly Ser Gly Gly Gly
    130                 135                 140

Ser Ser Gly Gly Ser Gly Gly Gly Ser Ala Gln Ala Val Leu
145                 150                 155                 160

Thr Gln Pro Ser Ser Val Ser Gly Ser Pro Gly Gln Ser Val Thr Ile
                165                 170                 175

Ser Cys Thr Gly Ala Ser Gly Asp Val Gly Ala Tyr Asn Phe Val Ser
            180                 185                 190

Trp Tyr Gln Gln His Pro Gly Lys Thr Pro Lys Leu Ile Ile Tyr Asp
        195                 200                 205

Val Asn Lys Arg Pro Ser Gly Val Ser Asn Arg Phe Ser Gly Ser Lys
    210                 215                 220

Ser Gly Asn Thr Ala Ser Leu Thr Ile Ser Arg Leu Gln Ala Glu Asp
225                 230                 235                 240

Glu Ser Asp Tyr Tyr Cys Ser Ser Tyr Thr Ser Arg Tyr Thr Thr Glu
                245                 250                 255

Phe Gly Gly Gly Thr Lys Val Thr Val Leu Gly Ala Ala Ala His
            260                 265                 270

<210> SEQ ID NO 188
<211> LENGTH: 5
<212> TYPE: PRT
<213> ORGANISM: Homo sapiens

<400> SEQUENCE: 188

Asp Tyr Gly Met Asn
1               5

<210> SEQ ID NO 189
<211> LENGTH: 17
<212> TYPE: PRT
<213> ORGANISM: Homo sapiens

<400> SEQUENCE: 189

```
Gly Val Asn Trp Asn Gly Gly Thr Arg Asp Tyr Ala Ala Ser Val Lys
1               5                   10                  15
Gly
```

<210> SEQ ID NO 190
<211> LENGTH: 12
<212> TYPE: PRT
<213> ORGANISM: Homo sapiens

<400> SEQUENCE: 190

```
Gly Trp Tyr Ser Gly Ser Pro Trp Ser Leu Gly His
1               5                   10
```

<210> SEQ ID NO 191
<211> LENGTH: 14
<212> TYPE: PRT
<213> ORGANISM: Homo sapiens

<400> SEQUENCE: 191

```
Thr Gly Ala Ser Gly Asp Val Gly Ala Tyr Asn Phe Val Ser
1               5                   10
```

<210> SEQ ID NO 192
<211> LENGTH: 7
<212> TYPE: PRT
<213> ORGANISM: Homo sapiens

<400> SEQUENCE: 192

```
Asp Val Asn Lys Arg Pro Ser
1               5
```

<210> SEQ ID NO 193
<211> LENGTH: 10
<212> TYPE: PRT
<213> ORGANISM: Homo sapiens

<400> SEQUENCE: 193

```
Ser Ser Tyr Thr Ser Arg Tyr Thr Thr Glu
1               5                   10
```

<210> SEQ ID NO 194
<211> LENGTH: 363
<212> TYPE: DNA
<213> ORGANISM: Homo sapiens

<400> SEQUENCE: 194

```
gaggtgcagc tggtggagtc cgggggaggt gtggtacggc ctgggggtc cctgagactc     60 tcctgtgcag cctctggatt cacctttgac gattatggca tgaactgggt ccgccaagct    120
ccagggaagg ggctggagtg gtctctggt gttaattgga atggtggtac cagagattat    180
gcagcctccg tgaagggccg attcaccatc tccagagaca acgccaagaa ctccctgtat    240
ctgcaaatga acagtctgag agccgaggac acggccttgt attactgtgc gagaggatgg    300
tatagtggga gcccgtggtc gctgggccac tggggccgag aaccctggt caccgtctcc    360 tca                                                                  363
```

<210> SEQ ID NO 195
<211> LENGTH: 333
<212> TYPE: DNA
<213> ORGANISM: Homo sapiens

<400> SEQUENCE: 195

```
caggctgtgc tgactcagcc gtcctccgtg tctgggtctc ctggacagtc ggtcaccatc    60
tcctgcactg gagccagcgg tgacgttggt gcttataact tgtctcctg gtaccaacaa    120 cacccaggca aaacccccaa actcataatt tatgatgtca ataagcggcc ctcaggggtt   180
tctaatcgct tctctggctc caagtctggc aacacggcct ccctgaccat ctctaggctc   240
caggccgagg acgagtctga ttattactgc agctcatata catcgaggta cacgaccgag   300
tttggcggag ggaccaaggt caccgtccta ggt                                 333
```

<210> SEQ ID NO 196
<211> LENGTH: 813
<212> TYPE: DNA
<213> ORGANISM: Homo sapiens

<400> SEQUENCE: 196

```
gaggtgcagc tggtggagtc cggggggaggt gtggtacggc ctgggggtc cctgagactc    60 tcctgtgcag cctctggatt cacctttgac gattatggca tgaactgggt ccgccaagct   120
ccagggaagg ggctggagtg ggtctctggt gttaattgga atggtggtac cagagattat   180
gcagcctccg tgaagggccg attcaccatc tccagagaca acgccaagaa ctccctgtat   240
ctgcaaatga acagtctgag agccgaggac acggccttgt attactgtgc gagaggatgg   300
tatagtggga gcccgtggtc gctgggccac tggggccgag gaaccctggt caccgtctcg   360
agtggaggcg gcggttcagg cggaggtggc tctggcggta gcgaggtggc tctggcggt   420 agcggaggtg gctctagcgg aggtggctct ggcggtggcg aagtgcaca ggctgtgctg   480 actcagccgt cctccgtgtc tgggtctcct ggacagtcgg tcaccatctc ctgcactgga   540
gccagcggtg acgttggtgc ttataacttt gtctcctggt accaacaaca cccaggcaaa   600 accccccaaac tcataattta tgatgtcaat aagcggccct caggggtttc taatcgcttc   660
tctggctcca gtctggcaa cacggcctcc ctgaccatct ctaggctcca ggccgaggac   720
gagtctgatt attactgcag ctcatataca tcgaggtaca cgaccgagtt tggcggaggg   780
accaaggtca ccgtcctagg tgcggccgca cat                                 813
```

<210> SEQ ID NO 197
<211> LENGTH: 15
<212> TYPE: DNA
<213> ORGANISM: Homo sapiens

<400> SEQUENCE: 197

```
gattatggca tgaac                                                      15
```

<210> SEQ ID NO 198
<211> LENGTH: 51
<212> TYPE: DNA
<213> ORGANISM: Homo sapiens

<400> SEQUENCE: 198

```
ggtgttaatt ggaatggtgg taccagagat tatgcagcct ccgtgaaggg c              51
```

<210> SEQ ID NO 199
<211> LENGTH: 36
<212> TYPE: DNA
<213> ORGANISM: Homo sapiens

<400> SEQUENCE: 199

```
ggatggtata gtgggagccc gtggtcgctg ggccac                              36
```

```
<210> SEQ ID NO 200
<211> LENGTH: 42
<212> TYPE: DNA
<213> ORGANISM: Homo sapiens

<400> SEQUENCE: 200
actggagcca gcggtgacgt tggtgcttat aactttgtct cc                           42

<210> SEQ ID NO 201
<211> LENGTH: 21
<212> TYPE: DNA
<213> ORGANISM: Homo sapiens

<400> SEQUENCE: 201
gatgtcaata agcggccctc a                                                  21

<210> SEQ ID NO 202
<211> LENGTH: 30
<212> TYPE: DNA
<213> ORGANISM: Homo sapiens

<400> SEQUENCE: 202
agctcatata catcgaggta cacgaccgag                                         30

<210> SEQ ID NO 203
<211> LENGTH: 121
<212> TYPE: PRT
<213> ORGANISM: Homo sapiens

<400> SEQUENCE: 203
```

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120

```
<210> SEQ ID NO 204
<211> LENGTH: 111
<212> TYPE: PRT
<213> ORGANISM: Homo sapiens

<400> SEQUENCE: 204
```

Gln Ala Val Leu Thr Gln Pro Ser Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Thr Pro Lys Leu
        35                  40                  45

Ile Ile Tyr Asp Val Asn Lys Arg Pro Ser Gly Val Ser Asn Arg Phe

```
                50                   55                   60
Ser Gly Ser Lys Ser Gly Asn Thr Ala Ser Leu Thr Ile Ser Gly Leu
 65                  70                  75                  80

Gln Ala Glu Asp Glu Ser Asp Tyr Tyr Cys Ala Ser Leu Val Ser Asp
                 85                  90                  95

Phe Ser Val Val Phe Gly Gly Gly Thr Lys Val Thr Val Leu Gly
            100                 105                 110
```

<210> SEQ ID NO 205
<211> LENGTH: 266
<212> TYPE: PRT
<213> ORGANISM: Homo sapiens

<400> SEQUENCE: 205

```
Glu Val Gln Leu Val Glu Ser Gly Gly Val Val Arg Pro Gly Gly
 1               5                  10                  15

Ser Leu Arg Leu Ser Cys Ala Ala Ser Gly Phe Thr Phe Asp Asp Tyr
                 20                  25                  30

Gly Met Asn Trp Val Arg Gln Ala Pro Gly Lys Gly Leu Glu Trp Val
             35                  40                  45

Ser Gly Val Asn Trp Asn Gly Gly Thr Arg Asp Tyr Ala Ala Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser Gly Gly Gly Gly Ser Gly Gly
            115                 120                 125

Gly Gly Ser Gly Gly Ser Gly Gly Ser Gly Gly Gly Gly Gly
            130                 135                 140

Ser Gly Gly Gly Gly Ser Ala Gln Ala Val Leu Thr Gln Pro Ser Ser
145                 150                 155                 160

Val Ser Gly Ser Pro Gly Gln Ser Ile Thr Ile Ser Cys Thr Gly Ala
                165                 170                 175

Ser Gly Asp Val Gly Ala Tyr Asn Phe Val Ser Trp Tyr Gln Gln His
            180                 185                 190

Pro Gly Lys Thr Pro Lys Leu Ile Ile Tyr Asp Val Asn Lys Arg Pro
            195                 200                 205

Ser Gly Val Ser Asn Arg Phe Ser Gly Ser Lys Ser Gly Asn Thr Ala
            210                 215                 220

Ser Leu Thr Ile Ser Gly Leu Gln Ala Glu Asp Glu Ser Asp Tyr Tyr
225                 230                 235                 240

Cys Ala Ser Leu Val Ser Asp Phe Ser Val Val Phe Gly Gly Gly Thr
                245                 250                 255

Lys Val Thr Val Leu Gly Ala Ala Ala His
            260                 265
```

<210> SEQ ID NO 206
<211> LENGTH: 5
<212> TYPE: PRT
<213> ORGANISM: Homo sapiens

<400> SEQUENCE: 206

Asp Tyr Gly Met Asn

```
<210> SEQ ID NO 207
<211> LENGTH: 17
<212> TYPE: PRT
<213> ORGANISM: Homo sapiens

<400> SEQUENCE: 207

Gly Val Asn Trp Asn Gly Gly Thr Arg Asp Tyr Ala Ala Ser Val Lys
 1               5                  10                  15
Gly

<210> SEQ ID NO 208
<211> LENGTH: 12
<212> TYPE: PRT
<213> ORGANISM: Homo sapiens

<400> SEQUENCE: 208

Gly Trp Tyr Ser Gly Ala Ala Trp Asn Met Gly Tyr
 1               5                  10

<210> SEQ ID NO 209
<211> LENGTH: 14
<212> TYPE: PRT
<213> ORGANISM: Homo sapiens

<400> SEQUENCE: 209

Thr Gly Ala Ser Gly Asp Val Gly Ala Tyr Asn Phe Val Ser
 1               5                  10

<210> SEQ ID NO 210
<211> LENGTH: 7
<212> TYPE: PRT
<213> ORGANISM: Homo sapiens

<400> SEQUENCE: 210

Asp Val Asn Lys Arg Pro Ser
 1               5

<210> SEQ ID NO 211
<211> LENGTH: 10
<212> TYPE: PRT
<213> ORGANISM: Homo sapiens

<400> SEQUENCE: 211

Ala Ser Leu Val Ser Asp Phe Ser Val Val
 1               5                  10

<210> SEQ ID NO 212
<211> LENGTH: 363
<212> TYPE: DNA
<213> ORGANISM: Homo sapiens

<400> SEQUENCE: 212
gaggtgcagc tggtggagtc cggggggaggt gtggtacggc ctggggggtc cctgagactc      60
tcctgtgcag cctctggatt cacctttgac gattatggca tgaactgggt ccgccaagct     120
ccagggaagg ggctggagtg gtctctggt gttaattgga tggtggtac cagagattat      180 gcagcctccg tgaagggccg attcaccatc tccagagaca cgccaagaa ctccctgtat      240 ctgcaaatga acagtctgag agccgaggac acggccttgt attactgtgc gagaggatgg     300
tatagtgggg ccgcgtggaa catgggctac tggggccgag aaccctggt caccgtctcc      360
```

```
tca                                                                  363

<210> SEQ ID NO 213
<211> LENGTH: 333
<212> TYPE: DNA
<213> ORGANISM: Homo sapiens

<400> SEQUENCE: 213
caggctgtgc tgactcagcc gtcctccgtg tctgggtccc ctggacagtc gatcaccatc    60
tcctgcactg gagccagcgg tgacgttggt gcttataact ttgtctcctg gtaccaacaa   120
cacccaggca aaaccccaa actcataatt tatgatgtca ataagcggcc ctcagggg tt   180 tctaatcgct ctctctggctc caagtctggc aacacggcct ccctgaccat ctctgggctc  240
caggccgagg acgagtctga ttattactgc gcctccctcg tctccgactt ctctgtggta   300
tttggcggag ggaccaaggt caccgtccta ggt                                333

<210> SEQ ID NO 214
<211> LENGTH: 798
<212> TYPE: DNA
<213> ORGANISM: Homo sapiens

<400> SEQUENCE: 214
gaggtgcagc tggtggagtc cggggggaggt gtggtacggc ctgggggtc cctgagactc    60 tcctgtgcag cctctggatt caccttt gac gattatggca tgaactgggt ccgccaagct   120
ccagggaagg ggctggagtg ggtctctggt gttaattgga atggtggtac cagagattat   180
gcagcctccg tgaagggccg attcaccatc tccagagaca cgccaagaa ctccctgtat    240 ctgcaaatga acagtctgag agccgaggac acggccttgt attactgtgc gagaggatgg   300
tatagtgggg ccgcgtggaa catgggctac tggggccgag gaaccctggt caccgtctcg   360
agtggaggcg gcggttcagg cggaggtggc tctggtggta gcggaggtgg ctctggcggt   420
ggcggaggtg gctctggcgg tggcggaagt gcacaggctg tgctgactca gccgtcctcc   480
gtgtctgggt cccctggaca gtcgatcacc atctcctgca ctggagccag cggtgacgtt   540
ggtgcttata actttgtctc ctggtaccaa caacacccag gcaaaacccc caaactcata   600
atttatgatg tcaataagcg gccctcaggg gtttctaatc gcttctctgg ctccaagtct   660
ggcaacacgg cctccctgac catctctggg ctccaggccg aggacgagtc tgattattac   720
tgcgcctccc tcgtctccga cttctctgtg gtatttggcg gagggaccaa ggtcaccgtc   780
ctaggtgcgg ccgcacat                                                 798

<210> SEQ ID NO 215
<211> LENGTH: 15
<212> TYPE: DNA
<213> ORGANISM: Homo sapiens

<400> SEQUENCE: 215
gattatggca tgaac                                                     15

<210> SEQ ID NO 216
<211> LENGTH: 51
<212> TYPE: DNA
<213> ORGANISM: Homo sapiens

<400> SEQUENCE: 216
ggtgttaatt ggaatggtgg taccagagat tatgcagcct ccgtgaaggg c              51
```

<210> SEQ ID NO 217
<211> LENGTH: 36
<212> TYPE: DNA
<213> ORGANISM: Homo sapiens

<400> SEQUENCE: 217
ggatggtata gtggggccgc gtggaacatg ggctac        36

<210> SEQ ID NO 218
<211> LENGTH: 42
<212> TYPE: DNA
<213> ORGANISM: Homo sapiens

<400> SEQUENCE: 218
actggagcca gcggtgacgt tggtgcttat aactttgtct cc        42

<210> SEQ ID NO 219
<211> LENGTH: 21
<212> TYPE: DNA
<213> ORGANISM: Homo sapiens

<400> SEQUENCE: 219
gatgtcaata agcggccctc a        21

<210> SEQ ID NO 220
<211> LENGTH: 30
<212> TYPE: DNA
<213> ORGANISM: Homo sapiens

<400> SEQUENCE: 220
gcctccctcg tctccgactt ctctgtggta        30

<210> SEQ ID NO 221
<211> LENGTH: 119
<212> TYPE: PRT
<213> ORGANISM: Homo sapiens

<400> SEQUENCE: 221

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
                20                  25                  30

Tyr Ile His Trp Val Arg Gln Thr Pro Gly Gln Gly Phe Glu Trp Met
            35                  40                  45

Gly Trp Val Asn Pro Asp Thr Gly Gly Thr Arg Tyr Ala Gln Lys Phe
        50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
                100                 105                 110

Thr Leu Val Thr Val Ser Ser
        115

<210> SEQ ID NO 222
<211> LENGTH: 109
<212> TYPE: PRT
<213> ORGANISM: Homo sapiens

<400> SEQUENCE: 222

Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
                20                  25                  30

His Trp Tyr Gln Gln Arg Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Leu Phe Asn Asp Asn
                85                  90                  95

Gly Val Phe Gly Gly Gly Thr Lys Leu Thr Val Leu Gly
                100                 105

<210> SEQ ID NO 223
<211> LENGTH: 248
<212> TYPE: PRT
<213> ORGANISM: Homo sapiens

<400> SEQUENCE: 223

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
                20                  25                  30

Tyr Ile His Trp Val Arg Gln Thr Pro Gly Gln Gly Phe Glu Trp Met
            35                  40                  45

Gly Trp Val Asn Pro Asp Thr Gly Gly Thr Arg Tyr Ala Gln Lys Phe
        50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
                100                 105                 110

Thr Leu Val Thr Val Ser Ser Gly Gly Ser Ser Gly Gly Gly
            115                 120                 125

Ser Gly Gly Gly Ser Ala Gln Ser Val Leu Thr Gln Pro Pro Ser
        130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
                180                 185                 190

Pro Glu Arg Phe Ser Gly Ser Arg Ser Gly Asn Thr Ala Thr Leu Thr
                195                 200                 205

Ile Ser Arg Val Glu Ala Gly Asp Glu Ala Asp Phe Tyr Cys Gln Val
            210                 215                 220

Trp Asp Leu Phe Asn Asp Asn Gly Val Phe Gly Gly Gly Thr Lys Leu
225                 230                 235                 240

Thr Val Leu Gly Ala Ala Ala His
                245

<210> SEQ ID NO 224

```
<211> LENGTH: 5
<212> TYPE: PRT
<213> ORGANISM: Homo sapiens

<400> SEQUENCE: 224

Asp Tyr Tyr Ile His
1               5

<210> SEQ ID NO 225
<211> LENGTH: 17
<212> TYPE: PRT
<213> ORGANISM: Homo sapiens

<400> SEQUENCE: 225

Trp Val Asn Pro Asp Thr Gly Gly Thr Arg Tyr Ala Gln Lys Phe Gln
1               5                   10                  15

Gly

<210> SEQ ID NO 226
<211> LENGTH: 10
<212> TYPE: PRT
<213> ORGANISM: Homo sapiens

<400> SEQUENCE: 226

Asp Leu Thr Gly Phe Asp Pro Phe Asp Ile
1               5                   10

<210> SEQ ID NO 227
<211> LENGTH: 11
<212> TYPE: PRT
<213> ORGANISM: Homo sapiens

<400> SEQUENCE: 227

Gly Gly Asn Asn Phe Arg Asn Lys Arg Val His
1               5                   10

<210> SEQ ID NO 228
<211> LENGTH: 7
<212> TYPE: PRT
<213> ORGANISM: Homo sapiens

<400> SEQUENCE: 228

Tyr Asp Ser Asp Arg Pro Ser
1               5

<210> SEQ ID NO 229
<211> LENGTH: 11
<212> TYPE: PRT
<213> ORGANISM: Homo sapiens

<400> SEQUENCE: 229

Gln Val Trp Asp Leu Phe Asn Asp Asn Gly Val
1               5                   10

<210> SEQ ID NO 230
<211> LENGTH: 357
<212> TYPE: DNA
<213> ORGANISM: Homo sapiens

<400> SEQUENCE: 230
gaggtgcagc tggtgcagtc tggggctgag gtgaagaagc ctggggcctc agtgaaggtc      60
tcctgtcagg cttctggata caccttcagc gattactata ttcactgggt gcgacagacc     120
cctggacaag ggtttgagtg gatgggatgg gtcaaccctg acactggtgg cacaagatac     180
```
gcgcagaagt tcagggctg ggtcacaatg accagggaca tgtccaacac cacagcctac      240
atggagctgc ccaggctgag agacgacgac acggccgtat attactgtgc gagagatcta      300
actggatttg atccttttga tatctggggc cagggaaccc tggtcaccgt ctcctca         357

<210> SEQ ID NO 231
<211> LENGTH: 327
<212> TYPE: DNA
<213> ORGANISM: Homo sapiens

<400> SEQUENCE: 231
cagtctgtgc tgactcagcc accctcagtg tcagtggccc caggaaagac ggccacgatt       60
acctgtgggg gaaacaactt tcgaaataaa agagtacact ggtatcagca gaggccaggc      120
caggcccctg tcctggtcat ctattatgac tcagaccggc cctcaggat cctgagcga       180 ttctctggct cccgctctgg gaacacggcc accctgacca tcagcagggt cgaggccggg      240
gatgaggccg acttttactg tcaggtgtgg gatctcttca cgacaacgg cgtgttcggc       300 ggagggacca agctgaccgt cctaggt                                          327

<210> SEQ ID NO 232
<211> LENGTH: 744
<212> TYPE: DNA
<213> ORGANISM: Homo sapiens

<400> SEQUENCE: 232
gaagtgcagc tggtgcagtc tggggctgag gtgaagaagc ctggggcctc agtgaaggtc       60
tcctgtcagg cttctggata caccttcagc gattactata ttcactgggt gcgacagacc      120
cctggacaag gtttgagtg gatgggatgg gtcaaccctg acactggtgg cacaagatac      180
gcgcagaagt tcagggctg ggtcacaatg accagggaca tgtccaacac cacagcctac      240
atggagctgc ccaggctgag agacgacgac acggccgtat attactgtgc gagagatcta      300
actggatttg atccttttga tatctggggc cagggaaccc tggtcaccgt ctcgagtgga      360
ggcggcagtt caggtggagg tggctctggc ggtggcggaa gtgcacagtc tgtgctgact      420
cagccaccct cagtgtcagt ggccccagga aagacgcca cgattacctg tggggaaac       480 aactttcgaa ataaaagagt acactggtat cagcagaggc caggccaggc ccctgtcctg      540
gtcatctatt atgattcaga ccggccctca gggatccctg agcgattctc tggctcccgc      600
tctgggaaca cggccaccct gaccatcagc agggtcgagg ccggggatga ggccgacttt      660
tactgtcagg tgtgggatct cttcaacgac aacggcgtgt tcggcggagg gaccaagctg      720
accgtcctag gtgcggccgc acat                                             744

<210> SEQ ID NO 233
<211> LENGTH: 15
<212> TYPE: DNA
<213> ORGANISM: Homo sapiens

<400> SEQUENCE: 233
gattactata ttcac                                                        15

<210> SEQ ID NO 234
<211> LENGTH: 51
<212> TYPE: DNA
<213> ORGANISM: Homo sapiens

<400> SEQUENCE: 234
tgggtcaacc ctgacactgg tggcacaaga tacgcgcaga agtttcaggg c                     51

<210> SEQ ID NO 235
<211> LENGTH: 30
<212> TYPE: DNA
<213> ORGANISM: Homo sapiens

<400> SEQUENCE: 235
gatctaactg gatttgatcc ttttgatatc                                             30

<210> SEQ ID NO 236
<211> LENGTH: 33
<212> TYPE: DNA
<213> ORGANISM: Homo sapiens

<400> SEQUENCE: 236
gggggaaaca actttcgaaa taaaagagta cac                                         33

<210> SEQ ID NO 237
<211> LENGTH: 21
<212> TYPE: DNA
<213> ORGANISM: Homo sapiens

<400> SEQUENCE: 237
tatgactcag accggccctc a                                                      21

<210> SEQ ID NO 238
<211> LENGTH: 33
<212> TYPE: DNA
<213> ORGANISM: Homo sapiens

<400> SEQUENCE: 238
caggtgtggg atctcttcaa cgacaacggc gtg                                         33

<210> SEQ ID NO 239
<211> LENGTH: 119
<212> TYPE: PRT
<213> ORGANISM: Homo sapiens

<400> SEQUENCE: 239

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 240
<211> LENGTH: 109
<212> TYPE: PRT
<213> ORGANISM: Homo sapiens -continued

```
<400> SEQUENCE: 240

Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Phe Leu Thr Asp Ser
                85                  90                  95

Gly Ser Phe Gly Gly Gly Thr Lys Leu Thr Val Leu Gly
            100                 105

<210> SEQ ID NO 241
<211> LENGTH: 248
<212> TYPE: PRT
<213> ORGANISM: Homo sapiens

<400> SEQUENCE: 241

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Ala Gln Ser Val Leu Thr Gln Pro Pro Ser
        130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
        195                 200                 205

Ile Ser Arg Val Glu Ala Gly Asp Glu Ala Asp Phe Tyr Cys Gln Val
    210                 215                 220

Trp Asp Phe Leu Thr Asp Ser Gly Ser Phe Gly Gly Gly Thr Lys Leu
225                 230                 235                 240

Thr Val Leu Gly Ala Ala Ala His
                245
```

<210> SEQ ID NO 242
<211> LENGTH: 5
<212> TYPE: PRT
<213> ORGANISM: Homo sapiens

<400> SEQUENCE: 242

Asp Tyr Tyr Ile His
1               5

<210> SEQ ID NO 243
<211> LENGTH: 17
<212> TYPE: PRT
<213> ORGANISM: Homo sapiens

<400> SEQUENCE: 243

Trp Val Asn Pro Asp Thr Gly Gly Thr Arg Tyr Ala Gln Lys Phe Gln
1               5                   10                  15

Gly

<210> SEQ ID NO 244
<211> LENGTH: 10
<212> TYPE: PRT
<213> ORGANISM: Homo sapiens

<400> SEQUENCE: 244

Asp Leu Thr Gly Phe Asp Pro Phe Asp Ile
1               5                   10

<210> SEQ ID NO 245
<211> LENGTH: 11
<212> TYPE: PRT
<213> ORGANISM: Homo sapiens

<400> SEQUENCE: 245

Gly Gly Asn Asn Phe Arg Asn Lys Arg Val His
1               5                   10

<210> SEQ ID NO 246
<211> LENGTH: 7
<212> TYPE: PRT
<213> ORGANISM: Homo sapiens

<400> SEQUENCE: 246

Tyr Asp Ser Asp Arg Pro Ser
1               5

<210> SEQ ID NO 247
<211> LENGTH: 11
<212> TYPE: PRT
<213> ORGANISM: Homo sapiens

<400> SEQUENCE: 247

Gln Val Trp Asp Phe Leu Thr Asp Ser Gly Ser
1               5                   10

<210> SEQ ID NO 248
<211> LENGTH: 357
<212> TYPE: DNA
<213> ORGANISM: Homo sapiens

<400> SEQUENCE: 248
gaggtgcagc tggtgcagtc tggggctgag gtgaagaagc ctggggcctc agtgaaggtc      60

```
tcctgtcagg cttctggata caccttcagc gattactata ttcactgggt gcgacagacc    120
cctggacaag ggtttgagtg gatgggatgg gtcaaccctg acactggtgg cacaagatac    180
gcgcagaagt ttcagggctg ggtcacaatg accagggaca tgtccaacac cacagcctac    240
atggagctgc ccaggctgag agacgacgac acggccgtat attactgtgc gagagatcta    300
actggatttg atccttttga tatctgggc cagggaaccc tggtcaccgt ctcctca        357
```

<210> SEQ ID NO 249
<211> LENGTH: 327
<212> TYPE: DNA
<213> ORGANISM: Homo sapiens

<400> SEQUENCE: 249

```
cagtctgtgc tgactcagcc acccctcagtg tcagtggccc caggaaagac ggccacaatt     60
acctgtgggg gaaacaactt tcgaaataaa agagtacact ggtatcagca gaggccaggc    120
caggcgcctg tcctggtcat ctattatgat tcagaccggc cctcagggat ccctgagcga    180
ttctctggct cccgctctgg gaacacggcc accctgacca tcagcagggt cgaggccggg    240
gatgaggccg acttttactg tcaggtgtgg gatttcctca ccgactcggg gtcgttcggc    300
ggagggacca agctgaccgt cctaggt                                        327
```

<210> SEQ ID NO 250
<211> LENGTH: 744
<212> TYPE: DNA
<213> ORGANISM: Homo sapiens

<400> SEQUENCE: 250

```
gaagtgcagc tggtgcagtc tggggctgag gtgaagaagc ctggggcctc agtgaaggtc     60
tcctgtcagg cttctggata caccttcagc gattactata ttcactgggt gcgacagacc    120
cctggacaag ggtttgagtg gatgggatgg gtcaaccctg acactggtgg cacaagatac    180
gcgcagaagt ttcagggctg ggtcacaatg accagggaca tgtccaacac cacagcctac    240
atggagctgc ccaggctgag agacgacgac acggccgtat attactgtgc gagagatcta    300
actggatttg atccttttga tatctgggc cagggaaccc tggtcaccgt ctcgagtgga    360
ggcggcggtt caggcggagg tggctctggc ggtggcggaa gtgcacagtc tgtgctgact    420 cagccacccct cagtgtcagt ggccccagga aagacggcca caattacctg tgggggaaac    480
aactttcgaa ataaaagagt acactggtat cagcagaggc caggccaggc gcctgtcctg    540
gtcatctatt atgattcaga ccggccctca gggatccctg agcgattctc tggctcccgc    600
tctgggaaca cggccaccct gaccatcagc agggtcgagg ccggggatga ggccgacttt    660
tactgtcagg tgtgggattt cctcaccgac tcggggtcgt tcggcggagg gaccaagctg    720
accgtcctag gtgcggccgc acat                                           744
```

<210> SEQ ID NO 251
<211> LENGTH: 15
<212> TYPE: DNA
<213> ORGANISM: Homo sapiens

<400> SEQUENCE: 251

```
gattactata ttcac                                                      15
```

<210> SEQ ID NO 252
<211> LENGTH: 51
<212> TYPE: DNA
<213> ORGANISM: Homo sapiens

<400> SEQUENCE: 252
tgggtcaacc ctgacactgg tggcacaaga tacgcgcaga agtttcaggg c  51

<210> SEQ ID NO 253
<211> LENGTH: 30
<212> TYPE: DNA
<213> ORGANISM: Homo sapiens

<400> SEQUENCE: 253
gatctaactg gatttgatcc ttttgatatc  30

<210> SEQ ID NO 254
<211> LENGTH: 33
<212> TYPE: DNA
<213> ORGANISM: Homo sapiens

<400> SEQUENCE: 254
gggggaaaca actttcgaaa taaaagagta cac  33

<210> SEQ ID NO 255
<211> LENGTH: 21
<212> TYPE: DNA
<213> ORGANISM: Homo sapiens

<400> SEQUENCE: 255
tatgattcag accggccctc a  21

<210> SEQ ID NO 256
<211> LENGTH: 33
<212> TYPE: DNA
<213> ORGANISM: Homo sapiens

<400> SEQUENCE: 256
caggtgtggg atttcctcac cgactcgggg tcg  33

<210> SEQ ID NO 257
<211> LENGTH: 119
<212> TYPE: PRT
<213> ORGANISM: Homo sapiens

<400> SEQUENCE: 257

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Tyr Asp Tyr Tyr Asp Arg Trp Gly Gln Gly
            100                 105                 110

Thr Leu Val Thr Val Ser Ser
        115

<210> SEQ ID NO 258

<211> LENGTH: 108
<212> TYPE: PRT
<213> ORGANISM: Homo sapiens

<400> SEQUENCE: 258

Gln Ser Val Leu Thr Gln Pro Pro Ser Met Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Phe Leu Ala Asp Glu
                85                  90                  95

Ala Met Phe Gly Gly Gly Thr Lys Leu Thr Val Leu
            100                 105

<210> SEQ ID NO 259
<211> LENGTH: 262
<212> TYPE: PRT
<213> ORGANISM: Homo sapiens

<400> SEQUENCE: 259

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
50                  55                  60

Gln Gly Trp Val Thr Met Thr Arg Asp Met Ser Asn Thr Thr Ala Tyr
65                  70                  75                  80

Met Glu Leu Pro Arg Leu Arg Asp Asp Thr Ala Val Tyr Tyr Cys
                85                  90                  95

Ala Arg Asp Leu Thr Gly Tyr Asp Tyr Tyr Asp Arg Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Gly Ser Gly Gly Gly Gly Gly Ser Gly
        130                 135                 140

Gly Gly Gly Ser Ala Gln Ser Val Leu Thr Gln Pro Pro Ser Met Ser
145                 150                 155                 160

Val Ala Pro Gly Lys Thr Ala Thr Ile Thr Cys Gly Gly Asn Asn Phe
                165                 170                 175

Arg Asn Lys Arg Val His Trp Tyr Gln Gln Arg Pro Gly Gln Ala Pro
            180                 185                 190

Val Leu Val Ile Tyr Tyr Asp Ser Asp Arg Pro Ser Gly Ile Pro Glu
        195                 200                 205

Arg Phe Ser Gly Ser Arg Ser Gly Asn Thr Ala Thr Leu Thr Ile Ser
210                 215                 220

Arg Val Glu Ala Gly Asp Glu Ala Asp Phe Tyr Cys Gln Val Trp Asp
225                 230                 235                 240

Phe Leu Ala Asp Glu Ala Met Phe Gly Gly Gly Thr Lys Leu Thr Val
            245                 250                 255

Leu Gly Ala Ala Ala His
        260

<210> SEQ ID NO 260
<211> LENGTH: 5
<212> TYPE: PRT
<213> ORGANISM: Homo sapiens

<400> SEQUENCE: 260

Asp Tyr Tyr Ile His
1               5

<210> SEQ ID NO 261
<211> LENGTH: 17
<212> TYPE: PRT
<213> ORGANISM: Homo sapiens

<400> SEQUENCE: 261

Trp Val Asn Pro Asp Thr Gly Gly Thr Arg Tyr Ala Gln Lys Phe Gln
1               5                   10                  15

Gly

<210> SEQ ID NO 262
<211> LENGTH: 10
<212> TYPE: PRT
<213> ORGANISM: Homo sapiens

<400> SEQUENCE: 262

Asp Leu Thr Gly Tyr Asp Tyr Tyr Asp Arg
1               5                   10

<210> SEQ ID NO 263
<211> LENGTH: 11
<212> TYPE: PRT
<213> ORGANISM: Homo sapiens

<400> SEQUENCE: 263

Gly Gly Asn Asn Phe Arg Asn Lys Arg Val His
1               5                   10

<210> SEQ ID NO 264
<211> LENGTH: 7
<212> TYPE: PRT
<213> ORGANISM: Homo sapiens

<400> SEQUENCE: 264

Tyr Asp Ser Asp Arg Pro Ser
1               5

<210> SEQ ID NO 265
<211> LENGTH: 11
<212> TYPE: PRT
<213> ORGANISM: Homo sapiens

<400> SEQUENCE: 265

Gln Val Trp Asp Phe Leu Ala Asp Glu Ala Met
1               5                   10

<210> SEQ ID NO 266
<211> LENGTH: 357
<212> TYPE: DNA

<213> ORGANISM: Homo sapiens

<400> SEQUENCE: 266

| | |
|---|---|
| gaggtgcagc tggtgcagtc tggggctgag gtgaagaagc ctggggcctc agtgaaggtc | 60 |
| tcctgtcagg cttctggata caccttcagc gattactata ttcactgggt gcgacagacc | 120 |
| cctggacaag ggtttgagtg gatgggatgg gtcaaccctg acactggtgg cacaagatac | 180 |
| gcgcagaagt tcagggctg gtcacaatg accagggaca tgtccaacac cacagcctac | 240 |
| atggagctgc ccaggctgag agacgacgac acggccgtat attactgtgc gagagatcta | 300 |
| actggatacg actactacga ccggtggggc cagggaaccc tggtcaccgt ctcctca | 357 |

<210> SEQ ID NO 267
<211> LENGTH: 327
<212> TYPE: DNA
<213> ORGANISM: Homo sapiens

<400> SEQUENCE: 267

| | |
|---|---|
| cagtctgtgc tgactcagcc gccctcaatg tcagtggccc caggaaagac ggccacgatt | 60 |
| acctgtgggg gaaacaactt tcgaaataaa agagtacact ggtatcagca gaggccaggc | 120 |
| caggcccctg tcctggtcat ctattatgat tcagaccggc cctcagggat ccctgagcga | 180 |
| ttctctggct cccgctctgg gaacacggcc accctgacca tcagcagggt cgaggccggg | 240 |
| gatgaggccg acttttactg tcaggtgtgg gatttcctcg ccgacgaggc gatgttcggc | 300 |
| ggagggacca agctgaccgt cctaggt | 327 |

<210> SEQ ID NO 268
<211> LENGTH: 786
<212> TYPE: DNA
<213> ORGANISM: Homo sapiens

<400> SEQUENCE: 268

| | |
|---|---|
| gaagtgcagc tggtgcagtc tggggctgag gtgaagaagc ctggggcctc agtgaaggtc | 60 |
| tcctgtcagg cttctggata caccttcagc gattactata ttcactgggt gcgacagacc | 120 |
| cctggacaag ggtttgagtg gatgggatgg gtcaaccctg acactggtgg cacaagatac | 180 |
| gcgcagaagt tcagggctg gtcacaatg accagggaca tgtccaacac cacagcctac | 240 |
| atggagctgc ccaggctgag agacgacgac acggccgtat attactgtgc gagagatcta | 300 |
| actggatacg actactacga ccggtggggc cagggaaccc tggtcaccgt ctcgagtgga | 360 |
| ggcggcggtt caggcggagg tggctctggc ggtggtggag gtggctctgg cggtggcgga | 420 |
| ggtggctctg gcggtggcgg aagtgcacag tctgtgctga ctcagccgcc ctcaatgtca | 480 |
| gtggccccag gaaagacggc cacgattacc tgtgggggaa acaactttcg aaataaaaga | 540 |
| gtacactggt atcagcagag gccaggccag gcccctgtcc tggtcatcta ttatgattca | 600 |
| gaccggccct cagggatccc tgagcgattc tctggctccc gctctgggaa cacggccacc | 660 |
| ctgaccatca gcagggtcga ggccggggat gaggccgact tttactgtca ggtgtgggat | 720 |
| ttcctcgccg acgaggcgat gttcggcgga gggaccaagc tgaccgtcct aggtgcggcc | 780 |
| gcacat | 786 |

<210> SEQ ID NO 269
<211> LENGTH: 15
<212> TYPE: DNA
<213> ORGANISM: Homo sapiens

<400> SEQUENCE: 269
gattactata ttcac    15

<210> SEQ ID NO 270
<211> LENGTH: 51
<212> TYPE: DNA
<213> ORGANISM: Homo sapiens

<400> SEQUENCE: 270
tgggtcaacc ctgacactgg tggcacaaga tacgcgcaga agtttcaggg c    51

<210> SEQ ID NO 271
<211> LENGTH: 30
<212> TYPE: DNA
<213> ORGANISM: Homo sapiens

<400> SEQUENCE: 271
gatctaactg gatacgacta ctacgaccgg    30

<210> SEQ ID NO 272
<211> LENGTH: 33
<212> TYPE: DNA
<213> ORGANISM: Homo sapiens

<400> SEQUENCE: 272
gggggaaaca actttcgaaa taaaagagta cac    33

<210> SEQ ID NO 273
<211> LENGTH: 21
<212> TYPE: DNA
<213> ORGANISM: Homo sapiens

<400> SEQUENCE: 273
tatgattcag accggccctc a    21

<210> SEQ ID NO 274
<211> LENGTH: 33
<212> TYPE: DNA
<213> ORGANISM: Homo sapiens

<400> SEQUENCE: 274
caggtgtggg atttcctcgc cgacgaggcg atg    33

<210> SEQ ID NO 275
<211> LENGTH: 119
<212> TYPE: PRT
<213> ORGANISM: Homo sapiens

<400> SEQUENCE: 275

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Gly Leu Arg Asp Asp Thr Ala Val Tyr Tyr Cys
                85                  90                  95

```
Ala Arg Asp Leu Thr Gly Tyr Asp Gln Tyr Thr Ala Trp Gly Gln Gly
            100                 105                 110

Thr Leu Val Thr Val Ser Ser
        115
```

<210> SEQ ID NO 276
<211> LENGTH: 109
<212> TYPE: PRT
<213> ORGANISM: Homo sapiens

<400> SEQUENCE: 276

```
Gln Ser Val Leu Thr Gln Pro Pro Ser Val Ser Val Ala Pro Gly Lys
1               5                   10                  15

Thr Ala Thr Ile Thr Cys Gly Gly Asn Asn Phe Arg Asn Lys Arg Val
            20                  25                  30

His Trp Tyr Gln Gln Arg Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Phe Tyr Cys Ser Thr Phe Asp Pro Thr Asp Arg
                85                  90                  95

Pro Leu Phe Gly Gly Gly Thr Lys Leu Thr Val Leu Gly
            100                 105
```

<210> SEQ ID NO 277
<211> LENGTH: 248
<212> TYPE: PRT
<213> ORGANISM: Homo sapiens

<400> SEQUENCE: 277

```
Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Ser Asp Tyr
            20                  25                  30

Tyr Ile His Trp Val Arg Gln Thr Pro Gly Gln Gly Phe Glu Trp Met
        35                  40                  45

Gly Trp Val Asn Pro Asp Thr Gly Gly Thr Arg Tyr Ala Gln Lys Phe
    50                  55                  60

Gln Gly Trp Val Thr Met Thr Arg Asp Met Ser Asn Thr Thr Ala Tyr
65                  70                  75                  80

Met Glu Leu Pro Gly Leu Arg Asp Asp Thr Ala Val Tyr Tyr Cys
                85                  90                  95

Ala Arg Asp Leu Thr Gly Tyr Asp Gln Tyr Thr Ala Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Gln Ser Val Leu Thr Gln Pro Pro Ser
    130                 135                 140

Val Ser Val Ala Pro Gly Lys Thr Ala Thr Ile Thr Cys Gly Gly Asn
145                 150                 155                 160

Asn Phe Arg Asn Lys Arg Val His Trp Tyr Gln Gln Arg Pro Gly Gln
                165                 170                 175

Ala Pro Val Leu Val Ile Tyr Tyr Asp Ser Asp Arg Pro Ser Gly Ile
            180                 185                 190
```

```
Pro Glu Arg Phe Ser Gly Ser Arg Ser Gly Asn Thr Ala Thr Leu Thr
            195                 200                 205

Ile Ser Arg Val Glu Ala Gly Asp Glu Ala Asp Phe Tyr Cys Ser Thr
        210                 215                 220

Phe Asp Pro Phe Thr Asp Arg Pro Leu Phe Gly Gly Gly Thr Lys Leu
225                 230                 235                 240

Thr Val Leu Gly Ala Ala Ala His
                245
```

```
<210> SEQ ID NO 278
<211> LENGTH: 5
<212> TYPE: PRT
<213> ORGANISM: Homo sapiens

<400> SEQUENCE: 278

Asp Tyr Tyr Ile His
1               5

<210> SEQ ID NO 279
<211> LENGTH: 17
<212> TYPE: PRT
<213> ORGANISM: Homo sapiens

<400> SEQUENCE: 279

Trp Val Asn Pro Asp Thr Gly Gly Thr Arg Tyr Ala Gln Lys Phe Gln
1               5                   10                  15

Gly

<210> SEQ ID NO 280
<211> LENGTH: 10
<212> TYPE: PRT
<213> ORGANISM: Homo sapiens

<400> SEQUENCE: 280

Asp Leu Thr Gly Tyr Asp Gln Tyr Thr Ala
1               5                   10

<210> SEQ ID NO 281
<211> LENGTH: 11
<212> TYPE: PRT
<213> ORGANISM: Homo sapiens

<400> SEQUENCE: 281

Gly Gly Asn Asn Phe Arg Asn Lys Arg Val His
1               5                   10

<210> SEQ ID NO 282
<211> LENGTH: 7
<212> TYPE: PRT
<213> ORGANISM: Homo sapiens

<400> SEQUENCE: 282

Tyr Asp Ser Asp Arg Pro Ser
1               5

<210> SEQ ID NO 283
<211> LENGTH: 11
<212> TYPE: PRT
<213> ORGANISM: Homo sapiens

<400> SEQUENCE: 283

Ser Thr Phe Asp Pro Phe Thr Asp Arg Pro Leu
1               5                   10
```

<210> SEQ ID NO 284
<211> LENGTH: 357
<212> TYPE: DNA
<213> ORGANISM: Homo sapiens

<400> SEQUENCE: 284

```
gaggtgcagc tggtgcagtc tggggctgag gtgaagaagc ctggggcctc agtgaaggtc      60
tcctgtcagg cttctggata cccttcagc gattactata ttcactgggt gcgacagacc     120
ccaggacaag ggtttgagtg gatgggatgg gtcaaccctg acactggtgg cacgagatac    180
gcgcagaagt tcagggctg gtcacaatg accaggaca tgtccaacac cacagcctac       240
atggagctgc ccgggctgag agacgacgac acggccgtat attactgtgc gagagatcta    300
actgggtacg accagtacac ggcctggggc cagggaaccc tggtcaccgt ctcctca       357
```

<210> SEQ ID NO 285
<211> LENGTH: 327
<212> TYPE: DNA
<213> ORGANISM: Homo sapiens

<400> SEQUENCE: 285

```
cagtctgtgc tgactcagcc accctcagtg tcagtggccc caggaaagac ggccacgatt     60
acctgtgggg gaaacaactt tcgaaataaa agagtacact ggtatcagca gaggccaggc    120
caggcccctg tcctggtcat ctattatgat tcagaccggc cctcagggat ccctgagcga    180
ttctctggct cccgctctgg gaacacggcc accctgacca tcagcagggt cgaggccggg    240
gatgaggccg acttttactg tagcaccttc gaccccttca ctgatcgtcc gctgttcggc    300
ggagggacca agctgaccgt cctaggt                                        327
```

<210> SEQ ID NO 286
<211> LENGTH: 744
<212> TYPE: DNA
<213> ORGANISM: Homo sapiens

<400> SEQUENCE: 286

```
gaagtgcagc tggtgcagtc tggggctgag gtgaagaagc ctggggcctc agtgaaggtc      60
tcctgtcagg cttctggata cccttcagc gattactata ttcactgggt gcgacagacc     120
ccaggacaag ggtttgagtg gatgggatgg gtcaaccctg acactggtgg cacgagatac    180
gcgcagaagt tcagggctg gtcacaatg accaggaca tgtccaacac cacagcctac       240
atggagctgc ccgggctgag agacgacgac acggccgtat attactgtgc gagagatcta    300
actgggtacg accagtacac ggcctggggc cagggaaccc tggtcaccgt ctcgagtgga    360
ggcggcggtt caggcggagg tggctctggc ggtggcggaa gtgcacagtc tgtgctgact    420
cagccaccct cagtgtcagt ggccccagga agacggcca cgattacctg tgggggaaac    480
aactttcgaa ataaaagagt acactggtat cagcagaggc caggccaggc ccctgtcctg    540
gtcatctatt atgattcaga ccggccctca gggatccctg agcgattctc tggctcccgc    600
tctgggaaca cggccaccct gaccatcagc agggtcgagg ccggggatga ggccgacttt    660
tactgtagca ccttcgaccc cttcactgat cgtccgctgt tcggcggagg gaccaagctg    720
accgtcctag gtgcggccgc acat                                           744
```

<210> SEQ ID NO 287
<211> LENGTH: 15
<212> TYPE: DNA

<213> ORGANISM: Homo sapiens

<400> SEQUENCE: 287
gattactata ttcac                                                    15

<210> SEQ ID NO 288
<211> LENGTH: 51
<212> TYPE: DNA
<213> ORGANISM: Homo sapiens

<400> SEQUENCE: 288
tgggtcaacc ctgacactgg tggcacgaga tacgcgcaga agtttcaggg c             51

<210> SEQ ID NO 289
<211> LENGTH: 30
<212> TYPE: DNA
<213> ORGANISM: Homo sapiens

<400> SEQUENCE: 289
gatctaactg ggtacgacca gtacacggcc                                    30

<210> SEQ ID NO 290
<211> LENGTH: 33
<212> TYPE: DNA
<213> ORGANISM: Homo sapiens

<400> SEQUENCE: 290
gggggaaaca actttcgaaa taaaagagta cac                                33

<210> SEQ ID NO 291
<211> LENGTH: 21
<212> TYPE: DNA
<213> ORGANISM: Homo sapiens

<400> SEQUENCE: 291
tatgattcag accggccctc a                                             21

<210> SEQ ID NO 292
<211> LENGTH: 33
<212> TYPE: DNA
<213> ORGANISM: Homo sapiens

<400> SEQUENCE: 292
agcaccttcg accccttcac tgatcgtccg ctg                                33

<210> SEQ ID NO 293
<211> LENGTH: 120
<212> TYPE: PRT
<213> ORGANISM: Homo sapiens

<400> SEQUENCE: 293

Gln Val Gln Leu Val Gln Ser Gly Ala Glu Lys Lys Pro Gly Ala Ser
1               5                   10                  15

Val Lys Val Ser Cys Lys Ala Ser Gly Tyr Thr Phe Thr Asp Tyr Tyr
            20                  25                  30

Met His Trp Val Arg Gln Ala Pro Gly Gln Gly Leu Glu Trp Val Gly
        35                  40                  45

Trp Ile Asn Pro Tyr Thr Gly Gly Ala Phe Tyr Ala Gln Lys Phe Arg
    50                  55                  60

Gly Arg Val Thr Met Thr Arg Asp Thr Ser Ile Asn Thr Ala Tyr Met
65                  70                  75                  80

```
Glu Leu Ser Arg Leu Gly Ser Asp Asp Thr Ala Val Tyr Tyr Cys Ala
             85                  90                  95

Arg Glu Pro Glu Arg Phe Gly Asp Ser Thr Gly Gln Val Trp Gly Arg
            100                 105                 110

Gly Thr Met Val Thr Val Ser Ser
        115                 120

<210> SEQ ID NO 294
<211> LENGTH: 113
<212> TYPE: PRT
<213> ORGANISM: Homo sapiens

<400> SEQUENCE: 294

Gln Ala Val Leu Thr Gln Pro Ser Ser Val Ser Gly Ala Pro Arg Gln
1               5                   10                  15

Arg Val Thr Ile Ser Cys Thr Gly Ser Ser Ser Asn Ile Gly Ala Gly
             20                  25                  30

Tyr Gly Val His Trp Tyr Gln Gln Leu Pro Gly Thr Ala Pro Lys Leu
         35                  40                  45

Leu Ile Tyr Gly Asn Ser Asn Arg Pro Ser Gly Val Pro Asp Arg Phe
     50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Tyr His Trp Asp Lys Glu
                85                  90                  95

Gln Ser Gly Tyr Val Phe Gly Thr Gly Thr Gln Leu Thr Val Leu Ser
            100                 105                 110

Ala

<210> SEQ ID NO 295
<211> LENGTH: 249
<212> TYPE: PRT
<213> ORGANISM: Homo sapiens

<400> SEQUENCE: 295

Gln Val Gln Leu Val Gln Ser Gly Ala Glu Lys Lys Pro Gly Ala Ser
1               5                   10                  15

Val Lys Val Ser Cys Lys Ala Ser Gly Tyr Thr Phe Thr Asp Tyr Tyr
             20                  25                  30

Met His Trp Val Arg Gln Ala Pro Gly Gln Gly Leu Glu Trp Val Gly
         35                  40                  45

Trp Ile Asn Pro Tyr Thr Gly Gly Ala Phe Tyr Ala Gln Lys Phe Arg
     50                  55                  60

Gly Arg Val Thr Met Thr Arg Asp Thr Ser Ile Asn Thr Ala Tyr Met
65                  70                  75                  80

Glu Leu Ser Arg Leu Gly Ser Asp Asp Thr Ala Val Tyr Tyr Cys Ala
                85                  90                  95

Arg Glu Pro Glu Arg Phe Gly Asp Ser Thr Gly Gln Val Trp Gly Arg
            100                 105                 110

Gly Thr Met Val Thr Val Ser Ser Gly Gly Gly Gly Ser Gly Gly Gly
        115                 120                 125

Gly Ser Gly Gly Ser Arg Ser Ala Gln Ala Val Leu Thr Gln Pro Ser
    130                 135                 140

Ser Val Ser Gly Ala Pro Arg Gln Arg Val Thr Ile Ser Cys Thr Gly
145                 150                 155                 160

Ser Ser Ser Asn Ile Gly Ala Gly Tyr Gly Val His Trp Tyr Gln Gln
```

```
                    165                 170                 175

Leu Pro Gly Thr Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Glu Ala Asp Tyr
    210                 215                 220

Tyr Cys Tyr His Trp Asp Lys Glu Gln Ser Gly Tyr Val Phe Gly Thr
225                 230                 235                 240

Gly Thr Gln Leu Thr Val Leu Ser Ala
                245

<210> SEQ ID NO 296
<211> LENGTH: 5
<212> TYPE: PRT
<213> ORGANISM: Homo sapiens

<400> SEQUENCE: 296

Asp Tyr Tyr Met His
1               5

<210> SEQ ID NO 297
<211> LENGTH: 17
<212> TYPE: PRT
<213> ORGANISM: Homo sapiens

<400> SEQUENCE: 297

Trp Ile Asn Pro Tyr Thr Gly Gly Ala Phe Tyr Ala Gln Lys Phe Arg
1               5                   10                  15

Gly

<210> SEQ ID NO 298
<211> LENGTH: 12
<212> TYPE: PRT
<213> ORGANISM: Homo sapiens

<400> SEQUENCE: 298

Glu Pro Glu Arg Phe Gly Asp Ser Thr Gly Gln Val
1               5                   10

<210> SEQ ID NO 299
<211> LENGTH: 14
<212> TYPE: PRT
<213> ORGANISM: Homo sapiens

<400> SEQUENCE: 299

Thr Gly Ser Ser Ser Asn Ile Gly Ala Gly Tyr Gly Val His
1               5                   10

<210> SEQ ID NO 300
<211> LENGTH: 7
<212> TYPE: PRT
<213> ORGANISM: Homo sapiens

<400> SEQUENCE: 300

Gly Asn Ser Asn Arg Pro Ser
1               5

<210> SEQ ID NO 301
<211> LENGTH: 11
<212> TYPE: PRT
<213> ORGANISM: Homo sapiens
```

<400> SEQUENCE: 301

Tyr His Trp Asp Lys Glu Gln Ser Gly Tyr Val
1               5                   10

<210> SEQ ID NO 302
<211> LENGTH: 363
<212> TYPE: DNA
<213> ORGANISM: Homo sapiens

<400> SEQUENCE: 302

```
caggtccagt tggtgcagtc tggggctgag gtgaagaagc ctggggcctc agtgaaggtc    60
tcctgcaagg cttctggata caccttcacc gactactata tgcactgggt gcgacaggcc   120
cctggacaag gcttgagtg gtgggatgg atcaacccttt atactggtgg cgcattctat    180
gcacagaagt ttcggggcag ggtcacaatg accagggaca cgtccatcaa cacagcctac   240
atggagctaa gcagactggg atctgacgac acggccgtgt attattgtgc gagagaacct   300
gaaagattcg gcgactccac ggggcaggtc tggggccggg gacaatggt caccgtctcg    360
agt                                                                 363
```

<210> SEQ ID NO 303
<211> LENGTH: 339
<212> TYPE: DNA
<213> ORGANISM: Homo sapiens

<400> SEQUENCE: 303

```
caggctgtgc tgactcagcc gtcctcagtg tctggggccc caaggcagag ggtcaccatc    60
tcctgcactg ggagcagctc aacatcggg gcaggttatg gtgtacactg gtaccaacag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc taccactggg acaaggagca gagtggttat   300
gtcttcggaa ctgggaccca gctcaccgtt ttaagtgcg                          339
```

<210> SEQ ID NO 304
<211> LENGTH: 750
<212> TYPE: DNA
<213> ORGANISM: Homo sapiens

<400> SEQUENCE: 304

```
caggtccagt tggtgcagtc tggggctgag gtgaagaagc ctggggcctc agtgaaggtc    60
tcctgcaagg cttctggata caccttcacc gactactata tgcactgggt gcgacaggcc   120
cctggacaag gcttgagtg gtgggatgg atcaacccttt atactggtgg cgcattctat    180
gcacagaagt ttcggggcag ggtcacaatg accagggaca cgtccatcaa cacagcctac   240
atggagctaa gcagactggg atctgacgac acggccgtgt attattgtgc gagagaacct   300
gaaagattcg gcgactccac ggggcaggtc tggggccggg gacaatggt caccgtctcg    360
agtggggcg gcggttcagg cggaggtggc tctggcggta gcagaagtgc acaggctgtg   420
ctgactcagc cgtcctcagt gtctggggcc ccaaggcaga gggtcaccat ctcctgcact   480
gggagcagct ccaacatcgg ggcaggttat ggtgtacact ggtaccaaca gcttccagga   540
acagccccca aactcctcat ctatggtaac agcaatcggc cctcaggggt ccctgaccga   600
ttctctggct ccaagtctgg cacctcagcc tccctggcca tcactgggct ccaggctgag   660
gatgaggctg attattactg ctaccactgg gacaaggagc agagtggtta tgtcttcgga   720
```

-continued

```
actgggaccc agctcaccgt tttaagtgcg                                      750
```

<210> SEQ ID NO 305
<211> LENGTH: 15
<212> TYPE: DNA
<213> ORGANISM: Homo sapiens

<400> SEQUENCE: 305

```
gactactata tgcac                                                       15
```

<210> SEQ ID NO 306
<211> LENGTH: 51
<212> TYPE: DNA
<213> ORGANISM: Homo sapiens

<400> SEQUENCE: 306

```
tggatcaacc cttatactgg tgcgcattc tatgcacaga agtttcgggg c                51
```

<210> SEQ ID NO 307
<211> LENGTH: 36
<212> TYPE: DNA
<213> ORGANISM: Homo sapiens

<400> SEQUENCE: 307

```
gaacctgaaa gattcggcga ctccacgggg caggtc                                36
```

<210> SEQ ID NO 308
<211> LENGTH: 42
<212> TYPE: DNA
<213> ORGANISM: Homo sapiens

<400> SEQUENCE: 308

```
actgggagca gctccaacat cggggcaggt tatggtgtac ac                         42
```

<210> SEQ ID NO 309
<211> LENGTH: 21
<212> TYPE: DNA
<213> ORGANISM: Homo sapiens

<400> SEQUENCE: 309

```
ggtaacagca atcggccctc a                                                21
```

<210> SEQ ID NO 310
<211> LENGTH: 33
<212> TYPE: DNA
<213> ORGANISM: Homo sapiens

<400> SEQUENCE: 310

```
taccactggg acaaggagca gagtggttat gtc                                   33
```

<210> SEQ ID NO 311
<211> LENGTH: 121
<212> TYPE: PRT
<213> ORGANISM: Homo sapiens

<400> SEQUENCE: 311

```
Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45
```

Gly Trp Ile Asn Pro Tyr Thr Gly Ser Ala Phe Tyr Ala Gln Lys Phe
        50                  55                  60

Arg Gly Arg Ala Thr Met Thr Arg Asn Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Gly Ser Ser Gly Gln Leu Trp Gly
            100                 105                 110

Arg Gly Thr Met Val Thr Ile Ser Ser
        115                 120

<210> SEQ ID NO 312
<211> LENGTH: 113
<212> TYPE: PRT
<213> ORGANISM: Homo sapiens

<400> SEQUENCE: 312

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Ile Gly Pro Gly
            20                  25                  30

Tyr Gly Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

Leu Ser Gly Tyr Val Phe Gly Thr Gly Thr Gln Leu Thr Val Leu Ser
            100                 105                 110

Ala

<210> SEQ ID NO 313
<211> LENGTH: 250
<212> TYPE: PRT
<213> ORGANISM: Homo sapiens

<400> SEQUENCE: 313

Glu Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Ala Thr Met Thr Arg Asn Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Gly Glu Ser Ser Gly Gln Leu Trp Gly
            100                 105                 110

Arg Gly Thr Met Val Thr Ile Ser Ser Gly Gly Gly Gly Ser Gly Gly
        115                 120                 125

```
Gly Gly Ser Gly Gly Ser Gly Ser Ala Gln Ala Val Leu Thr Gln Pro
        130                 135                 140

Ser Ser Val Ser Gly Ala Pro Gly Gln Arg Val Thr Ile Ser Cys Thr
145                 150                 155                 160

Gly Ser Ser Ser Asn Ile Gly Pro Gly Tyr Gly Val His Trp Tyr Gln
                165                 170                 175

Gln Leu Pro Gly Thr Ala Pro Lys Leu Leu Ile Tyr Gly Asp Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Gly Leu Ser Gly Tyr Val Phe Gly
225                 230                 235                 240

Thr Gly Thr Gln Leu Thr Val Leu Ser Ala
                245                 250

<210> SEQ ID NO 314
<211> LENGTH: 5
<212> TYPE: PRT
<213> ORGANISM: Homo sapiens

<400> SEQUENCE: 314

Asp Tyr Tyr Met His
1               5

<210> SEQ ID NO 315
<211> LENGTH: 17
<212> TYPE: PRT
<213> ORGANISM: Homo sapiens

<400> SEQUENCE: 315

Trp Ile Asn Pro Tyr Thr Gly Ser Ala Phe Tyr Ala Gln Lys Phe Arg
1               5                   10                  15

Gly

<210> SEQ ID NO 316
<211> LENGTH: 12
<212> TYPE: PRT
<213> ORGANISM: Homo sapiens

<400> SEQUENCE: 316

Glu Pro Glu Lys Phe Gly Glu Ser Ser Gly Gln Leu
1               5                   10

<210> SEQ ID NO 317
<211> LENGTH: 14
<212> TYPE: PRT
<213> ORGANISM: Homo sapiens

<400> SEQUENCE: 317

Thr Gly Ser Ser Ser Asn Ile Gly Pro Gly Tyr Gly Val His
1               5                   10

<210> SEQ ID NO 318
<211> LENGTH: 7
<212> TYPE: PRT
<213> ORGANISM: Homo sapiens

<400> SEQUENCE: 318

Gly Asp Ser Asn Arg Pro Ser
```

<210> SEQ ID NO 319
<211> LENGTH: 11
<212> TYPE: PRT
<213> ORGANISM: Homo sapiens

<400> SEQUENCE: 319

Gln Ser Tyr Asp Ser Gly Leu Ser Gly Tyr Val
1               5                   10

<210> SEQ ID NO 320
<211> LENGTH: 363
<212> TYPE: DNA
<213> ORGANISM: Homo sapiens

<400> SEQUENCE: 320

```
gaagtgcagc tggtgcagtc tggggctgag gtgaagaagc ctggggcctc agtgaaggtc      60
tcctgtcagg cttctggata caccttcacc gactactata tgcactgggt gcgacaggcc    120
cctggacaag gcttgagtg gtggggtgg atcaacccctt atactggtag cgcattctat     180
gcacagaagt tccggggcag ggccacaatg accaggaaca cgtccatcaa cacagcctac    240
atggagctga gcagactggg atctgacgac acggccgtgt attattgtgc gagagaacct    300
gaaaaattcg gcgagtccag cggccagttg tggggccggg ggacaatggt caccatctcg    360
agt                                                                  363
```

<210> SEQ ID NO 321
<211> LENGTH: 339
<212> TYPE: DNA
<213> ORGANISM: Homo sapiens

<400> SEQUENCE: 321

```
caggctgtgc tgactcagcc gtcctcagtg tctggggccc cagggcagag ggtcaccatc      60
tcctgcactg ggagcagctc caacatcggg gcaggttatg gtgtacactg gtaccaacag    120
cttccaggaa cagcccccaa actcctcatc tatggtgaca gcaatcggcc ctcaggggtc    180
cctgaccgat tctctggctc caagtctggc acctcagcct ccctggccat cactgggctc    240
caggccgagg atgaggctga ttattactgc cagtcctatg acagcggcct gagtggttat    300
gtcttcggaa ctgggaccca gctcaccgtt ttaagtgcg                            339
```

<210> SEQ ID NO 322
<211> LENGTH: 750
<212> TYPE: DNA
<213> ORGANISM: Homo sapiens

<400> SEQUENCE: 322

```
gaagtgcagc tggtgcagtc tggggctgag gtgaagaagc ctggggcctc agtgaaggtc      60
tcctgtcagg cttctggata caccttcacc gactactata tgcactgggt gcgacaggcc    120
cctggacaag gcttgagtg gtggggtgg atcaacccctt atactggtag cgcattctat     180
gcacagaagt tccggggcag ggccacaatg accaggaaca cgtccatcaa cacagcctac    240
atggagctga gcagactggg atctgacgac acggccgtgt attattgtgc gagagaacct    300
gaaaaattcg gcgagtccag cggccagttg tggggccggg ggacaatggt caccatctcg    360
agtggaggcg gcggttcagg cggaggtggc tctggcggta gcggaagtgc acaggctgtg    420
ctgactcagc cgtcctcagt gtctggggcc ccagggcaga gggtcaccat ctcctgcact    480
```

-continued

| | |
|---|---|
| gggagcagct ccaacatcgg ggcaggttat ggtgtacact ggtaccaaca gcttccagga | 540 |
| acagccccca aactcctcat ctatggtgac agcaatcggc cctcagggt ccctgaccga | 600 |
| ttctctggct ccaagtctgg cacctcagcc tccctggcca tcactgggct ccaggccgag | 660 |
| gatgaggctg attattactg ccagtcctat gacagcggcc tgagtggtta tgtcttcgga | 720 |
| actgggaccc agctcaccgt tttaagtgcg | 750 |

<210> SEQ ID NO 323
<211> LENGTH: 15
<212> TYPE: DNA
<213> ORGANISM: Homo sapiens

<400> SEQUENCE: 323

| | |
|---|---|
| gactactata tgcac | 15 |

<210> SEQ ID NO 324
<211> LENGTH: 51
<212> TYPE: DNA
<213> ORGANISM: Homo sapiens

<400> SEQUENCE: 324

| | |
|---|---|
| tggatcaacc cttatactgg tagcgcattc tatgcacaga gtttcggggg c | 51 |

<210> SEQ ID NO 325
<211> LENGTH: 36
<212> TYPE: DNA
<213> ORGANISM: Homo sapiens

<400> SEQUENCE: 325

| | |
|---|---|
| gaacctgaaa aattcggcga gtccagcggc cagttg | 36 |

<210> SEQ ID NO 326
<211> LENGTH: 42
<212> TYPE: DNA
<213> ORGANISM: Homo sapiens

<400> SEQUENCE: 326

| | |
|---|---|
| actgggagca gctccaacat cggggcaggt tatggtgtac ac | 42 |

<210> SEQ ID NO 327
<211> LENGTH: 21
<212> TYPE: DNA
<213> ORGANISM: Homo sapiens

<400> SEQUENCE: 327

| | |
|---|---|
| ggtgacagca atcggccctc a | 21 |

<210> SEQ ID NO 328
<211> LENGTH: 33
<212> TYPE: DNA
<213> ORGANISM: Homo sapiens

<400> SEQUENCE: 328

| | |
|---|---|
| cagtcctatg acagcggcct gagtggttat gtc | 33 |

<210> SEQ ID NO 329
<211> LENGTH: 121
<212> TYPE: PRT
<213> ORGANISM: Homo sapiens

<400> SEQUENCE: 329

Gln Val Gln Leu Val Gln Ser Gly Ala Glu Val Lys Lys Pro Gly Ala

-continued

```
              1               5                  10                 15
            Ser Val Lys Val Ser Cys Lys Ala Ser Gly Tyr Thr Phe Thr His Tyr
                            20                  25                 30

Tyr Met His Trp Val Arg Gln Ala Pro Gly Gln Gly Leu Glu Trp Val
                        35                  40                 45

Gly Trp Ile Asn Pro Tyr Thr Gly Ala Phe Tyr Ala Gln Lys Phe
                    50                  55                  60

Gln Gly Arg Val Thr Met Thr Arg Asp Thr Ser Ile Asn Thr Ala Tyr
            65                  70                  75                 80

Met Glu Leu Ser Arg Leu Gly Ser Asp Asp Thr Ala Val Tyr Tyr Cys
                            85                  90                 95

Ala Arg Glu Pro Glu Lys Phe Asp Ser Pro Asn Ala Glu Ile Trp Gly
                            100                 105                110

Arg Gly Thr Met Val Thr Ile Ser Ser
                        115                 120
```

<210> SEQ ID NO 330
<211> LENGTH: 113
<212> TYPE: PRT
<213> ORGANISM: Homo sapiens

<400> SEQUENCE: 330

```
            Gln Ala Val Leu Thr Gln Pro Ser Ser Val Ser Gly Ala Pro Gly Gln
            1               5                  10                 15

Arg Val Thr Ile Ser Cys Thr Gly Ser Ser Asn Ile Gly Ala Gly
                            20                  25                 30

Tyr Gly Val His Trp Tyr Gln Gln Leu Pro Gly Thr Ala Pro Lys Leu
                        35                  40                 45

Leu Ile Tyr Gly Asn Ser Asn Arg Pro Ser Gly Val Pro Asp Arg Phe
                    50                  55                  60

Ser Gly Ser Lys Ser Gly Thr Ser Ala Ser Leu Ala Ile Thr Gly Leu
            65                  70                  75                 80

Gln Ala Glu Asp Glu Ala Asp Tyr Tyr Cys Gln Ser Tyr Asp Ser Ser
                            85                  90                 95

Leu Ser Gly Tyr Val Phe Gly Thr Gly Thr Gln Leu Thr Val Leu Ser
                            100                 105                110

Ala
```

<210> SEQ ID NO 331
<211> LENGTH: 250
<212> TYPE: PRT
<213> ORGANISM: Homo sapiens

<400> SEQUENCE: 331

```
            Gln Val Gln Leu Val Gln Ser Gly Ala Glu Val Lys Lys Pro Gly Ala
            1               5                  10                 15

Ser Val Lys Val Ser Cys Lys Ala Ser Gly Tyr Thr Phe Thr His Tyr
                            20                  25                 30

Tyr Met His Trp Val Arg Gln Ala Pro Gly Gln Gly Leu Glu Trp Val
                        35                  40                 45

Gly Trp Ile Asn Pro Tyr Thr Gly Ala Phe Tyr Ala Gln Lys Phe
                    50                  55                  60

Gln Gly Arg Val Thr Met Thr Arg Asp Thr Ser Ile Asn Thr Ala Tyr
            65                  70                  75                 80

Met Glu Leu Ser Arg Leu Gly Ser Asp Asp Thr Ala Val Tyr Tyr Cys
                            85                  90                 95
```

```
Ala Arg Glu Pro Glu Lys Phe Asp Ser Pro Asn Ala Glu Ile Trp Gly
            100                 105                 110

Arg Gly Thr Met Val Thr Ile Ser Glu Gly Gly Ser Gly Gly
            115                 120                 125

Gly Gly Ser Gly Gly Ser Gly Ser Ala Gln Ala Val Leu Thr Gln Pro
        130                 135                 140

Ser Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
210                 215                 220

Tyr Tyr Cys Gln Ser Tyr Asp Ser Ser Leu Ser Gly Tyr Val Phe Gly
225                 230                 235                 240

Thr Gly Thr Gln Leu Thr Val Leu Ser Ala
            245                 250

<210> SEQ ID NO 332
<211> LENGTH: 5
<212> TYPE: PRT
<213> ORGANISM: Homo sapiens

<400> SEQUENCE: 332

His Tyr Tyr Met His
1               5

<210> SEQ ID NO 333
<211> LENGTH: 17
<212> TYPE: PRT
<213> ORGANISM: Homo sapiens

<400> SEQUENCE: 333

Trp Ile Asn Pro Tyr Thr Gly Gly Ala Phe Tyr Ala Gln Lys Phe Gln
1               5                   10                  15

Gly

<210> SEQ ID NO 334
<211> LENGTH: 12
<212> TYPE: PRT
<213> ORGANISM: Homo sapiens

<400> SEQUENCE: 334

Glu Pro Glu Lys Phe Asp Ser Pro Asn Ala Glu Ile
1               5                   10

<210> SEQ ID NO 335
<211> LENGTH: 14
<212> TYPE: PRT
<213> ORGANISM: Homo sapiens

<400> SEQUENCE: 335

Thr Gly Ser Ser Ser Asn Ile Gly Ala Gly Tyr Gly Val His
1               5                   10

<210> SEQ ID NO 336
```

<211> LENGTH: 7
<212> TYPE: PRT
<213> ORGANISM: Homo sapiens

<400> SEQUENCE: 336

Gly Asn Ser Asn Arg Pro Ser
1               5

<210> SEQ ID NO 337
<211> LENGTH: 11
<212> TYPE: PRT
<213> ORGANISM: Homo sapiens

<400> SEQUENCE: 337

Gln Ser Tyr Asp Ser Ser Leu Ser Gly Tyr Val
1               5                   10

<210> SEQ ID NO 338
<211> LENGTH: 363
<212> TYPE: DNA
<213> ORGANISM: Homo sapiens

<400> SEQUENCE: 338
caggtccagc tggtgcagtc tggggctgag gtgaaaaagc ctggggcctc agtgaaggtc      60
tcctgcaagg cttctggata caccttcacc cactactata tgcactgggt gcgacaggcc     120
cctggacaag gcttgagtg gtgggatgg atcaacccctt atactggtgg cgcattctat      180
gcacagaagt tcagggcag ggtcacaatg accagggaca cgtccatcaa cacagcctac     240
atggagctga gcagactggg atctgacgac acggccgtgt attattgtgc gagagaacct    300
gaaaaattcg actcgccgaa cgccgagatc tggggccggg ggacaatggt caccatctcg    360
agt                                                                   363

<210> SEQ ID NO 339
<211> LENGTH: 339
<212> TYPE: DNA
<213> ORGANISM: Homo sapiens

<400> SEQUENCE: 339
caggctgtgc tgactcagcc gtcctcagtg tctggggccc cagggcagag ggtcaccatc      60
tcctgcactg ggagcagctc caacatcggg gcaggttatg gtgtacactg gtaccaacag    120
cttccaggaa cagcccccaa actcctcatc tatggtaaca gcaatcggcc ctcaggggtc    180
cctgaccgat tctctggctc caagtctggc acctcagcct ccctggccat cactgggctc    240
caggctgagg atgaggctga ttattactgc cagtcctatg acagcagcct gagtggttat    300
gtcttcggaa ccgggaccca gctcaccgtt ttaagtgcg                            339

<210> SEQ ID NO 340
<211> LENGTH: 750
<212> TYPE: DNA
<213> ORGANISM: Homo sapiens

<400> SEQUENCE: 340
caggtccagc tggtgcagtc tggggctgag gtgaaaaagc ctggggcctc agtgaaggtc      60
tcctgcaagg cttctggata caccttcacc cactactata tgcactgggt gcgacaggcc     120
cctggacaag gcttgagtg gtgggatgg atcaacccctt atactggtgg cgcattctat      180
gcacagaagt tcagggcag ggtcacaatg accagggaca cgtccatcaa cacagcctac     240
atggagctga gcagactggg atctgacgac acggccgtgt attattgtgc gagagaacct    300

```
gaaaaattcg actcgccgaa cgccgagatc tggggccggg ggacaatggt caccatctcg    360
agtgaaggcg gcggttcagg cggaggtggc tctggcggta gcggaagtgc acaggctgtg    420
ctgactcagc cgtcctcagt gtctgggggcc ccagggcaga gggtcaccat ctcctgcact    480
gggagcagct ccaacatcgg ggcaggttat ggtgtacact ggtaccaaca gcttccagga    540
acagccccca aactcctcat ctatggtaac agcaatcggc cctcaggggt ccctgaccga    600
ttctctggct ccaagtctgg cacctcagcc tccctggcca tcactgggct ccaggctgag    660
gatgaggctg attattactg ccagtcctat gacagcagcc tgagtggtta tgtcttcgga    720
accgggaccc agctcaccgt tttaagtgcg                                     750
```

```
<210> SEQ ID NO 341
<211> LENGTH: 15
<212> TYPE: DNA
<213> ORGANISM: Homo sapiens

<400> SEQUENCE: 341
cactactata tgcac                                                     15

<210> SEQ ID NO 342
<211> LENGTH: 51
<212> TYPE: DNA
<213> ORGANISM: Homo sapiens

<400> SEQUENCE: 342
tggatcaacc cttatactgg tggcgcattc tatgcacaga gtttcaggg c              51

<210> SEQ ID NO 343
<211> LENGTH: 36
<212> TYPE: DNA
<213> ORGANISM: Homo sapiens

<400> SEQUENCE: 343
gaacctgaaa aattcgactc gccgaacgcc gagatc                              36

<210> SEQ ID NO 344
<211> LENGTH: 42
<212> TYPE: DNA
<213> ORGANISM: Homo sapiens

<400> SEQUENCE: 344
actgggagca gctccaacat cggggcaggt tatggtgtac ac                       42

<210> SEQ ID NO 345
<211> LENGTH: 21
<212> TYPE: DNA
<213> ORGANISM: Homo sapiens

<400> SEQUENCE: 345
ggtaacagca atcggccctc a                                              21

<210> SEQ ID NO 346
<211> LENGTH: 33
<212> TYPE: DNA
<213> ORGANISM: Homo sapiens

<400> SEQUENCE: 346
cagtcctatg acagcagcct gagtggttat gtc                                 33

<210> SEQ ID NO 347
```

```
<211> LENGTH: 121
<212> TYPE: PRT
<213> ORGANISM: Homo sapiens

<400> SEQUENCE: 347

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Asn Thr Ala Tyr
65                  70                  75                  80

Met Glu Leu Ser Arg Leu Gly Ser Asp Asp Thr Ala Val Tyr Tyr Cys
                85                  90                  95

Ala Arg Glu Pro Glu Lys Phe Asp Ser Asp Asp Ser Val Trp Gly
            100                 105                 110

Arg Gly Thr Met Val Thr Val Ser Gly
        115                 120

<210> SEQ ID NO 348
<211> LENGTH: 112
<212> TYPE: PRT
<213> ORGANISM: Homo sapiens

<400> SEQUENCE: 348

Gln Ala Val Leu Thr Pro Pro Ser Val Ser Gly Ala Pro Gly Gln Arg
1               5                   10                  15

Val Thr Ile Ser Cys Thr Gly Ser Ser Asn Ile Gly Ala Gly Tyr
            20                  25                  30

Gly Val His Trp Tyr Gln Gln Leu Pro Gly Thr Ala Pro Lys Leu Ile
        35                  40                  45

Ile Tyr Gly Asp Ser Ser Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Asn Ser Leu
                85                  90                  95

Ser Gly Tyr Val Phe Gly Thr Gly Thr Gln Leu Thr Val Leu Ser Ala
            100                 105                 110

<210> SEQ ID NO 349
<211> LENGTH: 249
<212> TYPE: PRT
<213> ORGANISM: Homo sapiens

<400> SEQUENCE: 349

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60
```

Arg Gly Arg Val Thr Met Thr Arg Asp Thr Ser Ile Asn Thr Ala Tyr
65                  70                  75                  80

Met Glu Leu Ser Arg Leu Gly Ser Asp Thr Ala Val Tyr Tyr Cys
                85                  90                  95

Ala Arg Glu Pro Glu Lys Phe Asp Ser Asp Ser Asp Val Trp Gly
            100                 105                 110

Arg Gly Thr Met Val Thr Val Ser Gly Gly Gly Ser Gly Gly
            115                 120                 125

Gly Gly Ser Gly Gly Ser Ser Ala Gln Ala Val Leu Thr Pro Pro
        130                 135                 140

Ser Val Ser Gly Ala Pro Gly Gln Arg Val Thr Ile Ser Cys Thr Gly
145                 150                 155                 160

Ser Ser Ser Asn Ile Gly Ala Gly Tyr Gly Val His Trp Tyr Gln Gln
                165                 170                 175

Leu Pro Gly Thr Ala Pro Lys Leu Ile Ile Tyr Gly Asp Ser Ser Arg
            180                 185                 190

Pro Ser Gly Val Pro Asp Arg Phe Ser Gly Ser Lys Ser Gly Thr Ser
        195                 200                 205

Ala Ser Leu Ala Ile Thr Gly Leu Gln Ala Glu Asp Glu Ala Asp Tyr
210                 215                 220

Tyr Cys Gln Ser Tyr Asp Asn Ser Leu Ser Gly Tyr Val Phe Gly Thr
225                 230                 235                 240

Gly Thr Gln Leu Thr Val Leu Ser Ala
                245

<210> SEQ ID NO 350
<211> LENGTH: 5
<212> TYPE: PRT
<213> ORGANISM: Homo sapiens

<400> SEQUENCE: 350

Asn Tyr Tyr Met His
1               5

<210> SEQ ID NO 351
<211> LENGTH: 17
<212> TYPE: PRT
<213> ORGANISM: Homo sapiens

<400> SEQUENCE: 351

Trp Ile Asn Pro Tyr Thr Gly Ser Ala Phe Tyr Ala Gln Lys Phe Arg
1               5                   10                  15

Gly

<210> SEQ ID NO 352
<211> LENGTH: 12
<212> TYPE: PRT
<213> ORGANISM: Homo sapiens

<400> SEQUENCE: 352

Glu Pro Glu Lys Phe Asp Ser Asp Ser Asp Val
1               5                   10

<210> SEQ ID NO 353
<211> LENGTH: 14
<212> TYPE: PRT
<213> ORGANISM: Homo sapiens

<400> SEQUENCE: 353

```
Thr Gly Ser Ser Ser Asn Ile Gly Ala Gly Tyr Gly Val His
1               5                  10
```

<210> SEQ ID NO 354
<211> LENGTH: 8
<212> TYPE: PRT
<213> ORGANISM: Homo sapiens

<400> SEQUENCE: 354

```
Gly Asp Ser Ser Arg Pro Ser Gly
1               5
```

<210> SEQ ID NO 355
<211> LENGTH: 11
<212> TYPE: PRT
<213> ORGANISM: Homo sapiens

<400> SEQUENCE: 355

```
Gln Ser Tyr Asp Asn Ser Leu Ser Gly Tyr Val
1               5                   10
```

<210> SEQ ID NO 356
<211> LENGTH: 363
<212> TYPE: DNA
<213> ORGANISM: Homo sapiens

<400> SEQUENCE: 356

| caggttcagc tggtgcagtc tggggctgag gtgaagaagc ctggggcctc agtgaaggtc | 60 |
| tcctgcaagg cttctggata caccttcacc aactactata tgcactgggt gcgacaggcc | 120 |
| cctggacagg ggcttgagtg gtgggatgg atcaacccttt atactggtag cgcattctat | 180 |
| gcacagaagt tcgggcag ggttacaatg accagggaca cgtccatcaa cacagcctac | 240 |
| atggagctga gcagactggg atctgacgac acggccgtgt attattgtgc gagagaacct | 300 |
| gaaaaattcg actccgacga ctccgacgtc tggggccgcg ggacaatggt caccgtctcg | 360 |
| ggt | 363 |

<210> SEQ ID NO 357
<211> LENGTH: 339
<212> TYPE: DNA
<213> ORGANISM: Homo sapiens

<400> SEQUENCE: 357

| caggctgtgc tgactcagcc gccctcagtg tctggggccc cagggcagag ggtcaccatc | 60 |
| tcctgcactg ggagcagctc caacatcggg gcaggttatg gtgtacactg gtaccaacag | 120 |
| cttccaggaa cagcccccaa actcatcatc tatggtgaca gcagtcggcc ctcagggggtc | 180 |
| cctgaccgat tctctggctc caagtctggc acctcagcct ccctggccat cactgggctc | 240 |
| caggctgagg atgaggctga ttattactgc cagtcctatg acaacagcct gagcggttat | 300 |
| gtcttcggaa ctgggaccca gctcaccgtt ttaagtgcg | 339 |

<210> SEQ ID NO 358
<211> LENGTH: 750
<212> TYPE: DNA
<213> ORGANISM: Homo sapiens

<400> SEQUENCE: 358

| caggttcagc tggtgcagtc tggggctgag gtgaagaagc ctggggcctc agtgaaggtc | 60 |
| tcctgcaagg cttctggata caccttcacc aactactata tgcactgggt gcgacaggcc | 120 |

```
cctggacagg ggcttgagtg ggtgggatgg atcaaccctt atactggtag cgcattctat    180
gcacagaagt ttcggggcag ggttacaatg accagggaca cgtccatcaa cacagcctac    240
atggagctga gcagactggg atctgacgac acggccgtgt attattgtgc gagagaacct    300
gaaaaattcg actccgacga ctccgacgtc tggggccgcg ggacaatggt caccgtctcg    360
ggtggaggcg gcagttcagg cggaggtggc tctggcggta gcggaagtgc acaggctgtg    420
ctgactcagc cgccctcagt gtctggggcc cagggcaga gggtcaccat ctcctgcact    480
gggagcagct ccaacatcgg ggcaggttat ggtgtacact ggtaccaaca gcttccagga    540
acagccccca aactcatcat ctatggtgac agcagtcggc cctcaggggt ccctgaccga    600
ttctctggct ccaagtctgg cacctcagcc tccctggcca tcactgggct ccaggctgag    660
gatgaggctg attattactg ccagtcctat gacaacagcc tgagcggtta tgtcttcgga    720
actgggaccc agctcaccgt tttaagtgcg                                     750

<210> SEQ ID NO 359
<211> LENGTH: 15
<212> TYPE: DNA
<213> ORGANISM: Homo sapiens

<400> SEQUENCE: 359
aactactata tgcac                                                      15

<210> SEQ ID NO 360
<211> LENGTH: 51
<212> TYPE: DNA
<213> ORGANISM: Homo sapiens

<400> SEQUENCE: 360
tggatcaacc cttatactgg tagcgcattc tatgcacaga gtttcggggg c              51

<210> SEQ ID NO 361
<211> LENGTH: 36
<212> TYPE: DNA
<213> ORGANISM: Homo sapiens

<400> SEQUENCE: 361
gaacctgaaa aattcgactc cgacgactcc gacgtc                               36

<210> SEQ ID NO 362
<211> LENGTH: 42
<212> TYPE: DNA
<213> ORGANISM: Homo sapiens

<400> SEQUENCE: 362
actgggagca gctccaacat cggggcaggt tatggtgtac ac                        42

<210> SEQ ID NO 363
<211> LENGTH: 24
<212> TYPE: DNA
<213> ORGANISM: Homo sapiens

<400> SEQUENCE: 363
ggtgacagca gtcggccctc aggg                                            24

<210> SEQ ID NO 364
<211> LENGTH: 33
<212> TYPE: DNA
<213> ORGANISM: Homo sapiens

<400> SEQUENCE: 364
```
cagtcctatg acaacagcct gagcggttat gtc                                33

<210> SEQ ID NO 365
<211> LENGTH: 119
<212> TYPE: PRT
<213> ORGANISM: Homo sapiens

<400> SEQUENCE: 365

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Ile Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Val Trp Asp Pro Leu Asp Tyr Trp Gly Arg Gly
            100                 105                 110

Thr Leu Val Thr Val Ser Ser
        115

<210> SEQ ID NO 366
<211> LENGTH: 108
<212> TYPE: PRT
<213> ORGANISM: Homo sapiens

<400> SEQUENCE: 366

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Val Glu Ile Lys Arg
            100                 105

<210> SEQ ID NO 367
<211> LENGTH: 243
<212> TYPE: PRT
<213> ORGANISM: Homo sapiens

<400> SEQUENCE: 367

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val

```
                 35                  40                  45
Ser Ala Ile Ser Gly Ser Gly Gly Ser Thr Tyr Tyr Ala Asp Ser Val
 50                  55                  60

Lys Gly Arg Ile Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Trp Val Trp Asp Pro Leu Asp Tyr Trp Gly Arg Gly
                100                 105                 110

Thr Leu Val Thr Val Ser Ser Gly Gly Gly Ser Gly Gly Gly
                115                 120                 125

Ser Gly Gly Gly Ser Asp Ile Gln Met Thr Gln Ser Pro Ser Thr
130                 135                 140

Leu Ser Ala Ser Val Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Val
                180                 185                 190

Pro Ser Arg Phe Ser Gly Ser Gly Ser Gly Thr Asp Phe Thr Leu Thr
                195                 200                 205

Ile Ser Ser Leu Gln Pro Asp Asp Phe Ala Thr Tyr Tyr Cys Gln Gln
210                 215                 220

Tyr Ser Asn Tyr Pro Leu Thr Phe Gly Gly Gly Thr Lys Val Glu Ile
225                 230                 235                 240

Lys Arg Ala

<210> SEQ ID NO 368
<211> LENGTH: 5
<212> TYPE: PRT
<213> ORGANISM: Homo sapiens

<400> SEQUENCE: 368

Asp Tyr Tyr Met Ser
1               5

<210> SEQ ID NO 369
<211> LENGTH: 17
<212> TYPE: PRT
<213> ORGANISM: Homo sapiens

<400> SEQUENCE: 369

Ala Ile Ser Gly Ser Gly Gly Ser Thr Tyr Tyr Ala Asp Ser Val Lys
1               5                   10                  15

Gly

<210> SEQ ID NO 370
<211> LENGTH: 10
<212> TYPE: PRT
<213> ORGANISM: Homo sapiens

<400> SEQUENCE: 370

Gly Leu Trp Val Trp Asp Pro Leu Asp Tyr
1               5                   10

<210> SEQ ID NO 371
<211> LENGTH: 11
<212> TYPE: PRT
```

<213> ORGANISM: Homo sapiens

<400> SEQUENCE: 371

Arg Ala Ser Glu Gly Ile Tyr His Trp Leu Ala
1               5                   10

<210> SEQ ID NO 372
<211> LENGTH: 7
<212> TYPE: PRT
<213> ORGANISM: Homo sapiens

<400> SEQUENCE: 372

Lys Ala Ser Ser Leu Ala Ser
1               5

<210> SEQ ID NO 373
<211> LENGTH: 9
<212> TYPE: PRT
<213> ORGANISM: Homo sapiens

<400> SEQUENCE: 373

Gln Gln Tyr Ser Asn Tyr Pro Leu Thr
1               5

<210> SEQ ID NO 374
<211> LENGTH: 357
<212> TYPE: DNA
<213> ORGANISM: Homo sapiens

<400> SEQUENCE: 374

```
caagtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtctcagct attagtggta gtggtggtag cacatactac     180
gcagactccg tgaagggccg gatcaccatc tccagagaca acgccaagaa ctcactgtat     240
ctgcaaatga acagcctgag agctgaggac acggccgtgt attactgtgc gagagggctt     300
tgggtttggg atcctcttga ctactggggc agaggaaccc tggtcaccgt ctcttca       357
```

<210> SEQ ID NO 375
<211> LENGTH: 324
<212> TYPE: DNA
<213> ORGANISM: Homo sapiens

<400> SEQUENCE: 375

```
gacatccaga tgacccagtc tccttccacc ctgtctgcat ctgttggaga cagagtcacc      60
atcacctgcc gggccagtga gggtatttat cactggttgg cctggtatca gcagaagcca     120
gggaaagccc ctaaactcct gatctataag gcctctagtt tagccagtgg ggtcccatca     180
aggttcagcg gcagtggatc tgggacagag ttcactctca ccatcagcag cctgcagcct     240
gatgattttg caacttatta ctgccaacaa tatagtaatt atccgctcac tttcggcgga     300
gggaccaagg tggagatcaa acgt                                            324
```

<210> SEQ ID NO 376
<211> LENGTH: 729
<212> TYPE: DNA
<213> ORGANISM: Homo sapiens

<400> SEQUENCE: 376

```
caagtgcagc tggtggagtc tgggggaggc ttggtcaagc ctggagggtc cctgagactc      60
```

-continued

| | | |
|---|---|---|
| tcctgtgcag cctctggatt caccttcagt gactactaca tgagctggat ccgccaggct | 120 | |
| ccagggaagg ggctggagtg ggtctcagct attagtggta gtggtggtag cacatactac | 180 | |
| gcagactccg tgaagggccg gatcaccatc tccagagaca acgccaagaa ctcactgtat | 240 | |
| ctgcaaatga acagcctgag agctgaggac acggccgtgt attactgtgc gagagggctt | 300 | |
| tgggtttggg atcctcttga ctactgggc agaggaaccc tggtcaccgt ctcttcaggt | 360 | |
| ggaggcggtt caggcggagg tggcagcggc ggtggcggat cggacatcca gatgacccag | 420 | |
| tctccttcca ccctgtctgc atctgttgga gacagagtca ccatcacctg ccgggccagt | 480 | |
| gagggtattt atcactggtt ggcctggtat cagcagaagc cagggaaagc ccctaaactc | 540 | |
| ctgatctata aggcctctag tttagccagt ggggtcccat caaggttcag cggcagtgga | 600 | |
| tctgggacag atttcactct caccatcagc agcctgcagc ctgatgattt tgcaacttat | 660 | |
| tactgccaac aatatagtaa ttatccgctc actttcggcg agggaccaa ggtggagatc | 720 | |
| aaacgtgcg | 729 | |

<210> SEQ ID NO 377
<211> LENGTH: 15
<212> TYPE: DNA
<213> ORGANISM: Homo sapiens

<400> SEQUENCE: 377
gactactaca tgagc    15

<210> SEQ ID NO 378
<211> LENGTH: 51
<212> TYPE: DNA
<213> ORGANISM: Homo sapiens

<400> SEQUENCE: 378
gctattagtg gtagtggtgg tagcacatac tacgcagact ccgtgaaggg c    51

<210> SEQ ID NO 379
<211> LENGTH: 30
<212> TYPE: DNA
<213> ORGANISM: Homo sapiens

<400> SEQUENCE: 379
gggctttggg tttgggatcc tcttgactac    30

<210> SEQ ID NO 380
<211> LENGTH: 33
<212> TYPE: DNA
<213> ORGANISM: Homo sapiens

<400> SEQUENCE: 380
cgggccagtg agggtattta tcactggttg gcc    33

<210> SEQ ID NO 381
<211> LENGTH: 21
<212> TYPE: DNA
<213> ORGANISM: Homo sapiens

<400> SEQUENCE: 381
aaggcctcta gtttagccag t    21

<210> SEQ ID NO 382
<211> LENGTH: 27
<212> TYPE: DNA
<213> ORGANISM: Homo sapiens -continued

```
<400> SEQUENCE: 382
caacaatata gtaattatcc gctcact                                              27

<210> SEQ ID NO 383
<211> LENGTH: 5
<212> TYPE: PRT
<213> ORGANISM: Homo sapiens

<400> SEQUENCE: 383

Ser Tyr Gly Ile Ser
1               5

<210> SEQ ID NO 384
<211> LENGTH: 108
<212> TYPE: PRT
<213> ORGANISM: Homo sapiens

<400> SEQUENCE: 384

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Asn Tyr Pro Leu
                85                  90                  95

Thr Phe Gly Gly Gly Thr Lys Val Glu Ile Lys Arg
            100                 105

<210> SEQ ID NO 385
<211> LENGTH: 243
<212> TYPE: PRT
<213> ORGANISM: Homo sapiens

<400> SEQUENCE: 385

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Arg Gly Tyr Tyr Ala Phe Asp Ile Trp Gly Gln Gly
            100                 105                 110

Thr Leu Val Thr Val Ser Ser Gly Gly Gly Ser Gly Gly Gly
        115                 120                 125

Ser Gly Gly Gly Gly Ser Asp Ile Gln Met Thr Gln Ser Pro Ser Thr
    130                 135                 140
```

```
Leu Ser Ala Ser Val Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Thr Tyr Tyr Cys Gln Gln
        210                 215                 220

Tyr Ser Asn Tyr Pro Leu Thr Phe Gly Gly Gly Thr Lys Val Glu Ile
225                 230                 235                 240

Lys Arg Ala

<210> SEQ ID NO 386
<211> LENGTH: 5
<212> TYPE: PRT
<213> ORGANISM: Homo sapiens

<400> SEQUENCE: 386

Ser Tyr Gly Ile Ser
1               5

<210> SEQ ID NO 387
<211> LENGTH: 17
<212> TYPE: PRT
<213> ORGANISM: Homo sapiens

<400> SEQUENCE: 387

Trp Ile Ser Ala Tyr Thr Gly Asn Thr Asn Tyr Ala Gln Lys Phe Gln
1               5                   10                  15

Gly

<210> SEQ ID NO 388
<211> LENGTH: 10
<212> TYPE: PRT
<213> ORGANISM: Homo sapiens

<400> SEQUENCE: 388

Asp Arg Gly Tyr Tyr Asp Ala Phe Asp Ile
1               5                   10

<210> SEQ ID NO 389
<211> LENGTH: 11
<212> TYPE: PRT
<213> ORGANISM: Homo sapiens

<400> SEQUENCE: 389

Arg Ala Ser Glu Gly Ile Tyr His Trp Leu Ala
1               5                   10

<210> SEQ ID NO 390
<211> LENGTH: 7
<212> TYPE: PRT
<213> ORGANISM: Homo sapiens

<400> SEQUENCE: 390

Lys Ala Ser Ser Leu Ala Ser
1               5
```

```
<210> SEQ ID NO 391
<211> LENGTH: 9
<212> TYPE: PRT
<213> ORGANISM: Homo sapiens

<400> SEQUENCE: 391

Gln Gln Tyr Ser Asn Tyr Pro Leu Thr
1               5

<210> SEQ ID NO 392
<211> LENGTH: 357
<212> TYPE: DNA
<213> ORGANISM: Homo sapiens

<400> SEQUENCE: 392
caggtgcagc tggtgcagtc tggagctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg atcagcgctt acactggtaa cacaaactat      180
gcacagaagt tccagggcag agtcaccatg accacagaca catccacgag cacagcctac     240
atggaactga ggagcctgag atctgacgac acggccgtgt attactgtgc gagagatcgt     300
ggatactatg atgcttttga tatctggggc caaggcaccc tggtcaccgt ctcctca       357

<210> SEQ ID NO 393
<211> LENGTH: 324
<212> TYPE: DNA
<213> ORGANISM: Homo sapiens

<400> SEQUENCE: 393
gacatccaga tgacccagtc tccttccacc ctgtctgcat ctgttggaga cagagtcacc      60
atcacctgcc gggccagtga gggtatttat cactggttgg cctggtatca gcagaagcca     120
gggaaagccc ctaaactcct gatctataag gcctctagtt tagccagtgg ggtcccatca     180
aggttcagcg gcagtggatc tgggacagag ttcactctca ccatcagcag cctgcagcct     240
gatgattttg caacttatta ctgccaacaa tatagtaatt atccgctcac tttcggcgga     300
gggaccaagg tggagatcaa acgt                                            324

<210> SEQ ID NO 394
<211> LENGTH: 729
<212> TYPE: DNA
<213> ORGANISM: Homo sapiens

<400> SEQUENCE: 394
caggtgcagc tggtgcagtc tggagctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg atcagcgctt acactggtaa cacaaactat      180
gcacagaagt tccagggcag agtcaccatg accacagaca catccacgag cacagcctac     240
atggaactga ggagcctgag atctgacgac acggccgtgt attactgtgc gagagatcgt     300
ggatactatg atgcttttga tatctggggc caaggcaccc tggtcaccgt ctcctcaggt     360
ggaggcggtt caggcggagg tggcagcggc ggtggcggat cggacatcca gatgacccag     420
tctccttcca ccctgtctgc atctgttgga cagagtca ccatcacctg ccgggccagt       480
gagggtattt atcactggtt ggcctggtat cagcagaagc agggaaagc ccctaaactc      540 ctgatctata aggcctctag tttagccagt ggggtcccat caaggttcag cggcagtgga     600
tctgggacag agttcactct caccatcagc agcctgcagc ctgatgattt tgcaacttat    660
```

```
tactgccaac aatatagtaa ttatccgctc actttcggcg gagggaccaa ggtggagatc      720
aaacgtgcg                                                              729
```

<210> SEQ ID NO 395
<211> LENGTH: 15
<212> TYPE: DNA
<213> ORGANISM: Homo sapiens

<400> SEQUENCE: 395

```
agttatggta tcagc                                                        15
```

<210> SEQ ID NO 396
<211> LENGTH: 51
<212> TYPE: DNA
<213> ORGANISM: Homo sapiens

<400> SEQUENCE: 396

```
tggatcagcg cttacactgg taacacaaac tatgcacaga agttccaggg c                51
```

<210> SEQ ID NO 397
<211> LENGTH: 30
<212> TYPE: DNA
<213> ORGANISM: Homo sapiens

<400> SEQUENCE: 397

```
gatcgtggat actatgatgc ttttgatatc                                        30
```

<210> SEQ ID NO 398
<211> LENGTH: 33
<212> TYPE: DNA
<213> ORGANISM: Homo sapiens

<400> SEQUENCE: 398

```
cgggccagtg agggtattta tcactggttg gcc                                    33
```

<210> SEQ ID NO 399
<211> LENGTH: 21
<212> TYPE: DNA
<213> ORGANISM: Homo sapiens

<400> SEQUENCE: 399

```
aaggcctcta gtttagccag t                                                 21
```

<210> SEQ ID NO 400
<211> LENGTH: 27
<212> TYPE: DNA
<213> ORGANISM: Homo sapiens

<400> SEQUENCE: 400

```
caacaatata gtaattatcc gctcact                                           27
```

<210> SEQ ID NO 401
<211> LENGTH: 119
<212> TYPE: PRT
<213> ORGANISM: Homo sapiens

<400> SEQUENCE: 401

```
Gln Met Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30
```

Gly Met Tyr Trp Val Arg Gln Ala Pro Gly Lys Gly Leu Glu Trp Val
         35                  40                  45

Ala His Ile Trp Tyr Asp Gly Ser Asn Glu Lys Tyr Ala Asp Ser Val
 50                      55                  60

Lys Gly Arg Met Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gln His Trp Ile Thr Ala Phe Asp Ile Trp Gly Lys Gly
             100                 105                 110

Thr Leu Val Thr Val Ser Ser
        115

<210> SEQ ID NO 402
<211> LENGTH: 111
<212> TYPE: PRT
<213> ORGANISM: Homo sapiens

<400> SEQUENCE: 402

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Glu Gly Ser Lys Arg Pro Ser Gly Val Ser Asn Arg Phe
 50                      55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Arg
                 85                  90                  95

Ser Thr Arg Val Phe Gly Gly Gly Thr Lys Leu Thr Val Leu Gly
             100                 105                 110

<210> SEQ ID NO 403
<211> LENGTH: 246
<212> TYPE: PRT
<213> ORGANISM: Homo sapiens

<400> SEQUENCE: 403

Gln Met Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
             20                  25                  30

Gly Met Tyr Trp Val Arg Gln Ala Pro Gly Lys Gly Leu Glu Trp Val
         35                  40                  45

Ala His Ile Trp Tyr Asp Gly Ser Asn Glu Lys Tyr Ala Asp Ser Val
 50                      55                  60

Lys Gly Arg Met Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gln His Trp Ile Thr Ala Phe Asp Ile Trp Gly Lys Gly
             100                 105                 110

Thr Leu Val Thr Val Ser Ser Gly Gly Gly Gly Ser Gly Ala Gly Gly
         115                 120                 125

```
Ser Gly Gly Gly Ser Gln Ser Ala Leu Thr Gln Pro Ala Ser Val
    130             135                 140
Ser Gly Ser Pro Gly Gln Ser Ile Thr Ile Ser Cys Thr Gly Thr Ser
145                 150                 155                 160
Ser Asp Val Gly Gly Tyr Asn Tyr Val Ser Trp Tyr Gln Gln His Pro
                165                 170                 175
Gly Lys Ala Pro Lys Leu Met Ile Tyr Glu Gly Ser Lys Arg Pro Ser
            180                 185                 190
Gly Val Ser Asn Arg Phe Ser Gly Ser Lys Ser Gly Asn Thr Ala Ser
        195                 200                 205
Leu Thr Ile Ser Gly Leu Gln Ala Glu Asp Glu Ala Asp Tyr Tyr Cys
    210                 215                 220
Ser Ser Tyr Thr Thr Arg Ser Thr Arg Val Phe Gly Gly Gly Thr Lys
225                 230                 235                 240
Leu Thr Val Leu Gly Ala
                245

<210> SEQ ID NO 404
<211> LENGTH: 5
<212> TYPE: PRT
<213> ORGANISM: Homo sapiens

<400> SEQUENCE: 404

Asn Tyr Gly Met Tyr
1               5

<210> SEQ ID NO 405
<211> LENGTH: 17
<212> TYPE: PRT
<213> ORGANISM: Homo sapiens

<400> SEQUENCE: 405

His Ile Trp Tyr Asp Gly Ser Asn Glu Lys Tyr Ala Asp Ser Val Lys
1               5                   10                  15
Gly

<210> SEQ ID NO 406
<211> LENGTH: 10
<212> TYPE: PRT
<213> ORGANISM: Homo sapiens

<400> SEQUENCE: 406

Glu Gln His Trp Ile Thr Ala Phe Asp Ile
1               5                   10

<210> SEQ ID NO 407
<211> LENGTH: 14
<212> TYPE: PRT
<213> ORGANISM: Homo sapiens

<400> SEQUENCE: 407

Thr Gly Thr Ser Ser Asp Val Gly Gly Tyr Asn Tyr Val Ser
1               5                   10

<210> SEQ ID NO 408
<211> LENGTH: 7
<212> TYPE: PRT
<213> ORGANISM: Homo sapiens

<400> SEQUENCE: 408

Glu Gly Ser Lys Arg Pro Ser
1               5
```

<210> SEQ ID NO 409
<211> LENGTH: 10
<212> TYPE: PRT
<213> ORGANISM: Homo sapiens

<400> SEQUENCE: 409

Ser Ser Tyr Thr Thr Arg Ser Thr Arg Val
1               5                   10

<210> SEQ ID NO 410
<211> LENGTH: 357
<212> TYPE: DNA
<213> ORGANISM: Homo sapiens

<400> SEQUENCE: 410
cagatgcagc tggtggagtc tgggggaggc gtggtccagc ctggaggtc cctgagactc      60 tcctgtgcag cctctggatt caccttcagt aactatggca tgtactgggt ccgccaggct    120
ccaggcaagg ggctggagtg ggtggcacat atttggtatg atggaagtaa tgaaaagtat    180
gcagactccg tgaagggccg aatgaccgtc tccagagaca attccaagaa cacgttgtat    240
ttgcaaatga acagcctgag agccgaggac acggctgtgt attactgtgc gacagagcaa    300
cactggatta ctgcttttga tatctggggc aaaggaaccc tggtcaccgt ctcctca      357

<210> SEQ ID NO 411
<211> LENGTH: 333
<212> TYPE: DNA
<213> ORGANISM: Homo sapiens

<400> SEQUENCE: 411
cagtctgccc tgactcagcc tgcctccgtg tctgggtctc ctggacagtc gatcaccatc     60
tcctgcactg gaaccagcag tgacgttggt ggttataact atgtctcctg gtaccaacaa    120
cacccaggca aagcccccaa actcatgatt tatgagggca gtaagcggcc ctcagggtt    180 tctaatcgct tctctggctc caagtctggc aacacggcct ccctgacaat ctctgggctc    240
caggctgagg acgaggctga ttactactgc agctcatata accaggagc actcgagtt    300 ttcggcggag ggaccaagct gaccgtccta ggt                                 333

<210> SEQ ID NO 412
<211> LENGTH: 738
<212> TYPE: DNA
<213> ORGANISM: Homo sapiens

<400> SEQUENCE: 412
cagatgcagc tggtggagtc tgggggaggc gtggtccagc ctggaggtc cctgagactc      60 tcctgtgcag cctctggatt caccttcagt aactatggca tgtactgggt ccgccaggct    120
ccaggcaagg ggctggagtg ggtggcacat atttggtatg atggaagtaa tgaaaagtat    180
gcagactccg tgaagggccg aatgaccgtc tccagagaca attccaagaa cacgttgtat    240
ttgcaaatga acagcctgag agccgaggac acggctgtgt attactgtgc gacagagcaa    300
cactggatta ctgcttttga tatctggggc aaaggcaccc tggtcaccgt ctcctcaggt    360
ggaggcggtt caggcgcagg tggcagcggc ggtggcggat cacagtctgc gctgactcag    420
cctgcctccg tgtctgggtc tcctggacag tcgatcacca tctcctgcac tggaaccagc    480
agtgacgttg gtggttataa ctatgtctcc tggtaccaac aacacccagg caaagccccc    540

```
aaactcatga tttatgaggg cagtaagcgg ccctcagggg tttctaatcg cttctctggc    600
tccaagtctg gcaacacggc ctccctgaca atctctgggc tccaggctga ggacgaggct    660
gattattact gcagctcata taaccaggag cactcgag ttttcggcgg agggaccaag     720
ctgaccgtcc taggtgcg                                                  738
```

<210> SEQ ID NO 413
<211> LENGTH: 15
<212> TYPE: DNA
<213> ORGANISM: Homo sapiens

<400> SEQUENCE: 413

```
aactatggca tgtac                                                     15
```

<210> SEQ ID NO 414
<211> LENGTH: 51
<212> TYPE: DNA
<213> ORGANISM: Homo sapiens

<400> SEQUENCE: 414

```
catatttggt atgatggaag taatgaaaag tatgcagact ccgtgaaggg c             51
```

<210> SEQ ID NO 415
<211> LENGTH: 30
<212> TYPE: DNA
<213> ORGANISM: Homo sapiens

<400> SEQUENCE: 415

```
gagcaacact ggattactgc ttttgatatc                                     30
```

<210> SEQ ID NO 416
<211> LENGTH: 42
<212> TYPE: DNA
<213> ORGANISM: Homo sapiens

<400> SEQUENCE: 416

```
actggaacca gcagtgacgt tggtggttat aactatgtct cc                       42
```

<210> SEQ ID NO 417
<211> LENGTH: 21
<212> TYPE: DNA
<213> ORGANISM: Homo sapiens

<400> SEQUENCE: 417

```
gagggcagta agcggccctc a                                              21
```

<210> SEQ ID NO 418
<211> LENGTH: 30
<212> TYPE: DNA
<213> ORGANISM: Homo sapiens

<400> SEQUENCE: 418

```
agctcatata caaccaggag cactcgagtt                                     30
```

<210> SEQ ID NO 419
<211> LENGTH: 121
<212> TYPE: PRT
<213> ORGANISM: Homo sapiens

<400> SEQUENCE: 419

Glu Val Gln Leu Val Glu Ser Gly Gly Gly Val Val Arg Pro Gly Gly
1               5                   10                  15

```
Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ser Phe Tyr Tyr Phe Gly Tyr Trp Gly
            100                 105                 110

Arg Gly Thr Leu Val Thr Val Ser Ser
            115                 120
```

<210> SEQ ID NO 420
<211> LENGTH: 111
<212> TYPE: PRT
<213> ORGANISM: Homo sapiens

<400> SEQUENCE: 420

```
Gln Ala Ala Leu Thr Gln Pro Ala Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Ala Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Phe Ser Val Val Phe Gly Gly Gly Thr Lys Leu Thr Val Leu Gly
            100                 105                 110
```

<210> SEQ ID NO 421
<211> LENGTH: 249
<212> TYPE: PRT
<213> ORGANISM: Homo sapiens

<400> SEQUENCE: 421

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ser Phe Tyr Tyr Phe Gly Tyr Trp Gly
            100                 105                 110
```

```
Arg Gly Thr Leu Val Thr Val Ser Ser Gly Gly Gly Ser Gly Gly
            115                 120                 125
Gly Gly Ser Gly Gly Gly Ser Ala Gln Ala Leu Thr Gln Pro
        130                 135                 140
Ala Ser Val Ser Gly Ser Pro Gly Gln Ser Ile Thr Ile Ser Cys Thr
145                 150                 155                 160
Gly Ala Ser Gly Asp Val Gly Ala Tyr Asn Phe Val Ser Trp Tyr Gln
                165                 170                 175
Gln His Pro Gly Lys Ala Pro Lys Leu Ile Ile Tyr Asp Val Asn Lys
                180                 185                 190
Arg Pro Ser Gly Val Ser Asn Arg Phe Ser Gly Ser Lys Ser Gly Asn
            195                 200                 205
Thr Ala Ser Leu Thr Ile Ser Gly Leu Gln Ala Glu Asp Glu Ala Asp
210                 215                 220
Tyr Tyr Cys Ser Ser Tyr Thr Ser Thr Phe Ser Val Val Phe Gly Gly
225                 230                 235                 240
Gly Thr Lys Leu Thr Val Leu Gly Ala
                245
```

<210> SEQ ID NO 422
<211> LENGTH: 5
<212> TYPE: PRT
<213> ORGANISM: Homo sapiens

<400> SEQUENCE: 422

```
Asp Tyr Gly Met Asn
1               5
```

<210> SEQ ID NO 423
<211> LENGTH: 17
<212> TYPE: PRT
<213> ORGANISM: Homo sapiens

<400> SEQUENCE: 423

```
Gly Val Asn Trp Asn Gly Gly Thr Arg Asp Tyr Ala Ala Ser Val Lys
1               5                   10                  15
Gly
```

<210> SEQ ID NO 424
<211> LENGTH: 12
<212> TYPE: PRT
<213> ORGANISM: Homo sapiens

<400> SEQUENCE: 424

```
Gly Trp Tyr Ser Gly Ser Phe Tyr Tyr Phe Gly Tyr
1               5                   10
```

<210> SEQ ID NO 425
<211> LENGTH: 14
<212> TYPE: PRT
<213> ORGANISM: Homo sapiens

<400> SEQUENCE: 425

```
Thr Gly Ala Ser Gly Asp Val Gly Ala Tyr Asn Phe Val Ser
1               5                   10
```

<210> SEQ ID NO 426
<211> LENGTH: 7
<212> TYPE: PRT
<213> ORGANISM: Homo sapiens

```
<400> SEQUENCE: 426

Asp Val Asn Lys Arg Pro Ser
1               5

<210> SEQ ID NO 427
<211> LENGTH: 10
<212> TYPE: PRT
<213> ORGANISM: Homo sapiens

<400> SEQUENCE: 427

Ser Ser Tyr Thr Ser Thr Phe Ser Val Val
1               5                   10

<210> SEQ ID NO 428
<211> LENGTH: 363
<212> TYPE: DNA
<213> ORGANISM: Homo sapiens

<400> SEQUENCE: 428
gaggtgcagc tggtggagag cggggggaggt gtggtacggc ctgggggggtc cctgagactc      60 tcctgtgcag cctctggatt cacctttgac gattatggca tgaactgggt ccgccaagct     120
ccagggaagg ggctgagtg gtctctggt gttaattgga atggtggtac cagagattat     180
gcagcctccg tgaagggccg attcaccatc tccagagaca acgccaagaa ctccctgtat     240
ctgcaaatga acagtctgag agccgaggac acggccttgt atcactgtgc gagaggatgg     300
tatagtggga gcttctacta ctttggctac tggggccgag aaccctggt caccgtctcc     360 tca                                                                   363

<210> SEQ ID NO 429
<211> LENGTH: 333
<212> TYPE: DNA
<213> ORGANISM: Homo sapiens

<400> SEQUENCE: 429
caggctgcgc tgactcagcc ggcctccgtg tctgggtctc ctggacagtc gatcaccatc      60
tcctgcactg gagccagcgg tgacgttggt gcttataact ttgtctcctg gtaccaacaa     120
cacccaggca aagcccccaa actcataatt tatgatgtca ataagcggcc ctcagggtt     180 tctaatcgct tctctggctc caagtctggc aacacggcct ccctgaccat ctctgggctc     240
caggccgagg acgaggctga ttattactgc agctcatata caagcacctt ctctgtggta     300
tttggcggag ggaccaagct gaccgtccta ggt                                   333

<210> SEQ ID NO 430
<211> LENGTH: 747
<212> TYPE: DNA
<213> ORGANISM: Homo sapiens

<400> SEQUENCE: 430
gaggtgcagc tggtggagtc cggggggaggt gtggtacggc ctgggggggtc cctgagactc      60 tcctgtgcag cctctggatt cacctttgac gattatggca tgaactgggt ccgccaagct     120
ccagggaagg ggctgagtg gtctctggt gttaattgga atggtggtac cagagattat     180
gcagcctccg tgaagggccg attcaccatc tccagagaca acgccaagaa ctccctgtat     240
ctgcaaatga acagtctgag agccgaggac acggccttgt atcactgtgc gagaggatgg     300
tatagtggga gcttctacta ctttggctac tggggccgag aaccctggt caccgtctcg     360 agtggaggcg gcggttcagg cggaggtggc tctggcggtg gcggaagtgc acaggctgcg     420
```

-continued

```
ctgactcagc cggcctccgt gtctgggtct cctggacagt cgatcaccat ctcctgcact      480
ggagccagcg gtgacgttgg tgcttataac tttgtctcct ggtaccaaca acacccaggc      540
aaagccccca aactcataat ttatgatgtc aataagcggc cctcagsggt tctaatcgc       600 ttctctggct ccaagtctgg caacacggcc tccctgacca tctctgggct ccaggccgag      660
gacgaggctg attattactg cagctcatat acaagcacct tctctgtggt atttggcgga      720
gggaccaagc tcaccgtcct aggtgcg                                          747
```

<210> SEQ ID NO 431
<211> LENGTH: 15
<212> TYPE: DNA
<213> ORGANISM: Homo sapiens

<400> SEQUENCE: 431

```
gattatggca tgaac                                                        15
```

<210> SEQ ID NO 432
<211> LENGTH: 51
<212> TYPE: DNA
<213> ORGANISM: Homo sapiens

<400> SEQUENCE: 432

```
ggtgttaatt ggaatggtgg taccagagat tatgcagcct ccgtgaaggg c                51
```

<210> SEQ ID NO 433
<211> LENGTH: 36
<212> TYPE: DNA
<213> ORGANISM: Homo sapiens

<400> SEQUENCE: 433

```
ggatggtata gtgggagctt ctactacttt ggctac                                 36
```

<210> SEQ ID NO 434
<211> LENGTH: 42
<212> TYPE: DNA
<213> ORGANISM: Homo sapiens

<400> SEQUENCE: 434

```
actggagcca gcggtgacgt tggtgcttat aactttgtct cc                          42
```

<210> SEQ ID NO 435
<211> LENGTH: 21
<212> TYPE: DNA
<213> ORGANISM: Homo sapiens

<400> SEQUENCE: 435

```
gatgtcaata agcggccctc a                                                 21
```

<210> SEQ ID NO 436
<211> LENGTH: 30
<212> TYPE: DNA
<213> ORGANISM: Homo sapiens

<400> SEQUENCE: 436

```
agctcatata caagcacctt ctctgtggta                                        30
```

<210> SEQ ID NO 437
<211> LENGTH: 119
<212> TYPE: PRT
<213> ORGANISM: Homo sapiens

<400> SEQUENCE: 437

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 438
<211> LENGTH: 109
<212> TYPE: PRT
<213> ORGANISM: Homo sapiens

<400> SEQUENCE: 438

Ser Ser Val Leu Thr Gln Pro Pro Ser Val Ser Val Ala Pro Gly Lys
1               5                   10                  15

Thr Ala Arg Ile Thr Cys Gly Gly Asn Asn Phe Arg Asn Lys Arg Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Thr Asp Arg
                85                  90                  95

Pro Leu Phe Gly Gly Gly Thr Lys Leu Thr Val Leu Gly
            100                 105

<210> SEQ ID NO 439
<211> LENGTH: 245
<212> TYPE: PRT
<213> ORGANISM: Homo sapiens

<400> SEQUENCE: 439

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys

```
                    85                  90                  95
Ala Arg Asp Leu Thr Gly Phe Asp Pro Phe Asp Ile Trp Gly Gln Gly
                100                 105                 110

Thr Leu Val Thr Val Ser Ser Gly Gly Gly Ser Gly Gly Gly
        115                 120                 125

Ser Gly Gly Gly Ser Ala Ser Val Leu Thr Gln Pro Pro Ser
    130                 135                 140

Val Ser Val Ala Pro Gly Lys Thr Ala Arg Ile Thr Cys Gly Gly Asn
145                 150                 155                 160

Asn Phe Arg Asn Lys Arg Val His Trp Tyr Gln Gln Lys Pro Gly Gln
                165                 170                 175

Ala Pro Val Leu Val Ile Tyr Tyr Asp Ser Asp Arg Pro Ser Gly Ile
                180                 185                 190

Pro Glu Arg Phe Ser Gly Ser Arg Ser Gly Asn Thr Ala Thr Leu Thr
                195                 200                 205

Ile Ser Arg Val Glu Ala Gly Asp Glu Ala Asp Tyr Tyr Cys Gln Val
210                 215                 220

Trp Asp Ser Ser Thr Ala Arg Pro Leu Phe Gly Gly Thr Lys Leu
225                 230                 235                 240

Thr Val Leu Gly Ala
                245

<210> SEQ ID NO 440
<211> LENGTH: 5
<212> TYPE: PRT
<213> ORGANISM: Homo sapiens

<400> SEQUENCE: 440

Asp Tyr Tyr Ile His
1               5

<210> SEQ ID NO 441
<211> LENGTH: 17
<212> TYPE: PRT
<213> ORGANISM: Homo sapiens

<400> SEQUENCE: 441

Trp Val Asn Pro Asp Thr Gly Gly Thr Arg Tyr Ala Gln Lys Phe Gln
1               5                   10                  15
Gly

<210> SEQ ID NO 442
<211> LENGTH: 10
<212> TYPE: PRT
<213> ORGANISM: Homo sapiens

<400> SEQUENCE: 442

Asp Leu Thr Gly Phe Asp Pro Phe Asp Ile
1               5                   10

<210> SEQ ID NO 443
<211> LENGTH: 11
<212> TYPE: PRT
<213> ORGANISM: Homo sapiens

<400> SEQUENCE: 443

Gly Gly Asn Asn Phe Arg Asn Lys Arg Val His
1               5                   10
```

```
<210> SEQ ID NO 444
<211> LENGTH: 7
<212> TYPE: PRT
<213> ORGANISM: Homo sapiens

<400> SEQUENCE: 444

Tyr Asp Ser Asp Arg Pro Ser
1               5

<210> SEQ ID NO 445
<211> LENGTH: 11
<212> TYPE: PRT
<213> ORGANISM: Homo sapiens

<400> SEQUENCE: 445

Gln Val Trp Asp Ser Ser Thr Asp Arg Pro Leu
1               5                   10

<210> SEQ ID NO 446
<211> LENGTH: 357
<212> TYPE: DNA
<213> ORGANISM: Homo sapiens

<400> SEQUENCE: 446
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt ttcagggccg ggtcacaatg accagggaca tgtccatctc cacagcctac     240
atggagctgt ccaggctgag aagcgacgac acggccgtat attactgtgc gagagatcta     300
actggatttg atccttttga tatctggggc cagggaaccc tggtcaccgt ctcctca        357

<210> SEQ ID NO 447
<211> LENGTH: 327
<212> TYPE: DNA
<213> ORGANISM: Homo sapiens

<400> SEQUENCE: 447
tcgtctgtgc tgactcagcc accctcagtg tcagtggccc caggaaagac ggcccgcatt      60
acctgtgggg gaaacaactt tcgaaataaa agagtacact ggtatcagca gaagccaggc     120
caggcccctg tcctggtcat ctattatgat tcagaccggc cctcagggat ccctgagcga     180
ttctctggct cccgctctgg gaacacggcc accctgacca tcagcagggt cgaggccggg     240
gatgaggccg actattactg tcaggtgtgg gatagtagta ctgatcgtcc gctgttcggc     300
ggagggacca agctgaccgt cctaggt                                         327

<210> SEQ ID NO 448
<211> LENGTH: 735
<212> TYPE: DNA
<213> ORGANISM: Homo sapiens

<400> SEQUENCE: 448
caagtgcagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt ttcagggccg ggtcacaatg accagggaca tgtccatctc cacagcctac     240
atggagctgt ccaggctgag aagcgacgac acggccgtat attactgtgc gagagatcta     300
```

```
actggatttg atccttttga tatctggggc cagggaaccc tggtcaccgt ctcgagtgga    360
ggcggcggtt caggcggagg tggctctggc ggtggcggaa gtgcatcgtc tgtgctgact    420
cagccaccct cagtgtcagt ggccccagga aagacggccc gcattacctg tgggggaaac    480
aactttcgaa ataaaagagt acactggtat cagcagaagc caggccaggc ccctgtcctg    540
gtcatctatt atgattcaga ccggccctca gggatccctg agcgattctc tggctcccgc    600
tctgggaaca cggccaccct gaccatcagc agggtcgagg ccggggatga ggccgactat    660
tactgtcagg tgtgggatag tagtactgat cgtccgctgt cggcggagg gaccaagctg    720 accgtcctag gtgcg                                                     735
```

```
<210> SEQ ID NO 449
<211> LENGTH: 15
<212> TYPE: DNA
<213> ORGANISM: Homo sapiens

<400> SEQUENCE: 449
gattactata ttcac                                                     15

<210> SEQ ID NO 450
<211> LENGTH: 51
<212> TYPE: DNA
<213> ORGANISM: Homo sapiens

<400> SEQUENCE: 450
tgggtcaacc ctgacactgg tggcacaaga tacgcgcaga gtttcaggg c               51

<210> SEQ ID NO 451
<211> LENGTH: 30
<212> TYPE: DNA
<213> ORGANISM: Homo sapiens

<400> SEQUENCE: 451
gatctaactg gatttgatcc ttttgatatc                                     30

<210> SEQ ID NO 452
<211> LENGTH: 33
<212> TYPE: DNA
<213> ORGANISM: Homo sapiens

<400> SEQUENCE: 452
gggggaaaca actttcgaaa taaaagagta cac                                 33

<210> SEQ ID NO 453
<211> LENGTH: 21
<212> TYPE: DNA
<213> ORGANISM: Homo sapiens

<400> SEQUENCE: 453
tatgattcag accggccctc a                                              21

<210> SEQ ID NO 454
<211> LENGTH: 33
<212> TYPE: DNA
<213> ORGANISM: Homo sapiens

<400> SEQUENCE: 454
caggtgtggg atagtagtac tgatcgtccg ctg                                 33

<210> SEQ ID NO 455
<211> LENGTH: 121
```

```
<212> TYPE: PRT
<213> ORGANISM: Homo sapiens

<400> SEQUENCE: 455

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Phe Trp Gly Gly Asp Asn Trp Gly
            100                 105                 110

Arg Gly Thr Leu Val Thr Val Ser Ser
        115                 120

<210> SEQ ID NO 456
<211> LENGTH: 112
<212> TYPE: PRT
<213> ORGANISM: Homo sapiens

<400> SEQUENCE: 456

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Gly Thr Gln Leu Thr Val Leu Gly
            100                 105                 110

<210> SEQ ID NO 457
<211> LENGTH: 250
<212> TYPE: PRT
<213> ORGANISM: Homo sapiens

<400> SEQUENCE: 457

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Ser Thr Ala Tyr
```

```
                65                  70                  75                  80
Met Glu Leu Ser Arg Leu Arg Ser Asp Asp Thr Ala Val Tyr Tyr Cys
                85                  90                  95

Ala Arg Glu Pro Glu Lys Phe Asp Phe Trp Gly Gly Asp Asn Trp Gly
            100                 105                 110

Arg Gly Thr Leu Val Thr Val Ser Gly Gly Gly Ser Gly Gly
        115                 120                 125

Gly Gly Ser Gly Gly Gly Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Gly Tyr Val Phe Gly
225                 230                 235                 240

Gly Gly Thr Gln Leu Thr Val Leu Ser Ala
                245                 250

<210> SEQ ID NO 458
<211> LENGTH: 5
<212> TYPE: PRT
<213> ORGANISM: Homo sapiens

<400> SEQUENCE: 458

Asp Tyr Tyr Met His
1               5

<210> SEQ ID NO 459
<211> LENGTH: 17
<212> TYPE: PRT
<213> ORGANISM: Homo sapiens

<400> SEQUENCE: 459

Trp Ile Asn Pro Tyr Thr Gly Gly Ala Phe Tyr Ala Gln Lys Phe Arg
1               5                   10                  15

Gly

<210> SEQ ID NO 460
<211> LENGTH: 12
<212> TYPE: PRT
<213> ORGANISM: Homo sapiens

<400> SEQUENCE: 460

Glu Pro Glu Lys Phe Asp Phe Trp Gly Gly Asp Asn
1               5                   10

<210> SEQ ID NO 461
<211> LENGTH: 14
<212> TYPE: PRT
<213> ORGANISM: Homo sapiens

<400> SEQUENCE: 461

Thr Gly Ser Ser Ser Asn Ile Gly Ala Gly Tyr Gly Val His
```

<210> SEQ ID NO 462
<211> LENGTH: 7
<212> TYPE: PRT
<213> ORGANISM: Homo sapiens

<400> SEQUENCE: 462

Gly Asn Ser Asn Arg Pro Ser
1               5

<210> SEQ ID NO 463
<211> LENGTH: 11
<212> TYPE: PRT
<213> ORGANISM: Homo sapiens

<400> SEQUENCE: 463

Gln Ser Tyr Asp Ser Ser Leu Ser Gly Tyr Val
1               5                   10

<210> SEQ ID NO 464
<211> LENGTH: 363
<212> TYPE: DNA
<213> ORGANISM: Homo sapiens

<400> SEQUENCE: 464
caggtgcagc tggtgcagtc tggggctgag gtgaagaagc ctggggcctc agtgaaggtc     60
tcctgcaagg cttctggata caccttcacc gactactata tgcactgggt gcgacaggcc    120
cctggacaag gcttgagtg gtgggatgg atcaacccctt atactggtgg cgcattctat    180
gcacagaagt tcggggcag ggtcacaatg accagggaca cgtccatcag cacagcctac    240
atggagctga gcagactgag atctgacgac acggccgtgt attattgtgc gagagaacct    300
gaaaaattcg attttttggg gggtgacaac tggggccggg ggacattggt caccgtctcc    360
tca                                                                  363

<210> SEQ ID NO 465
<211> LENGTH: 336
<212> TYPE: DNA
<213> ORGANISM: Homo sapiens

<400> SEQUENCE: 465
caggctgtgc tgactcagcc gccgtcagtg tctggggccc cagggcagag ggtcaccatc     60
tcctgcactg ggagcagctc caacatcggg gcaggttatg tgtacactg gtaccaacag    120 cttccaggaa cagcccccaa actcctcatc tatggtaaca gcaatcggcc ctcaggggtc    180
cctgaccgat tctctggctc caagtctggc acctcagcct ccctggccat cactgggctc    240
caggctgagg atgaggctga ttattactgc cagtcctatg acagcagcct gagtggttat    300
gtcttcggag gtgggaccca gctcaccgtc ctaggt                             336

<210> SEQ ID NO 466
<211> LENGTH: 750
<212> TYPE: DNA
<213> ORGANISM: Homo sapiens

<400> SEQUENCE: 466
caggtccagc tggtgcagtc tggggctgag gtgaagaagc ctggggcctc agtgaaggtc     60
tcctgcaagg cttctggata caccttcacc gactactata tgcactgggt gcgacaggcc    120
cctggacaag gcttgagtg gtgggatgg atcaacccctt atactggtgg cgcattctat    180

```
gcacagaagt tcggggcag ggtcacaatg accagggaca cgtccatcag cacagcctac    240
atggagctga gcagactgag atctgacgac acggccgtgt attattgtgc gagagaacct    300
gaaaaattcg attttggg gggtgacaac tggggccggg gacattggt caccgtctcg      360 agtggaggcg gcggttcagg cggaggtggc tctggcggtg gcggaagtgc acaggctgtg    420
ctgactcagc cgccgtcagt gtctgggggcc ccagggcaga gggtcaccat ctcctgcact   480
gggagcagct ccaacatcgg ggcaggttat ggtgtacact ggtaccaaca gcttccagga    540
acagccccca aactcctcat ctatggtaac agcaatcggc cctcaggggt ccctgaccga    600
ttctctggct ccaagtctgg cacctcagcc tccctggcca tcactgggct ccaggctgag    660
gatgaggctg attattactg ccagtcctat gacagcagcc tgagtggtta tgtcttcgga    720
ggtgggaccc agctcaccgt tttaagtgcg                                     750
```

<210> SEQ ID NO 467
<211> LENGTH: 15
<212> TYPE: DNA
<213> ORGANISM: Homo sapiens

<400> SEQUENCE: 467

```
gactactata tgcac                                                     15
```

<210> SEQ ID NO 468
<211> LENGTH: 51
<212> TYPE: DNA
<213> ORGANISM: Homo sapiens

<400> SEQUENCE: 468

```
tggatcaacc cttatactgg tggcgcattc tatgcacaga agtttcgggg c             51
```

<210> SEQ ID NO 469
<211> LENGTH: 36
<212> TYPE: DNA
<213> ORGANISM: Homo sapiens

<400> SEQUENCE: 469

```
gaacctgaaa aattcgattt tgggggggt gacaac                               36
```

<210> SEQ ID NO 470
<211> LENGTH: 42
<212> TYPE: DNA
<213> ORGANISM: Homo sapiens

<400> SEQUENCE: 470

```
actgggagca gctccaacat cggggcaggt tatggtgtac ac                       42
```

<210> SEQ ID NO 471
<211> LENGTH: 21
<212> TYPE: DNA
<213> ORGANISM: Homo sapiens

<400> SEQUENCE: 471

```
ggtaacagca atcggccctc a                                              21
```

<210> SEQ ID NO 472
<211> LENGTH: 33
<212> TYPE: DNA
<213> ORGANISM: Homo sapiens

<400> SEQUENCE: 472
cagtcctatg acagcagcct gagtggttat gtc                          33

<210> SEQ ID NO 473
<211> LENGTH: 119
<212> TYPE: PRT
<213> ORGANISM: Homo sapiens

<400> SEQUENCE: 473

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Ala Tyr Thr Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser
        115

<210> SEQ ID NO 474
<211> LENGTH: 108
<212> TYPE: PRT
<213> ORGANISM: Homo sapiens

<400> SEQUENCE: 474

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Met Gly Glu Tyr Asn Ala
                85                  90                  95

Thr Phe Gly Gly Gly Thr Lys Val Glu Ile Lys Arg
            100                 105

<210> SEQ ID NO 475
<211> LENGTH: 242
<212> TYPE: PRT
<213> ORGANISM: Homo sapiens

<400> SEQUENCE: 475

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

```
Gly Trp Val Ser Ala Tyr Thr Gly Asn Thr Asn Tyr Ala Gln Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Tyr Tyr Asp Ala Phe Asp Ile Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Asp Ile Gln Met Thr Gln Ser Pro Ser Thr
        130                 135                 140

Leu Ser Ala Ser Val Gly Asp Arg Val Thr Ile Thr Cys Arg Ala Ser
145                 150                 155                 160

Glu Gly Ile Tyr His Trp Leu Ala Trp Tyr Gln Gln Lys Pro Gly Lys
                165                 170                 175

Ala Pro Lys Leu Leu Ile Tyr Lys Ala Ser Ser Leu Ala Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Thr Tyr Tyr Cys Gln Gln
210                 215                 220

Met Gly Glu Tyr Asn Ala Thr Phe Gly Gly Gly Thr Lys Val Glu Ile
225                 230                 235                 240

Lys Arg

<210> SEQ ID NO 476
<211> LENGTH: 5
<212> TYPE: PRT
<213> ORGANISM: Homo sapiens

<400> SEQUENCE: 476

Ser Tyr Gly Ile Ser
1               5

<210> SEQ ID NO 477
<211> LENGTH: 17
<212> TYPE: PRT
<213> ORGANISM: Homo sapiens

<400> SEQUENCE: 477

Trp Val Ser Ala Tyr Thr Gly Asn Thr Asn Tyr Ala Gln Lys Phe Gln
1               5                   10                  15

Gly

<210> SEQ ID NO 478
<211> LENGTH: 10
<212> TYPE: PRT
<213> ORGANISM: Homo sapiens

<400> SEQUENCE: 478

Asp Arg Gly Tyr Tyr Asp Ala Phe Asp Ile
1               5                   10

<210> SEQ ID NO 479
<211> LENGTH: 11
<212> TYPE: PRT
<213> ORGANISM: Homo sapiens
```

<400> SEQUENCE: 479

Arg Ala Ser Glu Gly Ile Tyr His Trp Leu Ala
1               5                   10

<210> SEQ ID NO 480
<211> LENGTH: 7
<212> TYPE: PRT
<213> ORGANISM: Homo sapiens

<400> SEQUENCE: 480

Lys Ala Ser Ser Leu Ala Ser
1               5

<210> SEQ ID NO 481
<211> LENGTH: 9
<212> TYPE: PRT
<213> ORGANISM: Homo sapiens

<400> SEQUENCE: 481

Gln Gln Met Gly Glu Tyr Asn Ala Thr
1               5

<210> SEQ ID NO 482
<211> LENGTH: 357
<212> TYPE: DNA
<213> ORGANISM: Homo sapiens

<400> SEQUENCE: 482

```
caggtgcagc tggtgcagtc tggagctgag gtgaagaagc ctggggcctc agtgaaggtc      60
tcctgcaagg cttctggtta cacctttacc agttatggta tcagctgggt gcgacaggcc     120
cctggacaag gcttgagtg gatgggatgg gtcagcgctt acactggtaa cacaaactat     180
gcacagaagt tccagggcag agtcaccatg accacagaca catccacgag cacagcctac     240
atggaactga ggagcctgag atctgacgac acggccgtgt attactgtgc gagagatcgt     300
ggatactatg atgcttttga tatctggggc caaggcaccc tggtcaccgt ctcctca        357
```

<210> SEQ ID NO 483
<211> LENGTH: 324
<212> TYPE: DNA
<213> ORGANISM: Homo sapiens

<400> SEQUENCE: 483

```
gacatccaga tgacccagtc tccttccacc ctgtctgcat ctgttggaga cagagtcacc      60
atcacctgcc gggccagtga gggtatttat cactggttgg cctggtatca gcagaagcca     120
gggaaagccc ctaaactcct gatctataag gcctctagtt tagccagtgg ggtcccatca     180
aggttcagcg gcagtggatc tgggacagag ttcactctca ccatcagcag cctgcagcct     240
gatgattttg caacttatta ctgccaacaa atgggcgagt acaacgccac cttcggcgga     300
gggaccaagg tggagatcaa acgt                                            324
```

<210> SEQ ID NO 484
<211> LENGTH: 726
<212> TYPE: DNA
<213> ORGANISM: Homo sapiens

<400> SEQUENCE: 484

```
caggtgcagc tggtgcagtc tggagctgag gtgaagaagc ctggggcctc agtgaaggtc      60
tcctgcaagg cttctggtta cacctttacc agttatggta tcagctgggt gcgacaggcc     120
```

```
cctggacaag ggcttgagtg gatgggatgg gtcagcgctt acactggtaa cacaaactat    180
gcacagaagt tccagggcag agtcaccatg accacagaca catccacgag cacagcctac    240
atggaactga ggagcctgag atctgacgac acggccgtgt attactgtgc gagagatcgt    300
ggatactatg atgcttttga tatctggggc caaggcaccc tggtcaccgt ctcctcaggt    360
ggaggcggtt caggcggagg tggcagcggc ggtggcggat cggacatcca gatgacccag    420
tctccttcca ccctgtctgc atctgttgga gacagagtca ccatcacctg ccgggccagt    480
cagggtattt atcactggtt ggcctggtat cagcagaagc cagggaaagc ccctaaactc    540
ctgatctata aggcctctag tttagccagt ggggtcccat caaggttcag cggcagtgga    600
tctgggacag agttcactct caccatcagc agcctgcagc tgatgatttt gcaacttat     660 tactgccaac aaatgggcga gtacaacgcc accttcggcg agggaccaa ggtggagatc    720 aaacgt                                                               726
```

`<210>` SEQ ID NO 485
`<211>` LENGTH: 15
`<212>` TYPE: DNA
`<213>` ORGANISM: Homo sapiens

`<400>` SEQUENCE: 485

```
agttatggta tcagc                                                      15
```

`<210>` SEQ ID NO 486
`<211>` LENGTH: 51
`<212>` TYPE: DNA
`<213>` ORGANISM: Homo sapiens

`<400>` SEQUENCE: 486

```
tgggtcagcg cttacactgg taacacaaac tatgcacaga agttccaggg c              51
```

`<210>` SEQ ID NO 487
`<211>` LENGTH: 30
`<212>` TYPE: DNA
`<213>` ORGANISM: Homo sapiens

`<400>` SEQUENCE: 487

```
gatcgtggat actatgatgc ttttgatatc                                      30
```

`<210>` SEQ ID NO 488
`<211>` LENGTH: 33
`<212>` TYPE: DNA
`<213>` ORGANISM: Homo sapiens

`<400>` SEQUENCE: 488

```
cgggccagtg agggtattta tcactggttg gcc                                  33
```

`<210>` SEQ ID NO 489
`<211>` LENGTH: 21
`<212>` TYPE: DNA
`<213>` ORGANISM: Homo sapiens

`<400>` SEQUENCE: 489

```
aaggcctcta gtttagccag t                                               21
```

`<210>` SEQ ID NO 490
`<211>` LENGTH: 27
`<212>` TYPE: DNA
`<213>` ORGANISM: Homo sapiens

```
<400> SEQUENCE: 490
caacaaatgg gcgagtacaa cgccacc                                            27

<210> SEQ ID NO 491
<211> LENGTH: 121
<212> TYPE: PRT
<213> ORGANISM: Homo sapiens

<400> SEQUENCE: 491
```

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120

```
<210> SEQ ID NO 492
<211> LENGTH: 111
<212> TYPE: PRT
<213> ORGANISM: Homo sapiens

<400> SEQUENCE: 492
```

Gln Ala Ala Leu Thr Gln Pro Ala Ser Val Ser Gly Ser Pro Gly Gln
1               5                   10                  15

Ser Ile Thr Ile Ser Cys Thr Gly Ala Ser Gly Asp Val Gly Ala Tyr
            20                  25                  30

Asn Phe Val Ser Trp Tyr Gln Gln His Pro Gly Lys Ala Pro Lys Leu
        35                  40                  45

Ile Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Thr
                85                  90                  95

Phe Ser Val Val Phe Gly Gly Gly Thr Lys Leu Thr Val Leu Gly
            100                 105                 110

```
<210> SEQ ID NO 493
<211> LENGTH: 248
<212> TYPE: PRT
<213> ORGANISM: Homo sapiens

<400> SEQUENCE: 493
```

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
            35                  40                  45
Ser Gly Val Asn Trp Asn Gly Thr Arg Asp Tyr Ala Ala Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr His Cys
                85                  90                  95
Ala Arg Gly Trp Tyr Ser Gly Ala Ala Trp Asn Met Gly Tyr Trp Gly
                100                 105                 110
Arg Gly Thr Leu Val Thr Val Ser Ser Gly Gly Gly Ser Gly Gly
            115                 120                 125
Gly Gly Ser Gly Gly Gly Ser Ala Gln Ala Leu Thr Gln Pro
        130                 135                 140
Ala Ser Val Ser Gly Ser Pro Gly Gln Ser Ile Thr Ile Ser Cys Thr
 145                 150                 155                 160
Gly Ala Ser Gly Asp Val Gly Ala Tyr Asn Phe Val Ser Trp Tyr Gln
                165                 170                 175
Gln His Pro Gly Lys Ala Pro Lys Leu Ile Ile Tyr Asp Val Asn Lys
                180                 185                 190
Arg Pro Ser Gly Val Ser Asn Arg Phe Ser Gly Ser Lys Ser Gly Asn
            195                 200                 205
Thr Ala Ser Leu Thr Ile Ser Gly Leu Gln Ala Glu Asp Glu Ala Asp
 210                 215                 220
Tyr Tyr Cys Ser Ser Tyr Thr Ser Thr Phe Ser Val Val Phe Gly Gly
 225                 230                 235                 240
Gly Thr Lys Leu Thr Val Leu Gly
                245

<210> SEQ ID NO 494
<211> LENGTH: 5
<212> TYPE: PRT
<213> ORGANISM: Homo sapiens

<400> SEQUENCE: 494

Asp Tyr Gly Met Asn
 1               5

<210> SEQ ID NO 495
<211> LENGTH: 17
<212> TYPE: PRT
<213> ORGANISM: Homo sapiens

<400> SEQUENCE: 495

Gly Val Asn Trp Asn Gly Gly Thr Arg Asp Tyr Ala Ala Ser Val Lys
 1               5                   10                  15
Gly

<210> SEQ ID NO 496
<211> LENGTH: 12
<212> TYPE: PRT
<213> ORGANISM: Homo sapiens

<400> SEQUENCE: 496

Gly Trp Tyr Ser Gly Ala Ala Trp Asn Met Gly Tyr
 1               5                   10

<210> SEQ ID NO 497

```
<211> LENGTH: 14
<212> TYPE: PRT
<213> ORGANISM: Homo sapiens

<400> SEQUENCE: 497

Thr Gly Ala Ser Gly Asp Val Gly Ala Tyr Asn Phe Val Ser
1               5                   10

<210> SEQ ID NO 498
<211> LENGTH: 7
<212> TYPE: PRT
<213> ORGANISM: Homo sapiens

<400> SEQUENCE: 498

Asp Val Asn Lys Arg Pro Ser
1               5

<210> SEQ ID NO 499
<211> LENGTH: 10
<212> TYPE: PRT
<213> ORGANISM: Homo sapiens

<400> SEQUENCE: 499

Ser Ser Tyr Thr Ser Thr Phe Ser Val Val
1               5                   10

<210> SEQ ID NO 500
<211> LENGTH: 363
<212> TYPE: DNA
<213> ORGANISM: Homo sapiens

<400> SEQUENCE: 500
gaggtgcagc tggtggagag cggggaggt gtggtacggc ctgggggtc cctgagactc      60 tcctgtgcag cctctggatt cacctttgac gattatggca tgaactgggt ccgccaagct    120
ccagggaagg gctggagtg gtctctggt gttaattgga atggtggtac cagagattat     180
gcagcctccg tgaagggccg attcaccatc tccagagaca cgccaagaa ctccctgtat    240 ctgcaaatga acagtctgag agccgaggac acggccttgt atcactgtgc gagaggatgg   300
tatagtgggg ccgcgtggaa catgggctac tggggccgag aaccctggt caccgtctcc    360 tca                                                                 363

<210> SEQ ID NO 501
<211> LENGTH: 333
<212> TYPE: DNA
<213> ORGANISM: Homo sapiens

<400> SEQUENCE: 501
caggctgcgc tgactcagcc ggcctccgtg tctgggtctc ctggacagtc gatcaccatc    60
tcctgcactg gagccagcgg tgacgttggt gcttataact ttgtctcctg gtaccaacaa   120
cacccaggca agcccccaa actcataatt tatgatgtca ataagcggcc ctcaggggtt    180
tctaatcgct tctctggctc caagtctggc aacacggcct ccctgaccat ctctgggctc    240
caggccgagg acgaggctga ttattactgc agctcatata caagcacctt ctctgtggta    300
tttggcggag ggaccaagct gaccgtccta ggt                                 333

<210> SEQ ID NO 502
<211> LENGTH: 744
<212> TYPE: DNA
<213> ORGANISM: Homo sapiens
```

<400> SEQUENCE: 502

```
gaggtgcagc tggtggagag cgggggaggt gtggtacggc ctggggggtc cctgagactc      60
tcctgtgcag cctctggatt cacctttgac gattatggca tgaactgggt ccgccaagct     120
ccagggaagg gctggagtg gtctctggt gttaattgga atggtggtac cagagattat     180
gcagcctccg tgaagggccg attcaccatc tccagagaca cgccaagaa ctccctgtat     240
ctgcaaatga acagtctgag agccgaggac acggccttgt atcactgtgc gagaggatgg     300
tatagtgggg ccgcgtggaa catgggctac tggggccgag aaccctggt caccgtctcc     360
tcaggaggcg gcggttcagg cggaggtggc tctggcggtg gcggaagtgc acaggctgcg     420
ctgactcagc cggcctccgt gtctgggtct cctggacagt cgatcaccat ctcctgcact     480
ggagccagcg tgacgttgg tgcttataac tttgtctcct ggtaccaaca cacccaggc     540
aaagcccca aactcataat ttatgatgtc aataagcggc cctcaggggt ttctaatcgc     600
ttctctggct ccaagtctgg caacacggcc tccctgacca tctctgggct ccaggccgag     660
gacgaggctg attattactg cagctcatat acaagcacct tctctgtggt atttggcgga     720
gggaccaagc tgaccgtcct aggt                                            744
```

<210> SEQ ID NO 503
<211> LENGTH: 15
<212> TYPE: DNA
<213> ORGANISM: Homo sapiens

<400> SEQUENCE: 503

```
gattatggca tgaac                                                      15
```

<210> SEQ ID NO 504
<211> LENGTH: 51
<212> TYPE: DNA
<213> ORGANISM: Homo sapiens

<400> SEQUENCE: 504

```
ggtgttaatt ggaatggtgg taccagagat tatgcagcct ccgtgaaggg c              51
```

<210> SEQ ID NO 505
<211> LENGTH: 36
<212> TYPE: DNA
<213> ORGANISM: Homo sapiens

<400> SEQUENCE: 505

```
ggatggtata gtggggccgc gtggaacatg ggctac                               36
```

<210> SEQ ID NO 506
<211> LENGTH: 42
<212> TYPE: DNA
<213> ORGANISM: Homo sapiens

<400> SEQUENCE: 506

```
actggagcca gcggtgacgt tggtgcttat aactttgtct cc                        42
```

<210> SEQ ID NO 507
<211> LENGTH: 21
<212> TYPE: DNA
<213> ORGANISM: Homo sapiens

<400> SEQUENCE: 507

```
gatgtcaata agcggccctc a                                               21
```

-continued

<210> SEQ ID NO 508
<211> LENGTH: 30
<212> TYPE: DNA
<213> ORGANISM: Homo sapiens

<400> SEQUENCE: 508
agctcatata caagcacctt ctctgtggta                                        30

<210> SEQ ID NO 509
<211> LENGTH: 119
<212> TYPE: PRT
<213> ORGANISM: Homo sapiens

<400> SEQUENCE: 509

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 510
<211> LENGTH: 109
<212> TYPE: PRT
<213> ORGANISM: Homo sapiens

<400> SEQUENCE: 510

Ser Ser Val Leu Thr Gln Pro Pro Ser Val Ser Val Ala Pro Gly Lys
1               5                   10                  15

Thr Ala Arg Ile Thr Cys Gly Gly Asn Asn Phe Arg Asn Lys Arg Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Leu Phe Asn Asp Asn
                85                  90                  95

Gly Val Phe Gly Gly Gly Thr Lys Leu Thr Val Leu Gly
            100                 105

<210> SEQ ID NO 511
<211> LENGTH: 244
<212> TYPE: PRT
<213> ORGANISM: Homo sapiens

<400> SEQUENCE: 511

Gln Val Gln Leu Val Gln Ser Gly Ala Glu Val Lys Lys Pro Gly Ala

```
            1               5                  10                 15
          Ser Val Lys Val Ser Cys Lys Ala Ser Gly Tyr Thr Phe Ser Asp Tyr
                          20                  25                 30

Tyr Ile His Trp Val Arg Gln Ala Pro Gly Gln Gly Leu Glu Trp Met
                          35                  40                  45

Gly Trp Val Asn Pro Asp Thr Gly Gly Thr Arg Tyr Ala Gln Lys Phe
                  50                  55                  60

Gln Gly Arg Val Thr Met Thr Arg Asp Met Ser Ile Ser Thr Ala Tyr
           65                  70                  75                  80

Met Glu Leu Ser Arg Leu Arg Ser Asp Thr Ala Val Tyr Tyr Cys
                          85                  90                  95

Ala Arg Asp Leu Thr Gly Phe Asp Pro Phe Asp Ile Trp Gly Gln Gly
                          100                 105                110

Thr Leu Val Thr Val Ser Ser Gly Gly Gly Ser Gly Gly Gly Gly
                          115                 120                 125

Ser Gly Gly Gly Gly Ser Ala Ser Ser Val Leu Thr Gln Pro Pro Ser
           130                 135                 140

Val Ser Val Ala Pro Gly Lys Thr Ala Arg Ile Thr Cys Gly Gly Asn
          145                 150                 155                 160

Asn Phe Arg Asn Lys Arg Val His Trp Tyr Gln Gln Lys Pro Gly Gln
                          165                 170                 175

Ala Pro Val Leu Val Ile Tyr Tyr Asp Ser Asp Arg Pro Ser Gly Ile
                          180                 185                 190

Pro Glu Arg Phe Ser Gly Ser Arg Ser Gly Asn Thr Ala Thr Leu Thr
                          195                 200                 205

Ile Ser Arg Val Glu Ala Gly Asp Glu Ala Asp Tyr Tyr Cys Gln Val
           210                 215                 220

Trp Asp Leu Phe Asn Asp Asn Gly Val Phe Gly Gly Gly Thr Lys Leu
          225                 230                 235                 240

Thr Val Leu Gly

<210> SEQ ID NO 512
<211> LENGTH: 5
<212> TYPE: PRT
<213> ORGANISM: Homo sapiens

<400> SEQUENCE: 512

Asp Tyr Tyr Ile His
1               5

<210> SEQ ID NO 513
<211> LENGTH: 17
<212> TYPE: PRT
<213> ORGANISM: Homo sapiens

<400> SEQUENCE: 513

Trp Val Asn Pro Asp Thr Gly Gly Thr Arg Tyr Ala Gln Lys Phe Gln
1               5                   10                  15

Gly

<210> SEQ ID NO 514
<211> LENGTH: 10
<212> TYPE: PRT
<213> ORGANISM: Homo sapiens

<400> SEQUENCE: 514

Asp Leu Thr Gly Phe Asp Pro Phe Asp Ile
```

<210> SEQ ID NO 515
<211> LENGTH: 11
<212> TYPE: PRT
<213> ORGANISM: Homo sapiens

<400> SEQUENCE: 515

Gly Gly Asn Asn Phe Arg Asn Lys Arg Val His
1               5                   10

<210> SEQ ID NO 516
<211> LENGTH: 7
<212> TYPE: PRT
<213> ORGANISM: Homo sapiens

<400> SEQUENCE: 516

Tyr Asp Ser Asp Arg Pro Ser
1               5

<210> SEQ ID NO 517
<211> LENGTH: 11
<212> TYPE: PRT
<213> ORGANISM: Homo sapiens

<400> SEQUENCE: 517

Gln Val Trp Asp Leu Phe Asn Asp Asn Gly Val
1               5                   10

<210> SEQ ID NO 518
<211> LENGTH: 357
<212> TYPE: DNA
<213> ORGANISM: Homo sapiens

<400> SEQUENCE: 518
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt ttcagggccg ggtcacaatg accagggaca tgtccatctc cacagcctac     240
atggagctgt ccaggctgag aagcgacgac acggccgtat attactgtgc gagagatcta     300
actggatttg atccttttga tatctggggc cagggaaccc tggtcaccgt ctcctca       357

<210> SEQ ID NO 519
<211> LENGTH: 327
<212> TYPE: DNA
<213> ORGANISM: Homo sapiens

<400> SEQUENCE: 519
tcgtctgtgc tgactcagcc accctcagtg tcagtggccc caggaaagac ggcccgcatt      60
acctgtgggg gaaacaactt tcgaaataaa agagtacact ggtatcagca gaagccaggc     120
caggcccctg tcctggtcat ctattatgat tcagaccggc cctcagggat ccctgagcga     180
ttctctggct cccgctctgg gaacacggcc accctgacca tcagcagggt cgaggccggg     240
gatgaggccg actattactg tcaggtgtgg gatctcttca acgacaacgg cgtgttcggc     300
ggagggacca agctgaccgt cctaggt                                         327

<210> SEQ ID NO 520
<211> LENGTH: 732
<212> TYPE: DNA

```
<213> ORGANISM: Homo sapiens

<400> SEQUENCE: 520
caggtccagc tggtgcagtc tggggctgag gtgaagaagc ctggggcctc agtgaaggtc      60
tcctgtaagg cttctggata cccttcagc gattactata ttcactgggt gcgacaggcc     120
cctggacaag ggttggagtg gatgggatgg gtcaaccctg acactggtgg cacaagatac    180
gcgcagaagt ttcagggccg ggtcacaatg accaggaca tgtccatctc cacagcctac     240
atggagctgt ccaggctgag aagcgacgac acggccgtat attactgtgc gagagatcta    300
actggatttg atccttttga tatctggggc caggaaccc tggtcaccgt ctcctcagga     360
ggcggcagtt caggtggagg tggctctggc ggtggcggaa gtgcatcgtc tgtgctgact    420
cagccaccct cagtgtcagt ggccccagga aagacggccc gcattacctg tgggggaaac    480
aactttcgaa ataaaagagt acactggtat cagcagaagc caggccaggc ccctgtcctg    540
gtcatctatt atgattcaga ccggccctca gggatccctg agcgattctc tggctcccgc    600
tctgggaaca cggccaccct gaccatcagc agggtcgagg ccggggatga ggccgactat    660
tactgtcagg tgtgggatct cttcaacgac aacggcgtgt tcggcggagg gaccaagctg    720
accgtcctag gt                                                        732

<210> SEQ ID NO 521
<211> LENGTH: 15
<212> TYPE: DNA
<213> ORGANISM: Homo sapiens

<400> SEQUENCE: 521
gattactata ttcac                                                      15

<210> SEQ ID NO 522
<211> LENGTH: 51
<212> TYPE: DNA
<213> ORGANISM: Homo sapiens

<400> SEQUENCE: 522
tgggtcaacc ctgacactgg tggcacaaga tacgcgcaga agtttcaggg c               51

<210> SEQ ID NO 523
<211> LENGTH: 30
<212> TYPE: DNA
<213> ORGANISM: Homo sapiens

<400> SEQUENCE: 523
gatctaactg gatttgatcc ttttgatatc                                       30

<210> SEQ ID NO 524
<211> LENGTH: 33
<212> TYPE: DNA
<213> ORGANISM: Homo sapiens

<400> SEQUENCE: 524
gggggaaaca actttcgaaa taaaagagta cac                                   33

<210> SEQ ID NO 525
<211> LENGTH: 21
<212> TYPE: DNA
<213> ORGANISM: Homo sapiens

<400> SEQUENCE: 525
tatgattcag accggccctc a                                                21
```

<210> SEQ ID NO 526
<211> LENGTH: 33
<212> TYPE: DNA
<213> ORGANISM: Homo sapiens

<400> SEQUENCE: 526
caggtgtggg atctcttcaa cgacaacggc gtg                                    33

<210> SEQ ID NO 527
<211> LENGTH: 119
<212> TYPE: PRT
<213> ORGANISM: Homo sapiens

<400> SEQUENCE: 527

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
    50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser
        115

<210> SEQ ID NO 528
<211> LENGTH: 109
<212> TYPE: PRT
<213> ORGANISM: Homo sapiens

<400> SEQUENCE: 528

Ser Ser Val Leu Thr Gln Pro Pro Ser Val Ser Val Ala Pro Gly Lys
1               5                   10                  15

Thr Ala Arg Ile Thr Cys Gly Gly Asn Asn Phe Arg Asn Lys Arg Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Arg Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Phe Leu Thr Asp Ser
                85                  90                  95

Gly Ser Phe Gly Gly Gly Thr Lys Leu Thr Val Leu Gly
            100                 105

<210> SEQ ID NO 529
<211> LENGTH: 244
<212> TYPE: PRT
<213> ORGANISM: Homo sapiens

<400> SEQUENCE: 529

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Ile His Trp Val Arg Gln Ala Pro Gly Gln Gly Leu Glu Trp Met
        35                  40                  45

Gly Trp Val Asn Pro Asp Thr Gly Gly Thr Arg Tyr Ala Gln Lys Phe
50                  55                  60

Gln Gly Arg Val Thr Met Thr Arg Asp Met Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Thr Gly Phe Asp Pro Phe Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Ala Ser Ser Val Leu Thr Gln Pro Pro Ser
    130                 135                 140

Val Ser Val Ala Pro Gly Lys Thr Ala Arg Ile Thr Cys Gly Gly Asn
145                 150                 155                 160

Asn Phe Arg Asn Lys Arg Val His Trp Tyr Gln Gln Lys Pro Gly Gln
                165                 170                 175

Ala Pro Val Leu Val Ile Tyr Tyr Asp Ser Asp Arg Pro Ser Gly Ile
            180                 185                 190

Pro Glu Arg Phe Ser Gly Ser Arg Ser Gly Asn Thr Ala Thr Leu Thr
        195                 200                 205

Ile Ser Arg Val Glu Ala Gly Asp Glu Ala Asp Tyr Tyr Cys Gln Val
210                 215                 220

Trp Asp Phe Leu Thr Asp Ser Gly Ser Phe Gly Gly Gly Thr Lys Leu
225                 230                 235                 240

Thr Val Leu Gly

<210> SEQ ID NO 530
<211> LENGTH: 5
<212> TYPE: PRT
<213> ORGANISM: Homo sapiens

<400> SEQUENCE: 530

Asp Tyr Tyr Ile His
1               5

<210> SEQ ID NO 531
<211> LENGTH: 17
<212> TYPE: PRT
<213> ORGANISM: Homo sapiens

<400> SEQUENCE: 531

Trp Val Asn Pro Asp Thr Gly Gly Thr Arg Tyr Ala Gln Lys Phe Gln
1               5                   10                  15

Gly

<210> SEQ ID NO 532
<211> LENGTH: 10
<212> TYPE: PRT
<213> ORGANISM: Homo sapiens

<400> SEQUENCE: 532
```

```
Asp Leu Thr Gly Phe Asp Pro Phe Asp Ile
1               5                   10

<210> SEQ ID NO 533
<211> LENGTH: 11
<212> TYPE: PRT
<213> ORGANISM: Homo sapiens

<400> SEQUENCE: 533

Gly Gly Asn Asn Phe Arg Asn Lys Arg Val His
1               5                   10

<210> SEQ ID NO 534
<211> LENGTH: 7
<212> TYPE: PRT
<213> ORGANISM: Homo sapiens

<400> SEQUENCE: 534

Tyr Asp Ser Asp Arg Pro Ser
1               5

<210> SEQ ID NO 535
<211> LENGTH: 11
<212> TYPE: PRT
<213> ORGANISM: Homo sapiens

<400> SEQUENCE: 535

Gln Val Trp Asp Phe Leu Thr Asp Ser Gly Ser
1               5                   10

<210> SEQ ID NO 536
<211> LENGTH: 357
<212> TYPE: DNA
<213> ORGANISM: Homo sapiens

<400> SEQUENCE: 536
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt ttcagggccg ggtcacaatg accagggaca tgtccatctc cacagcctac     240
atggagctgt ccaggctgag aagcgacgac acggccgtat attactgtgc gagagatcta     300
actggatttg atccttttga tatctggggc cagggaaccc tggtcaccgt ctcctca        357

<210> SEQ ID NO 537
<211> LENGTH: 327
<212> TYPE: DNA
<213> ORGANISM: Homo sapiens

<400> SEQUENCE: 537
tcgtctgtgc tgactcagcc accctcagtg tcagtggccc caggaaagac ggcccgcatt      60
acctgtgggg gaaacaactt tcgaaataaa agagtacact ggtatcagca gaagccaggc     120
caggcccctg tcctggtcat ctattatgat tcagaccggc cctcagggat ccctgagcga     180
ttctctggct cccgctctgg gaacacggcc accctgacca tcagcagggt cgaggccggg     240
gatgaggccg actattactg tcaggtgtgg gatttcctca ccgactcggg gtcgttcggc     300
ggagggacca agctgaccgt cctaggt                                         327

<210> SEQ ID NO 538
```

```
<211> LENGTH: 732
<212> TYPE: DNA
<213> ORGANISM: Homo sapiens

<400> SEQUENCE: 538
caggtccagc tggtgcagtc tggggctgag gtgaagaagc ctggggcctc agtgaaggtc      60
tcctgtaagg cttctggata caccttcagc gattactata ttcactgggt gcgacaggcc     120
cctggacaag ggttggagtg gatgggatgg gtcaaccctg acactggtgg cacaagatac     180
gcgcagaagt ttcagggccg ggtcacaatg accagggaca tgtccatctc cacagcctac     240
atggagctgt ccaggctgag aagcgacgac acggccgtat attactgtgc gagagatcta     300
actggatttg atccttttga tatctggggc caggaaccc tggtcaccgt ctcctcagga      360
ggcggcggtt caggcggagg tggctctggc ggtggcggaa gtgcatcgtc tgtgctgact     420
cagccaccct cagtgtcagt gccccagga agacggccc gcattacctg tggggaaaac       480
aactttcgaa ataaaagagt acactggtat cagcagaagc caggccaggc ccctgtcctg     540
gtcatctatt atgattcaga ccggccctca gggatccctg agcgattctc tggctcccgc     600
tctgggaaca cggccaccct gaccatcagc agggtcgagg ccggggatga ggccgactat     660
tactgtcagg tgtgggattt cctcaccgac tcggggtcgt tcggcggagg gaccaagctg     720
accgtcctag gt                                                         732

<210> SEQ ID NO 539
<211> LENGTH: 15
<212> TYPE: DNA
<213> ORGANISM: Homo sapiens

<400> SEQUENCE: 539
gattactata ttcac                                                       15

<210> SEQ ID NO 540
<211> LENGTH: 51
<212> TYPE: DNA
<213> ORGANISM: Homo sapiens

<400> SEQUENCE: 540
tgggtcaacc ctgacactgg tggcacaaga tacgcgcaga gtttcaggg c                51

<210> SEQ ID NO 541
<211> LENGTH: 30
<212> TYPE: DNA
<213> ORGANISM: Homo sapiens

<400> SEQUENCE: 541
gatctaactg gatttgatcc ttttgatatc                                       30

<210> SEQ ID NO 542
<211> LENGTH: 33
<212> TYPE: DNA
<213> ORGANISM: Homo sapiens

<400> SEQUENCE: 542
gggggaaaca actttcgaaa taaaagagta cac                                   33

<210> SEQ ID NO 543
<211> LENGTH: 21
<212> TYPE: DNA
<213> ORGANISM: Homo sapiens

<400> SEQUENCE: 543
```
tatgattcag accggccctc a 21

<210> SEQ ID NO 544
<211> LENGTH: 33
<212> TYPE: DNA
<213> ORGANISM: Homo sapiens

<400> SEQUENCE: 544
caggtgtggg atttcctcac cgactcgggg tcg 33

<210> SEQ ID NO 545
<211> LENGTH: 121
<212> TYPE: PRT
<213> ORGANISM: Homo sapiens

<400> SEQUENCE: 545

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Met His Trp Val Arg Gln Ala Pro Gly Gln Gly Leu Glu Trp Val
        35                  40                  45
Gly Trp Ile Asn Pro Tyr Thr Gly Gly Ala Phe Tyr Ala Gln Lys Phe
    50                  55                  60
Arg Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Pro Glu Arg Phe Gly Asp Ser Thr Gly Gln Val Trp Gly
            100                 105                 110
Arg Gly Thr Leu Val Thr Val Ser Ser
        115                 120
```

<210> SEQ ID NO 546
<211> LENGTH: 112
<212> TYPE: PRT
<213> ORGANISM: Homo sapiens

<400> SEQUENCE: 546

```
Gln Ala Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Gly Val His Trp Tyr Gln Gln Leu Pro Gly Thr Ala Pro Lys Leu
        35                  40                  45
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Tyr His Trp Asp Lys Glu
                85                  90                  95
Gln Ser Gly Tyr Val Phe Gly Gly Thr Gln Leu Thr Val Leu Gly
            100                 105                 110
```

<210> SEQ ID NO 547
<211> LENGTH: 249
<212> TYPE: PRT
<213> ORGANISM: Homo sapiens

<400> SEQUENCE: 547

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Glu Pro Glu Arg Phe Gly Asp Ser Thr Gly Gln Val Trp Gly
            100                 105                 110

Arg Gly Thr Leu Val Thr Val Ser Ser Gly Gly Gly Ser Gly Gly
            115                 120                 125

Gly Gly Ser Gly Gly Ser Arg Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Tyr His Trp Asp Lys Glu Gln Ser Gly Tyr Val Phe Gly
225                 230                 235                 240

Gly Gly Thr Gln Leu Thr Val Leu Gly
                245

<210> SEQ ID NO 548
<211> LENGTH: 5
<212> TYPE: PRT
<213> ORGANISM: Homo sapiens

<400> SEQUENCE: 548

Asp Tyr Tyr Met His
1               5

<210> SEQ ID NO 549
<211> LENGTH: 17
<212> TYPE: PRT
<213> ORGANISM: Homo sapiens

<400> SEQUENCE: 549

Trp Ile Asn Pro Tyr Thr Gly Gly Ala Phe Tyr Ala Gln Lys Phe Arg
1               5                   10                  15

Gly

<210> SEQ ID NO 550
<211> LENGTH: 12
<212> TYPE: PRT

<210> SEQ ID NO 550
<211> LENGTH: 11
<212> TYPE: PRT
<213> ORGANISM: Homo sapiens

<400> SEQUENCE: 550

Glu Pro Glu Arg Phe Gly Asp Ser Thr Gly Gln Val
1               5                   10

<210> SEQ ID NO 551
<211> LENGTH: 14
<212> TYPE: PRT
<213> ORGANISM: Homo sapiens

<400> SEQUENCE: 551

Thr Gly Ser Ser Ser Asn Ile Gly Ala Gly Tyr Gly Val His
1               5                   10

<210> SEQ ID NO 552
<211> LENGTH: 7
<212> TYPE: PRT
<213> ORGANISM: Homo sapiens

<400> SEQUENCE: 552

Gly Asn Ser Asn Arg Pro Ser
1               5

<210> SEQ ID NO 553
<211> LENGTH: 11
<212> TYPE: PRT
<213> ORGANISM: Homo sapiens

<400> SEQUENCE: 553

Tyr His Trp Asp Lys Glu Gln Ser Gly Tyr Val
1               5                   10

<210> SEQ ID NO 554
<211> LENGTH: 363
<212> TYPE: DNA
<213> ORGANISM: Homo sapiens

<400> SEQUENCE: 554
caggtgcagc tggtgcagtc tggggctgag gtgaagaagc ctggggcctc agtgaaggtc      60
tcctgcaagg cttctggata caccttcacc gactactata tgcactgggt gcgacaggcc     120
cctggacaag gcttgagtg gatgggatgg atcaacccctt atactggtgg cgcattctat     180
gcacagaagt tcggggcag ggtcacaatg accagggaca cgtccatcag cacagcctac     240
atggagctga gcagactgag atctgacgac acggccgtgt attattgtgc gagagaacct     300
gaaagattcg gcgactccac ggggcaggtc tggggccggg ggacattggt caccgtctcc     360
tca                                                                    363

<210> SEQ ID NO 555
<211> LENGTH: 336
<212> TYPE: DNA
<213> ORGANISM: Homo sapiens

<400> SEQUENCE: 555
caggctgtgc tgactcagcc gccgtcagtg tctggggccc cagggcagag ggtcaccatc      60
tcctgcactg ggagcagctc caacatcggg gcaggttatg gtgtacactg gtaccaacag     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc taccactggg acaaggagca gagtggttat     300

```
gtcttcggag gtgggaccca gctcaccgtc ctaggt                                    336
```

<210> SEQ ID NO 556
<211> LENGTH: 747
<212> TYPE: DNA
<213> ORGANISM: Homo sapiens

<400> SEQUENCE: 556

```
caggtgcagc tggtgcagtc tggggctgag gtgaagaagc ctggggcctc agtgaaggtc     60
tcctgcaagg cttctggata caccttcacc gactactata tgcactgggt gcgacaggcc    120
cctggacaag gcttgagtg gtgggatgg atcaacccctt atactggtgg cgcattctat     180
gcacagaagt ttcggggcag gtcacaatg accagggaca cgtccatcag cacagcctac    240
atggagctga gcagactgag atctgacgac acggccgtgt attattgtgc gagagaacct    300
gaaagattcg gcgactccac ggggcaggtc tggggccggg ggacattggt caccgtctcc    360
tcagggggcg gcggttcagg cggaggtggc tctggcggta gcagaagtgc acaggctgtg    420
ctgactcagc cgccgtcagt gtctggggcc ccagggcaga gggtcaccat ctcctgcact    480
gggagcagct ccaacatcgg ggcaggttat ggtgtacact ggtaccaaca gcttccagga    540
acagcccca aactcctcat ctatggtaac agcaatcggc cctcaggggt ccctgaccga    600
ttctctggct ccaagtctgg cacctcagcc tccctggcca tcactgggct ccaggctgag    660
gatgaggctg attattactg ctaccactgg gacaaggagc agagtggtta tgtcttcgga    720
ggtgggaccc agctcaccgt cctaggt                                        747
```

<210> SEQ ID NO 557
<211> LENGTH: 15
<212> TYPE: DNA
<213> ORGANISM: Homo sapiens

<400> SEQUENCE: 557

```
gactactata tgcac                                                      15
```

<210> SEQ ID NO 558
<211> LENGTH: 51
<212> TYPE: DNA
<213> ORGANISM: Homo sapiens

<400> SEQUENCE: 558

```
tggatcaacc cttatactgg tggcgcattc tatgcacaga gtttcggggc                51
```

<210> SEQ ID NO 559
<211> LENGTH: 36
<212> TYPE: DNA
<213> ORGANISM: Homo sapiens

<400> SEQUENCE: 559

```
gaacctgaaa gattcggcga ctccacgggg caggtc                               36
```

<210> SEQ ID NO 560
<211> LENGTH: 42
<212> TYPE: DNA
<213> ORGANISM: Homo sapiens

<400> SEQUENCE: 560

```
actgggagca gctccaacat cggggcaggt tatggtgtac ac                        42
```

<210> SEQ ID NO 561

```
<211> LENGTH: 21
<212> TYPE: DNA
<213> ORGANISM: Homo sapiens

<400> SEQUENCE: 561
ggtaacagca atcggccctc a                                              21

<210> SEQ ID NO 562
<211> LENGTH: 33
<212> TYPE: DNA
<213> ORGANISM: Homo sapiens

<400> SEQUENCE: 562
taccactggg acaaggagca gagtggttat gtc                                 33

<210> SEQ ID NO 563
<211> LENGTH: 121
<212> TYPE: PRT
<213> ORGANISM: Homo sapiens

<400> SEQUENCE: 563
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Gly Glu Ser Ser Gly Gln Leu Trp Gly
            100                 105                 110

Arg Gly Thr Leu Val Thr Val Ser Ser
        115                 120

```
<210> SEQ ID NO 564
<211> LENGTH: 112
<212> TYPE: PRT
<213> ORGANISM: Homo sapiens

<400> SEQUENCE: 564
```

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Gly
                85                  90                  95

Leu Ser Gly Tyr Val Phe Gly Gly Thr Gln Leu Thr Val Leu Gly
            100                 105                 110

<210> SEQ ID NO 565
<211> LENGTH: 249
<212> TYPE: PRT
<213> ORGANISM: Homo sapiens

<400> SEQUENCE: 565

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Met His Trp Val Arg Gln Ala Pro Gly Gln Gly Leu Glu Trp Val
        35                  40                  45
Gly Trp Ile Asn Pro Tyr Thr Gly Ser Ala Phe Tyr Ala Gln Lys Phe
    50                  55                  60
Arg Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Pro Glu Lys Phe Gly Glu Ser Ser Gly Gln Leu Trp Gly
            100                 105                 110
Arg Gly Thr Leu Val Thr Val Ser Gly Gly Gly Ser Gly Gly
        115                 120                 125
Gly Gly Ser Gly Gly Ser Gly Ser Ala Gln Ala Val Leu Thr Gln Pro
    130                 135                 140
Pro Ser Val Ser Gly Ala Pro Gly Gln Arg Val Thr Ile Ser Cys Thr
145                 150                 155                 160
Gly Ser Ser Ser Asn Ile Gly Ala Gly Tyr Gly Val His Trp Tyr Gln
                165                 170                 175
Gln Leu Pro Gly Thr Ala Pro Lys Leu Leu Ile Tyr Gly Asp Ser Asn
            180                 185                 190
Arg Pro Ser Gly Val Pro Asp Arg Phe Ser Gly Ser Lys Ser Gly Thr
        195                 200                 205
Ser Ala Ser Leu Ala Ile Thr Gly Leu Gln Ala Glu Asp Glu Ala Asp
    210                 215                 220
Tyr Tyr Cys Gln Ser Tyr Asp Ser Gly Leu Ser Gly Tyr Val Phe Gly
225                 230                 235                 240
Gly Gly Thr Gln Leu Thr Val Leu Gly
                245

<210> SEQ ID NO 566
<211> LENGTH: 5
<212> TYPE: PRT
<213> ORGANISM: Homo sapiens

<400> SEQUENCE: 566

Asp Tyr Tyr Met His
1               5

<210> SEQ ID NO 567
<211> LENGTH: 17
<212> TYPE: PRT
<213> ORGANISM: Homo sapiens

<400> SEQUENCE: 567

Trp Ile Asn Pro Tyr Thr Gly Ser Ala Phe Tyr Ala Gln Lys Phe Arg
1               5                   10                  15
Gly

<210> SEQ ID NO 568
<211> LENGTH: 12
<212> TYPE: PRT
<213> ORGANISM: Homo sapiens

<400> SEQUENCE: 568

Glu Pro Glu Lys Phe Gly Glu Ser Ser Gly Gln Leu
1               5                   10

<210> SEQ ID NO 569
<211> LENGTH: 14
<212> TYPE: PRT
<213> ORGANISM: Homo sapiens

<400> SEQUENCE: 569

Thr Gly Ser Ser Ser Asn Ile Gly Ala Gly Tyr Gly Val His
1               5                   10

<210> SEQ ID NO 570
<211> LENGTH: 7
<212> TYPE: PRT
<213> ORGANISM: Homo sapiens

<400> SEQUENCE: 570

Gly Asp Ser Asn Arg Pro Ser
1               5

<210> SEQ ID NO 571
<211> LENGTH: 11
<212> TYPE: PRT
<213> ORGANISM: Homo sapiens

<400> SEQUENCE: 571

Gln Ser Tyr Asp Ser Gly Leu Ser Gly Tyr Val
1               5                   10

<210> SEQ ID NO 572
<211> LENGTH: 363
<212> TYPE: DNA
<213> ORGANISM: Homo sapiens

<400> SEQUENCE: 572
caggtgcagc tggtgcagtc tggggctgag gtgaagaagc ctggggcctc agtgaaggtc      60
tcctgcaagg cttctggata caccttcacc gactactata tgcactgggt gcgacaggcc     120
cctggacaag gcttgagtg gtgggatgg atcaacccctt atactggtag cgctttctat     180
gcacagaagt tcggggcag ggtcacaatg accagggaca cgtccatcag cacagcctac     240
atggagctga gcagactgag atctgacgac acggccgtgt attattgtgc gagagaacct     300
gaaaaattcg gcgagtccag cggccagttg tggggccggg ggacattggt caccgtctcc     360
tca                                                                    363

<210> SEQ ID NO 573
<211> LENGTH: 336
<212> TYPE: DNA
<213> ORGANISM: Homo sapiens

<400> SEQUENCE: 573
caggctgtgc tgactcagcc gccgtcagtg tctggggccc cagggcagag ggtcaccatc      60
tcctgcactg ggagcagctc caacatcggg gcaggttatg gtgtacactg gtaccaacag     120

-continued

```
cttccaggaa cagcccccaa actcctcatc tatggtgaca gcaatcggcc ctcaggggtc    180
cctgaccgat tctctggctc caagtctggc acctcagcct ccctggccat cactgggctc    240
caggctgagg atgaggctga ttattactgc cagtcctatg acagcggcct gagtggttat    300
gtcttcggag gtgggaccca gctcaccgtc ctaggt                              336
```

<210> SEQ ID NO 574
<211> LENGTH: 747
<212> TYPE: DNA
<213> ORGANISM: Homo sapiens

<400> SEQUENCE: 574

```
caggtgcagc tggtgcagtc tggggctgag gtgaagaagc ctggggcctc agtgaaggtc     60
tcctgcaagg cttctggata caccttcacc gactactata tgcactgggt gcgacaggcc    120
cctggacaag gcttgagtg gtgggatgg atcaaccctt atactggtag cgctttctat      180
gcacagaagt tcgggcag ggtcacaatg accaggaca cgtccatcag cacagcctac       240
atggagctga gcagactgag atctgacgac acggccgtgt attattgtgc gagagaacct    300
gaaaaattcg gcgagtccag cggccagttg tggggccggg ggacattggt caccgtctcc    360
tcaggaggcg gcggttcagg cggaggtggc tctggcggta gcggaagtgc acaggctgtg    420
ctgactcagc cgccgtcagt gtctggggcc ccagggcaga gggtcaccat ctcctgcact    480
gggagcagct ccaacatcgg ggcaggttat ggtgtacact ggtaccaaca gcttccagga    540
acagccccca aactcctcat ctatggtgac agcaatcggc cctcagggt  ccctgaccga    600 ttctctggct ccaagtctgg cacctcagcc tccctggcca tcactgggct ccaggctgag    660
gatgaggctg attattactg ccagtcctat gacagcggcc tgagtggtta tgtcttcgga    720
ggtgggaccc agctcaccgt cctaggt                                       747
```

<210> SEQ ID NO 575
<211> LENGTH: 15
<212> TYPE: DNA
<213> ORGANISM: Homo sapiens

<400> SEQUENCE: 575

```
gactactata tgcac                                                     15
```

<210> SEQ ID NO 576
<211> LENGTH: 51
<212> TYPE: DNA
<213> ORGANISM: Homo sapiens

<400> SEQUENCE: 576

```
tggatcaacc cttatactgg tagcgctttc tatgcacaga agtttcgggg c              51
```

<210> SEQ ID NO 577
<211> LENGTH: 36
<212> TYPE: DNA
<213> ORGANISM: Homo sapiens

<400> SEQUENCE: 577

```
gaacctgaaa aattcggcga gtccagcggc cagttg                              36
```

<210> SEQ ID NO 578
<211> LENGTH: 42
<212> TYPE: DNA
<213> ORGANISM: Homo sapiens

<400> SEQUENCE: 578

```
actgggagca gctccaacat cggggcaggt tatggtgtac ac                    42
```

<210> SEQ ID NO 579
<211> LENGTH: 21
<212> TYPE: DNA
<213> ORGANISM: Homo sapiens

<400> SEQUENCE: 579

```
ggtgacagca atcggccctc a                                           21
```

<210> SEQ ID NO 580
<211> LENGTH: 33
<212> TYPE: DNA
<213> ORGANISM: Homo sapiens

<400> SEQUENCE: 580

```
cagtcctatg acagcggcct gagtggttat gtc                              33
```

<210> SEQ ID NO 581
<211> LENGTH: 121
<212> TYPE: PRT
<213> ORGANISM: Homo sapiens

<400> SEQUENCE: 581

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | His | Tyr |
|---|---|---|---|---|---|---|---|---|---|---|---|---|---|---|---|
| | | | 20 | | | | | 25 | | | | | 30 | | |

| Tyr | Met | His | Trp | Val | Arg | Gln | Ala | Pro | Gly | Gln | Gly | Leu | Glu | Trp | Val |
|---|---|---|---|---|---|---|---|---|---|---|---|---|---|---|---|
| | | 35 | | | | | 40 | | | | | 45 | | | |

| Gly | Trp | Ile | Asn | Pro | Tyr | Thr | Gly | Gly | Ala | Phe | Tyr | Ala | Gln | Lys | Phe |
|---|---|---|---|---|---|---|---|---|---|---|---|---|---|---|---|
| 50 | | | | | 55 | | | | | 60 | | | | | |

| Gln | Gly | Arg | Val | Thr | Met | Thr | Arg | Asp | Thr | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Arg | Leu | Arg | Ser | Asp | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Pro | Glu | Lys | Phe | Asp | Ser | Pro | Asn | Ala | Glu | Ile | Trp | Gly |
|---|---|---|---|---|---|---|---|---|---|---|---|---|---|---|---|
| | | | 100 | | | | | 105 | | | | | 110 | | |

| Arg | Gly | Thr | Leu | Val | Thr | Val | Ser | Ser |
|---|---|---|---|---|---|---|---|---|
| | | | 115 | | | | | 120 |

<210> SEQ ID NO 582
<211> LENGTH: 112
<212> TYPE: PRT
<213> ORGANISM: Homo sapiens

<400> SEQUENCE: 582

| Gln | Ala | Val | Leu | Thr | Gln | Pro | Pro | Ser | Val | Ser | Gly | Ala | Pro | Gly | Gln |
|---|---|---|---|---|---|---|---|---|---|---|---|---|---|---|---|
| 1 | | | | 5 | | | | | 10 | | | | | 15 | |

| Arg | Val | Thr | Ile | Ser | Cys | Thr | Gly | Ser | Ser | Ser | Asn | Ile | Gly | Ala | Gly |
|---|---|---|---|---|---|---|---|---|---|---|---|---|---|---|---|
| | | | 20 | | | | | 25 | | | | | 30 | | |

| Tyr | Gly | Val | His | Trp | Tyr | Gln | Gln | Leu | Pro | Gly | Thr | Ala | Pro | Lys | Leu |
|---|---|---|---|---|---|---|---|---|---|---|---|---|---|---|---|
| | | 35 | | | | | 40 | | | | | 45 | | | |

| Leu | Ile | Tyr | Gly | Asn | Ser | Asn | Arg | Pro | Ser | Gly | Val | Pro | Asp | Arg | Phe |
|---|---|---|---|---|---|---|---|---|---|---|---|---|---|---|---|
| 50 | | | | | 55 | | | | | 60 | | | | | |

| Ser | Gly | Ser | Lys | Ser | Gly | Thr | Ser | Ala | Ser | Leu | Ala | Ile | Thr | Gly | Leu |
|---|---|---|---|---|---|---|---|---|---|---|---|---|---|---|---|
| 65 | | | | | 70 | | | | | 75 | | | | | 80 |

| Gln | Ala | Glu | Asp | Glu | Ala | Asp | Tyr | Tyr | Cys | Gln | Ser | Tyr | Asp | Ser | Ser |

85                  90                  95

Leu Ser Gly Tyr Val Phe Gly Gly Thr Gln Leu Thr Val Leu Gly
            100                 105                 110

<210> SEQ ID NO 583
<211> LENGTH: 249
<212> TYPE: PRT
<213> ORGANISM: Homo sapiens

<400> SEQUENCE: 583

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Gly Ala Phe Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Pro Asn Ala Glu Ile Trp Gly
            100                 105                 110

Arg Gly Thr Leu Val Thr Val Ser Glu Gly Gly Ser Gly Gly
        115                 120                 125

Gly Gly Ser Gly Gly Ser Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Gly Tyr Val Phe Gly
225                 230                 235                 240

Gly Gly Thr Gln Leu Thr Val Leu Gly
                245

<210> SEQ ID NO 584
<211> LENGTH: 5
<212> TYPE: PRT
<213> ORGANISM: Homo sapiens

<400> SEQUENCE: 584

His Tyr Tyr Met His
1               5

<210> SEQ ID NO 585
<211> LENGTH: 17
<212> TYPE: PRT
<213> ORGANISM: Homo sapiens

<400> SEQUENCE: 585

-continued

Trp Ile Asn Pro Tyr Thr Gly Gly Ala Phe Tyr Ala Gln Lys Phe Gln
1               5                   10                  15

Gly

<210> SEQ ID NO 586
<211> LENGTH: 12
<212> TYPE: PRT
<213> ORGANISM: Homo sapiens

<400> SEQUENCE: 586

Glu Pro Glu Lys Phe Asp Ser Pro Asn Ala Glu Ile
1               5                   10

<210> SEQ ID NO 587
<211> LENGTH: 14
<212> TYPE: PRT
<213> ORGANISM: Homo sapiens

<400> SEQUENCE: 587

Thr Gly Ser Ser Ser Asn Ile Gly Ala Gly Tyr Gly Val His
1               5                   10

<210> SEQ ID NO 588
<211> LENGTH: 7
<212> TYPE: PRT
<213> ORGANISM: Homo sapiens

<400> SEQUENCE: 588

Gly Asn Ser Asn Arg Pro Ser
1               5

<210> SEQ ID NO 589
<211> LENGTH: 11
<212> TYPE: PRT
<213> ORGANISM: Homo sapiens

<400> SEQUENCE: 589

Gln Ser Tyr Asp Ser Ser Leu Ser Gly Tyr Val
1               5                   10

<210> SEQ ID NO 590
<211> LENGTH: 363
<212> TYPE: DNA
<213> ORGANISM: Homo sapiens

<400> SEQUENCE: 590
caggtgcagc tggtgcagtc tggggctgag gtgaagaagc ctggggcctc agtgaaggtc      60
tcctgcaagg cttctggata caccttcacc cactactata tgcactgggt gcgacaggcc     120
cctggacaag ggcttgagtg gtgggatgg atcaaccctt atactggtgg cgcattctat      180
gcacagaagt tcagggcag ggtcacaatg accaggaca cgtccatcag cacagcctac      240
atggagctga gcagactgag atctgacgac acggccgtgt attattgtgc gagagaacct     300
gaaaaattcg actcgccgaa cgccgagatc tggggccggg ggacattggt caccgtctcc     360
tca                                                                    363

<210> SEQ ID NO 591
<211> LENGTH: 336
<212> TYPE: DNA
<213> ORGANISM: Homo sapiens

<400> SEQUENCE: 591

```
caggctgtgc tgactcagcc gccgtcagtg tctggggccc cagggcagag ggtcaccatc      60
tcctgcactg ggagcagctc caacatcggg gcaggttatg gtgtacactg gtaccaacag     120
cttccaggaa cagcccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggttat     300
gtcttcggag gtgggaccca gctcaccgtc ctaggt                               336

<210> SEQ ID NO 592
<211> LENGTH: 747
<212> TYPE: DNA
<213> ORGANISM: Homo sapiens

<400> SEQUENCE: 592
caggtgcagc tggtgcagtc tggggctgag gtgaagaagc ctggggcctc agtgaaggtc      60
tcctgcaagg cttctggata caccttcacc cactactata tgcactgggt gcgacaggcc     120
cctggacaag ggcttgagtg ggtgggatgg atcaacccctt atactggtgg cgcattctat    180
gcacagaagt tcagggcag ggtcacaatg accaggaca cgtccatcag cacagcctac      240
atggagctga gcagactgag atctgacgac acggccgtgt attattgtgc gagagaacct     300
gaaaaattcg actcgccgaa cgccgagatc tgggccggg ggacattggt caccgtctcc     360
tcagaaggcg gcggttcagg cggaggtggc tctggcggta gcggaagtgc acaggctgtg    420
ctgactcagc cgccgtcagt gtctggggcc cagggcaga gggtcaccat ctcctgcact     480
gggagcagct ccaacatcgg ggcaggttat ggtgtacact ggtaccaaca gcttccagga     540
acagccccca aactcctcat ctatggtaac agcaatcggc cctcagggt ccctgaccga      600 ttctctggct ccaagtctgg cacctcagcc tccctggcca tcactgggct ccaggctgag     660
gatgaggctg attattactg ccagtcctat gacagcagcc tgagtggtta tgtcttcgga     720
ggtgggaccc agctcaccgt cctaggt                                         747

<210> SEQ ID NO 593
<211> LENGTH: 15
<212> TYPE: DNA
<213> ORGANISM: Homo sapiens

<400> SEQUENCE: 593
cactactata tgcac                                                       15

<210> SEQ ID NO 594
<211> LENGTH: 51
<212> TYPE: DNA
<213> ORGANISM: Homo sapiens

<400> SEQUENCE: 594
tggatcaacc cttatactgg tggcgcattc tatgcacaga agtttcaggg c               51

<210> SEQ ID NO 595
<211> LENGTH: 36
<212> TYPE: DNA
<213> ORGANISM: Homo sapiens

<400> SEQUENCE: 595
gaacctgaaa aattcgactc gccgaacgcc gagatc                                36

<210> SEQ ID NO 596
```

-continued

<210> SEQ ID NO 596
<211> LENGTH: 42
<212> TYPE: DNA
<213> ORGANISM: Homo sapiens

<400> SEQUENCE: 596
actgggagca gctccaacat cggggcaggt tatggtgtac ac 42

<210> SEQ ID NO 597
<211> LENGTH: 21
<212> TYPE: DNA
<213> ORGANISM: Homo sapiens

<400> SEQUENCE: 597
ggtaacagca atcggccctc a 21

<210> SEQ ID NO 598
<211> LENGTH: 33
<212> TYPE: DNA
<213> ORGANISM: Homo sapiens

<400> SEQUENCE: 598
cagtcctatg acagcagcct gagtggttat gtc 33

<210> SEQ ID NO 599
<211> LENGTH: 121
<212> TYPE: PRT
<213> ORGANISM: Homo sapiens

<400> SEQUENCE: 599

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Asp Ser Asp Val Trp Gly
            100                 105                 110

Arg Gly Thr Leu Val Thr Val Ser Ser
        115                 120

<210> SEQ ID NO 600
<211> LENGTH: 112
<212> TYPE: PRT
<213> ORGANISM: Homo sapiens

<400> SEQUENCE: 600

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
        35                  40                  45

Leu Ile Tyr Gly Asp Ser Asn Arg Pro Ser Gly Val Pro Asp Arg Phe
    50                  55                  60

```
Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Asn Ser
                 85                  90                  95

Leu Ser Gly Tyr Val Phe Gly Gly Gly Thr Gln Leu Thr Val Leu Gly
            100                 105                 110

<210> SEQ ID NO 601
<211> LENGTH: 249
<212> TYPE: PRT
<213> ORGANISM: Homo sapiens

<400> SEQUENCE: 601

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                 20                  25                  30

Tyr Met His Trp Val Arg Gln Ala Pro Gly Gln Gly Leu Glu Trp Val
             35                  40                  45

Gly Trp Ile Asn Pro Tyr Thr Gly Ser Ala Phe Tyr Ala Gln Lys Phe
 50                  55                  60

Arg Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Pro Glu Lys Phe Asp Ser Asp Ser Asp Val Trp Gly
            100                 105                 110

Arg Gly Thr Leu Val Thr Val Ser Ser Gly Gly Gly Ser Gly Gly
            115                 120                 125

Gly Gly Ser Gly Gly Ser Ala Gln Ala Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Gly Val His Trp Tyr Gln
                165                 170                 175

Gln Leu Pro Gly Thr Ala Pro Lys Leu Leu Ile Tyr Gly Asp Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Asn Ser Leu Ser Gly Tyr Val Phe Gly
225                 230                 235                 240

Gly Gly Thr Gln Leu Thr Val Leu Gly
                245

<210> SEQ ID NO 602
<211> LENGTH: 5
<212> TYPE: PRT
<213> ORGANISM: Homo sapiens

<400> SEQUENCE: 602

Asn Tyr Tyr Met His
1               5

<210> SEQ ID NO 603
```

```
<211> LENGTH: 17
<212> TYPE: PRT
<213> ORGANISM: Homo sapiens

<400> SEQUENCE: 603

Trp Ile Asn Pro Tyr Thr Gly Ser Ala Phe Tyr Ala Gln Lys Phe Arg
1               5                   10                  15

Gly

<210> SEQ ID NO 604
<211> LENGTH: 12
<212> TYPE: PRT
<213> ORGANISM: Homo sapiens

<400> SEQUENCE: 604

Glu Pro Glu Lys Phe Asp Ser Asp Asp Ser Asp Val
1               5                   10

<210> SEQ ID NO 605
<211> LENGTH: 14
<212> TYPE: PRT
<213> ORGANISM: Homo sapiens

<400> SEQUENCE: 605

Thr Gly Ser Ser Ser Asn Ile Gly Ala Gly Tyr Gly Val His
1               5                   10

<210> SEQ ID NO 606
<211> LENGTH: 7
<212> TYPE: PRT
<213> ORGANISM: Homo sapiens

<400> SEQUENCE: 606

Gly Asp Ser Asn Arg Pro Ser
1               5

<210> SEQ ID NO 607
<211> LENGTH: 11
<212> TYPE: PRT
<213> ORGANISM: Homo sapiens

<400> SEQUENCE: 607

Gln Ser Tyr Asp Asn Ser Leu Ser Gly Tyr Val
1               5                   10

<210> SEQ ID NO 608
<211> LENGTH: 363
<212> TYPE: DNA
<213> ORGANISM: Homo sapiens

<400> SEQUENCE: 608
caggtgcagc tggtgcagtc tggggctgag gtgaagaagc ctggggcctc agtgaaggtc      60
tcctgcaagg cttctggata caccttcacc aactactata tgcactgggt gcgacaggcc     120
cctggacaag ggcttgagtg gtgggatgg atcaacccctt atactggtag cgcattctat     180
gcacagaagt tcgggggcag ggtcacaatg accaggggaca cgtccatcag cacagcctac     240
atggagctga gcagactgag atctgacgac acggccgtgt attattgtgc gagagaacct     300
gaaaaattcg actccgacga ctccgacgtc tggggccgcg gacattggt caccgtctcc     360 tca                                                                   363

<210> SEQ ID NO 609
```

```
<211> LENGTH: 336
<212> TYPE: DNA
<213> ORGANISM: Homo sapiens

<400> SEQUENCE: 609
caggctgtgc tgactcagcc gccgtcagtg tctggggccc cagggcagag ggtcaccatc      60
tcctgcactg ggagcagctc caacatcggg gcaggttatg gtgtacactg gtaccaacag     120
cttccaggaa cagcccccaa actcctcatc tatggtgaca gcaatcggcc ctcaggggtc     180
cctgaccgat tctctggctc caagtctggc acctcagcct ccctggccat cactgggctc     240
caggctgagg atgaggctga ttattactgc cagtcctatg acaacagcct gagcggttat     300
gtcttcggag gtgggaccca gctcaccgtc ctaggt                               336

<210> SEQ ID NO 610
<211> LENGTH: 747
<212> TYPE: DNA
<213> ORGANISM: Homo sapiens

<400> SEQUENCE: 610
caggtgcagc tggtgcagtc tggggctgag gtgaagaagc ctgggcctc agtgaaggtc       60 tcctgcaagg cttctggata caccttcacc aactactata tgcactgggt gcgacaggcc     120
cctggacaag gcttgagtg gtgggatgg atcaaccctt atactggtag cgcattctat       180
gcacagaagt tcgggcag gtcacaatg accaggaca cgtccatcag cacagcctac         240
atggagctga gcagactgag atctgacgac acggccgtgt attattgtgc gagagaacct     300
gaaaaattcg actccgacga ctccgacgtc tggggccgcg ggacattggt caccgtctcc     360
tcaggaggcg gcagttcagg cggaggtggc tctggcggta gcggaagtgc acaggctgtg     420
ctgactcagc cgccgtcagt gtctggggcc cagggcaga gggtcaccat ctcctgcact       480
gggagcagct ccaacatcgg ggcaggttat ggtgtacact ggtaccaaca gcttccagga     540 acagcccca aactcctcat ctatggtgac agcaatcggc cctcagggt ccctgaccga        600 ttctctggct ccaagtctgg cacctcagcc tccctggcca tcactgggct ccaggctgag     660
gatgaggctg attattactg ccagtcctat gacaacagcc tgagcggtta tgtcttcgga     720
ggtgggaccc agctcaccgt cctaggt                                         747

<210> SEQ ID NO 611
<211> LENGTH: 15
<212> TYPE: DNA
<213> ORGANISM: Homo sapiens

<400> SEQUENCE: 611
aactactata tgcac                                                       15

<210> SEQ ID NO 612
<211> LENGTH: 51
<212> TYPE: DNA
<213> ORGANISM: Homo sapiens

<400> SEQUENCE: 612
tggatcaacc cttatactgg tagcgcattc tatgcacaga gtttcgggg c                51

<210> SEQ ID NO 613
<211> LENGTH: 36
<212> TYPE: DNA
<213> ORGANISM: Homo sapiens

<400> SEQUENCE: 613
```

```
gaacctgaaa aattcgactc cgacgactcc gacgtc                                   36
```

<210> SEQ ID NO 614
<211> LENGTH: 42
<212> TYPE: DNA
<213> ORGANISM: Homo sapiens

<400> SEQUENCE: 614

```
actgggagca gctccaacat cggggcaggt tatggtgtac ac                            42
```

<210> SEQ ID NO 615
<211> LENGTH: 21
<212> TYPE: DNA
<213> ORGANISM: Homo sapiens

<400> SEQUENCE: 615

```
ggtgacagca atcggccctc a                                                   21
```

<210> SEQ ID NO 616
<211> LENGTH: 33
<212> TYPE: DNA
<213> ORGANISM: Homo sapiens

<400> SEQUENCE: 616

```
cagtcctatg acaacagcct gagcggttat gtc                                      33
```

<210> SEQ ID NO 617
<211> LENGTH: 121
<212> TYPE: PRT
<213> ORGANISM: Homo sapiens

<400> SEQUENCE: 617

```
Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Asp Asp Tyr
            20                  25                  30

Gly Met Asn Trp Val Arg Gln Ala Pro Gly Lys Gly Leu Glu Trp Val
        35                  40                  45

Ser Gly Val Asn Trp Asn Gly Gly Thr Arg Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Trp Tyr Ser Gly Ala Ala Trp Asn Met Gly Tyr Trp Gly
            100                 105                 110

Arg Gly Thr Leu Val Thr Val Ser Ser
        115                 120
```

<210> SEQ ID NO 618
<211> LENGTH: 110
<212> TYPE: PRT
<213> ORGANISM: Homo sapiens

<400> SEQUENCE: 618

```
Gln Ala Ala Leu Thr Gln Pro Ala Ser Val Ser Gly Ser Pro Gly Gln
 1               5                  10                  15

Ser Ile Thr Ile Ser Cys Thr Gly Ala Ser Gly Asp Val Gly Ala Tyr
            20                  25                  30
```

Asn Phe Val Ser Trp Tyr Gln Gln His Pro Gly Lys Ala Pro Lys Leu
                35                  40                  45

Ile Ile Tyr Asp Val Asn Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Leu Val Ser Asp
                 85                  90                  95

Phe Ser Val Val Phe Gly Gly Thr Lys Leu Thr Val Leu
                100                 105                 110

<210> SEQ ID NO 619
<211> LENGTH: 261
<212> TYPE: PRT
<213> ORGANISM: Homo sapiens

<400> SEQUENCE: 619

Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Asp Asp Tyr
                20                  25                  30

Gly Met Asn Trp Val Arg Gln Ala Pro Gly Lys Gly Leu Glu Trp Val
                35                  40                  45

Ser Gly Val Asn Trp Asn Gly Gly Thr Arg Asp Tyr Ala Ala Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Gly Trp Tyr Ser Gly Ala Ala Trp Asn Met Gly Tyr Trp Gly
                100                 105                 110

Arg Gly Thr Leu Val Thr Val Ser Ser Gly Gly Gly Ser Gly Gly
                115                 120                 125

Gly Gly Ser Gly Gly Ser Gly Gly Ser Gly Gly Gly Gly Gly
                130                 135                 140

Ser Gly Gly Gly Gly Ser Ala Gln Ala Ala Leu Thr Gln Pro Ala Ser
145                 150                 155                 160

Val Ser Gly Ser Pro Gly Gln Ser Ile Thr Ile Ser Cys Thr Gly Ala
                165                 170                 175

Ser Gly Asp Val Gly Ala Tyr Asn Phe Val Ser Trp Tyr Gln Gln His
                180                 185                 190

Pro Gly Lys Ala Pro Lys Leu Ile Ile Tyr Asp Val Asn Lys Arg Pro
                195                 200                 205

Ser Gly Val Ser Asn Arg Phe Ser Gly Ser Lys Ser Gly Asn Thr Ala
                210                 215                 220

Ser Leu Thr Ile Ser Gly Leu Gln Ala Glu Asp Glu Ala Asp Tyr Tyr
225                 230                 235                 240

Cys Ala Ser Leu Val Ser Asp Phe Ser Val Val Phe Gly Gly Gly Thr
                245                 250                 255

Lys Leu Thr Val Leu
            260

<210> SEQ ID NO 620
<211> LENGTH: 5
<212> TYPE: PRT
<213> ORGANISM: Homo sapiens

<400> SEQUENCE: 620

Asp Tyr Gly Met Asn
1               5

<210> SEQ ID NO 621
<211> LENGTH: 17
<212> TYPE: PRT
<213> ORGANISM: Homo sapiens

<400> SEQUENCE: 621

Gly Val Asn Trp Asn Gly Gly Thr Arg Asp Tyr Ala Ala Ser Val Lys
1               5                   10                  15

Gly

<210> SEQ ID NO 622
<211> LENGTH: 12
<212> TYPE: PRT
<213> ORGANISM: Homo sapiens

<400> SEQUENCE: 622

Gly Trp Tyr Ser Gly Ala Ala Trp Asn Met Gly Tyr
1               5                   10

<210> SEQ ID NO 623
<211> LENGTH: 16
<212> TYPE: PRT
<213> ORGANISM: Homo sapiens

<400> SEQUENCE: 623

Ser Cys Thr Gly Ala Ser Gly Asp Val Gly Ala Tyr Asn Phe Val Ser
1               5                   10                  15

<210> SEQ ID NO 624
<211> LENGTH: 7
<212> TYPE: PRT
<213> ORGANISM: Homo sapiens

<400> SEQUENCE: 624

Asp Val Asn Lys Arg Pro Ser
1               5

<210> SEQ ID NO 625
<211> LENGTH: 10
<212> TYPE: PRT
<213> ORGANISM: Homo sapiens

<400> SEQUENCE: 625

Ala Ser Leu Val Ser Asp Phe Ser Val Val
1               5                   10

<210> SEQ ID NO 626
<211> LENGTH: 363
<212> TYPE: DNA
<213> ORGANISM: Homo sapiens

<400> SEQUENCE: 626
gaggtgcagc tggtggagag cggcggaggc gtggtgagac caggcggcag cctgagactg      60
agctgcgccg ccagcggctt caccttcgac gactacggca tgaactgggt gaggcaggcc     120
ccaggcaagg gcctggagtg ggtgtccggc gtgaactgga acggcggcac cagagactac     180
gccgcctctg tgaagggcag attcaccatc agccgggaca cgccaagaa cagcctgtac      240

```
ctgcagatga acagcctgag agccgaggac accgccctgt accactgcgc cagaggctgg    300
tacagcggag ccgcctggaa catgggctac tggggcagag gcaccctggt gaccgtgtcc    360
agc                                                                  363

<210> SEQ ID NO 627
<211> LENGTH: 330
<212> TYPE: DNA
<213> ORGANISM: Homo sapiens

<400> SEQUENCE: 627
caggccgccc tgacccagcc cgccagcgtg tctggcagcc caggccagag catcaccatc     60
agctgcaccg gcgccagcgg cgatgtgggc gcctacaact tcgtgtcctg gtatcagcag    120
caccccggca aggccccccaa gctgatcatc tacgacgtga acaagagacc cagcggcgtg    180
tccaacagat tcagcggcag caagagcggc aacaccgcca gcctgaccat cagcggactg    240
caggccgagg acgaggccga ctactactgc gccagcctgg tgtccgactt cagcgtggtg    300
ttcggcggag gcaccaagct gaccgtgctg                                     330

<210> SEQ ID NO 628
<211> LENGTH: 783
<212> TYPE: DNA
<213> ORGANISM: Homo sapiens

<400> SEQUENCE: 628
gaggtgcagc tggtggagag cggcggaggc gtggtgagac aggcggcag cctgagactg      60 agctgcgccg ccagcggctt caccttcgac gactacggca tgaactgggt gaggcaggcc    120
ccaggcaagg gcctggagtg ggtgtccggc gtgaactgga acggcggcac cagagactac    180
gccgcctctg tgaagggcag attcaccatc agccgggaca cgccaagaa cagcctgtac    240 ctgcagatga acagcctgag agccgaggac accgccctgt accactgcgc cagaggctgg    300
tacagcggag ccgcctggaa catgggctac tggggcagag gcaccctggt gaccgtgtcc    360
agcggaggcg gcggttcagg cggaggtggc tctggtggta gcggaggtgg ctctggcggt    420
ggcggaggtg gctctggcgg tggcggaagt gcacaggccg ccctgaccca gcccgccagc    480
gtgtctggca gccaggccaga gagcatcacc atcagctgca ccggcgccag cggcgatgtg    540
ggcgcctaca acttcgtgtc ctggtatcag cagcaccccg gcaaggcccc caagctgatc    600
atctacgacg tgaacaagag acccagcggc gtgtccaaca gattcagcgg cagcaagagc    660
ggcaacaccg ccagcctgac catcagcgga ctgcaggccg aggacgaggc cgactactac    720
tgcgccagcc tggtgtccga cttcagcgtg gtgttcggcg gaggcaccaa gctgaccgtg    780
ctg                                                                  783

<210> SEQ ID NO 629
<211> LENGTH: 15
<212> TYPE: DNA
<213> ORGANISM: Homo sapiens

<400> SEQUENCE: 629
gactacggca tgaac                                                      15

<210> SEQ ID NO 630
<211> LENGTH: 51
<212> TYPE: DNA
<213> ORGANISM: Homo sapiens

<400> SEQUENCE: 630
```

```
ggcgtgaact ggaacggcgg caccagagac tacgccgcct ctgtgaaggg c        51

<210> SEQ ID NO 631
<211> LENGTH: 36
<212> TYPE: DNA
<213> ORGANISM: Homo sapiens

<400> SEQUENCE: 631
ggctggtaca gcggagccgc ctggaacatg ggctac                         36

<210> SEQ ID NO 632
<211> LENGTH: 42
<212> TYPE: DNA
<213> ORGANISM: Homo sapiens

<400> SEQUENCE: 632
accggcgcca gcggcgatgt gggcgcctac aacttcgtgt cc                  42

<210> SEQ ID NO 633
<211> LENGTH: 21
<212> TYPE: DNA
<213> ORGANISM: Homo sapiens

<400> SEQUENCE: 633
gacgtgaaca agagacccag c                                         21

<210> SEQ ID NO 634
<211> LENGTH: 30
<212> TYPE: DNA
<213> ORGANISM: Homo sapiens

<400> SEQUENCE: 634
gccagcctgg tgtccgactt cagcgtggtg                                30
```

METHODS OF USING ANTIBODIES AGAINST HUMAN IL-22

CROSS REFERENCE TO RELATED APPLICATIONS

The present application is a continuation application of U.S. application Ser. No. 12/474,479, filed 29 May 2009 (allowed), which is a divisional application of U.S. application Ser. No. 11/707,986, filed 20 Feb. 2007 (now U.S. Pat. No. 7,811,567), which claims the benefit of U.S. provisional application No. 60/774,595, filed Feb. 21, 2006, the entire disclosure of which is relied upon and incorporated by reference.

TECHNICAL FIELD

This invention relates to antibodies, e.g., human antibodies, and antigen-binding fragments thereof that bind interleukin-22 (IL-22), in particular, human IL-22, and their use in regulating IL-22-associated activities. The antibodies disclosed herein are useful in diagnosing, preventing, and/or treating IL-22 associated disorders, e.g., autoimmune disorders, including arthritis.

BACKGROUND OF THE INVENTION

Antigens initiate immune responses and activate the two largest populations of lymphocytes: T cells and B cells. After encountering antigen, T cells proliferate and differentiate into effector cells, while B cells proliferate and differentiate into antibody-secreting plasma cells. These effector cells secrete and/or respond to cytokines, which are small proteins (<about 30 kDa) secreted by lymphocytes and other cell types.

Interleukin-22 (IL-22) is a class II cytokine that shows sequence homology to IL-10. Its expression is up-regulated in T cells by IL-9 or ConA (Dumoutier L. et al. (2000) *Proc Natl Acad Sci USA* 97(18):10144-9). Further studies have shown that expression of IL-22 mRNA is induced in vivo in response to LPS administration, and that IL-22 modulates parameters indicative of an acute phase response (Dumoutier L. et al. (2000); Pittman D. et al. (2001) *Genes and Immunity* 2:172). In addition, IL-22 enhances the expression of antimicrobial peptides associated with host defense, including β-defensin, S100A7, S100A8, and S100A. Wolk et al., *Immunity*, 21:241-54 (2004); Boniface et al., *J. Immunol.* 174:3695-3702 (2005); Liang et al., *J. Exp. Med.*, 203(10):2271-79 (2006). Taken together, these observations indicate that IL-22 plays a role in inflammation (Kotenko S. V. (2002) *Cytokine & Growth Factor Reviews* 13(3):223-40).

IL-22 is believed to bind to a receptor complex consisting of IL-22R and IL-10R2, two members of the type II cytokine receptor family (CRF2) (Xie M. H. et al. (2000) *J Biol Chem* 275(40):31335-9; Kotenko S. V. et al. (2001) *J Biol Chem* 276(4):2725-32). Both chains of the IL-22 receptor are expressed constitutively in a number of organs. Epithelial cell lines derived form these organs are responsive to IL-22 in vitro (Kotenko S. V. (2002) *Cytokine & Growth Factor Reviews* 13(3):223-40). IL-22 induces activation of the JAK/STAT3 and ERK pathways, as well as intermediates of other MAPK pathways (Dumoutier L. et al. (2000) supra; Xie M. H. et al. (2000) supra; Dumoutier L. et al. (2000) *J Immunol* 164(4):1814-9; Kotenko S. V. et al. (2001) *J Biol Chem* 276 (4):2725-32; Lejeune, D. et al. (2002) *J Biol Chem* 277(37): 33676-82).

CRF2 members are receptors for IFNα/β, IFNγ, coagulation factor VIIa, IL-10 and the IL-10 related proteins IL-19, IL-20, IL-22, IL-24, IL-26, as well as the recently identified IFN-like cytokines, IL-28 and IL-29 (Kotenko S. V. (2002) *Cytokine & Growth Factor Reviews* 13(3):223-40; Kotenko, S. V. et al. (2000) *Oncogene* 19(21):2557-65; Sheppard, P. et al. (2003) *Nature Immunology* 4(1):63-8; Kotenko, S. V. et al. (2003) *Nature Immunology* 4(1):69-77). In addition to these membrane receptors, the CRF2 family also includes a soluble protein, IL-22 binding protein (IL-22BP), which is specific for IL-22 and blocks its activity (Dumoutier, L. et al. (2001) *J Immunol* 166(12):7090-5; Kotenko, S. V. et al. (2001) *J Immunol* 166(12):7096-103; Xu, W. et al. (2001) *Proc Natl Acad Sci USA* 98(17):9511-6; Gruenberg, B. H. et al. (2001) *Genes & Immunity* 2(6):329-34; Wei C-C et al. (2003) *Genes & Immunity* 4:204-211). While the IL-22 receptor complex is unique for IL-22, each chain (i.e., IL-22R and IL-10R2) is shared with other CRF2 members to define functional receptors for other cytokines, including IL-20, IL-24 (IL-22R/IL-20R2), IL-28, IL-29 (IFN-λR1/IL-10R2) and IL-10 (IL-10R1/IL-10R2) (Dumoutier, L. et al. (2001) *J. Immunol.* 167 (7):3545-9; Wang, M. et al. (2002) *J Biol Chem* 277(9):7341-7; Parrish-Novak, J. et al. (2002) *J Biol Chem* 277(49):47517-23; Kotenko, S. V. et al. (1997) *EMBO J.* 16(19):5894-903; Spencer, S. D. et al. (1998) *J Exp Med* 187(4):571-8).

Both chains of the CRF2-composed receptor are necessary for signal transduction. One chain of the composed receptor has been historically defined as a ligand binding chain (e.g., IFNγR1) based on its high affinity for the cytokine. The other chain (e.g., IFNγR2) has been characterized as a helper or accessory chain, and shows minimal affinity for the cytokine alone (Kotenko, S. V. et al. (2000) *Oncogene* 19(21):2557-65). For IL-22, IL-22R is the high affinity receptor subunit with IL-10R2 subsequently binding to the IL-22/IL-22R complex (Li, J. et al. (2004) *Int. Immunopharmacol.* 4(5): 673-708; Logsdon, N. J. et al. (2002) *J. Interferon Cytokine Res* 22(11):1099-1112).

SUMMARY OF THE INVENTION

The present application provides, at least in part, IL-22 binding agents such as antibodies and antigen-binding fragments thereof that bind to interleukin-22 ("IL-22"), in particular, human IL-22, with high affinity and specificity. The antibodies and antigen-binding fragments thereof of the present invention are also referred to herein as "anti-IL-22 antibodies" and "fragments thereof," respectively. In one embodiment, the antibody or fragment thereof reduces, inhibits, or antagonizes IL-22 activity. Such antibodies can be used to regulate immune responses or IL-22-associated disorders by antagonizing IL-22 activity. In other embodiments, the anti-IL-22 antibody can be used diagnostically, or as a targeting antibody to deliver a therapeutic or a cytotoxic agent to an IL-22-expressing cell. Thus, the anti-IL-22 antibodies of the invention are useful in diagnosing, treating, and/or preventing IL-22-associated disorders, e.g., autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD.

Accordingly, in one aspect, the invention features an isolated antibody that binds to IL-22, in particular, human IL-22. In certain embodiments, the anti-IL-22 antibody may have at least one of the following characteristics: (1) it is a monoclonal or single specificity antibody; (2) it is a human antibody; (3) it is an in vitro generated antibody; (4) it is an in vivo generated antibody (e.g., transgenic system); (5) it binds to IL-22 with an association constant of at least $10^{12}$ M$^{-1}$; (6) it binds to IL-22 with an association constant of at least $10^{11}$ M$^{-1}$; (7) it binds to IL-22 with an association constant of at least $10^{10}$ M$^{-1}$; (8) it binds to IL-22 with an association constant of at least $10^{9}$ M$^{-1}$; (9) it binds to IL-22 with an association constant of at least $10^{6}$ M$^{-1}$; (10) it binds to IL-22 with a dissociation constant of 500 nM or less; (11) it binds to IL-22 with a dissociation constant of 10 nM or less; (12) it binds to IL-22 with a dissociation constant of 150 pM or less; (13) it binds to IL-22 with a dissociation constant of 60 pM or less; (14) it inhibits binding of IL-22 to IL-22R or a receptor complex of IL-22R and IL-10R2 with an IC$_{50}$ of 10 nM or less; (15) it blocks IL-22 mediated proliferation of IL-22 receptor engineered BaF3 cells with an IC$_{50}$ of 1 nM or less in one embodiment, with an IC$_{50}$ of 150 pM or less in another embodiment, with an IC$_{50}$ of 100 pM or less in another embodiment, and with an IC$_{50}$ of 10 pM or less in another embodiment; and (16) it blocks IL-22 mediated GROa secretion from HT29 cells with an IC$_{50}$ of 1 nM or less in one embodiment, with an IC$_{50}$ of 150 pM or less in another embodiment, and with an IC$_{50}$ of 10 pM or less in another embodiment. IL-22 mediated BaF3 cell proliferation and IL-22 mediated GROa secretion from HT29 cells can be measured as described in the examples.

Nonlimiting illustrative embodiments of the antibodies of the invention are referred to herein as "GIL01," "GIL16," "GIL45," "GIL60," "GIL68," "GIL92," "097D09," "062A09," "062G05," "087B03," "367D04," "368D04," "166B06," "166G05," "375G06," "376B10," "354A08," "355B06," "355E04," and "356A11." These antibodies can be germlined or non-germlined. In another embodiment, the antibody is chosen from 356A11, 354A08, 087B03, and 368D04. The antibodies of the invention may specifically bind to the same IL-22 epitope or a similar epitope (e.g., an overlapping epitope) that GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 binds to. In other embodiments, the antibodies specifically bind to a fragment of an IL-22, e.g., a fragment of at least 10, 20, 50, 75, 100, 150, or 200 amino acids contiguous to the amino acid sequence set forth in SEQ ID NO:1, or a sequence that is at least 85%, 90%, 95%, 96%, 97%, 98%, 99% or more identical thereto. In other embodiments, the antibody competitively inhibits the binding of at least one of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 to its target epitope.

In one embodiment, the antibody of the present invention includes a $V_H$ domain, $V_L$ domain, or combination thereof, of the $F_v$ fragment of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11. For example, the antibody includes a $V_H$ and/or a $V_L$ domain having amino acid sequence as set forth in Tables 1 and 7 (SEQ ID NO:5, 23, 41, 59, 77, 95, 113, 131, 149, 167, 185, 203, 221, 239, 257, 275, 293, 311, 329, 347, 365, 383, 401, 419, 437, 455, 473, 491, 509, 527, 545, 563, 581, 599, or 617 for $V_H$ and SEQ ID NO:6, 24, 42, 60, 78, 96, 114, 132, 150, 168, 186, 204, 222, 240, 258, 276, 294, 312, 330, 348, 366, 384, 402, 420, 438, 456, 474, 492, 510, 528, 546, 564, 582, 600, or 618 for $V_L$), or a sequence substantially identical thereto (e.g., a sequence at least about 85%, 90%, 95%, 96%, 97%, 98%, 99% or more identical thereto, or which differs by no more than 1, 2, 5, 10 or 15 amino acid residues from SEQ ID NO:5, 6, 23, 24, 41, 42, 59, 60, 77, 78, 95, 96, 113, 114, 131, 132, 149, 150, 167, 168, 185, 186, 203, 204, 221, 222, 239, 240, 257, 258, 275, 276, 293, 294, 311, 312, 329, 330, 347, 348, 365, 366, 383, 384, 401, 402, 419, 420, 437, 438, 455, 456, 473, 474, 491, 492, 509, 510, 527, 528, 545, 546, 563, 564, 581, 582, 599, 600, 617, or 618).

In another embodiment, the antibody of the present invention includes a $V_H$ domain, $V_L$ domain, or combination thereof, of the $F_v$ fragment of an antibody chosen from 356A11, 354A08, 087B03, and 368D04. In this embodiment, the antibody, or antigen-binding fragment thereof, comprises:

a $V_H$ domain comprising the amino acid sequence set out in SEQ ID NO:167 or 491 and/or a $V_L$ domain comprising the amino acid sequence set out in SEQ ID NO:168 or 492 (087B03);

a $V_H$ domain comprising the amino acid sequence set out in SEQ ID NO:293 or 545 and/or a $V_L$ domain having the amino acid sequence set out in SEQ ID NO:294 or 546 (354A08);

a $V_H$ domain comprising the amino acid sequence set out in SEQ ID NO:203 or 617 and/or a $V_L$ domain comprising the amino acid sequence set out in SEQ ID NO:204 or 618 (368D04); or a $V_H$ domain comprising the amino acid sequence set out in SEQ ID NO:347 or 599 and/or a $V_L$ domain comprising the amino acid sequence set out in SEQ ID NO:348 or 600 (356A11).

In another embodiment, the antibody includes a $V_H$ and/or $V_L$ domain encoded by a nucleic acid having a nucleotide sequence as set forth in Tables 1 and 7 (SEQ ID NO:14, 32, 50, 68, 86, 104, 122, 140, 158, 176, 194, 212, 230, 248, 266, 284, 302, 320, 338, 356, 374, 392, 410, 428, 446, 464, 482, 500, 518, 536, 554, 572, 590, 608, or 626 for $V_H$ and SEQ ID NO:15, 33, 51, 69, 87, 105, 123, 141, 159, 177, 195, 213, 231, 249, 267, 285, 303, 321, 339, 357, 375, 393, 411, 429, 447, 465, 483, 501, 519, 537, 555, 573, 591, 609, or 627 for $V_L$), or a sequence substantially identical thereto (e.g., a sequence at least about 85%, 90%, 95%, 96%, 97%, 98%, 99% or more identical thereto, or which differs by no more than 1, 2, 3, 6, 15, 30 or 45 nucleotides from SEQ ID NO: 14, 15, 32, 33, 50, 51, 68, 69, 86, 87, 104, 105, 122, 123, 140, 141, 158, 159, 176, 177, 194, 195, 212, 213, 230, 231, 248, 249, 266, 267, 284, 285, 302, 303, 320, 321, 338, 339, 356, 357, 374, 375, 392, 393, 410, 411, 428, 429, 446, 447, 464, 465, 482, 483, 500, 501, 518, 519, 536, 537, 554, 555, 572, 573, 590, 591, 608, 609, 626, or 627).

In other embodiments, the antibody includes an Fv domain having an amino acid sequence as set forth in Tables 1 and 7 (SEQ ID NO:7, 25, 43, 61, 79, 97, 115, 133, 151, 169, 187, 205, 223, 241, 259, 277, 295, 313, 331, 349, 367, 385, 403, 421, 439, 457, 475, 493, 511, 529, 547, 565, 583, 601, or 619), or a sequence substantially identical thereto (e.g., a sequence at least about 85%, 90%, 95%, 96%, 97%, 98%, 99% or more identical thereto, or which differs by no more than 1, 2, 5, 10, 15, 20, 30 or 35 amino acid residues from SEQ ID NO:7, 25, 43, 61, 79, 97, 115, 133, 151, 169, 187, 205, 223, 241, 259, 277, 295, 313, 331, 349, 367, 385, 403, 421, 439, 457, 475, 493, 511, 529, 547, 565, 583, 601, or 619). In another embodiment, the antibody of the present invention includes an Fv domain of an antibody chosen from 356A11 (SEQ ID NO:349 or 601), 354A08 (SEQ ID NO:295 or 547), 087B03 (SEQ ID NO:169 or 493), and 368D04 (SEQ ID NO:205 or 619). In another embodiment, the antibody includes an Fv domain encoded by a nucleic acid having a nucleotide sequence as set forth in Tables 1 and 7 (SEQ ID NO:16, 34, 52, 70, 88, 106, 124, 142, 160, 178, 196, 214, 232, 250, 268, 286, 304, 322, 340, 358, 376, 394, 412, 430, 448, 466, 484, 502, 520, 538, 556, 574, 592, 610, or 628), or a sequence substantially identical thereto (e.g., a sequence at least about 85%, 90%, 95%, 96%, 97%, 98%, 99% or more identical thereto, or which differs by no more than 1, 2, 3, 6, 15, 30, 45, 60, 90 or 105 nucleotides from SEQ ID NO: 16, 34, 52, 70, 88, 106, 124, 142, 160, 178, 196, 214, 232, 250, 268, 286, 304, 322, 340, 358, 376, 394, 412, 430, 448, 466, 484, 502, 520, 538, 556, 574, 592, 610, or 628). In yet other embodiments, the antibody comprises at least one complementarity determining region (CDR) of these $V_H$ and $V_L$ domains. For example, the antibody can include one, two, or three CDR's of the $V_H$ domain having an amino acid sequence as set forth in or included within the sequences in Tables 1 and 7 (SEQ ID NO:5, 7, 8, 9, 10, 23, 25, 26, 27, 28, 41, 43, 44, 45, 46, 59, 61, 62, 63, 64, 77, 79, 80, 81, 82, 95, 97, 98, 99, 100, 113, 115, 116, 117, 118, 131, 133, 134, 135, 136, 149, 151, 152, 153, 154, 167, 169, 170, 171, 172, 185, 187, 188, 189, 190, 203, 205, 206, 207, 208, 221, 223, 224, 225, 226, 239, 241, 242, 243, 244, 257, 259, 260, 261, 262, 275, 277, 278, 279, 280, 293, 295, 296, 297, 298, 311, 313, 314, 315, 316, 329, 331, 332, 333, 334, 347, 349, 350, 351, 352, 365, 367, 368, 369, 370, 383, 385, 386, 387, 388, 401, 403, 404, 405, 406, 419, 421, 422, 423, 424, 437, 439, 440, 441, 442, 455, 457, 458, 459, 460, 473, 475, 476, 477, 478, 491, 493, 494, 495, 496, 509, 511, 512, 513, 514, 527, 529, 530, 531, 532, 545, 547, 548, 549, 550, 563, 565, 566, 567, 568, 581, 583, 584, 585, 586, 599, 601, 602, 603, 604, 617, 619, 620, 621, or 622), or a sequence substantially homologous thereto (e.g., a sequence at least about 85%, 90%, 95%, 96%, 97%, 98%, 99% or more identical thereto). In another embodiment, the antibody of the present invention includes one, two, or three CDR's of the $V_H$ domain of an antibody chosen from 356A11, 354A08, 087B03, and 368D04. In this embodiment, the antibody, or antigen-binding fragment thereof, comprises a heavy chain variable region comprising:

a) SEQ ID NO:170 or 494; b) SEQ ID NO: 171 or 495; and/or c) SEQ ID NO: 172 or 496 (087B03);

a) SEQ ID NO:296 or 548; b) SEQ ID NO:297 or 549; and/or c) SEQ ID NO:298 or 550 (354A08);

a) SEQ ID NO:206 or 620; b) SEQ ID NO:207 or 621; and/or c) SEQ ID NO:208 or 622 (368D04); or a) SEQ ID NO:350 or 602; b) SEQ ID NO:351 or 603; and/or c) SEQ ID NO:352 or 604 (356A11).

In another embodiment, the antibody can include one, two, or three CDR's of the $V_L$ domain having an amino acid sequence as set forth in or included within the sequences in Tables 1 and 7 (SEQ ID NO:6, 7, 11, 12, 13, 24, 25, 29, 30, 31, 42, 43, 47, 48, 49, 60, 61, 65, 66, 67, 78, 79, 83, 84, 85, 96, 97, 101, 102, 103, 114, 115, 119, 120, 121, 132, 133, 137, 138, 139, 150, 151, 155, 156, 157, 168, 169, 173, 174, 175, 186, 187, 191, 192, 193, 204, 205, 209, 210, 211, 222, 223, 227, 228, 229, 240, 241, 245, 246, 247, 258, 259, 263, 264, 265, 276, 277, 281, 282, 283, 294, 295, 299, 300, 301, 312, 313, 317, 318, 319, 330, 331, 335, 336, 337, 348, 349, 353, 354, 355, 366, 367, 371, 372, 373, 384, 385, 389, 390, 391, 402, 403, 407, 408, 409, 420, 421, 425, 426, 427, 438, 439, 443, 444, 445, 456, 457, 461, 462, 463, 474, 475, 479, 480, 481, 492, 493, 497, 498, 499, 510, 511, 515, 516, 517, 528, 529, 533, 534, 535, 546, 547, 551, 552, 553, 564, 565, 569, 570, 571, 582, 583, 587, 588, 589, 600, 601, 605, 606, 607, 618, 619, 623, 624, or 625), or a sequence substantially identical thereto (e.g., a sequence at least about 85%, 90%, 95%, 96%, 97%, 98%, 99% or more identical thereto). In another embodiment, the antibody of the present invention includes one, two, or three CDR's of the $V_L$ domain of an antibody chosen from 356A11, 354A08, 087B03, and 368D04. In this embodiment, the antibody, or antigen-binding fragment thereof, comprises a light chain variable region comprising:

a) SEQ ID NO:173 or 497; b) SEQ ID NO: 174 or 498; and/or c) SEQ ID NO:175 or 499 (087B03);

a) SEQ ID NO:299 or 551; b) SEQ ID NO:300 or 552; and/or c) SEQ ID NO:301 or 553 (354A08);

a) SEQ ID NO:209 or 623; b) SEQ ID NO:210 or 624; and/or c) SEQ ID NO:211 or 625 (368D04); or a) SEQ ID NO:353 or 605; b) SEQ ID NO:354 or 606; and/or c) SEQ ID NO:355 or 607 (356A11).

In a still further embodiment, the antibody comprises an H3 fragment of the $V_H$ domain of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11, e.g., an H3 fragment having the amino acid sequence as set forth in Tables 1 and 7 (SEQ ID NO:10, 28, 46, 64, 82, 100, 118, 136, 154, 172, 190, 208, 226, 244, 262, 280, 298, 316, 334, 352, 370, 388, 406, 424, 442, 460, 478, 496, 514, 532, 550, 568, 586, 604, or 622), or a sequence substantially identical thereto (e.g., a sequence at least about 85%, 90%, 95%, 96%, 97%, 98%, 99% or more identical thereto).

The antibody of the invention can be full-length (e.g., include at least one complete heavy chain and at least one complete light chain) or can include only an antigen-binding fragment (e.g., a Fab, F(ab')$_2$, Fv, a single chain Fv fragment, a Fd fragment, or a dAb fragment). The antibody can include a constant region, or a portion thereof, chosen from any of: the kappa, lambda, alpha, gamma, delta, epsilon and mu constant region genes. For example, heavy chain constant regions of the various isotypes can be used, including: IgG$_1$, IgG$_2$, IgG$_3$, IgG$_4$, IgM, IgA$_1$, IgA$_2$, IgD, and IgE. The light chain constant region can be chosen from kappa or lambda. The antibody may be an IgG, or it may also be IgG$_{1\kappa}$ or IgG$_{1\gamma}$.

The anti-IL-22 antibody described herein can be derivatized or linked to another functional molecule (such as another peptide or protein (e.g., a Fab fragment)). For example, an antibody of the invention can be functionally linked (e.g., by chemical coupling, genetic fusion, non-covalent association or otherwise) to at least one other molecular entity, such as another antibody (e.g., a bispecific or a multispecific antibody), toxin, radioisotope, cytotoxic or cytostatic agent, among others.

In another aspect, the invention features a pharmaceutical composition containing at least one anti-IL-22 antibody and a pharmaceutically acceptable carrier. The pharmaceutical composition can further include a combination of at least one anti-IL-22 antibody and at least one therapeutic agent (e.g., cytokine and growth factor inhibitors, immunosuppressants, anti-inflammatory agents, metabolic inhibitors, enzyme inhibitors, cytotoxic agents, cytostatic agents, or combinations thereof, as described in more detail herein). Combinations of the anti-IL-22 antibody and a therapeutic agent are also within the scope of the invention. The compositions and combinations of the invention can be used to regulate IL-22-associated inflammatory conditions, e.g., by modulating IL-22 signaling through its receptors located on epithelial cells of a variety of tissues, including, but not limited to, those of the pancreas, skin, lung, gut, liver, kidney, salivary gland, and vascular endothelia, in addition to potentially activated and tissue localized immune cells.

In another aspect, the invention features a method of treating a subject with an IL-22-associated disorder. The method includes administering to the subject an anti-IL-22 antibody in an amount sufficient to inhibit at least one IL-22 activity of immune cells, thereby treating the IL-22-associated disorder.

The anti-IL-22 antibody can be administered to the subject, alone or in combination, with other therapeutic agents as described herein. The subject may be a mammal, e.g. human. For example, the method can be used to treat a subject with an IL-22-associated disorder such as autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD.

In another aspect, the invention features a method of decreasing, inhibiting or reducing an acute phase response in a subject. The method includes administering to the subject an IL-22 binding agent, e.g., an IL-22 antagonist, (e.g., an anti-IL-22 antibody or fragment thereof as described herein), in an amount sufficient to decrease, inhibit or reduce the acute phase response in the subject. In one embodiment, the subject is a mammal, e.g., a human suffering from an IL-22-associated disorder, including, e.g., respiratory disorders, inflammatory disorders and autoimmune disorders. In one embodiment, the IL-22 binding agent is administered locally, e.g., topically, subcutaneously, or other administrations that are not in the general circulation.

In another aspect, an IL-22 binding agent can be used to alter the type of immune response and/or increase the efficacy of a vaccine formulation used to immunize a subject. For example, an anti-IL-22 antibody of the present invention can be administered before, during and/or after an immunization to increase vaccine efficacy. In one embodiment, the vaccine formulation contains one or more IL-22 antagonists and an antigen, i.e., an immunogen, including, for example, viral, bacterial, or tumor antigens. In another embodiment, the IL-22 antagonist and the immunogen are administered separately, e.g., within one hour, three hours, one day or two days of each other.

In another aspect, the invention provides a method for detecting the presence of IL-22 in a sample in vitro. Samples may include biological samples such as serum, plasma, tissue and biopsy. The subject method can be used to diagnose a disorder, such as an IL-22-associated disorder as described herein. The method includes: (1) contacting the sample or a control sample with an anti-IL-22 antibody, and (2) detecting formation of a complex between the anti-IL-22 antibody and the sample or the control sample, wherein a statistically significant change in the formation of the complex in the sample relative to a control sample, is indicative of the presence of the IL-22 in the sample.

In another aspect, the invention provides a method for detecting the presence of IL-22 in vivo (e.g., in vivo imaging in a subject). The method can be used to diagnose a disorder, e.g., an IL-22-associated disorder as described herein. The method includes: (1) administering an anti-IL-22 antibody to a subject or a control subject under conditions that allow binding of the antibody to IL-22, and (2) detecting formation of a complex between the antibody and IL-22, wherein a statistically significant change in the formation of the complex in the subject relative to a control, e.g., a control subject, is indicative of the presence of IL-22.

The antibody may be directly or indirectly labeled with a detectable substance to facilitate detection of the bound or unbound antibody. Suitable detectable substances include various enzymes, prosthetic groups, fluorescent materials, luminescent materials and radioactive materials.

In another aspect, the invention provides a method for delivering or targeting an agent, e.g., a therapeutic or a cytotoxic agent, to an IL-22-expressing cell in vivo. The method includes administering an anti-IL-22 antibody to a subject under conditions that allow binding of the antibody to IL-22. The antibody may be coupled to a second therapeutic moiety, such as a toxin.

The disclosure provides nucleic acid sequences from the $V_H$ and $V_L$ domains of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11. Also provided are nucleic acid sequences that comprise at least one CDR from GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11. The disclosure also provides vectors and host cells comprising such nucleic acids.

The disclosure further provides methods of producing new $V_H$ and $V_L$ domains and functional antibodies comprising all or a portion of such domains derived from the $V_H$ or $V_L$ domains of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11.

Additional aspects of the disclosure will be set forth in part in the description, and in part will be obvious from the description, or may be learned by practicing the invention. The invention is set forth and particularly pointed out in the claims, and the disclosure should not be construed as limiting the scope of the claims. The following detailed description includes exemplary representations of various embodiments of the invention, which are not restrictive of the invention as claimed. The accompanying figures constitute a part of this specification and, together with the description, serve only to illustrate embodiments and not limit the invention.

BRIEF DESCRIPTION OF THE FIGURES

FIG. 5. Amino acid and nucleotide sequences of human IL-22. The nucleotide sequence of human IL-22 is SEQ ID NO:2 and includes a poly (A) tail. The disclosed nucleotide sequence includes an open reading frame and the amino acid sequence of full-length IL-22 protein corresponding to the foregoing nucleotide sequence is reported in SEQ ID NO:1. The amino acid sequence of mature IL-22 corresponds to about amino acids 34-179 of SEQ ID NO:1.

FIG. 6. Amino acid and nucleotide sequences of mouse IL-22.

FIG. 7. Amino acid and nucleotide sequences of non-germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11, including $V_H$ and $V_L$ domains, and CDRs (H1, H2, H3, L1, L2, and L3).

FIG. 8. Amino acid and nucleotide sequences of germlined GIL01, GIL16, GIL45, GIL60, GIL68, GIL92, 062A09, 087B03, 166B06, 166G05, 354A08, 355B06, 355E04, 356A11, and 368D04, including $V_H$ and $V_L$ domains, and CDRs (H1, H2, H3, L1, L2, and L3).

FIG. 9. Amino acid and nucleotide sequences of scFv's for non-germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11, with CDRs underlined (H1, H2, H3, L1, L2, and L3).

FIG. 10. Amino acid and nucleotide sequences of scFv's for germlined GIL01, GIL16, GIL45, GIL60, GIL68, GIL92, 062A09, 087B03, 166B06, 166G05, 354A08, 355B06, 355E04, 356A11, and 368D04 with CDRs underlined (H1, H2, H3, L1, L2, and L3).

FIG. 20. Disease evaluation of in mice treated with 16 mg/kg of 356A11, 368D04, or control antibody in murine model of psoriasis. (A) Clinical disease progression over 10 weeks. (B) Clinical score at 10 weeks.

FIG. 21. Detection of in vivo serum levels of IL-22 (pg/mL) in psoriatic mice treated with 16 mg/kg of 356A11, 368D04, or a control antibody.

FIG. 27. Disease evaluation of in mice treated with 16 mg/kg of 356A11 or control antibody in murine model of psoriasis. Mice treated with IL-12 and LPS at day 1 following adoptive transfer of T cells. (A) Clinical disease progression over 10 weeks. (B) Clinical score at 10 weeks.

FIG. 28. Detection of in vivo serum levels of IL-22 (ng/mL) in psoriatic mice treated with 16 mg/kg of 356A11 or a control antibody. Mice treated with IL-12 and LPS at day 1 following adoptive transfer of T cells.

FIG. 29. Detection of in vivo serum levels of (A) IL-17A, (B) IL-17F, (C) IL-17A/F; and (D) IL-6 in psoriatic mice treated with 16 mg/kg of 356A11 or a control antibody. Mice treated with IL-12 and LPS at day 1 following adoptive transfer of T cells.

FIG. 30. Cytokine gene expression in the ears of psoriatic mice treated with 16 mg/kg of 356A11 or a control antibody.

(A) IL-17. (B) IL-22. (C) IL-17F. (D) IFNγ. (E) IL-6. Mice treated with IL-12 and LPS at day 1 following adoptive transfer of T cells.

Figure 31:
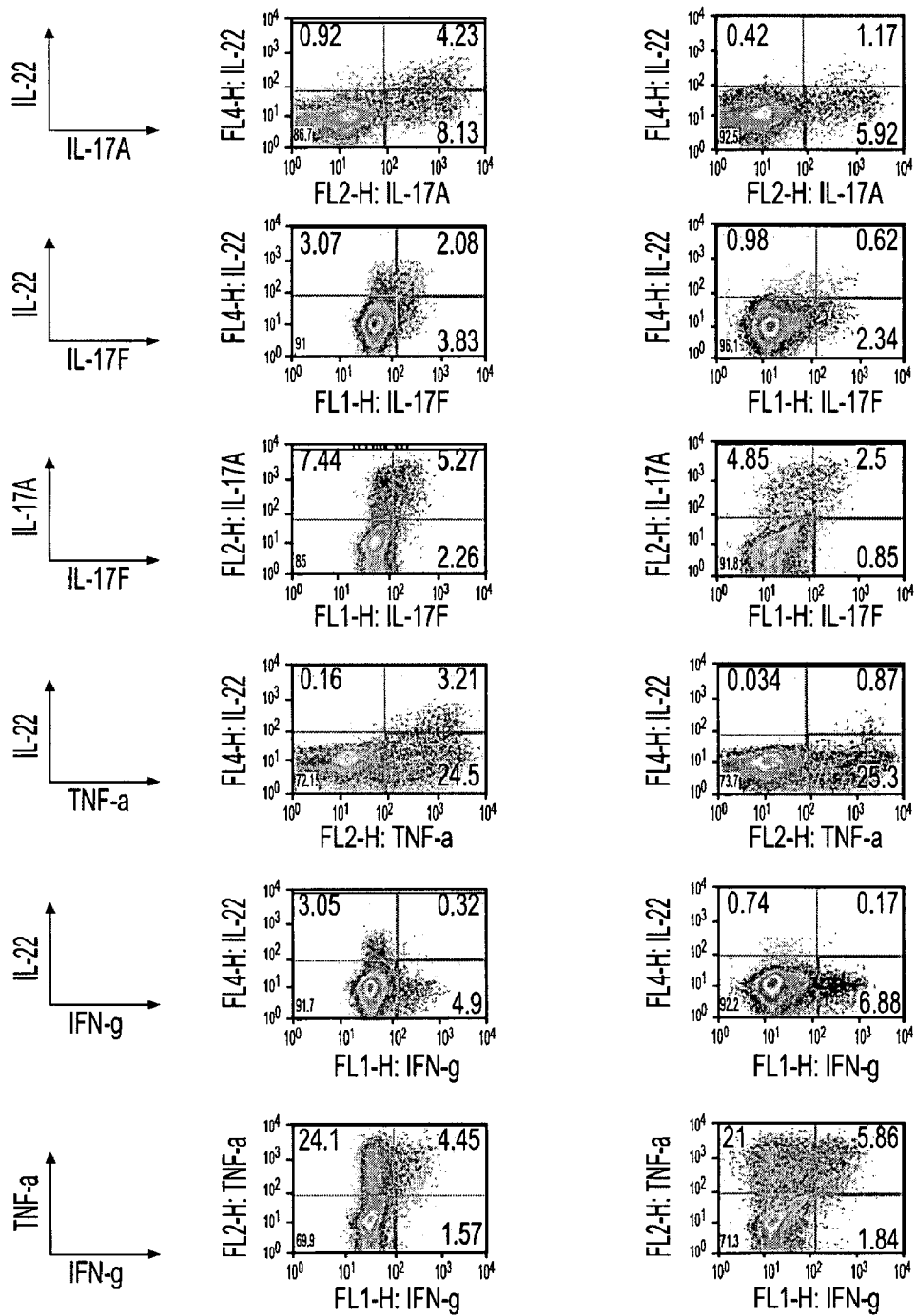
Figure 32A:
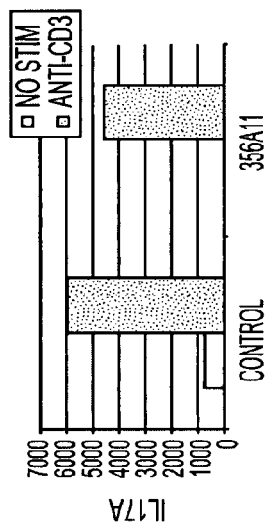
Figure 32B:
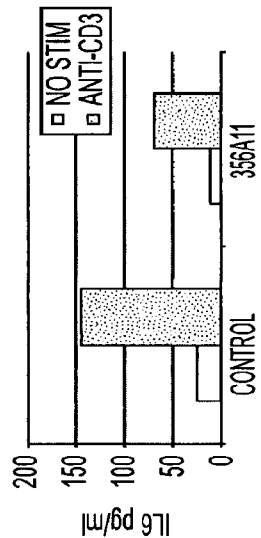
Figure 32C:
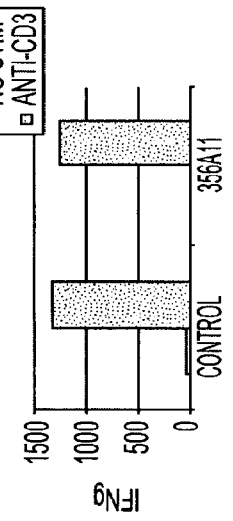
Figure 32D:
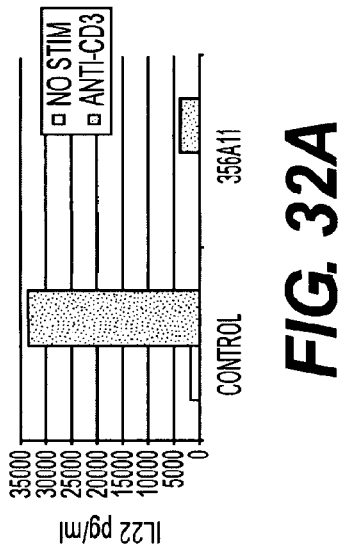
Figure 32E:
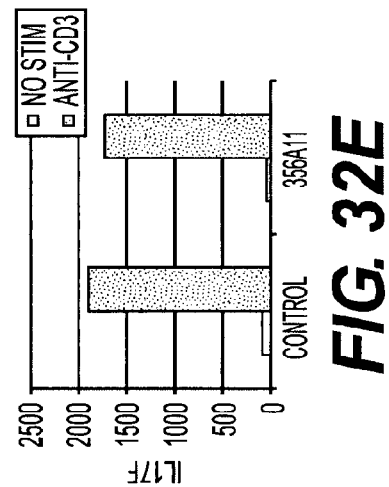
Figure 33A:
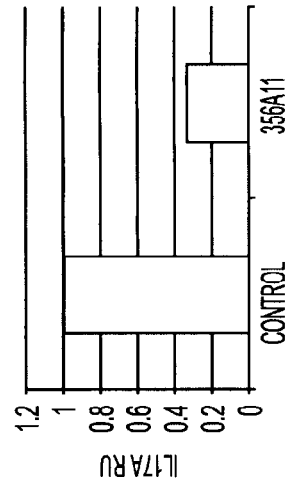
Figure 33D:
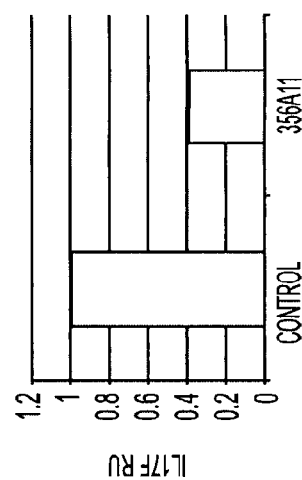
Figure 33B:
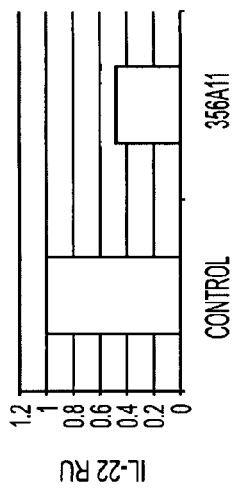
Figure 33E:
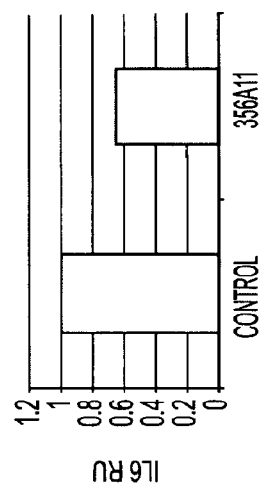
Figure 33C:
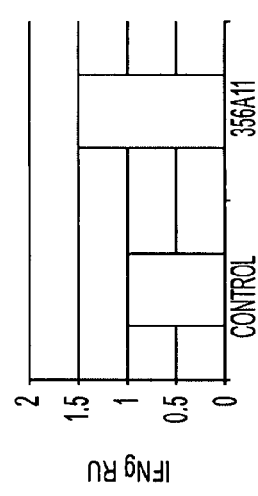
Figure 36E:
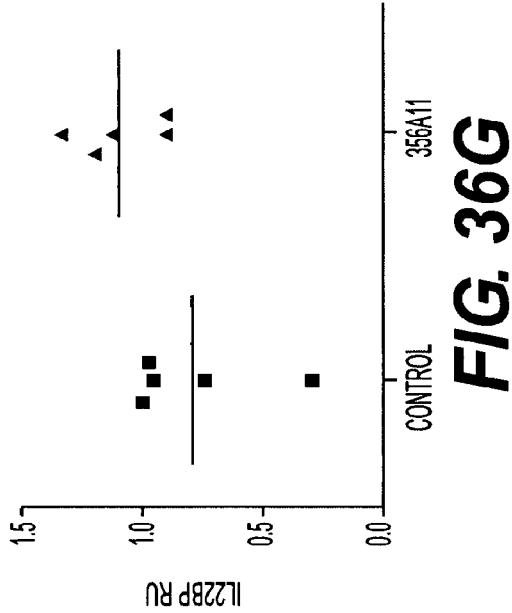
Figure 36G:
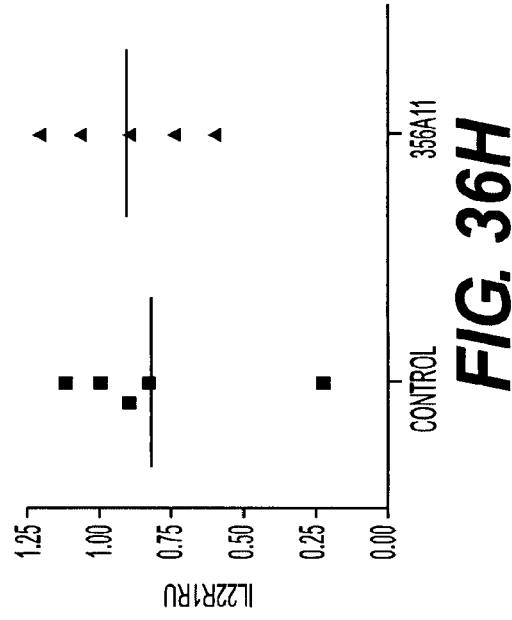
Figure 36F:
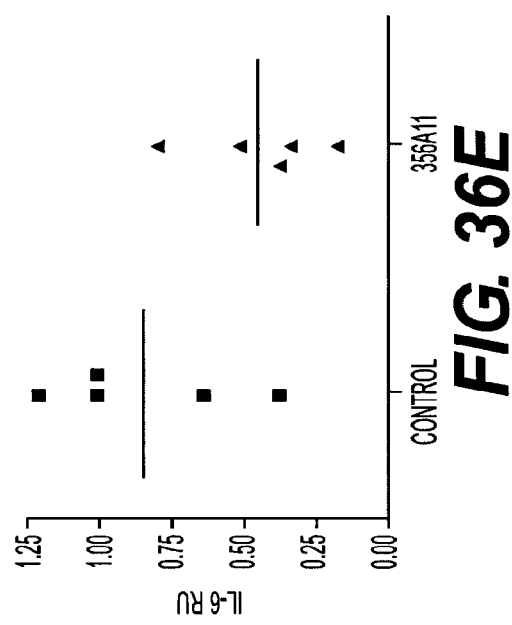
Figure 36H:
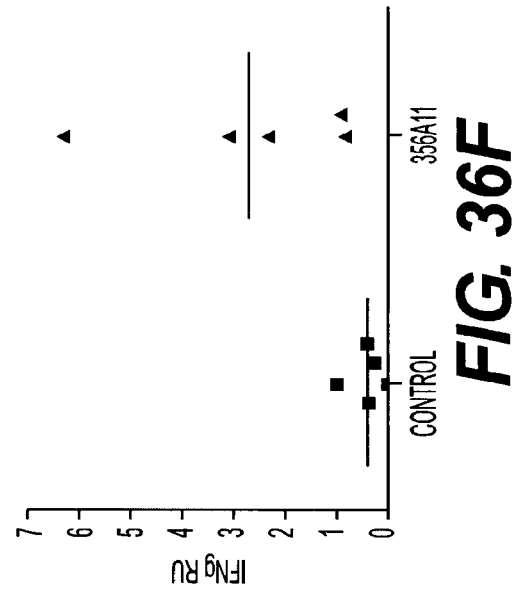
Figure 39C:
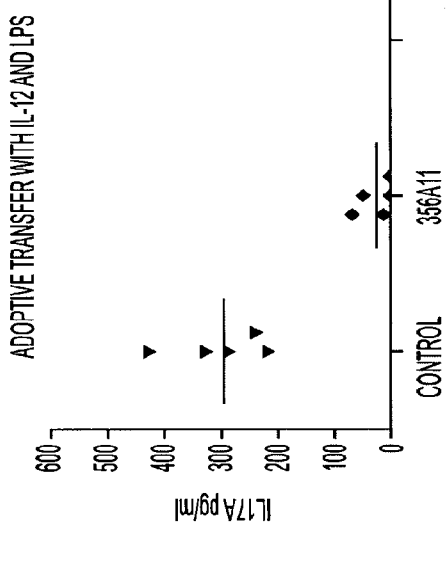
Figure 39D:
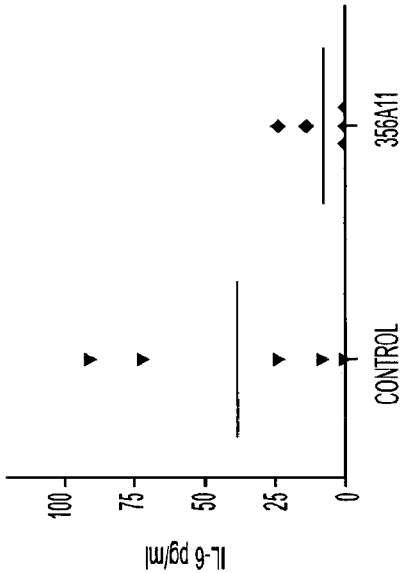
Figure 39A:
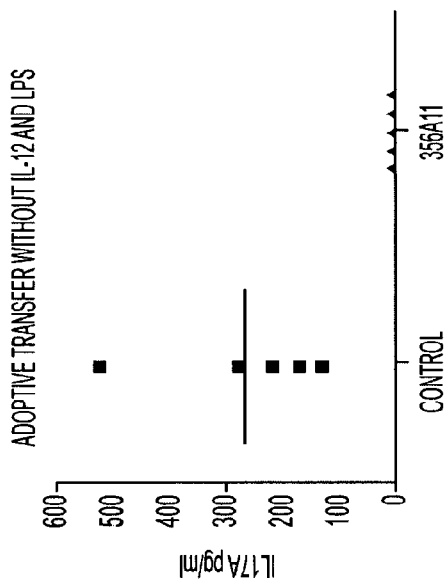
Figure 39B:
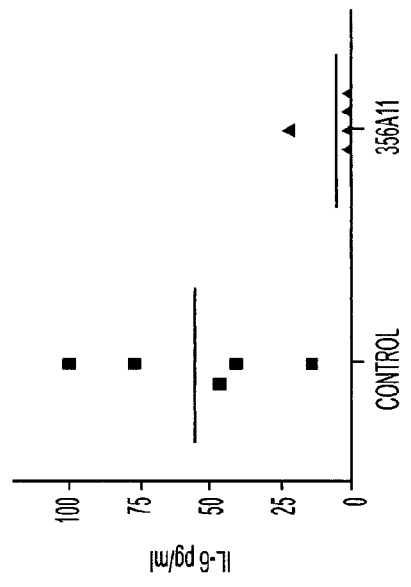

FIG. 31. Flow cytometric analysis of pooled CD4+ lymph node cells treated with PMA and ionomycin following isolation from psoriatic mice treated with 16 mg/kg of 356A11 or a control antibody and stained for IL-22 and IL-17A; IL-22 and IL-17F; IL-17A and IL-17F; IL-22 and TNFα; IL-22 and IFNγ; or TNFα and IFNγ. Mice treated with IL-12 and LPS at day 1 following adoptive transfer of T cells.

FIG. 32. Cytokine detection in the supernatants of pooled lymph node cells isolated from psoriatic mice treated with 16 mg/kg of 356A11 or a control antibody and stimulated ex vivo with or without platebound, anti-CD3 antibody. (A) IL-22. (B) IL-6. (C) IFNγ (D) IL-17A. (E) IL-17F. Mice treated with IL-12 and LPS at day 1 following adoptive transfer of T cells.

FIG. 33. Cytokine gene expression in pooled lymph node cells isolated from psoriatic mice treated with 16 mg/kg of 356A11 or a control antibody and stimulated ex vivo with platebound, anti-CD3 antibody. (A) IL-22. (B) IL-6. (C) IFNγ (D) IL-17A. (E) IL-17F. Mice treated with IL-12 and LPS at day 1 following adoptive transfer of T cells.

FIG. 34. Disease evaluation of in mice treated with 16 mg/kg of 356A11 or control antibody in murine model of psoriasis. (A) Clinical disease progression over 10 weeks. (B) Clinical score at 10 weeks.

FIG. 35. Detection of in vivo serum levels of IL-22 (ng/mL) in psoriatic mice treated with 16 mg/kg of 356A11 or a control antibody.

FIG. 36. Cytokine gene expression in the ears of psoriatic mice treated with 16 mg/kg of 356A11 or a control antibody. (A) IL-22, (B) IL-17, (C) IL-17F, (D) IL-1F6 (IL-1 family member 6), (E) IL-6, (F) IFNγ, (G) IL-22 BP (IL-22 binding protein), or (H) IL-22R1 (IL-22 receptor subunit).

FIG. 37. Disease evaluation of in mice treated with 16 mg/kg of 356A11 or control antibody in murine model of psoriasis. (A) Clinical disease progression over 10 weeks. (B) Clinical score at 10 weeks. Mice treated with IL-12 and LPS at day 1 following adoptive transfer of T cells.

FIG. 38. Detection of in vivo serum levels of IL-22 (ng/mL) in psoriatic mice treated with 16 mg/kg of 356A11 or a control antibody. Mice treated with IL-12 and LPS at day 1 following adoptive transfer of T cells.

FIG. 39. Detection of in vivo serum levels of (A) IL-17A and (B) IL-6 in psoriatic mice treated with 16 mg/kg of 356A11 or a control antibody (without coadministration of IL-12 and LPS) and (C) IL-17A and (D) IL-6 in psoriatic mice treated with 16 mg/kg of 356A11 or a control antibody (IL-12 and LPS coadministered at day 1 following adoptive transfer of T cells).

Figure 40A:
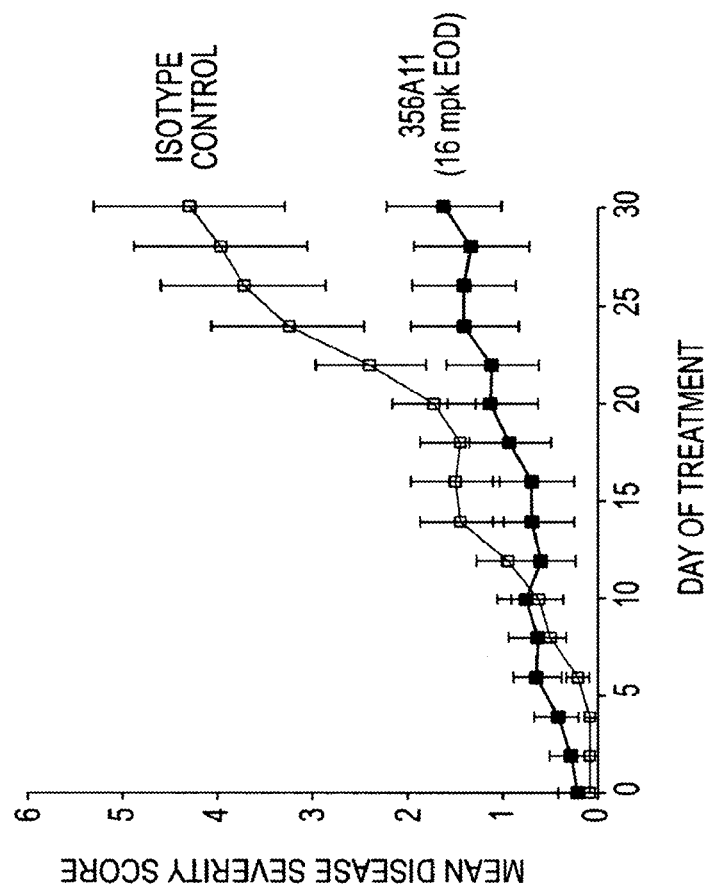
Figure 40B:
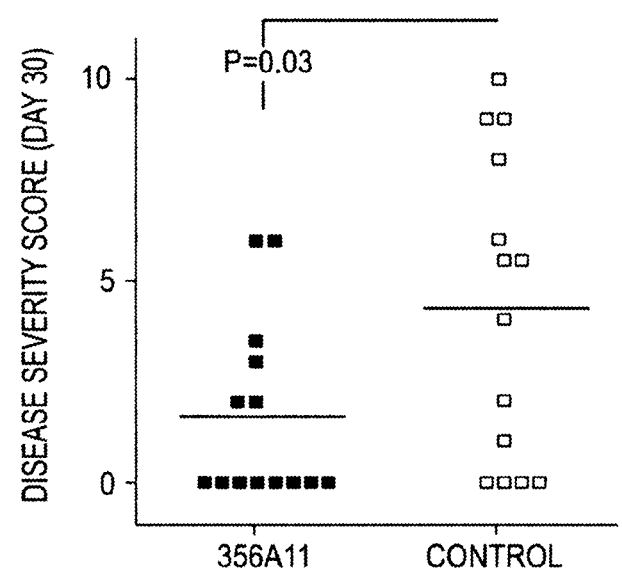

FIG. 40. (A) Mean disease severity score or (B) disease severity score at day 30 of 16 mg kg$^{-1}$ of 356A11 administered every other day in murine CIA model.

Figure 41:
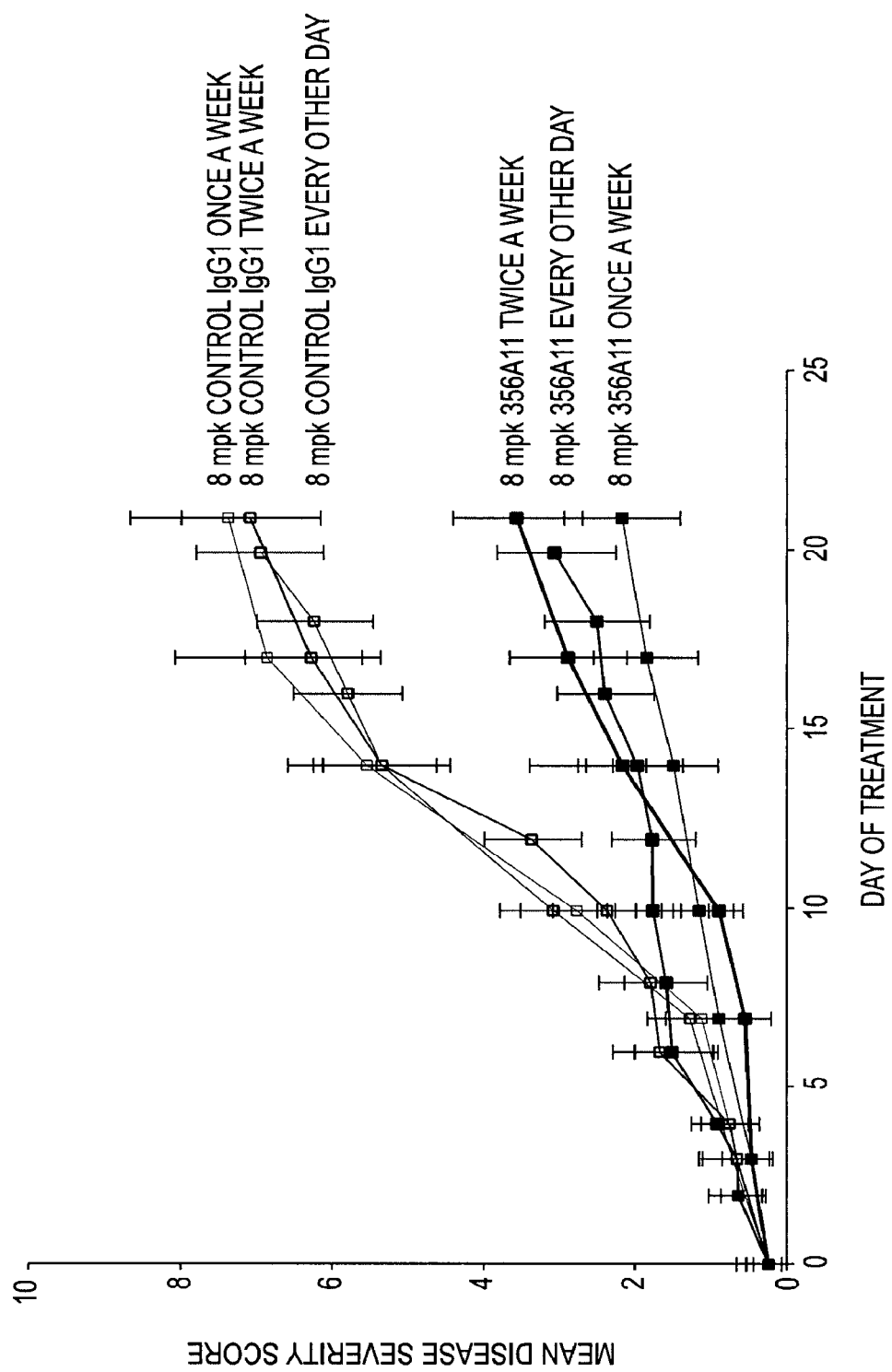

FIG. 41. Mean disease severity score of 8 mg kg$^{-1}$ of 356A11 administered every other day, once a week, or twice a week in murine CIA model.

Figure 42A:
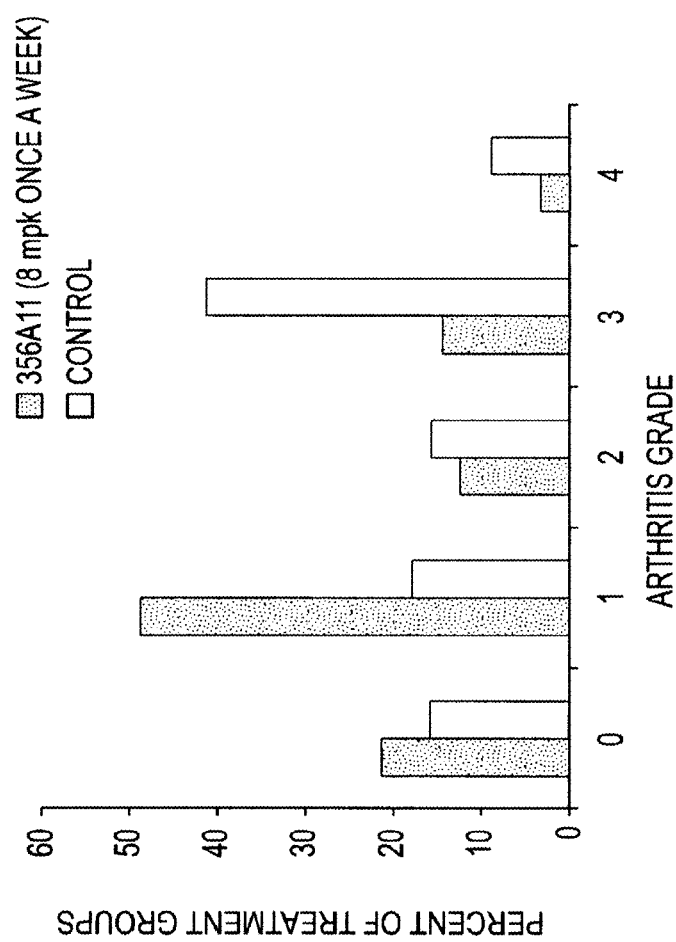
Figure 42B:
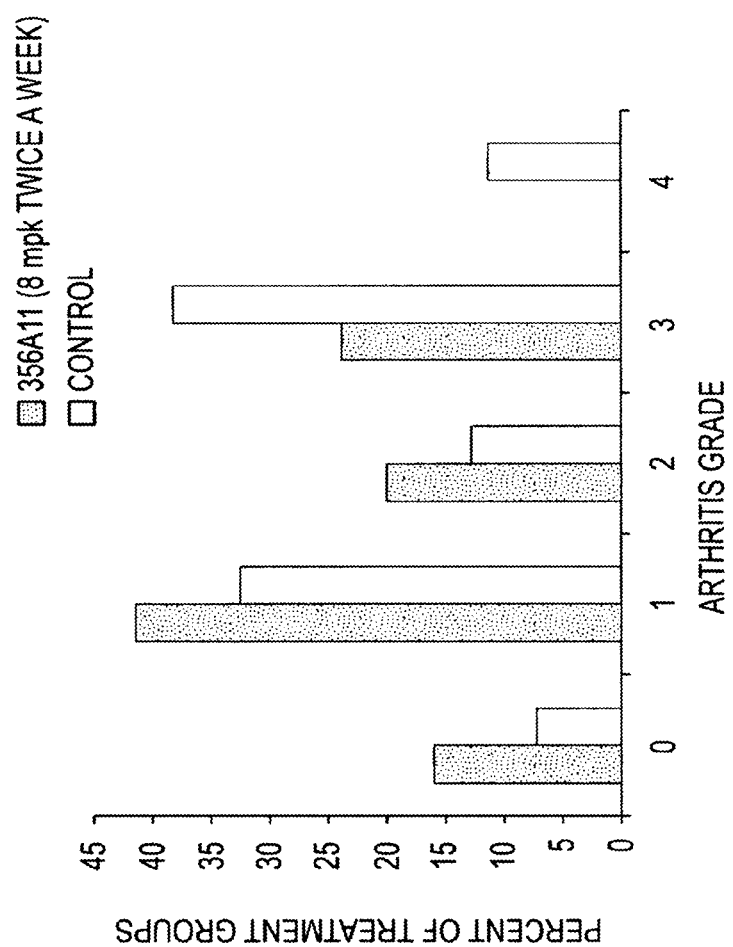
Figure 42C:
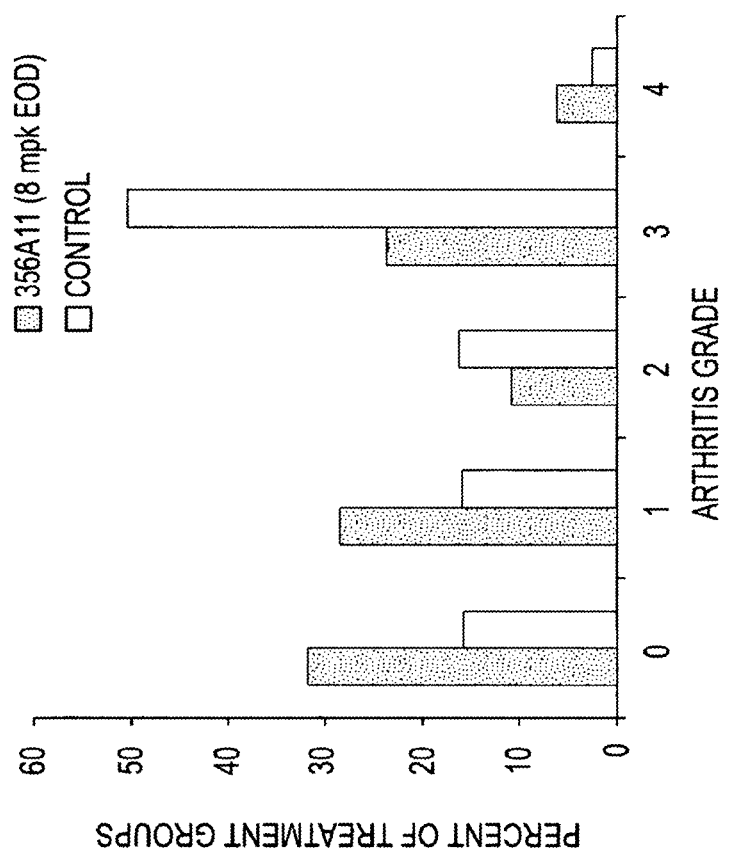

FIG. 42. Histological evaluation (paw) of disease progression in mice treated with (A) 8 mg kg$^{-1}$ of 356A11 once a week, (B) 8 mg kg$^{-1}$ of 356A11 twice a week, or (C) 8 mg kg$^{-1}$ of 356A11 every other day.

Figure 43:
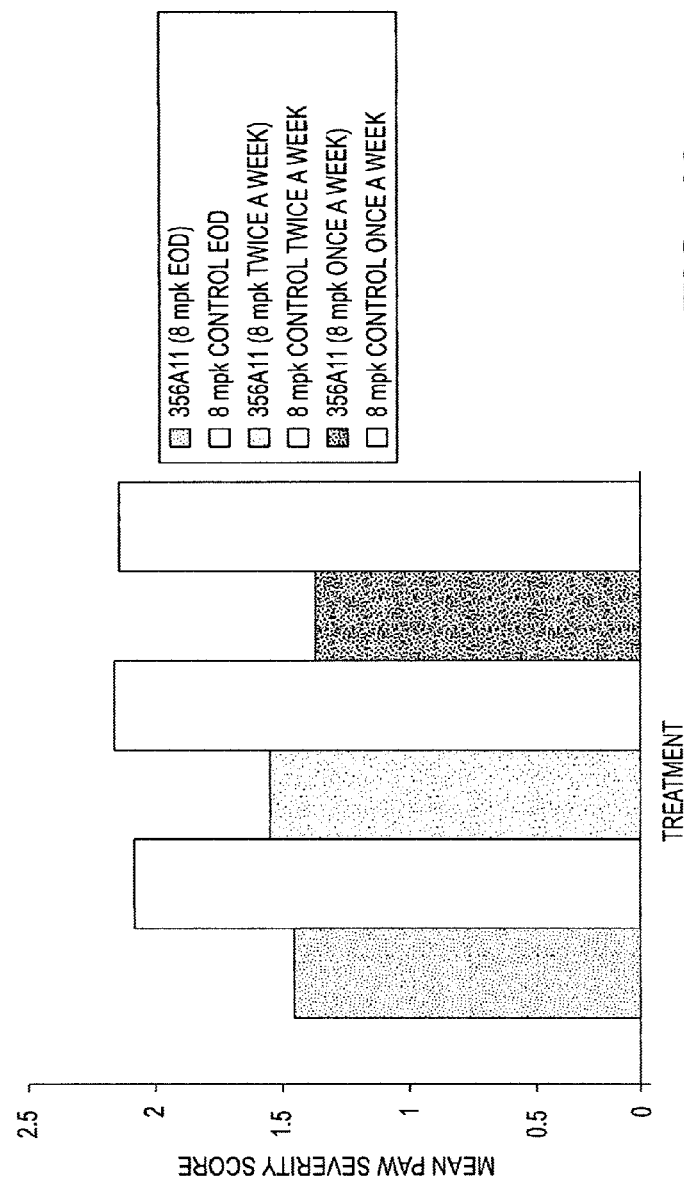

FIG. 43. Histological evaluation (mean paw severity score) of disease progression in mice treated with 8 mg kg$^{-1}$ of 356A11 once a week, twice a week, or every other day.

Figure 44A:
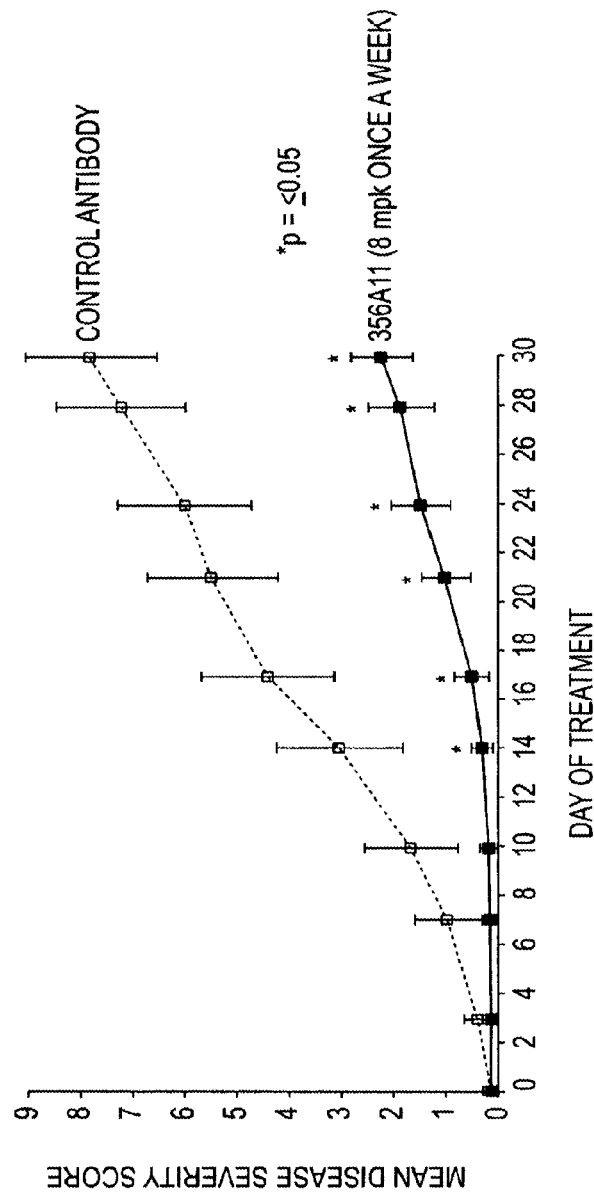

FIGS. 44A-B. Mean disease severity scores from two separate studies of 8 mg kg$^{-1}$ of 356A11 administered once a week in murine CIA model.

Figure 45A:
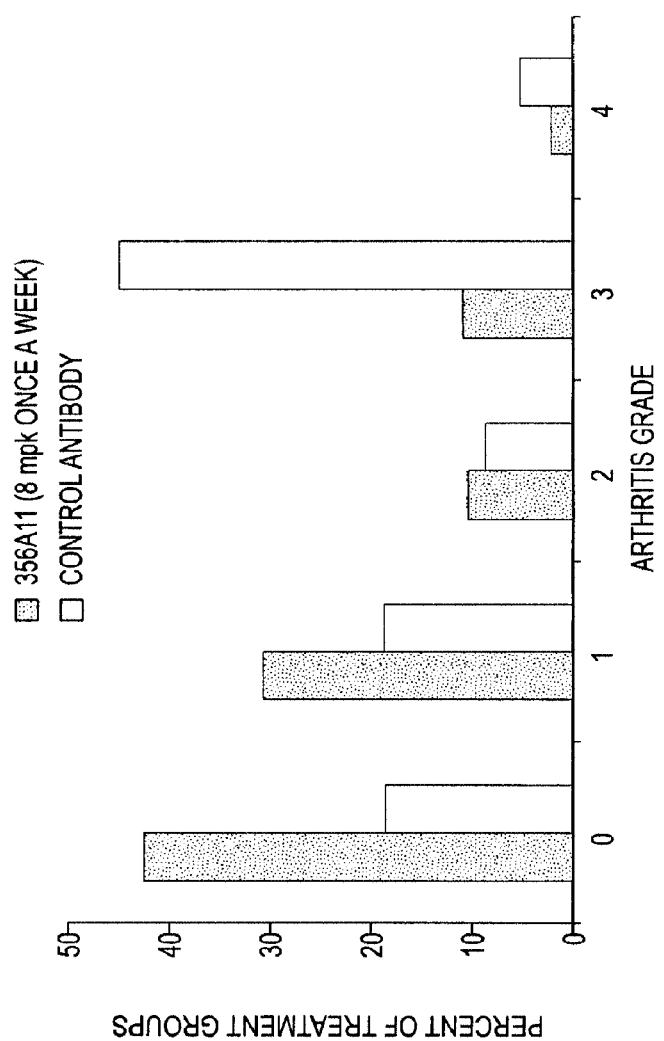
Figure 45B:
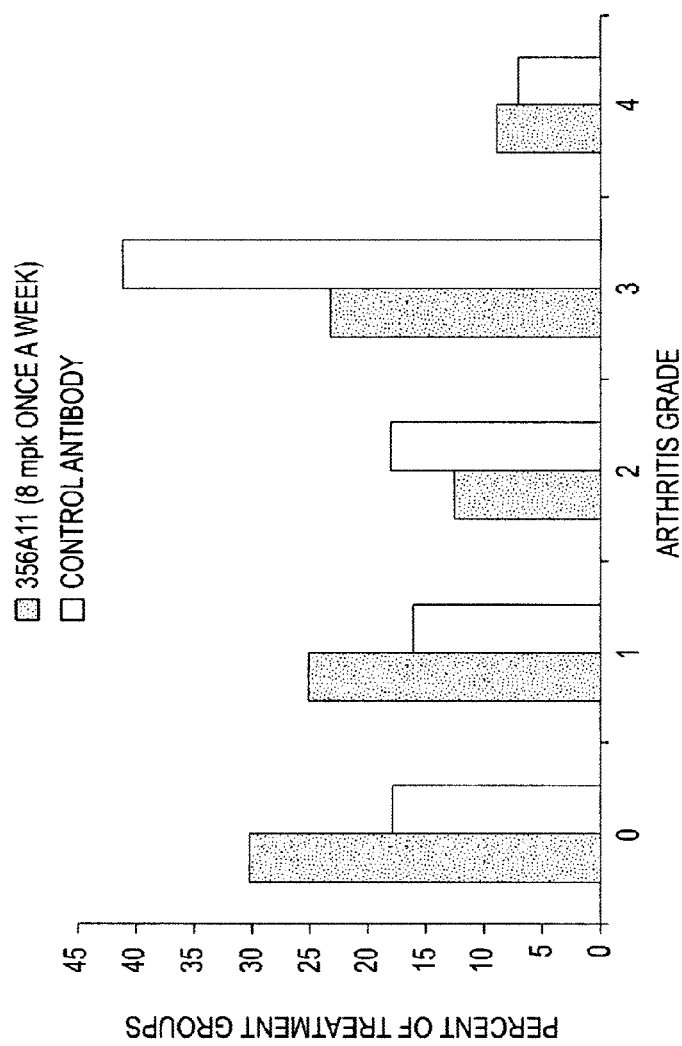

FIGS. 45A-B. Histological evaluation (paw) of disease progression from two separate studies in mice treated with 8 mg kg$^{-1}$ of 356A11 once a week in murine CIA model.

Figure 46A:
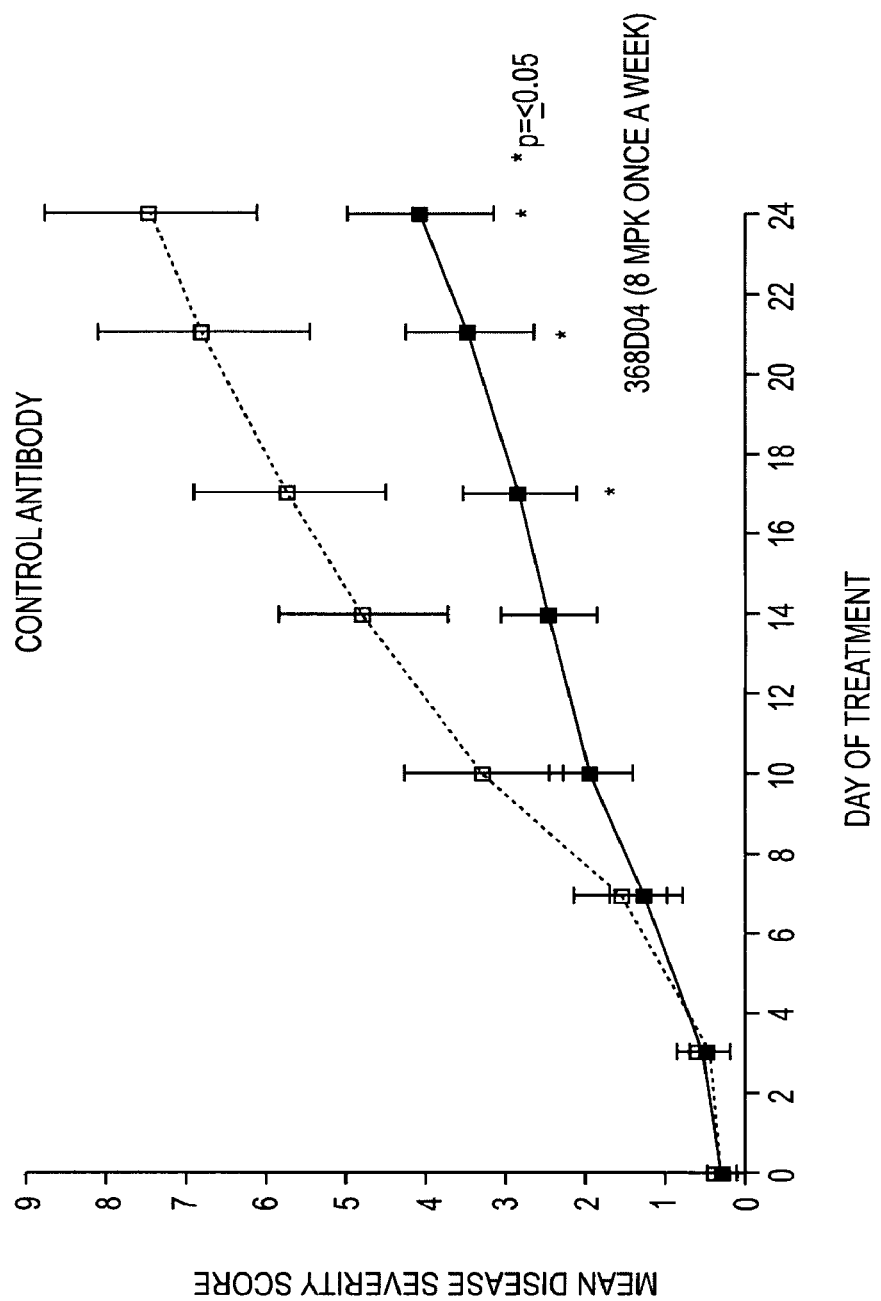
Figure 46B:
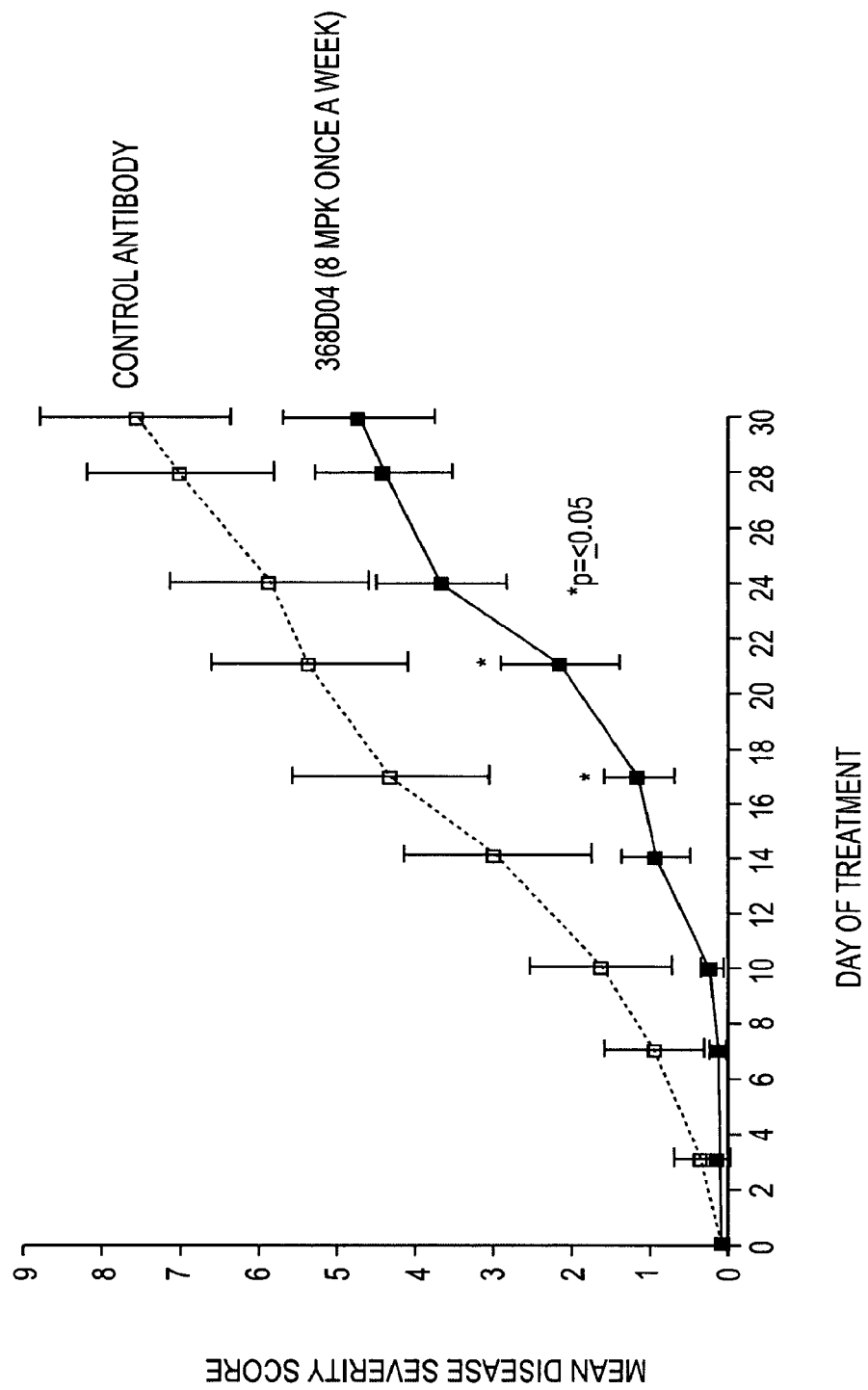
Figure 46C:
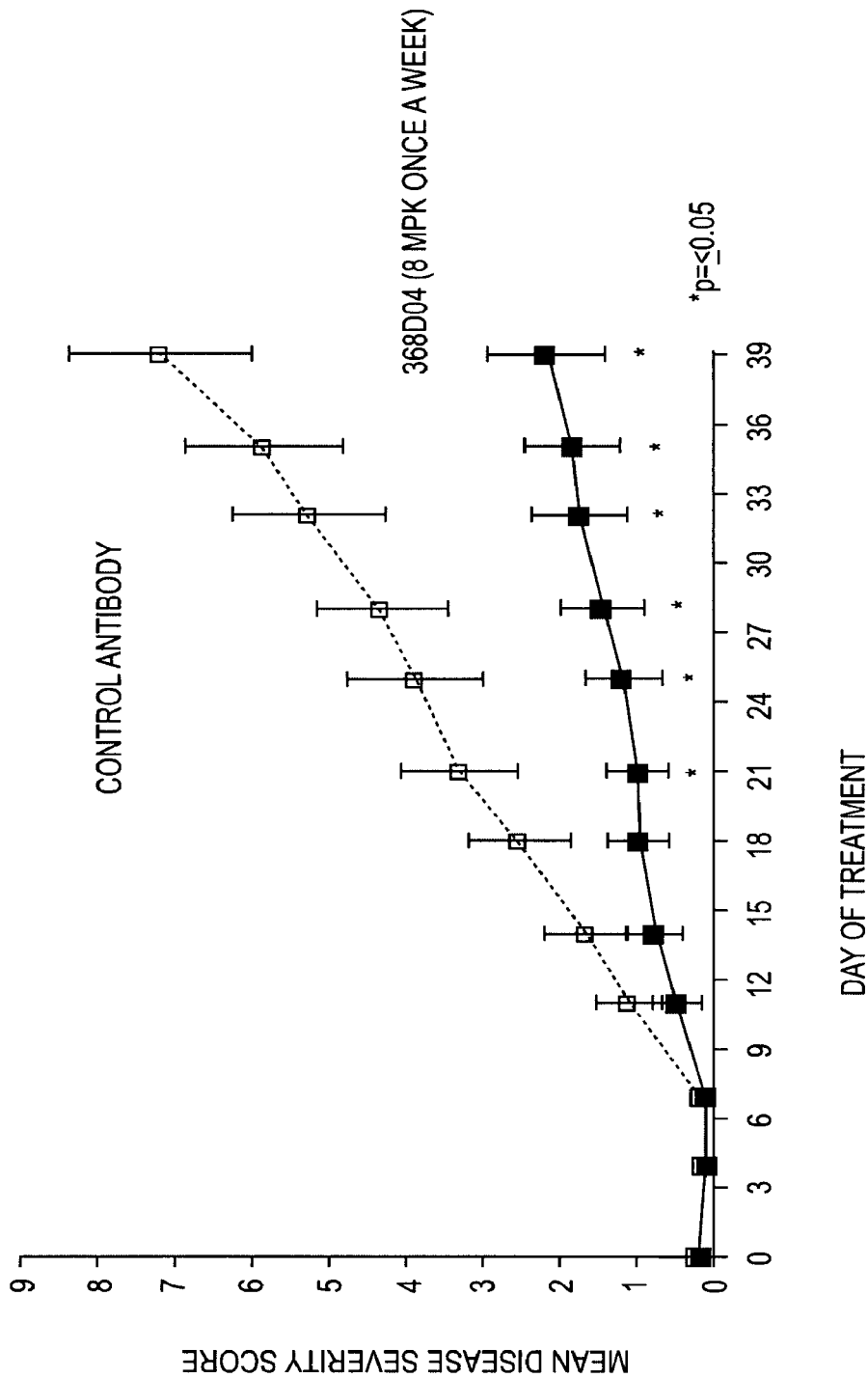

FIGS. 46A-C. Mean disease severity scores from three separate studies of 8 mg kg$^{-1}$ of 368D04 administered once a week in murine CIA model.

Figure 47A:
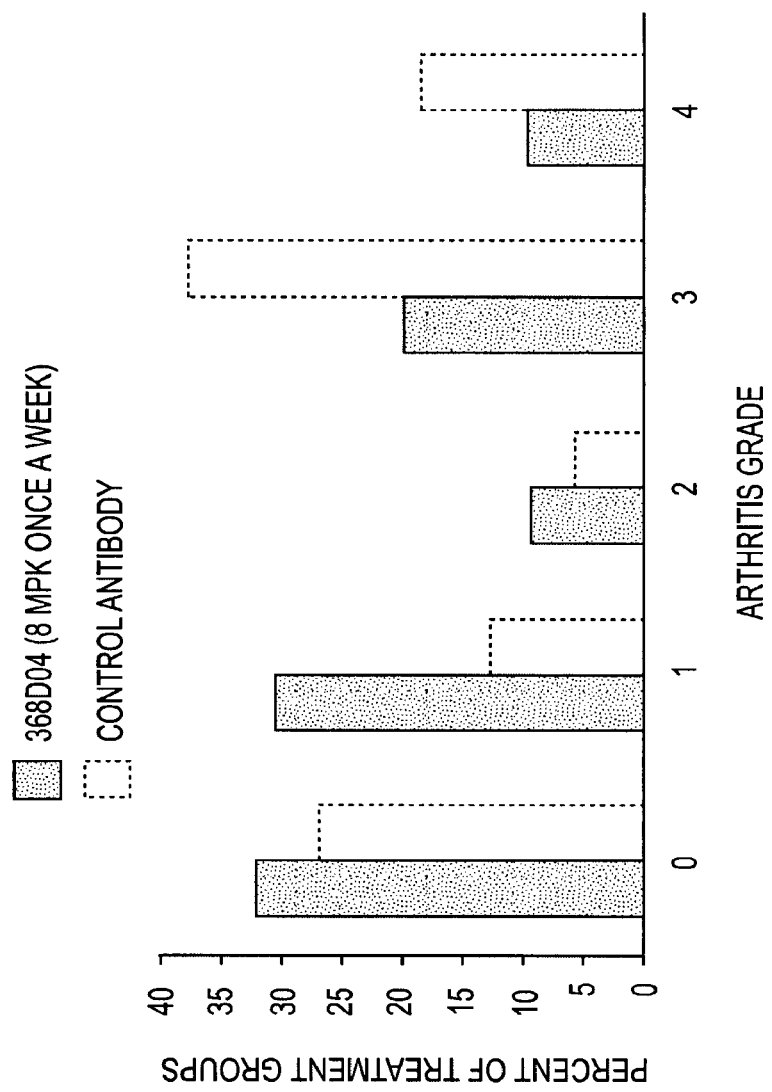
Figure 47B:
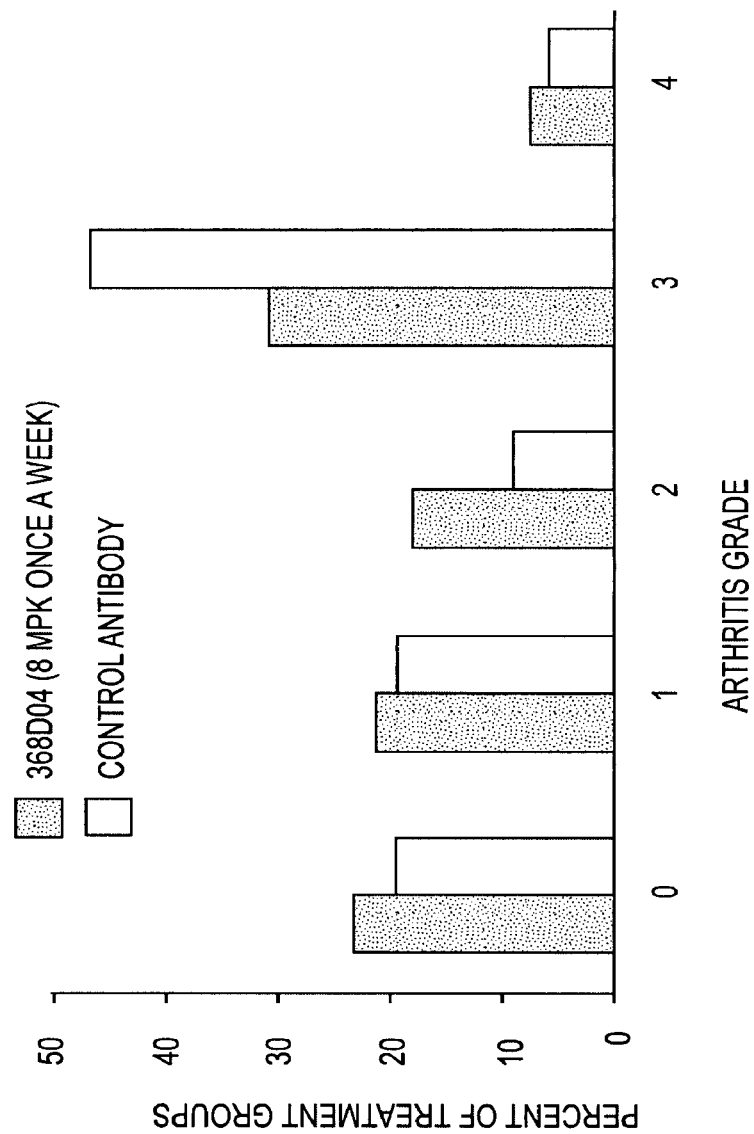

FIGS. 47A-C. Histological evaluation (paw) of disease progression from three separate studies in mice treated with 8 mg kg$^{-1}$ of 368D04 once a week in murine CIA model.

Figure 48A:
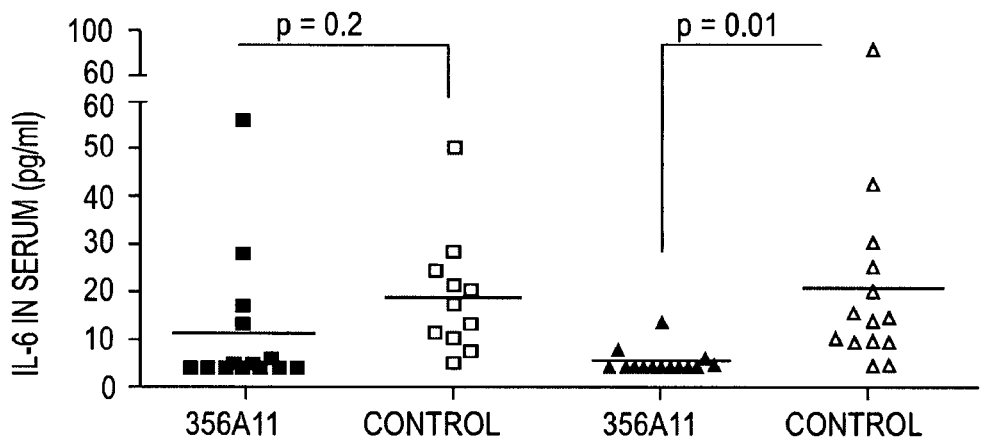
Figure 48B:
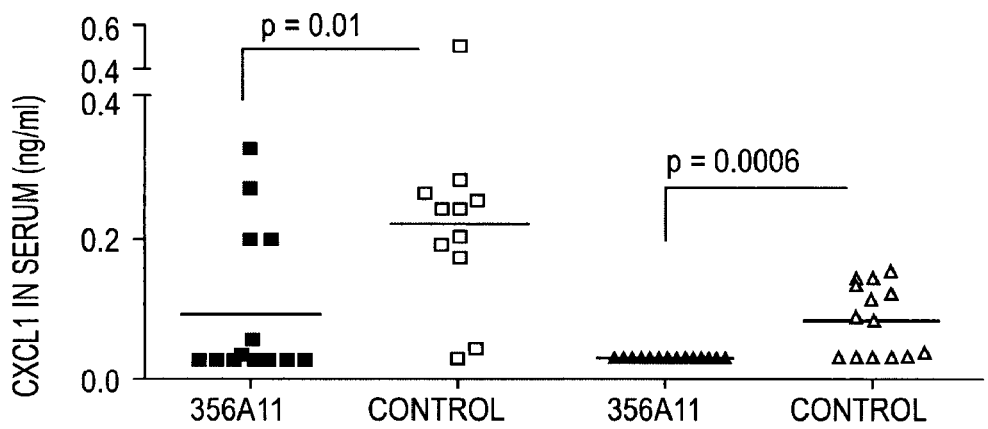

FIG. 48. Serum levels of (A) IL-6 (pg/ml) and (B) CXCL1 (ng/ml) from mice treated with 356A11 (8 mpk once a week) in murine CIA model.

DETAILED DESCRIPTION

I. Definitions

In order that the present invention may be more readily understood, certain terms are first defined. Additional definitions are set forth throughout the detailed description.

The term "antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')$_2$, Fv, scFv, Fd, dAb, and other antibody fragments that retain antigen-binding function. Typically, such fragments would comprise an antigen-binding domain.

The terms "antigen-binding domain" and "antigen-binding fragment" refer to a part of an antibody molecule that comprises-amino acids responsible for the specific binding between antibody and antigen. The part of the antigen that is specifically recognized and bound by the antibody is referred to as the "epitope." An antigen-binding domain may comprise an antibody light chain variable region ($V_L$) and an antibody heavy chain variable region ($V_H$); however, it does not have to comprise both. Fd fragments, for example, have two $V_H$ regions and often retain some antigen-binding function of the intact antigen-binding domain. Examples of antigen-binding fragments of an antibody include (1) a Fab fragment, a monovalent fragment having the $V_L$, $V_H$, $C_L$ and $C_H1$ domains; (2) a F(ab')$_2$ fragment, a bivalent fragment having two Fab fragments linked by a disulfide bridge at the hinge region; (3) a Fd fragment having the two $V_H$ and $C_H1$ domains; (4) a Fv fragment having the $V_L$ and $V_H$ domains of a single arm of an antibody, (5) a dAb fragment (Ward et al., (1989) Nature 341:544-546), which has a $V_H$ domain; (6) an isolated complementarity determining region (CDR); and (7) a single chain Fv (scFv). Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). These antibody fragments are obtained using conventional techniques known to those with skill in the art, and the fragments are evaluated for function in the same manner as are intact antibodies.

The term "effective amount" refers to a dosage or amount that is sufficient to regulate IL-22 activity to ameliorate clinical symptoms or achieve a desired biological outcome, e.g., decreased T cell and/or B cell activity, suppression of autoimmunity, suppression of transplant rejection, etc.

The term "human antibody" includes antibodies having variable and constant regions corresponding substantially to human germline immunoglobulin sequences known in the art, including, for example, those described by Kabat et al. (See Kabat, et al. (1991) Sequences of Proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

The phrase "inhibit" or "antagonize" IL-22 activity and its cognates refer to a reduction, inhibition, or otherwise diminution of at least one activity of IL-22 due to binding an anti-IL-22 antibody, wherein the reduction is relative to the activity of IL-22 in the absence of the same antibody. The activity can be measured using any technique known in the art, including, for example, as described in Examples 7 and 9. Inhibition or antagonism does not necessarily indicate a total elimination of the IL-22 polypeptide biological activity. A reduction in activity may be about 10%, 20%, 30%, 40%, 50%, 60%, 70%, 80%, 90%, or more.

The term "interleukin-22" or "IL-22" refers to a class II cytokine (which may be mammalian) capable of binding to IL-22R and/or a receptor complex of IL-22R and IL-10R2, and has at least one of the following features: (1) an amino acid sequence of a naturally occurring mammalian IL-22 polypeptide (full length or mature form) or a fragment thereof, e.g., an amino acid sequence shown as SEQ ID NO:1 (human) or SEQ ID NO:3 (murine) or a fragment thereof; (2) an amino acid sequence substantially identical to, e.g., at least 85%, 90%, 95%, 96%, 97%, 98%, 99% identical to, an amino acid sequence shown as SEQ ID NO:1 or amino acids 34-179 thereof (human) or SEQ ID NO:3 (murine) or a fragment thereof; (3) an amino acid sequence which is encoded by a naturally occurring mammalian IL-22 nucleotide sequence or a fragment thereof (e.g., SEQ ID NO:2 or nucleotides 71 to 610 (human) or SEQ ID NO:4 (murine) or a fragment thereof); (4) an amino acid sequence encoded by a nucleotide sequence which is substantially identical to, e.g., at least 85%, 90%, 95%, 96%, 97%, 98%, 99% identical to, a nucleotide sequence shown as SEQ ID NO:2 or nucleotides 71 to 610 thereof (human) or SEQ ID NO:4 (murine) or a fragment thereof; (5) an amino acid sequence encoded by a nucleotide sequence degenerate to a naturally occurring IL-22 nucleotide sequence or a fragment thereof, e.g., SEQ ID NO:2 (human) or SEQ ID NO:4 (murine) or a fragment thereof; or (6) a nucleotide sequence that hybridizes to one of the foregoing nucleotide sequences under stringent conditions, e.g., highly stringent conditions. The IL-22 may bind to IL-22R and/or a receptor complex of IL-22R and IL-10R2 of mammalian origin, e.g., human or mouse.

The nucleotide sequence and the predicted amino acid sequence of human IL-22 are shown in SEQ ID NO:2 and SEQ ID NO:1, respectively. The amino acid sequence of mature human IL-22 corresponds to amino acids 34-179 of SEQ ID NO:1. Analysis of recombinant human IL-22 reveals many structural domains. (Nagem et al. (2002) Structure, 10:1051-62; U.S. Patent Application No. US 2002/0187512 A1).

The term "IL-22 activity" refers to at least one cellular process initiated or interrupted as a result of IL-22 binding to a receptor complex consisting of IL-22R and IL-10R2 on the cell. IL-22 activities include at least one of, but are not limited to: (1) binding IL-22R or a receptor complex of IL-22R and IL-10R2 (e.g., human IL-22R with or without human IL-10R2); (2) associating with signal transduction molecules (e.g., JAK-1); (3) stimulating phosphorylation of STAT proteins (e.g., STAT5, STAT3, or combination thereof); (4) activating STAT proteins; and (5) modulating (e.g., increasing or decreasing) proliferation, differentiation, effector cell function, cytolytic activity, cytokine secretion, survival, or combinations thereof, of epithelial cells, fibroblasts, or immune cells. Epithelial cells include, but are not limited to, cells of the skin, gut, liver, and kidney, as well as endothelial cells. Fibroblasts include, but are not limited to, synovial fibroblasts. Immune cells may include CD8+ and CD4+ T cells, NK cells, B cells, macrophages, and megakaryocytes. IL-22 activity can be determined in vitro, for example, using the IL-22 receptor inhibition assay as described in Examples 2 and 6, the GROa secretion assay in Example 9, or the BAF3 proliferation assay of Example 7. IL-22 activity can also be determined in vivo, for example, by scoring progression of an immune response or disorder as described in Example 13.

As used herein, "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term excludes sequences generated by genomic rearrangement in an immune cell.

The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The phrase "percent identical" or "percent identity" refers to the similarity between at least two different sequences. This percent identity can be determined by standard alignment algorithms, for example, the Basic Local Alignment Tool (BLAST) described by Altshul et al. ((1990) J. Mol. Biol., 215: 403-410); the algorithm of Needleman et al. ((1970) J. Mol. Biol., 48: 444-453); or the algorithm of Meyers et al. ((1988) Comput. Appl. Biosci., 4: 11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4: 11-17) which has been incorporated into the ALIGN program (version 2.0), using a PAM120 weight residue table, a gap length penalty of 12 and a gap penalty of 4. The percent identity is usually calculated by comparing sequences of similar length.

The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat.

No. 5,565,332. A repertoire may include only one sequence or may include a plurality of sequences, including ones in a genetically diverse collection.

The terms "specific binding" or "specifically binds" refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the association constant $K_A$ is higher than $10^6 M^{-1}$. If necessary, nonspecific binding can be reduced without substantially affecting specific binding by varying the binding conditions. The appropriate binding conditions, such as concentration of antibodies, ionic strength of the solution, temperature, time allowed for binding, concentration of a blocking agent (e.g., serum albumin, milk casein), etc., may be optimized by a skilled artisan using routine techniques. Illustrative conditions are set forth in Example 3, but other conditions known to the person of ordinary skill in the art fall within the scope of this invention.

As used herein, the term "stringent" describes conditions for hybridization and washing. Stringent conditions are known to those skilled in the art and can be found in *Current Protocols in Molecular Biology*, John Wiley & Sons, N.Y. (1989), 6.3.1-6.3.6. Aqueous and nonaqueous methods are described in that reference and either can be used. One example of stringent hybridization conditions is hybridization in 6× sodium chloride/sodium citrate (SSC) at about 45° C., followed by at least one wash in 0.2×SSC, 0.1% SDS at 50° C. A second example of stringent hybridization conditions is hybridization in 6×SSC at about 45° C., followed by at least one wash in 0.2×SSC, 0.1% SDS at 55° C. Another example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. High stringent conditions include hybridization in 0.5M sodium phosphate, 7% SDS at 65° C., followed by at least one wash at 0.2×SSC, 1% SDS at 65° C.

The phrase "substantially as set out," "substantially identical" or "substantially homologous" means that the relevant amino acid or nucleotide sequence (e.g., CDR(s), $V_H$, or $V_L$ domain) will be identical to or have insubstantial differences (through conserved amino acid substitutions) in comparison to the sequences which are set out. Insubstantial differences include minor amino acid changes, such as 1 or 2 substitutions in a 5 amino acid sequence of a specified region. In the case of antibodies, the second antibody has the same specificity and has at least 50% of the affinity of the first antibody.

Sequences substantially identical or homologous (e.g., at least about 85% sequence identity) to the sequences disclosed herein are also part of this application. In some embodiment, the sequence identity can be about 85%, 90%, 95%, 96%, 97%, 98%, 99% or higher. Alternatively, substantial identity or homology exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

The term "therapeutic agent" is a substance that treats or assists in treating a medical disorder. Therapeutic agents may include, but are not limited to, substances that modulate immune cells or immune responses in a manner that complements the IL-22 activity of anti-IL-22 antibodies. Non-limiting examples and uses of therapeutic agents are described herein.

As used herein, a "therapeutically effective amount" of an anti-IL-22 antibody refers to an amount of an antibody which is effective, upon single or multiple dose administration to a subject (such as a human patient) at treating, preventing, curing, delaying, reducing the severity of, and/or ameliorating at least one symptom of a disorder or recurring disorder, or prolonging the survival of the subject beyond that expected in the absence of such treatment.

The term "treatment" refers to a therapeutic or preventative measure. The treatment may be administered to a subject having a medical disorder or who ultimately may acquire the disorder, in order to prevent, cure, delay, reduce the severity of, and/or ameliorate one or more symptoms of a disorder or recurring disorder, or in order to prolong the survival of a subject beyond that expected in the absence of such treatment.

II. Anti-IL-22 Antibodies

The disclosure provides novel anti-IL-22 antibodies that comprise novel antigen-binding fragments.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas (see e.g., Kohler and Milstein (1975) *Nature*, 256: 495-499) in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) *Science* 228:1315-1317; Clackson et al. (1991) *Nature*, 352: 624-628; Marks et al. (1991) *J. Mol. Biol.*, 222: 581-597 WO 92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) *Science* 229:1202-1207; by Oi et al. (1986) *BioTechniques* 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.*, 80: 7308-7312, 1983; Kozbor et al., *Immunology Today*, 4: 7279, 1983; Olsson et al., *Meth. Enzymol.*, 92: 3-16, 1982), and may be made according to the teachings of PCT Publication WO92/06193 or EP 0239400).

An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

In certain embodiments, an antibody can contain an altered immunoglobulin constant or Fc region. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, *Annu. Rev. Immunol* 9:457-92, 1991; Capel et al., *Immunomethods* 4:25-34, 1994; and de Haas et al., *J. Lab. Clin. Med.* 126:330-41, 1995).

For additional antibody production techniques, see Antibodies: A Laboratory Manual, eds. Harlow et al., Cold Spring Harbor Laboratory, 1988. The present invention is not necessarily limited to any particular source, method of production, or other special characteristics of an antibody.

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see *Antibodies: A Laboratory Manual, Cold Spring Harbor Laboratory*, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in *Sequences of Proteins of Immunological Interest, US Department of Health and Human Services* (1991), eds. Kabat et al. Another standard for characterizing the antigen binding site is to refer to the hypervariable loops as described by Chothia. See, e.g., Chothia, D. et al. (1992) *J. Mol.* 227:799-817; and Tomlinson et al. (1995) *EMBO J.* 14:4628-4638. Still another standard is the AbM definition used by Oxford Molecular's AbM antibody modelling software. See, generally, e.g., *Protein Sequence and Structure Analysis of Antibody Variable Domains.* In: *Antibody Engineering Lab Manual* (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

The Fab fragment (Fragment antigen-binding) consists of $V_H$-$C_H1$ and $V_L$-$C_L$ domains covalently linked by a disulfide bond between the constant regions. The $F_v$ fragment is smaller and consists of $V_H$ and $V_L$ domains non-covalently linked. To overcome the tendency of non-covalently linked domains to dissociate, a single chain $F_v$ fragment (sc$F_v$) can be constructed. The sc$F_v$ contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide may be used as a linker, but other linkers are known in the art.

The sequence of antibody genes after assembly and somatic mutation is highly varied, and these varied genes are estimated to encode $10^{10}$ different antibody molecules (Immunoglobulin Genes, 2nd ed., eds. Jonio et al., Academic Press, San Diego, Calif., 1995).

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992). In one embodiment, the bispecific antibody comprises a first binding domain polypeptide, such as a Fab' fragment, linked via an immunoglobulin constant region to a second binding domain polypeptide.

Small Modular ImmunoPharmaceuticals (SMIP™) provide an example of a variant molecule comprising a binding domain polypeptide. SMIPs and their uses and applications are disclosed in e.g., U.S. Published Patent Application. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

A SMIP™ typically refers to a binding domain-immunoglobulin fusion protein that includes a binding domain polypeptide that is fused or otherwise connected to an immunoglobulin hinge or hinge-acting region polypeptide, which in turn is fused or otherwise connected to a region comprising one or more native or engineered constant regions from an immunoglobulin heavy chain, other than CH1, for example, the CH2 and CH3 regions of IgG and IgA, or the CH3 and CH4 regions of IgE (see e.g., U.S. 2005/0136049 by Ledbetter, J. et al., which is incorporated by reference, for a more complete description). The binding domain-immunoglobulin fusion protein can further include a region that includes a native or engineered immunoglobulin heavy chain CH2 constant region polypeptide (or CH3 in the case of a construct derived in whole or in part from IgE) that is fused or otherwise connected to the hinge region polypeptide and a native or engineered immunoglobulin heavy chain CH3 constant region polypeptide (or CH4 in the case of a construct derived in whole or in part from IgE) that is fused or otherwise connected to the CH2 constant region polypeptide (or CH3 in the case of a construct derived in whole or in part from IgE). Typically, such binding domain-immunoglobulin fusion proteins are capable of at least one immunological activity selected from the group consisting of antibody dependent cell-mediated cytotoxicity, complement fixation, and/or binding to a target, for example, a target antigen, such as human IL-22.

Therapeutic proteins, i.e., a protein or peptide that has a biological effect on a region in the body on which it acts or on a region of the body on which it remotely acts via intermediates, are also useful for practicing the invention. A therapeutic protein can include peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and potentially improved characteristics.

Other embodiments of therapeutic proteins include fusion proteins. These molecules generally have all or a substantial portion of a targeting peptide, for example, IL-22 or an anti-IL-22 antibody, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments of antibodies, antigens, receptor proteins, enzymes, lectins, MHC proteins, cell adhesion proteins and binding proteins. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

In one embodiment, the targeting peptide, for example, IL-22 or an anti-IL-22 antibody, is fused with an immunoglobulin heavy chain constant region, such as an Fc fragment, which contains two constant region domains and a hinge region but lacks the variable region (See, U.S. Pat. Nos. 6,018,026 and 5,750,375, incorporated herein by reference). The Fc region may be a naturally occurring Fc region, or may be altered to improve certain qualities, such as therapeutic qualities, circulation time, reduced aggregation, etc. Peptides and proteins fused to an Fc region typically exhibit a greater half-life in vivo than the unfused counterpart. Also, a fusion to an Fc region permits dimerization/multimerization of the fusion polypeptide.

VHH molecules (or nanobodies), as known to the skilled artisan, are heavy chain variable domains derived from immunoglobulins naturally devoid of light chains, such as those derived from *Camelidae* as described in WO 9404678, incorporated herein by reference. Such a VHH molecule can be derived from antibodies raised in *Camelidae* species, for example in camel, llama, dromedary, alpaca and guanaco and is sometomes called a camelid or camelized variable domain. See e.g., Muyldermans., *J. Biotechnology* (2001) 74(4):277-302, incorporated herein by reference. Other species besides *Camelidae* may produce heavy chain antibodies naturally devoid of light chain. VHH molecules are about 10 times smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognized by antibodies generated in vitro through the use of antibody libraries or via immunization of mammals other than Camelids (see WO 9749805, which is incorporated herein by reference).

One aspect of the present invention comprises antibodies and antigen binding fragments that bind IL-22. The disclosure provides novel CDRs derived from human immunoglobulin gene libraries. The structure for carrying a CDR is generally an antibody heavy or light chain or portion thereof, where the CDR is located to a naturally occurring CDR region. The structures and locations of variable domains may be determined as described in Kabat et al., Sequences of Proteins of Immunological Interest, No. 91-3242, National Institutes of Health Publications, Bethesda, Md. (1991).

DNA and amino acid (AA) sequences of illustrative embodiments of the anti-IL-22 antibodies of this invention, including their $scF_v$ fragments, $V_H$ and $V_L$ domains, and CDRs, are set forth in FIGS. 7-10 and enumerated in Tables 1 and 7. Twenty specific embodiments of the non-germlined antibodies are identified as GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11. The CDR positions in the $V_H$ and $V_L$ domains of the non-germlined antibodies are listed in Table 2. Fifteen specific embodiments of the germlined antibodies are identified as GIL01, GIL16, GIL45, GIL60, GIL68, GIL92, 062A09, 087B03, 166B06, 166G05, 354A08, 355B06, 355E04, 356A11, and 368D04.

TABLE 1

Amino acid and Nucleotide Sequences of $V_H$ and $V_L$ Domains, Fv, and CDRs of Non-germlined Antibodies

| Region | Type | GIL01 SEQ ID | GIL16 SEQ ID | GIL45 SEQ ID | GIL60 SEQ ID | GIL68 SEQ ID | GIL92 SEQ ID | 097D09 SEQ ID | 062A09 SEQ ID | 062G05 SEQ ID | 087B03 SEQ ID |
|---|---|---|---|---|---|---|---|---|---|---|---|
| $V_H$ | AA | NO: 5 | NO: 23 | NO: 41 | NO: 59 | NO: 77 | NO: 95 | NO: 113 | NO: 131 | NO: 149 | NO: 167 |
| $V_L$ | AA | NO: 6 | NO: 24 | NO: 42 | NO: 60 | NO: 78 | NO: 96 | NO: 114 | NO: 132 | NO: 150 | NO: 168 |
| scFv | AA | NO: 7 | NO: 25 | NO: 43 | NO: 61 | NO: 79 | NO: 97 | NO: 115 | NO: 133 | NO: 151 | NO: 169 |
| H1 | AA | NO: 8 | NO: 26 | NO: 44 | NO: 62 | NO: 80 | NO: 98 | NO: 116 | NO: 134 | NO: 152 | NO: 170 |
| H2 | AA | NO: 9 | NO: 27 | NO: 45 | NO: 63 | NO: 81 | NO: 99 | NO: 117 | NO: 135 | NO: 153 | NO: 171 |
| H3 | AA | NO: 10 | NO: 28 | NO: 46 | NO: 64 | NO: 82 | NO: 100 | NO: 118 | NO: 136 | NO: 154 | NO: 172 |
| L1 | AA | NO: 11 | NO: 29 | NO: 47 | NO: 65 | NO: 83 | NO: 101 | NO: 119 | NO: 137 | NO: 155 | NO: 173 |
| L2 | AA | NO: 12 | NO: 30 | NO: 48 | NO: 66 | NO: 84 | NO: 102 | NO: 120 | NO: 138 | NO: 156 | NO: 174 |
| L3 | AA | NO: 13 | NO: 31 | NO: 49 | NO: 67 | NO: 85 | NO: 103 | NO: 121 | NO: 139 | NO: 157 | NO: 175 |
| $V_H$ | DNA | NO: 14 | NO: 32 | NO: 50 | NO: 68 | NO: 86 | NO: 104 | NO: 122 | NO: 140 | NO: 158 | NO: 176 |
| $V_L$ | DNA | NO: 15 | NO: 33 | NO: 51 | NO: 69 | NO: 87 | NO: 105 | NO: 123 | NO: 141 | NO: 159 | NO: 177 |
| $scF_v$ | DNA | NO: 16 | NO: 34 | NO: 52 | NO: 70 | NO: 88 | NO: 106 | NO: 124 | NO: 142 | NO: 160 | NO: 178 |
| H1 | DNA | NO: 17 | NO: 35 | NO: 53 | NO: 71 | NO: 89 | NO: 107 | NO: 125 | NO: 143 | NO: 161 | NO: 179 |
| H2 | DNA | NO: 18 | NO: 36 | NO: 54 | NO: 72 | NO: 90 | NO: 108 | NO: 126 | NO: 144 | NO: 162 | NO: 180 |
| H3 | DNA | NO: 19 | NO: 37 | NO: 55 | NO: 73 | NO: 91 | NO: 109 | NO: 127 | NO: 145 | NO: 163 | NO: 181 |
| L1 | DNA | NO: 20 | NO: 38 | NO: 56 | NO: 74 | NO: 92 | NO: 110 | NO: 128 | NO: 146 | NO: 164 | NO: 182 |
| L2 | DNA | NO: 21 | NO: 39 | NO: 57 | NO: 75 | NO: 93 | NO: 111 | NO: 129 | NO: 147 | NO: 165 | NO: 183 |
| L3 | DNA | NO: 22 | NO: 40 | NO: 58 | NO: 76 | NO: 94 | NO: 112 | NO: 130 | NO: 148 | NO: 166 | NO: 184 |

| Region | Type | 367D04 SEQ ID | 368D04 SEQ ID | 166B06 SEQ ID | 166G05 SEQ ID | 375G06 SEQ ID | 376B10 SEQ ID | 354A08 SEQ ID | 355B06 SEQ ID | 355E04 SEQ ID | 356A11 SEQ ID |
|---|---|---|---|---|---|---|---|---|---|---|---|
| $V_H$ | AA | NO: 185 | NO: 203 | NO: 221 | NO: 239 | NO: 257 | NO: 275 | NO: 293 | NO: 311 | NO: 329 | NO: 347 |
| $V_L$ | AA | NO: 186 | NO: 204 | NO: 222 | NO: 240 | NO: 258 | NO: 276 | NO: 294 | NO: 312 | NO: 330 | NO: 348 |
| $scF_v$ | AA | NO: 187 | NO: 205 | NO: 223 | NO: 241 | NO: 259 | NO: 277 | NO: 295 | NO: 313 | NO: 331 | NO: 349 |
| H1 | AA | NO: 188 | NO: 206 | NO: 224 | NO: 242 | NO: 260 | NO: 278 | NO: 296 | NO: 314 | NO: 332 | NO: 350 |
| H2 | AA | NO: 189 | NO: 207 | NO: 225 | NO: 243 | NO: 261 | NO: 279 | NO: 297 | NO: 315 | NO: 333 | NO: 351 |
| H3 | AA | NO: 190 | NO: 208 | NO: 226 | NO: 244 | NO: 262 | NO: 280 | NO: 298 | NO: 316 | NO: 334 | NO: 352 |
| L1 | AA | NO: 191 | NO: 209 | NO: 227 | NO: 245 | NO: 263 | NO: 281 | NO: 299 | NO: 317 | NO: 335 | NO: 353 |
| L2 | AA | NO: 192 | NO: 210 | NO: 228 | NO: 246 | NO: 264 | NO: 282 | NO: 300 | NO: 318 | NO: 336 | NO: 354 |
| L3 | AA | NO: 193 | NO: 211 | NO: 229 | NO: 247 | NO: 265 | NO: 283 | NO: 301 | NO: 319 | NO: 337 | NO: 355 |
| $V_H$ | DNA | NO: 194 | NO: 212 | NO: 230 | NO: 248 | NO: 266 | NO: 284 | NO: 302 | NO: 320 | NO: 338 | NO: 356 |
| $V_L$ | DNA | NO: 195 | NO: 213 | NO: 231 | NO: 249 | NO: 267 | NO: 285 | NO: 303 | NO: 321 | NO: 339 | NO: 357 |
| $scF_v$ | DNA | NO: 196 | NO: 214 | NO: 232 | NO: 250 | NO: 268 | NO: 286 | NO: 304 | NO: 322 | NO: 340 | NO: 358 |
| H1 | DNA | NO: 197 | NO: 215 | NO: 233 | NO: 251 | NO: 269 | NO: 287 | NO: 305 | NO: 323 | NO: 341 | NO: 359 |
| H2 | DNA | NO: 198 | NO: 216 | NO: 234 | NO: 252 | NO: 270 | NO: 288 | NO: 306 | NO: 324 | NO: 342 | NO: 360 |
| H3 | DNA | NO: 199 | NO: 217 | NO: 235 | NO: 253 | NO: 271 | NO: 289 | NO: 307 | NO: 325 | NO: 343 | NO: 361 |
| L1 | DNA | NO: 200 | NO: 218 | NO: 236 | NO: 254 | NO: 272 | NO: 290 | NO: 308 | NO: 326 | NO: 344 | NO: 362 |
| L2 | DNA | NO: 201 | NO: 219 | NO: 237 | NO: 255 | NO: 273 | NO: 291 | NO: 309 | NO: 327 | NO: 345 | NO: 363 |
| L3 | DNA | NO: 202 | NO: 220 | NO: 238 | NO: 256 | NO: 274 | NO: 292 | NO: 310 | NO: 328 | NO: 346 | NO: 364 |

TABLE 2

Positions of CDRs within Non-germlined Antibody Amino Acid Sequences of $V_H$ and $V_L$ Domains

| CDR | GIL01 | GIL16 | GIL45 | GIL60 | GIL68 | GIL92 | 097D09 | 062A09 | 062G05 | 087B03 |
|---|---|---|---|---|---|---|---|---|---|---|
| H1 | 31-35 | 31-35 | 31-35 | 31-35 | 31-35 | 31-35 | 31-35 | 31-35 | 31-35 | 31-35 |
| H2 | 50-66 | 50-66 | 50-66 | 50-66 | 50-66 | 50-66 | 50-66 | 50-66 | 50-66 | 50-66 |
| H3 | 99-108 | 99-108 | 99-108 | 99-110 | 99-108 | 99-110 | 99-108 | 99-108 | 99-108 | 99-110 |
| L1 | 24-34 | 24-34 | 23-36 | 23-36 | 23-33 | 23-36 | 24-34 | 24-34 | 24-34 | 23-36 |
| L2 | 50-56 | 50-56 | 52-58 | 52-58 | 49-55 | 52-58 | 50-56 | 50-56 | 50-56 | 52-58 |
| L3 | 89-97 | 89-97 | 91-100 | 91-100 | 88-98 | 91-101 | 89-97 | 89-97 | 89-97 | 91-100 |

| CDR | 367D04 | 368D04 | 166B06 | 166G05 | 375G06 | 376B10 | 354A08 | 355B06 | 355E04 | 356A11 |
|---|---|---|---|---|---|---|---|---|---|---|
| H1 | 31-35 | 31-35 | 31-35 | 31-35 | 31-35 | 31-35 | 30-34 | 31-35 | 31-35 | 31-35 |
| H2 | 50-66 | 50-66 | 50-66 | 50-66 | 50-66 | 50-66 | 49-65 | 50-66 | 50-66 | 50-66 |
| H3 | 99-110 | 99-110 | 99-108 | 99-108 | 99-108 | 99-108 | 98-110 | 99-110 | 99-110 | 99-110 |
| L1 | 23-36 | 23-36 | 23-33 | 23-33 | 23-33 | 23-33 | 23-36 | 23-36 | 23-36 | 22-35 |
| L2 | 52-58 | 52-58 | 49-55 | 49-55 | 49-55 | 49-55 | 52-58 | 52-58 | 52-58 | 51-58 |
| L3 | 91-100 | 91-100 | 88-98 | 88-98 | 88-98 | 88-98 | 91-101 | 91-101 | 91-101 | 90-100 |

Anti-IL-22 antibodies of this invention may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Constant regions are known in the art (see, for example, Kabat et al., Sequences of Proteins of Immunological Interest, No. 91-3242, National Institutes of Health Publications, Bethesda, Md. (1991)). Therefore, antibodies within the scope of this invention include $V_H$ and $V_L$ domains, or a portion thereof, combined with constant regions known in the art.

Certain embodiments comprise a $V_H$ domain, a $V_L$ domain, or a combination thereof, of the $F_v$ fragment from GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11. Another embodiment comprises a $V_H$ domain, a $V_L$ domain, or a combination thereof, of the $F_v$ fragment from an antibody chosen from 356A11, 354A08, 087B03, and 368D04. Further embodiments comprise one, two, three, four, five or six complementarity determining regions (CDRs) from the $V_H$ and $V_1$ domains. Antibodies whose CDR sequences are included within SEQ ID NO:5-13, 23-31, 41-49, 59-67, 77-85, 95-103, 113-121, 131-139, 149-157, 167-175, 185-193, 203-211, 221-229, 239-247, 257-265, 275-283, 293-301, 311-319, 329-337, 347-355, 365-373, 383-391, 401-409, 419-427, 437-445, 455-463, 473-481, 491-499, 509-517, 527-535, 545-553, 563-571, 581-589, 599-607, or 617-625 are encompassed within the scope of this invention. For example, in one embodiment, an antibody comprises a H3 fragment of the $V_H$ domain of germlined or non-germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 or from an antibody chosen from 356A11, 354A08, 087B03, and 368D04.

In certain embodiments, the $V_H$ and/or $V_L$ domains may be germlined, i.e., the framework regions (FR) of these domains are mutated using conventional molecular biology techniques to match those produced by the germline cells. In other embodiments, the FR sequences remain diverged from the consensus germline sequences. In one embodiment of this invention, germlined antibodies are shown in Table 7.

In one embodiment, the invention provides amino acid and nucleic acid sequences for the germlined GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11. Amino acid and nucleotide sequences for the $V_H$ domain of the germlined GIL01, GIL16, GIL45, GIL60, GIL68, GIL92, 062A09, 087B03, 166B06, 166G05, 354A08, 355B06, 355E04, 356A11, and 368D04 are depicted in Table 7 and FIG. 8. Amino acid and nucleotide sequences for the $V_L$ domain of the germlined GIL01, GIL16, GIL45, GIL60, GIL68, GIL92, 062A09, 087B03, 166B06, 166G05, 354A08, 355B06, 355E04, 356A11, and 368D04 are also depicted in Table 7 and FIG. 8.

In one embodiment, mutagenesis is used to make an antibody more similar to one or more germline sequences. This may be desirable when mutations are introduced into the framework region of an antibody through somatic mutagenesis or through error prone PCR. Germline sequences for the $V_H$ and $V_L$ domains can be identified by performing amino acid and nucleic acid sequence alignments against the VBASE database (MRC Center for Protein Engineering, UK). VBASE is a comprehensive directory of all human germline variable region sequences compiled from over a thousand published sequences, including those in the current releases of the Genbank and EMBL data libraries. In some embodiments, the FR regions of the scFvs are mutated in conformity with the closest matches in the VBASE database and the CDR portions are kept intact.

In certain embodiments, antibodies of this invention specifically react with an epitope that is the same as the epitope recognized by GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11, such that they competitively inhibit the binding of GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 to human IL-22. Such antibodies can be determined in competitive binding assays. In one embodiment, the antibody, or antigen binding fragment thereof, binds to an IL-22 epitope that is recognized by 368D04, such that the antibody competitively inhibits the binding of 368D04 to human IL-22. In another embodiment, the antibody, or antigen binding fragment thereof, binds to an IL-22 epitope that is recognized by 356A11, such that the antibody competitively inhibits the binding of 356A11 to human IL-22. In another embodiment, the antibody, or antigen binding fragment thereof, binds to an IL-22 epitope that is recognized by 354A08, such that the antibody competitively inhibits the binding of 354A08 to human IL-22. In another embodiment, the antibody, or antigen binding fragment thereof, binds to an IL-22 epitope that is recognized by 087B03, such that the antibody competitively inhibits the binding of 087B03 to human IL-22. In one embodiment, the association constant ($K_A$) of these antibodies for human IL-22 is at least $10^6$ $M^{-1}$. In another embodiment, the association constant of these antibodies for human IL-22 is at least $10^9$ $M^{-1}$. In other embodiments, the association constant of these antibodies for human IL-22 is at least $10^{10}$ $M^{-1}$, at least $10^{11}$ $M^{-1}$, or at least $10^{12}$ $M^{-1}$. The binding affinity may be determined using techniques known in the art, such as ELISA, biosensor technology, such as biospecific interaction analysis, or other techniques including those described in this application.

It is contemplated that antibodies of this invention may bind other proteins, such as, for example, recombinant proteins comprising all or a portion of IL-22.

One of ordinary skill in the art will recognize that the disclosed antibodies may be used to detect, measure, and/or inhibit proteins that differ somewhat from IL-22. For example, these proteins may be homologs of IL-22. Anti-IL-22 antibodies are expected to bind proteins that comprise a sequence which is at least about 60%, 70%, 80%, 90%, 95%, or more identical to any sequence of at least 100, 80, 60, 40, or 20 contiguous amino acids in the sequence set forth SEQ ID NO:1.

In addition to sequence homology analyses, epitope mapping (see, e.g., Epitope Mapping Protocols, ed. Morris, Humana Press, 1996), and secondary and tertiary structure analyses can be carried out to identify specific 3D structures assumed by the presently disclosed antibodies and their complexes with antigens. Such methods include, but are not limited to, X-ray crystallography (Engstom (1974) Biochem. Exp. Biol., 11:7-13) and computer modeling of virtual representations of the present antibodies (Fletterick et al. (1986) Computer Graphics and Molecular Modeling, in Current Communications in Molecular Biology, Cold Spring Harbor Laboratory, Cold Spring Harbor, N.Y.).

The disclosure provides a method for obtaining anti-IL-22 antibodies that comprises creating antibodies with altered Table 1$V_H$ and/or $V_L$ sequence(s). Such antibodies may be derived by a skilled artisan using techniques known in the art. For example, amino acid substitutions, deletions, or additions can be introduced in FR and/or CDR regions. FR changes are usually designed to improve the stability and immunogenicity of the antibody, while CDR changes are typically designed to increase antibody affinity for its antigen. The changes that increase affinity may be tested by altering CDR sequence and measuring antibody affinity for its target (see Antibody Engineering, 2nd ed., Oxford University Press, ed. Borrebaeck, 1995).

Antibodies whose CDR sequences differ insubstantially from those included in or included within the sequences in SEQ ID NO: 5-13, 23-31, 41-49, 59-67, 77-85, 95-103, 113-121, 131-139, 149-157, 167-175, 185-193, 203-211, 221-229, 239-247, 257-265, 275-283, 293-301, 311-319, 329-337, 347-355, 365-373, 383-391, 401-409, 419-427, 437-445, 455-463, 473-481, 491-499, 509-517, 527-535, 545-553, 563-571, 581-589, 599-607, or 617-625, are encompassed within the scope of this invention. Typically, this involves substitution of an amino acid with an amino acid having similar charge, hydrophobic, or stereochemical characteristics. More drastic substitutions in FR regions, in contrast to CDR regions, may also be made as long as they do not adversely affect (e.g., reduce affinity by more than 50% as compared to unsubstituted antibody) the binding properties of the antibody. Substitutions may also be made to germline the antibody or stabilize the antigen binding site.

Conservative modifications will produce molecules having functional and chemical characteristics similar to those of the molecule from which such modifications are made. In contrast, substantial modifications in the functional and/or chemical characteristics of the molecules may be accomplished by selecting substitutions in the amino acid sequence that differ significantly in their effect on maintaining (1) the structure of the molecular backbone in the area of the substitution, for example, as a sheet or helical conformation, (2) the charge or hydrophobicity of the molecule at the target site, or (3) the size of the molecule.

For example, a "conservative amino acid substitution" may involve a substitution of a native amino acid residue with a normative residue such that there is little or no effect on the polarity or charge of the amino acid residue at that position. (See, for example, MacLennan et al., 1998, Acta Physiol. Scand. Suppl. 643:55-67; Sasaki et al., 1998, Adv. Biophys. 35:1-24).

Desired amino acid substitutions (whether conservative or non-conservative) can be determined by those skilled in the art at the time such substitutions are desired. For example, amino acid substitutions can be used to identify important residues of the molecule sequence, or to increase or decrease the affinity of the molecules described herein. Exemplary amino acid substitutions include, but are not limited to, those set forth in Table 3.

TABLE 3

Amino Acid Substitutions

| Original Residues | Exemplary Substitutions | More Conservative Substitutions |
| --- | --- | --- |
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

In one embodiment, the method for making a variant $V_H$ domain comprises adding, deleting, or substituting at least one amino acid in the disclosed $V_H$ domains, or combining the disclosed $V_H$ domains with at least one $V_L$ domain, and testing the variant $V_H$ domain for IL-22 binding or modulation of IL-22 activity.

An analogous method for making a variant V$_L$ domain comprises adding, deleting, or substituting at least one amino acid in the disclosed V$_L$ domains, or combining the disclosed V$_L$ domains with at least one V$_H$ domain, and testing the variant V$_L$ domain for IL-22 binding or modulation of IL-22 activity.

A further aspect of the disclosure provides a method for preparing antibodies or antigen-binding fragments that specifically bind IL-22. The method comprises:

(a) providing a starting repertoire of nucleic acids encoding a V$_H$ domain which lacks at least one CDR or contains at least one CDR to be replaced;

(b) inserting into or replacing the CDR region of the starting repertoire with at least one donor nucleic acid encoding an amino acid sequence as substantially set out herein for a V$_H$ CDR, yielding a product repertoire;

(c) expressing the nucleic acids of the product repertoire;

(d) selecting a specific antigen-binding fragment that binds to IL-22; and (e) recovering the specific antigen-binding fragment or nucleic acid encoding it.

In an analogous method at least one V$_L$ CDR of the invention is combined with a repertoire of nucleic acids encoding a V$_L$ domain which lacks at least one CDR or contains at least one CDR to be replaced. The at least one V$_H$ or V$_L$ CDR may be a CDR1, a CDR2, a CDR3, or a combination thereof, including combinations of V$_H$ and V$_L$ CDRs, such as those set forth in Tables 1 or 7, including those set out in SEQ ID NO:8, 9, 10, 11, 12, 13, 26, 27, 28, 29, 30, 31, 44, 45, 46, 47, 48, 49, 62, 63, 64, 65, 66, 67, 80, 81, 82, 83, 84, 85, 98, 99, 100, 101, 102, 103, 116, 117, 118, 119, 120, 121, 134, 135, 136, 137, 138, 139, 152, 153, 154, 155, 156, 157, 170, 171, 172, 173, 174, 175, 188, 189, 190, 191, 192, 193, 206, 207, 208, 209, 210, 211, 224, 225, 226, 227, 228, 229, 242, 243, 244, 245, 246, 247, 260, 261, 262, 263, 264, 265, 278, 279, 280, 281, 282, 283, 296, 297, 298, 299, 300, 301, 314, 315, 316, 317, 318, 319, 332, 333, 334, 335, 336, 337, 350, 351, 352, 353, 354, 355, 368, 369, 370, 371, 372, 373, 386, 387, 388, 389, 390, 391, 404, 405, 406, 407, 408, 409, 422, 423, 424, 425, 426, 427, 440, 441, 442, 443, 444, 445, 458, 459, 460, 461, 462, 463, 476, 477, 478, 479, 480, 481, 494, 495, 496, 497, 498, 499, 512, 513, 514, 515, 516, 517, 530, 531, 532, 533, 534, 535, 548, 549, 550, 551, 552, 553, 566, 567, 568, 569, 570, 571, 584, 585, 586, 587, 588, 589, 602, 603, 604, 605, 606, 607, 620, 621, 622, 623, 624, or 625.

In one embodiment, the variable domain includes a CDR3 to be replaced or lacks a CDR3 encoding region and the at least one donor nucleic acid encodes an amino acid substantially as set out in SEQ ID NO:10, 13, 28, 31, 46, 49, 64, 67, 82, 85, 100, 103, 118, 121, 136, 139, 154, 157, 172, 175, 190, 193, 208, 211, 226, 229, 244, 247, 262, 265, 280, 283, 298, 301, 316, 319, 334, 337, 352, 355, 370, 373, 388, 391, 406, 409, 424, 427, 442, 445, 460, 463, 478, 481, 496, 499, 514, 517, 532, 535, 550, 553, 568, 571, 586, 589, 604, 607, 622, or 625.

In another embodiment, the variable domain includes a CDR1 to be replaced or lacks a CDR1 encoding region and the at least one donor nucleic acid encodes an amino acid sequence substantially as set out in SEQ ID NO:8, 11, 26, 29, 44, 47, 62, 65, 80, 83, 98, 101, 116, 119, 134, 137, 152, 155, 170, 173, 188, 191, 206, 209, 224, 227, 242, 245, 260, 263, 278, 281, 296, 299, 314, 317, 332, 335, 350, 353, 368, 371, 386, 389, 404, 407, 422, 425, 440, 443, 458, 461, 476, 479, 494, 497, 512, 515, 530, 533, 548, 551, 566, 569, 584, 587, 602, 605, 620, or 623.

In another embodiment, the variable domain includes a CDR2 to be replaced or lacks a CDR2 encoding region and the at least one donor nucleic acid encodes an amino acid sequence substantially as set out in SEQ ID NO:9, 12, 27, 30, 45, 48, 63, 66, 81, 84, 99, 102, 117, 120, 135, 138, 153, 156, 171, 174, 189, 192, 207, 210, 225, 228, 243, 246, 261, 264, 279, 282, 297, 300, 315, 318, 333, 336, 351, 354, 369, 372, 387, 390, 405, 408, 423, 426, 441, 444, 459, 462, 477, 480, 495, 498, 513, 516, 531, 534, 549, 552, 567, 570, 585, 588, 603, 606, 621, or 624.

In another embodiment, the variable domain includes a CDR3 to be replaced or lacks a CDR3 encoding region and further comprises a CDR1 to be replaced or lacks a CDR1 encoding region, where the at least one donor nucleic acid encodes an amino acid sequence substantially as set out in Tables 1 or 7.

In another embodiment, the variable domain includes a CDR3 to be replaced or lacks a CDR3 encoding region and further comprises a CDR2 to be replaced or lacks a CDR2 encoding region, where the at least one donor nucleic acid encodes an amino acid sequence substantially as set out in Tables 1 or 7.

In another embodiment, the variable domain includes a CDR3 to be replaced or lacks a CDR3 encoding region and further comprises a CDR1 and a CDR2 to be replaced or lacks a CDR1 and a CDR2 encoding region, where the at least one donor nucleic acid encodes an amino acid sequence substantially as set out in Tables 1 or 7.

Using recombinant DNA methodology, a disclosed CDR sequence may be introduced into a repertoire of V$_H$ or V$_L$ domains lacking the respective CDR (Marks et al. (BioTechnology (1992) 10: 779-783). For example, a primer adjacent to the 5' end of the variable domain and a primer to the third FR can be used to generate a repertoire of variable domain sequences lacking CDR3. This repertoire can be combined with a CDR3 of a disclosed antibody. Using analogous techniques, portions of a disclosed CDR sequence may be shuffled with portions of CDR sequences from other antibodies to provide a repertoire of antigen-binding fragments that bind IL-22. Either repertoire can be expressed in a host system such as phage display (described in WO 92/01047 and its corresponding U.S. Pat. No. 5,969,108) so suitable antigen-binding fragments that bind to IL-22 can be selected.

A further alternative uses random mutagenesis of the disclosed V$_H$ or V$_L$ sequences to generate variant V$_H$ or V$_L$ domains still capable of binding IL-22. A technique using error-prone PCR is described by Gram et al. (Proc. Nat. Acad. Sci. U.S.A. (1992) 89: 3576-3580).

Another method uses direct mutagenesis of the disclosed V$_H$ or V$_L$ sequences. Such techniques are disclosed by Barbas et al. (Proc. Nat. Acad. Sci. U.S.A. (1994) 91: 3809-3813) and Schier et al. (J. Mol. Biol. (1996) 263: 551-567).

A portion of a variable domain will comprise at least one CDR region substantially as set out herein and, optionally, intervening framework regions from the V$_H$ or V$_L$ domains as set out herein. The portion may include the C-terminal half of FR1 and/or the N-terminal half of FR4. Additional residues at the N-terminal or C-terminal end of the variable domain may not be the same residues found in naturally occurring antibodies. For example, construction of antibodies by recombinant DNA techniques often introduces N- or C-terminal residues from its use of linkers. Some linkers may be used to join variable domains to other variable domains (e.g., diabodies), constant domains, or proteinaceous labels.

Although the embodiments illustrated in the Examples comprise a "matching" pair of V$_H$ and V$_L$ domains, a skilled artisan will recognize that alternative embodiments may comprise antigen-binding fragments containing only a single CDR from either V$_L$ or V$_H$ domain. Either one of the single chain specific antigen-binding domains can be used to screen for complementary domains capable of forming a two-domain specific antigen-binding fragment capable of, for example, binding to IL-22. The screening may be accomplished by phage display screening methods using the so-called hierarchical dual combinatorial approach disclosed in WO 92/01047. In this approach, an individual colony containing either a H or L chain clone is used to infect a complete library of clones encoding the other chain (L or H), and the resulting two-chain specific antigen-binding domain is selected in accordance with phage display techniques as described.

In some alternative embodiments, the anti-IL-22 antibodies can be linked to a protein (e.g., albumin) by chemical cross-linking or recombinant methods. The disclosed antibodies may also be linked to a variety of nonproteinaceous polymers (e.g., polyethylene glycol, polypropylene glycol, or polyoxyalkylenes) in manners set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their half-life in blood circulation. Exemplary polymers and attachment methods are shown in U.S. Pat. Nos. 4,766,106; 4,179,337; 4,495,285; and 4,609,546.

The disclosed antibodies can be modified to alter their glycosylation; that is, at least one carbohydrate moiety can be deleted or added to the antibody. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the antibody (see WO 87/05330 and Aplin et al. (1981) *CRC Crit. Rev. Biochem.*, 22: 259-306). Removal of carbohydrate moieties can also be accomplished chemically or enzymatically (see Hakimuddin et al. (1987) *Arch. Biochem. Biophys.*, 259: 52; Edge et al. (1981) *Anal. Biochem.*, 118: 131; Thotakura et al. (1987) *Meth. Enzymol.*, 138: 350).

Methods for altering an antibody constant region are known in the art. Antibodies with altered function (e.g., altered affinity for an effector ligand such as FcR on a cell or the C1 component of complement) can be produced by replacing at least one amino acid residue in the constant portion of the antibody with a different residue (see e.g., EP 388,151 A1, U.S. Pat. No. 5,624,821 and U.S. Pat. No. 5,648,260). Similar types of alterations could be described which if applied to a murine or other species antibody would reduce or eliminate similar functions.

For example, it is possible to alter the affinity of an Fc region of an antibody (e.g., an IgG, such as a human IgG) for FcR (e.g., Fc gamma R1) or C1q. The affinity may be altered by replacing at least one specified residue with at least one residue having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821).

For example, replacing residue 297 (asparagine) with alanine in the IgG constant region significantly inhibits recruitment of effector cells, while only slightly reducing (about three fold weaker) affinity for C1q (see e.g., U.S. Pat. No. 5,624,821). The numbering of the residues in the heavy chain is that of the EU index (see Kabat et al., 1991 supra). This alteration destroys the glycosylation site and it is believed that the presence of carbohydrate is required for Fc receptor binding. Any other substitution at this site that destroys the glycosylation site is believed to cause a similar decrease in lytic activity. Other amino acid substitutions, e.g., changing any one of residues 318 (Glu), 320 (Lys) and 322 (Lys), to Ala, are also known to abolish C1q binding to the Fc region of IgG antibodies (see e.g., U.S. Pat. No. 5,624,821).

Modified antibodies can be produced which have a reduced interaction with an Fc receptor. For example, it has been shown that in human $IgG_3$, which binds to the human Fc gamma R1 receptor, changing Leu 235 to Glu destroys its interaction with the receptor. Mutations on adjacent or close sites in the hinge link region of an antibody (e.g., replacing residues 234, 236 or 237 with Ala) can also be used to affect antibody affinity for the Fc gamma R1 receptor. The numbering of the residues in the heavy chain is based in the EU index (see Kabat et al., 1991 supra).

Additional methods for altering the lytic activity of an antibody, for example, by altering at least one amino acid in the N-terminal region of the CH2 domain, are described in WO 94/29351 by Morgan et al. and U.S. Pat. No. 5,624,821.

The antibodies of this invention may be tagged with a detectable or functional label. These labels include radiolabels (e.g., $^{131}I$ or $^{99}Tc$), enzymatic labels (e.g., horseradish peroxidase or alkaline phosphatase), and other chemical moieties (e.g., biotin).

The invention may also feature an isolated antibody that binds to IL-22, in particular, human IL-22. In certain embodiments, the anti-IL-22 antibody may have at least one of the following characteristics: (1) it is a monoclonal or single specificity antibody; (2) it is a human antibody; (3) it is an in vitro generated antibody; (4) it is an in vivo generated antibody (e.g., transgenic mouse system); (5) it binds to IL-22 with an association constant of at least $10^{12}$ $M^{-1}$; (6) it binds to IL-22 with an association constant of at least $10^{11}$ $M^{-1}$; (7) it binds to IL-22 with an association constant of at least $10^{10}$ $M^{-1}$; (8) it binds to IL-22 with an association constant of at least $10^9$ $M^{-1}$; (9) it binds to IL-22 with an association constant of at least $10^6$ $M^{-1}$; (10) it binds to IL-22 with a dissociation constant of 500 nM or less; (11) it binds to IL-22 with a dissociation constant of 10 nM or less; (12) it binds to IL-22 with a dissociation constant of 150 pM or less; (13) it binds to IL-22 with a dissociation constant of 60 pM or less; (14) it inhibits binding of IL-22 to IL-22R or a receptor complex of IL-22R and IL-10R2 with an $IC_{50}$ of 10 nM or less; (15) it blocks IL-22 mediated proliferation of IL-22 receptor engineered BaF3 cells with an $IC_{50}$ of 1 nM or less in one embodiment, with an $IC_{50}$ of 150 pM or less in another embodiment, with an $IC_{50}$ of 100 pM or less in another embodiment, and with an $IC_{50}$ of 10 pM or less in another embodiment; and (16) it blocks IL-22 mediated GROa secretion from HT29 with an $IC_{50}$ of 1 nM or less in one embodiment, with an $IC_{50}$ of 150 pM or less in another embodiment, and with an $IC_{50}$ of 10 pM or less in another embodiment.

One of skill in the art will appreciate that the modifications described above are not all-exhaustive, and that many other modifications are obvious to a skilled artisan in light of the teachings of the present disclosure.

III. Nucleic Acids, Cloning and Expression Systems

The disclosure provides isolated nucleic acids encoding the disclosed antibodies. The nucleic acids may comprise DNA or RNA, and they may be synthetic (completely or partially) or recombinant (completely or partially). Reference to a nucleotide sequence as set out herein encompasses a DNA molecule with the specified sequence, and encompasses a RNA molecule with the specified sequence in which U is substituted for T.

Also provided are nucleic acids that comprise a coding sequence for one, two, or three CDR's, a $V_H$ domain, a $V_L$ domain, or combinations thereof, as disclosed herein, or a sequence substantially identical thereto (e.g., a sequence at least 85%, 90%, 95%, 96%, 97%, 98%, 99% or higher identical thereto, or which is capable of hybridizing under stringent conditions to the sequences disclosed).

In one embodiment, the isolated nucleic acids have nucleotide sequences encoding heavy chain and light chain variable regions of an anti-IL-22 antibody having at least one CDR chosen from the amino acid sequences of SEQ ID NO: 8-13, 26-31, 44-49, 62-67, 80-85, 98-103, 116-121, 134-139, 152-157, 170-175, 188-193, 206-211, 224-229, 242-247, 260-265, 278-283, 296-301, 314-319, 332-337, 350-355, 368-373, 386-391, 404-409, 422-427, 440-445, 458-463, 476-481, 494-499, 512-517, 530-535, 548-553, 566-571, 584-589, 602-607, or 620-625; or sequence encoding a CDR which differs by one or two amino acids from the sequences described herein.

The nucleic acid can encode only the light chain or the heavy chain variable region, or can also encode an antibody light or heavy chain constant region, operatively linked to the corresponding variable region. In one embodiment, the light chain variable region is linked to a constant region chosen from a kappa or a lambda constant region. The light chain constant region may also be a human kappa or lambda type. In another embodiment, the heavy chain variable region is linked to a heavy chain constant region of an antibody isotype chosen from IgG (e.g., $IgG_1$, $IgG_2$, $IgG_3$, $IgG_4$), IgM, $IgA_1$, $IgA_2$, IgD, and IgE. The heavy chain constant region may be an IgG (e.g., an $IgG_1$) isotype.

The nucleic acid compositions of the present invention, while often in the native sequence (of cDNA or genomic DNA or mixtures thereof) except for modified restriction sites and the like, may be mutated in accordance with standard techniques to provide gene sequences. For coding sequences, these mutations, may affect amino acid sequence as desired. In particular, nucleotide sequences substantially identical to or derived from native V, D, J, constant, switches and other such sequences described herein are contemplated (where "derived" indicates that a sequence is identical or modified from another sequence).

In one embodiment, the nucleic acid differs (e.g., differs by substitution, insertion, or deletion) from that of the sequences provided (e.g., as follows: by at least one but less than 10, 20, 30, or 40 nucleotides; at least one but less than 1%, 5%, 10% or 20% of the nucleotides in the subject nucleic acid). If necessary for this analysis the sequences should be aligned for maximum homology. "Looped" out sequences from deletions or insertions, or mismatches, are considered differences. The difference may be at a nucleotide(s) encoding a non-essential residue(s), or the difference may be a conservative substitution(s).

The disclosure also provides nucleic acid constructs in the form of plasmids, vectors, transcription or expression cassettes, which comprise at least one nucleic acid as described herein.

The disclosure further provides a host cell that comprises at least one nucleic acid construct described herein.

Also provided are the methods of making the encoded protein(s) from the nucleic acid(s) comprising sequence described herein. The method comprises culturing host cells under appropriate conditions so they express the protein from the nucleic acid. Following expression and production, the $V_H$ or $V_L$ domain, or specific binding member may be isolated and/or purified using any suitable technique, then used as appropriate. The method can also include the steps of fusing a nucleic acid encoding a scFv with nucleic acids encoding a Fc portion of an antibody and expressing the fused nucleic acid in a cell. The method can also include a step of germlining.

Antigen-binding fragments, $V_H$ and/or $V_L$ domains, and encoding nucleic acid molecules and vectors may be isolated and/or purified from their natural environment, in substantially pure or homogenous form, or, in the case of nucleic acid, free or substantially free of nucleic acid or genes of origin other than the sequence encoding a polypeptide with the require function.

Systems for cloning and expressing polypeptides in a variety of host cells are known in the art. Cells suitable for producing antibodies are described in, for example, Fernandez et al. (1999) Gene Expression Systems, Academic Press, eds. In brief, suitable host cells include mammalian cells, insect cells, plant cells, yeast cells, or prokaryotic cells, e.g., *E. coli*. Mammalian cells available in the art for heterologous polypeptide expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cell. In one embodiment, the GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, and 356A11 antibodies are expressed in HEK293 or CHO cells. In another embodiment, a selection of antibodies chosen from 365A11, 354A08, 087B03, and 368D04 are, expressed in HEK293 or CHO cells. In other embodiments, the nucleic acids encoding the antibodies of the invention are placed under the control of a tissue-specific promoter (e.g., a mammary specific promoter) and the antibodies are produced in transgenic animals. For example, the antibodies are secreted into the milk of the transgenic animal, such as a transgenic cow, pig, horse, sheep, goat or rodent.

Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone. For details, see Sambrook et al., Molecular Cloning: A Laboratory Manual, 2nd ed., Cold Spring Harbor Laboratory Press (1989). Many established techniques used with vectors, including the manipulation, preparation, mutagenesis, sequencing, and transfection of DNA, are described in Current Protocols in Molecular Biology, Second Edition, Ausubel et al. eds., John Wiley & Sons (1992).

A further aspect of the disclosure provides a method of introducing the nucleic acid into a host cell. For eukaryotic cells, suitable transfection techniques may include calcium phosphate, DEAE-Dextran, electroporation, liposome-mediated transfection, and transduction using retrovirus or other viruses, e.g., vaccinia or baculovirus. For bacterial cells, suitable techniques may include calcium chloride transformation, electroporation, and transfection using bacteriophage. DNA introduction may be followed by a selection method (e.g., drug resistance) to select cells that contain the nucleic acid.

IV. Uses of Anti-IL-22 Antibodies

Anti-IL-22 antibodies that act as antagonists to IL-22 can be used to regulate at least one IL-22-mediated immune response, such as acting on epithelial cells in solid tissue and indirectly modulating downstream immune responses, such as blocking expansion of T cell subsets, including, for example, $T_H17$ T cells. In one embodiment, antibodies of the invention are used in a method for regulating an immune response, the method comprising contacting IL-22 with an antibody of the invention thereby regulating the immune response. In one embodiment, the immune response comprises cell proliferation, cytolytic activity, cytokine secretion, or chemokine secretion.

Accordingly, the antibodies of the invention can be used to directly or indirectly inhibit the activity (e.g., proliferation, differentiation, and/or survival) of an immune or hematopoietic cell (e.g., a cell of myeloid, lymphoid, or erythroid lineage, or precursor cells thereof), and, thus, can be used to treat a variety of immune disorders and hyperproliferative disorders. Non-limiting examples of immune disorders that can be treated include, but are not limited to, autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy. In one embodiment, the IL-22-associated disorder is, an arthritic disorder, e.g., a disorder chosen from one or more of rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); or an inflammatory condition of, e.g., the skin (e.g., psoriasis), cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD; acute inflammatory conditions, e.g., endotoxemia, sepsis and septicaemia, toxic shock syndrome and infectious disease; multiple organ failure; respiratory disease (ARD); amyloidosis; nephropathies such as glomerulosclerosis, membranous neuropathy, renal arteriosclerosis, glomerulonephritis, fibroproliferative diseases of the kidney, as well as other kidney disfunctions and renal tumors. Because of IL-22's effects on epithelia, anti-IL-22 antibodies can be used to treat epithelial cancers, e.g., carcinoma, melanoma and others. For a description of a rationale for IL-22 inhibition in these and other disease states see WO 03/083062 (pages 58-75).

Multiple sclerosis is a central nervous system disease that is characterized by inflammation and loss of myelin sheaths—the fatty material that insulates nerves and is needed for proper nerve function. Inflammation that results from an immune response that is dependent on IL-22 can be treated with the antibodies and compositions of this invention. In the experimental autoimmune encephalitis (EAE) mouse model for multiple sclerosis (Tuohy et al. (J. Immunol. (1988) 141: 1126-1130), Sobel et al. (J. Immunol. (1984) 132: 2393-2401), and Traugott (Cell Immunol. (1989) 119: 114-129), treatment of mice with GIL01, GIL16, GIL45, GIL60, GIL68, GIL92, 097D09, 062A09, 062G05, 087B03, 367D04, 368D04, 166B06, 166G05, 375G06, 376B10, 354A08, 355B06, 355E04, or 356A11 injections prior (and continuously) to EAE induction may profoundly delay the onset of the disease. This can serve as a model for confirming use of the antibody of the invention. The antibodies of this invention may similarly be used to treat multiple sclerosis in humans.

Arthritis is a disease characterized by inflammation in the joints. Rheumatoid Arthritis (RA) is the most frequent form of arthritis, involving inflammation of connective tissue and the synovial membrane, a membrane that lines the joint. The inflamed synovial membrane often infiltrates the joint and damages joint cartilage and bone. IL-22 and IL-22R protein and/or transcript is associated with both human diseases. In RA synovial biopsies, IL-22 protein is detected in vimentin$^+$ synovial fibroblasts and some CD68$^+$ macrophages while IL-22R is detected in synovial fibroblasts. Treatment of synovial fibroblasts with IL-22 induces the production of monocyte chemoattractant protein-1, MCP-1, as well as general metabolic activity (Ikeuchi, H., et al. (2005) *Arthritis Rheum.* 52:1037-46). Inhibitors of IL-22 ameliorate symptoms of rheumatoid arthritis (WO 2005/000897 A2; U.S. Pat. No. 6,939,545). Increased secretion of inflammatory cytokines and chemokines, and more importantly, increased disease resulting from immune responses that are dependent on IL-22 may be treated with the antibodies of this invention. Similarly, the antibodies and compositions of this invention may be used to treat RA or other arthritic diseases in humans.

Transplant rejection is the immunological phenomenon where tissues from a donor are specifically "attacked" by immune cells of the host. The principle "attacking" cells are T cells, whose T cell receptors recognize the donor's MHC molecules as "foreign." This recognition activates the T cells, which proliferate and secrete a variety of cytokines and cytolytic proteins that ultimately destroy the transplant. MLR and transplantation models have been described by Current Protocols in Immunology, Second Edition, Coligan et al. eds., John Wiley & Sons, 1994; Kasaian et al. (Immunity (2002) 16: 559-569); Fulmer et al. (Am. J. Anat. (1963) 113: 273-285), and Lenschow et al. (Science (1992) 257: 789-792). The antibodies and compositions of this invention may be used to reduce the MLR and treat transplant rejection and related diseases (e.g., graft versus host disease) in humans that are dependent on IL-22.

The antibodies of this invention can also be used to treat hyperproliferative disorders associated with aberrant activity of IL-22-responsive cells and IL-22R/IL-10R2-responsive cells by administering the antibodies in an amount sufficient to inhibit or reduce hyperproliferation of IL-22 and/or IL-22R and/or IL-10R2-responsive cells in a subject and allowing the antibodies to treat or prevent the disorder. IL-22 and IL-22R expression is constitutive on epithelial cells in a number of tissues including, but not limited to, pancreas, lung, skin, gut, liver, kidney (Kotenko, S. V. et al. (2001) *J. Biol. Chem.* 276:2725-32; Xie, M. H. et al. (2000) *J. Biol. Chem.* 275: 31335-9; Wolk, K. et al. (2004) *Immunity* 21:241-54). In addition, IL-22 receptor complex is also expressed on the surface of fibroblasts from the diseased joint and normal gut (Ikeuchi, H. et al. (2005) *Arthritis Rheum.* 52:1037-46; Andoh, A. et al. (2005) *Gastroenterology* 129:969-84). Neoplastic derivatives of these cell types may be hyper responsive to IL-22, modulating these cells ability to survive in the organism. Hence antibodies to IL-22 may be used to inhibit the progression of such neoplasms, e.g. squamous cell carcinomas, basal cell carcinomas, transitional cell papillomas and carcinomas, adenomas, adenocarcinoma, linitis plastica, insulinoma, glucagonoma, gastrinoma, vipoma, cholangiocarcinoma, hepatocellular carcinoma, adenoid cyctic carcinoma, carcinoid tumor of appendix, prolactinoma, oncocytoma, hurthle cell adenoma, renal cell carcinoma, Grawitz tumor, multiple endocrine adenomas, endometroid adenoma, adnexal and skin appendage neoplasms, mucoepidermoid neoplams, cystic, mucinous and serous neoplasms, cystadenoma, pseudomyxoma peritonei, ductal, lobular and medullary neoplasms, acinar cell neoplasns, complex epithelial neoplasms, Warthin's tumor, thymoma, specialized gonadal neoplasms, sex cord-stromal tumor, thecoma, granulosa cell tumor, arrhenoblastoma, sertoli-leydig cell tumor, paraganglioma, pheochromocytoma, glomus tumor, malanocytic nevus, malignant melanoma, melanoma, nodular melanoma, dysplastic nevus, lentigo maligna, superficial spreading melanoma, or acral lentiginous melanoma. While the IL-22 receptor is not detected on ex vivo naïve or activated immune cells, dysregulation of the receptor might make such derivative neoplastic cells responsive to IL-22 and thus inhibition by an antibody to IL-22.

In another aspect, the invention features a method of decreasing, inhibiting or reducing an acute phase response in a subject. The method includes administering to the subject an anti-IL-22 antibody or fragment thereof as described herein, in an amount sufficient to decrease, inhibit or reduce the acute phase response in the subject. In one embodiment, the subject is a mammal, e.g., a human suffering from an IL-22-associated disorder as described herein, including, e.g., respiratory disorders, inflammatory disorders and autoimmune disorders. In one embodiment, the IL-22 binding agent is administered locally, e.g., topically, subcutaneously, or other administrations that are not in the general circulation.

IL-22 is believed to exert its inflammatory effects locally, e.g. by acting (e.g., directly acting) as a modular or a regulator of tissue inflammation as opposed to direct systemic effects. Accordingly, inhibition of IL-22 activity using, e.g. an anti-IL-22 antibody of the present invention may provide a more effective (e.g., less toxic) tissue-specific, anti-inflammatory agent than systemic anti-inflammatory modalities. Furthermore, inhibition of local IL-22 using, e.g., an anti-IL-22 antibody or fragment thereof described herein, may provide a useful candidate for combination with systemic anti-inflammatory modalities.

V. Combination Therapy

In one embodiment, a pharmaceutical composition comprising at least one anti-IL-22 antibody and at least one therapeutic agent is administered in combination therapy. The therapy is useful for treating pathological conditions or disorders, such as immune and inflammatory disorders. The term "in combination" in this context means that the antibody composition and the therapeutic agent are given substantially contemporaneously, either simultaneously or sequentially. In one embodiment, if given sequentially, at the onset of administration of the second compound, the first of the two compounds is still detectable at effective concentrations at the site of treatment. In another embodiment, if given sequentially, at the onset of administration of the second compound, the first of the two compounds is not detectable at effective concentrations at the site of treatment.

For example, the combination therapy can include at least one anti-IL-22 antibody co-formulated with, and/or co-administered with, at least one additional therapeutic agent. The additional agents may include at least one cytokine inhibitor, growth factor inhibitor, immunosuppressant, anti-inflammatory agent, metabolic inhibitor, enzyme inhibitor, cytotoxic agent, and cytostatic agent, as described in more detail below.

In one embodiment, the additional agent is a standard treatment for arthritis, including, but not limited to, non-steroidal anti-inflammatory agents (NSAIDs); corticosteroids, including prednisolone, prednisone, cortisone, and triamcinolone; and disease modifying anti-rheumatic drugs (DMARDs), such as methotrexate, hydroxychloroquine (Plaquenil) and sulfasalazine, leflunomide (Araya), tumor necrosis factor inhibitors, including etanercept (Enbrel), infliximab (Remicade) (with or without methotrexate), and adalimumab (Humira), anti-CD20 antibody (e.g., Rituxan), soluble interleukin-1 receptor, such as anakinra (Kineret), gold, minocycline (Minocin), penicillamine, and cytotoxic agents, including azathioprine, cyclophosphamide, and cyclosporine. Such combination therapies may advantageously utilize lower dosages of the administered therapeutic agents, thus avoiding possible toxicities or complications associated with the various monotherapies. Moreover, the additional therapeutic agents disclosed herein act on pathways in addition to or that differ from the IL-22/IL-22R/IL-10R2 pathway, and thus are expected to enhance and/or synergize with the effects of the anti-IL-22 antibodies.

Therapeutic agents used in combination with anti-IL-22 antibodies may be those agents that interfere at different stages in the autoimmune and subsequent inflammatory response. In one embodiment, at least one anti-IL-22 antibody described herein may be co-formulated with, and/or co-administered with, at least one cytokine and/or growth factor antagonist. The antagonists may include soluble receptors, peptide inhibitors, small molecules, ligand fusions, antibodies and binding fragments thereof (that bind cytokines or growth factors or their receptors or other cell surface molecules), and "anti-inflammatory cytokines" and agonists thereof.

Non-limiting examples of the agents that can be used in combination with the anti-IL-22 antibodies described herein, include, but are not limited to, antagonists of at least one interleukin (e.g., IL-1, IL-2, IL-6, IL-7, IL-8, IL-12 (or one of its subunits p35 or p40), IL-13, IL-15, IL-16, IL-17A-F (including heterodimers thereof, for example, IL-17A/IL-17F heterodimer), IL-18, IL-19, IL-20, IL-21, and IL-23 (or one of its subunits p19 or p40); cytokine (e.g., TNFα, LT, EMAP-II, and GM-CSF); and growth factor (e.g., FGF and PDGF). The agents may also include, but not limited to, antagonists of at least one receptor for an interleukin, cytokine, and growth factor. Anti-IL-22 antibodies can also be combined with inhibitors (e.g., antibodies or binding fragments thereof) to cell surface molecules such as CD2, CD3, CD4, CD8, CD20 (e.g. Rituxan), CD25, CD28, CD30, CD40, CD45, CD69, CD80 (B7.1), CD86 (B7.2), CD90, or their ligands (e.g., CD154 (gp39, CD40L)), or LFA-1/ICAM-1 and VLA-4NCAM-1 (Yusuf-Makagiansar et al. (2002) *Med Res Rev* 22(2):146-67)). In certain embodiments, antagonists that can be used in combination with anti-IL-22 antibodies described herein may include antagonists of IL-1, IL-12 (or one of its subunits p35 or p40), TNFα, IL-15, IL-17A-F (including heterodimers thereof, for example, IL-17A/IL-17F heterodimer), IL-18, IL-19, IL-20, IL-21, and IL-23 (or one of its subunits p19 or p40), and their receptors.

Examples of those agents include IL-12 antagonists (such as antibodies that bind IL-12 (see e.g., WO 00/56772) or one of its subunits p35 or p40); IL-12 receptor inhibitors (such as antibodies to the IL-12 receptor); and soluble IL-12 receptor and fragments thereof. Examples of IL-15 antagonists include antibodies against IL-15 or its receptor, soluble fragments of the IL-15 receptor, and IL-15-binding proteins. Examples of IL-18 antagonists include antibodies to IL-18, soluble fragments of the IL-18 receptor, and IL-18 binding proteins (IL-18BP, Mallet et al. (2001) Circ. Res. 28). Examples of IL-1 antagonists include Interleukin-1-Converting Enzyme (ICE) inhibitors (such as Vx740), IL-1 antagonists (e.g., IL-1 RA (ANIKINRA (or Kineret), AMGEN)), sIL-1RII (Immunex), and anti-IL-1 receptor antibodies.

In one embodiment, the combination therapy includes at least one anti-IL-22 antibody co-formulated with, and/or co-administered with an antagonist, such as an antibody or antigen binding fragment thereof or a soluble receptor, of at least one of IL-17A, IL-17F, IL-17A/IL-17F heterodimer, or IL-23 (or one of its subunits p19 or p40).

Examples of TNF antagonists include antibodies to TNF (e.g., human TNFα), such as D2E7 (human anti-TNFα antibody, U.S. Pat. No. 6,258,562, Humira™, BASF); CDP-571/CDP-870/BAY-10-3356 (humanized anti-TNFα antibodies, Celltech/Pharmacia); cA2 (chimeric anti-TNFα antibody, Remicade™, Centocor); and anti-TNF antibody fragments (e.g., CPD870). Other examples include soluble TNF receptor (e.g., human p55 or p75) fragments and derivatives, such as p55 kdTNFR-IgG (55 kD TNF receptor-IgG fusion protein, Lenercept™) and 75 kdTNFR-IgG (75 kD TNF receptor-IgG fusion protein, Enbrel™, Immunex, see, e.g., Arthritis & Rheumatism (1994) Vol. 37, S295; J. Invest. Med. (1996) Vol. 44, 235A). Further examples include enzyme antagonists (e.g., TNFα converting enzyme inhibitors (TACE) such as alpha-sulfonyl hydroxamic acid derivative (WO 01/55112) or N-hydroxyformamide inhibitor (GW 3333, -005, or -022)) and TNF-bp/s-TNFR (soluble TNF binding protein, see e.g., Arthritis & Rheumatism (1996) Vol. 39, No. 9 (supplement), S284; and Am. J. Physiol. Heart Circ. Physiol. (1995) Vol. 268, pp. 37-42). TNF antagonists may be soluble TNF receptor (e.g., human p55 or p75) fragments and derivatives, such as 75 kdTNFR-IgG; and TNFα converting enzyme (TACE) inhibitors.

In other embodiments, the anti-IL-22 antibodies described herein can be administered in combination with at least one of the following: IL-13 antagonists, such as soluble IL-13 receptors and/or anti-IL-13 antibodies; and IL-2 antagonists, such as IL-2 fusion proteins (e.g., DAB 486-IL-2 and/or DAB 389-IL-2, Seragen, see e.g., Arthritis & Rheumatism (1993) Vol. 36, 1223) and anti-IL-2R antibodies (e.g., anti-Tac (humanized antibody, Protein Design Labs, see Cancer Res. 1990 Mar. 1; 50(5):1495-502)). Another combination includes anti-IL-22 antibodies in combination with non-depleting anti-CD4 inhibitors such as IDEC-CE9.1/SB 210396 (anti-CD4 antibody, IDEC/SmithKline). Yet other combinations include anti-IL-22 antibodies with antagonists (such as antibodies, soluble receptors, or antagonistic ligands) of costimulatory molecules, such as CD80 (B7.1) and CD86 (B7.2); ICOSL, ICOS, CD28, and CTLA4 (e.g., CTLA4-Ig (atabacept)); P-selectin glycoprotein ligand (PSGL); and anti-inflammatory cytokines and agonists thereof (e.g., antibodies). The anti-inflammatory cytokines may include IL-4 (DNAX/Schering); IL-10 (SCH 52000, recombinant IL-10, DNAX/Schering); IL-13; and TGF.

In other embodiments, at least one anti-IL-22 antibody can be co-formulated with, and/or co-administered with, at least one anti-inflammatory drug, immunosuppressant, metabolic inhibitor, and enzymatic inhibitor. Non-limiting examples of the drugs or inhibitors that can be used in combination with the IL-22 antagonists described herein, include, but are not limited to, at least one of: non-steroidal anti-inflammatory drug (NSAID) (such as ibuprofen, Tenidap (see e.g., Arthritis & Rheumatism (1996) Vol. 39, No. 9 (supplement), S280)), Naproxen (see e.g., Neuro Report (1996) Vol. 7, pp. 1209-1213), Meloxicam, Piroxicam, Diclofenac, and Indomethacin); Sulfasalazine (see e.g., Arthritis & Rheumatism (1996) Vol. 39, No. 9 (supplement), S281); corticosteroid (such as prednisolone); cytokine suppressive anti-inflammatory drug (CSAID); and an inhibitor of nucleotide biosynthesis (such as an inhibitor of purine biosynthesis (e.g., folate antagonist such as methotrexate) and an inhibitor of pyrimidine biosynthesis (e.g., a dihydroorotate dehydrogenase (DHODH) inhibitor such as leflunomide (see e.g., *Arthritis & Rheumatism* (1996) Vol. 39, No. 9 (supplement), S131; Inflammation Research (1996) Vol. 45, pp. 103-107)). Therapeutic agents for use in combination with IL-22/IL-22R or IL-22/IL-10R2 antagonists may include NSAIDs, CSAIDs, DHODH inhibitors (such as leflunomide), and folate antagonists (such as methotrexate).

Examples of additional inhibitors include at least one of: corticosteroid (oral, inhaled and local injection); immunosuppressant (such as cyclosporin and tacrolimus (FK-506)); a mTOR inhibitor (such as sirolimus (rapamycin) or a rapamycin derivative (e.g., ester rapamycin derivative such as CCI-779 (Elit. L. (2002) *Current Opinion Investig. Drugs* 3(8): 1249-53; Huang, S. et al. (2002) *Current Opinion Investig. Drugs* 3(2):295-304))); an agent which interferes with the signaling of proinflammatory cytokines such as TNFα and IL-1 (e.g., IRAK, NIK, IKK, p38 or a MAP kinase inhibitor); a COX2 inhibitor (e.g., celecoxib and variants thereof (MK-966), see e.g., Arthritis & Rheumatism (1996) Vol. 39, No. 9 (supplement), S81); a phosphodiesterase inhibitor (such as R973401, see e.g., Arthritis & Rheumatism (1996) Vol. 39, No. 9 (supplement), S282)); a phospholipase inhibitor (e.g., an inhibitor of cytosolic phospholipase 2 (cPLA2) such as trifluoromethyl ketone analogs (U.S. Pat. No. 6,350,892)); an inhibitor of vascular endothelial cell growth factor (VEGF); an inhibitor of the VEGF receptor; and an inhibitor of angiogenesis. Therapeutic agents for use in combination with anti-IL-22 antibodies may include immunosuppresants (such as cyclosporine and tacrolimus (FK-506)); and mTOR inhibitors (such as sirolimus (rapamycin) or rapamycin derivatives (e.g., ester rapamycin derivatives such as CCI-779)); COX2 inhibitors (such as celecoxib and variants thereof); and phospholipase inhibitors (such as inhibitors of cytosolic phospholipase 2 (cPLA2) (e.g., trifluoromethyl ketone analogs)).

Examples of therapeutic agents that can be co-administered and/or co-formulated with at least one anti-IL-22 antibody, include, but are not limited to, at least one of: TNF antagonists (such as anti-TNF antibodies); soluble fragments of TNF receptors (e.g., human p55 and p75) and derivatives thereof (such as p55 kdTNFR-IgG (55 kD TNF receptor-IgG fusion protein, Lenercept™) and 75 kdTNFR-IgG (75 kD TNF receptor-IgG fusion protein, Enbrel™)); TNF enzyme antagonists (such as TACE inhibitors); antagonists of IL-12 (or one of its subunits p35 or p40), IL-15, IL-17A-F (including heterodimers thereof, for example, IL-17A/IL-17F heterodimer), IL-18, IL-19, IL-20, IL-21, IL-22, and IL-23 (or one of its subunits p19 or p40); T cell and B cell depleting agents (such as anti-CD4 or anti-CD22 antibodies); small molecule inhibitors (such as methotrexate and leflunomide); sirolimus (rapamycin) and analogs thereof (such as CCI-779); Cox-2 and cPLA2 inhibitors; p38, TPL-2, Mk-2 and NFκB inhibitors; RAGE and soluble RAGE; P-selectin and PSGL-1 inhibitors (such as antibodies to and small molecule inhibitors); and estrogen receptor beta (ERB) agonists, and ERB-NFkb antagonists. Therapeutic agents that can be co-administered and/or co-formulated with at least one anti-IL-22 antibody may include at least one of: a soluble fragment of a TNF receptor (e.g., human p55 or p75) such as 75 kdTNFR-IgG (75 kD TNF receptor-IgG fusion protein, Enbrel™); methotrexate; leflunomide; and sirolimus (rapamycin) and analogs thereof (such as CCI-779).

The anti-IL-22 antibodies disclosed herein can be used in combination with other therapeutic agents to treat specific immune disorders as discussed in further detail below.

Non-limiting examples of agents for treating arthritic disorders (e.g., rheumatoid arthritis, inflammatory arthritis, rheumatoid arthritis, juvenile rheumatoid arthritis, osteoarthritis and psoriatic arthritis), with which an anti-IL-22 antibody can be combined include at least one of the following: TNF antagonists (such as anti-TNF antibodies); soluble fragments of TNF receptors (e.g., human p55 and p75) and derivatives thereof (such as p55 kdTNFR-IgG (55 kD TNF receptor-IgG fusion protein, Lenercept™) and 75 kdTNFR-IgG (75 kD TNF receptor-IgG fusion protein, Enbrel™)); TNF enzyme antagonists (such as TACE inhibitors); antagonists of IL-12 (or one of its subunits p35 or p40), IL-15, IL-17A-F (including heterodimers thereof, for example, IL-17A/IL-17F heterodimer), IL-18, IL-19, IL-20, IL-21, IL-23 (or one of its subunits p19 or p40), and IL-24; T cell and B cell depleting agents (such as anti-CD4, anti-CD20, or anti-CD22 antibodies); small molecule inhibitors (such as methotrexate and leflunomide); sirolimus (rapamycin) and analogs thereof (e.g., CCI-779); Cox-2 and cPLA2 inhibitors; NSAIDs; p38, TPL-2, Mk-2, and NFκB inhibitors; RAGE or soluble RAGE; P-selectin or PSGL-1 inhibitors (such as small molecule inhibitors and antibodies to); estrogen receptor beta (ERB) agonists, and ERB-NFκB antagonists. Therapeutic agents that can be co-administered and/or co-formulated with at least one IL-22/IL-22R/IL-10R2 antagonist may include at least one of: a soluble fragment of a TNF receptor (e.g., human p55 or p75) such as 75 kdTNFR-IgG (75 kD TNF receptor-IgG fusion protein, Enbrel™); methotrexate; leflunomide; and sirolimus (rapamycin) or an analog thereof (e.g., CCI-779).

Non-limiting examples of agents for treating multiple sclerosis with which anti-IL-22 antibody can be combined include interferon-β for example, IFNβ-1a and IFNβ-1b), copaxone, corticosteroids, IL-1 inhibitors, TNF inhibitors, antibodies to CD40 ligand, antibodies to CD80, and IL-12 antagonists, including antibodies that bind IL-12 (or one of its subunits p35 or p40).

Non-limiting examples of agents for treating inflammatory bowel disease or Crohn's disease with which an anti-IL-22 antibody can be combined include budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13, and/or TGFβ or agonists thereof (e.g., agonist antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

In other embodiments, an anti-IL-22 antibody can be used in combination with at least one antibody directed at other targets involved in regulating immune responses, e.g., transplant rejection or graft versus host disease. Non-limiting examples of agents for treating immune responses with which an IL-22/IL-22R/IL10R2 antagonist of the invention can be combined include the following: antibodies against cell surface molecules, including but not limited to CD25 (IL-2 receptor α), CD11a (LFA-1), CD54 (ICAM-1), CD4, CD45, CD28/CTLA4, CD80 (B7-1), CD86 (B7-2), or combinations thereof. In another embodiment, an anti-IL-22 antibody is used in combination with at least one general immunosuppressive agent, such as cyclosporin A or FK506.

Another aspect of the present invention accordingly relates to kits for carrying out the combined administration of the anti-IL-22 antibodies with other therapeutic agents. In one embodiment, the kit comprises at least one anti-IL-22 antibody formulated in a pharmaceutical carrier, and at least one therapeutic agent, formulated as appropriate in one or more separate pharmaceutical preparations.

VI. Diagnostic Uses

The antibodies may also be used to detect the presence of IL-22 in biological samples. By correlating the presence or level of these proteins with a medical condition, one of skill in the art can diagnose the associated medical condition. For example, IL-22 induces changes associated with those caused by inflammatory cytokines (such as IL-1 and TNFα), and inhibitors of IL-22 ameliorate symptoms of rheumatoid arthritis (WO 2005/000897 A2). Illustrative medical conditions that may be diagnosed by the antibodies of this invention include multiple sclerosis, rheumatoid arthritis, psoriasis, inflammatory bowel disease, pancreatitis, and transplant rejection.

Antibody-based detection methods are well known in the art, and include ELISA, radioimmunoassays, immunoblots, Western blots, flow cytometry, immunofluorescence, immunoprecipitation, and other related techniques. The antibodies may be provided in a diagnostic kit that incorporates at least one of these procedures to detect IL-22. The kit may contain other components, packaging, instructions, or other material to aid the detection of the protein and use of the kit.

Antibodies may be modified with detectable markers, including ligand groups (e.g., biotin), fluorophores and chromophores, radioisotopes, electron-dense reagents, or enzymes. Enzymes are detected by their activity. For example, horseradish peroxidase is detected by its ability to convert tetramethylbenzidine (TMB) to a blue pigment, quantifiable with a spectrophotometer. Other suitable binding partners include biotin and avidin, IgG and protein A, and other receptor-ligand pairs known in the art.

Antibodies can also be functionally linked (e.g., by chemical coupling, genetic fusion, non-covalent association or otherwise) to at least one other molecular entity, such as another antibody (e.g., a bispecific or a multispecific antibody), toxins, radioisotopes, cytotoxic or cytostatic agents, among others. Other permutations and possibilities are apparent to those of ordinary skill in the art, and they are considered equivalents within the scope of this invention.

VII. Pharmaceutical Compositions and Methods of Administration

Certain embodiments of the invention include compositions comprising the disclosed antibodies. The compositions may be suitable for pharmaceutical use and administration to patients. The compositions comprise an antibody of the present invention and a pharmaceutical excipient. As used herein, "pharmaceutical excipient" includes solvents, dispersion media, coatings, antibacterial and antifungal agents, isotonic and absorption delaying agents, etc., that are compatible with pharmaceutical administration. Use of these agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

A pharmaceutical composition of the invention is formulated to be compatible with its intended route of administration. Methods to accomplish the administration are known to those of ordinary skill in the art. Pharmaceutical compositions may be topically or orally administered, or capable of transmission across mucous membranes. Examples of administration of a pharmaceutical composition include oral ingestion or inhalation. Administration may also be intravenous, intraperitoneal, intramuscular, intracavity, subcutaneous, cutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous administration include a carrier such as physiological saline, bacteriostatic water, Cremophor EL™ (BASF, Parsippany, N.J.), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminum monostearate and gelatin.

Oral compositions include an inert diluent or edible carrier. The composition can be enclosed in gelatin or compressed into tablets. For the purpose of oral administration, the antibodies can be incorporated with excipients and placed in tablets, troches, or capsules. Pharmaceutically compatible binding agents or adjuvant materials can be included in the composition. The tablets, troches, and capsules, may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; or (6) a sweetening agent or a flavoring agent.

The composition may also be administered by a transmucosal or transdermal route. For example, antibodies that comprise a Fc portion may be capable of crossing mucous membranes in the intestine, mouth, or lungs (via Fc receptors). Transmucosal administration can be accomplished through the use of lozenges, nasal sprays, inhalers, or suppositories. Transdermal administration can also be accomplished through the use of a composition containing ointments, salves, gels, or creams known in the art. For transmucosal or transdermal administration, penetrants appropriate to the barrier to be permeated are used. For administration by inhalation, the antibodies are delivered in an aerosol spray from a pressured container or dispenser, which contains a propellant (e.g., liquid or gas) or a nebulizer.

In certain embodiments, the antibodies of this invention are prepared with carriers to protect the antibodies against rapid elimination from the body. Biodegradable polymers (e.g., ethylene vinyl acetate, polyanhydrides, polyglycolic acid, collagen, polyorthoesters, polylactic acid) are often used. Methods for the preparation of such formulations are known by those skilled in the art. Liposomal suspensions can be used as pharmaceutically acceptable carriers too. The liposomes can be prepared according to established methods known in the art (U.S. Pat. No. 4,522,811).

The antibodies or antibody compositions of the invention are administered in therapeutically effective amounts as described. Therapeutically effective amounts may vary with the subject's age, condition, sex, and severity of medical condition. Appropriate dosage may be determined by a physician based on clinical indications. The antibodies or compositions may be given as a bolus dose to maximize the circulating levels of antibodies for the greatest length of time. Continuous infusion may also be used after the bolus dose.

As used herein, the term "subject" is intended to include human and non-human animals. Subjects may include a human patient having a disorder characterized by cells that express IL-22, e.g., a cancer cell or an immune cell. The term "non-human animals" of the invention includes all vertebrates, such as non-human primates, sheep, dogs, cows, chickens, amphibians, reptiles, etc.

Examples of dosage ranges that can be administered to a subject can be chosen from: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject characteristics. Dosages can also be administered via continuous infusion (such as through a pump). The administered dose may also depend on the route of administration. For example, subcutaneous administration may require a higher dosage than intravenous administration.

In certain circumstances, it may be advantageous to formulate compositions in dosage unit form for ease of administration and uniformity of dosage. Dosage unit form as used herein refers to physically discrete units suited for the patient. Each dosage unit contains a predetermined quantity of antibody calculated to produce a therapeutic effect in association with the carrier. The dosage unit depends on the characteristics of the antibodies and the particular therapeutic effect to be achieved.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Antibodies that exhibit large therapeutic indices may be less toxic and/or more therapeutically effective.

The data obtained from the cell culture assays and animal studies can be used to formulate a dosage range in humans. The dosage of these compounds may lie within the range of circulating antibody concentrations in the blood, that includes an $ED_{50}$ with little or no toxicity. The dosage may vary within this range depending upon the dosage composition form employed and the route of administration. For any antibody used in the present invention, the therapeutically effective dose can be estimated initially using cell culture assays. A dose may be formulated in animal models to achieve a circulating plasma concentration range that includes the $IC_{50}$ (i.e., the concentration of antibody which achieves a half-maximal inhibition of symptoms). The effects of any particular dosage can be monitored by a suitable bioassay. Examples of suitable bioassays include DNA replication assays, transcription-based assays, IL-22/IL-22R binding assays, IL-22/IL-10R2 binding assays, IL-22/IL-22R/IL-10R2, and other immunological assays.

EXAMPLES

Example 1

Selection of Anti-IL-22 scFv's

Selection of Parents GIL01 and GIL68

GIL01 and GIL68 were isolated from scFv libraries by soluble selection on IL-22. Soluble selections were carried out using biotinylated IL-22 with an N-terminal His/FLAG tagged protein (bio.IL-22 H/F). Bio.IL-22 H/F was initially used at a concentration of 100 nM. An scFv phagemid library, which is an expanded version of the $1.38 \times 10^{10}$ library described (Vaughan et al., 1996), was used to select antibodies specific for IL-22. Purified scFv phage ($10^{12}$ transducing units (tu)) were blocked for 30 minutes in 100 µl 3% MPBS (3% milk powder in PBS), then bio.IL-22 H/F was added and incubated at room temperature for 1 hour. Phage/antigen was added to 50 µl of Dynal M280 Streptavidin magnetic beads, which had been blocked for 1 hour at 37° C. in 1 ml of 3% MPBS, then incubated for a further 15 minutes at room temperature. Beads were captured using a magnetic rack and washed 4× in 1 ml of 3% MPBS/0.1% (v/v) Tween 20 followed by three washes in PBS. After the last wash, beads were resuspended in 100 µl PBS and used to infect 5 ml exponentially growing *E. coli* TG-1 cells. Cells and phage on beads were incubated for 1 hour at 37° C. (30 minutes stationary, 30 minutes shaking at 250 rpm), then spread on 2TYAG plates. Plates were incubated at 30° C. overnight and colonies visualized the next day. Colonies were scraped off the plates into 10 ml 2TY broth and 15% glycerol added for storage at −70° C.

Glycerol stock cultures from the first round panning selection were superinfected with helper phage and rescued to give scFv antibody-expressing phage particles for the second round of selection. A second and third round of soluble selection was carried out as described above, dropping the concentration of bio.IL-22 H/F to 50 nM.

Isolation of Parents GIL16, GIL45, GIL60 and GIL92

GIL16, GIL45, GIL60 and GIL92 were isolated from scFv libraries by a combination of panning on an IL-22 fusion protein and soluble selection on bio.IL-22 H/F. Wells of a microtiter plate were coated with 10 µg/ml (Dulbecco's PBS, pH 7.4) human IL-22 fusion protein and incubated overnight at 4° C. Wells were washed in PBS and blocked for 2 hours at 37° C. in 3% MPBS. Purified phage ($10^{12}$ tu) in 100 µl of 3% MPBS were added to blocked wells and incubated at room temperature for 1 hour. Wells were washed 10 times with PBST (PBS containing 0.1% v/v Tween20), then 10 times with PBS. Bound phage particles were eluted with 100 µl trypsin solution (0.5 µg/ml trypsin in 50 mM Tris pH 8, 1 mM $CaCl_2$) for 30 minutes at 37° C. The eluted phage were used to infect 10 ml exponentially growing *E. coli* TG1. Infected cells were grown in 2TY broth for 1 hour at 37° C., as above, then streaked onto 2TYAG plates and incubated overnight at 30° C. Output colonies were scraped off the plates and phage rescued as described above. A second round of soluble selection was carried out as described above, using 100 nM bio.IL-22 H/F.

Example 2

ScFv Blocks Binding of IL-22 to IL-22R

Inhibition assays were performed on the parent antibodies GIL01, GIL16, GIL45, GIL60, GIL68, and GIL92 to identify antibodies that block or alter binding of IL-22 to IL-22R and/or IL-22 receptor complex. Crude scFv containing periplasmic extracts were screened for the ability to inhibit the binding of bio.IL-22 H/F to a human IL-22 receptor protein (hIL-22R). Output colonies from selections were picked into 96 well plates containing 100 µl 2TYAG. ScFv production was induced by addition of 1 mM IPTG to exponentially growing cultures and overnight incubation at 30° C. Periplasmic extracts were prepared (Griffiths et al., 1993) in 50 mM MOPS pH 7.4/0.5 mM EDTA/0.5M Sorbitol.

Microtiter plates were coated with 1.25 µg/ml of an IL-22 receptor protein antibody (in PBS) for 1.5 hours at room temperature. Plates were then washed three times in PBS, and blocked for 1 hour at room temperature with PBS containing 2% milk powder (2% MPBS). After a further 3 washes, 50 µl of 25% cell conditioned medium containing IL-22 receptor protein was added to each well, and incubated overnight at 4° C. The following day, 25 µl of sample and 25 µl of bio.IL-22 H/F (54 ng/ml in PBS/0.05% BSA/0.05% Tween) were added to the washed plates, and incubated for 1.5 hours at room temperature. After 3 washes in PBST, binding of bio.IL-22 H/F was detected with Europium-Streptavidin and TRF detected with the DELFIA® reagent kit and Victor 2™ Plate Reader (Perkin Elmer).

Figure 1:
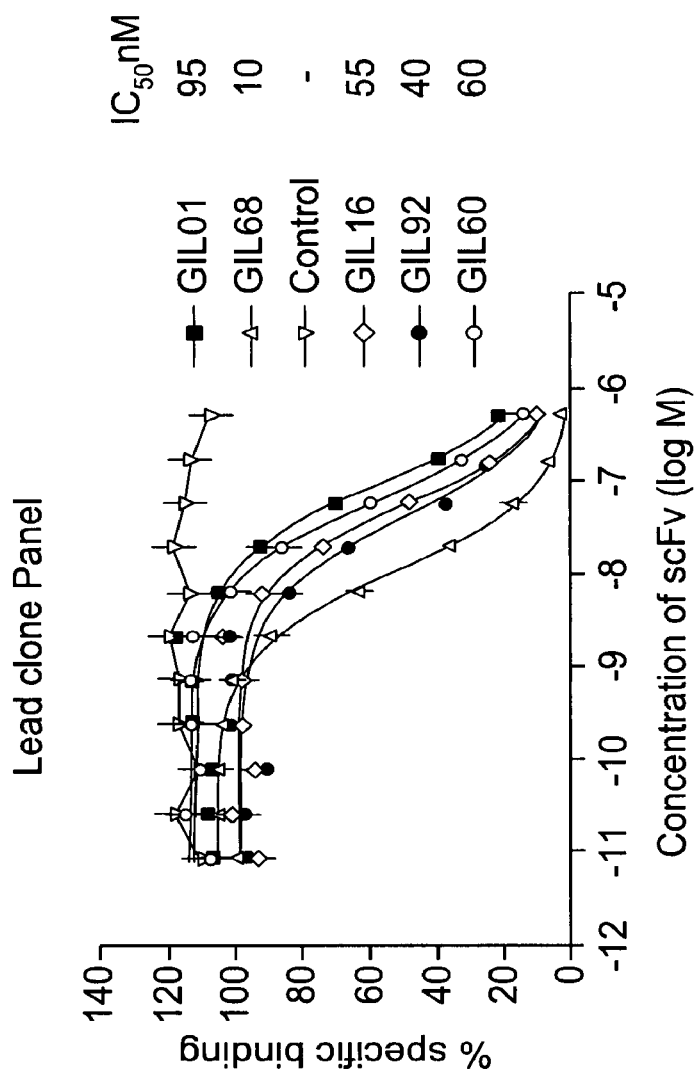
FIG. 1. Potency of parent anti-IL-22 scFv clones in the IL-22 receptor complex assay: bio.IL-22 binding IL-22 receptor complex DELFIA competition assay.
Figure 2A:
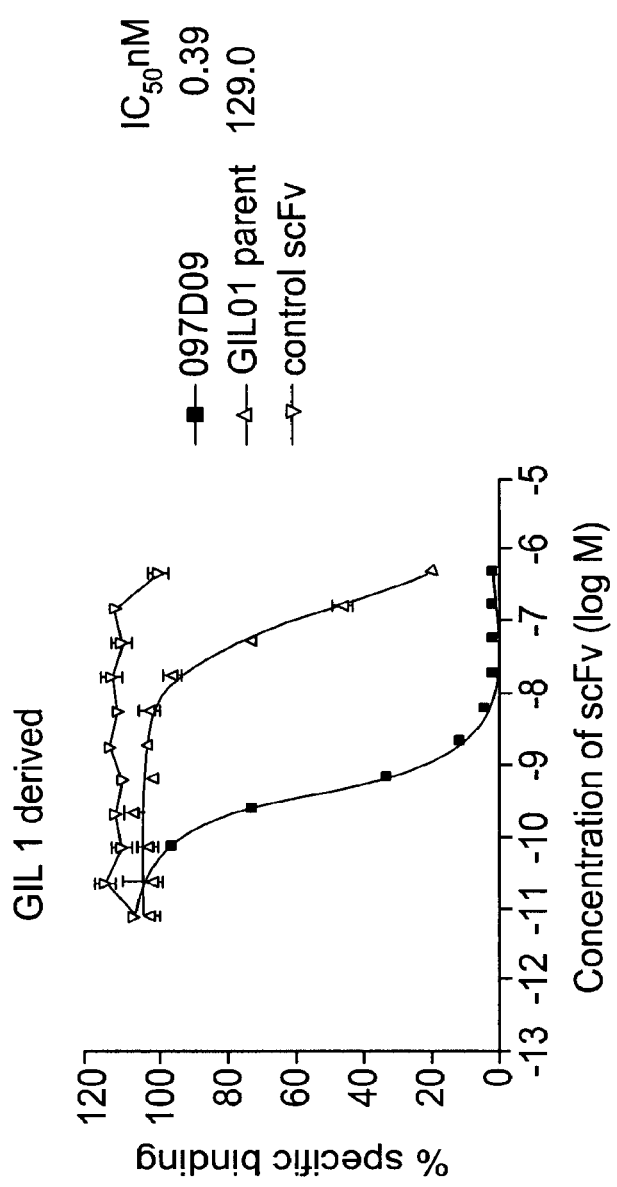
FIG. 2. Profiling of lead scFv clones in IL-22 receptor complex assay: bio.IL-22 binding IL-22 receptor complex DELFIA competition assay. (A) GIL 1 derived. (B) GIL 16 derived. (C) GIL 16, GIL 60, and GIL 68 derived. (D) GIL 60 derived. (E) GIL 68 derived. (F) GIL 68 derived. (G) GIL 92 derived.
Figure 2B:
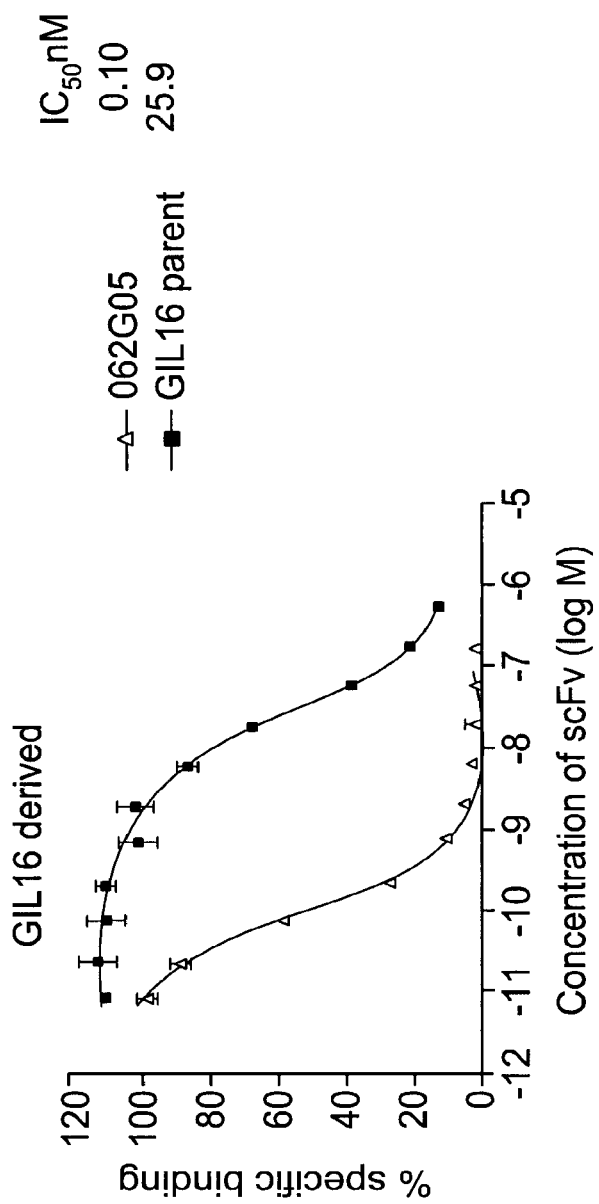
Figure 2C:
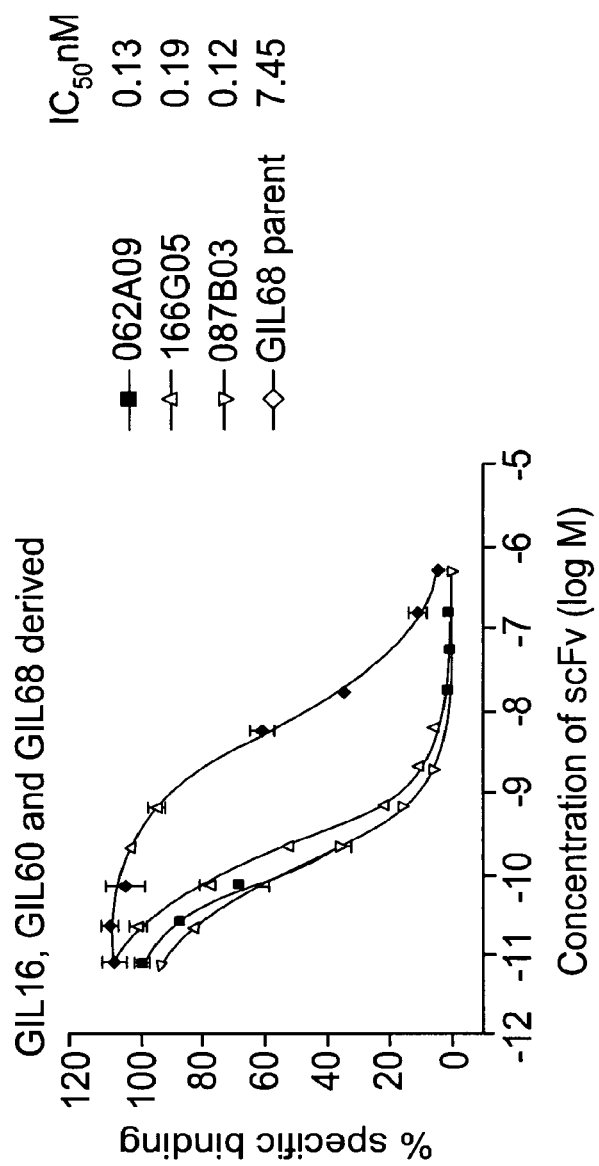
Figure 2D:
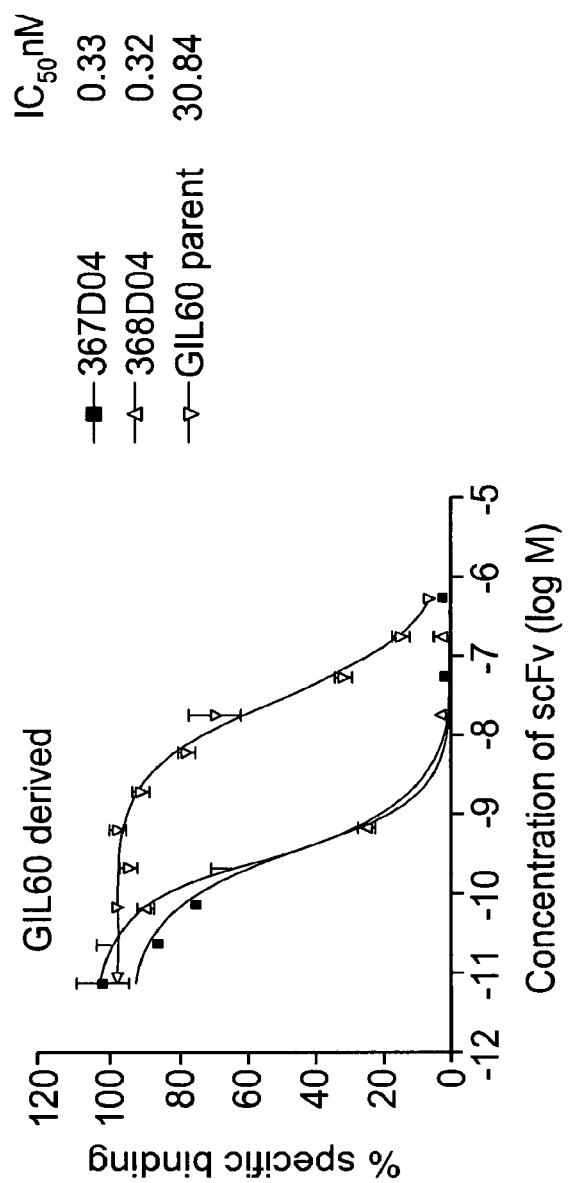
Figure 2E:
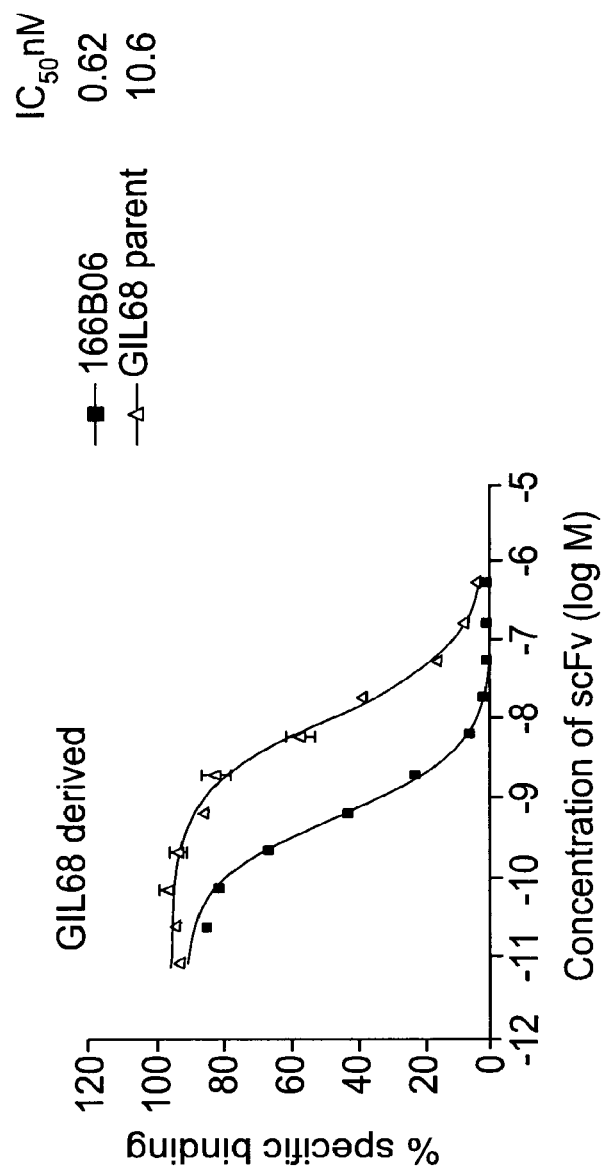
Figure 2F:
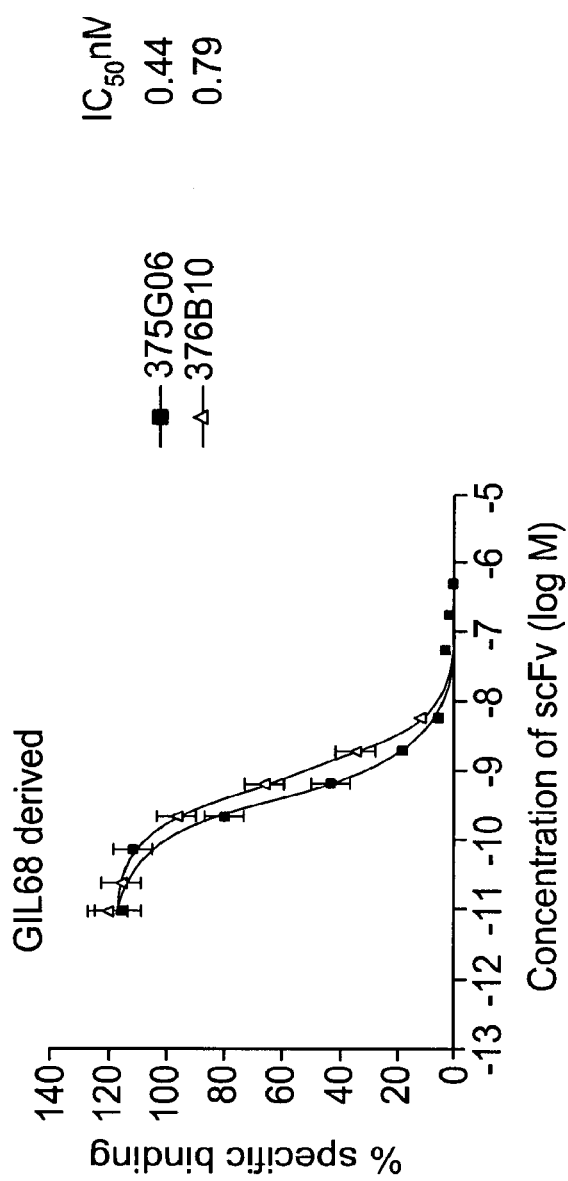
Figure 2G:
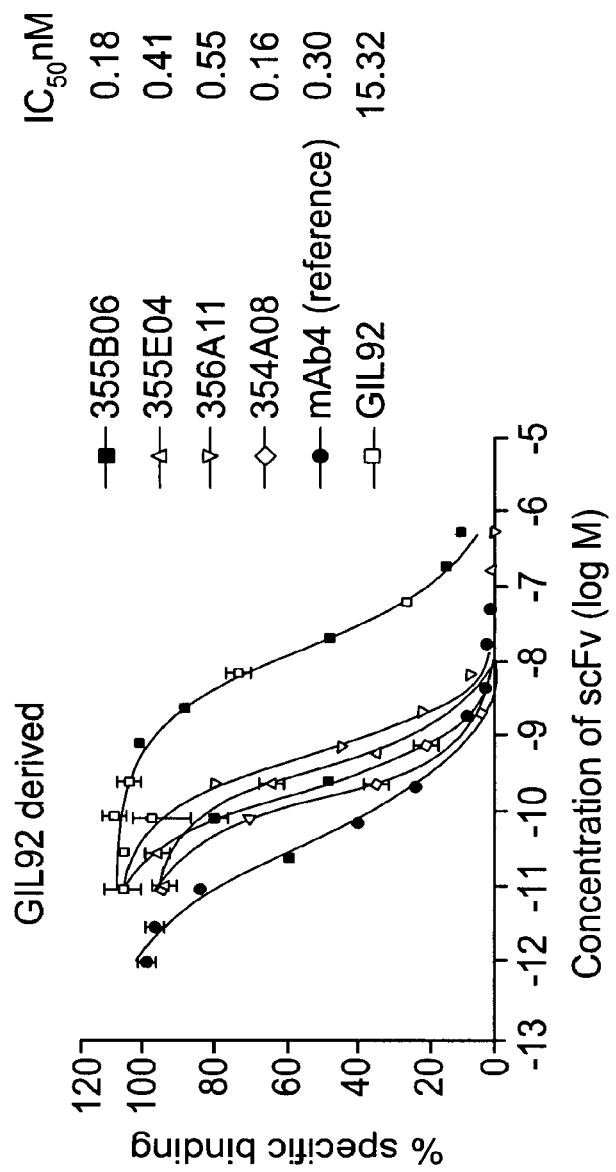

Clones that showed inhibition of IL-22 binding were retested as purified scFv. Both the IL-22/IL-22R binding assay (described above) and the IL-22/IL-22 receptor complex assay (described below) were used. ScFv concentrations were titrated in order to establish the clone potencies as measured by assay $IC_{50}$ values. These were determined using GraphPad Prism software and four-parameter logistic equation curve fitting. Sample results from the IL-22 receptor complex assay are shown in FIG. 1.

Example 3

Verification of IL-22 Binding by Phage ELISA

To establish the specificity of the scFv's for IL-22, a phage ELISA was performed using IL-22 fusion protein, IL-22 H/F and an unrelated protein. Individual *E. coli* colonies containing phagemid were inoculated into 96 well plates containing 100 µl 2TYAG medium per well. M13K07 helper phage were added to a multiplicity of infection (moi) of 10 to the exponentially growing culture and the plates incubated an additional 1 hour at 37° C. Plates were centrifuged in a benchtop centrifuge at 2000 rpm for 10 minutes. The supernatant was removed and cell pellets were resuspended in 100 µl 2TYAK and incubated at 30° C. overnight with shaking. The next day, plates were centrifuged at 2000 rpm for 10 minutes and 100 µl phage-containing supernatant from each well was transferred to a fresh 96 well plate. Phage samples were blocked in a final concentration of 3% MPBS for 1 hour at room temperature.

Microtiter plates were coated with 1 µg/ml IL-22 fusion protein, IL-22 H/F or an unrelated protein and incubated overnight at 4° C. After coating, the solutions were removed from the wells, and the plates blocked for 1 hour at room temperature in 3% MPBS. Plates were rinsed with PBS then 50 µl of pre-blocked phage was added to each well. The plates were incubated at room temperature for 1 hour, then washed with 3 changes of PBST followed by 3 changes of PBS. To each well, 50 µl of a 1:5000 dilution of anti-M13-HRP conjugate (Pharmacia) was added and the plates incubated at room temperature for 1 hour. Plates were washed 3 times with PBST then 3 times with PBS. Fifty µl of TMB substrate was added to each well and incubated until color development. The reaction was stopped by the addition of 25 µl of 0.5 M $H_2SO_4$, and the absorbance at 450 nm measured. These experiments confirmed the specific binding of scFv clones to IL-22.

Example 4

Conversion of $scF_v$ to IgG

Heavy and light chain V regions from scFv clones were amplified with clone-specific primers. PCR products were digested with appropriate restriction enzymes and subcloned into vectors containing human IgG4 heavy chain constant domain (for $V_H$ domains) or vectors containing human lambda or kappa light chain constant domains as appropriate ($V_L$ domains). The closest human germlines of the $V_H$ and $V_L$ segments were determined and this information was used to indicate whether kappa or lambda light chain constant domains were used (Table 4). Correct insertion of V region domains into plasmids was verified by sequencing of plasmid DNA from individual *E. coli* colonies. Plasmids were prepared from *E. coli* cultures by standard techniques and heavy and light chain constructs co-transfected into HEK 293 EBNA cells using standard techniques. Secreted IgG was purified using protein A sepharose (Pharmacia) and buffer exchanged into PBS.

TABLE 4

$V_H$ and $V_L$ germlines of IL-22 neutralizing clones

| Clone | $V_H$ germline | $V_L$ germline |
|---|---|---|
| GIL01 | 3-11 (DP35) | Vk1:L12 |
| GIL16 | 1-18 (DP14) | Vk1:L12 |
| GIL45 | 3-33 (DP50) | VL2:2a2 (DPL11) |
| GIL60 | 3-20 (DP32) | VL2:2a2 (DPL11) |
| GIL68 | 1-2 (DP8) | VL3:3h |
| GIL92 | 1-2 (DP8) | VL1:1e (DPL8) |

Potency of purified IgG was verified in the biochemical IL-22 receptor complex inhibition assay as described below. IgG concentrations were titrated in order to obtain potency values. Sample potency data is shown in Table 5.

TABLE 5

Potency of IL-22 scFv and IgG in the IL-22 receptor complex inhibition assay

| Clone | ScFv potency (nM) | IgG potency (nM) |
|---|---|---|
| GIL01 | 104 | 13 |
| GIL16 | 49 | 10 |
| GIL60 | 43 | 15 |
| GIL68 | 7 | 2 |
| GIL92 | 16 | unobtainable |
| GIL45 | 358 | 180 |

Example 5

IL-22 Antibody Optimization

Large ribosome display libraries were created and screened for scFv's that specifically recognized recombinant human IL-22, essentially as described in Hanes et al. (2000). Initially the five parent clones (GIL01, GIL16, GIL60, GIL68 and GIL92) were converted to ribosome display format, and this template was subsequently used for library creation. On the DNA level, a T7 promoter was added at the 5'-end for efficient transcription to mRNA. On the mRNA level, the construct contained a prokaryotic ribosome-binding site (Shine-Dalgarno sequence) and 5' & 3' stem loops for mRNA stability. At the 3' end of the single chain, the stop codon was removed and a portion of gill was added to act as a spacer, allowing folding of the scFv away from the ribosomal tunnel (Hanes et al. 2000).

Ribosome display libraries derived from the lead clones were created by mutagenesis of the single chain complementarity determining regions (CDRs) using PCR with non-proofreading Taq DNA polymerase. Affinity based selections were performed where the library was incubated with bio.IL-22H/F, followed by streptavidin coated paramagnetic beads. (Dynal M280). Tertiary complexes (mRNA-ribosome-scFv) were recovered by magnetic separation, while unbound complexes were washed away. The mRNAs encoding the bound scFvs were then rescued by RT-PCR as described (Hanes et al., 2000) and the selection process repeated with decreasing concentrations (100 nM-10 pM over 5 rounds) of bio.IL-22H/F.

Error prone PCR was introduced to further increase library size. The error rate that was employed created, on average, 7.2 mutations per 1,000 bp after a standard PCR reaction based on the method of Cadwell and Joyce (1992). Initial error prone PCR reactions took place between the first and second rounds of selection.

$V_H/V_L$ recombination libraries for each parent clone were prepared from the $V_H$ and $V_L$ CDR ribosome display outputs after either the second or fourth round of selections. The $V_H$ portion of the $V_H$ CDR selection output for a particular lineage was specifically PCR amplified, using clone specific primers. The $V_L$ portion of the $V_L$ CDR selection output for the same lineage was amplified separately. These two PCR products were recombined via an overlapping PCR reaction. This created a complete library of scFv products containing all components required for further rounds of ribosome display selection.

For some clones, phage display libraries were also utilized. Phage libraries were created by mutagenesis of single chain CDRs using PCR reactions with appropriate primers, and selected as described above. These outputs were also combined with ribosome display selection outputs to create $V_H N_L$ recombination libraries. The $V_H$ selection outputs from the fourth round of ribosome display, together with the outputs from the third round of phage display, were recombined with the $V_L$ outputs from the same lineage. This was achieved using clone specific primers and over-lapping PCR to produce $V_H/V_L$ recombination libraries. Selections with soluble bio.IL-22 H/F continued in ribosome display format, as described above. The scFv regions of selection outputs were directionally cloned into pCANTAB6 for production of scFv for biochemical high throughput screening.

Example 6

Identification of Optimized Clones

Two assays were used for high throughput screening of selection outputs. Outputs derived from clones GIL01, GIL16 and GIL68 were screened in a homogeneous time resolved fluorescence assay (HTRF®, Cis Biointernational), while GIL60 and GIL92 outputs were screened in a DELFIA® (Perkin Elmer) assay.

HTRF® Epitope Competition Assay

Crude scFv containing culture supernatants from GIL01, GIL16 and GIL68 output clones were prepared as described above and screened for inhibition of bio.IL-22H/F binding GIL68 in an HTRF assay.

Cryptate labeled GIL68 IgG (labeling kit from Cis Biointernational) was diluted 400 fold in assay buffer (PBS/0.4M KF/0.05% BSA/0.05% Tween), followed by the addition of 7.5 nM Streptavidin XL665 (Xlent, C is Biointernational). This solution was mixed with crude scFv sample (diluted 125×), and bio.IL-22H/F in a Packard black 384 well Optiplate (Perkin Elmer). Plates were incubated for 1 hour at room temperature then read using a Victor 2™ Plate Reader (Perkin Elmer). The 665 nM/620 nM emission ratio was used to calculate the percentage of specific binding in each well.

DELFIA® Time Resolved Fluorescence assay

GIL60 and GIL92 output clones were screened for inhibition of bio.IL-22H/F binding to an IL-22 receptor complex.

Microtiter plates were coated with IL-22 receptor complex antibody (1 μg/ml in PBS), and incubated for 1.5 hours at room temperature. Plates were washed three times in PBST, and blocked for 1 hour at room temperature with 2% MPBS. After a further 3 washes, diluted cell conditioned medium containing an IL-22 receptor complex was added and incubated overnight at 4° C. Crude scFv supernatants were prepared as described above. The following day, 25 μl of diluted scFv sample and 25 μl of bio.IL-22 H/F (6 ng/ml) were added to the washed plates, and incubated for 1.5 hours at room temperature. Plates were washed 3 times in PBST, then binding of bio.IL-22H/F to the IL-22 receptor complex was detected with Europium-Streptavidin and the DELFIA® reagent kit (PerkinElmer). Time Resolved Fluorescence was measured using a Victor 2™ Plate Reader (Perkin Elmer).

Purified scFv from positive clones identified from the screening were tested in the DELFIA® IL-22 receptor complex competition assay as described above. A titration of scFv concentrations was used in order to establish the clone potency as measured by $IC_{50}$ values in the assay. Sample results are shown in FIG. 2. Fourteen optimized clones were designated 097D09, 062A09, 062G05, 087B03, 367D04, 368D04, 166B06, 166G05, 375G06, 376B10, 354A08, 355B06, 355E04, and 356A11.

Example 7

Ranking of Optimized Clones in the BAF3-IL-22 Proliferation Assay

Proliferation assays were performed to assess the antibody's ability to block the IL-22 mediated BaF3 cell proliferation. BaF3 cells expressing hIL22R/hIL10R2 were generated by co-transfection of BaF3 cells with hIL22R-GFP and hIL10R2-YFP. BaF3 cells expressing both hIL22R and hIL10R2 (BaF3-IL-22 receptor cells) were sorted and collected by FACS.

BaF3-IL-22 receptor cells were routinely maintained in RPMI1640 with 10% FBS and 1 ng/mL murine IL-J. Immediately before assay setup, cells were washed 4 times in assay medium (RPMI1640 with 10% FBS, 100 U/ml Penicillin and 100 μg/ml Streptomycin), resuspended in assay medium and incubated at 37° C., 5% $CO_2$ for 6-8 hours. To prepare assay plates, 100 μl of cells (1×10⁵/ml in assay medium) were added to the central 60 wells of a 96 well flat-bottomed tissue culture plate (Costar). Test scFv or IgG samples were prepared by diluting the stock sample in assay medium followed by filtration through a 0.22 μM filter. Serial 5-fold dilutions of samples were prepared in a separate dilution plate. Cell containing wells were treated with 50 μl of sample followed by 50 μl of human IL-22, (40 ng/ml in assay medium), and were then incubated for 40 hours at 37° C. in 5% $CO_2$. Control wells included media alone and cells either alone or in the presence of 10 ng/mL human IL-22.

Cell proliferation was detected by the addition of 20 μl of Alamar Blue (Serotec) to wells, followed by incubation for 5 hours±30 mins at 37° C. in 5% $CO_2$. Plates were mixed by gentle tapping to ensure even signal throughout the wells before measurement of fluorescence (excitation=560 nM, emission=590 nM). $EC_{50}$ and $IC_{50}$ values were estimated using four-parameter logistic curve fitting (Graphpad Prism 2 Software) and were used to rank antibodies. Sample potency data for optimized scFvs and IgGs are shown in Table 6.

TABLE 6

$IC_{50}$ values of scFv and IgG clones in BaF3-IL-22 proliferation assay

| Clone | Parent | $IC_{50}$ of scFv (pM) | $IC_{50}$ of IgG (pM) |
|---|---|---|---|
| 097D09 | GIL01 | 298 ± 246 | 197 ± 42 |
| 062A09 | GIL16 | 267 | 83 ± 37 |
| 062G05 | GIL16 | 182 | 112 ± 30 |
| 087B03 | GIL60 | 212 | 105 ± 17 |
| 367D04 | GIL60 | 160 ± 49 | 126 ± 6 |
| 368D04 | GIL60 | 186 ± 66 | 127 ± 10 |
| 166B06 | GIL68 | 460 | 71 ± 23 |
| 166G05 | GIL68 | 204 | 97 ± 23 |
| 375G06 | GIL68 | 118 ± 98 | 100 ± 1 |
| 376B10 | GIL68 | 104 ± 47 | 119 ± 6 |
| 354A08 | GIL92 | 219 ± 83 | 79 ± 15* |
| 355B06 | GIL92 | 183 ± 3 | 92 ± 14* |
| 355E04 | GIL92 | 192 ± 47 | 100 ± 14* |
| 356A11 | GIL92 | 124 ± 21 | 53 ± 5* |

*GIL92-derived clones were tested as germlined IgGs.

Example 8

Germlining

Sequence data for the six parent clones was used to identify the nearest germline sequence for the heavy and light chain of each clone. Appropriate mutations were made using standard site directed mutagenesis techniques with the appropriate mutagenic primers. Mutation of sequences was confirmed by sequence analysis. The sequences for the germlined clones and their scFv and $V_H$ and $V_L$ domains are shown in Table 7. Purified scFv from the germlined parent clones were tested in the biotinylated IL-22 binding IL-22 receptor complex competition assay as described earlier, in order to establish the clone potency as measured by $IC_{50}$ values in the assay. Results are summarized in Table 8.

TABLE 7

Amino Acid and Nucleotide Sequences of $V_H$ and $V_L$ Domains, $F_v$, and CDRs of Germlined Antibodies (GIL01, GIL16, GIL45, GIL60, GIL68, GIL92, 062A09, and 087B03)

| Region | Type | GIL01 SEQ ID | GIL16 SEQ ID | GIL45 SEQ ID | GIL60 SEQ ID | GIL68 SEQ ID | GIL92 SEQ ID | 062A09 SEQ ID | 087B03 SEQ ID |
|---|---|---|---|---|---|---|---|---|---|
| $V_H$ | AA | NO: 365 | NO: 383 | NO: 401 | NO: 419 | NO: 437 | NO: 455 | NO: 473 | NO: 491 |
| $V_L$ | AA | NO: 366 | NO: 384 | NO: 402 | NO: 420 | NO: 438 | NO: 456 | NO: 474 | NO: 492 |
| scF$_v$ | AA | NO: 367 | NO: 385 | NO: 403 | NO: 421 | NO: 439 | NO: 457 | NO: 475 | NO: 493 |
| H1 | AA | NO: 368 | NO: 386 | NO: 404 | NO: 422 | NO: 440 | NO: 458 | NO: 476 | NO: 494 |
| H2 | AA | NO: 369 | NO: 387 | NO: 405 | NO: 423 | NO: 441 | NO: 459 | NO: 477 | NO: 495 |
| H3 | AA | NO: 370 | NO: 388 | NO: 406 | NO: 424 | NO: 442 | NO: 460 | NO: 478 | NO: 496 |
| L1 | AA | NO: 371 | NO: 389 | NO: 407 | NO: 425 | NO: 443 | NO: 461 | NO: 479 | NO: 497 |
| L2 | AA | NO: 372 | NO: 390 | NO: 408 | NO: 426 | NO: 444 | NO: 462 | NO: 480 | NO: 498 |
| L3 | AA | NO: 373 | NO: 391 | NO: 409 | NO: 427 | NO: 445 | NO: 463 | NO: 481 | NO: 499 |
| $V_H$ | DNA | NO: 374 | NO: 392 | NO: 410 | NO: 428 | NO: 446 | NO: 464 | NO: 482 | NO: 500 |
| $V_L$ | DNA | NO: 375 | NO: 393 | NO: 411 | NO: 429 | NO: 447 | NO: 465 | NO: 483 | NO: 501 |
| scF$_v$ | DNA | NO: 376 | NO: 394 | NO: 412 | NO: 430 | NO: 448 | NO: 466 | NO: 484 | NO: 502 |
| H1 | DNA | NO: 377 | NO: 395 | NO: 413 | NO: 431 | NO: 449 | NO: 467 | NO: 485 | NO: 503 |
| H2 | DNA | NO: 378 | NO: 396 | NO: 414 | NO: 432 | NO: 450 | NO: 468 | NO: 486 | NO: 504 |
| H3 | DNA | NO: 379 | NO: 397 | NO: 415 | NO: 433 | NO: 451 | NO: 469 | NO: 487 | NO: 505 |
| L1 | DNA | NO: 380 | NO: 398 | NO: 416 | NO: 434 | NO: 452 | NO: 470 | NO: 488 | NO: 506 |
| L2 | DNA | NO: 381 | NO: 399 | NO: 417 | NO: 435 | NO: 453 | NO: 471 | NO: 489 | NO: 507 |
| L3 | DNA | NO: 382 | NO: 400 | NO: 418 | NO: 436 | NO: 454 | NO: 472 | NO: 490 | NO: 508 |

Amino Acid and Nucleotide Sequences of $V_H$ and $V_L$ Domains, $F_v$, and CDRs of Germlined Antibodies (166B06, 166G05, 354A08, 355B06, 355E04, 356A11, and 368D04)

| Region | Type | 166B06 SEQ ID | 166G05 SEQ ID | 354A08 SEQ ID | 355E06 SEQ ID | 355E04 SEQ ID | 356A11 SEQ ID | 368D04 SEQ ID |
|---|---|---|---|---|---|---|---|---|
| $V_H$ | AA | NO: 509 | NO: 527 | NO: 545 | NO: 563 | NO: 581 | NO: 599 | NO: 617 |
| $V_L$ | AA | NO: 510 | NO: 528 | NO: 546 | NO: 564 | NO: 582 | NO: 600 | NO: 618 |
| scF$_v$ | AA | NO: 511 | NO: 529 | NO: 547 | NO: 565 | NO: 583 | NO: 601 | NO: 619 |
| H1 | AA | NO: 512 | NO: 530 | NO: 548 | NO: 566 | NO: 584 | NO: 602 | NO: 620 |
| H2 | AA | NO: 513 | NO: 531 | NO: 549 | NO: 567 | NO: 585 | NO: 603 | NO: 621 |
| H3 | AA | NO: 514 | NO: 532 | NO: 550 | NO: 568 | NO: 586 | NO: 604 | NO: 622 |
| L1 | AA | NO: 515 | NO: 533 | NO: 551 | NO: 569 | NO: 587 | NO: 605 | NO: 623 |
| L2 | AA | NO: 516 | NO: 534 | NO: 552 | NO: 570 | NO: 588 | NO: 606 | NO: 624 |
| L3 | AA | NO: 517 | NO: 535 | NO: 553 | NO: 571 | NO: 589 | NO: 607 | NO: 625 |
| $V_H$ | DNA | NO: 518 | NO: 536 | NO: 554 | NO: 572 | NO: 590 | NO: 608 | NO: 626 |
| $V_L$ | DNA | NO: 519 | NO: 537 | NO: 555 | NO: 573 | NO: 591 | NO: 609 | NO: 627 |
| scF$_v$ | DNA | NO: 520 | NO: 538 | NO: 556 | NO: 574 | NO: 592 | NO: 610 | NO: 628 |
| H1 | DNA | NO: 521 | NO: 539 | NO: 557 | NO: 575 | NO: 593 | NO: 611 | NO: 629 |
| H2 | DNA | NO: 522 | NO: 540 | NO: 558 | NO: 576 | NO: 594 | NO: 612 | NO: 630 |
| H3 | DNA | NO: 523 | NO: 541 | NO: 559 | NO: 577 | NO: 595 | NO: 613 | NO: 631 |
| L1 | DNA | NO: 524 | NO: 542 | NO: 560 | NO: 578 | NO: 596 | NO: 614 | NO: 632 |
| L2 | DNA | NO: 525 | NO: 543 | NO: 561 | NO: 579 | NO: 597 | NO: 615 | NO: 633 |
| L3 | DNA | NO: 526 | NO: 544 | NO: 562 | NO: 580 | NO: 598 | NO: 616 | NO: 634 |

TABLE 8

ScFv potencies of ungermlined and germlined parent clones in the IL-22 receptor competition assay

| Parent clone scFv | Average IC$_{50}$ nM in IL-22 competition assay | |
|---|---|---|
| | Parent | Fully germlined |
| GIL01 | 124 ± 50 | 143 ± 45 |
| GIL16 | 44 ± 1 | 38 ± 1 |
| GIL60 | 51 ± 16 | 82 ± 3 |
| GIL68 | 9 ± 1 | 14 + 1 |
| GIL92 | 18 ± 2 | 40 ± 11 |

Nine of the optimized antibodies were germlined as described above. Eight germlined IgGs were tested in the BaF3-IL-22 proliferation assay as described above. Antibody IC$_{50}$ values from a representative experiment are shown in Table 9.

Antibody sequences were then sent to GENEART North America (28 Kirk Bradden Rd. East, Toronto, ON, Canada M8Y2E6), where they were synthesized for optimized expression in CHO cells using GENEART's proprietary optimization algorithm.

TABLE 9

IgG potencies of germlined optimized clones in the BaF3-IL-22R proliferation assay

| Clone | Parent | IC$_{50}$ (pM) of non-germlined IgG | IC$_{50}$ (pM) of germlined IgG |
|---|---|---|---|
| 087B03 | GIL60 | 72 ± 6 | 118 ± 19 |
| 166B06 | GIL68 | 109 ± 16 | 169 ± 32 |
| 166G05 | GIL68 | 366 ± 226* | 109 ± 31 |
| 356A11 | GIL92 | ND | 53 ± 5 |
| 355B06 | GIL92 | ND | 92 ± 14 |
| 355E04 | GIL92 | ND | 100 ± 14 |
| 354A08 | GIL92 | ND | 79 ± 15 |
| 062A09 | GIL16 | 108 ± 23 | unobtainable |

*sample contained precipitate
ND = not determined

Example 9

Antibody Inhibits IL-22 Induced GROa Secretion from HT29 Cells

GROa assays were performed to assess the antibody's ability to block the IL-22 induced GROa secretion from HT29 cells. HT29 cells were seeded in 96 well flat bottom tissue culture plate (Corning Inc. Cat. #3595) in DMEM medium (DMEM+10% FBS+100 unit/ml penicillin and streptomycin+2 mM Glutamine) at $5 \times 10^4$/well. 10 ng/ml IL-22 was mixed with serially diluted antibody in DMEM medium and incubated for 30 min at 37° C. 24 hours after seeding, medium was removed from HT29 cells and pre-mixed IL-22 and antibody were added to the cells in 96 well plate.

Figure 3A:
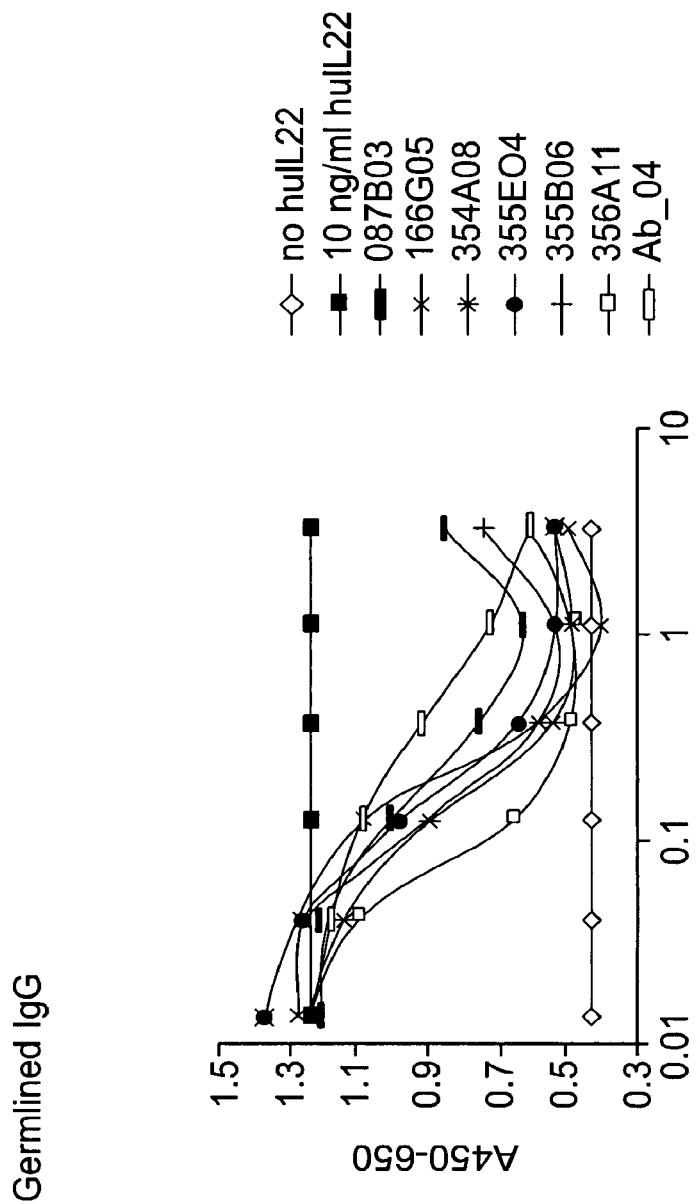
FIG. 3. IgG potency in GROa cell based assays. Optimized GIL-IgGs in huIL-22 GROa assay. (A) Germlined IgG. (B) Non-germlined IgG.
Figure 3B:
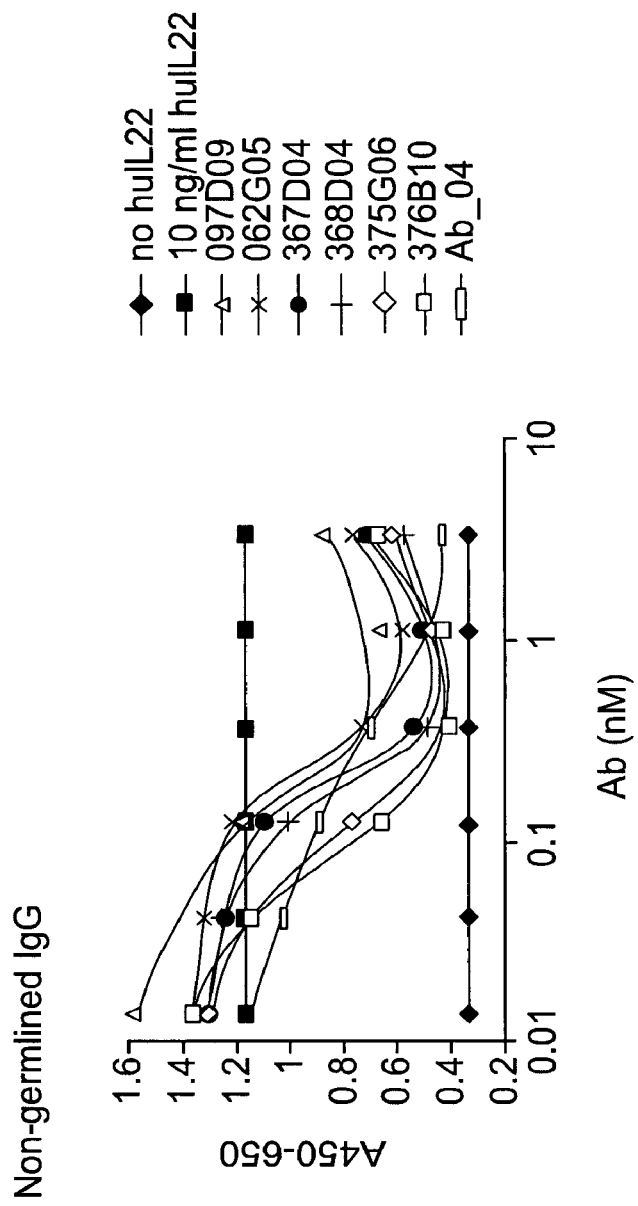

After 48 hours of incubation at 37° C. with 5% $CO_2$, medium was collected and secreted GROa was tested using Human GROa Immunoassay kit (R&D Systems, Cat. DGR00), according to the manufacturer's directions. Results are presented in FIG. 3.

Example 10

Antibody Binds to and Inhibits Different Species IL-22

Figure 4A:
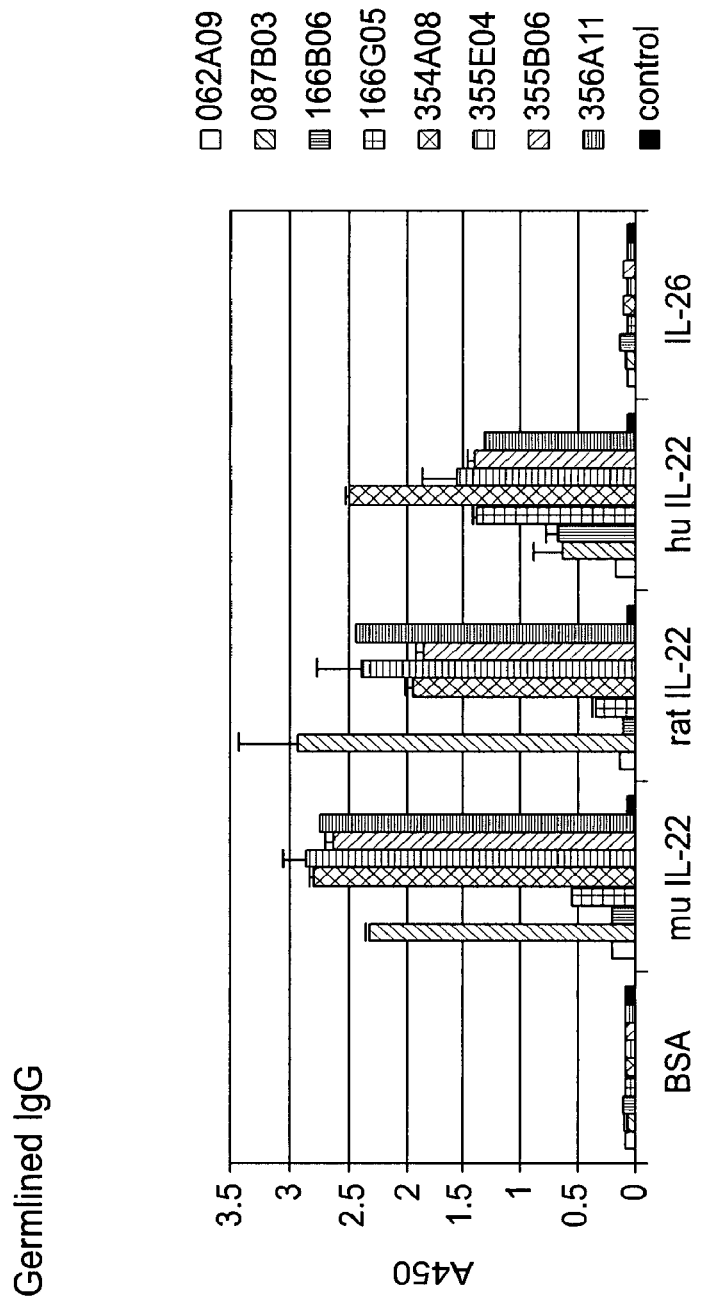
FIG. 4. Cross species reactivity of IL-22 antibodies by ELISA. Optimized GIL-IgGs specifically bind to IL-22. (A) Germlined IgG. (B) Non-germlined IgG.
Figure 4B:
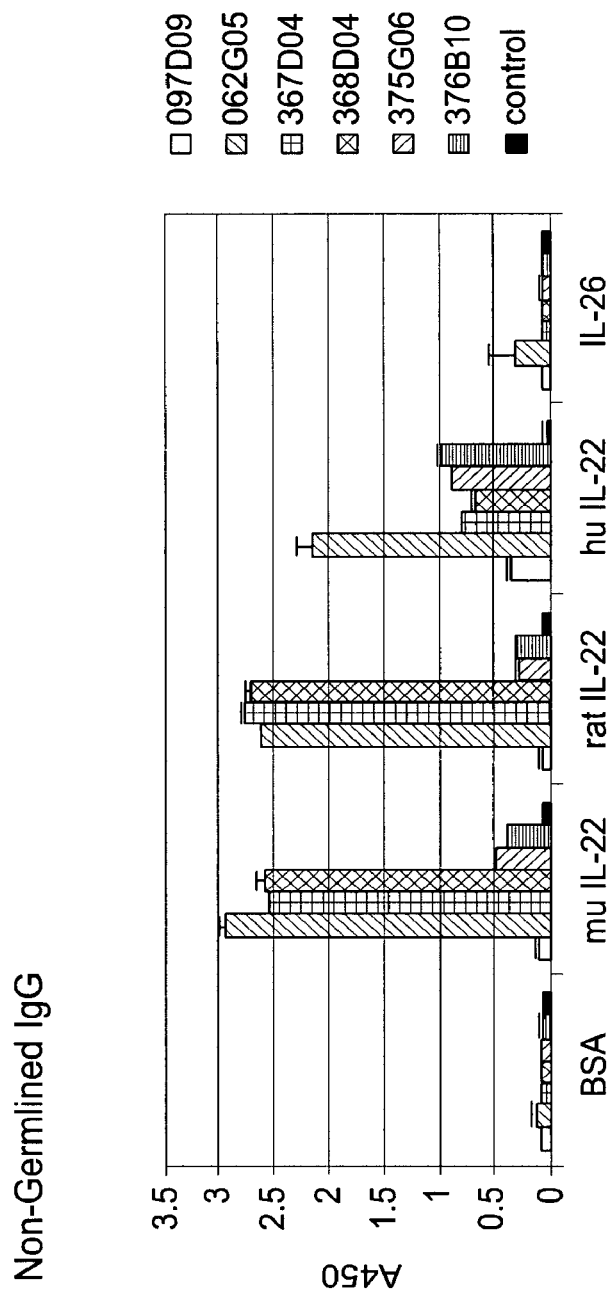

Cross species reactivity of germlined and non-germlined optimized antibodies were determined as follows: ELISA plates (Costar, Cat. #3590) were coated overnight with 1 μg/ml of rat, mouse, or human IL-22 or human IL-26 in PBS buffer. Plates were washed with PBST buffer (0.05% Tween20 in PBS) 3 times, then blocked with 1% BSA (Sigma A8918)/PBST for 1 hr at RT. Antibodies were added at 1 μg/ml, incubated 1 hr at 25° C. The plates were washed, then HRP-conjugated goat anti-human IgG antibody (Southern Biotech Association, Cat. #2040-05) was added. The plates were incubated for 1 hour at 25° C., then washed with PBST, and developed with TMB (KPL, Cat. #50-76-04). Reaction was stopped with 0.18 M $H_2SO_4$. Plates were read at OD 450 nm. Results are presented in FIG. 4.

These antibodies were also evaluated in both the GROa cell assay and BaF3-IL-22 proliferation assay. As shown in Tables 10(a) and 10(b), the antibodies blocked the activity of human, monkey, rat, and mouse IL-22 signalling via a human IL-22 receptor. 356A11 and 368D04 also demonstrated cross-species reactivity against murine, rat, and monkey IL-22 using real-time biospecific interaction analysis (BIA), as discussed further in Example 11.

TABLE 10(a)

IL-22 antibodies are highly potent for blocking other species of IL-22 as shown in the GROa cell based assay system. Values shown represent $IC_{50}$ values in pM.

| Protein ID | human IL-22 | murine IL-22 | rat IL-22 | monkey IL-22 |
|---|---|---|---|---|
| 356A11 | 123.64 | 143.76 | 210.91 | 89.57 |
| 368D04 | 154.07 | 156.25 | 281.12 | 184.10 |
| control 1 | 353.18 | 468.34 | 1161.57 | 343.19 |
| control 2 | 1955.80 | 3399.79 | 10697.17 | 1459.27 |

TABLE 10(b)

IL-22 antibodies are highly potent for blocking other species of IL-22 as shown in the BaF3 cell based assay system. Values shown represent $IC_{50}$ values in pM.

| Protein ID | human IL-22 | murine IL-22 | rat IL-22 | monkey IL-22 |
|---|---|---|---|---|
| 356A11 | 3.57 | 2.53 | 10.69 | 2.58 |
| 368D04 | 3.63 | 1.47 | 12.07 | 3.87 |
| control 1 | 6.40 | 5~6 | 27.37 | 7.18 |
| control 2 | 204.98 | 1033.26 | 2500.00 | 134.27 |

Example 11

Comparison of Binding Kinetics Between Rat Anti-IL-22 Monoclonal Antibodies and Human Anti-IL-22 Monoclonal Antibodies The binding kinetics of human, monoclonal anti-IL-22 antibodies (356A11 and 368D04) and rat, monoclonal anti-IL-22 antibodies (P3/3 (Ab-02) and P3/2 (Ab-04) from WO 2005/000897 and WO 02/068476) to human IL-22 were evaluated by real-time biospecific interaction analysis (BIA) using surface plasmon resonance technology.

To prepare the biosensor surface for the rat monoclonal antibodies, Protein A/G (Pierce #21186, Rockford, Ill.) was immobilized onto a research-grade carboxymethyl dextran chip (CM5) using amine coupling. The surface was activated with EDC/NHS. The protein A/G was injected at a concentration of 50 μg/ml in sodium acetate buffer (pH 4.0). The immobilization was done using the wizard tools with aim of 3000 (RUs) for the protein A/G. Remaining activated groups were blocked with 1.0 M ethanolamine (pH 8.0). The first flow cell was used as a reference surface to correct for bulk refractive index, matrix effects, and non-specific binding. The second, third, and fourth flow cells were coated with the capturing molecule. The rat monoclonal antibodies Ab-02 and Ab-04, which bind to protein A/G, were captured onto the protein A/G surface by injecting 30 μl of a 1 μg/ml solution. The net difference between the baseline and the point approximately 90 seconds after completing Ab-02 or Ab-04 injection was used to represent the amount of ligand bound.

To prepare the biosensor surface for the human monoclonal antibodies, either human monoclonal antibody (356A11 or 368D04) or control antibody were immobilized onto a research-grade carboxymethyl dextran chip (CM5) using standard amine coupling. The surface was activated with EDC/NHS. The capturing antibodies were injected at a concentration of 1 μg/ml in sodium acetate buffer (pH 5.5). Remaining activated groups were blocked with 1.0 M ethanolamine (pH 8.0). The first flow cell was used as a reference surface to correct for bulk refractive index, matrix effects, and non-specific binding. The second, third, and fourth flow cells were coated with the capturing molecule.

For Ab-02 and Ab-04, solutions of human IL-22 at 300, 100, 50, 25, 12.5, 6.4, 3.2, 1.6 and 0 nM concentrations were injected in triplicates at a flow rate of 30 μl per minute for 3 minutes and the amount of bound material as a function of time was recorded as sensorgrams. The dissociation phase was monitored in HBS/EP buffer for 10 minutes at the same flow rate followed by a 5 μl injection of 0.1% TFA and a 5 μl injection of glycine pH 1.5 to regenerate a fully active capturing surface.

For 356A11 and 368D04, solutions of human IL-22 at 400, 200, 100, 50, 25, 12.5, 6.25 and 0 nM were injected in triplicates at a flow rate of 100 μl per minute (high flow to avoid non specific binding) for 3 minutes, and the amount of bound material as a function of time was recorded as sensorgrams. The dissociation phase was monitored in HBS/EP buffer for 60 minutes at the same flow rate followed by two 5 µl injections of glycine pH 1.5 to regenerate a fully active capturing surface.

All kinetic experiments were done at 22.5° C. in HBS/EP buffer. Blank and buffer effects were subtracted for each sensorgram using double referencing. In control experiments the first injection contained buffer.

The kinetic data were analyzed using BIAevaluation software 3.0.2 applied to a 1:1 model. The apparent dissociation ($K_d$) and association ($K_a$) rate constants were calculated from the appropriate regions of the sensorgrams using a global analysis. The affinity constants of the interaction between antibody and analyte were calculated from the kinetic rate constants by the following formulae: $K_D=K_d/K_a$, where $K_D$ is the dissociation constant, and $K_A=K_a/K_d$, where $K_A$ is the association constant. The binding data for Ab-02 and AB-04 are summarized in Tables 11A and 11B. The binding data for 356A11 and 368D04 are summarized in Table 12.

TABLE 11A

Kinetic parameters for the interaction between human IL-22 and anti-IL-22 antibodies Ab-02 and Ab-04

|  | Ab-02 $k_a$ ($M^{-1}s^{-1}$) | Ab-02 $k_d$ ($s^{-1}$) | Ab-04 $k_a$ ($M^{-1}s^{-1}$) | Ab-04 $k_d$ ($s^{-1}$) |
|---|---|---|---|---|
| Protein A/G | 2.78E+05 | 1.45E−03 | 5.15E+05 | 1.23E−03 |

TABLE 11B

Kinetic data of rat monoclonal antibodies for human IL-22

| Antibody | Ka (1/Ms) | Kd (1/s) | KA (1/M) | KD (M) | Chi2 |
|---|---|---|---|---|---|
| Ab-02 | 2.78E+05 | 1.45E−03 | 1.92E+08 | 5.22E−08 | 0.49 |
| Ab-04 | 5.15E+05 | 1.23E−03 | 4.22E+08 | 2.38E−09 | 0.53 |

TABLE 12

Kinetic data of human monoclonal antibodies for human IL-22

| Antibody | Ka (1/Ms) | Kd (1/s) | KA (1/M) | KD (M) | Chi2 |
|---|---|---|---|---|---|
| 356A11 | 7.91E+04 | 4.27E−06 | 1.85E+10 | 5.40E−11 | 0.223 |
| 368D04 | 1.89E+05 | 2.50E−05 | 7.56E+09 | 1.32E−10 | 0.298 |

These results show that the human monoclonal anti-IL-22 antibodies of this invention have a significantly higher affinity for human IL-22 than the rat monoclonal anti-IL-22 antibodies Ab-02 and Ab-04, described in WO 2005/000897 and WO 02/068476 as having the ability to neutralize human IL-22. Specifically, the dissociation constant of 356A11 ($K_D$=5.40× $10^{-11}$ M or 0.054 nM) for human IL-22 is approximately 1000-fold and more than 40-fold greater than the dissociation constants of Ab-02 ($K_D$=5.22×$10^{-8}$M or 52 nM) and Ab-04 ($K_D$=2.38×$10^{-9}$M or 2.38 nM), respectively. Similarly, 368D04 ($K_D$=1.32×$10^{-10}$ M or 0.132 nM) has an approximately 400-fold and 18-fold stronger affinity for human IL-22 than Ab-02 and Ab-04, respectively. The binding profiles of 356A11 and 36804 for monkey, murine, and rat IL-22 were similar to that of human IL-22 (data not shown).

The binding specificities of 356A11 and 368D04 were also evaluated using BIA. Neither antibody showed cross reactivity with human IL-10, human IL-19, human IL-20, human IL-24, human IL-28A, human IL-29, human IFN-α2c, or human IFN-ω (data not shown).

Example 12

In Vivo Half Life of Anti-Human IL-22 Antibodies

Figure 11A:
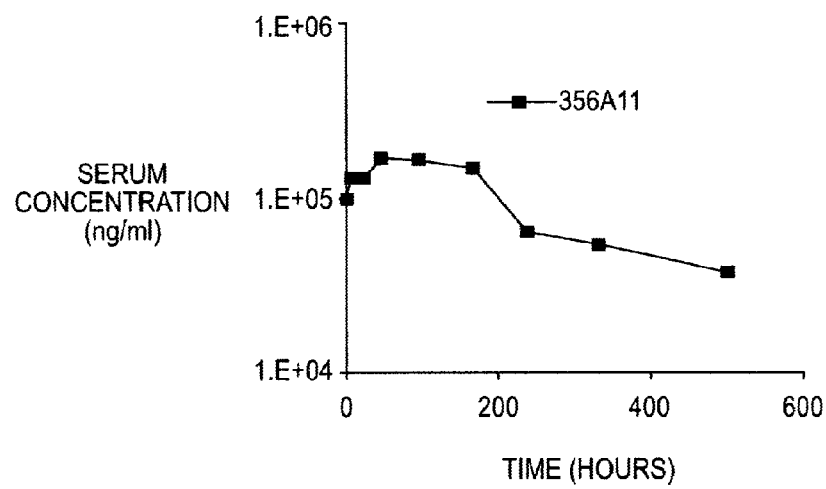
FIGS. 11A-B. In vivo half life of (A) 356A11 and (B) 368D04.
Figure 11B:
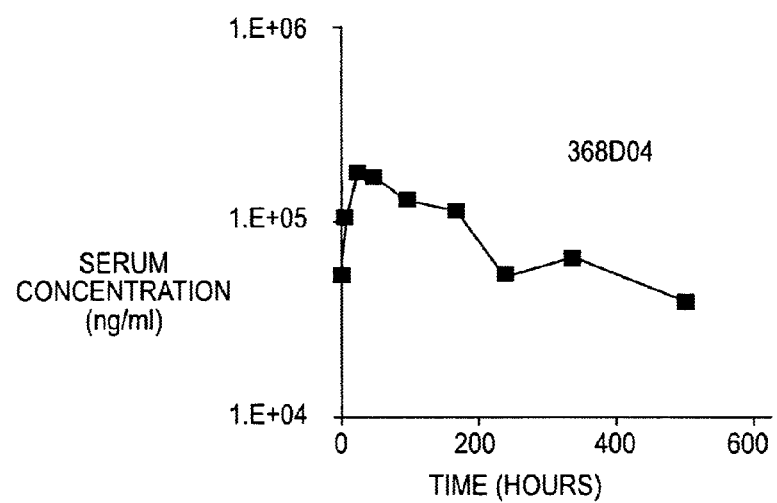
Figure 12A:
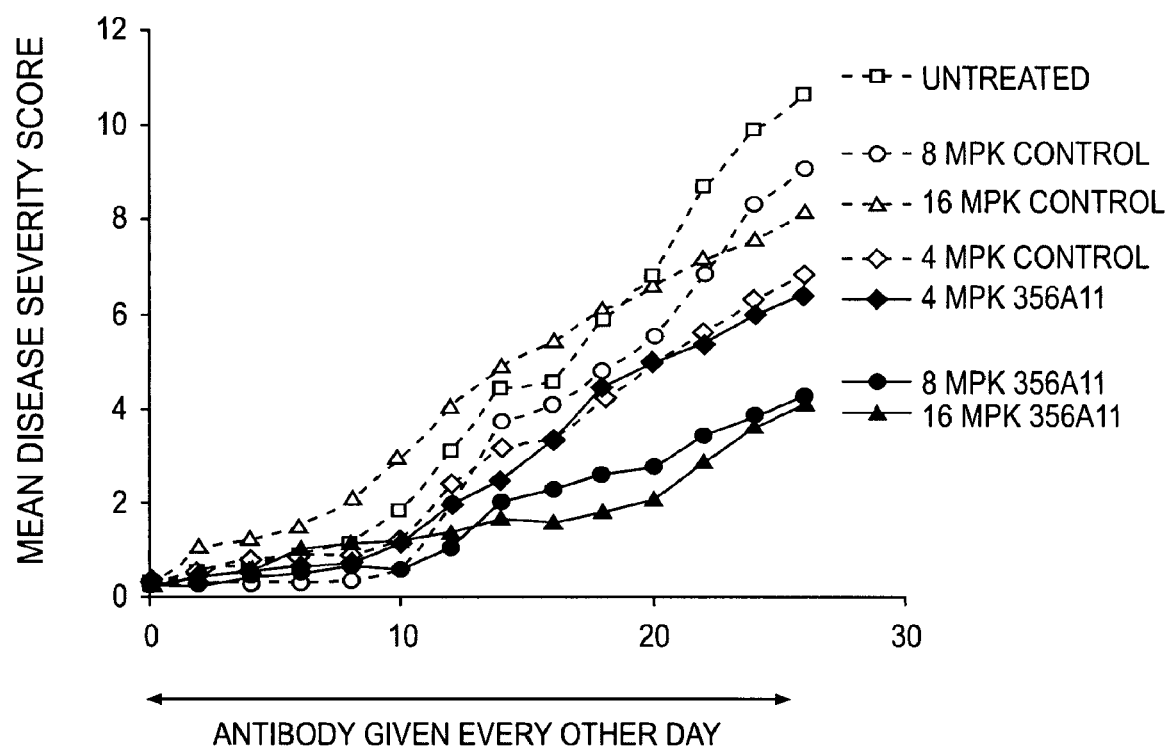
FIGS. 12A-B. Mean disease severity scores (A) or disease severity scores (B) with various doses of 356A11 administered every other day in murine CIA model.
Figure 12B:
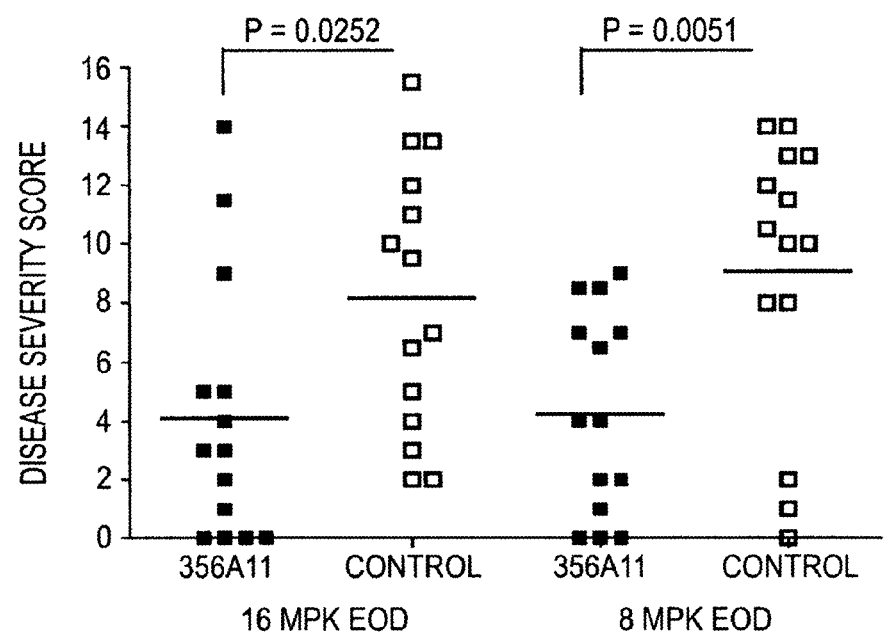
Figure 13A:
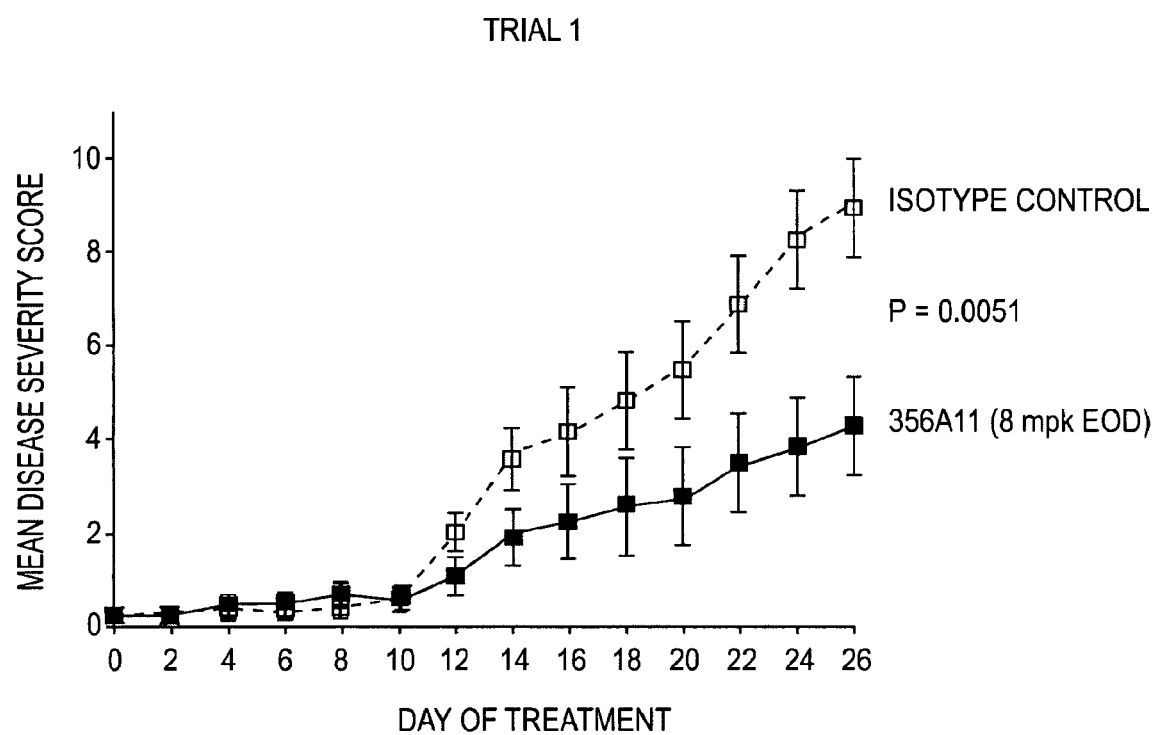
FIGS. 13A-D. Mean disease severity scores of 8 mg kg$^{-1}$ of 356A11 administered every other day in murine CIA model in multiple studies.
Figure 13B:
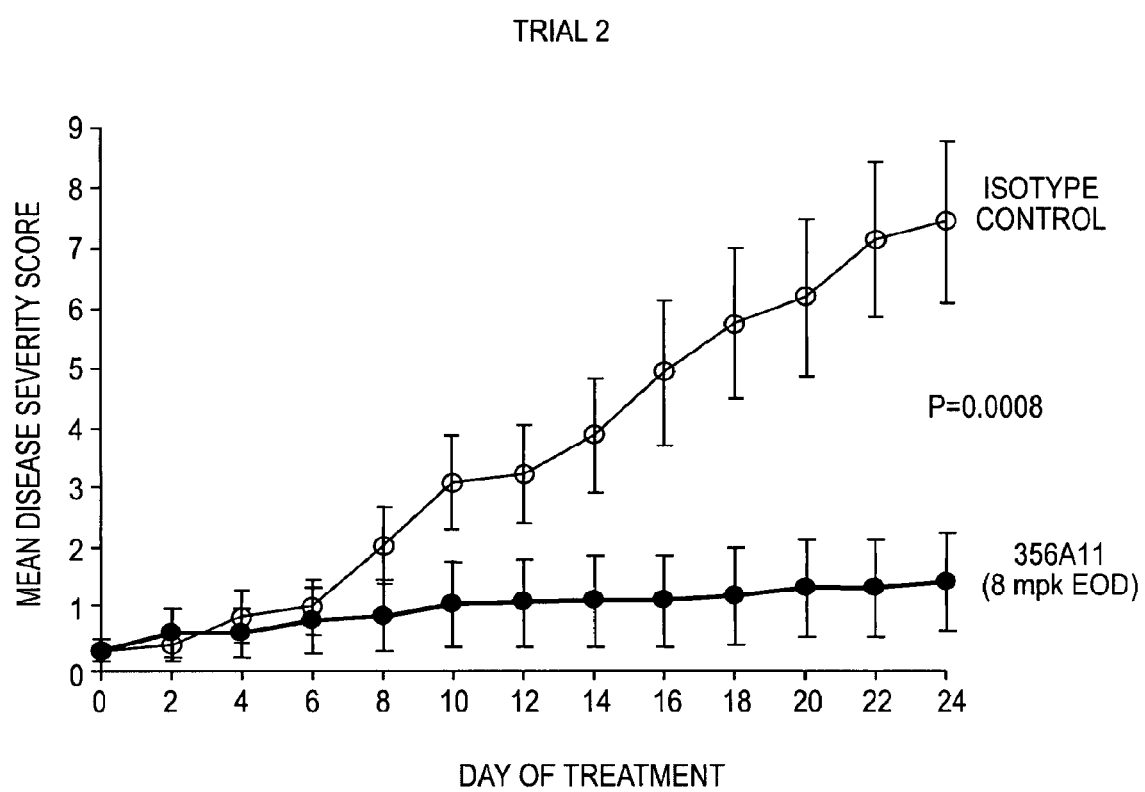
Figure 13C:
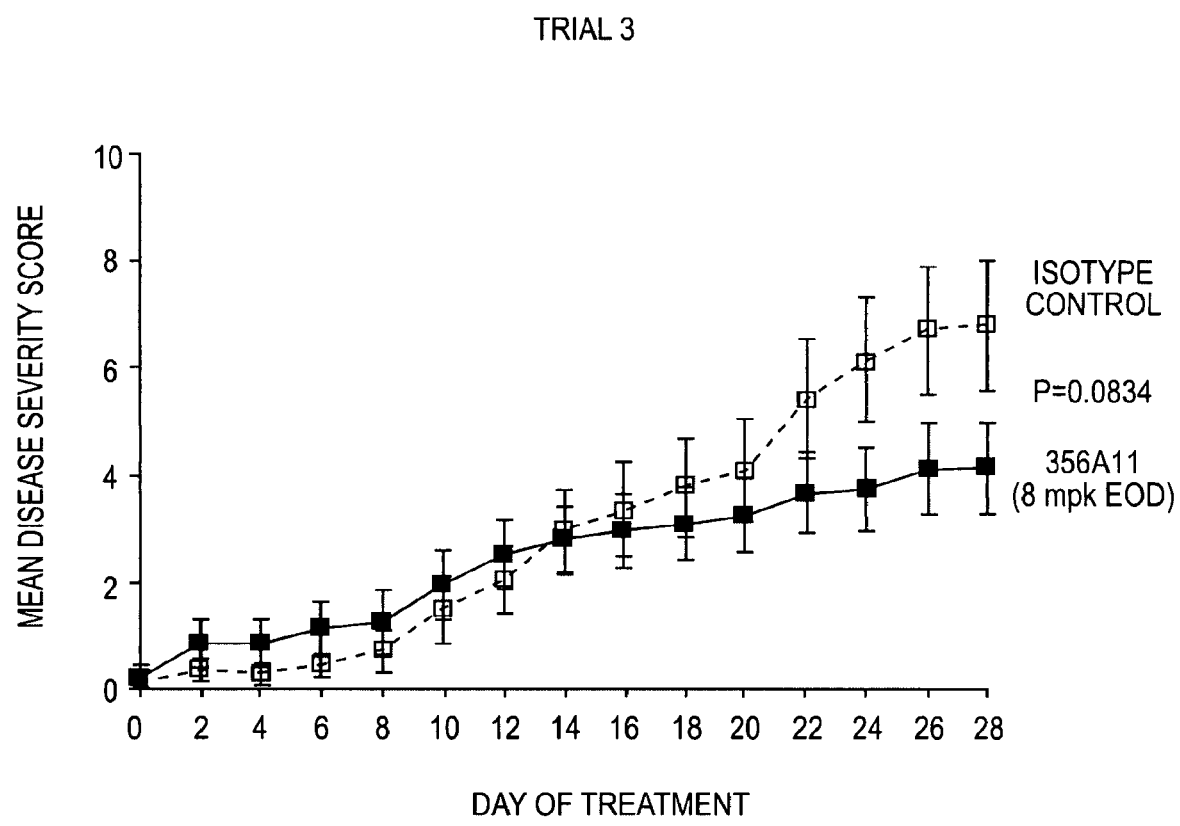
Figure 13D:
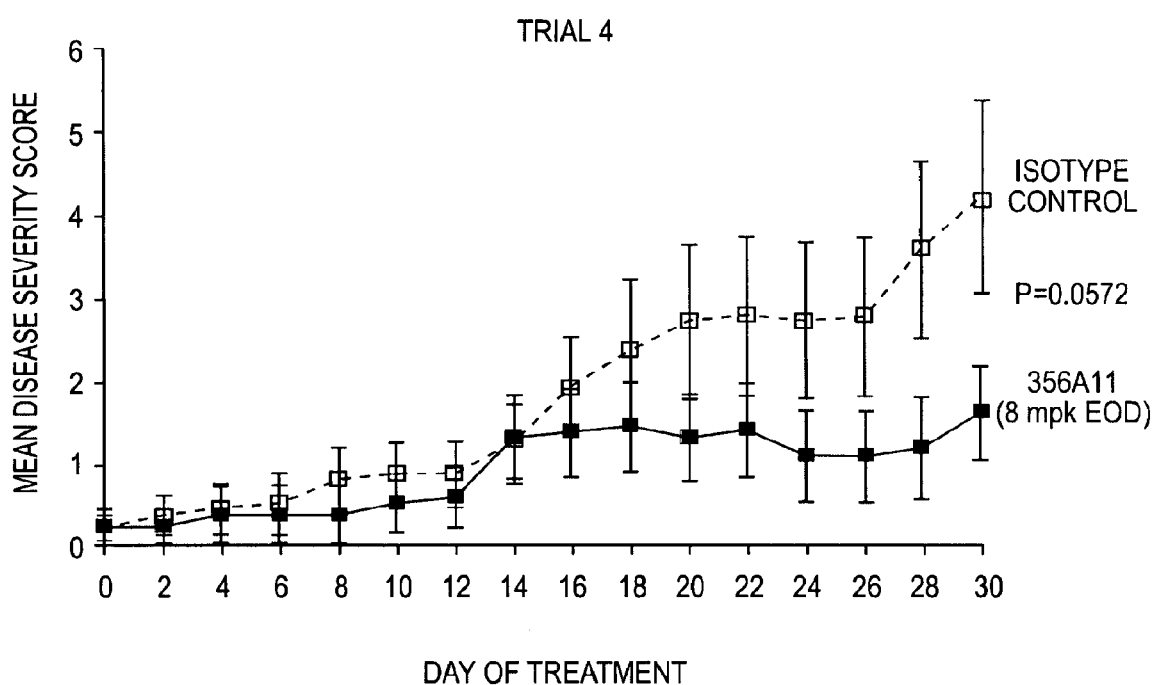
Figure 14A:
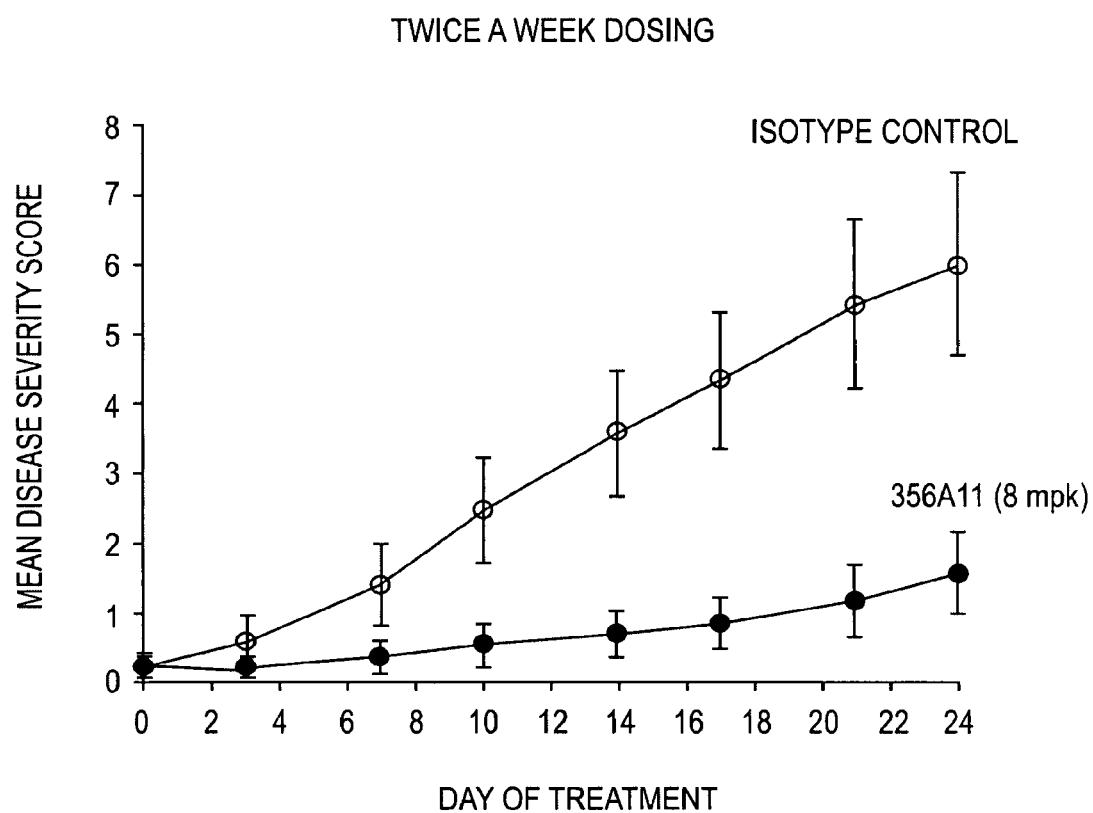
FIGS. 14A-B. Mean disease severity scores of 8 mg kg$^{-1}$ of 356A11 administered once or twice a week in murine CIA model.
Figure 14B:
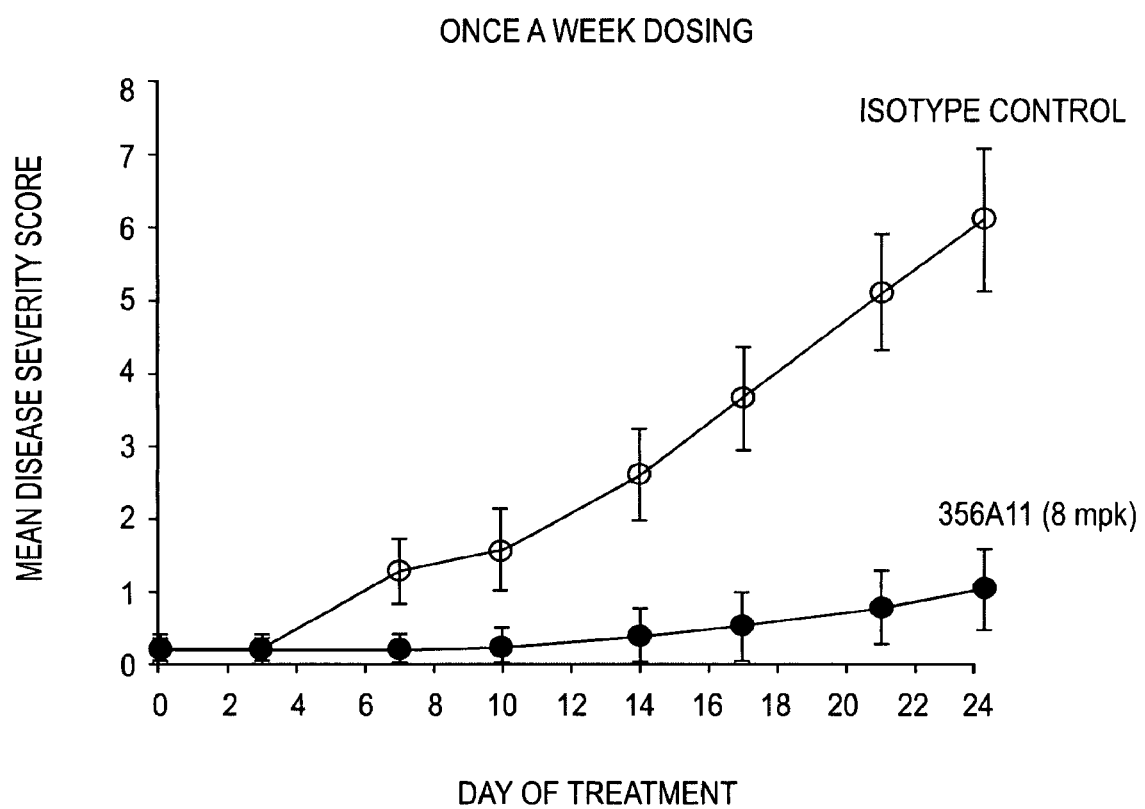
Figure 15A:
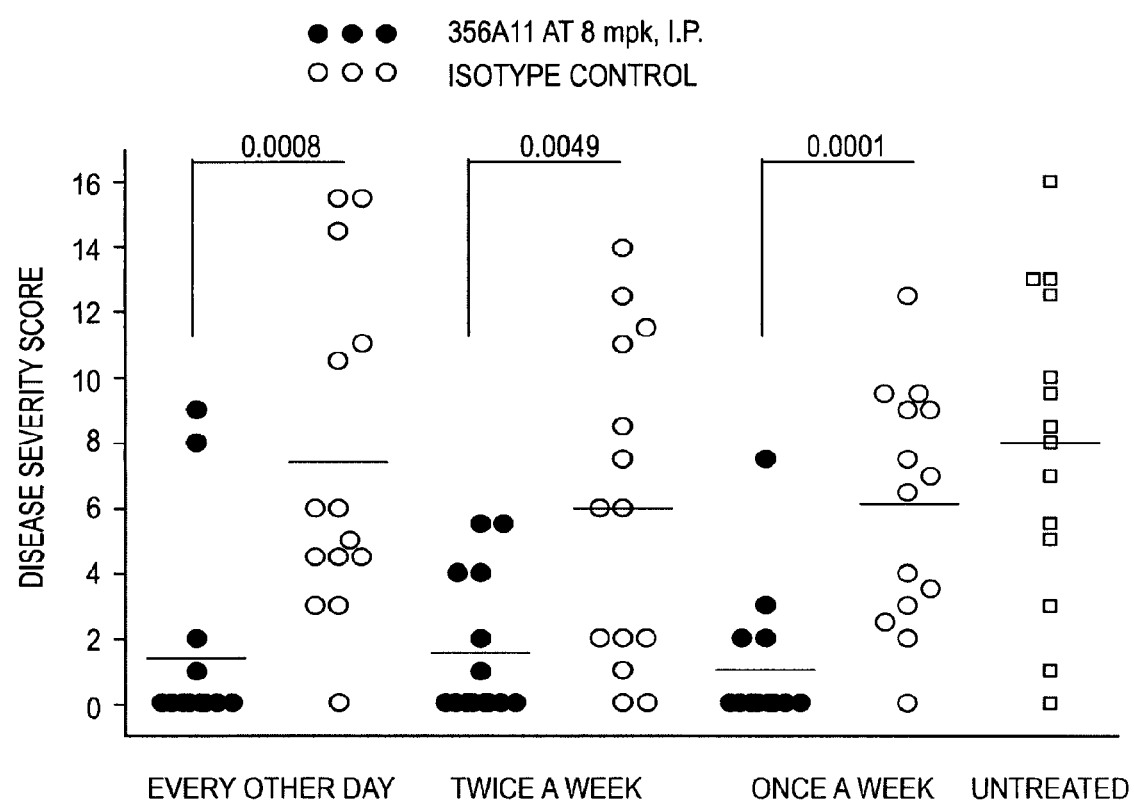
FIGS. 15A-B. Disease severity scores from two separate studies of 8 mg kg$^{-1}$ of 356A11 administered every other day, twice a week, or once a week in murine CIA model.
Figure 15B:
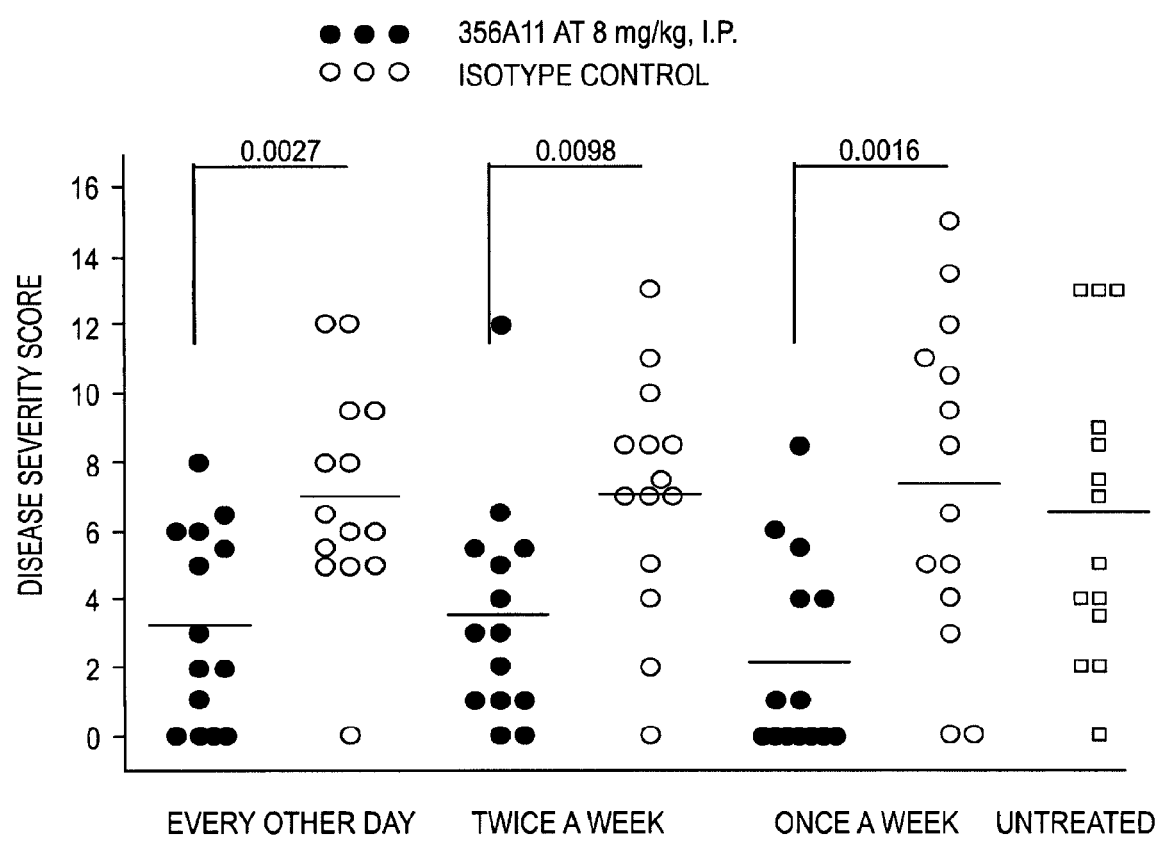
Figure 16A:
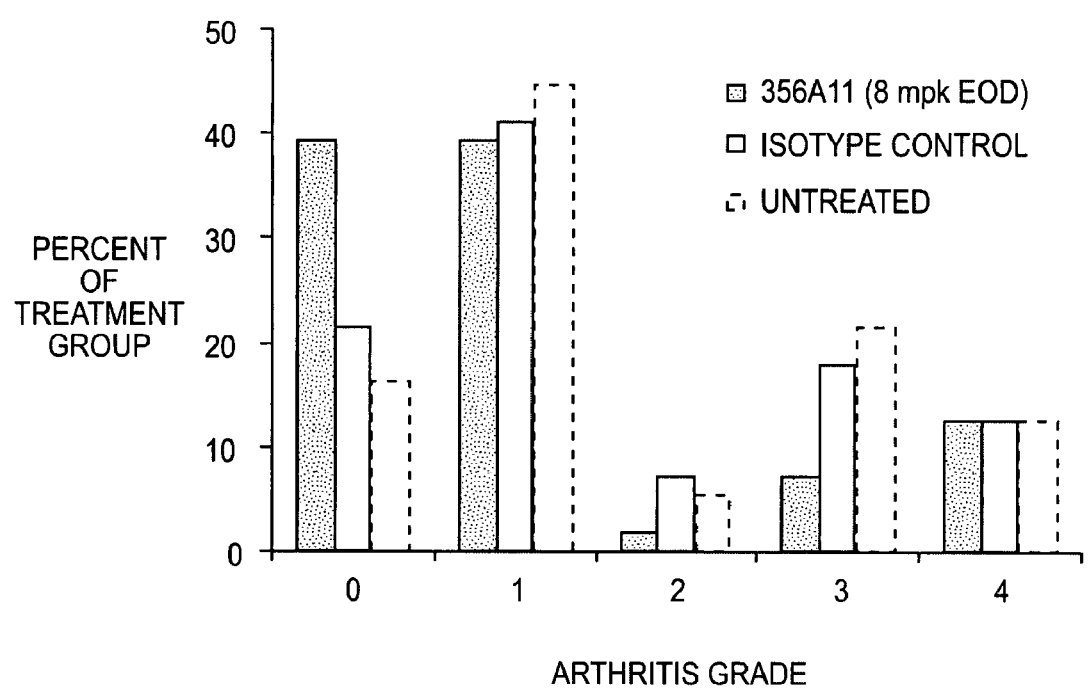
FIGS. 16A-F. Histological evaluation (paw) of disease progression in multiple studies using mice treated with (A) 8 mg kg$^{-1}$ of 356A11 every other day or (B) 16 mg kg$^{-1}$ of 356A11 every other day, (C) 8 mg kg$^{-1}$ of 356A11 every other day, once a week, or twice a week, (D) 8 mg kg$^{-1}$ of 356A11 once a week, (E) 8 mg kg$^{-1}$ of 356A11 twice a week, or (F) 8 mg kg$^{-1}$ of 356A11 every other day in murine CIA model.
Figure 16B:
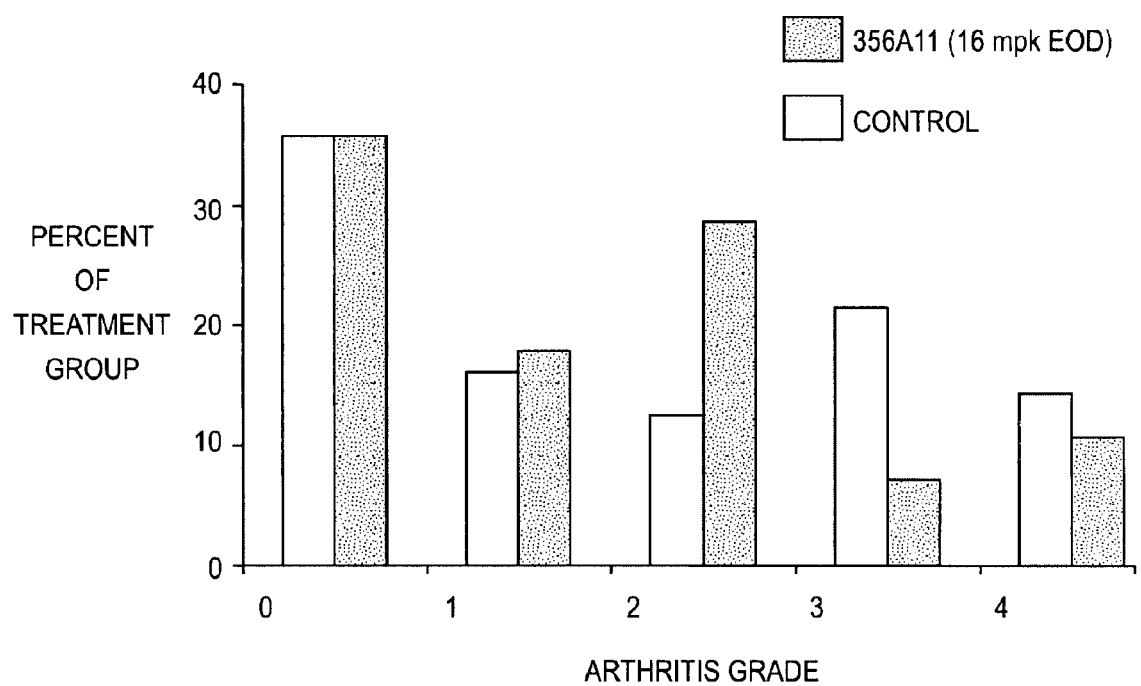
Figure 16C:
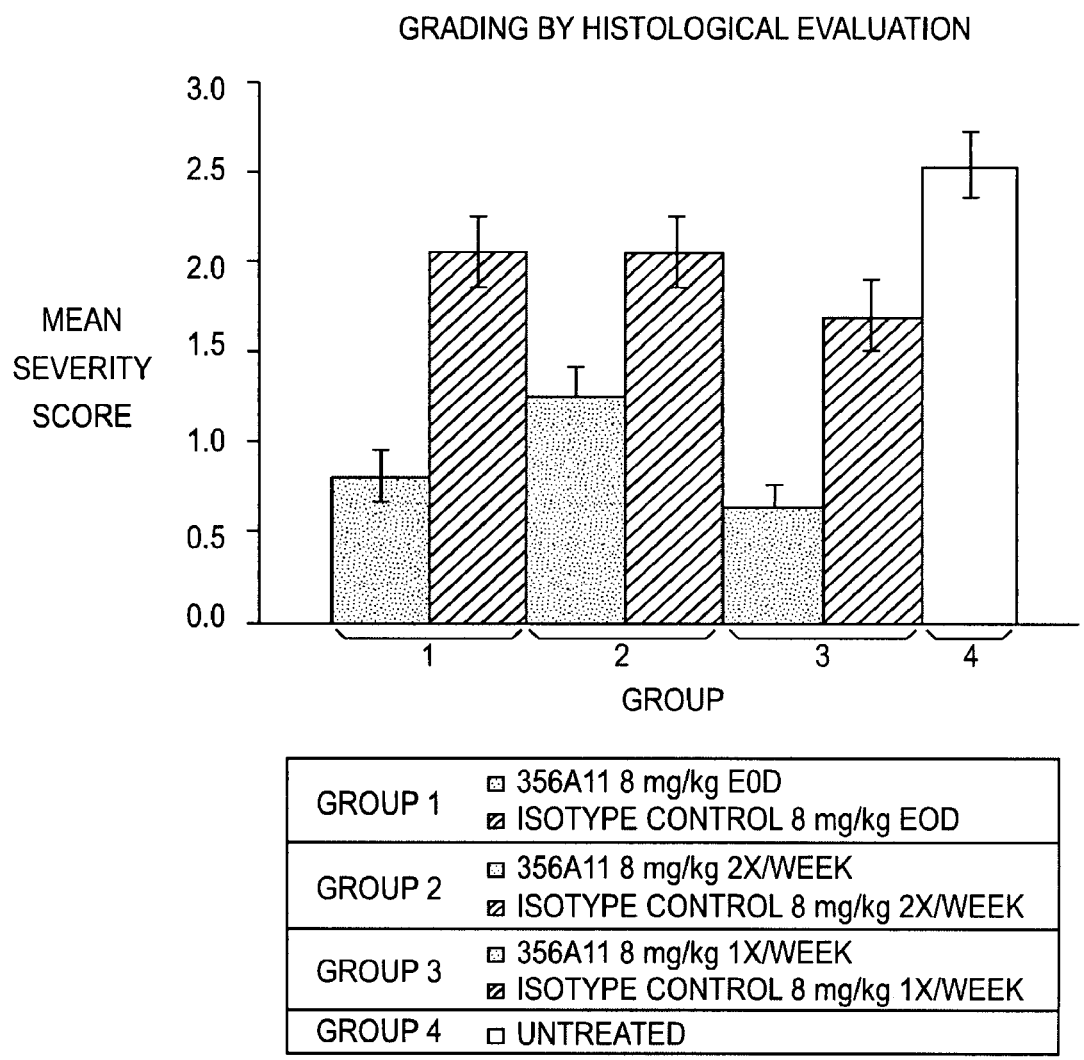
Figure 16D:
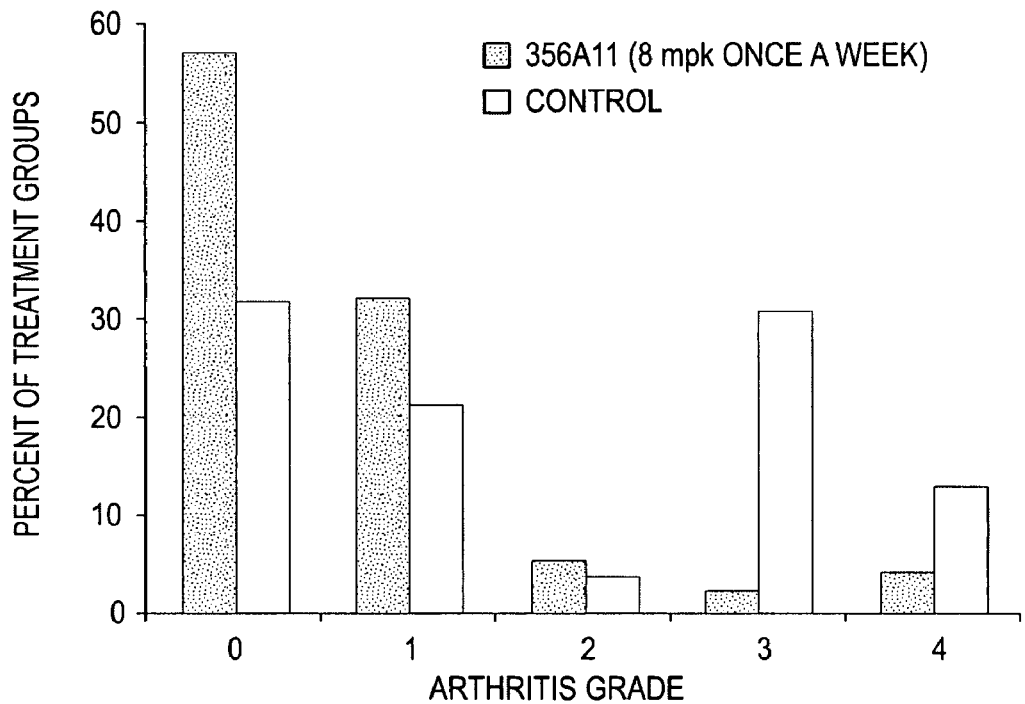
Figure 16E:
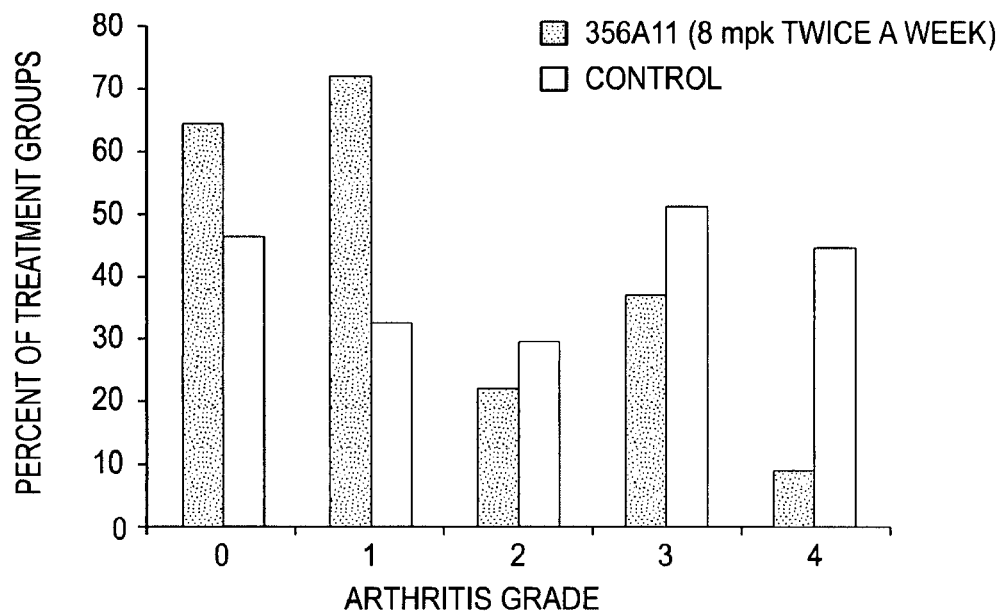
Figure 16F:
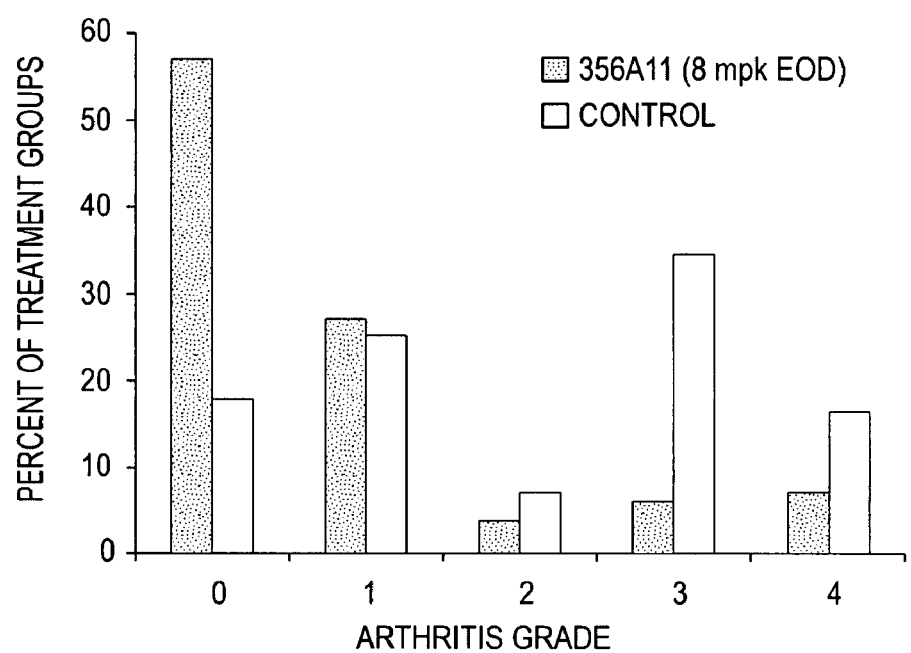

The anti human IL-22 antibodies of the invention have long in vivo half lives. For example, the in vivo half life of both 356A11 and 368D04 in DBA/1 mice was eight days. Specifically, a single dose of either 356A11 or 368D04 (16 mg/kg) was administered intraperitoneally to DBA/1 mice. The 356A11 and 368D04 antibodies were detected in serum from the mice using a human IgG1 ELISA. The time courses of 356A11 and 368D04 serum concentrations are shown in FIGS. 11A and B. The PK parameters of 356A11 and 368D04 are summarized in the Table 13 below.

TABLE 13

PK Parameters of 3536A11 and 368D04

| PK Parameter | 356A11 | 368D04 |
|---|---|---|
| AUC (ng · hr/mL) | 57273471 | 54052982 |
| Cmax (ng/mL) | 169854 | 177161 |
| Tmax (hr) | 48 | 24 |
| t½ (hr) | 192 | 206 |
| t½ (days) | 8 | 8.6 |

Example 13

Treatment of Arthritis

Arthritis is a disease characterized by inflammation in the joints. Rheumatoid Arthritis (RA) is the most frequent form of arthritis, involving inflammation of connective tissue and the synovial membrane, a membrane that lines the joint. The inflamed synovial membrane often infiltrates the joint and damages joint cartilage and bone. Both IL-22 and IL-22R protein and/or transcript are associated with human disease. In RA synovial biopsies, IL-22 protein is detected in vimentin$^+$ synovial fibroblasts and some CD68$^+$ macrophages while IL-22R is detected in synovial fibroblasts. Treatment of synovial fibroblasts with IL-22 induces the production of monocyte chemoattractant protein-1, MCP-1, as well as general metabolic activity (Ikeuchi, H. et al. (2005) *Arthritis Rheum.* 52:1037-46).

IL-22 is used to study its effect on cells from the synovial membrane, the membrane that lines the joints. Human fibroblast-like synoviocytes (HFLS) (Cell Applications (San Diego, Calif.)) are isolated from synovial tissues of rheumatoid arthritis patients undergoing joint surgery. HFLS are cultured with human IL-22 for 48 hours, and the supernatants are removed and tested for chemokines and cytokines by ELISA. IL-22 will increase HFLS secretion of chemokines MCP-1, Eotaxin, and IP-10, and cytokines TNFα, IL-6, and IL-8. These chemokines and cytokines are known in the art to promote inflammation through a number of activities, and increased concentrations in the joints caused by IL-22 exacerbates inflammation and RA.

The ability of human anti IL-22 antibody to ameliorate symptoms in collagen induced arthritis (CIA) was examined using the 356A11 and 368D04 antibodies. CIA is the standard mouse and rat model for studying rheumatoid arthritis, see e.g., Holmdahl et al., (2002) Ageing Res. Rev., 1:135. On day 0, male DBA/1 (Jackson Laboratory, Bar Harbor, Me.) mice were injected subcutaneously in the base of the tail with 100 μg of bovine Collagen Type II (Chondrex, Redmond, Wash.) in complete Freund's adjuvant, and on day 21, the mice were boosted with 100 μg of bovine Collagen Type II in incomplete Freund's adjuvant.

Mice were monitored at least two times a week for disease progression. The disease severity was scored using gross paw evaluation as follows: 0=no swelling, 1=1 to 2 swollen digits or swollen ankle, 2=more than 2 swollen digits or mild paw swelling, 3=extensive paw swelling, and 4=ankylosis of paw. Mice injected with an isotype control antibody after the collagen injections progressively developed disease. Treatment with either 356A11 or 368D04 significantly reduced disease progression. These were blind studies so the investigators did not know which animal group received which antibody until the end of the study.

Various doses of 356A11 and 368D04 were evaluated. The treatments of 356A11 or 368D04 (or a human IgG1λ isotype control antibody) were initiated when 10% of the mice in the treatment group had a disease severity score of at least 1. The antibody was administered at various frequencies: every other day, once a week, or twice a week, and the mice were monitored for disease progression. Administering either 8 or 16 mg $kg^{-1}$ of 356A11 every other day significantly blocked progression of CIA in multiple studies as shown in FIGS. 12A-B, 13, and 40-41. Four separate CIA studies (FIGS. 13A-D), testing with 8 mg $kg^{-1}$ of 356A11 every other day, show that the 356A11 antibody consistently blocked disease progression in the murine CIA model. Surprisingly, twice weekly and even weekly dosing with 8 mg $kg^{-1}$ of 356A11 was also sufficient in multiple studies to significantly block disease progression as shown in FIGS. 14-15, 41, and 44A-B.

In the first CIA study with 368D04 (administered every other day at 16 mg $kg^{-1}$), little or no efficacy was observed. However, administering 8 mg $kg^{-1}$ of 368D04 once a week in multiple studies significantly blocked disease progression as shown in FIGS. 46A-C.

The human anti IL-22 antibody's ability to significantly block disease progression when administered once a week in the CIA model indicates that the antibody could be administered with a similar dosing frequency, or an even further extended dosing frequency, such as once every two weeks, when administered in humans.

Treatment effects of the anti-IL-22 antibody were also evaluated by histopathological analysis of the paws. At the end of the study, animals were euthanized, paws were harvested and fixed with 10% formalin for histology, decalcified, and embedded in paraffin for sectioning and standard H&E staining. The paws were scored on a 5-grade scoring method (0-4) to characterize intensity and extent of arthritis. Inflammatory infilitrates were used for scoring in addition to other changes related to the inflammation, such as pannus formation, fibrous of the synovial membrane, articular cartilage erosin and/or subchondral bone destruction. Histology grades were determined using readings of individual paws: NAD=0 or nothing abnormal discovered; 1=slight to moderate; 2=miled to moderate; 3=marked; 4=massive. The histological effect of the therapeutic administration of the anti-IL-22 antibodies are shown in FIGS. 16A-F, 42A-C, 43, and 45A-B. As shown in FIGS. 16A-F, 42A-C, 43, and 45A-B, administering 356A111 in multiple studies ameliorated symptoms of collagen induced arthritis in mice. Similarly, administering 368D04 every other day at 8 mg $kg^{-1}$ in multiple studies ameliorated symptoms of collagen induced arthritis in mice. FIGS. 47A-C.

In addition to histopathological evaluations, bone destruction in treated mice was also examined. At the end of the study, paws were fixed in a lateral position and X-ray pictures were taken with a Faxitron machine. The Faxitron provides high resolution x-ray radiographs, and the high magnification capability provides enhanced imaging performance. The Faxitron radiographs correlated with visual gross paw evaluation scores and showed that treatment with anti-IL-22 antibody prevented bone destruction as compared to treatment with the isotype control antibody (data not shown).

Example 14

Detection of Serum IL-22 by ELISA and Increased Detection of Serum IL-22 In Vivo with 356A11 Treatment To date, the detection of IL-22 gene expression has only been reported at the RNA level. With the ELISA described below, IL-22 is not detected in normal mice. We have discovered, though, that this ELISA allows the detection of IL-22 in the circulation of arthritic mice. Furthermore, administration of the 356A11 antibody enables the detection of IL-22 at ten-fold higher levels. The 356A11 antibody at the doses given sequesters the cytokine, thus neutralizing its activity as shown in prior examples. With the circulation of this antibody within the blood stream, the antibody-sequestered IL-22 is now detected at higher levels with this ELISA. This is due to the unique and distinct epitopes of the capture and detector antibodies that constitute this mIL-22 ELISA. This ELISA detects IL-22/356A11, IL-22BP/IL-22, IL-22BP/356A11/IL-22 and naked IL-22, equivalently.

In the context of the CIA studies discussed previously (Example 13), arthritic mice were treated every other day with 16 mg $kg^{-1}$ of 356A11 antibody. At day 30 after the collagen boost, serum was collected from the mice after sacrifice. Levels of IL-22 in the serum samples were then measured by ELISA.

For this ELISA format, 1mGIL19P3/1, a rat IgG1k monoclonal anti-murine IL-22 antibody, was coated on a 96-well microtiter ELISA plate to be used as the capture antibody. Serum samples obtained from arthritic mice were serially diluted and then added to the coated microtiter plates. After allowing the samples to incubate with 1mGIL19P3/1 in the microtiter plates, the plates were washed and 2hmGIL19P3/5-bio, a rat IgG2ak monoclonal anti-IL-22 antibody conjugated to biotin was added to the plates as a detection antibody. After another incubating and washing step, streptavidin conjugated to horseradish peroxidase (HRP), which converts tetramethylbenzidine (TMB) to a blue pigment and is quantifiable with a spectrophotometer, was added, incubated and the plate washed. After the final incubation with TMB followed by addition of diluted $H_2SO_4$ to stop the enzymatic reaction, absorbance was measured at 450 nm using a spectrometer. Alternatively, and because the detector antibody's isotype, rat IgG2ak, is distinct from the coat antibody isotype, an HRP-conjugated secondary antibody that binds to rat IgG2a antibody can also be used. Using this sandwich ELISA, we demonstrated that the addition of increasing amounts of either mIL-22BP and/or 356A11 does not affect the ability to detect a fixed concentration of murine IL-22. This ELISA has been used to detect IL-22 in the serum of mice after an i.p., LPS injection.

When CIA mice were administered the 356A11 antibody, as indicated above, IL-22 was detected in the serum at levels ranging from about 1 ng/mL to about 9 ng/mL. See FIG. 17. Conversely, the arthritic mice in the control treatment group, receiving a human IgG1λ isotype control antibody, recorded significantly lower in vivo levels of IL-22 (less than 1 ng/mL).

Figure 17:
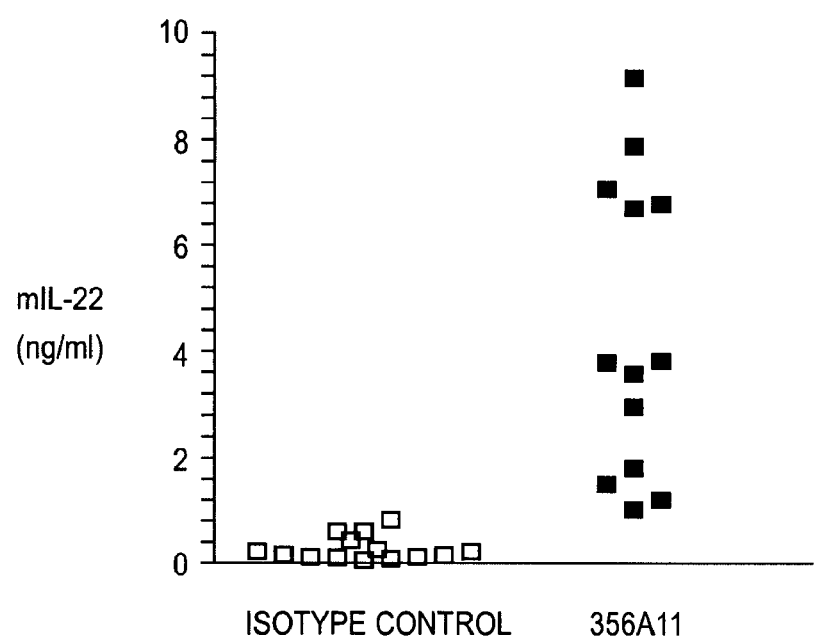
FIG. 17. Detection and stabilization of in vivo IL-22 (ng/mL) in arthritic mice treated with 356A11.
Figure 18:
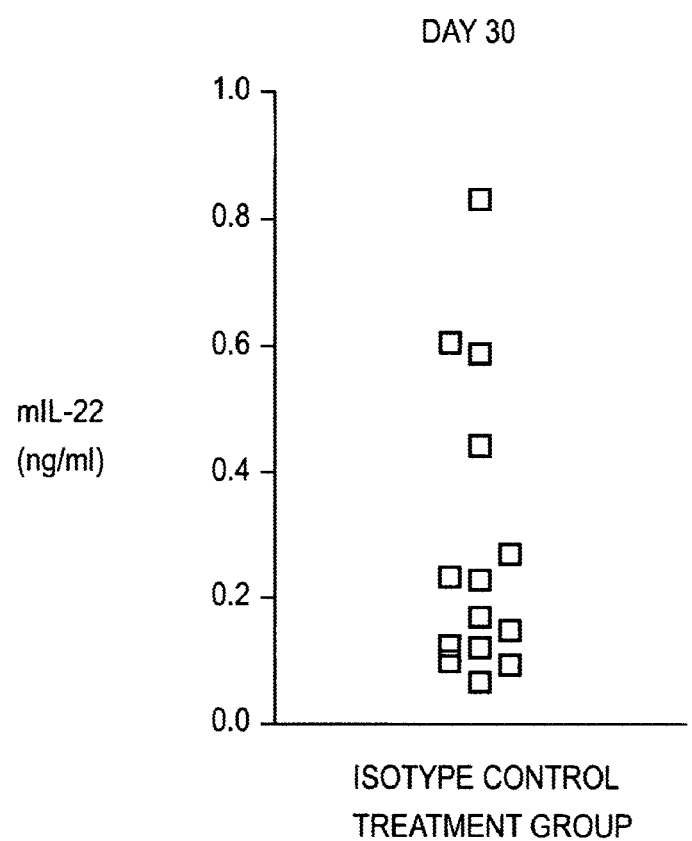
FIG. 18. Detection of in vivo IL-22 (ng/mL) in arthritic mice administered an isotype control antibody.

See FIGS. 17 and 18. Thus, the 356A11 antibody captures IL-22 in vivo to produce a stabilized antibody/cytokine complex that circulates. This in turn permits the detection of in vivo IL-22 with increased sensitivity as shown in FIG. 16. In contrast to the large amounts of antibody used in the above study, it is proposed that 356A11 at considerably lower levels could also be administered and have the same effect.

Example 15

Treatment of Psoriasis

Figure 19:
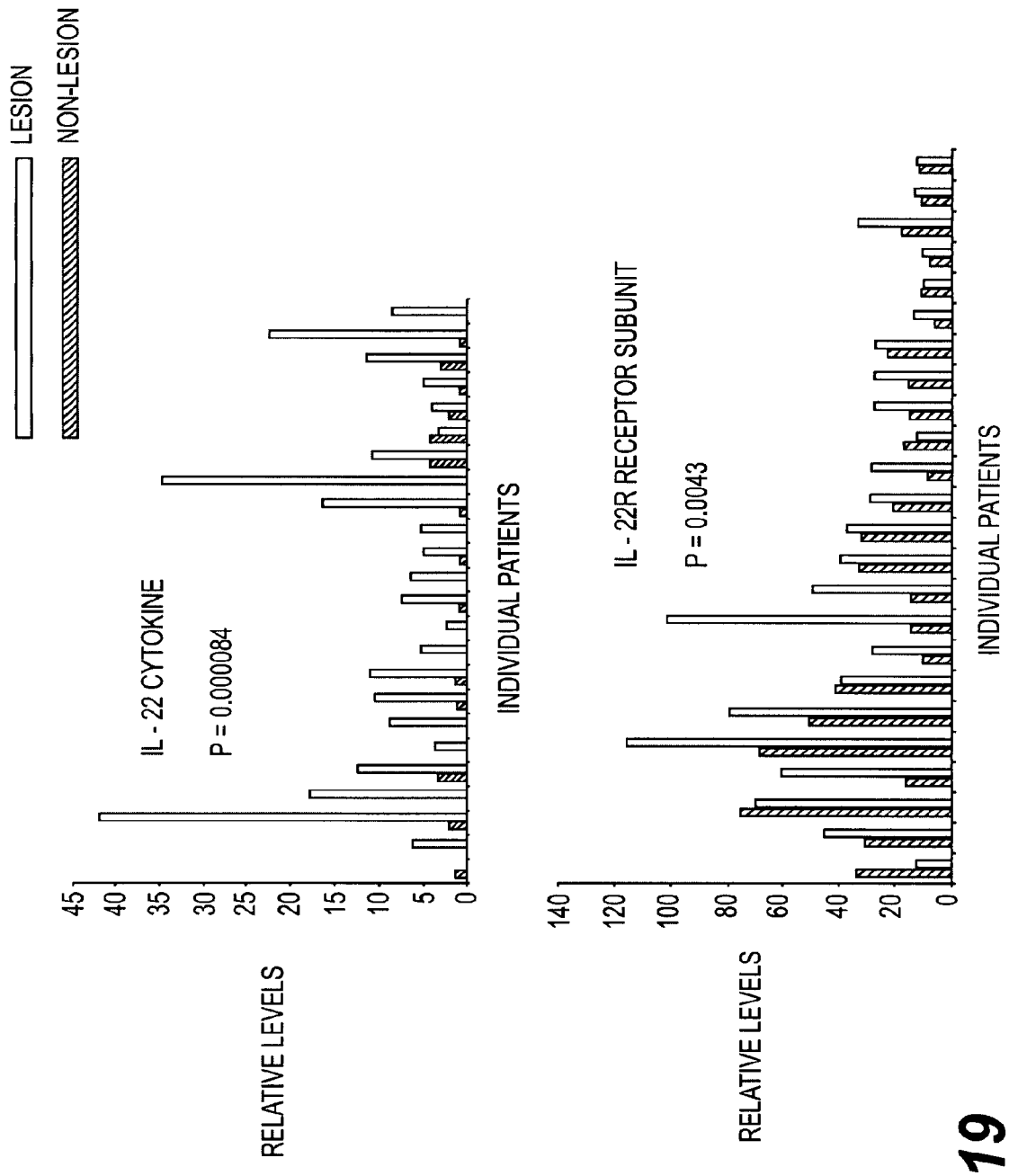
FIG. 19. Upregulation of IL-22 and IL-22R protein in human psoriatic lesions.

Levels of IL-22 and IL-22R RNA were measured in paired tissue samples (lesion vs. non-lesion) from human psoriatic patients using quantitative PCR. This study demonstrated that levels of IL-22 and IL-22R were upregulated in psoriatic lesions. FIG. 19. Other evidence implicates IL-22 in the development of psoriasis. For example, transgenic mice that constitutively express IL-22 present with thick skin, mononuclear immune cell infiltrates, characteristic of psoriatic lesions, and die soon after birth. WO 03/083062. Similarly, administering IL-22 to mice induces thickening of skin and mononuclear immune cell infiltrates. WO 03/083062. IL-22 also induces human keratinocyte hyperplasia, suggesting an important role in skin inflammatory processes. Boniface et al., J. Immunol., 2005174:3695-3702.

Xenogenic transplantation in SCID mice is a recognized model for studying psoriasis, see e.g., Boehncke et al. Br. J. Dermatol. 2005, 153(4):758-66. Under local anesthesia, lesional split-skin (thickness about 0.5 mm) is exised from a patient with chronic plaque-stage psoriasis. Human split grafts are transplanted on the back of 6-8 week old SCID mice. Mice are given 3 weeks to accept the graft and heal. At 22 days following transplantation, mice are injected intraperitoneally with 8 mg kg$^{-1}$ of human anti-Il-22 antibodies, such as germlined 087B03, 368D04, 354A08 or 356A11, every other day. As a negative control, mice receive daily intragastric applications of 200 µL PBS. As a positive control, mice receive daily intragastric application of 2 mg kg$^{-1}$ dexamethasone in 200 µL PBS. The negative controls develop hallmarks of psoriasis, including acanthosis, papillomatosis, parakeratosis, and a dense mononuclear infiltrate. Mice are sacrificed at day 50 following transplantation and the grafts with surrounding skin are excised. One half of the graft is fixed in formalin and the other half is frozen in liquid nitrogen. Routine hematoxylin and eosin stainings are performed and the pathological changes of the grafts are analysed both qualitatively (epidermal differentiation) and quantitatively (epidermal thickness, inflammatory infiltrate). The mean epidermal thickness may be measured from the tip of the rete ridges to the border of the viable epidermis using an ocular micrometer. The density of the inflammatory infiltrate may be determined by counting the number of cells in three adjacent power fields. Disease progression may be evaluated using histological analysis to measure hallmarks of psoriasis, such as acanthosis, papillomatosis, parakeratosis, inflammatory infiltrates, and the appearance of the corneal and granular layers.

Negative control mice injected with 200 µL PBS or an isotype-matched control antibody following graft transplantation progressively develop psoriasis. Because psoriatic lesions express higher levels of IL-22, treatment with anti-IL-22 antibodies, for example with germlined 087B03, 368D04, 354A08 or 356A11, is expected to suppress or delay psoriasis, as confirmed in the adoptive transfer study reported below.

Adoptive transfer of CD4+CD45rb$^{high}$ Tcells in scid/scid mice is another recognized model for studying psoriasis in mice. Hong et al., J. Immunol., 162(1):7480-91 (1999). In this model, coadministration of LPS and IL-12 or staphylococcal enterotoxin B into scid/scid mice 1 day after adoptive transfer of CD4+CD45rb$^{high}$ Tcells induces skin lesions exhibiting the hallmarks observed in human psoriasis.

Using a slight modification of this model, CD4+CD45rb$^{high}$CD25-Tcells were transferred to scid/scid mice with or without coadmistration of LPS and IL-12 at day one following adoptive transfer. CD4+CD45rb$^{high}$CD25-Tcells were able to induce psoriatic lesions when transferred into scid/scid mice even when they were administered without LPS and IL-12. Thus, administration of IL-12 and LPS following adoptive transfer did not seem to alter the efficacy of anti IL-22 antibodies in this model.

Cells for adoptive transfer were prepared as described before with slight modification. Spleens were collected from 6- to 8-wk-old BALB/cBy donor mice (Jackson Laboratory, Bar Harbor, Me.) and splenocytes were isolated by mechanical homogenization of whole spleens. CD4$^+$ T cells were selected using murine CD4 enrichment kit (R&D) according to the manufacturer's instruction. CD4 enriched T cells were labeled with anti-CD4-PE (Pharmingen), anti-CD45RB-FITC and anti-CD25-APC (Pharmingen). Cells were sorted using a Moflo (Becton Dickinson, San Jose, Calif.) cell sorter. CD4+CD45Rb$^{high}$CD25-cells were collected and were >95% pure. Cells were re-suspended in saline at 2×10$^6$ cells/ml and 4×10$^5$ cells were injected i.p. into C.B-17/Prkdc scid/scid mice (Jackson Laboratory, Bar Harbor, Me.). In some cases, 10 ng IL-12 and 20 ug LPS were administrated i.p. to the recipient mice that received CD4$^+$CD45Rb$^{high}$ cells on day 1 and an additional dose of IL-12 was administered on day 3. Mice were dosed with 16 mg/kg of either an isotype control antibody or anti-IL-22 antibodies (356A11 or 368D04) on the day of adoptive transfer and once a week thereafter for 10 weeks. Mice were monitored for clinical symptoms of skin lesions twice a week. At termination of the study, mouse ear, skin, lymph nodes, and spleen were harvested for further ex-vivo studies.

Clinical Evaluation

Mice were evaluated by blinded investigators twice per week starting 10 days post adoptive transfer. To record disease progression semiquantitative clinical scores from 0 to 6 were given based on physical appearance: 0=no skin or ear symptoms; 0.5=slight erythema on ear or eye lid, 1=mild, moderate erythema on ears or eyelids with mild thickening of the ear (<2% of the body surface); 2=moderate to severe erythema on 2-10% of the body surface, mild scaling; 3=severe erythema and scaling on 10%-20% of the body surface; 4=very severe, extensive erythema and scaling on 20%-40% of the body surface. 5=very severe, extensive erythema and scaling on 40%-60% of the body surface. 6=very severe, extensive erythema and scaling and scaling on greater than 60% of the body surface. Specific observations were noted based on fur condition, ear manifestations, eyelid appearance, and presence of inflammation on limbs and tail.

In the study without coadministration of LPS and IL-12, antibodies 356A11 and 368D04 significantly suppressed skin inflammation, when compared to control antibody treated mice, starting as early as day 21 for 356A11 and day 35 for 368D04 (FIGS. 20A-B). Similar results were observed in the study with coadministration of LPS and IL-12 at day one following adoptive transfer, with 356A11 and 368D04 significantly suppressing skin lesions, when compared to the control antibody, starting as early as day 28 post adoptive transfer. (FIGS. 27A and B). In a separate study, 356A11, without (FIGS. 34A-B) or with (Figures and 37A-B) coadministration of LPS and IL-12 at day one following adoptive transfer, significantly suppressed skin inflammation, when compared to control antibody treated mice, starting as early as day 21.

Cytokine Detection

Mouse serum or supernatants from the cell culture were quantitated for IL-6, IFNγ, and TNFα using an ELISA kit (R&D system). ELISA for IL-22, IL-17A, IL-17F, and IL-17 A/F heterodimer involved coating a 96-well flat-bottom plate (Costar) overnight at 4° C. with 100 μl of a 2 μg/ml solution of anti-IL-22 (Ab-01), anti-IL-17A (R&D), or anti-IL-17F (RK015-01) antibody in PBS. Plates were then washed with PBS/Tween (0.05% Tween-20 in PBS) and blocked with 200 μl PBS plus 1% BSA for 1 h at RT. Antibodies to murine IL-22 (Ab-01, Ab-02, and Ab-03) and murine IL-17F (RK015-01) were generated by methods described in Li et al., *Int. Immunopharmacol.* 4:693-708 (2004). In between all of the following steps, plates were washed with PBS/Tween. IL-22 (R&D), IL-17A (R&D), IL-17F, and IL-17A/F standards, sample supernatants and serum samples (diluted with PBS 1:5) were then added. Biotinylated secondary antibodies for anti-IL-22 (Ab-03), anti-IL-17A (R&D), and anti-IL-17F (RK015-01) were then added to the respective plates at 0.5 μg/ml in 1% BSA/PBS solution and incubated for 1 h at 37° C. Poly HRP-labeled streptavidin (Pierce) was added according to manufacturer's instruction for 15 minutes. The plate was developed by adding TMB substrate for 15-30 minutes. Assay was then read on a Molecular Devices (Sunnyvale, Calif.) plate reader and data were analyzed using SOFTmax software.

In the study without coadministration of LPS and IL-12, higher levels of serum IL-22 were detected in mice treated with 356A11 than in mice treated with control antibody, indicating that 356A11 captures and stabilizes IL-22 in vivo (FIG. 21), as discussed in Example 14. Similar results were also observed in 356A11 treated mice with coadministration of LPS and IL-12 at day one following adoptive transfer. (FIG. 28). These results were replicated in a separate study with 356A11 without (FIG. 35) and with (FIG. 38) coadministration of LPS and IL-12 at day one following adoptive transfer. Serum IL-22 was not detected in 368D04 treated mice (FIG. 21).

Figure 22A:
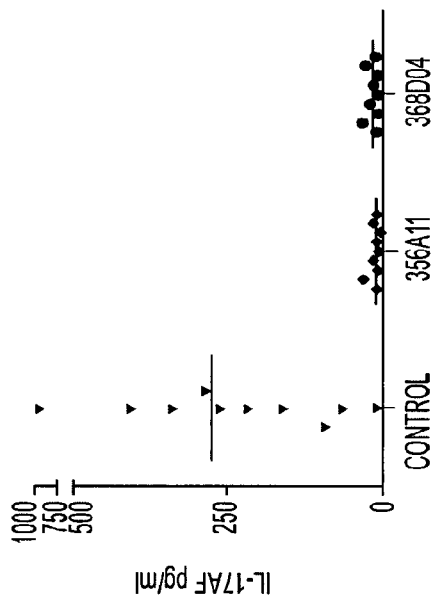
FIG. 22. Detection of in vivo serum levels of (A) IL-17A, (B) IL-17F, (C) IL-17A/F; and (D) IL-6 in psoriatic mice treated with 16 mg/kg of 356A11, 368D04, or a control antibody.
Figure 22C:
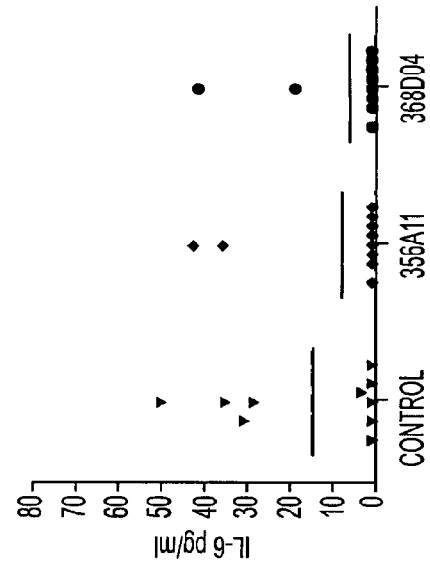
Figure 22B:
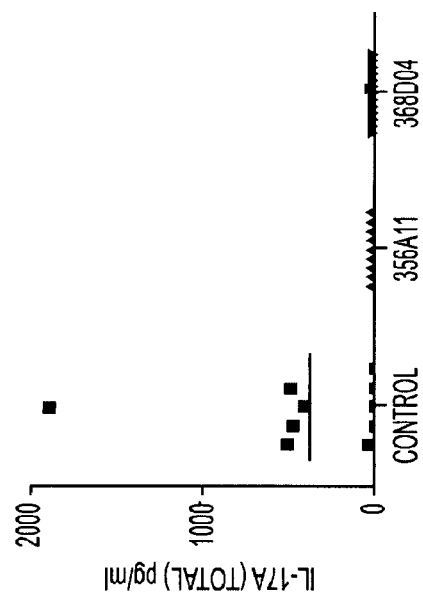
Figure 22D:
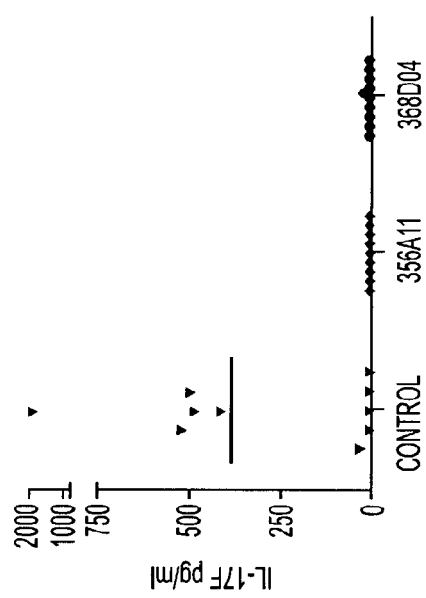

In the study without coadministration of LPS and IL-12, significantly lower serum levels of IL-17F, IL-17A, IL-17A/F were detected in mice treated with 356A11 and 368D04 (FIGS. 22A-C). Also observed was a trend of decreasing IL-6 serum levels in mice treated with 356A11 and 368D04 (FIG. 22D). IFNγ and TNFα were below the detection limit in serum from mice treated with control, 356A11, or 368D04 antibodies. Similar results were also observed in 356A11 treated mice with coadministration of LPS and IL-12 at day one following adoptive transfer. (FIGS. 29A-D). In a separate study, significantly lower serum levels of IL-17A and IL-6 were also observed in mice treated with 356A11 without (FIGS. 39A-B) and with (FIGS. 39C-D) coadministration, of LPS and IL-12 at day one following adoptive transfer.

Lymph Node Cell Isolation and Stimulation

Psoriatic lesions in this model usually progress from the ear, eye, face and neck to the rest of the body. Mice treated with therapeutics usually develop mild skin lesions around the eye and ear only. Therefore, cervical lymph nodes that drain the face were isolated from each mouse to obtain the highest number of activated cells. Lymph node (LN) cells were recovered by mechanical homogenization. LN cells were pooled from about 9 to 10 mice per group and resuspended at $1 \times 10^6$/ml in complete RPMI 1640 medium supplemented with 10% FBS (HyClone), $5 \times 10^{-5}$ M 2-ME (Sigma), 2 mM glutamine (Life Technologies, Gaithersburg, Md.), 10 U/ml penicillin, 100 μg streptomycin (Life Technologies), and 15 mM HEPES. A total of 200 μg/well of this suspension was then placed in a 96-well plate and stimulated with anti-CD3 plus anti-CD28 (1 μg/ml each) for 48 hours.

Intracellular Cytokine Staining

To examine the effects of IL-22 neutralization on the effector T cell population, intracellular cytokine staining was performed on cervical lymph node cells. Cells were stimulated with 50 ng/ml PMA (Sigma), 1 μg/ml ionomycin (Sigma), and GolgiPlug (Pharmingen) for 12 hours. Cells were first stained for surface antigen (CD4) and then treated with Cytofix/Cytoperm (Pharmingen) according to manufacturer's directions. Intracellular cytokine staining was performed using antibodies to IFNγ, IL-22, IL-17A, IL-17F, TNFα, and relevant IgG isotype controls. Anti-IL-22 (Ab-02) was labeled with Alexa 647 (Molecular Probes) and anti-IL-17F (RK015-01) was labeled with FITC (Pierce Biotechnologies) according to manufacturer's directions.

Figure 23:
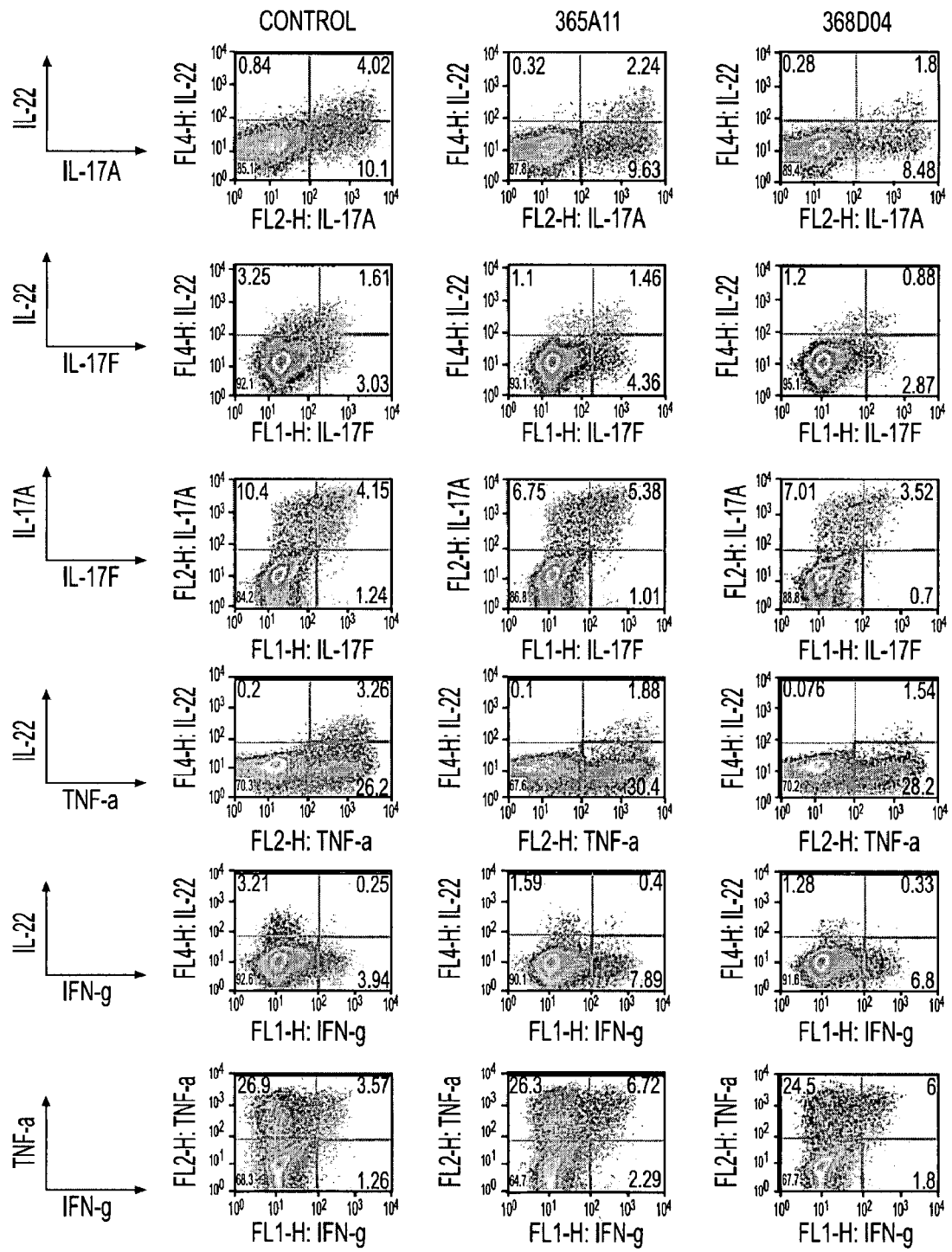
FIG. 23. Flow cytometric analysis of pooled CD4+ lymph node cells treated with PMA and ionomycin following isolation from psoriatic mice treated with 16 mg/kg of 356A11, 368D04, or a control antibody and stained for IL-22 and IL-17A; IL-22 and IL-17F; IL-17A and IL-17F; IL-22 and TNFα; IL-22 and IFNγ; or TNFα and IFNγ.
Figure 24A:
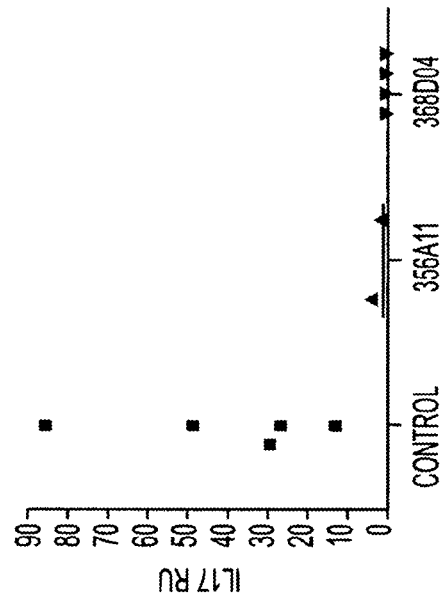
FIG. 24. Cytokine gene expression in the ears of psoriatic mice treated with 16 mg/kg of 356A11, 368D04, or a control antibody. (A) IL-22. (B) IL-17. (C) IFNγ. (D) IL-17F. (E) IL-6.
Figure 24B:
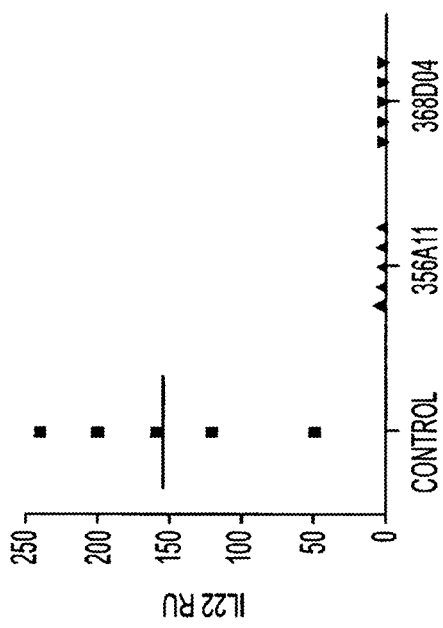
Figure 24C:
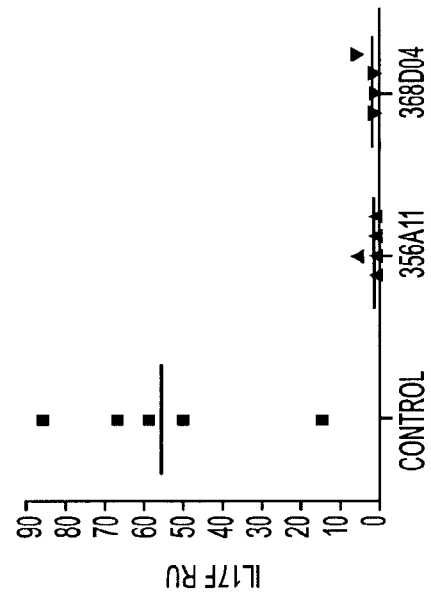
Figure 24D:
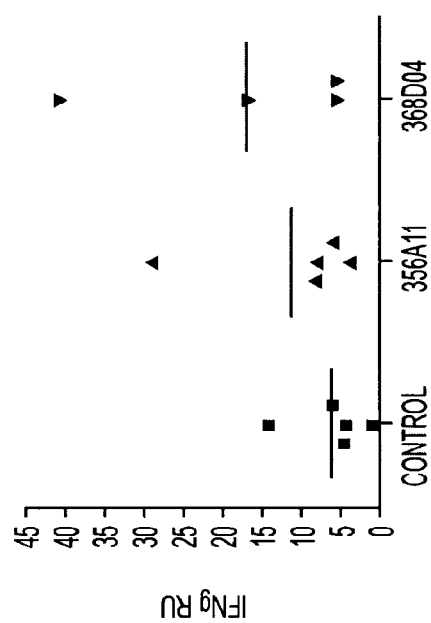
Figure 24E:
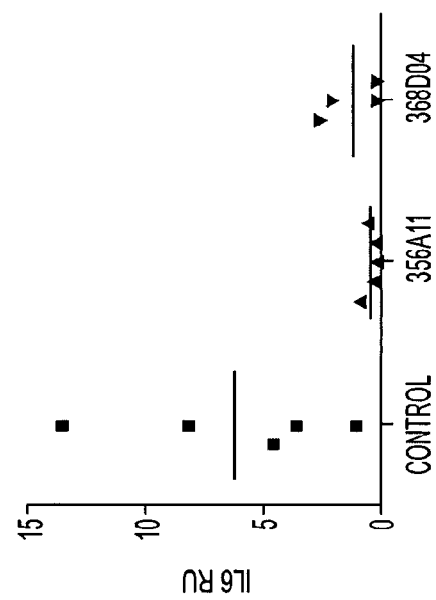
Figure 25A:
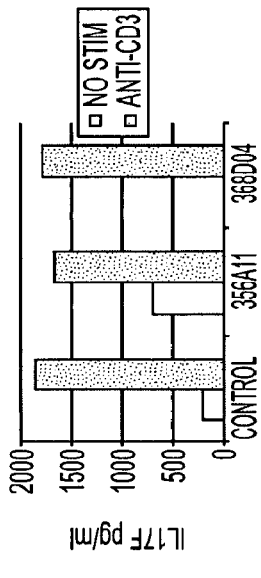
FIG. 25. Cytokine detection in the supernatants of pooled lymph node cells isolated from psoriatic mice treated with 16 mg/kg of 356A11, 368D04, or a control antibody and stimulated ex vivo with and without platebound, anti-CD3 antibody. (A) IL-22. (B) IL-6. (C) IFNγ (D) IL-17F. (E) IL-17A/F. (F) IL-17A.
Figure 25B:
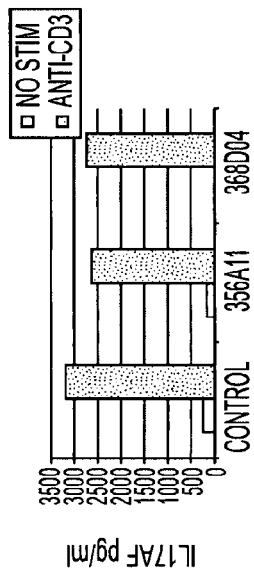
Figure 25C:
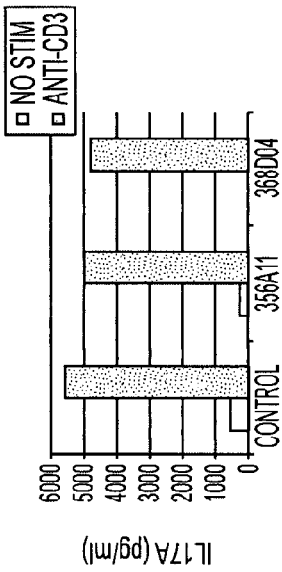
Figure 25D:
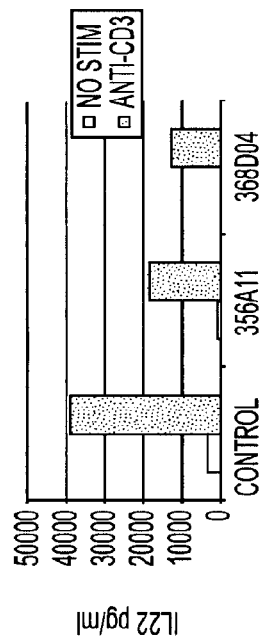
Figure 25E:
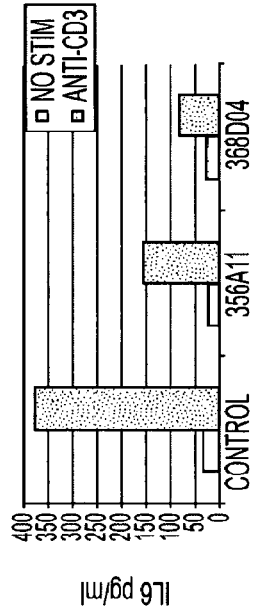
Figure 25F:
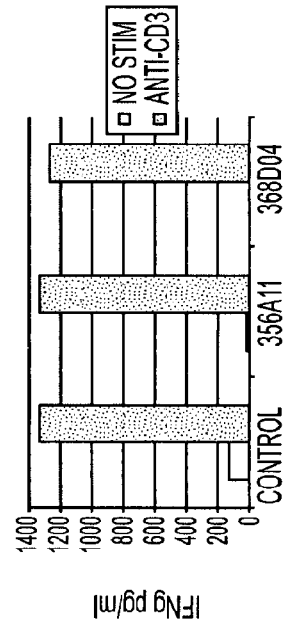
Figure 26A:
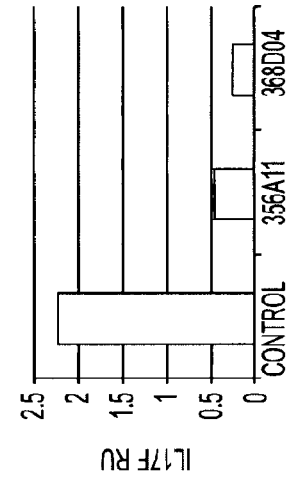
FIG. 26. Cytokine gene expression in pooled lymph node cells isolated from psoriatic mice treated with 16 mg/kg of 356A11, 368D04, or a control antibody and stimulated ex vivo with platebound, anti-CD3 antibody. (A) IL-22. (B) IL-6. (C) IFNγ (D) IL-17F. (E) IL-17A.
Figure 26D:
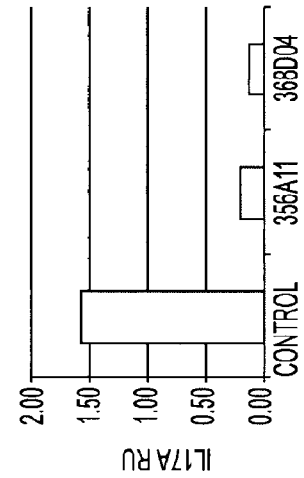
Figure 26B:
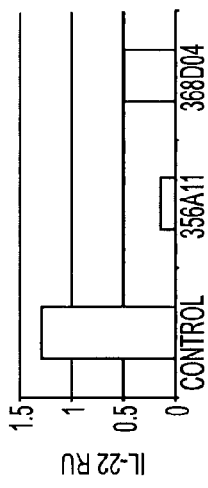
Figure 26C:
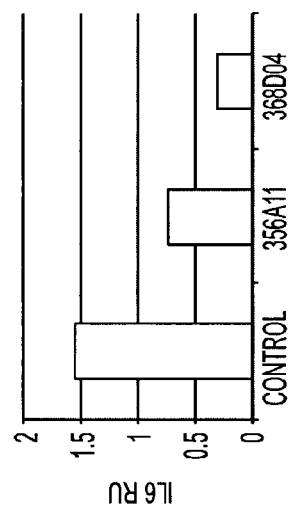
Figure 26E:
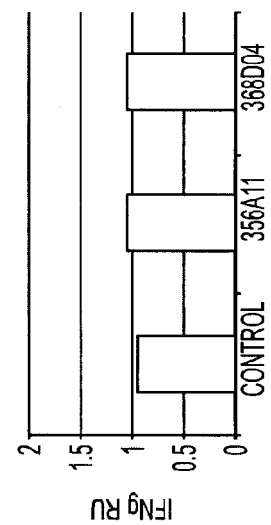

Cells were analysed on a gated CD4+ population. FACS analysis results show that in mice treated with 356A11 and 368D04 (without coadministration of LPS and IL-12), there were lower percentages of CD4+ T cells producing IL-22, IL-17A, and both IL-22 and IL-17F, but higher percentages of CD4+ T cells producing IFNγ when compared to the isotype control treated mice (FIG. 23). Similar results were also observed in 356A11 treated mice with coadministration of LPS and IL-12 at day one following adoptive transfer. (FIG. 31).

Quantitation of Cytokine Transcripts.

RNA was isolated from the mouse ears or LN cells (after stimulation) using the Qiagen Rneasy kit (Qiagen). Quantitative PCR for cytokine transcripts was performed using prequalified primers and probes (Applied Biosystems). The ΔΔCt method was used to normalize transcript to GAPDH and to calculate fold induction relative to control mice.

The quantitative PCR results using RNA from mouse ears show that mice treated with 356A11 and 368D04 had lower IL-22, IL-17F, IL-17A, and IL-6 gene expression but enhanced IFNγ expression when compared to mice treated with the control antibody (FIGS. 24A-E). Similar results were also observed in 356A11 treated mice with coadministration of LPS and IL-12 at day one following adoptive transfer. (FIGS. 30A-E). These results were replicated in a separate study with 356A11 (without coadministration of LPS and IL-12), where it was also observed that 356A11 treated mice had lower IL-1 family 6 protein (IL-1F6) gene expression and unchanged IL-22 binding protein and IL-22 receptor subunit (IL-22R1) gene expression, as compared to mice treated with the control antibody. (FIGS. 36A-H).

The quantitative PCR results using RNA from lymph node cells, stimulated with anti-CD3 and anti-CD28 for 48 hrs, as described above, show that 356A11 and 368D04 suppressed IL-22, IL-6, IL-17A, and IL-17F gene expression ex vivo but affected no significant changes in IFNγ gene expression. (FIGS. 26A-E). Similar results were observed in 356A11 treated mice with coadministration of LPS and IL-12 at day one following adoptive transfer. (FIGS. 33A-E).

Supernatants from the lymph node cells stimulated with anti-CD3 and anti-CD28, as described above, were collected for cytokine analysis using ELISA kits (R&D system) as discussed previously. Cytokine ELISA results mirrored the LN gene expression data, showing that 356A11 and 368D04 suppressed IL-22, IL-6, IL-17A, and IL-17F secretion ex vivo but produced no significant changes in IFNγ secretion from stimulated cells. (FIGS. 25A-F). Similar results were observed in 356A11 treated mice with coadministration of LPS and IL-12 at day one following adoptive transfer. (FIGS. 32A-E).

Histopathologic Analysis

Necropsies were performed on mouse tissue upon in vivo study termination. Tissue samples from ear, trunck skin were collected and fixed in 10% formalin solution for section preparation and analysis. To record disease severity, semi-quantitive histological scores from 0 to 5 were assigned based on the severity of inflammation. Histological evaluation was performed in a blinded fashion by a board certified pathologist. 0=within normal limit; 1=minimal; 2=mild, 3=moderate, 4=marked, and 5=severe.

Immunohistochemistry Analysis

Tissue samples were collected and embedded in Tissue Tek OCT (Miles, Elkhurt, Ind.) compound and frozen with dry ice for cryostat-cut sections. Tissue sections (5 µm) were fixed in 100% acetone and stained with anti-CD4, anti-CD11b and anti-neutrophil antibody (PharMingen). Tissues were evaluated as negative=0, mild=1, moderate=2, and severe=3 based on visual fluorescent microscopy detection.

Histology findings demonstrate that mice treated with 356A11 and 368D04 experienced lesser keratinocyte proliferation, rete pegs, and inflammatory cell infiltrates in the skin when compared to the isotype control treatment. Additionally, immunohistochemistry results showed that 356A11 decreased the number of CD4+, CD11b+ (macrophages) and neutrophils in the epidermal, dermal, and sub cutis layers. The histological results mirrored that of the clinical findings and support using IL-22 antagonists, such as the antibodies of this invention, as therapeutic agents for the treatment of psoriasis and other psorasis-like skin diseases.

Overall results demonstrate that antibodies of this invention, such as 087B03, 368D04, 354A08 or 356A11, are efficacious in this murine model of psoriasis and indicates that treatment with anti-IL-22 antibodies, including 087B03, 368D04, 354A08 or 356A11, provides an efficacious strategy for therapeutic intervention in human psoriasis.

Example 16

Treatment of Patients

Patients with an autoimmune disorder, respiratory disorder, inflammatory condition of the skin, cardiovascular system, nervous system, kidneys, liver and pancreas or transplant patients are among the type of patients that may be treated with the antibodies of the invention. Exemplary treatment regimens and expected outcomes are provided below. Dosages and frequencies of administration other than those in Table 14 may also be used. The skilled artisan can adjust treatment regimens as necessary based on route of administration or other known variables, such as the age, weight, condition, sex, severity of medical condition, etc. of the patient to be treated.

TABLE 14

Treatment Regimens

| Disorder | Treated with | Dosage Range | Frequency | Expected Outcome |
| --- | --- | --- | --- | --- |
| Multiple Sclerosis | 087B03, 368D04, 356A11, or 354A08 | 250 µg/kg to 2 mg/kg | weekly, biweekly, or monthly | improvement or stabilization of condition |
| Rheumatoid Arthritis | 087B03, 368D04, 356A11, or 354A08 | 250 µg/kg to 2 mg/kg | weekly, biweekly, or monthly | improvement or stabilization of condition |
| Psoriasis | 087B03, 368D04, 356A11, or 354A08 | 250 µg/kg to 2 mg/kg | weekly, biweekly, or monthly | improvement or stabilization of condition |
| IBD | 087B03, 368D04, 356A11, or 354A08 | 250 µg/kg to 2 mg/kg | monthly, biweekly, or monthly | improvement or stabilization of condition |
| Alzheimer's Disease | 087B03, 368D04, 356A11, or 354A08 | 250 µg/kg to 2 mg/kg | monthly, biweekly, or monthly | improvement or stabilization of condition |

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supercede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The names of the parties to the joint research agreement are 1) Wyeth and 2) Cambridge Antibody Technology Limited.

We claim:

1. A method of treating an interleukin-22 (IL-22)-associated disorder, in a subject, wherein the IL-22-associated disorder is atopic dermatitis, said method comprising, administering to the subject an antibody, or antigen-binding fragment thereof, that specifically binds to human IL-22, in an amount sufficient to inhibit or reduce immune cell activity in the subject, thereby treating the disorder, wherein the antibody, or antigen-binding fragment thereof, comprises a $V_H$ domain comprising three complementary determining regions (CDRs) comprising the amino acid sequences of SEQ ID NO:620, 621, and 622 and a $V_L$ domain comprising three CDRs comprising the amino acid sequences of SEQ ID NO: 623, 624, and 625, or wherein the antibody, or antigen-binding fragment thereof, comprises a $V_H$ domain comprising three complementary determining regions (CDRs) comprising the amino acid sequences of SEQ ID NO:602, 603, and 604 and a $V_L$ domain comprising three CDRs comprising the amino acid sequences of SEQ ID NO:605, 606, and 607.

2. The method of claim 1, wherein the $V_L$ domain comprises the amino acid sequence of SEQ ID NO: 600 or 618.

3. The method of claim 2, wherein the $V_H$ domain comprises the amino acid sequence of SEQ ID NO: 599 or 617.

4. The method of claim 1, wherein the $V_H$ domain comprises the amino acid sequence of SEQ ID NO: 617 and the $V_L$ domain comprises the sequence of SEQ ID NO: 618.

5. The method of claim 1, wherein the $V_H$ domain comprises the amino acid sequence of SEQ ID NO: 599 and the $V_L$ domain comprises the sequence of SEQ ID NO: 600.

6. The method of claim 1, wherein the antibody, or antigen-binding fragment thereof, has an association constant for human IL-22 of at least $10^{10}$ $M^{-1}$.

7. The method of claim 6, wherein the association constant for human IL-22 is at least $10^{11}$ $M^{-1}$.

8. The method of claim 1, wherein the antibody, or antigen-binding fragment thereof, blocks IL-22 mediated BAF3 cell proliferation with an $IC_{50}$ of 150 pM or less, wherein the BAF3 cells comprise a human IL-22 receptor.

9. The method of claim 8, wherein the antibody, or antigen-binding fragment thereof, blocks IL-22 mediated BAF3 cell proliferation with an $IC_{50}$ of 100 pM or less.

10. The method of claim 1, wherein the antibody, or antigen-binding fragment thereof, blocks IL-22 mediated GROa secretion from HT29 cells with an $IC_{50}$ of 1 nM or less.

11. The method of claim 10, wherein the antibody, or antigen-binding fragment thereof, blocks IL-22 mediated GROa secretion from HT29 cells with an $IC_{50}$ of 150 pM or less.

12. The method of claim 1, wherein the subject is a mammal.

13. The method of claim 1, wherein the subject is a human.

14. The method of claim 13, wherein the antibody is administered in a range chosen from 1 μg/kg to 20 mg/kg, 1 μg/kg to 10 mg/kg, 1 μg/kg to 1 mg/kg, 10 μg/kg to 1 mg/kg, 10 μg/kg to 100 μg/kg, 100 μg to 1 mg/kg, 250 μg/kg to 2 mg/kg, 950 μg/kg to 1 mg/kg, 500 μg/kg to 2 mg/kg, 1 mg/kg to 5 mg/kg, 5 mg/kg to 10 mg/kg, 10 mg/kg to 20 mg/kg, 10 mg/kg to 25 mg/kg, and 20 mg/kg to 30 mg/kg.

15. A method of treating atopic dermatitis in a subject, said method comprising, administering to the subject an antibody, or antigen-binding fragment thereof, that specifically binds to human IL-22, in an amount sufficient to inhibit or reduce immune cell activity in the subject, thereby treating the atopic dermatitis, wherein the antibody, or antigen-binding fragment thereof, comprises a $V_H$ domain comprising an amino acid sequence that is at least 85% identical to SEQ ID NO:617 and a $V_L$ domain comprising an amino acid sequence that is at least 85% identical to SEQ ID NO:618 or wherein the antibody, or antigen-binding fragment thereof, comprises a $V_H$ domain comprising an amino acid sequence that is at least 85% identical to SEQ ID NO:599 and a $V_L$ domain comprising an amino acid sequence that is at least 85% identical to SEQ ID NO:600.

16. The method of claim 15, wherein the $V_H$ domain comprises an amino acid sequence that is at least 90% identical to SEQ ID NO:617 and the $V_L$ domain comprises an amino acid sequence that is at least 90% identical to SEQ ID NO:618 or wherein the $V_H$ domain comprises an amino acid sequence that is at least 90% identical to SEQ ID NO:599 and the $V_L$ domain comprises an amino acid sequence that is at least 90% identical to SEQ ID NO:600.

17. The method of claim 15, wherein the $V_H$ domain comprises an amino acid sequence that is at least 95% identical to SEQ ID NO:617 and the $V_L$ domain comprises an amino acid sequence that is at least 95% identical to SEQ ID NO:618 or wherein the $V_H$ domain comprises an amino acid sequence that is at least 95% identical to SEQ ID NO:599 and the $V_L$ domain comprises an amino acid sequence that is at least 95% identical to SEQ ID NO:600.

18. The method of claim 15, wherein the $V_H$ domain comprises an amino acid sequence that is at least 98% identical to SEQ ID NO:617 and the $V_L$ domain comprises an amino acid sequence that is at least 98% identical to SEQ ID NO:618 or wherein the $V_H$ domain comprises an amino acid sequence that is at least 98% identical to SEQ ID NO:599 and the $V_L$ domain comprises an amino acid sequence that is at least 98% identical to SEQ ID NO:600.

19. The method of claim 15, wherein the $V_H$ domain differs by no more than 5 amino acids from the amino acid sequence of SEQ ID NO:617 and wherein the $V_L$ domain differs by no more than 5 amino acids from the amino acid sequence of SEQ ID NO:618 or wherein the $V_H$ domain differs by no more than 5 amino acids from the amino acid sequence of SEQ ID NO:599 and wherein the $V_L$ domain differs by no more than 5 amino acids from the amino acid sequence of SEQ ID NO:600.

20. The method of claim 15, wherein the $V_H$ domain comprises the amino acid sequence of SEQ ID NO:617 and the $V_L$ domain comprises the amino acid sequence of SEQ ID NO:618.

21. The method of claim 15, wherein the $V_H$ domain comprises the amino acid sequence of SEQ ID NO:599 and the $V_L$ domain comprises the amino acid sequence of SEQ ID NO:600.

22. A method of treating atopic dermatitis in a subject, said method comprising, administering to the subject an antibody, or antigen-binding fragment thereof, that specifically binds to human IL-22, in an amount sufficient to inhibit or reduce immune cell activity in the subject, thereby treating the atopic dermatitis, wherein the antibody, or antigen-binding fragment thereof, comprises a $V_H$ domain comprising an amino acid sequence that is at least 85% identical to SEQ ID NO:599 or SEQ ID NO:617.

23. The method of claim 22, wherein the $V_H$ domain comprises an amino acid sequence that is at least 95% identical to SEQ ID NO:599 or SEQ ID NO:617.

24. The method of claim 22, wherein the $V_H$ domain comprises an amino acid sequence that is at least 98% identical to SEQ ID NO:599 or SEQ ID NO:617.

25. The method of claim 22, wherein the $V_H$ domain comprises the amino acid sequence of SEQ ID NO:599 or SEQ ID NO:617.

26. A method of treating atopic dermatitis in a subject, said method comprising, administering to the subject an antibody, or antigen-binding fragment thereof, that specifically binds to human IL-22, in an amount sufficient to inhibit or reduce immune cell activity in the subject, thereby treating the atopic dermatitis, wherein the antibody, or antigen-binding fragment thereof, comprises a $V_L$ domain comprising an amino acid sequence that is at least 85% identical to SEQ ID NO:600 or SEQ ID NO:618.

27. The method of claim 26, wherein the $V_L$ domain comprises an amino acid sequence that is at least 95% identical to SEQ ID NO:600 or SEQ ID NO:618.

28. The method of claim 26, wherein the $V_L$ domain comprises an amino acid sequence that is at least 98% identical to SEQ ID NO:600 or SEQ ID NO:618.

29. The method of claim 26, wherein the $V_L$ domain comprises the amino acid sequence of SEQ ID NO:600 or SEQ ID NO:618.

* * * * *

UNITED STATES PATENT AND TRADEMARK OFFICE
CERTIFICATE OF CORRECTION

| | | |
|---|---|---|
| PATENT NO. | : 8,906,375 B2 | Page 1 of 1 |
| APPLICATION NO. | : 12/951734 | |
| DATED | : December 9, 2014 | |
| INVENTOR(S) | : Lynette A. Fouser et al. | |

It is certified that error appears in the above-identified patent and that said Letters Patent is hereby corrected as shown below:

On The Title Page, Inventors (75): City for First Named Inventor, Lynette A. Fouser, "Action" should read --Acton--.

In The Claims

In Claim 14 (Column 350, line 65), "950" should read --250--.

Signed and Sealed this
Twelfth Day of May, 2015

Michelle K. Lee
*Director of the United States Patent and Trademark Office*